United States Patent
Bregman et al.

(10) Patent No.: US 9,505,749 B2
(45) Date of Patent: Nov. 29, 2016

(54) QUINAZOLINONE COMPOUNDS AND DERIVATIVES THEREOF

(71) Applicant: AMGEN INC., Thousand Oaks, CA (US)

(72) Inventors: Howard Bregman, Melrose, MA (US); John L. Buchanan, Newton, MA (US); Nagasree Chakka, Lexington, MA (US); Erin F. Dimauro, Cambridge, MA (US); Hakan Gunaydin, Somerville, MA (US); Angel Guzman-Perez, Belmont, MA (US); Zihao Hua, Andover, MA (US); Xin Huang, Wellesley, MA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 14/423,078

(22) PCT Filed: Aug. 27, 2013

(86) PCT No.: PCT/US2013/056884
§ 371 (c)(1),
(2) Date: Feb. 20, 2015

(87) PCT Pub. No.: WO2014/036022
PCT Pub. Date: Mar. 6, 2014

(65) Prior Publication Data
US 2015/0225396 A1      Aug. 13, 2015

Related U.S. Application Data

(60) Provisional application No. 61/694,560, filed on Aug. 29, 2012.

(51) Int. Cl.
| | | |
|---|---|---|
| *C07D 471/02* | (2006.01) |
| *C07D 403/12* | (2006.01) |
| *C07D 401/14* | (2006.01) |
| *C07D 413/14* | (2006.01) |
| *C07D 401/12* | (2006.01) |
| *C07D 239/90* | (2006.01) |
| *C07D 239/95* | (2006.01) |
| *C07D 413/12* | (2006.01) |
| *C07D 417/12* | (2006.01) |
| *C07D 417/14* | (2006.01) |
| *C07D 471/04* | (2006.01) |

(52) U.S. Cl.
CPC ........... *C07D 471/02* (2013.01); *C07D 239/90* (2013.01); *C07D 239/95* (2013.01); *C07D 401/12* (2013.01); *C07D 401/14* (2013.01); *C07D 403/12* (2013.01); *C07D 413/12* (2013.01); *C07D 413/14* (2013.01); *C07D 417/12* (2013.01); *C07D 417/14* (2013.01); *C07D 471/04* (2013.01)

(58) Field of Classification Search
CPC .................................................. C07D 401/207
See application file for complete search history.

(56) References Cited

U.S. PATENT DOCUMENTS

| 2009/0163545 A1 | 6/2009 | Goldfarb |
| 2010/0168065 A1 | 7/2010 | Vialard et al. |

FOREIGN PATENT DOCUMENTS

| WO | 2006/127550 A1 | 11/2006 |
| WO | 2007/133108 A1 | 11/2007 |
| WO | 2009/102537 A1 | 8/2009 |
| WO | 2013/117288 A1 | 8/2013 |

OTHER PUBLICATIONS

Pinedo et al. (2000).*
McMahon et al. (2000).*
International Search Report for parent PCT Application No. PCT/US2013/056884, mailed on Feb. 4, 2014.
International Preliminary Report on Patentability and Written Opinion for parent PCT Application No. PCT/US2013/056884 dated Mar. 3, 2015.
Huang, S-M A. et al., "Tankyrase Inhibition Stabilizes Axin and Antagonizes Wnt Signalling", Nature, vol. 461(7264), pp. 614-620 (2009).
Willems, E. et al., "Small-Molecule Inhibitors of the Wnt Pathway Potently Promote Cardiomyocytes from Human Embryonic Stem Cell-Derived Mesoderm" Circulation Research, vol. 109(4), pp. 360-364 (2011).
Waaler, J. et al., "A Novel Tankyrase Inhibitor Decreases Canonical Wnt Signaling in Colon Carcinoma Cells and Reduces Tumor Growth in Conditional APC Mutant Mice", Cancer Research, American Association for Cancer Research, vol. 72(11), pp. 2822-2832 (2012).
Bregman, H. et al., "Discovery of a Class of Novel Tankyrase Inhibitors that Bind to Both the Nicotinamide Pocket and the Induced Pocket", Journal of Medicinal Chemistry, vol. 56(3), pp. 1341-1345 (2013).
Lindgren, A. E. G. et al., "PARP Inhibitor with Selectivity Toward ADP-Ribosyltransferase ARTD3/PARP3", ACS Chemical Biology, American Chemical Society, Washington, DC, US vol. 8(8), pp. 1698-1703 (2013).
Barker, N. et al., "Mining the Wnt Pathway for Cancer Therapeutics", Nature Reviews Drug Discovery, vol. 5, pp. 997-1014 (2006).
Sammour, A. et al., "Reactions of 2-Ethyl-4H-3,1-benzoaxin-4-one", Acta Chimica Academiae Scientiarum Hungaricae, vol. 78(3), pp. 293-303 (1973).

(Continued)

*Primary Examiner* — Paul V Ward
(74) *Attorney, Agent, or Firm* — Bernard P. Friedrichsen

(57) ABSTRACT

Compounds of Formula I are useful inhibitors of tankyrase. Compounds of Formula I have the following structure: where the definitions of the variables are provided herein.

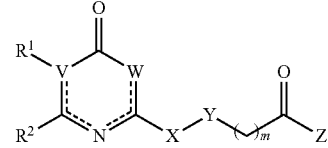

49 Claims, No Drawings

(56) References Cited

OTHER PUBLICATIONS

Chen, et. al. "Small Molecule-Mediated Disruption of Wnt-Dependent Signaling in Tissue Regeneration and Cancer", Nature Chemical Biology, vol. 5(2), pp. 100-107 (2009).
Narwal, M. et al., "Structural Basis of Selective Inhibition of Human Tankyrases", J. Medicinal Chemistry, vol. 55 (3), pp. 1360-1367 (2012).
Gunaydin, H. et al., "Novel Binding Mode of a Potent and Selective Tankyrase Inhibitor", PLoS One, e33740 (2012).
Hua, Z. et al., "Development of Novel Dual Binders as Potent, Selective, and Orally Bioavailable Tankyrase Inhibitors", J. Medicinal Chemistry, pp. 10003-10015 (2013).
Bregman, H. et al. "Discovery of Novel, Induced-Pocket Binding Oxazolidinones as Potent, Selective, and Orally Bioavailable Tankyrase Inhibitors", J. Medicinal Chemistry, vol. 56, pp. 4320-4342 (2013).
Huang, H. et al. "Structure-Based Design of 2-Aminopyridine Oxazolidinones as Potent and Selective Tankyrase Inhibitors", ACS Med. Chem. Lett., vol. 4, pp. 1218-1223 (2013).
Lau, T. et al., "A Novel Tankyrase Small-Molecule Inhibitor Suppresses APC Mutation-Driven Colorectal Tumor Growth", Cancer Research, vol. 73(10), pp. 3132-3144 (2013).
Schultz, M.D et al., "Structure-Efficiency Relationship of [1,2,4]Trazol-3-ylamines as novel Nicotinamide Isosteres that Inhibit Tankyrases", J. Medicinal Chemistry, vol. 56, pp. 7049-7059 (2013).
Schultz, M. D. et al., "[1,2,4]Triazol-3-ylsulfanylmethyl)-3-phenyl-[1,2,4]oxadiazoles: Antagonists of the Wnt Pathway That Inhibit Tankyrases 1 and 2 via Novel Adenosine Pocket Binding", J. Medicinal Chemistry, vol. 55, pp. 1127-1136 (2012).
Larsson, A. E. et al., "Fragment-Based Ligand Design of Novel Potent Inhibitors of Tankyrases",J. Medicinal Chemistry, vol. 56, pp. 4497-4508 (2013).
Voronkov, A. et al., "Structural Basis and SAR for G007-LK, a Lead Stage 1,2,4-Triazole Based Specific Takyrase 1/2 Inhibitor", J. Medicinal Chemistry, vol. 56, pp. 3012-3023 (2013).
Schultz, M. D et al., "identification of NVP-TNKS656: The use of Structure-Efficiency Relationships to Generate a Highly Potent, Selective, ad Orally Active Tankyrase Inhibitor", J. Medicinal Chemistry, vol. 56, pp. 6495-6511 (2013).
Haiarainen, T. et al., "Structural Basis and Selectivity of Tankyrase Inhibition by a Wnt Signaling Inhibitor WIKI4", PLoS One, vol. 8(6), e65404 (2013).
Results from SciFinder® Structure Search with quinazolinone bonded to chain with amide (N in ring (Class 3) performed on Aug. 17, 2011.
Results from SciFinder® Stricture Search with S bonded to quinazolinone (Class 1) performed on Aug. 17, 2011.
Results from SciFinder® Structure Search with C bonded to quinazolinone (Class 2) performed on Aug. 17, 2011.
Results from SciFinder® Structure Search with quinazolinone and lactam (Class 4) performed on Aug. 17, 2011.

* cited by examiner

QUINAZOLINONE COMPOUNDS AND DERIVATIVES THEREOF

CROSS REFERENCES TO RELATED APPLICATIONS

This application is a 371 National Phase Application of PCT/US2013/056884 filed Aug. 27, 2013, which claims the benefit of U.S. Provisional Application No. 61/694,560 filed Aug. 29, 2012.

FIELD OF THE INVENTION

The present invention relates to compounds capable of inhibiting the kinase activity of tankyrase 1 and/or tankyrase 2, and compositions that include compounds that inhibit tankyrase 1 and/or tankyrase 2. The compounds and compositions may be used to treat diseases or conditions modulated by tankyrase 1 and/or tankyrase 2 such as cancer and are especially useful in treating patients with conditions or diseases related to tankyrase expression.

BACKGROUND OF THE INVENTION

Tankyrase (TNKS) is a member of the poly-ADP-ribose polymerase (PARP) family, which uses NAD+ as a substrate to transfer ADP-ribose polymers onto target proteins, resulting in a post-translational modification referred to as PARsylation. TNKS was first identified as a binding partner for telomerase repeat binding factor 1 (TRF1), which is a key player in the regulation of telomere length at the chromosome ends. Telomere length is maintained by the reverse transcriptase telomerase. The TRF1 and TRF2 proteins are DNA binding proteins that regulate the length and stability of telomeres. Poly-ADP-ribosylation (PARsylation) of TRF1 by TNKS inhibits the ability of TRF1 to bind telomeric DNA thereby allowing telomerase access to telomeric DNA. Thus, TNKS proteins function as positive regulators of telomere length. In addition, it has been reported that TNKS regulates sister chromatid separation during mitosis as well as vesicle trafficking. Additional binding partners of TNKS have recently been identified including CASC3 and BLZF1 (Golgin-45) suggesting roles for TNKS in diverse cellular processes including mRNA metabolism and Golgi structure maintenance.

There are two TNKS genes, TNKS1 and TNKS2, in the human and mouse genomes. Individual and double-knockout of TNKS1 and TNKS2 in mice suggests that they share significant functional redundancy (Chiang Y. J. et. al., "Tankyrase 1 and Tankyrase 2 are Essential but Redundant for Mouse Embryonic Development," PLoS ONE 3(7): e2639. Pp. 1-10 (2008)) as the single homozygous TNKS1 or TNKS2 mice had relatively mild growth phenotypes and no defects in telomere maintenance, whereas the double knockout caused early embryonic lethality.

More recently, TNKS proteins were shown to bind directly to AXIN1 and AXIN2 proteins, which are negative regulators of the Wnt pathway, and regulate their steady state levels by PARsylation and ubiquitination (Huang, S. M. et al. "Tankyrase Inhibition Stabilizes Axin and Antagonizes Wnt Signalling," Nature, 461, pp 614-620 (2009)). Small-molecule inhibitors of tankyrases TNKS1 and TNKS2 can downregulate Wnt signaling (Huang, S. M. et al. "Tankyrase Inhibition Stabilizes Axin and Antagonizes Wnt Signalling," Nature, 461, pp 614-620 (2009); Chen, B. et. al. "Small Molecule-Mediated Disruption of Wnt-Dependent Signaling in Tissue Regeneration and Cancer," Nature Chem. Biol., 5(2), pp 100-107, (2009)) in several immortalized and malignant human cell lines. These inhibitors of TNKS also regulate the Wnt pathway in vivo in a Wnt signaling-dependent zebrafish model of fin regeneration.

Signaling by the Wnt family of secreted proteins plays an essential, evolutionarily conserved role in embryonic development and adult tissue homeostasis in a vast array of organisms including, flies, worms, chickens, frogs and mammals. Wnt signaling is a fundamental morphogenetic pathway that is deployed in diverse settings throughout development to regulate processes such as cell fate specification, tissue patterning, polarity, gastrulation, stem cell maintenance, and cell migration. The Wnt pathway is extraordinarily complex and the binding of Wnt ligands can lead to a variety of biological outcomes depending on the molecular and cellular context. Wnt signaling is often described in terms of either the canonical pathway or one of several non-canonical pathways.

In the canonical or β-catenin-dependent Wnt pathway, specific Wnt ligands regulate the level and sub-cellular localization of β-catenin. In the absence of an activating Wnt signal, glycogen synthase kinase 3β (GSK3β) collaborates with the AXIN and APC (adenomatous polyposis coli) proteins and other factors to phosphorylate β-catenin at its amino (N)-terminal domain. The phosphorylated β-catenin is recognized and ubiquitinated by a complex containing a β-transducin repeat-containing protein (βTrCP), and is then degraded by the proteasome. Wnt binding to the Frizzled-low density lipoprotein-related protein (LRP)-5/6 co-receptor complex on the cell surface leads to the recruitment of disheveled and the inhibition the AXIN/GSK3β complex. This, in turn, leads to the stabilization of the free pools of β-catenin which can enter the nucleus, bind to T cell factor (TCF) transcriptional regulators along with other cofactors and modulate transcription of various genes.

Wnt pathway deregulation has been implicated in many human diseases including cancer as well as many non-oncogenic disorders such as cardiac disease, osteoporosis, osteoarthritis, diabetes, fibrotic/proliferative diseases, Alzheimer's disease and schizophrenia. Wnt/β-catenin signaling is of particular relevance to colorectal cancers (CRC), which are the second leading cause of cancer death in Western societies. Mutations in the tumor suppressor gene, APC, are responsible for Familial Adenomatous Polyposis. Truncating mutations APC are also the most prevalent genetic alterations in sporadic CRC. Inactivating mutations of AXIN1/2 and oncogenic mutations in β-catenin, all of which lead to the stabilization of β-catenin and to altered expression of β-catenin/TCF-regulated genes in the absence of exogenous Wnt signals, have also been identified in human cancers including CRC. Indeed, aberrant activation of Wnt/β-catenin signaling is likely an obligatory step in the initiation of the majority, if not all, human CRC.

There is also good evidence for Wnt pathway hyperactivation in the initiation and/or progression on a variety of other human cancers including gastric, pancreatic, kidney (Wilms), medulloblastoma, melanoma, lung, thyroid, breast and prostate cancer. This pathway activation is achieved by either oncogenic mutations in β-catenin, or loss of function mutations in APC or AXIN. In addition, mutations or epigenetic silencing of extracellular negative regulators such as SFRP's, DKK's and WIF can also lead to abnormal pathway activity and have been widely reported in a large number of different human cancers.

Blocking canonical Wnt signaling in CRC and other Wnt-dependent tumors such as lung, breast and teratocarcinomas has been shown to inhibit tumor growth in human xenografts grown in mice or in transgenic mouse models. Several classes of small molecules have been shown to act as Wnt signaling inhibitors at various "nodes" of the pathway including the disruption of dishevelled activity and b-catenin interaction surfaces with TCF/LEF or pygopus. The efficient assembly of the multi-protein β-catenin destruction complex is dependent on the steady-state levels of its principal constituents. AXIN has been reported to be the concentration-limiting factor in regulating the efficiency of the β-catenin destruction complex and overexpression of AXIN induces β-catenin degradation even in cell lines expressing truncated APC (Hart, M. J. et. al. "Downregulation of Beta-Catenin by Human Axin and its Association with the APC Tumor Suppressor, Beta-Catenin and GSK3 Beta," Curr. Biol., 8(10) pp 573-581 (1998)). Thus, AXIN protein levels need to be tightly regulated to ensure proper Wnt pathway signaling and regulation of AXIN stability by TNKS therefore represents a good therapeutic target.

Cancer stem cells, found in many types of cancer, are rare populations of malignant cells with the capacity for endless self-renewal. They are believed to be responsible for tumor growth, recurrence and metastasis. Also referred to as "tumor-initiating cells," these cells have been identified in many types of solid tumor cancers, including cancer of head and neck, breast, lung, prostate, pancreas and glioblastoma. Cancer stem cells appear to be preferentially resistant to both standard chemotherapy and radiotherapy. One important therapeutic strategy is to specifically target the key biological pathways which are thought to be critical to the activity and survival of cancer stem cells. Since the Wnt pathway has been shown to be critical for cancer stem cells in many types of malignancies (e.g. squamous cancer stem cells), TNKS inhibitors are promising therapeutic compounds for use in treating human disease where cancer stem cells are thought to play a role (i.e. in recurrent or resistant disease). TNKS inhibitors could be either used alone or in combination with current chemotherapies.

Upregulation of telomerase and telomere maintenance is necessary for most cancer cells to replicate indefinitely and thereby enable tumor growth and metastasis. One strategy for the development of anti-cancer therapies is to inhibit telomerase activity in cancer cells Inhibiting telomerase activity should result in telomere shortening which can cause senescence and death of cancer cells. Another, strategy to inhibit the telomere elongation in cancer cells would be to effectively inhibit telomerase by exclusion by preventing the PARsylation of TRF1 by TNKS. Thus, TNKS inhibitors would be suitable cancer therapies either alone or in combination with telomerase inhibitors by targeting teleomeres and driving cancer cells towards senescence.

A need therefore exists for potent and selective inhibitors of TNKS that may be used to treat cancer. The present application discloses such potent and selective tankyrase inhibitors with good drug-like properties that are suitable for inhibiting the growth of cancer cells. These compounds are especially appropriate for inhibiting CRC or any other human tumor that has evidence of Wnt pathway activation and/or dependence.

SUMMARY OF THE INVENTION

In one aspect, the invention provides a compound of Formula I:

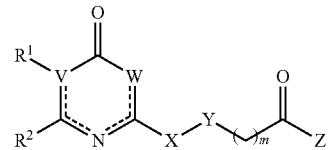

or a pharmaceutically acceptable salt thereof, a tautomer thereof, a pharmaceutically acceptable salt of the tautomer, a stereoisomer of any of the foregoing, or a mixture thereof, wherein:

$R^1$ is selected from —H, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —($C_1$-$C_6$ alkyl)-S—($C_1$-$C_6$ alkyl), —($C_1$-$C_6$ alkyl)-NH—($C_1$-$C_6$ alkyl), or —($C_1$-$C_6$ alkyl)-$NH_2$, or when V is C, then $R^1$ may additionally be selected from —O—($C_1$-$C_6$ alkyl), —NH—($C_1$-$C_6$ alkyl), or —N($C_1$-$C_6$ alkyl)$_2$;

$R^2$ is selected from —H, —$NH_2$, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —($C_1$-$C_6$ alkyl)-S—($C_1$-$C_6$ alkyl), —($C_1$-$C_6$ alkyl)-NH—($C_1$-$C_6$ alkyl), or —($C_1$-$C_6$ alkyl)-$NH_2$;

or $R^1$ and $R^2$, together with the atoms to which they are attached, join to form a 6 membered ring comprising 0, 1, or 2 heteroatoms selected from N, O, or S; wherein the 6-membered ring is optionally substituted with one or two substituents selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), or —$NH_2$;

V is C or N;
W is CH or NH;
X is $CH_2$, S, or $SO_2$;
Y is $CH_2$ or S;
one or two of X and Y are $CH_2$;
m is 0, 1, or 2;
Z is a group of formula II or formula III

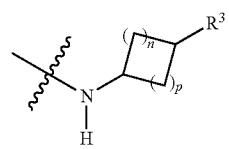

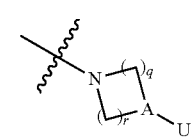

wherein
$R^3$ is selected from —O—$R^{4a}$, —O—$CH_2$—$R^{4a}$ or —$R^{4a}$;

$R^{4a}$ is selected from a $C_6$-$C_{10}$ aryl group, a heteroaryl group with 5 to 10 ring members containing 1, 2, or 3 heteroatoms independently selected from N, O, or S, or a heterocyclyl group with 5 to 10 ring members containing 1, 2, 3, or 4 heteroatoms independently selected from N, O, or S, or a —$CH_2$-phenyl group, wherein the $C_6$-$C_{10}$ aryl group, the heteroaryl group, or the heterocyclyl group are unsubstituted or are substituted with 1, 2, or 3 substituents independently selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —$R^{4b}$, —$OCH_2$—$R^{4b}$, —CH$_2$O—R$^{4b}$, or —(C$_1$-C$_4$ alkylene)-R$^{4b}$, and the heterocyclyl group may be further substituted with 1 oxo substituent;

R$^{4b}$ is selected from C$_6$-C$_{10}$ aryl group, a C$_3$-C$_8$ cycloalkyl group, a heteroaryl group with 5 to 10 ring members containing 1, 2, or 3 heteroatoms independently selected from N, O, or S, or a heterocyclyl group with 5 to 10 ring members containing 1, 2, 3, or 4 heteroatoms independently selected from N, O, or S, wherein the C$_6$-C$_{10}$ aryl group, the C$_3$-C$_8$ cycloalkyl group, the heteroaryl group, and the heterocyclyl group are unsubstituted or are substituted with 1, 2, or 3 substituents independently selected from —F, —Cl, —Br, —I, —CN, —C$_1$-C$_6$ alkyl, —C$_1$-C$_6$ haloalkyl, —C$_1$-C$_6$ perhaloalkyl, —OH, or —O—(C$_1$-C$_6$ alkyl, and the heterocyclyl group or cycloalkyl group may be further substituted with 1 oxo substituent n is 0, 1, 2, or 3;
p is 1, 2, or 3;
q is 1 or 2;
r is 1, 2, or 3;
A is CH or N;

wherein when Z is a group of formula III, R$^1$ and R$^2$, together with the atoms to which they are attached, join to form a 6-membered ring;

wherein the ring that includes the A variable in the group of formula III may include 0 or 1 double bond and A is C if the bond between an adjacent ring member and A is a double bond;

U is a heterocyclic or heteroaromatic group selected from

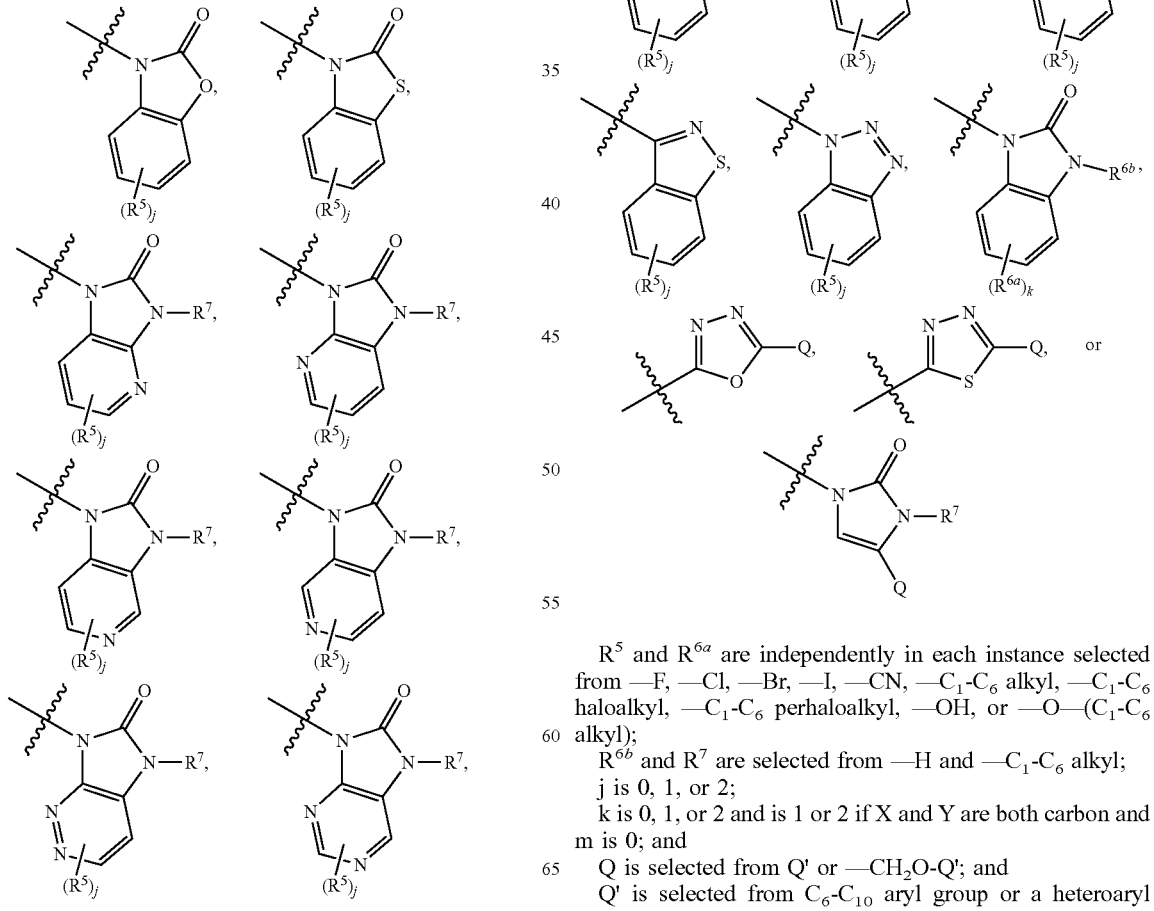

R$^5$ and R$^{6a}$ are independently in each instance selected from —F, —Cl, —Br, —I, —CN, —C$_1$-C$_6$ alkyl, —C$_1$-C$_6$ haloalkyl, —C$_1$-C$_6$ perhaloalkyl, —OH, or —O—(C$_1$-C$_6$ alkyl);

R$^{6b}$ and R$^7$ are selected from —H and —C$_1$-C$_6$ alkyl;
j is 0, 1, or 2;
k is 0, 1, or 2 and is 1 or 2 if X and Y are both carbon and m is 0; and
Q is selected from Q' or —CH$_2$O-Q'; and
Q' is selected from C$_6$-C$_{10}$ aryl group or a heteroaryl group with 5 to 10 ring members containing 1, 2, or 3 heteroatoms independently selected from N, O, or S, wherein the $C_6$-$C_{10}$ aryl group and the heteroaryl group are unsubstituted or are substituted with 1, 2, or 3 substituents independently selected from —F, —Cl, —Br, —I, —CN, —$C_1$-$C_6$ alkyl, —$C_1$-$C_6$ haloalkyl, —$C_1$-$C_6$ perhaloalkyl, —OH, or —O—($C_1$-$C_6$ alkyl);

wherein the symbol ~~~, when drawn across a bond, indicates the point of attachment to the rest of the molecule.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, $R^1$ is selected from —H, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —($C_1$-$C_6$ alkyl)-S—($C_1$-$C_6$ alkyl), —($C_1$-$C_6$ alkyl)-NH—($C_1$-$C_6$ alkyl), or —($C_1$-$C_6$ alkyl)-$NH_2$, or when V is C, then $R^1$ may additionally be selected from —O—($C_1$-$C_6$ alkyl), —NH—($C_1$-$C_6$ alkyl), or —N($C_1$-$C_6$ alkyl)$_2$; and $R^2$ is selected from —H, —$CH_3$, or —$NH_2$.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, $R^1$ is —H.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, the compound of formula I, has the formula IA

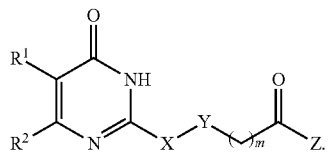

IA

In some embodiments of the compound of formula I or the pharmaceutically acceptable salt thereof, the tautomer thereof, the pharmaceutically acceptable salt of the tautomer, the stereoisomer of any of the foregoing, or the mixture thereof, $R^1$ and $R^2$, together with the atoms to which they are attached, join to form a 6 membered ring comprising 0 or 1 heteroatoms selected from N, O, or S; wherein the 6-membered ring is optionally substituted with one or two substituents selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), or —$NH_2$. In some such embodiments, $R^1$ and $R^2$, together with the atoms to which they are attached, join to form a 6 membered ring comprising 0 heteroatoms, wherein the 6-membered ring is optionally substituted with one or two substituents selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), or —$NH_2$.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, the compound of formula I, has the formula IB

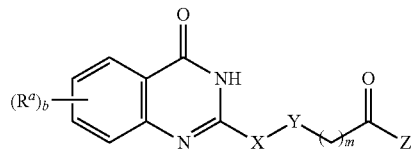

IB wherein b is 0, 1, or 2; and $R^a$ is independently selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), or —$NH_2$.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, the compound of formula I, has the formula IC

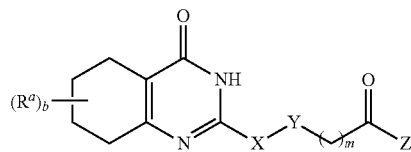

IC wherein b is 0, 1, or 2; and $R^a$ is independently selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), or —$NH_2$.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, the compound of formula I, has the formula ID

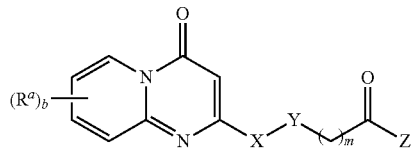

ID wherein b is 0, 1, or 2; and $R^a$ is independently selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), or —$NH_2$.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, b is 0, or b is 1 and $R^a$ is —F.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, V is C, and W is NH.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, X is S and Y is CH$_2$.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, Y is S and X is CH$_2$.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, X is CH$_2$ and Y is CH$_2$.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, X is SO$_2$ and Y is CH$_2$.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, m is 0. In other embodiments, m is 1, and in still other embodiments, m is 2.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, Z is a group of formula II.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, Z is

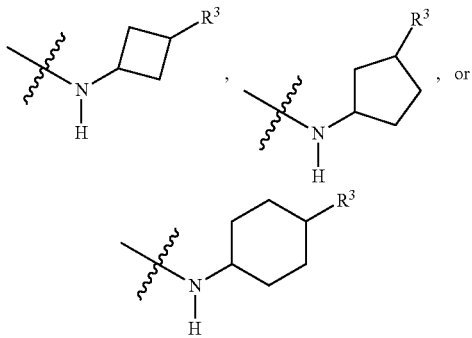

and the symbol ⌇, when drawn across a bond, indicates the point of attachment to the rest of the molecule.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, Z is

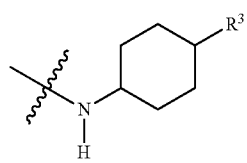

and the symbol ⌇, when drawn across a bond, indicates the point of attachment to the rest of the molecule.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, Z is

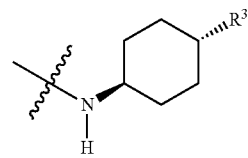

and the symbol ⌇, when drawn across a bond, indicates the point of attachment to the rest of the molecule.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, Z is

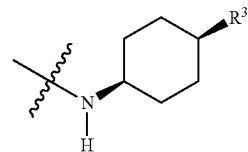

and the symbol ⌇, when drawn across a bond, indicates the point of attachment to the rest of the molecule.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, R$^3$ is

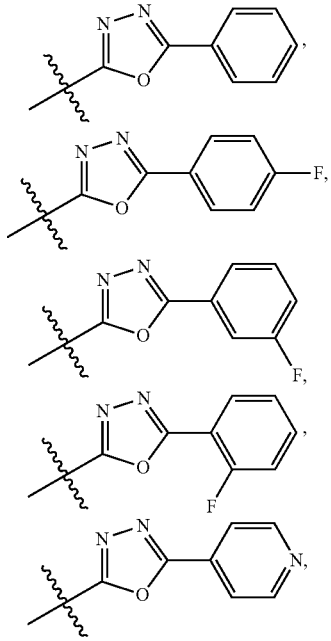

-continued
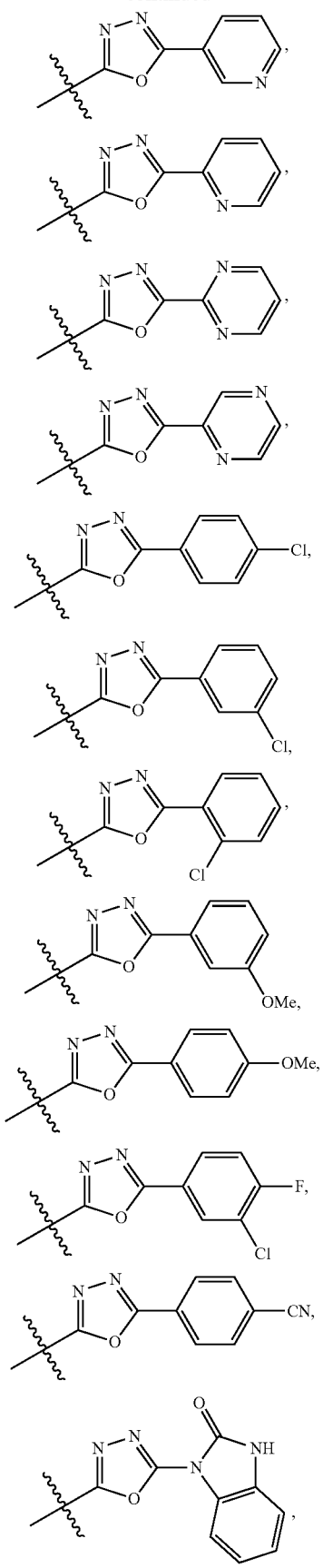
-continued
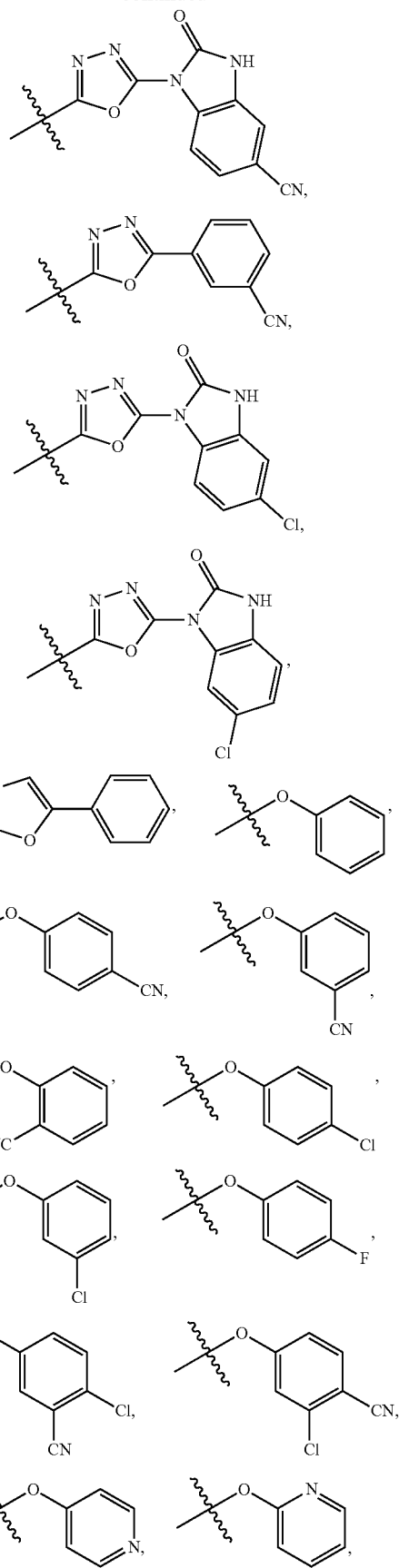

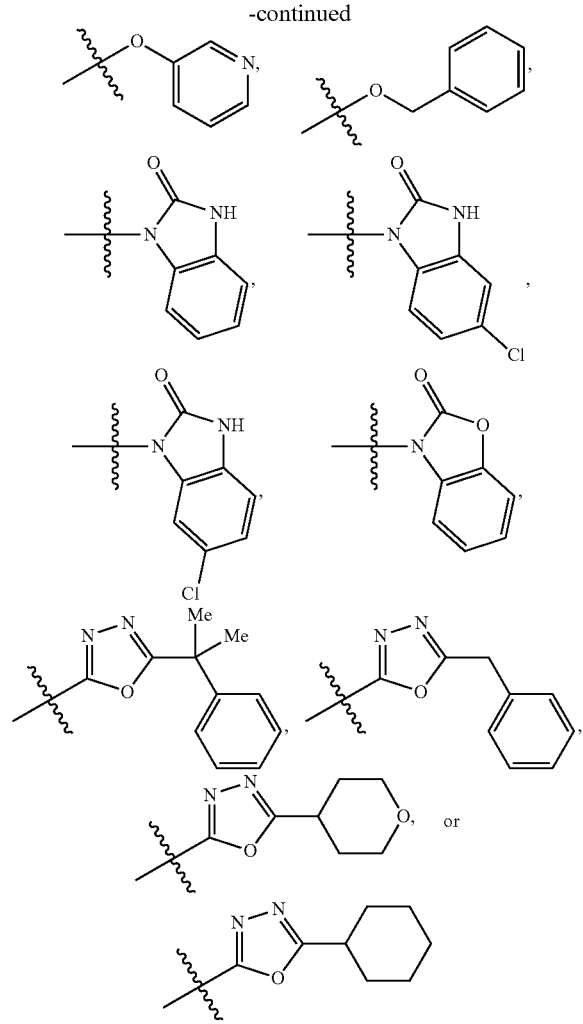

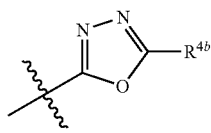

and the symbol ⌇, when drawn across a bond, indicates the point of attachment to the rest of the molecule.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, $R^3$ is —O—$R^{4a}$ or —$R^{4a}$. In some such embodiments, $R^3$ is —O—$R^{4a}$ whereas in other embodiments, $R^3$ is —$R^{4a}$.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, —$R^{4a}$ is

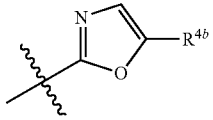

and the symbol ⌇, when drawn across a bond, indicates the point of attachment to the rest of the molecule. In some such embodiments, $R^{4b}$ is a $C_6$-$C_{10}$ aryl group or a heteroaryl group with 5 to 10 ring members containing 1, 2, or 3 heteroatoms independently selected from N, O, or S, and the $C_6$-$C_{10}$ aryl group and the heteroaryl group are unsubstituted or are substituted with 1, 2, or 3 substituents independently selected from —F, —Cl, —CN, —$C_1$-$C_6$ alkyl, —$C_1$-$C_6$ haloalkyl, —$C_1$-$C_6$ perhaloalkyl, or —O—($C_1$-$C_6$ alkyl).

In some embodiments of the compound of formula I or the pharmaceutically acceptable salt thereof, the tautomer thereof, the pharmaceutically acceptable salt of the tautomer, the stereoisomer of any of the foregoing, or the mixture thereof, —$R^{4a}$ is

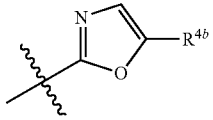

and the symbol ⌇, when drawn across a bond, indicates the point of attachment to the rest of the molecule.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, —$R^{4a}$ is

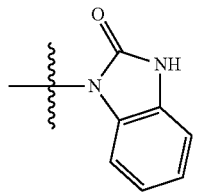 [SMILES: *n1c(=O)[nH]c2ccccc21]

and $R^{4a}$ is unsubstituted or is substituted with 1, 2, or 3 substituents independently selected from —F, —Cl, —CN, —$C_1$-$C_6$ alkyl, —$C_1$-$C_6$ haloalkyl, —$C_1$-$C_6$ perhaloalkyl, or —O—($C_1$-$C_6$ alkyl), and the symbol ⌇, when drawn across a bond, indicates the point of attachment to the rest of the molecule.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, —$R^{4a}$ is selected from a heteroaryl group with 5 to 10 ring members containing 1, 2, or 3 heteroatoms independently selected from N, O, or S, or a heterocyclyl group with 5 to 10 ring members containing 1, 2, 3, or 4 heteroatoms independently selected from N, O, or S, wherein the heteroaryl group or the heterocyclyl group are unsubstituted or are substituted with 1, 2, or 3 substituents independently selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), or —$R^{4b}$, and the heterocyclyl group may additionally be substituted with 1 oxo substituent.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, —$R^{4a}$ is a heteroaryl group with 5 ring members comprising 2 or 3 heteroatoms independently selected from N, O, or S, or —$R^{4a}$ is a heterocyclyl group with 9 ring members comprising 1, 2, or 3 heteroatoms independently selected from N, O, or S, wherein the heteroaryl group or the heterocyclyl group are unsubstituted or are substituted with 1, 2, or 3 substituents independently selected from —F, —Cl, —Br, —I, —CN, —CH$_3$, —CF$_3$, —OH, —O—CH$_3$, or —R$^{4b}$ and the heterocyclyl group may additionally be substituted with 1 oxo substituent.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, wherein —R$^{4a}$ is substituted with an —R$^{4b}$ substituent and —R$^{4b}$ is selected from a phenyl, pyridyl, pyrazinyl, pyrimidinyl, or benzoimidazolonyl group, wherein the phenyl, pyridyl, pyrazinyl, pyrimidinyl, or benzoimidazolonyl group are unsubstituted or are substituted with 1, 2, or 3 substituents independently selected from —F, —Cl, —CN, —CH$_3$, —CF$_3$, or —O—CH$_3$.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, n is 1 or 2. In some such embodiments, n is 1 whereas in other embodiments, n is 2.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, p is 1 or 2. In some such embodiments, p is 1 whereas in other embodiments, p is 2.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, Z is a group of formula III.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, q is 1 or 2. In some such embodiments, q is 1 whereas in other embodiments, q is 2.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, r is 1 or 2. In some such embodiments, r is 1 whereas in other embodiments, r is 2.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, Z is

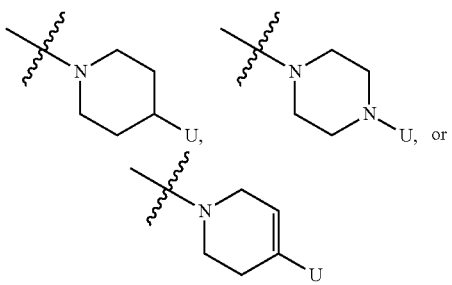

and the symbol ∼∼, when drawn across a bond, indicates the point of attachment to the rest of the molecule.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, U is

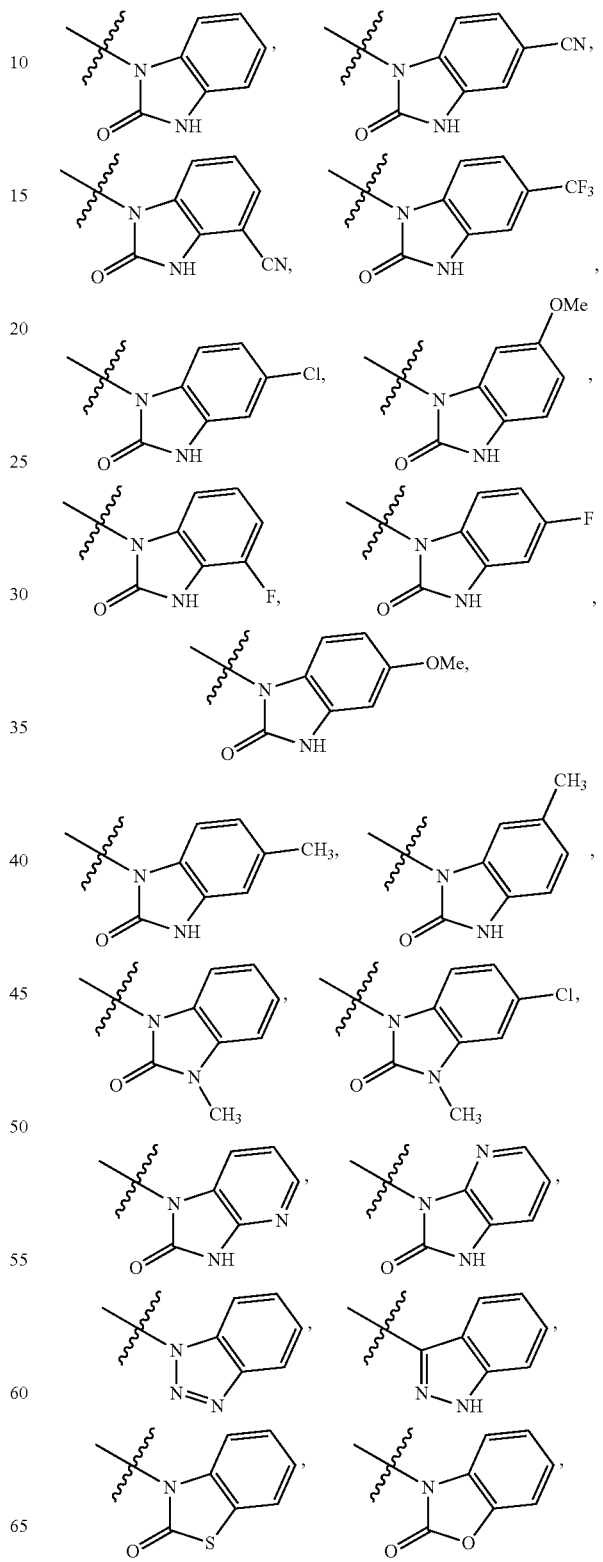

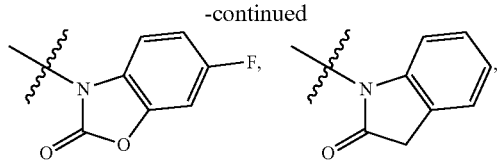
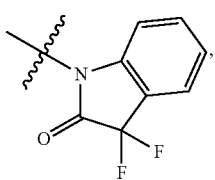
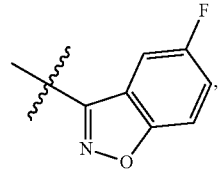
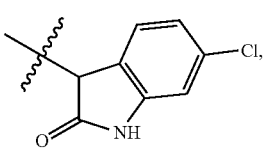
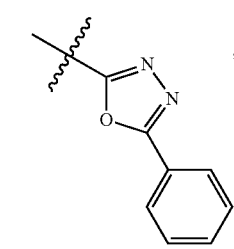
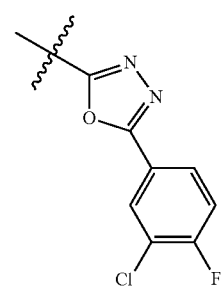
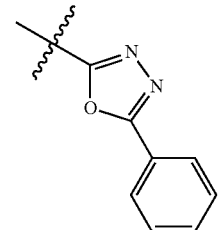
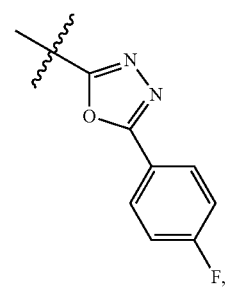
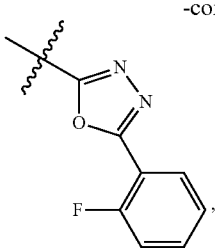
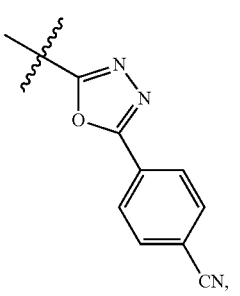
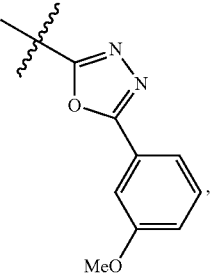
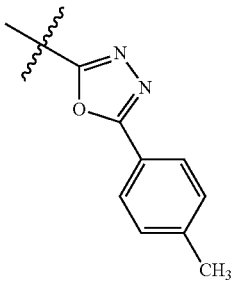
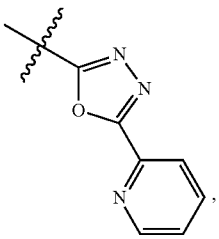
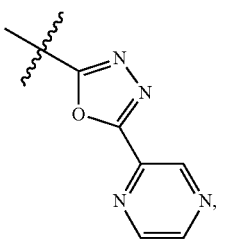

-continued

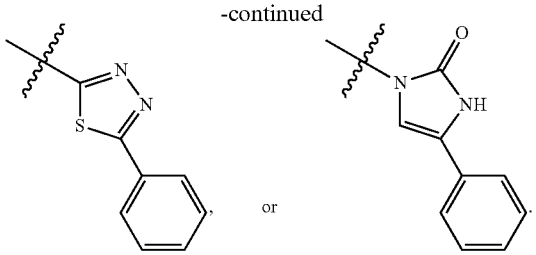, or

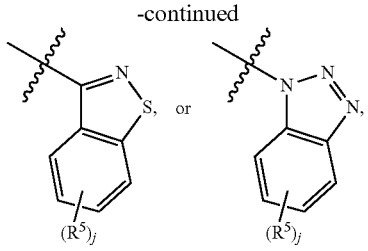

and the symbol ⌇, when drawn across a bond, indicates the point of attachment to the rest of the molecule.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, U is

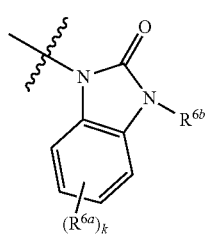

where $R^{6a}$ is independently selected from —F, —Cl, —CN, —$C_1$-$C_6$ alkyl, —$C_1$-$C_6$ perhaloalkyl, or —O—($C_1$-$C_6$ alkyl);

k is 1 or 2;

$R^{6b}$ is —H; and the symbol ⌇, when drawn across a bond, indicates the point of attachment to the rest of the molecule. In some such embodiments, $R^{6a}$ is —F, —Cl, —CN, —$CF_3$, —$CH_3$, or —O—$CH_3$. In other such embodiments, $R^{6a}$ is —F, —Cl, —CN, —$CF_3$, or —O—$CH_3$.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, U is

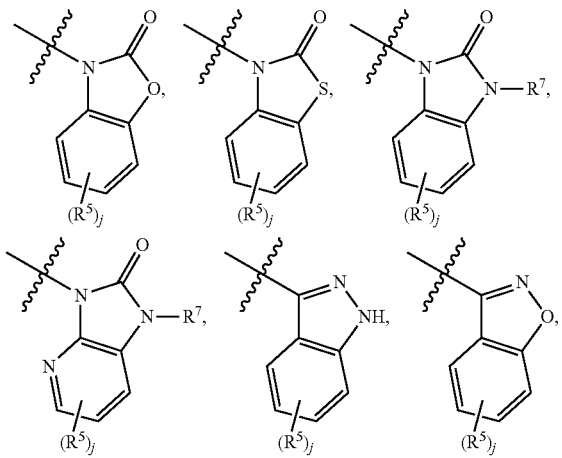

and the symbol ⌇, when drawn across a bond, indicates the point of attachment to the rest of the molecule.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, U is

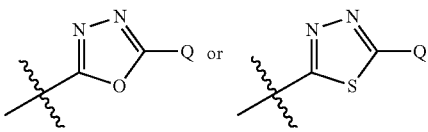

and the symbol ⌇, when drawn across a bond, indicates the point of attachment to the rest of the molecule. In some such embodiments, Q is Q' and Q' is a phenyl or a heteroaryl group with 6 ring members containing 1 or 2 N heteroatoms, wherein the phenyl group and the heteroaryl group are unsubstituted or are substituted with 1 or 2 substituents independently selected from —F, —Cl, —CN, —$CH_3$, —$CF_3$, or —$OCH_3$.

In some embodiments of the compound of formula I or the pharmaceutically acceptable salt thereof, the tautomer thereof, the pharmaceutically acceptable salt of the tautomer, the stereoisomer of any of the foregoing, or the mixture thereof, U is

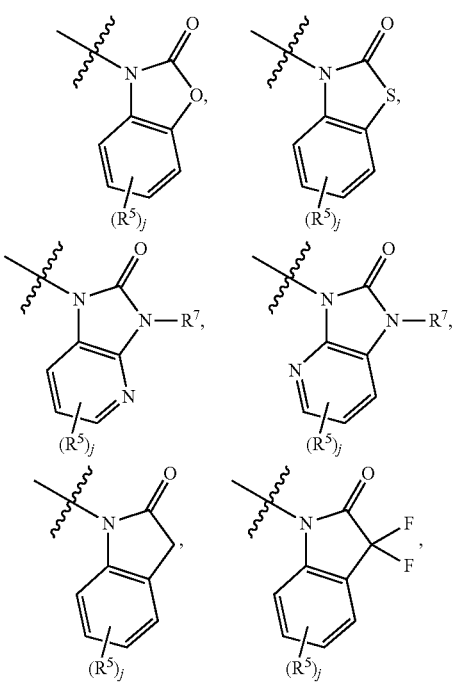

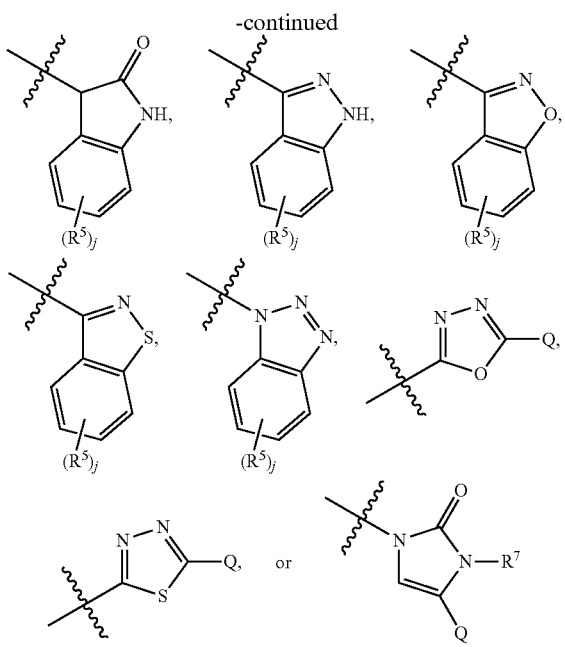

and the symbol ∼∼∼, when drawn across a bond, indicates the point of attachment to the rest of the molecule.

In some embodiments, the compound is a salt. Such salts may be anhydrous or associated with water as a hydrate. In other embodiments, the compound is a neutral compound.

Also provided are pharmaceutical compositions that include at least one pharmaceutically acceptable excipient, carrier or diluent and the compound or the pharmaceutically acceptable salt thereof, the tautomer thereof, the pharmaceutically acceptable salt of the tautomer, the stereoisomer of any of the foregoing, or the mixture thereof according to any one of the embodiments. In some such embodiments, the compound or the pharmaceutically acceptable salt thereof, the tautomer thereof, the pharmaceutically acceptable salt of the tautomer, the stereoisomer of any of the foregoing, or the mixture thereof according to any one of the embodiments is present in an amount effective for the treatment of cancer or for inhibiting tankyrase 1 and or tankyrase 2.

In other embodiments, the invention provides a method of treating cancer. Such methods typically include administering to a subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments. In some such embodiments, the cancer os colon cancer and in still other such embodiments is APC colon cancer. In some embodiments, the subject is a human cancer patient, and the cancer is selected from colon cancer. In still other embodiments, the cancer is selected from colon, pancreatic, ovarian, gastric, lung, or leukemia. In still other embodiments the cancer is any other cancer that relies on the Wnt pathway for growth or survival.

In still other embodiments, the invention provides a method of treating a condition where it is desired to inhibit tankyrase 1 or tankyrase 2 activity. Such methods typically include administering to a subject an effective amount of the compound or the pharmaceutically acceptable salt thereof, the tautomer thereof, the pharmaceutically acceptable salt of the tautomer, the stereoisomer of any of the foregoing, or the mixture thereof according to any one of any of the embodiments.

In some embodiments, the compound or the pharmaceutically acceptable salt thereof, the tautomer thereof, the pharmaceutically acceptable salt of the tautomer, the stereoisomer of any of the foregoing, or the mixture thereof according to any one of any of the embodiments is used in the preparation of a medicament. In some such embodiments, the medicament is for use in treating cancer. In some such embodiments, a medicament is for use in inhibiting tankyrase 1 or tankyrase 2. In still other such embodiments, the medicament is for use in treating a cancer in a human cancer patient such as a human with colon cancer.

In some such embodiments, the compound or the pharmaceutically acceptable salt thereof, the tautomer thereof, the pharmaceutically acceptable salt of the tautomer, the stereoisomer of any of the foregoing, or the mixture thereof according to any one of any of the embodiments is provided for use in treating cancer. In some such embodiments, the cancer is colon cancer. In still other embodiments the use is for treating cancer in a human patient.

Other objects, features and advantages of the invention will become apparent to those skilled in the art from the following description and claims.

DETAILED DESCRIPTION OF THE INVENTION

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, if any variable occurs more than one time in a chemical formula, its definition on each occurrence is independent of its definition at every other occurrence. If the chemical structure and chemical name conflict, the chemical structure is determinative of the identity of the compound. The compounds of the present disclosure may contain one or more chiral centers and/or double bonds and therefore, may exist as stereoisomers, such as double-bond isomers (i.e., geometric isomers), enantiomers or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into the component enantiomers or stereoisomers using separation techniques or chiral synthesis techniques well known to the skilled artisan.

Certain compounds of the invention may possess asymmetric carbon atoms (optical centers) or double bonds; the racemates, enantiomers, diastereomers, geometric isomers and individual isomers are all intended to be encompassed within the scope of the invention. Furthermore, atropisomers and mixtures thereof such as those resulting from restricted rotation about two aromatic or heteroaromatic rings bonded to one another are intended to be encompassed within the scope of the invention.

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line indicates that both stereoisomers are encompassed.

Various compounds of the invention contain one or more chiral centers, and can exist as racemic mixtures of enantiomers, mixtures of diastereomers or enantiomerically or optically pure compounds. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al. (1997) Tetrahedron 33:2725; Eliel, E. L., Stereochemistry of Carbon Compounds (McGraw-Hill, NY, 1962); and Wilen, S. H., Tables of Resolving Agents and Optical Resolutions p. 268 (E. L. Eliel, Ed., Univ. of Notre Dame Press, Notre Dame, Ind., 1972).

As known by those skilled in the art, certain compounds of the invention may exist in one or more tautomeric forms. Because one chemical structure may only be used to represent one tautomeric form, it will be understood that for convenience, referral to a compound of a given structural formula includes tautomers of the structure represented by the structural formula.

Compounds of the present disclosure include, but are not limited to, compounds of Formula I and all pharmaceutically acceptable forms thereof. Pharmaceutically acceptable forms of the compounds recited herein include pharmaceutically acceptable salts, solvates, crystal forms (including polymorphs and clathrates), chelates, non-covalent complexes, prodrugs, and mixtures thereof. In certain embodiments, the compounds described herein are in the form of pharmaceutically acceptable salts. As used herein, the term "compound" encompasses not only the compound itself, but also a pharmaceutically acceptable salt thereof, a solvate thereof, a chelate thereof, a non-covalent complex thereof, a prodrug thereof, and mixtures of any of the foregoing. In some embodiments, the term "compound" encompasses the compound itself, pharmaceutically acceptable salts thereof, tautomers of the compound, pharmaceutically acceptable salts of the tautomers, and ester prodrugs such as ($C_1$-$C_4$) alkyl esters. In other embodiments, the term "compound" encompasses the compound itself, pharmaceutically acceptable salts thereof, tautomers of the compound, pharmaceutically acceptable salts of the tautomers.

The term "solvate" refers to the compound formed by the interaction of a solvent and a compound. Suitable solvates are pharmaceutically acceptable solvates, such as hydrates, including monohydrates and hemi-hydrates.

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). Radiolabeled compounds are useful as therapeutic or prophylactic agents, research reagents, e.g., GPR40 assay reagents, and diagnostic agents, e.g., in vivo imaging agents. All isotopic variations of the compounds of the invention, whether radioactive or not, are intended to be encompassed within the scope of the invention. For example, if a variable is said to be H, this means that variable may also be deuterium (D) or tritium (T).

"Alkyl" refers to a saturated branched or straight-chain monovalent hydrocarbon group derived by the removal of one hydrogen atom from a single carbon atom of a parent alkane. Typical alkyl groups include, but are not limited to, methyl, ethyl, propyls such as propan-1-yl and propan-2-yl, butyls such as butan-1-yl, butan-2-yl, 2-methyl-propan-1-yl, 2-methyl-propan-2-yl, tert-butyl, and the like. In certain embodiments, an alkyl group comprises 1 to 20 carbon atoms. In some embodiments, alkyl groups include 1 to 6 carbon atoms whereas in other embodiments, alkyl groups include 1 to 4 carbon atoms. In still other embodiments, an alkyl group includes 1 or 2 carbon atoms. Branched chain alkyl groups include at least 3 carbon atoms and typically include 3 to 7, or in some embodiments, 3 to 6 carbon atoms. An alkyl group having 1 to 6 carbon atoms may be referred to as a ($C_1$-$C_6$)alkyl group and an alkyl group having 1 to 4 carbon atoms may be referred to as a ($C_1$-$C_4$)alkyl. This nomenclature may also be used for alkyl groups with differing numbers of carbon atoms.

"Alkenyl" refers to an unsaturated branched or straight-chain hydrocarbon group having at least one carbon-carbon double bond derived by the removal of one hydrogen atom from a single carbon atom of a parent alkene. The group may be in either the Z- or E-form (cis or trans) about the double bond(s). Typical alkenyl groups include, but are not limited to, ethenyl; propenyls such as prop-1-en-1-yl, prop-1-en-2-yl, prop-2-en-1-yl(allyl), and prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, and buta-1,3-dien-2-yl; and the like. In certain embodiments, an alkenyl group has 2 to 20 carbon atoms and in other embodiments, has 2 to 6 carbon atoms. An alkenyl group having 2 to 6 carbon atoms may be referred to as a ($C_2$-$C_6$)alkenyl group.

"Alkynyl" refers to an unsaturated branched or straight-chain hydrocarbon having at least one carbon-carbon triple bond derived by the removal of one hydrogen atom from a single carbon atom of a parent alkyne. Typical alkynyl groups include, but are not limited to, ethynyl; propynyl; butyryl, 2-pentynyl, 3-pentynyl, 2-hexynyl, 3-hexynyl and the like. In certain embodiments, an alkynyl group has 2 to 20 carbon atoms and in other embodiments, has 2 to 6 carbon atoms. An alkynyl group having 2 to 6 carbon atoms may be referred to as a —($C_2$-$C_6$)alkynyl group.

"Alkoxy" refers to a radical —OR where R represents an alkyl group as defined herein. Representative examples include, but are not limited to, methoxy, ethoxy, propoxy, butoxy, cyclohexyloxy, and the like. Typical alkoxy groups include 1 to 10 carbon atoms, 1 to 6 carbon atoms or 1 to 4 carbon atoms in the R group. Alkoxy groups that include 1 to 6 carbon atoms may be designated as —O($C_{1-6}$) alkyl or as —O—($C_{1-6}$) alkyl groups. In some embodiments, an alkoxy group may include 1 to 4 carbon atoms and may be designated as —O($C_{1-4}$) alkyl or as an —O—($C_{1-4}$) alkyl group.

"Alkylene" refers to a divalent saturated hydrocarbon group derived from a parent alkane by removal of two hydrogen atoms. Examples of alkylene group include, but are not limited to, —$CH_2$—, —$CH_2CH_2$—, —$CH(CH_3)$—, —$CH_2CH_2CH_2$—, —$CH_2C(CH_3)(H)$—, and the like. In some embodiments an alkylene may include 1 to 6 carbon atoms and in other embodiments may include 1 to 4 carbon atoms. Such groups may be designated as —($C_1$-$C_6$)alkylene- and —($C_1$-$C_4$)alkylene-groups.

"Aryl" refers to a monovalent aromatic hydrocarbon group derived by the removal of one hydrogen atom from a single carbon atom of a parent aromatic ring system. Aryl encompasses monocyclic carbocyclic aromatic rings, for example, benzene. Aryl also encompasses bicyclic carbocyclic aromatic ring systems where each of the rings is aromatic, for example, naphthalene. Aryl groups may thus include fused ring systems where each ring is a carbocyclic aromatic ring. In certain embodiments, an aryl group includes 6 to 10 carbon atoms. Such groups may be referred to as $C_6$-$C_{10}$ aryl groups. Aryl, however, does not encompass or overlap in any way with heteroaryl as separately defined below. Hence, if one or more carbocyclic aromatic rings is fused with an aromatic ring that includes at least one heteroatom, the resulting ring system is heteroaryl, not aryl, as defined herein.

"Carbonyl" refers to the radical —C(O) or —C(=O) group.

"Carboxy" refers to the radical —C(O)OH.

"Cyano" refers to the radical —CN.

"Cycloalkyl" refers to a saturated cyclic alkyl group derived by the removal of one hydrogen atom from a single carbon atom of a parent cycloalkane. Typical cycloalkyl groups include, but are not limited to, groups derived from cyclopropane, cyclobutane, cyclopentane, cyclohexane, cycloheptane, cyclooctane, and the like. Cycloalkyl groups may be described by the number of carbon atoms in the ring. For example a cycloalkyl group having 3 to 7 ring members may be referred to as a ($C_3$-$C_7$)cycloalkyl and a cycloalkyl group having 4 to 7 ring members may be referred to as a ($C_4$-$C_7$)cycloalkyl. In certain embodiments, the cycloalkyl group can be a ($C_3$-$C_{10}$)cycloalkyl, a ($C_3$-$C_7$)cycloalkyl, a ($C_3$-$C_6$)cycloalkyl, or a ($C_4$-$C_7$)cycloalkyl group.

"Heterocyclyl" refers to a cyclic group that includes at least one saturated or unsaturated, but non-aromatic, cyclic ring. Heterocyclyl groups include at least one heteroatom as a ring member. Typical heteroatoms include, but are not limited to, O, S and N and are independently chosen. Heterocyclyl groups include monocyclic ring systems and bicyclic ring systems. Bicyclic heterocyclyl groups include at least one non-aromatic ring with at least one heteroatom ring member that may be fused to a cycloalkyl ring or may be fused to an aromatic ring where the aromatic ring may be carbocyclic or may include one or more heteroatoms. The point of attachment of a bicyclic heterocyclyl group may be at the non-aromatic cyclic ring that includes at least one heteroatom or at another ring of the heterocyclyl group. For example, a heterocyclyl group derived by removal of a hydrogen atom from one of the 9 membered heterocyclic compounds shown below may be attached to the rest of the molecule at the 5-membered ring or at the 6-membered ring.

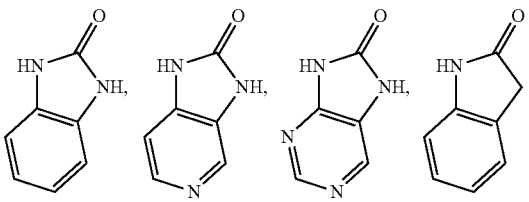 [SMILES: O=c1[nH]c2ccccc2[nH]1 ; O=c1[nH]c2ccncc2[nH]1 ; O=c1[nH]c2cncnc2[nH]1 ; O=C1Cc2ccccc2N1]

In some embodiments, a heterocyclyl group includes 3 to 10 ring members of which 1, 2, or 3 ring members are independently selected from O, S, or N. In other embodiments, a heterocyclyl group includes 4 to 10 ring members of which 1, 2, or 3 are heteroatoms independently selected from O, S, or N. In other embodiments, a heterocyclyl group includes 5 to 10 ring members of which 1, 2, 3 or 4 are heteroatoms independently selected from O, S, or N. In other embodiments, a heterocyclyl group includes 4 to 7 ring members comprising 1 heteroatom selected from O, S, or N. In still other embodiments, a heterocyclyl group includes 3 or 4 ring members of which 1 is a heteroatom selected from O, S, or N. In still other embodiments, a heterocyclyl group includes rings with 5 to 10 ring members of which 1, 2, 3, or 4 are heteroatoms selected from O, S, or N and rings with 3 or 4 ring members of which 1 is a heteroatom selected from O, S, or N. In other embodiments, a heterocyclyl group includes 5 to 7 ring members of which 1, 2, or 3 are heteroatoms independently selected from O, S, or N. Typical heterocyclyl groups include, but are not limited to, groups derived from epoxides, aziridine, azetidine, imidazolidine, morpholine, piperazine, piperidine, hexahydropyrimidine, 1,4,5,6-tetrahydropyrimidine, pyrazolidine, pyrrolidine, quinuclidine, tetrahydrofuran, tetrahydropyran, benzimidazolone, pyridinone, and the like. Substituted heterocyclyl also includes ring systems substituted with one or more oxo (=O) or oxide (—O⁻) substituents, such as piperidinyl N-oxide, morpholinyl-N-oxide, 1-oxo-1-thiomorpholinyl, pyridinonyl, benzimidazolonyl, benzo[d]oxazol-2(3H)-only, 3,4-dihydroisoquinolin-1(2H)-only, indolin-only, 1H-imidazo[4,5-c]pyridin-2(3H)-only, 7H-purin-8(9H)-only, imidazolidin-2-only, 1H-imidazol-2(3H)-only, 1,1-dioxo-1-thiomorpholinyl, and the like.

"Disease" refers to any disease, disorder, condition, symptom, or indication.

"Halo" or "halogen" refers to a fluoro, chloro, bromo, or iodo group.

"Haloalkyl" refers to an alkyl group in which at least one hydrogen is replaced with a halogen. Thus, the term "haloalkyl" includes monohaloalkyl (alkyl substituted with one halogen atom) and polyhaloalkyl (alkyl substituted with two or more halogen atoms). Representative "haloalkyl" groups include difluoromethyl, 2,2,2-trifluoroethyl, 2,2,2-trichloroethyl, and the like. The term "perhaloalkyl" means, unless otherwise stated, an alkyl group in which each of the hydrogen atoms is replaced with a halogen atom. For example, the term "perhaloalkyl", includes, but is not limited to, trifluoromethyl, pentachloroethyl, 1,1,1-trifluoro-2-bromo-2-chloroethyl, and the like.

"Heteroaryl" refers to a monovalent heteroaromatic group derived by the removal of one hydrogen atom from a single atom of a parent heteroaromatic ring system. Heteroaryl groups typically include 5- to 14-membered, but more typically include 5- to 10-membered aromatic, monocyclic, bicyclic, and tricyclic rings containing one or more, for example, 1, 2, 3, or 4, or in certain embodiments, 1, 2, or 3, heteroatoms chosen from O, S, and N, with the remaining ring atoms being carbon. In monocyclic heteroaryl groups, the single ring is aromatic and includes at least one heteroatom. In bicyclic aromatic rings, both rings are aromatic. In bicyclic heteroaryl groups, at least one of the rings must include a heteroatom, but it is not necessary that both rings include a heteroatom although it is permitted for them to do so. For example, heteroaryl includes a 5- to 7-membered heteroaromatic ring fused to a carbocyclic aromatic ring or fused to a heteroaromatic ring. In tricyclic aromatic rings, all three of the rings are aromatic and at least one of the rings includes at least one heteroatom. For fused, bicyclic and tricyclic heteroaryl ring systems where only one of the rings contains one or more heteroatoms, the point of attachment may be at the ring including at least one heteroatom or at a carbocyclic ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Heteroaryl does not encompass or overlap with aryl as defined above. Examples of heteroaryl groups include, but are not limited to, groups derived from acridine, carbazole, cinnoline, furan, imidazole, indazole, indole, indolizine, isobenzofuran, isochromene, isoindole, isoquinoline, isothiazole, 2H-benzo[d][1,2,3]triazole, isoxazole, naphthyridine, oxadiazole, oxazole, perimidine, phenanthridine, phenanthroline, phenazine, phthalazine, pteridine, purine, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, and the like. In certain embodiments, the heteroaryl group can be between 5 to 20 membered heteroaryl, such as, for example, a 5 to 14 membered or 5 to 10 membered heteroaryl. In certain embodiments, heteroaryl groups can be those derived from thiophene, pyrrole, benzothiophene, 2H-benzo[d][1,2,3]triazole benzofuran, indole, pyridine, quinoline, imidazole, benzimidazole, oxazole, tetrazole, and pyrazine.

"Sulfonyl" refers to a radical —S(O)$_2$R where R is an alkyl, substituted alkyl, substituted cycloalkyl, substituted heterocyclyl, substituted aryl, or substituted heteroaryl group as defined herein. Representative examples include, but are not limited to, methylsulfonyl, ethylsulfonyl, propylsulfonyl, butylsulfonyl, and the like.

"Sulfanyl" refers to a radical —SR where R is an alkyl, substituted alkyl, substituted cycloalkyl, substituted heterocyclyl, substituted aryl, or substituted heteroaryl group as defined herein that may be optionally substituted as defined herein. Representative examples include, but are not limited to, methylthio, ethylthio, propylthio, butylthio, and the like.

"Pharmaceutically acceptable" refers to generally recognized for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable excipient," "pharmaceutically acceptable carrier," or "pharmaceutically acceptable adjuvant" refer, respectively, to an excipient, carrier or adjuvant with which at least one compound of the present disclosure is administered. "Pharmaceutically acceptable vehicle" refers to any of a diluent, adjuvant, excipient or carrier with which at least one compound of the present disclosure is administered.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereomers."

"Subject" includes mammals and humans. The terms "human" and "subject" are used interchangeably herein.

"Therapeutically effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

EMBODIMENTS

The embodiments listed below are presented in numbered form for convenience and in ease and clarity of reference in referring back to multiple embodiments.

1. In a first embodiment, the invention provides a compound of Formula I:

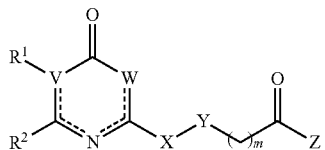

I or a pharmaceutically acceptable salt thereof, a tautomer thereof, a pharmaceutically acceptable salt of the tautomer, a stereoisomer of any of the foregoing, or a mixture thereof, wherein:

$R^1$ is selected from —H, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —($C_1$-$C_6$ alkyl)-S—($C_1$-$C_6$ alkyl), —($C_1$-$C_6$ alkyl)-NH—($C_1$-$C_6$ alkyl), or —($C_1$-$C_6$ alkyl)-$NH_2$, or when V is C, then $R^1$ may additionally be selected from —O—($C_1$-$C_6$ alkyl), —NH—($C_1$-$C_6$ alkyl), or —N($C_1$-$C_6$ alkyl)$_2$;

$R^2$ is selected from —H, —$NH_2$, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —($C_1$-$C_6$ alkyl)-S—($C_1$-$C_6$ alkyl), —($C_1$-$C_6$ alkyl)-NH—($C_1$-$C_6$ alkyl), or —($C_1$-$C_6$ alkyl)-$NH_2$;

or $R^1$ and $R^2$, together with the atoms to which they are attached, join to form a 6 membered ring comprising 0, 1, or 2 heteroatoms selected from N, O, or S; wherein the 6-membered ring is optionally substituted with one or two substituents selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), or —$NH_2$;

V is C or N;
W is CH or NH;
X is $CH_2$, S, or $SO_2$;
Y is $CH_2$ or S;
one or two of X and Y are $CH_2$;
m is 0, 1, or 2;
Z is a group of formula II or formula III

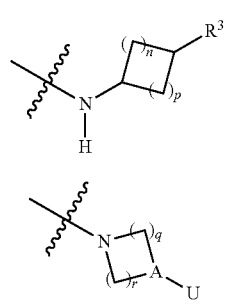

II

III wherein
$R^3$ is selected from —O—$R^{4a}$, —O—$CH_2$—$R^{4a}$ or —$R^{4a}$;

$R^{4a}$ is selected from a $C_6$-$C_{10}$ aryl group, a heteroaryl group with 5 to 10 ring members containing 1, 2, or 3 heteroatoms independently selected from N, O, or S, or a heterocyclyl group with 5 to 10 ring members containing 1, 2, 3, or 4 heteroatoms independently selected from N, O, or S, or a —$CH_2$-phenyl group, wherein the $C_6$-$C_{10}$ aryl group, the heteroaryl group, or the heterocyclyl group are unsubstituted or are substituted with 1, 2, or 3 substituents independently selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —$R^{4b}$, —$OCH_2$—$R^{4b}$, —$CH_2O$—$R^{4b}$, or —($C_1$-$C_4$ alkylene)-$R^{4b}$, and the heterocyclyl group may be further substituted with 1 oxo substituent;

$R^{4b}$ is selected from $C_6$-$C_{10}$ aryl group, a $C_3$-$C_8$ cycloalkyl group, a heteroaryl group with 5 to 10 ring members containing 1, 2, or 3 heteroatoms independently selected from N, O, or S, or a heterocyclyl group with 5 to 10 ring members containing 1, 2, 3, or 4 heteroatoms independently selected from N, O, or S, wherein the $C_6$-$C_{10}$ aryl group, the $C_3$-$C_8$ cycloalkyl group, the heteroaryl group, and the heterocyclyl group are unsubstituted or are substituted with 1, 2, or 3 substituents independently selected from —F, —Cl, —Br, —I, —CN, —$C_1$-$C_6$ alkyl, —$C_1$-$C_6$ haloalkyl, —$C_1$-$C_6$ perhaloalkyl, —OH, or —O—($C_1$-$C_6$ alkyl), and the heterocyclyl group or cycloalkyl group may be further substituted with 1 oxo substituent n is 0, 1, 2, or 3;
p is 1, 2, or 3;
q is 1 or 2;
r is 1, 2, or 3;
A is CH or N;

wherein when Z is a group of formula III, $R^1$ and $R^2$, together with the atoms to which they are attached, join to form a 6-membered ring;

wherein the ring that includes the A variable in the group of formula III may include 0 or 1 double bond and A is C if the bond between an adjacent ring member and A is a double bond;

U is a heterocyclic or heteroaromatic group selected from

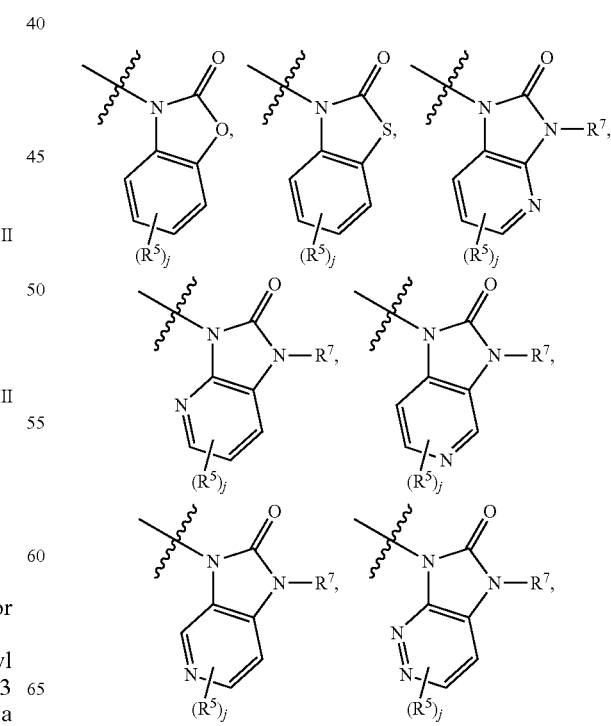

-continued

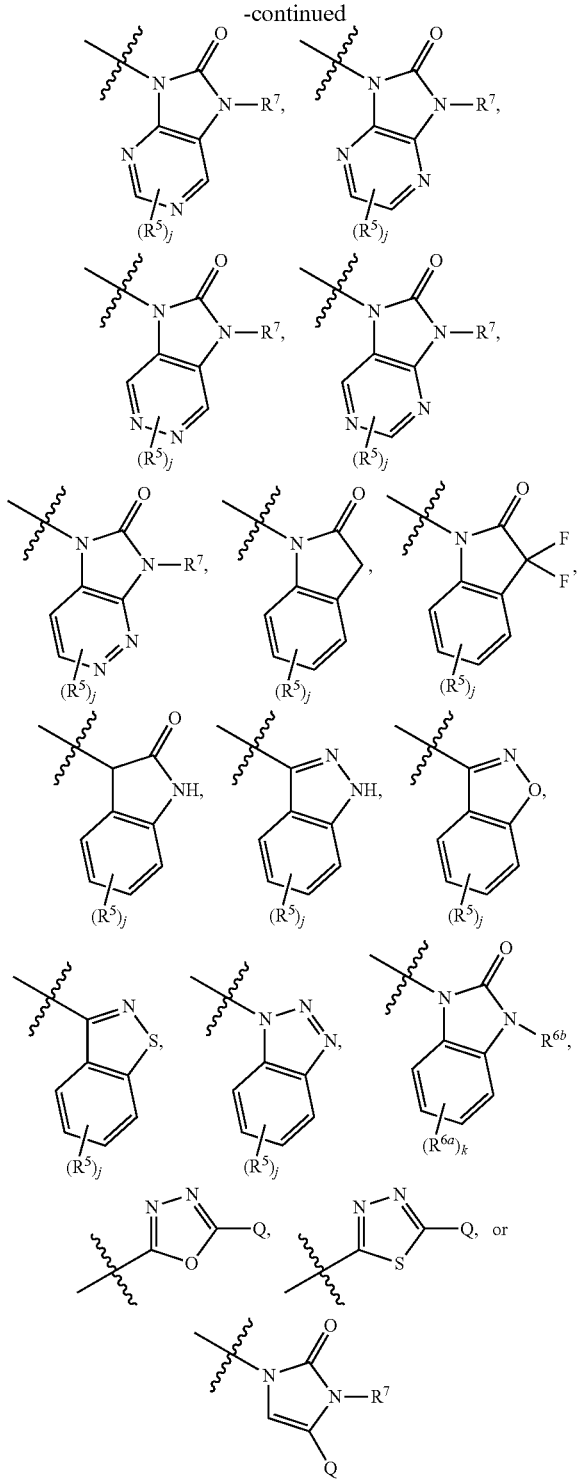

$R^5$ and $R^{6a}$ are independently in each instance selected from —F, —Cl, —Br, —I, —CN, —$C_1$-$C_6$ alkyl, —$C_1$-$C_6$ haloalkyl, —$C_1$-$C_6$ perhaloalkyl, —OH, or —O—($C_1$-$C_6$ alkyl);

$R^{6b}$ and $R^7$ are selected from —H and —$C_1$-$C_6$ alkyl;

j is 0, 1, or 2;

k is 0, 1, or 2 and is 1 or 2 if X and Y are both carbon and m is 0; and

Q is selected from Q' or —$CH_2O$-Q'; and

Q' is selected from $C_6$-$C_{10}$ aryl group or a heteroaryl group with 5 to 10 ring members containing 1, 2, or 3 heteroatoms independently selected from N, O, or S, wherein the $C_6$-$C_{10}$ aryl group and the heteroaryl group are unsubstituted or are substituted with 1, 2, or 3 substituents independently selected from —F, —Cl, —Br, —I, —CN, —$C_1$-$C_6$ alkyl, —$C_1$-$C_6$ haloalkyl, —$C_1$-$C_6$ perhaloalkyl, —OH, or —O—($C_1$-$C_6$ alkyl);

wherein the symbol ~~~, when drawn across a bond, indicates the point of attachment to the rest of the molecule.

2. The compound of embodiment 1 or the pharmaceutically acceptable salt thereof, the tautomer thereof, the pharmaceutically acceptable salt of the tautomer, the stereoisomer of any of the foregoing, or the mixture thereof, wherein $R^1$ is selected from —H, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —($C_1$-$C_6$ alkyl)-S—($C_1$-$C_6$ alkyl), —($C_1$-$C_6$ alkyl)-NH—($C_1$-$C_6$ alkyl), or —($C_1$-$C_6$ alkyl)-$NH_2$, or when V is C, then $R^1$ may additionally be selected from —O—($C_1$-$C_6$ alkyl), —NH—($C_1$-$C_6$ alkyl), or —N($C_1$-$C_6$ alkyl)$_2$; and $R^2$ is selected from —H, —$CH_3$, or —$NH_2$.

3. The compound of embodiment 1 or embodiment 2 or the pharmaceutically acceptable salt thereof, the tautomer thereof, the pharmaceutically acceptable salt of the tautomer, the stereoisomer of any of the foregoing, or the mixture thereof, wherein $R^1$ is —H.

4. The compound of embodiment 1 or the pharmaceutically acceptable salt thereof, the tautomer thereof, the pharmaceutically acceptable salt of the tautomer, the stereoisomer of any of the foregoing, or the mixture thereof, wherein the compound of formula I, has the formula IA

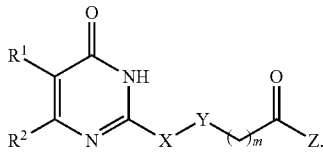

IA

5. The compound of embodiment 1 or the pharmaceutically acceptable salt thereof, the tautomer thereof, the pharmaceutically acceptable salt of the tautomer, the stereoisomer of any of the foregoing, or the mixture thereof, wherein $R^1$ and $R^2$, together with the atoms to which they are attached, join to form a 6 membered ring comprising 0 or 1 heteroatoms selected from N, O, or S; wherein the 6-membered ring is optionally substituted with one or two substituents selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), or —$NH_2$.

6. The compound of embodiment 1 or the pharmaceutically acceptable salt thereof, the tautomer thereof, the pharmaceutically acceptable salt of the tautomer, the stereoisomer of any of the foregoing, or the mixture thereof, wherein $R^1$ and $R^2$, together with the atoms to which they are attached, join to form a 6 membered ring comprising 0 heteroatoms, wherein the 6-membered ring is optionally substituted with one or two substituents selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), or —$NH_2$.

7. The compound of embodiment 1 or the pharmaceutically acceptable salt thereof, the tautomer thereof, the pharmaceutically acceptable salt of the tautomer, the stereoisomer of any of the foregoing, or the mixture thereof, wherein the compound of formula I, has the formula IB

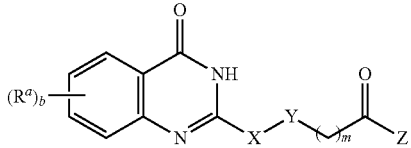

wherein b is 0, 1, or 2; and
$R^a$ is independently selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), or —$NH_2$.

8. The compound of embodiment 1 or the pharmaceutically acceptable salt thereof, the tautomer thereof, the pharmaceutically acceptable salt of the tautomer, the stereoisomer of any of the foregoing, or the mixture thereof, wherein the compound of formula I, has the formula IC

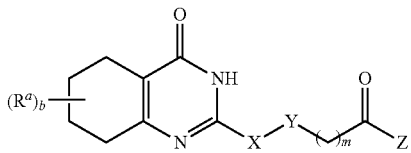

wherein b is 0, 1, or 2; and
$R^a$ is independently selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), or —$NH_2$.

9. The compound of embodiment 1 or the pharmaceutically acceptable salt thereof, the tautomer thereof, the pharmaceutically acceptable salt of the tautomer, the stereoisomer of any of the foregoing, or the mixture thereof, wherein the compound of formula I, has the formula ID

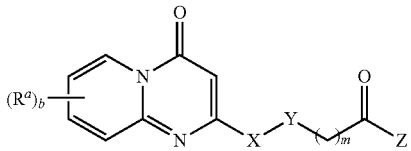

wherein b is 0, 1, or 2; and
$R^a$ is independently selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), or —$NH_2$.

10. The compound of any one of embodiments 7-9 or the pharmaceutically acceptable salt thereof, the tautomer thereof, the pharmaceutically acceptable salt of the tautomer, the stereoisomer of any of the foregoing, or the mixture thereof, wherein b is 0, or b is 1 and $R^a$ is —F.

11. The compound of any one of embodiments 1, 2, 5, or 6 or the pharmaceutically acceptable salt thereof, the tautomer thereof, the pharmaceutically acceptable salt of the tautomer, the stereoisomer of any of the foregoing, or the mixture thereof, wherein V is C, and W is NH.

12. The compound of any of embodiments 1-11 or the pharmaceutically acceptable salt thereof, the tautomer thereof, the pharmaceutically acceptable salt of the tautomer, the stereoisomer of any of the foregoing, or the mixture thereof, wherein X is S and Y is $CH_2$.

13. The compound of any of embodiments 1-11 or the pharmaceutically acceptable salt thereof, the tautomer thereof, the pharmaceutically acceptable salt of the tautomer, the stereoisomer of any of the foregoing, or the mixture thereof, wherein Y is S and X is $CH_2$.

14. The compound of any of embodiments 1-11 or the pharmaceutically acceptable salt thereof, the tautomer thereof, the pharmaceutically acceptable salt of the tautomer, the stereoisomer of any of the foregoing, or the mixture thereof, wherein X is $CH_2$ and Y is $CH_2$.

15. The compound of any of embodiments 1-11 or the pharmaceutically acceptable salt thereof, the tautomer thereof, the pharmaceutically acceptable salt of the tautomer, the stereoisomer of any of the foregoing, or the mixture thereof, wherein X is $SO_2$ and Y is $CH_2$.

16. The compound of any one of embodiments 1-15 or the pharmaceutically acceptable salt thereof, the tautomer thereof, the pharmaceutically acceptable salt of the tautomer, the stereoisomer of any of the foregoing, or the mixture thereof, wherein m is 0.

17. The compound of any one of embodiments 1-15 or the pharmaceutically acceptable salt thereof, the tautomer thereof, the pharmaceutically acceptable salt of the tautomer, the stereoisomer of any of the foregoing, or the mixture thereof, wherein m is 1.

18. The compound of any one of embodiments 1-15 or the pharmaceutically acceptable salt thereof, the tautomer thereof, the pharmaceutically acceptable salt of the tautomer, the stereoisomer of any of the foregoing, or the mixture thereof, wherein m is 2.

19. The compound of any one of embodiments 1-18 or the pharmaceutically acceptable salt thereof, the tautomer thereof, the pharmaceutically acceptable salt of the tautomer, the stereoisomer of any of the foregoing, or the mixture thereof, wherein Z is a group of formula II.

20. The compound of embodiment 19 or the pharmaceutically acceptable salt thereof, the tautomer thereof, the pharmaceutically acceptable salt of the tautomer, the stereoisomer of any of the foregoing, or the mixture thereof, wherein Z is

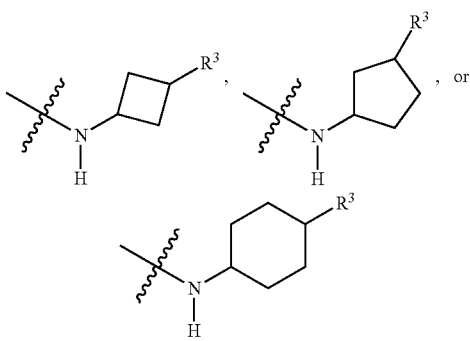

and the symbol ∼∼∼, when drawn across a bond, indicates the point of attachment to the rest of the molecule.

21. The compound of embodiment 21 or the pharmaceutically acceptable salt thereof, the tautomer thereof, the pharmaceutically acceptable salt of the tautomer, the stereoisomer of any of the foregoing, or the mixture thereof, wherein Z is

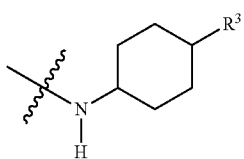

and the symbol ⌇, when drawn across a bond, indicates the point of attachment to the rest of the molecule.

22. The compound of embodiment 21 or the pharmaceutically acceptable salt thereof, the tautomer thereof, the pharmaceutically acceptable salt of the tautomer or the mixture thereof, wherein Z is

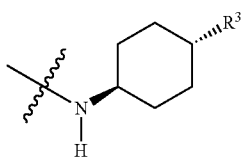

and the symbol ⌇, when drawn across a bond, indicates the point of attachment to the rest of the molecule.

23. The compound of embodiment 21 or the pharmaceutically acceptable salt thereof, the tautomer thereof, the pharmaceutically acceptable salt of the tautomer, or the mixture thereof, wherein Z is

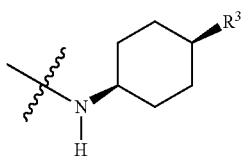

and the symbol ⌇, when drawn across a bond, indicates the point of attachment to the rest of the molecule.

24. The compound of any one of embodiments 1-23 or the pharmaceutically acceptable salt thereof, the tautomer thereof, the pharmaceutically acceptable salt of the tautomer, the stereoisomer of any of the foregoing, or the mixture thereof, wherein $R^3$ is

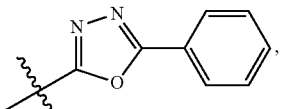

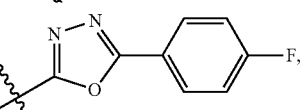

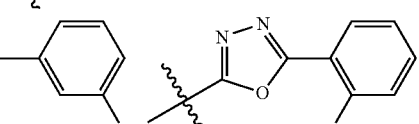

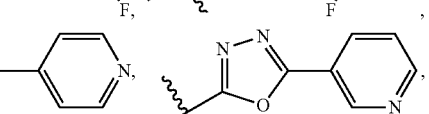

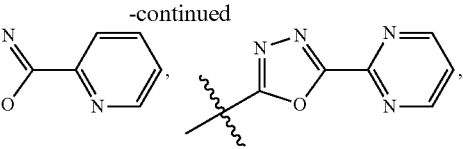

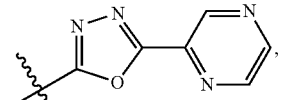

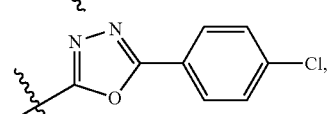

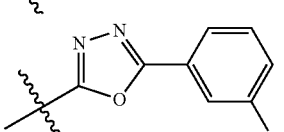

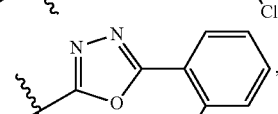

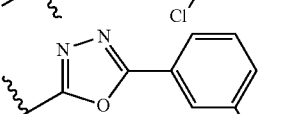

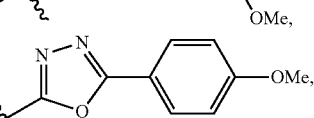

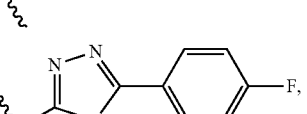

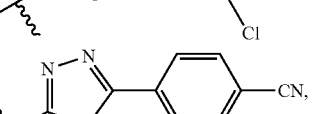

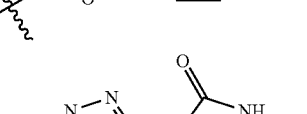

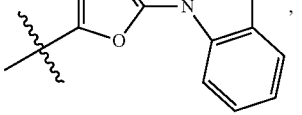

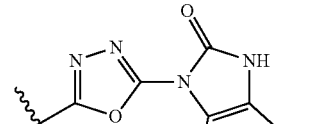

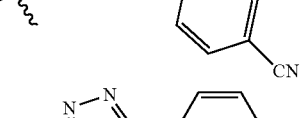

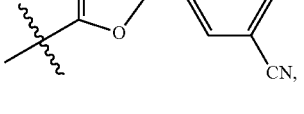

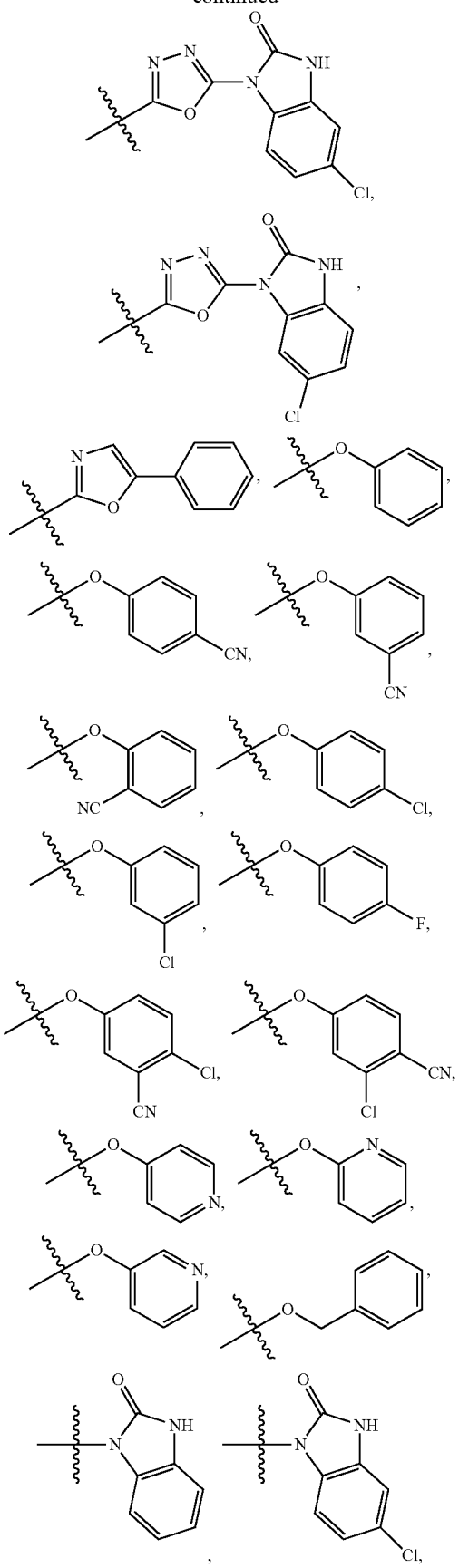

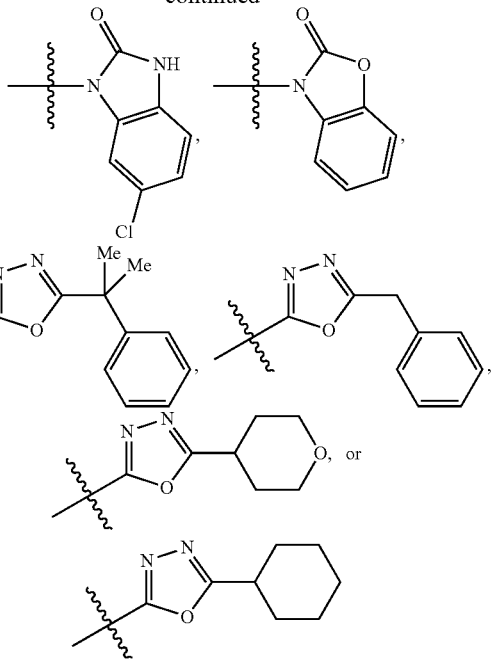

and the symbol ∿∿∿, when drawn across a bond, indicates the point of attachment to the rest of the molecule.

25. The compound of any one of embodiments 1-23 or the pharmaceutically acceptable salt thereof, the tautomer thereof, the pharmaceutically acceptable salt of the tautomer, the stereoisomer of any of the foregoing, or the mixture thereof, wherein $R^3$ is —O—$R^{4a}$ or —$R^{4a}$.

26. The compound of embodiment 25 or the pharmaceutically acceptable salt thereof, the tautomer thereof, the pharmaceutically acceptable salt of the tautomer, the stereoisomer of any of the foregoing, or the mixture thereof, wherein $R^3$ is —O—$R^{4a}$.

27. The compound of embodiment 25 or the pharmaceutically acceptable salt thereof, the tautomer thereof, the pharmaceutically acceptable salt of the tautomer, the stereoisomer of any of the foregoing, or the mixture thereof, wherein $R^3$ is —$R^{4a}$.

28. The compound of embodiment 27 or the pharmaceutically acceptable salt thereof, the tautomer thereof, the pharmaceutically acceptable salt of the tautomer, the stereoisomer of any of the foregoing, or the mixture thereof, wherein —$R^{4a}$ is

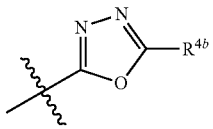

and the symbol ∿∿∿, when drawn across a bond, indicates the point of attachment to the rest of the molecule.

29. The compound of embodiment 28 or the pharmaceutically acceptable salt thereof, the tautomer thereof, the pharmaceutically acceptable salt of the tautomer, the stereoisomer of any of the foregoing, or the mixture thereof, wherein $R^{4b}$ is a $C_6$-$C_{10}$ aryl group or a heteroaryl group with 5 to 10 ring members containing 1, 2, or 3 heteroatoms independently selected from N, O, or S, and the $C_6$-$C_{10}$ aryl group and the heteroaryl group are unsubstituted or are substituted with 1, 2, or 3 substituents independently selected from —F, —Cl, —CN, —$C_1$-$C_6$ alkyl, —$C_1$-$C_6$ haloalkyl, —$C_1$-$C_6$ perhaloalkyl, or —O—($C_1$-$C_6$ alkyl).

30. The compound of embodiment 27 or the pharmaceutically acceptable salt thereof, the tautomer thereof, the pharmaceutically acceptable salt of the tautomer, the stereoisomer of any of the foregoing, or the mixture thereof, wherein —$R^{4a}$ is

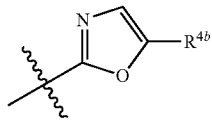

and the symbol ⌇, when drawn across a bond, indicates the point of attachment to the rest of the molecule.

31. The compound of embodiment 27 or the pharmaceutically acceptable salt thereof, the tautomer thereof, the pharmaceutically acceptable salt of the tautomer, the stereoisomer of any of the foregoing, or the mixture thereof, wherein —$R^{4a}$ is

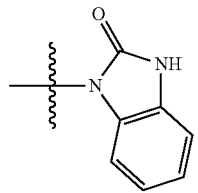 [SMILES: *n1c(=O)[nH]c2ccccc21]

and $R^{4a}$ is unsubstituted or is substituted with 1, 2, or 3 substituents independently selected from —F, —Cl, —CN, —$C_1$-$C_6$ alkyl, —$C_1$-$C_6$ haloalkyl, —$C_1$-$C_6$ perhaloalkyl, or —O—($C_1$-$C_6$ alkyl), and the symbol ⌇, when drawn across a bond, indicates the point of attachment to the rest of the molecule.

32. The compound of embodiment 27 or the pharmaceutically acceptable salt thereof, the tautomer thereof, the pharmaceutically acceptable salt of the tautomer, the stereoisomer of any of the foregoing, or the mixture thereof, wherein —$R^{4a}$ is selected from a heteroaryl group with 5 to 10 ring members containing 1, 2, or 3 heteroatoms independently selected from N, O, or S, or a heterocyclyl group with 5 to 10 ring members containing 1, 2, 3, or 4 heteroatoms independently selected from N, O, or S, wherein the heteroaryl group or the heterocyclyl group are unsubstituted or are substituted with 1, 2, or 3 substituents independently selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), or —$R^{4b}$, and the heterocyclyl group may additionally be substituted with 1 oxo substituent.

33. The compound of embodiment 32 or the pharmaceutically acceptable salt thereof, the tautomer thereof, the pharmaceutically acceptable salt of the tautomer, the stereoisomer of any of the foregoing, or the mixture thereof, wherein —$R^{4a}$ is a heteroaryl group with 5 ring members comprising 2 or 3 heteroatoms independently selected from N, O, or S, or —$R^{4a}$ is a heterocyclyl group with 9 ring members comprising 1, 2, or 3 heteroatoms independently selected from N, O, or S, wherein the heteroaryl group or the heterocyclyl group are unsubstituted or are substituted with 1, 2, or 3 substituents independently selected from —F, —Cl, —Br, —I, —CN, —$CH_3$, —$CF_3$, —OH, —O—$CH_3$, or —$R^{4b}$ and the heterocyclyl group may additionally be substituted with 1 oxo substituent.

34. The compound of embodiment 32 or 33 or the pharmaceutically acceptable salt thereof, the tautomer thereof, the pharmaceutically acceptable salt of the tautomer, the stereoisomer of any of the foregoing, or the mixture thereof, wherein —$R^{4a}$ is substituted with an —$R^{4b}$ substituent and —$R^{4b}$ is selected from a phenyl, pyridyl, pyrazinyl, pyrimidinyl, or benzoimidazolonyl group, wherein the phenyl, pyridyl, pyrazinyl, pyrimidinyl, or benzoimidazolonyl group are unsubstituted or are substituted with 1, 2, or 3 substituents independently selected from —F, —Cl, —CN, —$CH_3$, —$CF_3$, or —O—$CH_3$.

35. The compound of embodiment 19 or the pharmaceutically acceptable salt thereof, the tautomer thereof, the pharmaceutically acceptable salt of the tautomer, the stereoisomer of any of the foregoing, or the mixture thereof, wherein n is 1 or 2.

36. The compound of embodiment 19 or embodiment 35, or the pharmaceutically acceptable salt thereof, the tautomer thereof, the pharmaceutically acceptable salt of the tautomer, the stereoisomer of any of the foregoing, or the mixture thereof, wherein p is 1 or 2.

37 The compound of any one of embodiments 1-18 or the pharmaceutically acceptable salt thereof, the tautomer thereof, the pharmaceutically acceptable salt of the tautomer, the stereoisomer of any of the foregoing, or the mixture thereof, wherein Z is a group of formula III.

38. The compound of embodiment 37 or the pharmaceutically acceptable salt thereof, the tautomer thereof, the pharmaceutically acceptable salt of the tautomer, the stereoisomer of any of the foregoing, or the mixture thereof, wherein q is 1 or 2.

39. The compound of embodiment 37 or embodiment 38 or the pharmaceutically acceptable salt thereof, the tautomer thereof, the pharmaceutically acceptable salt of the tautomer, the stereoisomer of any of the foregoing, or the mixture thereof, wherein r is 1 or 2

40. The compound of embodiment 37 or the pharmaceutically acceptable salt thereof, the tautomer thereof, the pharmaceutically acceptable salt of the tautomer, the stereoisomer of any of the foregoing, or the mixture thereof, wherein Z is

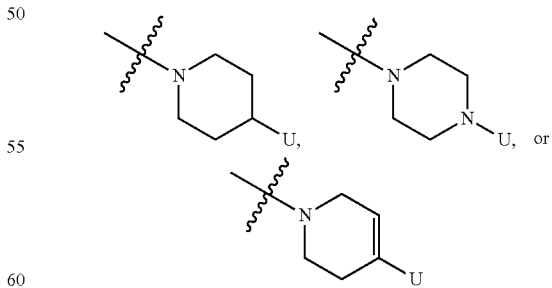

and the symbol ⌇, when drawn across a bond, indicates the point of attachment to the rest of the molecule.

41. The compound of any one of embodiments 1-18 or 37-40 or the pharmaceutically acceptable salt thereof, the tautomer thereof, the pharmaceutically acceptable salt of the tautomer, the stereoisomer of any of the foregoing, or the mixture thereof, wherein U is selected from
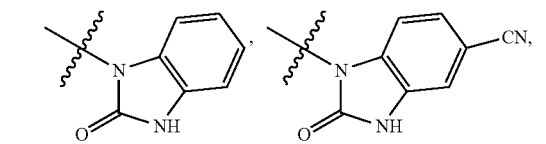
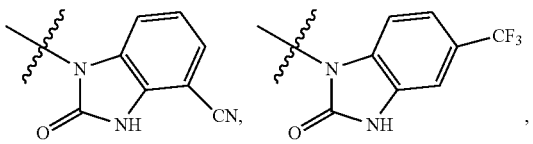
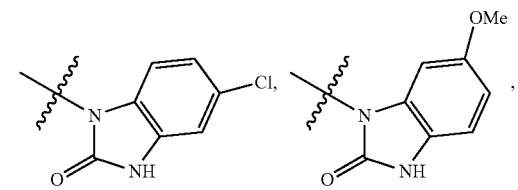
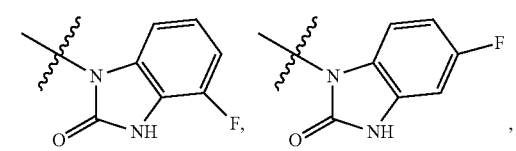
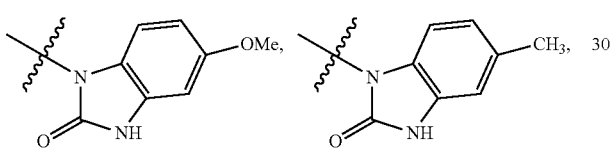
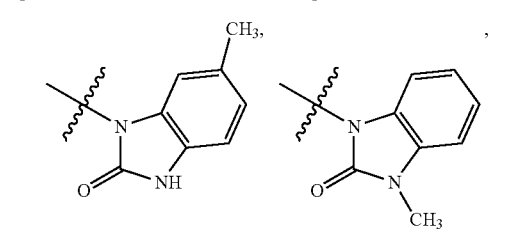
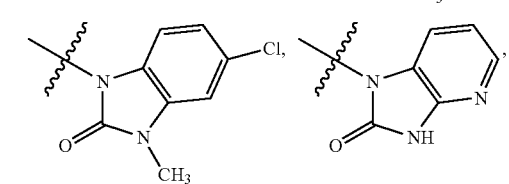
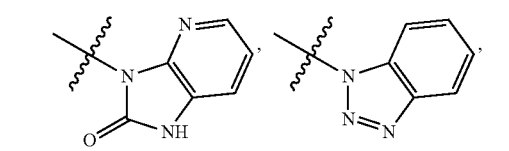
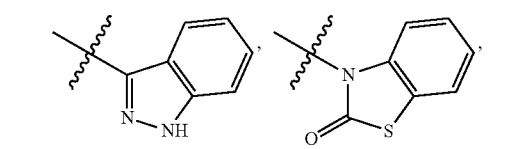
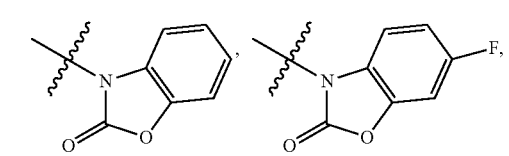
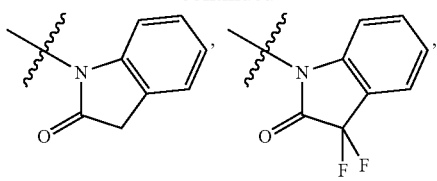
-continued
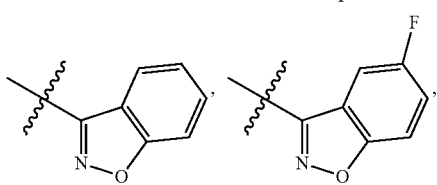
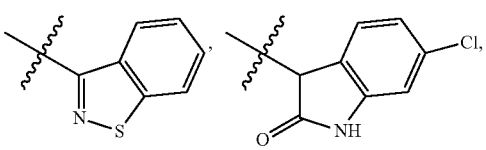
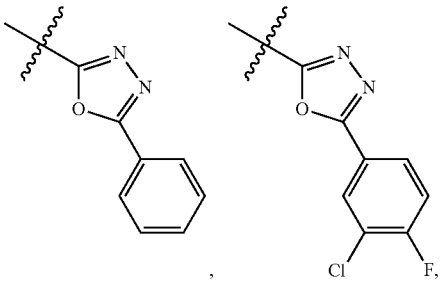
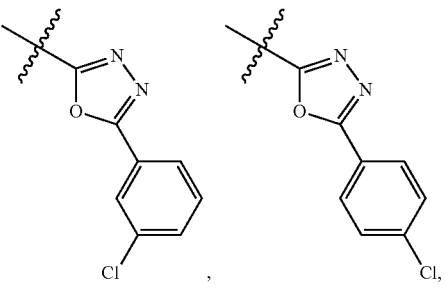
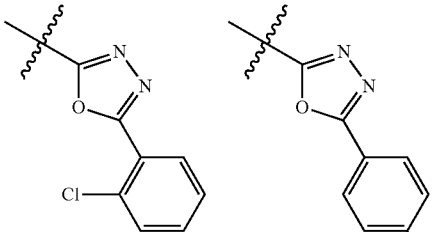
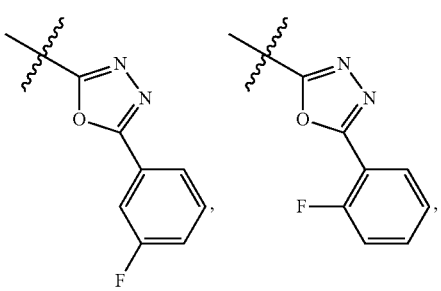

-continued

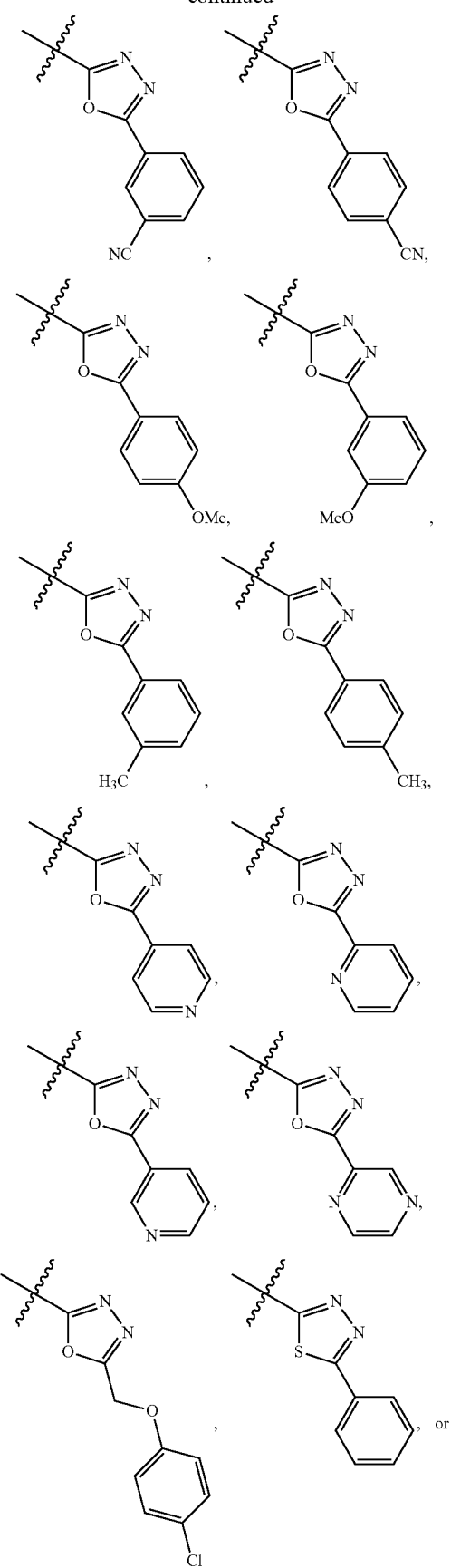

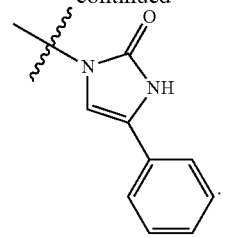

and the symbol ⌇, when drawn across a bond, indicates the point of attachment to the rest of the molecule.

42. The compound of any one of embodiments 1-18 or 37-40 or the pharmaceutically acceptable salt thereof, the tautomer thereof, the pharmaceutically acceptable salt of the tautomer, the stereoisomer of any of the foregoing, or the mixture thereof, wherein U is

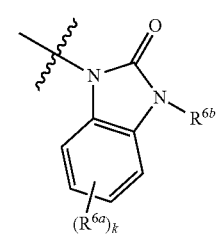

wherein
$R^{6a}$ is independently selected from —F, —Cl, —CN, —$C_1$-$C_6$ alkyl, —$C_1$-$C_6$ perhaloalkyl, or —O—($C_1$-$C_6$ alkyl);
k is 1 or 2;
$R^{6b}$ is —H; and
the symbol ⌇, when drawn across a bond, indicates the point of attachment to the rest of the molecule.

43. The compound of embodiment 42 or the pharmaceutically acceptable salt thereof, the tautomer thereof, the pharmaceutically acceptable salt of the tautomer, the stereoisomer of any of the foregoing, or the mixture thereof, wherein $R^{6a}$ is —F, —Cl, —CN, —$CF_3$, —$CH_3$, or —O—$CH_3$.

44. The compound of embodiment 43 or the pharmaceutically acceptable salt thereof, the tautomer thereof, the pharmaceutically acceptable salt of the tautomer, the stereoisomer of any of the foregoing, or the mixture thereof, wherein $R^{6a}$ is —F, —Cl, —CN, —$CF_3$, or —O—$CH_3$.

45. The compound of any one of embodiments 1-18 or 37-40 or the pharmaceutically acceptable salt thereof, the tautomer thereof, the pharmaceutically acceptable salt of the tautomer, the stereoisomer of any of the foregoing, or the mixture thereof, wherein U is

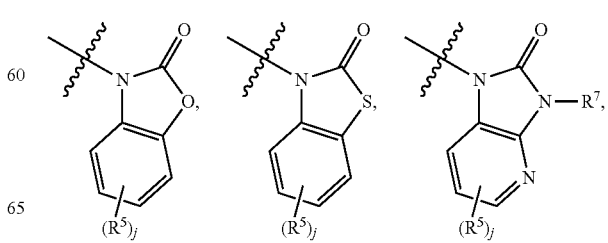

-continued

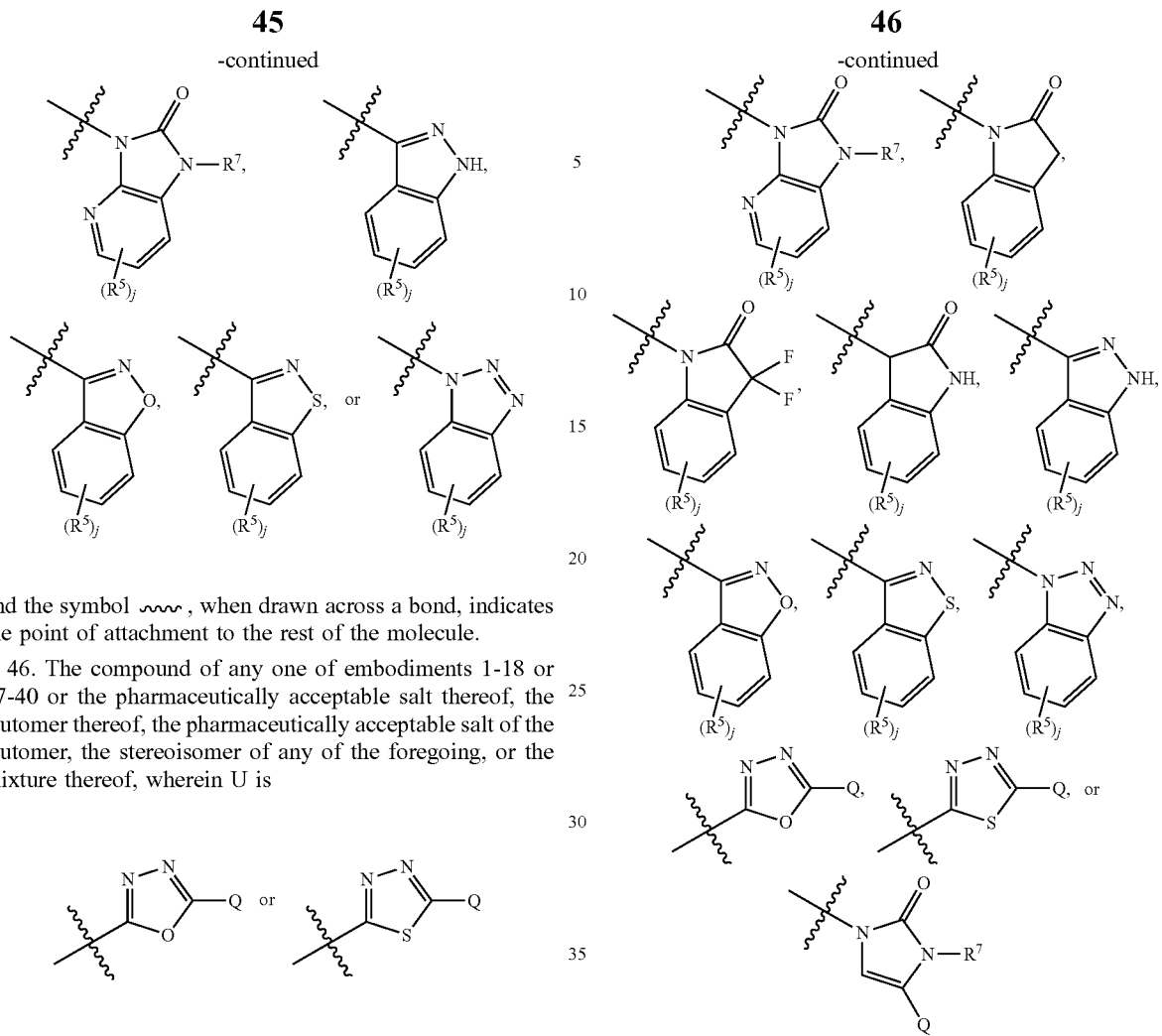

and the symbol ⌇, when drawn across a bond, indicates the point of attachment to the rest of the molecule.

46. The compound of any one of embodiments 1-18 or 37-40 or the pharmaceutically acceptable salt thereof, the tautomer thereof, the pharmaceutically acceptable salt of the tautomer, the stereoisomer of any of the foregoing, or the mixture thereof, wherein U is and the symbol ⌇, when drawn across a bond, indicates the point of attachment to the rest of the molecule.

47. The compound of embodiment 46 or the pharmaceutically acceptable salt thereof, the tautomer thereof, the pharmaceutically acceptable salt of the tautomer, the stereoisomer of any of the foregoing, or the mixture thereof, wherein Q is Q' and Q' is a phenyl or a heteroaryl group with 6 ring members containing 1 or 2 N heteroatoms, wherein the phenyl group and the heteroaryl group are unsubstituted or are substituted with 1 or 2 substituents independently selected from —F, —Cl, —CN, —CH$_3$, —CF$_3$, or —OCH$_3$.

48. The compound of any one of embodiments 1-18 or 37-40 or the pharmaceutically acceptable salt thereof, the tautomer thereof, the pharmaceutically acceptable salt of the tautomer, the stereoisomer of any of the foregoing, or the mixture thereof, wherein U is

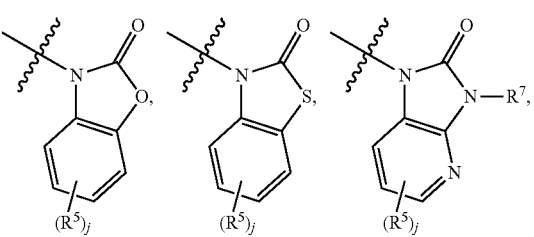

49. The compound of embodiment 1 or the pharmaceutically acceptable salt thereof, the tautomer thereof, the pharmaceutically acceptable salt of the tautomer, the stereoisomer of any of the foregoing, or the mixture thereof, wherein the compound is trans-N-(2-(4-oxo-3,4-dihydro-2-quinazolinyl)ethyl)-4-(5-phenyl-1,3,4-oxadiazol-2-yl)cyclohexanecarboxamide;
3-(4-oxo-3,4-dihydro-2-quinazolinyl)-N-(trans-4-(5-phenyl-1,3,4-oxadiazol-2-yl)cyclohexyl)propanamide;
2-(4-(4-(5-(3-chlorophenyl)-1,3,4-oxadiazol-2-yl)-1-piperidinyl)-4-oxobutyl)-4(3H)-quinazolinone;
2-(4-(4-(5-(4-chlorophenyl)-1,3,4-oxadiazol-2-yl)-1-piperidinyl)-4-oxobutyl)-4(3H)-quinazolinone;
2-(4-(4-(5-(3-fluorophenyl)-1,3,4-oxadiazol-2-yl)-1-piperidinyl)-4-oxobutyl)-4(3H)-quinazolinone;
2-(4-(4-(5-(4-fluorophenyl)-1,3,4-oxadiazol-2-yl)-1-piperidinyl)-4-oxobutyl)-4(3H)-quinazolinone;
2-(4-(4-(6-methyl-2-oxo-2,3-dihydro-1H-benzimidazol-1-yl)-1-piperidinyl)-4-oxobutyl)-4(3H)-quinazolinone;
2-(4-(4-(5-methoxy-2-oxo-2,3-dihydro-1H-benzimidazol-1-yl)-1-piperidinyl)-4-oxobutyl)-4(3H)-quinazolinone;
2-(4-oxo-4-(4-(5-phenyl-1,3,4-thiadiazol-2-yl)-1-piperidinyl)butyl)-4(3H)-quinazolinone;
4-(4-oxo-3,4-dihydro-2-quinazolinyl)-N-(trans-4-(5-phenyl-1,3,4-oxadiazol-2-yl)cyclohexyl)butanamide;

2-(4-(4-(5-methyl-2-oxo-2,3-dihydro-1H-benzimidazol-1-yl)-1-piperidinyl)-4-oxobutyl)-4(3H)-quinazolinone;
2-(4-oxo-4-(4-(5-(2-pyridinyl)-1,3,4-oxadiazol-2-yl)-1-piperidinyl)butyl)-4(3H)-quinazolinone;
2-(4-oxo-4-(4-(5-(3-pyridinyl)-1,3,4-oxadiazol-2-yl)-1-piperidinyl)butyl)-4(3H)-quinazolinone;
2-(4-oxo-4-(4-(5-(2-pyrazinyl)-1,3,4-oxadiazol-2-yl)-1-piperidinyl)butyl)-4(3H)-quinazolinone;
2-(4-(4-(5-(4-methoxyphenyl)-1,3,4-oxadiazol-2-yl)-1-piperidinyl)-4-oxobutyl)-4(3H)-quinazolinone;
2-(4-(4-(5-(2-chlorophenyl)-1,3,4-oxadiazol-2-yl)-1-piperidinyl)-4-oxobutyl)-4(3H)-quinazolinone;
2-(4-(4-(5-((4-chlorophenoxy)methyl)-1,3,4-oxadiazol-2-yl)-1-piperidinyl)-4-oxobutyl)-4(3H)-quinazolinone;
2-(4-(4-(5-(2-fluorophenyl)-1,3,4-oxadiazol-2-yl)-1-piperidinyl)-4-oxobutyl)-4(3H)-quinazolinone;
2-(4-oxo-4-(4-(5-(4-pyridinyl)-1,3,4-oxadiazol-2-yl)-1-piperidinyl)butyl)-4(3H)-quinazolinone;
3-(5-(1-(4-(4-oxo-3,4-dihydro-2-quinazolinyl)butanoyl)-4-piperidinyl)-1,3,4-oxadiazol-2-yl)benzonitrile;
4-(5-(1-(4-(4-oxo-3,4-dihydro-2-quinazolinyl)butanoyl)-4-piperidinyl)-1,3,4-oxadiazol-2-yl)benzonitrile;
2-(4-(4-(5-(3-methylphenyl)-1,3,4-oxadiazol-2-yl)-1-piperidinyl)-4-oxobutyl)-4(3H)-quinazolinone;
2-(4-(4-(5-(4-methylphenyl)-1,3,4-oxadiazol-2-yl)-1-piperidinyl)-4-oxobutyl)-4(3H)-quinazolinone;
2-(4-(4-(5-(3-methoxyphenyl)-1,3,4-oxadiazol-2-yl)-1-piperidinyl)-4-oxobutyl)-4(3H)-quinazolinone;
2-(4-(4-(5-(3-chloro-4-fluorophenyl)-1,3,4-oxadiazol-2-yl)-1-piperidinyl)-4-oxobutyl)-4(3H)-quinazolinone;
2-(4-oxo-4-(4-(2-oxo-1,2-dihydro-3H-imidazo[4,5-b]pyridin-3-yl)-1-piperidinyl)butyl)-4(3H)-quinazolinone;
2-(4-(4-(5-chloro-2-oxo-2,3-dihydro-1H-benzimidazol-1-yl)-1-piperidinyl)-4-oxobutyl)-4(3H)-quinazolinone;
N-(trans-4-(5-(4-fluorophenyl)-1,3,4-oxadiazol-2-yl)cyclohexyl)-4-(4-oxo-3,4-dihydro-2-quinazolinyl)butanamide;
N-(trans-4-(5-(4-chlorophenyl)-1,3,4-oxadiazol-2-yl)cyclohexyl)-4-(4-oxo-3,4-dihydro-2-quinazolinyl)butanamide;
N-(trans-4-(5-(4-methoxyphenyl)-1,3,4-oxadiazol-2-yl)cyclohexyl)-4-(4-oxo-3,4-dihydro-2-quinazolinyl)butanamide;
N-(trans-4-(5-(3-fluorophenyl)-1,3,4-oxadiazol-2-yl)cyclohexyl)-4-(4-oxo-3,4-dihydro-2-quinazolinyl)butanamide;
N-(trans-4-(5-(3-methoxyphenyl)-1,3,4-oxadiazol-2-yl)cyclohexyl)-4-(4-oxo-3,4-dihydro-2-quinazolinyl)butanamide;
4-(4-oxo-3,4-dihydro-2-quinazolinyl)-N-(trans-4-(5-(4-pyridinyl)-1,3,4-oxadiazol-2-yl)cyclohexyl)butanamide;
2-(4-(4-(6-methoxy-2-oxo-2,3-dihydro-1H-benzimidazol-1-yl)-1-piperidinyl)-4-oxobutyl)-4(3H)-quinazolinone;
N-(trans-4-(5-(3-chloro-4-fluorophenyl)-1,3,4-oxadiazol-2-yl)cyclohexyl)-4-(4-oxo-3,4-dihydro-2-quinazolinyl)butanamide;
N-(trans-4-(5-(3-chlorophenyl)-1,3,4-oxadiazol-2-yl)cyclohexyl)-4-(4-oxo-3,4-dihydro-2-quinazolinyl)butanamide;
3-((4-methyl-6-oxo-1,6-dihydropyrimidin-2-yl)thio)-N-((1r,4r)-4-(5-phenyl-1,3,4-oxadiazol-2-yl)cyclohexyl)propanamide;
3-(4-oxo-4H-pyrido[1,2-a]pyrimidin-2-yl)-N-(trans-4-(5-phenyl-1,3,4-oxadiazol-2-yl)cyclohexyl)propanamide;
3-((4-oxo-3,4-dihydroquinazolin-2-yl)thio)-N-((1s,3s)-3-(5-phenyl-1,3,4-oxadiazol-2-yl)cyclobutyl)propanamide;
3-((4-oxo-3,4-dihydroquinazolin-2-yl)thio)-N-((1r,3r)-3-(5-phenyl-1,3,4-oxadiazol-2-yl)cyclobutyl)propanamide;
2-(4-oxo-4-(4-(2-oxo-2,3-dihydro-1H-benzimidazol-1-yl)-1-piperidinyl)butyl)-4(3H)-quinazolinone;
2-(4-oxo-4-(4-(5-phenyl-1,3,4-oxadiazol-2-yl)-1-piperidinyl)butyl)-4(3H)-quinazolinone;
2-(4-oxo-4-(4-(2-oxo-2,3-dihydro-1H-indol-1-yl)-1-piperidinyl)butyl)-4(3H)-quinazolinone;
2-(4-oxo-4-(4-(2-oxo-1,3-benzoxazol-3(2H)-yl)-1-piperidinyl)butyl)-4(3H)-quinazolinone;
2-(4-(4-(5-chloro-3-methyl-2-oxo-2,3-dihydro-1H-benzimidazol-1-yl)-1-piperidinyl)-4-oxobutyl)-4(3H)-quinazolinone;
2-(4-oxo-4-(4-(2-oxo-2,3-dihydro-1H-benzimidazol-1-yl)-3,6-dihydro-1(2H)-pyridinyl)butyl)-4(3H)-quinazolinone;
2-(4-oxo-4-(4-(2-oxo-2,3-dihydro-1H-imidazo[4,5-b]pyridin-1-yl)-1-piperidinyl)butyl)-4(3H)-quinazolinone;
2-(4-(4-(1H-indazol-3-yl)-1-piperidinyl)-4-oxobutyl)-4(3H)-quinazolinone;
2-(4-oxo-4-(4-(2-oxo-4-phenyl-2,3-dihydro-1H-imidazol-1-yl)-1-piperidinyl)butyl)-4(3H)-quinazolinone;
2-(4-oxo-4-(4-(2-oxo-1,3-benzothiazol-3(2H)-yl)-1-piperidinyl)butyl)-4(3H)-quinazolinone;
2-(4-(4-(5-fluoro-2-oxo-2,3-dihydro-1H-benzimidazol-1-yl)-1-piperidinyl)-4-oxobutyl)-4(3H)-quinazolinone;
2-(4-oxo-4-(4-(2-oxo-5-(trifluoromethyl)-2,3-dihydro-1H-benzimidazol-1-yl)-1-piperidinyl)butyl)-4(3H)-quinazolinone;
2-(4-(4-(6-fluoro-2-oxo-1,3-benzoxazol-3(2H)-yl)-1-piperidinyl)-4-oxobutyl)-4(3H)-quinazolinone;
2-(4-(4-(3-methyl-2-oxo-2,3-dihydro-1H-benzimidazol-1-yl)-1-piperidinyl)-4-oxobutyl)-4(3H)-quinazolinone;
2-(4-(4-(1H-indazol-3-yl)-1-piperazinyl)-4-oxobutyl)-4(3H)-quinazolinone;
4-(4-oxo-3,4-dihydro-2-quinazolinyl)-N-(trans-4-(2-pyridinyloxyl)cyclohexyl)butanamide;
N-(trans-4-(2-cyanophenoxy)cyclohexyl)-4-(4-oxo-3,4-dihydro-2-quinazolinyl)butanamide;
N-(trans-4-(3-cyanophenoxy)cyclohexyl)-4-(4-oxo-3,4-dihydro-2-quinazolinyl)butanamide;
4-(4-oxo-3,4-dihydro-2-quinazolinyl)-N-(trans-4-(3-pyridinyloxyl)cyclohexyl)butanamide;
2-(4-(4-(3,3-difluoro-2-oxo-2,3-dihydro-1H-indol-1-yl)-1-piperidinyl)-4-oxobutyl)-4(3H)-quinazolinone;
2-oxo-1-(1-(4-(4-oxo-3,4-dihydro-2-quinazolinyl)butanoyl)-4-piperidinyl)-2,3-dihydro-1H-benzimidazole-4-carbonitrile;
N-((1R,3R)-3-(benzyloxy)cyclopentyl)-4-(4-oxo-3,4-dihydro-2-quinazolinyl)butanamide;
N-((1S,3S)-3-(benzyloxy)cyclopentyl)-4-(4-oxo-3,4-dihydro-2-quinazolinyl)butanamide;
N-(trans-4-(4-chloro-3-cyanophenoxy)cyclohexyl)-4-(4-oxo-3,4-dihydro-2-quinazolinyl)butanamide;
N-(trans-4-(3-chloro-4-cyanophenoxy)cyclohexyl)-4-(4-oxo-3,4-dihydro-2-quinazolinyl)butanamide;
4-(4-oxo-3,4-dihydro-2-quinazolinyl)-N-((1S,3S)-3-phenoxycyclopentyl)butanamide;
4-(4-oxo-3,4-dihydro-2-quinazolinyl)-N-((1R,3R)-3-phenoxycyclopentyl)butanamide;
N-(trans-4-(3-chlorophenoxy)cyclohexyl)-4-(4-oxo-3,4-dihydro-2-quinazolinyl)butanamide;
2-(4-(4-(4-fluoro-2-oxo-2,3-dihydro-1H-benzimidazol-1-yl)-1-piperidinyl)-4-oxobutyl)-4(3H)-quinazolinone;
2-oxo-1-(1-(4-(4-oxo-3,4-dihydro-2-quinazolinyl)butanoyl)-4-piperidinyl)-2,3-dihydro-1H-benzimidazole-5-carbonitrile;
2-(4-(4-(1,2-benzisothiazol-3-yl)-1-piperazinyl)-4-oxobutyl)-4(3H)-quinazolinone;
4-(4-oxo-3,4-dihydro-2-quinazolinyl)-N-(trans-4-(4-pyridinyloxyl)cyclohexyl)butanamide;

2-(4-(4-(1,2-benzisoxazol-3-yl)-1-piperazinyl)-4-oxobutyl)-4(3H)-quinazolinone;
2-(4-(4-(5-fluoro-1,2-benzisoxazol-3-yl)-1-piperidinyl)-4-oxobutyl)-4(3H)-quinazolinone;
N-(trans-4-(2-oxo-2,3-dihydro-1H-benzimidazol-1-yl)cyclohexyl)-4-(4-oxo-3,4-dihydro-2-quinazolinyl)butanamide;
N-(trans-4-(5-chloro-2-oxo-2,3-dihydro-1H-benzimidazol-1-yl)cyclohexyl)-4-(4-oxo-3,4-dihydro-2-quinazolinyl)butanamide;
2-(4-(4-(1H-benzotriazol-1-yl)-1-piperidinyl)-4-oxobutyl)-4(3H)-quinazolinone;
2-(4-(4-((3S)-6-chloro-2-oxo-2,3-dihydro-1H-indol-3-yl)-1-piperidinyl)-4-oxobutyl)-4(3H)-quinazolinone;
2-(4-(4-((3R)-6-chloro-2-oxo-2,3-dihydro-1H-indol-3-yl)-1-piperidinyl)-4-oxobutyl)-4(3H)-quinazolinone;
N-(trans-4-(4-fluorophenoxy)cyclohexyl)-4-(4-oxo-3,4-dihydro-2-quinazolinyl)butanamide;
N-(trans-4-(4-cyanophenoxy)cyclohexyl)-4-(4-oxo-3,4-dihydro-2-quinazolinyl)butanamide;
N-(trans-4-(4-chlorophenoxy)cyclohexyl)-4-(4-oxo-3,4-dihydro-2-quinazolinyl)butanamide;
N-(trans-4-(2-oxo-1,3-benzoxazol-3 (2H)-yl)cyclohexyl)-3-(4-oxo-3,4-dihydro-2-quinazolinyl)propanamide;
3-(4-oxo-3,4-dihydropyrido[2,3-d]pyrimidin-2-yl)-N-(trans-4-(5-phenyl-1,3,4-oxadiazol-2-yl)cyclohexyl)propanamide;
2-((3-(4-(5-chloro-2-oxo-2,3-dihydro-1H-benzimidazol-1-yl)-1-piperidinyl)-3-oxopropyl)sulfanyl)-4(3H)-quinazolinone;
2-((3-oxo-3-(4-(5-phenyl-1,3,4-oxadiazol-2-yl)-1-piperidinyl)propyl)sulfanyl)-4(3H)-quinazolinone;
N-(trans-4-(2-oxo-2,3-dihydro-1H-benzimidazol-1-yl)cyclohexyl)-3-(4-oxo-3,4-dihydro-2-quinazolinyl)propanamide;
N-(trans-4-(5-chloro-2-oxo-2,3-dihydro-1H-benzimidazol-1-yl)cyclohexyl)-3-(4-oxo-3,4-dihydro-2-quinazolinyl)propanamide;
N-(trans-4-(6-chloro-2-oxo-2,3-dihydro-1H-benzimidazol-1-yl)cyclohexyl)-3-(4-oxo-3,4-dihydro-2-quinazolinyl)propanamide;
N-(trans-4-(5-chloro-2-oxo-2,3-dihydro-1H-benzimidazol-1-yl)cyclohexyl)-2-((4-oxo-3,4-dihydro-2-quinazolinyl)sulfanyl)acetamide;
3-(4-oxo-3,4,5,6,7,8-hexahydropyrido[2,3-d]pyrimidin-2-yl)-N-(trans-4-(5-phenyl-1,3,4-oxadiazol-2-yl)cyclohexyl)propanamide;
2-((2-oxo-2-(4-(5-phenyl-1,3,4-oxadiazol-2-yl)-1-piperidinyl)ethyl)sulfanyl)-4(3H)-quinazolinone;
N-(trans-4-(5-chloro-2-oxo-2,3-dihydro-1H-benzimidazol-1-yl)cyclohexyl)-3-((4-oxo-3,4-dihydro-2-quinazolinyl)sulfanyl)propanamide;
3-((4-amino-6-oxo-1,6-dihydro-2-pyrimidinyl)sulfanyl)-N-(trans-4-(5-phenyl-1,3,4-oxadiazol-2-yl)cyclohexyl)propanamide;
3-(((4-oxo-3,4-dihydro-2-quinazolinyl)methyl)sulfanyl)-N-(trans-4-(5-phenyl-1,3,4-oxadiazol-2-yl)cyclohexyl)propanamide;
2-(((3-(4-(5-(4-fluorophenyl)-1,3,4-oxadiazol-2-yl)-1-piperidinyl)-3-oxopropyl)sulfanyl)methyl)-4(3H)-quinazolinone;
2-((3-(4-(1H-indazol-3-yl)-1-piperazinyl)-3-oxopropyl)sulfanyl)-4(3H)-quinazolinone;
4-(4-oxo-3,4-dihydro-2-quinazolinyl)-N-(trans-4-(5-phenyl-1,3-oxazol-2-yl)cyclohexyl)butanamide;
2-((4-oxo-3,4-dihydro-2-quinazolinyl)sulfanyl)-N-(trans-4-(5-phenyl-1,3,4-oxadiazol-2-yl)cyclohexyl)acetamide;
3-((4-oxo-3,4-dihydro-2-quinazolinyl)sulfanyl)-N-(trans-4-(5-phenyl-1,3,4-oxadiazol-2-yl)cyclohexyl)propanamide;
2-(3-oxo-3-(4-(5-phenyl-1,3,4-oxadiazol-2-yl)-1-piperidinyl)propyl)-4(3H)-quinazolinone;
N-(trans-4-(4-fluorophenoxy)cyclohexyl)-2-((4-oxo-3,4-dihydro-2-quinazolinyl)sulfanyl)acetamide;
N-(trans-4-(4-fluorophenoxy)cyclohexyl)-3-((4-oxo-3,4-dihydro-2-quinazolinyl)sulfanyl)propanamide;
3-(6-fluoro-4-oxo-3,4-dihydro-2-quinazolinyl)-N-(trans-4-(5-phenyl-1,3,4-oxadiazol-2-yl)cyclohexyl)propanamide;
N-(trans-4-(6-chloro-2-oxo-2,3-dihydro-1H-benzimidazol-1-yl)cyclohexyl)-2-((4-oxo-3,4-dihydro-2-quinazolinyl)sulfanyl)acetamide;
N-(trans-4-(5-cyano-2-oxo-2,3-dihydro-1H-benzimidazol-1-yl)cyclohexyl)-2-((4-oxo-3,4-dihydro-2-quinazolinyl)sulfanyl)acetamide;
N-(trans-4-(5-cyano-2-oxo-2,3-dihydro-1H-benzimidazol-1-yl)cyclohexyl)-3-((4-oxo-3,4-dihydro-2-quinazolinyl)sulfanyl)propanamide;
N-(trans-4-(4-chlorophenoxy)cyclohexyl)-3-((4-oxo-3,4-dihydro-2-quinazolinyl)sulfanyl)propanamide;
N-(trans-4-(4-cyanophenoxy)cyclohexyl)-3-((4-oxo-3,4-dihydro-2-quinazolinyl)sulfanyl)propanamide;
3-((4-oxo-3,4-dihydro-2-quinazolinyl)sulfanyl)-N-(trans-4-(2-pyridinyloxyl)cyclohexyl)propanamide;
3-((4-oxo-3,4-dihydro-2-quinazolinyl)sulfanyl)-N-(trans-4-(4-pyridinyloxyl)cyclohexyl)propanamide;
N-(trans-4-(3-cyanophenoxy)cyclohexyl)-3-((4-oxo-3,4-dihydro-2-quinazolinyl)sulfanyl)propanamide;
4-((4-oxo-3,4-dihydro-2-quinazolinyl)sulfanyl)-N-(trans-4-(5-phenyl-1,3,4-oxadiazol-2-yl)cyclohexyl)butanamide;
2-((4-oxo-4-(4-(5-phenyl-1,3,4-oxadiazol-2-yl)-1-piperidinyl)butyl)sulfanyl)-4(3H)-quinazolinone;
N-(trans-4-(3-chlorophenoxy)cyclohexyl)-3-((4-oxo-3,4-dihydro-2-quinazolinyl)sulfanyl)propanamide;
N-(trans-4-(4-chloro-3-cyanophenoxy)cyclohexyl)-3-((4-oxo-3,4-dihydro-2-quinazolinyl)sulfanyl)propanamide;
N-(trans-4-(3-chloro-4-cyanophenoxy)cyclohexyl)-3-((4-oxo-3,4-dihydro-2-quinazolinyl)sulfanyl)propanamide;
3-((4-oxo-3,4,5,6,7,8-hexahydro-2-quinazolinyl)sulfanyl)-N-(trans-4-(5-phenyl-1,3,4-oxadiazol-2-yl)cyclohexyl)propanamide;
N-(trans-4-(4-cyanophenoxy)cyclohexyl)-3-((4-oxo-3,4,5,6,7,8-hexahydro-2-quinazolinyl)sulfanyl)propanamide;
N-(trans-4-(5-(4-fluorophenyl)-1,3,4-oxadiazol-2-yl)cyclohexyl)-3-((4-oxo-3,4-dihydro-2-quinazolinyl)sulfanyl)propanamide;
N-(trans-4-(5-(3-chlorophenyl)-1,3,4-oxadiazol-2-yl)cyclohexyl)-3-((4-oxo-3,4-dihydro-2-quinazolinyl)sulfanyl)propanamide;
N-(trans-4-(5-(3-fluorophenyl)-1,3,4-oxadiazol-2-yl)cyclohexyl)-3-((4-oxo-3,4-dihydro-2-quinazolinyl)sulfanyl)propanamide;
N-(trans-4-(5-(3-methoxyphenyl)-1,3,4-oxadiazol-2-yl)cyclohexyl)-3-((4-oxo-3,4-dihydro-2-quinazolinyl)sulfanyl)propanamide;
N-(trans-4-(5-(4-methoxyphenyl)-1,3,4-oxadiazol-2-yl)cyclohexyl)-3-((4-oxo-3,4-dihydro-2-quinazolinyl)sulfanyl)propanamide;
N-(trans-4-(5-(3-chloro-4-fluorophenyl)-1,3,4-oxadiazol-2-yl)cyclohexyl)-3-((4-oxo-3,4-dihydro-2-quinazolinyl)sulfanyl)propanamide;
3-((6-oxo-1,6-dihydro-2-pyrimidinyl)sulfanyl)-N-(trans-4-(5-phenyl-1,3,4-oxadiazol-2-yl)cyclohexyl)propanamide;
3-((4-oxo-3,4-dihydro-2-quinazolinyl)sulfanyl)-N-(trans-4-(5-(4-pyridinyl)-1,3,4-oxadiazol-2-yl)cyclohexyl)propanamide;

N-(trans-4-(5-(4-chlorophenyl)-1,3,4-oxadiazol-2-yl)cyclohexyl)-3-((4-oxo-3,4-dihydro-2-quinazolinyl)sulfanyl)propanamide;

N-(trans-4-(5-(2-fluorophenyl)-1,3,4-oxadiazol-2-yl)cyclohexyl)-3-(4-oxo-3,4-dihydro-2-quinazolinyl)propanamide;

N-(trans-4-(5-(4-fluorophenyl)-1,3,4-oxadiazol-2-yl)cyclohexyl)-3-(4-oxo-3,4-dihydro-2-quinazolinyl)propanamide;

N-(trans-4-(5-(2-chlorophenyl)-1,3,4-oxadiazol-2-yl)cyclohexyl)-3-(4-oxo-3,4-dihydro-2-quinazolinyl)propanamide;

N-(trans-4-(5-(3-fluorophenyl)-1,3,4-oxadiazol-2-yl)cyclohexyl)-3-(4-oxo-3,4-dihydro-2-quinazolinyl)propanamide;

N-(trans-4-(5-(3-chlorophenyl)-1,3,4-oxadiazol-2-yl)cyclohexyl)-3-(4-oxo-3,4-dihydro-2-quinazolinyl)propanamide;

3-(4-oxo-3,4-dihydro-2-quinazolinyl)-N-(trans-4-(5-(2-pyridinyl)-1,3,4-oxadiazol-2-yl)cyclohexyl)propanamide;

3-(4-oxo-3,4-dihydro-2-quinazolinyl)-N-(trans-4-(5-(4-pyridinyl)-1,3,4-oxadiazol-2-yl)cyclohexyl)propanamide;

3-(4-oxo-3,4-dihydro-2-quinazolinyl)-N-(trans-4-(5-(2-pyrimidinyl)-1,3,4-oxadiazol-2-yl)cyclohexyl)propanamide;

N-((1r,4r)-4-(5-(4-cyanophenyl)-1,3,4-oxadiazol-2-yl)cyclohexyl)-3-(4-oxo-3,4-dihydroquinazolin-2-yl)propanamide;

3-(4-oxo-3,4-dihydroquinazolin-2-yl)-N-((1 r,4r)-4-(5-(tetrahydro-2H-pyran-4-yl)-1,3,4-oxadiazol-2-yl)cyclohexyl)propanamide;

3-(4-oxo-3,4-dihydro-2-quinazolinyl)-N-(trans-4-(5-(3-pyridinyl)-1,3,4-oxadiazol-2-yl)cyclohexyl)propanamide;

N-(trans-4-(5-(3-cyanophenyl)-1,3,4-oxadiazol-2-yl)cyclohexyl)-3-(4-oxo-3,4-dihydro-2-quinazolinyl)propanamide;

N-(trans-4-(5-cyclohexyl-1,3,4-oxadiazol-2-yl)cyclohexyl)-3-(4-oxo-3,4-dihydro-2-quinazolinyl)propanamide;

N-(trans-4-(5-benzyl-1,3,4-oxadiazol-2-yl)cyclohexyl)-3-(4-oxo-3,4-dihydro-2-quinazolinyl)propanamide;

3-(4-oxo-3,4-dihydroquinazolin-2-yl)-N-((1r,4r)-4-(5-(2-phenylpropan-2-yl)-1,3,4-oxadiazol-2-yl)cyclohexyl)propanamide;

N-(trans-4-(5-(4-chlorophenyl)-1,3,4-oxadiazol-2-yl)cyclohexyl)-3-(4-oxo-3,4-dihydro-2-quinazolinyl)propanamide;

3-(4-oxo-3,4-dihydro-2-quinazolinyl)-N-(trans-4-(5-(2-pyrazinyl)-1,3,4-oxadiazol-2-yl)cyclohexyl)propanamide;

3-((4-oxo-3,4-dihydro-2-quinazolinyl)sulfinyl)-N-(trans-4-(5-phenyl-1,3,4-oxadiazol-2-yl)cyclohexyl)propanamide;

3-((4-oxo-4H-pyrido[1,2-a]pyrimidin-2-yl)sulfanyl)-N-(trans-4-(5-phenyl-1,3,4-oxadiazol-2-yl)cyclohexyl)propanamide; or 3-((6-fluoro-4-oxo-3,4-dihydro-2-quinazolinyl)sulfanyl)-N-(trans-4-(5-phenyl-1,3,4-oxadiazol-2-yl)cyclohexyl)propanamide.

50. A pharmaceutical composition, comprising the compound of any one of embodiments 1-49 or the pharmaceutically acceptable salt thereof, the tautomer thereof, the pharmaceutically acceptable salt of the tautomer, the stereoisomer of any of the foregoing, or the mixture thereof, and at least one pharmaceutically acceptable excipient, carrier, or diluent.

51. A method of treating cancer, the method comprising: administering to a subject an effective amount of the compound of any one of embodiments 1-49 or the pharmaceutically acceptable salt thereof, the tautomer thereof, the pharmaceutically acceptable salt of the tautomer, the stereoisomer of any of the foregoing, or the mixture thereof, or the pharmaceutical composition of embodiment 50.

52. The method of embodiment 51, wherein the subject is a human cancer patient, and the cancer is selected from colon cancer.

53. The method of embodiment 52, wherein the colon cancer is APC colon cancer.

54. A method of treating a condition where it is desired to inhibit tankyrase 1 or tankyrase 2 activity, comprising administering to a subject an effective amount of the compound of any one of embodiments 1-49 or the pharmaceutically acceptable salt thereof, the tautomer thereof, the pharmaceutically acceptable salt of the tautomer, the stereoisomer of any of the foregoing, or the mixture thereof or the pharmaceutical composition of embodiment 50.

55. The compound of any one of embodiments 1-49 or the pharmaceutically acceptable salt thereof, the tautomer thereof, the pharmaceutically acceptable salt of the tautomer, the stereoisomer of any of the foregoing, or the mixture thereof, or the pharmaceutical composition of embodiment 50 for use in treating cancer.

56. The compound of any one of embodiments 1-49 or the pharmaceutically acceptable salt thereof, the tautomer thereof, the pharmaceutically acceptable salt of the tautomer, the stereoisomer of any of the foregoing, or the mixture thereof, or the pharmaceutical composition of embodiment 50 for use in inhibiting tankyrase 1 or tankyrase 2.

57. The use of the compound of any one of embodiments 1-49 or the pharmaceutically acceptable salt thereof, the tautomer thereof, the pharmaceutically acceptable salt of the tautomer, the stereoisomer of any of the foregoing, or the mixture thereof in the preparation of a medicament for treating cancer.

58. The use of the compound of any one of embodiments 1-49 or the pharmaceutically acceptable salt thereof, the tautomer thereof, the pharmaceutically acceptable salt of the tautomer, the stereoisomer of any of the foregoing, or the mixture thereof in the preparation of a medicament for inhibiting tankyrase 1 or tankyrase 2.

In some embodiments, the compound is a salt. Such salts may be anhydrous or associated with water as a hydrate.

Also provided are pharmaceutical compositions that include the compound or the pharmaceutically acceptable salt thereof, the tautomer thereof, the pharmaceutically acceptable salt of the tautomer, the stereoisomer of any of the foregoing, or the mixture thereof according to any one of the embodiments and at least one pharmaceutically acceptable excipient, carrier or diluent. In some such embodiments, the compound or the pharmaceutically acceptable salt thereof, the tautomer thereof, the pharmaceutically acceptable salt of the tautomer, the stereoisomer of any of the foregoing, or the mixture thereof according to any one of the embodiments is present in an amount effective for the treatment of cancer or, in some embodiments, for inhibiting tankyrase 1 and or tankyrase 2.

In other embodiments, the invention provides a method of treating cancer. Such methods typically include administering to a subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments. In some such embodiments, the cancer os colon cancer and in still other such embodiments is APC colon cancer. In some embodiments, the subject is a human cancer patient, and the cancer is selected from colon cancer. In still other embodiments, the cancer is selected from colon, pancreatic, ovarian, gastric, lung, or leukemia. In still other embodiments the cancer is any other cancer that relies on the Wnt pathway for growth or survival.

In still other embodiments, the invention provides a method of treating a condition where it is desired to inhibit tankyrase 1 or tankyrase 2 activity. Such methods typically include administering to a subject an effective amount of the compound or the pharmaceutically acceptable salt thereof, the tautomer thereof, the pharmaceutically acceptable salt of the tautomer, the stereoisomer of any of the foregoing, or the mixture thereof according to any one of any of the embodiments.

In some embodiments, the compound or the pharmaceutically acceptable salt thereof, the tautomer thereof, the pharmaceutically acceptable salt of the tautomer, the stereoisomer of any of the foregoing, or the mixture thereof according to any one of any of the embodiments is used in the preparation of a medicament. In some such embodiments, the medicament is for use in treating cancer. In some such embodiments, a medicament is for use in inhibiting tankyrase 1 or tankyrase 2. In still other such embodiments, the medicament is for use in treating a cancer in a human cancer patient such as a human with colon cancer.

In some such embodiments, the compound or the pharmaceutically acceptable salt thereof, the tautomer thereof, the pharmaceutically acceptable salt of the tautomer, the stereoisomer of any of the foregoing, or the mixture thereof according to any one of any of the embodiments is provided for use in treating cancer. In some such embodiments, the cancer is colon cancer. In still other embodiments the use is for treating cancer in a human patient.

In one embodiment, the invention provides a method of treating a proliferation-related disorder in a mammal in need thereof. Such methods include administering to the mammal a therapeutically effective amount of a compound of any of the embodiments described herein or a pharmaceutical composition comprising the compound. Another embodiment of the invention comprises treating abnormal cell growth by administering a therapeutically effective amount of a compound of the invention or a pharmaceutical composition of the invention to a subject in need thereof. In some embodiments, the invention provides the use of a compound of any of the embodiments or a pharmaceutical composition of the invention for treating abnormal cell growth. The abnormal cell growth can be a benign growth or a malignant growth. In particular, the abnormal cell growth can be a carcinoma, sarcoma, lymphoma, or leukemia. In one embodiment of this method, the abnormal cell growth is a cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. The method of the invention also comprises treating a patient having cancer wherein the cancer is selected from the group consisting of small cell lung carcinoma, non-small cell lung carcinoma, esophageal cancer, kidney cancer, pancreatic cancer, melanoma, bladder cancer, breast cancer, colon cancer, liver cancer, lung cancer, sarcoma, stomach cancer, cholangiocarcinoma, mesothelioma, or prostate cancer. In another embodiment of said method, said abnormal cell growth is a benign proliferative disease, including, but not limited to, psoriasis, benign prostatic hypertrophy or restenosis.

The pharmaceutical compositions or formulations for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

The compounds of the invention may be used to treat or prevent various kinase-related disorders. Thus, the present invention provides methods for treating or preventing such disorders. In some embodiments, the invention provides a method for treating a kinase-mediated disorder in a subject that includes administering a therapeutically effective amount of a compound of any of the embodiments of the invention or a pharmaceutical composition to the subject. In some embodiments, the subject is a mammal, and in some such embodiments is a human. In some embodiments the disorder is mediated by IGF-1R, Insulin Receptor, tankyrase 1, tankyrase 2, ALK, KDR, Tie2, EGFR, PKA, PKB, PKC, FKHR, TSC1/2, SGK, LCK, BTK, Erk, MSK, MK2, MSK, p38, P70S6K, PIM1, PIM2, ROCK2, GSK3, or a CDK complex. In some such embodiments, the disorder is mediated by tankyrase 1 or tankyrase 2. In some such embodiments, the administration of the compound or pharmaceutical composition produces selective inhibition of tankyrase 1 and or tankyrase 2. In some embodiments, the disorder is cancer. The present invention thus provides methods for treating or preventing tankyrase 1 and or tankyrase 2 mediated disease states, such as cancer. In some embodiments, the cancer is a tumor such as a solid tumor.

The compounds of the invention may also be used to treat proliferation-related disorders. Thus, the invention further provides methods for treating such proliferation-related disorders in a subject. Such methods include administering to a subject in need thereof a therapeutically effective amount of the compound or pharmaceutical composition of any of the embodiments. In some embodiments, the subject is a mammal. In some such embodiments, the mammal is a human. In some embodiments, the proliferation-related disorder is abnormal cell growth. In other embodiments, the disorder is inflammation or an inflammation-related disorder. In still other embodiments, the disorder is a metabolic disease such as diabetes. In still other embodiments, the disorder is cancer. In some such embodiments, the cancer is a solid tumor.

The magnitude of a prophylactic or therapeutic dose of a compound of any of the embodiments or a pharmaceutically acceptable salt, solvate, hydrate, or stereoisomer thereof in the acute or chronic treatment or prevention of a cancer or other disease or condition will vary with the nature and aggressiveness of the condition, and the route by which the active ingredient is administered. The dose, and in some cases the dose frequency, will also vary according to the condition to be treated, the age, body weight, and response of the individual patient. Suitable dosing regimens can be readily selected by those skilled in the art with due consideration of such factors. In one embodiment, the dose administered depends upon the specific compound to be used, and the weight and condition of the patient. In general, the dose per day is in the range of from about 0.001 to 100 mg/kg, preferably about 1 to 25 mg/kg, more preferably about 1 to about 5 mg/kg. For treatment of humans having a cancer, about 0.1 mg to about 15 g per day is administered in about one to four divisions a day, preferably 10 mg to 12 g per day, more preferably from 40 mg to 500 mg per day. In one embodiment the compounds of the invention are administered from 40 mg to 500 mg per day in about one to four divisions a day. Additionally, the recommended daily dose can be administered in cycles as single agents or in combination with other therapeutic agents. In one embodiment, the daily dose is administered in a single dose or in equally divided doses. In a related embodiment, the recommended daily dose can be administered one time per week, two times per week, three times per week, four times per week or five times per week.

The compounds of the invention can be administered to provide systemic distribution of the compound within the patient. Therefore, in some embodiments, the compounds of the invention are administered to produce a systemic effect in the body.

The compounds of the invention may also be administered directly to a site affected by a condition, as, for example, an in the treatment of an accessible area of skin or an esophageal cancer.

As indicated above, the compounds of the invention may be administered via oral, mucosal (including sublingual, buccal, rectal, nasal, or vaginal), parenteral (including subcutaneous, intramuscular, bolus injection, intra-arterial, or intravenous), transdermal, or topical administration. In some embodiments, the compounds of the invention are administered via mucosal (including sublingual, buccal, rectal, nasal, or vaginal), parenteral (including subcutaneous, intramuscular, bolus injection, intra-arterial, or intravenous), transdermal, or topical administration. In other embodiments, the compounds of the invention are administered via oral administration. In still other embodiments, the compounds of the invention are not administered via oral administration.

Different therapeutically effective amounts may be applicable for different conditions, as will be readily known by those of ordinary skill in the art. Similarly, amounts sufficient to treat or prevent such conditions, but insufficient to cause, or sufficient to reduce, adverse effects associated with conventional therapies are also encompassed by the above described dosage amounts and dose frequency schedules.

Some methods of the invention comprise the administration of a compound of the invention and an additional therapeutic agent (i.e., a therapeutic agent other than a compound of the invention). Thus, the compounds of the invention can be used in combination with at least one other therapeutic agent. Examples of additional therapeutic agents include, but are not limited to, antibiotics, anti-emetic agents, antidepressants, antifungal agents, anti-inflammatory agents, antineoplastic agents, antiviral agents, cytotoxic agents, and other anticancer agents, immunomodulatory agents, alpha-interferons, β-interferons, alkylating agents, hormones, and cytokines. In one embodiment, the invention encompasses administration of an additional therapeutic agent that demonstrates anti-cancer activity. In another embodiment, an additional therapeutic agent that demonstrates cytotoxic activity is administered to a subject such as a cancer patient.

The compounds of the invention and the other therapeutics agent can act additively or, preferably, synergistically. In some embodiments, a composition comprising a compound of the invention is administered concurrently with the administration of another therapeutic agent, which can be part of the same composition or can be in a different composition from the one that comprises the compound of the invention. In other embodiments, a compound of the invention is administered prior to, or subsequent to, administration of another therapeutic agent. In still other embodiments, a compound of the invention is administered to a patient who has not previously undergone or is not currently undergoing treatment with another therapeutic agent. A compound of the invention may be administered to a subject that has had, is currently undergoing, or is scheduled to receive radiation therapy. In some such embodiments, the subject is a cancer patient.

When administered as a combination, the therapeutic agents can be formulated as separate compositions that are administered at the same time or sequentially at different times, or the therapeutic agents can be given as a single composition. The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent. Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of any of the embodiments described herein may also be administered sequentially with known anticancer or cytotoxic agents when a combination formulation is inappropriate. The invention is not limited in the sequence of administration as compounds of the invention may be administered either prior to, simultaneous with, or after administration of a known anticancer or cytotoxic agent.

There are large numbers of antineoplastic agents available in commercial use, in clinical evaluation and in pre-clinical development, which may be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from, but are not limited to, the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT, and uricytin.

A second family of antineoplastic agents which may be used in combination with compounds of the present invention consists of alkylating-type antineoplastic agents. Suitable alkylating-type antineoplastic agents may be selected from, but are not limited to, the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP (Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin, and trimelamol.

A third family of antineoplastic agents which may be used in combination with compounds of the present invention consists of antibiotic-type antineoplastic agents. Suitable antibiotic-type antineoplastic agents may be selected from, but are not limited to, the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024, and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from, but not limited to, the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SDO1 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

The compounds of the invention may further be used with VEGFR inhibitors. Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. No. 6,630,500, U.S. Pat. No. 6,515,004, U.S. Pat. No. 6,713,485, U.S. Pat. No. 5,521,184, U.S. Pat. No. 5,770,599, U.S. Pat. No. 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089, and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-tumor agents include HERCEPTIN™ (trastuzumab), which may be used to treat breast cancer and other forms of cancer, and RITUXAN™ (rituximab), ZEVALIN™ (ibritumomab tiuxetan), and LYMPHOCIDE™ (epratuzumab), which may be used to treat non-Hodgkin's lymphoma and other forms of cancer, GLEEVAC™ which may be used to treat chronic myeloid leukemia and gastrointestinal stromal tumors, and BEXXAR™ (iodine 131 tositumomab) which may be used for treatment of non-Hodgkins's lymphoma.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., U.S. Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., U.S. Publication No. 2002/0042368), specifically binding anti-eph receptor and/or anti-ephrin antibodies or antigen binding regions (U.S. Pat. Nos. 5,981,245; 5,728, 813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D 148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); cancer therapy, (University of South Carolina, USA); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Alternatively, the present compounds may also be used in co-therapies with other anti-neoplastic agents, such as VEGF antagonists, other kinase inhibitors including p38 inhibitors, c-met inhibitors, KDR inhibitors, EGF inhibitors and CDK inhibitors, TNF inhibitors, matrix metalloproteinases (MMP) inhibitors, COX-2 inhibitors including celecoxib, NSAID's, or $\alpha_v\beta_3$ inhibitors.

The invention is further described by reference to the following examples, which are intended to exemplify the claimed invention but not to limit it in any way.

EXAMPLES

Unless otherwise noted, all materials were obtained from commercial suppliers and were used without further purification. Anhydrous solvents were obtained from Sigma-Aldrich (Milwaukee, Wis.) and used directly. All reactions involving air- or moisture-sensitive reagents were performed under a nitrogen or argon atmosphere. Purity was measured using Agilent 1100 Series high performance liquid chromatography (HPLC) systems with UV detection at 254 nm and 215 nm (System A: Agilent Zorbax Eclipse XDB-C8 4.6× 150 mm, 5 micron, 5 to 100% ACN in $H_2O$ with 0.1% TFA for 15 minutes at 1.5 mL/minute; System B: Zorbax SB-C8, 4.6×75 mm, 10 to 90% ACN in $H_2O$ with 0.1% formic acid for 12 minutes at 1.0 mL/minute). Silica gel chromatography was generally performed with prepacked silica gel cartridges (Biotage or Teledyne-Isco). $^1$H NMR spectra were recorded on a Bruker AV-400 (400 MHz) spectrometer or a Varian 400 MHz spectrometer at ambient temperature, or the NMR spectra were collected with a Bruker Avance III spectrometer operating at a proton frequency of 500.13 MHz using a 10 µL Protasis CapNMR flow probe. NMR samples were delivered to the flow probe using a Protasis One-Minute NMR™ Automation system comprised of a Discovery Tower™ Sample Manager and a Waters Liquid Handler made by CTC, Switzerland (Model 2777). All observed protons are reported as parts per million (ppm) downfield from tetramethylsilane (TMS) or another internal reference in the appropriate solvent indicated. Data are reported as follows: chemical shift, multiplicity (s=singlet, d=doublet, t=triplet, q=quartet, br=broad, m=multiplet), coupling constants, and number of protons. Low-resolution mass spectral (MS) data were determined on an Agilent 1100 Series LC-MS with UV detection at 254 nm and 215 nm and a low resonance electrospray mode (ESI).

The following Abbreviations are used to refer to various reagents and solvents:
ACN Acetonitrile
AcOH Acetic Acid
DCM Dichloromethane
DIEA N,N-Diisopropylethylamine
DMF N,N-Dimethylformamide
DMSO Dimethylsulfoxide
EtOAc Ethyl Acetate
EtOH Ethanol
HATU 0-(7-Azabenzotriazol-1-yl)-N,N,N',N'-tetramethyluronium hexafluorophosphate
IPA Isopropanol
MeOH Methanol
RT Room temperature
TEA Triethylamine
TFA Trifluoroacetic acid
THF Tetrahydrofuran
TLC Thin Layer Chromatography

SYNTHESIS OF INTERMEDIATES

Intermediate A 1-((1r,4r)-4-aminocyclohexyl)-1H-benzo[d]imidazol-2(3H)-one hydrochloride

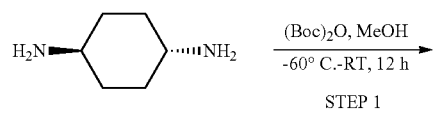

STEP 1

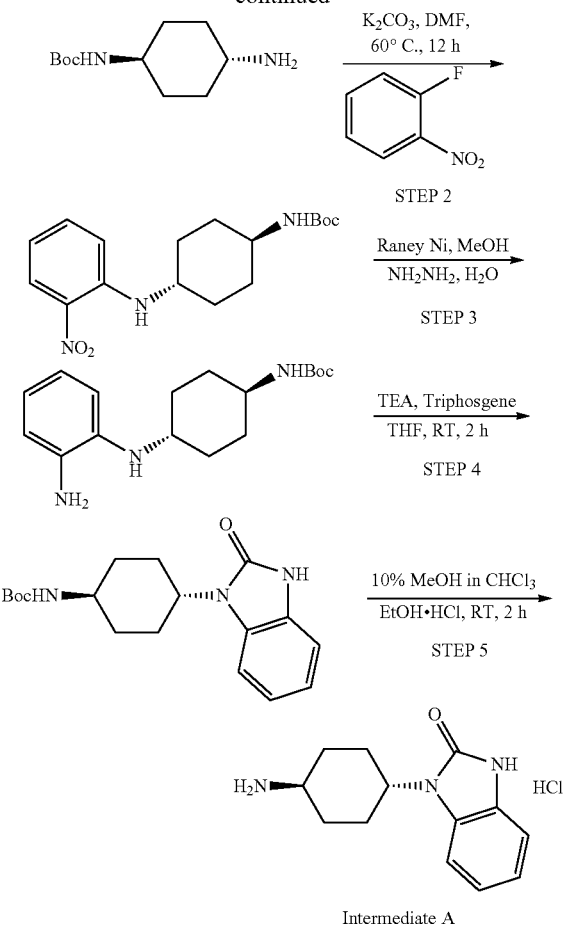

Intermediate A

Step 1:
tert-butyl((1r,4r)-4-aminocyclohexyl)carbamate

To a solution of trans-1,4-diaminocyclohexane (5 g, 43.78 mmol) in MeOH (100 mL) was added a solution of di-tert-butyl dicarbonate (4.77 g, 21.89 mmol) in MeOH (50 mL) at −60° C. over 90 min. The temperature was slowly allowed to warm to ambient temperature. The reaction mixture was stirred for 12 h at ambient temperature. After completion of the reaction (monitored by TLC (TLC eluent: 10% MeOH in $CHCl_3$, ninhydrin stain active)), the reaction mixture was concentrated and water was added to afford a white precipitate. The slurry was further stirred for 10 min, and then the precipitate was filtered and washed with water. The filtrate (aqueous layer) was extracted with EtOAc (2×150 mL). The extract was washed with saturated NaCl solution and separated and further dried with anhydrous sodium sulfate. Following filtration, the organics were concentrated under reduced pressure to afford tert-butyl((1r,4r)-4-aminocyclohexyl)carbamate as a white solid, 2.6 g (27.70%). NOTE:— Filtered solid (3 g) product was bisboc protected compound and unreacted starting material remained in the aqueous layer. $^1$H NMR (400 MHz, DMSO-$d_6$): δ 6.67 (d, J=7.6 Hz, 1H), 3.12 (m, 1H), 2.44 (m, 1H), 1.71 (m, 4H), 1.36 (s, 9H), 1.17 (m, 2H), 1.04 (m, 2H).

Step 2: tert-butyl((1r,4r)-4-((2-nitrophenyl)amino)cyclohexyl)carbamate

To a solution of tert-butyl((1r,4r)-4-aminocyclohexyl)carbamate (1 g, 4.66 mmol) and 1-fluoro-2-nitrobenzene (0.658 g, 4.66 mmol) in DMF (5 mL) was added potassium carbonate (1.28 g, 9.32 mmol) at ambient temperature. The resulting reaction mixture was stirred for 12 h at 60° C. After completion of reaction (monitored by TLC (TLC eluent: 30% EtOAc in petroleum ether)), the reaction mixture was cooled to ambient temperature and water was added to obtain a yellow precipitate. After stirring for 10 mins, the mixture was filtered and washed with water, then dried under vacuum to afford tert-butyl((1r,4r)-4-((2-nitrophenyl)amino)cyclohexyl)carbamate as a yellow solid, 1.5 g (95.84%). $^1$H NMR (300 MHz, DMSO-$d_6$) δ 8.03 (d, J=8.6 Hz, 1H), 7.87 (d, J=7.6 Hz, 1H), 7.52-7.43 (m, 1H), 7.11 (d, J=8.7 Hz, 1H), 6.83 (d, J=7.6 Hz, 1H), 6.71-6.57 (m, 1H), 3.42 (m, 1H), 1.99 (s, 2H), 1.81 (s, 2H), 1.45-1.20 (m, 2H+2H+1H+9H=14H). m/z (ESI) 336.3 (M+H)$^+$.

Step 3: tert-butyl((1r,4r)-4-((2-aminophenyl)amino)cyclohexyl)carbamate

To a stirred suspension of Raney Nickel (1.5 g) in MeOH (30 mL) was added tert-butyl((1r,4r)-4-((2-nitrophenyl)amino)cyclohexyl)carbamate (1.5 g, 4.47 mmol) at ambient temperature, and the temperature was raised to 56° C. Hydrazine hydrate (1.5 mL) was then added very slowly over 10 min (exothermic reaction). The reaction mixture was stirred for 10 min at 56° C. After completion of reaction (monitored by TLC (TLC eluent: 50% EtOAc in petroleum ether)), the reaction mixture was cooled to ambient temperature, and then was filtered through Celite® brand filter aid and concentrated. The residue was then placed under high vacuum to remove excess hydrazine hydrate. The product thus obtained was washed with petroleum ether to provide tert-butyl((1r,4r)-4-((2-aminophenyl)amino)cyclohexyl)carbamate as a grey solid, 1.1 g (80.58%). $^1$H NMR (300 MHz, DMSO-$d_6$): 6.85 (d, J=4.5 Hz, 1H), 6.52-6.34 (m, 3H), 4.45 (br s, 2H), 7.08 (d, J=7.5 Hz, 1H), 3.21-3.06 (m, 2H), 2.00-1.96 (m, 2H), 1.81-1.77 (m, 2H), 1.37 (s, 9H), 1.28-1.15 (m, 3H). m/z (ESI) 306.2 (M+H)$^+$.

Step 4: tert-butyl((1r,4r)-4-(2-oxo-2,3-dihydro-1H-benzo[d]imidazol-1-yl)cyclohexyl)carbamate To a solution of tert-butyl((1r,4r)-4-((2-aminophenyl)amino)cyclohexyl)carbamate (24.8 g, 81.20 mmol) in THF (250 mL) was added TEA (8.21 g, 81.20 mmol) and triphosgene (24 g, 81.20 mmol) at 0° C. The reaction mixture was stirred for 2 h at ambient temperature. After completion of the reaction (monitored by TLC (TLC eluent: 50% EtOAc in petroleum ether)), the reaction mixture was quenched with saturated NaHCO$_3$ solution and extracted with 20% THF in EtOAc (3×200 mL). The extract was washed with brine and dried on anhydrous sodium sulfate. After filtration, the organic layer was concentrated under vacuum to afford tert-butyl((1r,4r)-4-(2-oxo-2,3-dihydro-1H-benzo[d]imidazol-1-yl)cyclohexyl)carbamate as an off-white solid, 16 g+8 g (89.18%). NOTE:—Insoluble aqueous layer was filtered and washed with water and dried under vacuum (8 g). $^1$H NMR (400 MHz, DMSO-$d_6$): δ 7.31 (m, 1H), 6.97 (m, 4H), 6.81 (d, J=8 Hz, 1H), 4.13 (m, 1H), 2.25 (m, 2H), 1.91 (d, J=11.2 Hz, 2H), 1.67 (d, J=10.8 Hz, 2H), 1.39 (s, 9H), 1.35 (m, 2H). m/z (ESI) 276.1 (NHCOOH).

Step 5: 1-((1r,4r)-4-aminocyclohexyl)-1H-benzo[d]imidazol-2(3H)-one hydrochloride To a solution of tert-butyl((1r,4r)-4-(2-oxo-2,3-dihydro-1H-benzo[d]imidazol-1-yl)cyclohexyl)carbamate (12.5 g, 37.71 mmol) in 10% MeOH in CHCl$_3$ (125 mL) was added saturated ethanolic HCl (125 mL) at ambient temperature. The reaction mixture was stirred for 2 h at the same temperature. After completion of reaction (monitored by TLC (TLC eluent: 100% EtOAc)), the reaction mixture was concentrated, diethyl ether (50 mL) was added, and the resulting mixture was stirred for 10 mins. The resulting precipitate was filtered and the solid was washed with diethyl ether to afford 1-(4-amino-cyclohexyl)-1,3-dihydro-benzoimidazol-2-one hydrochloride as a tan solid. 9.1 g (90.18%). $^1$H NMR (400 MHz, DMSO-$d_6$): δ 10.90 (bs, 1H), 8.19 (bs, 3H), 7.38 (q, J=5.6 Hz & J=2.4 Hz, 1H), 6.97 (m, 3H), 4.18 (m, 1H), 3.23 (m, 1H), 2.30 (m, 2H), 2.11 (d, J=11.6 Hz, 2H), 1.75 (d, J=10.8 Hz, 2H), 1.59 (m, 2H). m/z (ESI) 232.

Intermediate B (1r, 4r)-4-(4-fluorophenoxy)cyclohexanamine

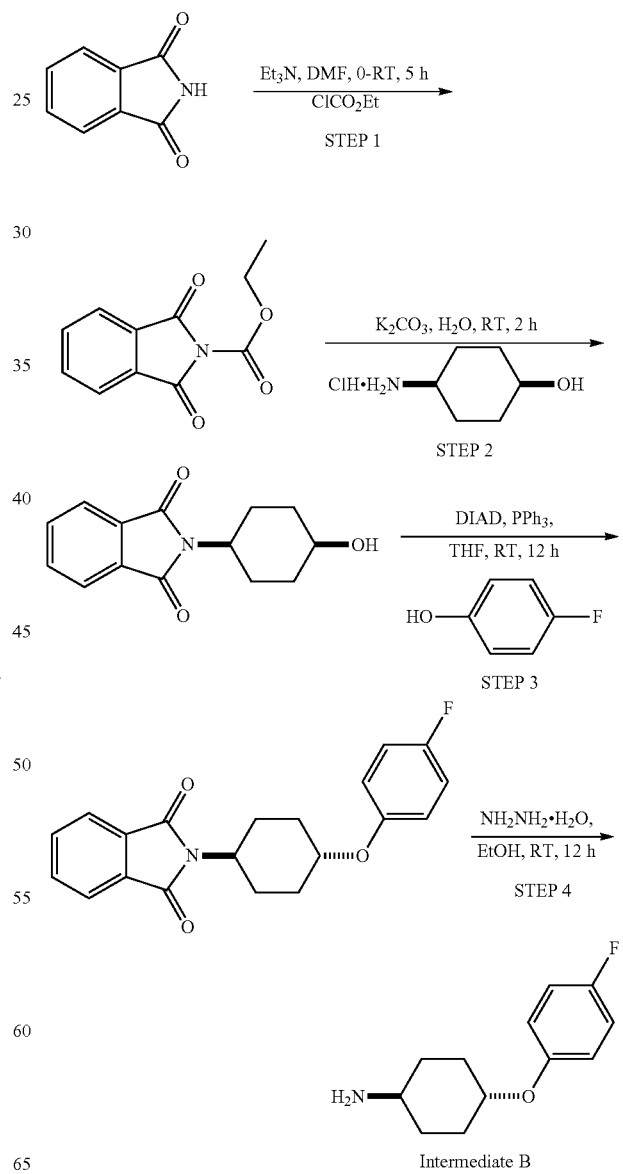

Intermediate B

Step 1: Synthesis of ethyl 1,3-dioxoisoindoline-2-carboxylate

To a solution of phthalimide (2 g, 13.59 mmol) and TEA (2.75 g, 27.18 mmol) in DMF (10 mL) at 0-5° C. in a 100 mL round bottom flask under an argon atmosphere, was added ethyl chloroformate dropwise over a period of 30 min. After complete addition, the reaction mixture was allowed to warm to ambient temperature and further stirred for 2 h. After completion of reaction (TLC was used to monitor the reaction using 30% EtOAc in petroleum ether, UV active), the reaction mixture was treated with ice water to afford a white precipitate. The precipitate was filtered and washed with ice water to obtain ethyl 1,3-dioxoisoindoline-2-carboxylate as a white solid. Yield 1.5 g (50.34%). m/z (ESI): 220.2.

Step 2: Synthesis of 2-((1s,4s)-4-hydroxycyclohexyl)isoindoline-1,3-dione

To a solution of ethyl 1,3-dioxoisoindoline-2-carboxylate (400 mg, 1.82 mmol) and (1s,4s)-4-aminocyclohexanol hydrochloride (275 mg, 1.82 mmol) in water (4 mL) at 0° C. in a 50 mL round bottom flask, was added $K_2CO_3$ (756 mg, 5.48 mmol) in portions. After 30 min, the reaction mixture was allowed to warm to ambient temperature and stirred further for 1 h at ambient temperature affording a white precipitate. The progress of reaction was monitored by TLC (EtOAc, ninhydrine active). The precipitate was filtered and dried to obtain 2-((1r, 4r)-4-hydroxycyclohexyl) isoindoline-1,3-dione as a white solid. Yield 300 mg (67.04%). m/z (ESI): 246.2.

Step 3: Synthesis of 2-((1r, 4r)-4-(4-fluorophenoxy)cyclohexyl)isoindoline-1,3-dione To a mixture of 2-((1r, 4r)-4-hydroxycyclohexyl) isoindoline-1,3-dione (4 g, 16.32 mmol), 4-fluorophenol (2.2 g, 19.52 mmol), and triphenyl phosphine (6.86 g, 26.12 mmol) in dry THF (50 mL) in a 100 mL round bottom flask, was added DIAD (5.27 g, 26.12 mmol) dropwise. The resulting mixture was stirred for 12 h at ambient temperature. The progress of reaction was monitored using TLC (20% EtOAc in petroleum ether). After completion of reaction, the reaction mixture was treated with water and the product was extracted in EtOAc. The water layer was back extracted using EtOAc. The organic layers were combined and dried over anhydrous sodium sulfate, and the organic layer was concentrated under reduced pressure to obtain 2-((1s,4s)-4-(4-fluorophenoxy)cyclohexyl)isoindoline-1,3-dione (7) as a thick yellow liquid. The product thus obtained was purified using 60-120 mesh silica column chromatography using 6% EtOAc in petroleum ether as an eluent providing 2-((1r,4r)-4-(4-fluorophenoxy)cyclohexyl)isoindoline-1,3-dione as a thick yellow liquid after concentration. Yield 2.8 g, (50.58%). m/z (ESI): 340.2.

Step 4: Synthesis of (1r,4r)-4-(4-fluorophenoxy)cyclohexanamine

To a solution of 2-((1r,4r)-4-(4-fluorophenoxy)cyclohexyl)isoindoline-1,3-dione (2.8 g, 8.23 mmol) in EtOH (20 mL) in a 100 mL round bottom flask was added hydrazine hydrate dropwise at ambient temperature. The resulting mixture was stirred for 12 h at ambient temperature. The progress of reaction was monitored by TLC (EtOAc, ninhydrin active). After completion of reaction, the white solid precipitate from the reaction mixture was filtered and the filtrate was treated with 5% dil. HCl and DCM. The layers were separated, and the aqueous layer (which contains the product in the hydrochloride form) was further basified to pH ~8-9 using cool 10% $NaHCO_3$ solution. After basification, the aqueous layer was extracted in DCM and concentrated to obtain (1r, 4r)-4-(4-fluorophenoxy)cyclohexanamine as a colorless oil. Yield 1.5 g (94.58%).

$^1$H NMR (400 MHz, CHLOROFORM-d) δ ppm 1.18-1.27 (m, 2H) 1.42-1.54 (m, 2H) 1.87-1.99 (m, 2H) 2.05-2.16 (m, 2H) 2.79 (tt, J=10.64, 3.94 Hz, 1H) 4.08 (ft, J=10.47, 4.16 Hz, 1H) 6.79-6.86 (m, 2H) 6.90-6.99 (m, 2H). m/z (ESI): 210.2.

Intermediate C (1r,4r)-4-(5-phenyl-1,3,4-oxadiazol-2-yl)cyclohexanamine

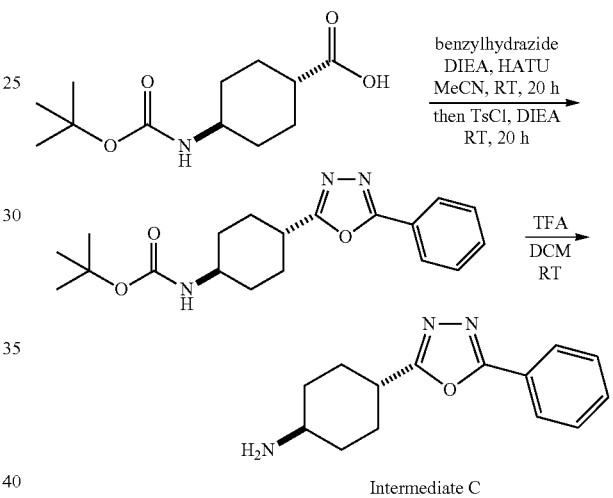

Intermediate C

Step 1: Synthesis of tert-butyl((1r,4r)-4-(5-phenyl-1,3,4-oxadiazol-2-yl)cyclohexyl)carbamate To (1r,4r)-4-((tert-butoxycarbonyl)amino)cyclohexanecarboxylic acid (TCI, Oakwood, Astatech) (514.6 mg, 2.115 mmol) and benzhydrazide (Aldrich) (288 mg, 2.115 mmol) in ACN (2.12E+04 µl) at RT was added DIEA (1105 µl, 6.35 mmol), followed by HATU (885 mg, 2.327 mmol). The resulting mixture was stirred at RT for 19 h, when 2 eq DIEA (368 uL) followed by para-toluene sulfonyl chloride (1210 mg, 6.35 mmol) were added and the mixture was stirred at RT for 24 h. The reaction mixture was then poured into 14% aq. $NH_3$ (DCM flask rinse), stirred for 15 min, and then transferred to a separatory funnel with DCM and water. The organic layer was washed with water. The combined aqueous layers were extracted with DCM. The combined organic layers were dried and concentrated. The product thus obtained was purified (ISCO: 25 g cartridge, 12 g column, 0 to 85% EtOAc-heptanes). The product-containing fractions were concentrated and loaded onto a 70 mL SCX-2 column with MeOH-DCM, and eluted with 2.0 M $NH_3$ in MeOH. The material (726.0 mg theoretical yield) thus obtained was taken directly on to the next step. m/z (ESI) 344.4 (M+H)$^+$.

Step 2: Synthesis of (1r,4r)-4-(5-phenyl-1,3,4-oxadiazol-2-yl)cyclohexanamine

To tert-butyl((1r,4r)-4-(5-phenyl-1,3,4-oxadiazol-2-yl)cyclohexyl)carbamate (726.0 mg, 2.114 mmol) in DCM (1.06E+04 µl) at RT was added TFA (489 µl, 6.34 mmol). The resulting mixture was stirred at RT for 19 h when additional TFA (489 µl, 6.34 mmol) was added. The mixture was then heated at 30° C. for 5.5 h, and then it was concentrated. The residue thus obtained was loaded onto a 70 mL SCX-2 column with MeOH-DCM, and eluted with 2.0 M $NH_3$ in MeOH. Yield 0.451 g (88%). $^1$H NMR (300 MHz, $d_6$-DMSO) δ ppm 8.05-7.90 (m, 2H), 7.65-7.50 (m, 3H), 4.80 (br, 2H), 3.35-3.20 (m, 1H), 3.00-2.80 (m, 1H), 2.13 (d, J=12.3 Hz, 2H), 1.91 (d, J=12.3 Hz, 2H), 1.60 (q, J=12.3 Hz, 2H), 1.30 (q, J=12.3 Hz, 2H). m/z (ESI): m/z: 244.0 (M+1).

Intermediate D 3-((1r,4r)-4-aminocyclohexyl)benzo[d]oxazol-2(3H)-one

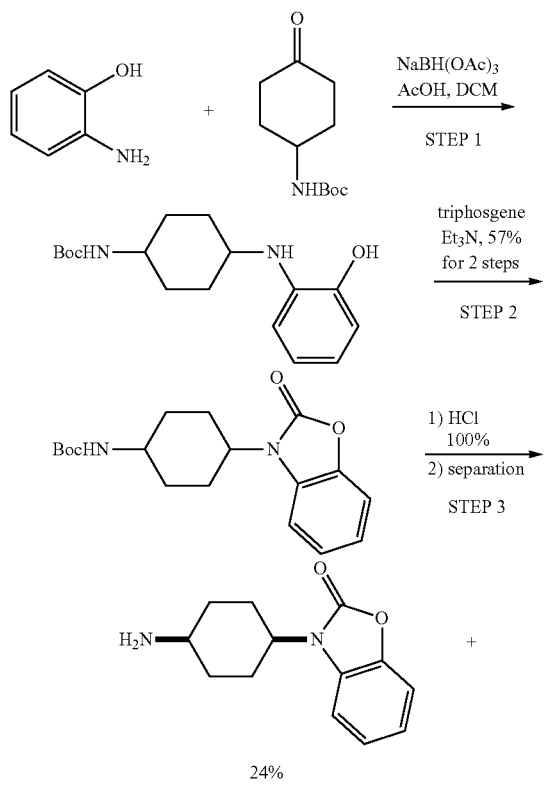

STEP 1: To a mixture of 4-N-boc-aminocyclohexanone (1.076 g, 5.05 mmol) and 2-aminophenol (0.829 mL, 10.09 mmol) in DCM (25.2 mL), were added AcOH (0.291 mL, 5.05 mmol) and sodium triacetoxyborohydride (1.497 g, 7.06 mmol). The resulting mixture was stirred at RT overnight. To the mixture was added saturated sodium carbonate solution, and the resulting solution was transferred to a separatory funnel. The organic layer was separated and the aqueous layer was washed with EtOAc (2×). The combined organic layers were dried with $Na_2SO_4$, filtered and dried under reduced pressure providing a residual oil. The residual oil was adsorbed onto a plug of silica gel and purified by chromatography through a Redi-Sep pre-packed silica gel column (80 g), eluting with a gradient of 0% to 35% 1M $NH_3$.MeOH in $CH_2Cl_2$, to provide tert-butyl(4-((2-hydroxyphenyl)amino)cyclohexyl)carbamate (1.80 g, 5.87 mmol, 116% yield) with certain amount of impurities as orange solid which was used without further purification. m/z (ESI) 307.2.

STEP 2: Triphosgene (1.424 g, 4.80 mmol) was added to a mixture of tert-butyl(4-((2-hydroxyphenyl)amino)cyclohexyl)carbamate (1.547 g, 5.05 mmol) and TEA (1.408 mL, 10.10 mmol) in THF (33.7 mL). The mixture was stirred at RT for 1 h. The reaction was quenched by adding saturated $NaHCO_3$ solution. The mixture was extracted with EtOAc. The combined organic layers were washed with saturated $NaHCO_3$ solution and brine, dried over anhydrous magnesium sulfate, and concentrated in vacuo. The residue thus obtained was adsorbed onto a plug of silica gel and purified by chromatography through a Redi-Sep pre-packed silica gel column (80 g), eluting with a gradient of 0% to 25% 1M $NH_3$.MeOH in $CH_2Cl_2$, to provide tert-butyl(4-(2-oxobenzo[d]oxazol-3(2H)-yl)cyclohexyl)carbamate (0.961 g, 2.89 mmol, 57.3% yield) as white solid. m/z (ESI) 355.2.

STEP 3: To a mixture of tert-butyl(4-(2-oxobenzo[d]oxazol-3(2H)-yl)cyclohexyl) carbamate (0.904 g, 2.72 mmol) in MeOH (27.2 mL) was added hydrogen chloride (4.0 N solution in 1,4-dioxane) (13.60 mL, 54.4 mmol). The mixture was stirred at RT for 1 h. The solvent was evaporated and the material thus obtained separated with chiral HPLC: ChiralPak OD-H (2×20 cm), 22% IPA/$CO_2$ (0.2% diethylamine), 100 bar, 65 ml/min, detection at 220 nm, inj. Volume, 0.5 ml, 30 mg/ml in MeOH:DCM (2:1) to give ((1r,4r)-4-aminocyclohexyl)benzo[d]oxazol-2(3H)-one (0.285 g, 1.22 mmol, 45% yield) as white solid. $^1$H NMR (400 MHz, DMSO-$d_6$) δ ppm 7.48 (dd, J=7.87, 0.83 Hz, 1H) 7.30-7.38 (m, 1H) 7.17-7.25 (m, 1H) 7.07-7.17 (m, 1H) 4.47 (br. s., 2H) 4.07 (tt, J=12.39, 4.05 Hz, 1H) 2.89 (tt, J=11.39, 3.77 Hz, 1H) 2.15 (qd, J=12.86, 3.37 Hz, 2H) 1.89-2.04 (m, 2H) 1.73-1.89 (m, 2H) 1.24-1.45 (m, 2H). m/z (ESI) 233.2.

Intermediate E 1-((1r,4r)-4-aminocyclohexyl)-5-chloro-1H-benzo[d]imidazol-2(3H)-one hydrochloride

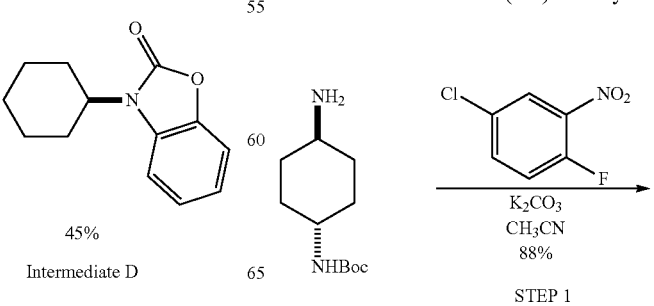

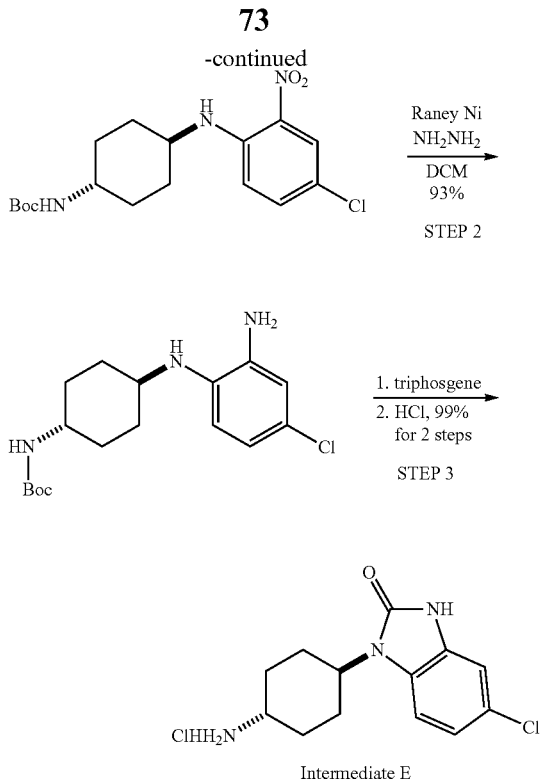

STEP 1: To a flask charged with 5-chloro-2-fluoronitrobenzene (1.05 g, 5.98 mmol) in ACN (20 mL) was added trans-N-boc-1,4-cyclohexanediamine (1.282 g, 5.98 mmol) and TEA (1.667 mL, 11.96 mmol). The resulting mixture was stirred at 80° C. for 5 h leading to conversion to single new spot on TLC. The mixture was cooled to RT. The resulting solid was filtered, washed with water and dried to give tert-butyl((1r,4r)-4-((4-chloro-2-nitrophenyl)amino)cyclohexyl) carbamate (1.95 g, 5.27 mmol, 88% yield) as a yellow solid. $^1$H NMR (400 MHz, DMSO-$d_6$) δ ppm 8.05 (d, J=2.54 Hz, 1H) 7.88 (d, J=7.82 Hz, 1H) 7.54 (dd, J=9.29, 2.54 Hz, 1H) 7.22 (d, J=9.49 Hz, 1H) 6.80 (d, J=8.12 Hz, 1H) 3.55 (dd, J=6.90, 3.77 Hz, 1H) 3.25 (br. s., 1H) 2.01 (d, J=11.35 Hz, 2H) 1.83 (d, J=11.25 Hz, 2H) 1.28-1.48 (m, 13H). m/z (ESI) 392.2.

STEP 2: tert-Butyl((1r,4r)-4-((4-chloro-2-nitrophenyl)amino)cyclohexyl) carbamate (1.08 g, 2.92 mmol) was dissolved in EtOH and Raney 3202 nickel slurry in water (3.22 mL, 488 mmol) was added at RT. The mixture was heated to 40° C. and hydrazine hydrate (1.364 mL, 43.8 mmol) was added dropwise at 40° C. The reaction was then stirred at 40° C. overnight (LC-MS indicated complete conversion to desired product). The reaction mixture was then cooled to RT, filtered through Celite® brand filter aid and the solvent was evaporated. The residual material was absorbed onto a plug of silica gel and purified by chromatography through a Redi-Sep pre-packed silica gel column (40 g), eluting with a gradient of 0% to 80% EtOAc in hexane, to provide tert-butyl((1r,4r)-4-((2-amino-4-chlorophenyl)amino)cyclohexyl)carbamate (0.927 g, 2.73 mmol, 93% yield) as off-white solid. $^1$H NMR (400 MHz, DMSO-$d_6$) δ ppm 6.74 (d, J=6.85 Hz, 1H) 6.54 (d, J=2.45 Hz, 1H) 6.45 (dd, J=8.41, 2.45 Hz, 1H) 6.39 (d, J=8.51 Hz, 1H) 4.81 (s, 2H) 4.21 (d, J=7.63 Hz, 1H) 3.24 (d, J=10.86 Hz, 1H) 3.00-3.15 (m, 1H) 1.98 (d, J=12.62 Hz, 2H) 1.81 (d, J=11.05 Hz, 2H) 1.39 (s, 9H) 1.08-1.33 (m, 4H). m/z (ESI) 340.2.

STEP 3: To a solution of tert-butyl((1r,4r)-4-((2-amino-4-chlorophenyl)amino)cyclohexyl) carbamate (0.927 g, 2.73 mmol) in THF was added TEA (0.760 mL, 5.46 mmol) and tri-phosgene (0.324 g, 1.091 mmol). The reaction was stirred at RT for 2 h. The starting material was consumed completely based on LC-MS. Saturated NaHCO$_3$ solution was added, and the white precipitate was filtered, washed with water and dried in air. The aqueous solution was extracted with EtOAc three times. The combined extracts were then washed and dried. The solvent was evaporated, and the resulting solid was filtered, washed with a small amount of EtOAc and dried, and combined with the previous solid to give tert-butyl((1r,4r)-4-(5-chloro-2-oxo-2,3-dihydro-1H-benzo[d]imidazol-1-yl)cyclohexyl)carbamate (0.99 g, 2.71 mmol, 99% yield) as an off-white solid. m/z (ESI) 388.2.

To a mixture of tert-butyl((1r,4r)-4-(5-chloro-2-oxo-2,3-dihydro-1H-benzo[d]imidazol-1-yl)cyclohexyl)carbamate (0.76 g, 2.077 mmol) in MeOH (20.77 mL) was added hydrogen chloride (4.0 M solution in 1,4-dioxane (10.39 mL, 41.5 mmol)). The reaction mixture was then stirred at RT for 3 h. The solvent was evaporated to give 1-((1r,4r)-4-aminocyclohexyl)-5-chloro-1H-benzo[d]imidazol-2(3H)-one hydrochloride (0.62 g, 2.07 mmol, 99% yield) as off-white solid. $^1$H NMR (400 MHz, DMSO-$d_6$) δ ppm 11.05 (s, 1H) 7.96 (br. s., 3H) 7.39 (d, J=8.02 Hz, 1H) 6.97-7.04 (m, 2H) 4.03-4.25 (m, 1H) 3.18-3.27 (m, 1H) 2.16-2.33 (m, 2H) 2.07 (d, J=10.95 Hz, 2H) 1.76 (d, J=10.17 Hz, 2H) 1.43-1.64 (m, 2H). m/z (ESI) 266.2.

Intermediate F 1-((1r,4r)-4-aminocyclohexyl)-6-chloro-1H-benzo[d]imidazol-2(3H)-one hydrochloride

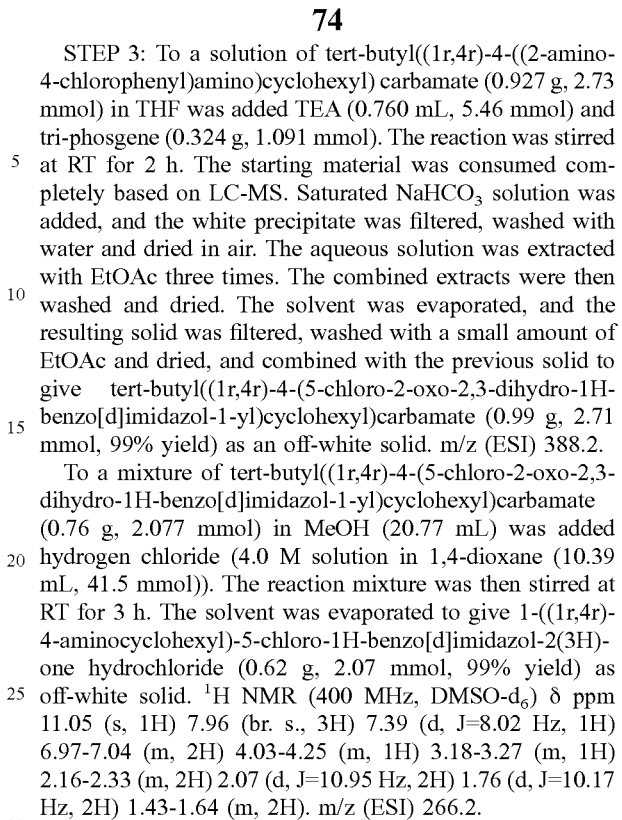

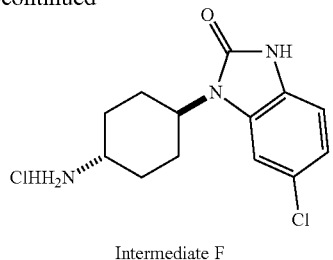

Intermediate F

STEP 1: To a flask charged with 4-chloro-2-fluoronitrobenzene (3.185 g, 18.14 mmol) in ACN (60.5 mL), was added trans-N-boc-1,4-cyclohexanediamine (3.89 g, 18.14 mmol) and TEA (5.06 mL, 36.3 mmol). The resulting bright yellow solution was at 80° C. for 5 h leading to conversion to single new spot on TLC. The mixture was cooled to RT. The resulting solid was filtered, washed with water and dried to give tert-butyl((1r,4r)-4-((5-chloro-2-nitrophenyl)amino)cyclohexyl)carbamate (6.02 g, 16.28 mmol, 90% yield) as yellow solid. $^1$H NMR (400 MHz, DMSO-d$_6$) δ ppm 8.08 (d, J=9.10 Hz, 1H) 7.93 (d, J=7.82 Hz, 1H) 7.24 (d, J=1.96 Hz, 1H) 6.82 (d, J=5.28 Hz, 1H) 6.70 (dd, J=9.19, 2.15 Hz, 1H) 3.62 (br. s., 1H) 3.30 (br. s., 1H) 1.99 (br. s., 2H) 1.83 (br. s., 2H) 1.35-1.51 (m, 13H). m/z (ESI) 392.2.

STEP 2: tert-butyl((1r,4r)-4-(5-chloro-2-nitrophenyl)amino)cyclohexyl)carbamate (0.343 g, 0.927 mmol) was dissolved in EtOH and Raney 3202 nickel slurry in water (1.021 mL, 155 mmol) was added at RT. The mixture was heated to 40° C. and hydrazine hydrate (0.433 mL, 13.91 mmol) was added over 20 min at 40° C. The reaction was stirred at 40° C. overnight (LC-MS indicated complete conversion to the desired product). The reaction mixture was then cooled to RT, filtered through Celite® brand filter aid and the solvent was evaporated. The residual material was absorbed onto a plug of silica gel and purified by chromatography through a Redi-Sep pre-packed silica gel column (12 g), eluting with a gradient of 0% to 40% 1M NH$_3$.MeOH in CH$_2$Cl$_2$, to provide tert-butyl((1r,4r)-4-((2-amino-5-chlorophenyl)amino)cyclohexyl) carbamate (0.31 g, 0.912 mmol, 98% yield) as tan solid. $^1$H NMR (400 MHz, DMSO-d$_6$) δ ppm 6.74 (d, J=6.75 Hz, 1H) 6.49 (d, J=8.80 Hz, 1H) 6.29-6.44 (m, 2H) 4.62 (br. s., 2H) 4.39 (d, J=7.43 Hz, 1H) 3.25 (br. s., 1H) 3.03-3.17 (m, 1H) 1.97 (br. s., 2H) 1.82 (d, J=11.25 Hz, 2H) 1.39 (s, 9H) 1.09-1.35 (m, 4H). m/z (ESI) 340.2.

STEP 3: To a solution of tert-butyl((1r,4r)-4-((2-amino-5-chlorophenyl)amino)cyclohexyl) carbamate (0.31 g, 0.912 mmol) in THF was added TEA (0.254 mL, 1.824 mmol) and triphosgene (0.108 g, 0.365 mmol). The reaction was stirred at RT for 2 h. The starting material was consumed completely based on LC-MS. Saturated NaHCO$_3$ solution was added and the mixture was extracted with EtOAc. The combined extracts were washed with brine and dried over anhydrous sodium sulfate. The solvent was evaporated and the resulting solid was filtered, washed with small amount of EtOAc and dried to give tert-butyl((1r,4r)-4-(6-chloro-2-oxo-2,3-dihydro-1H-benzo[d]imidazol-1-yl)cyclohexyl)carbamate as a tan solid.

To a mixture of tert-butyl((1r,4r)-4-(6-chloro-2-oxo-2,3-dihydro-1H-benzo[d]imidazol-1-yl)cyclohexyl)carbamate (0.28 g, 0.765 mmol) in MeOH (7.65 mL) was added hydrogen chloride (4.0 M solution in 1,4-dioxane) (3.83 mL, 15.31 mmol). The mixture was then stirred at RT for 1 h. The solvent was evaporated to give 1-((1r,4r)-4-aminocyclohexyl)-6-chloro-1H-benzo[d]imidazol-2(3H)-one hydrochloride (0.26 g, 0.860 mmol, 94% yield) as tan solid. $^1$H NMR (400 MHz, DMSO-d$_6$) δ ppm 11.04 (s, 1H) 8.15 (br. s., 3H) 7.51 (d, J=1.57 Hz, 1H) 6.91-7.06 (m, 2H) 4.16 (ddd, J=12.40, 8.39, 3.96 Hz, 1H) 3.27 (br. s., 1H) 2.18-2.36 (m, 2H) 2.09 (d, J=11.64 Hz, 2H) 1.74 (d, J=10.86 Hz, 2H) 1.44-1.65 (m, 2H). m/z (ESI) 266.2.

Intermediate G 1-((1r,4r)-4-aminocyclohexyl)-2-oxo-2,3-dihydro-1H-benzo[d]imidazole-5-carbonitrile hydrochloride

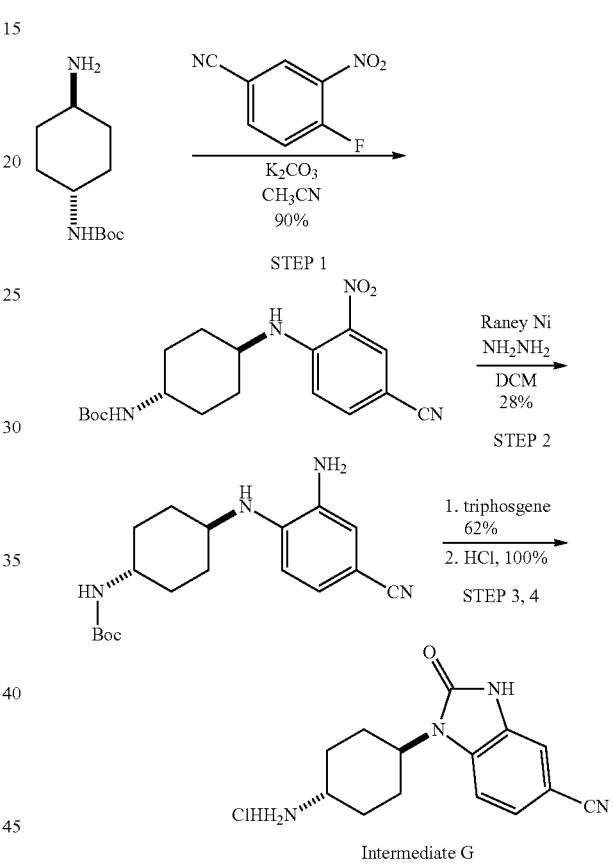

Intermediate G

STEP 1: To a flask charged with 4-fluoro-3-nitrobenzonitrile (0.984 g, 5.92 mmol) in ACN (19.75 mL), was added trans-n-boc-1,4-cyclohexanediamine (1.269 g, 5.92 mmol) and TEA (1.651 mL, 11.85 mmol). The resulting mixture was stirred at 80° C. for 3 h leading to complete conversion. The mixture was cooled to RT. The resulting solid was filtered, washed with water and dried to give tert-butyl((1r,4r)-4-((4-cyano-2-nitrophenyl)amino)cyclohexyl)carbamate (1.93 g, 5.36 mmol, 90% yield) as yellow solid, which was used for next step without further purification. $^1$H NMR (400 MHz, DMSO-d$_6$) δ ppm 8.29-8.37 (m, 1H) 7.96-8.10 (m, 1H) 7.53-7.71 (m, 1H) 7.13 (d, J=9.29 Hz, 1H) 6.64 (d, J=7.82 Hz, 1H) 3.34-3.62 (m, 1H) 3.09 (d, J=2.25 Hz, 1H) 1.81 (d, J=10.27 Hz, 2H) 1.65 (d, J=10.47 Hz, 2H) 1.09-1.38 (m, 13H). m/z (ESI) 361.2.

STEP 2: tert-butyl((1 r,4r)-4-((4-cyano-2-nitrophenyl)amino)cyclohexyl)carbamate (1.93 g, 5.36 mmol) was dissolved in EtOH and Raney 3202 nickel slurry in water (5.90 mL, 894 mmol) was added at RT. The mixture was heated to 40° C. and hydrazine hydrate (2.502 mL, 80 mmol) was added dropwise at 40° C. The reaction was stirred at 40° C. overnight (LC-MS indicated complete consumption of starting material). The reaction mixture was then cooled to RT, filtered through Celite® brand filter aid and the solvent was evaporated. The residual material was absorbed onto a plug of silica gel and purified by chromatography through a Redi-Sep pre-packed silica gel column (80 g), eluting with a gradient of 0% to 40% 1M NH3.MeOH in CH$_2$Cl$_2$, to provide tert-butyl((1r,4r)-4-((2-amino-4-cyanophenyl)amino)cyclohexyl)carbamate (0.50 g, 1.513 mmol, 28.3% yield) as orange solid. $^1$H NMR (400 MHz, DMSO-d$_6$) δ ppm 6.89 (dd, J=8.17, 2.01 Hz, 1H) 6.71-6.81 (m, 2H) 6.50 (d, J=8.51 Hz, 1H) 5.06 (d, J=7.92 Hz, 1H) 4.95 (s, 2H) 3.15-3.28 (m, 2H) 1.93-2.04 (m, 2H) 1.82 (d, J=10.07 Hz, 2H) 1.21-1.33 (m, 4H). m/z (ESI) 275.2.

STEP 3: To a mixture of tert-butyl((1r,4r)-4-((2-amino-4-cyanophenyl)amino)cyclohexyl) carbamate (0.50 g, 1.513 mmol) in THF were added TEA (0.421 mL, 3.03 mmol) and triphosgene (0.180 g, 0.605 mmol). The mixture was stirred at RT overnight. Saturated aqueous NaHCO$_3$ was added, and the mixture was then extracted with EtOAc three times. The combined organic layers were washed and dried. The solvent was then removed. The residual material was absorbed onto a plug of silica gel and purified by chromatography through a Redi-Sep pre-packed silica gel column (40 g), eluting with a gradient of 10% to 90% 1M NH3.MeOH in DCM, to provide tert-butyl((1r,4r)-4-(5-cyano-2-oxo-2,3-dihydro-1H-benzo[d]imidazol-1-yl)cyclohexyl) carbamate (0.336 g, 0.943 mmol, 62.3% yield) as light-yellow solid. $^1$H NMR (400 MHz, DMSO-d$_6$) δ ppm 11.29 (br. s., 1H) 7.51-7.58 (m, 1H) 7.44 (dd, J=8.22, 1.66 Hz, 1H) 7.35 (d, J=1.56 Hz, 1H) 6.77 (d, J=6.16 Hz, 1H) 4.15 (tt, J=12.43, 3.80 Hz, 1H) 3.42 (br. s., 1H) 2.13-2.28 (m, 2H) 1.91 (d, J=10.56 Hz, 2H) 1.70 (d, J=9.88 Hz, 2H) 1.27-1.44 (m, 13H). m/z (ESI) 301.2.

STEP 4: To a mixture of tert-butyl((1r,4r)-4-(5-cyano-2-oxo-2,3-dihydro-1H-benzo[d]imidazol-1-yl)cyclohexyl)carbamate (0.336 g, 0.943 mmol) in MeOH (9.43 mL) was added hydrogen chloride (4.0 M solution in 1,4-dioxane) (4.71 mL, 18.85 mmol). The reaction mixture was stirred at RT for 3 h. The solvent was evaporated to give 1-((1r,4r)-4-aminocyclohexyl)-2-oxo-2,3-dihydro-1H-benzo[d]imidazole-5-carbonitrile hydrochloride (0.27 g, 0.94 mmol, 100% yield) as a light yellow solid. $^1$H NMR (400 MHz, DMSO-d$_6$) δ ppm 11.36 (s, 1H) 8.06 (br. s., 2H) 7.58 (d, J=8.31 Hz, 1H) 7.47 (dd, J=8.31, 1.37 Hz, 1H) 7.38 (d, J=1.37 Hz, 1H) 4.10-4.31 (m, 1H) 3.23 (br. s., 1H) 2.17-2.35 (m, 2H) 2.09 (d, J=9.98 Hz, 2H) 1.77 (d, J=9.98 Hz, 2H) 1.46-1.64 (m, 2H). m/z (ESI) 257.2.

Intermediates H, I, J

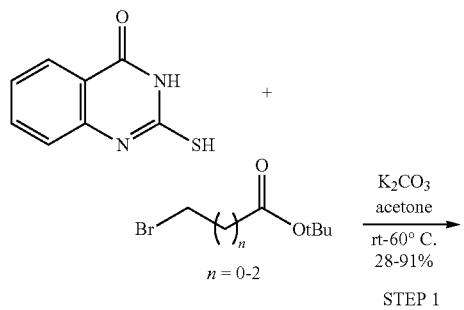

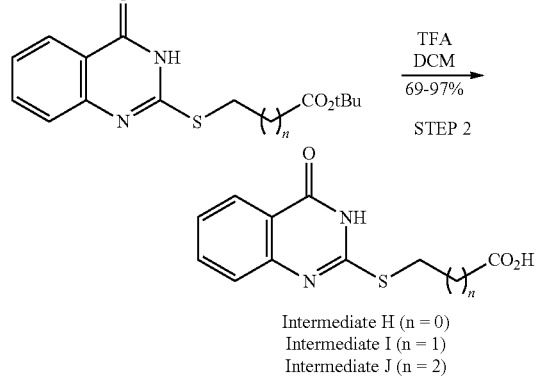

Intermediate H (n = 0)
Intermediate I (n = 1)
Intermediate J (n = 2)

2-((4-oxo-3,4-dihydroquinazolin-2-yl)thio)acetic acid (n=0)

STEP 1: To a mixture of 2-mercapto-4(3H)-quinazolinone (6.13 g, 34.4 mmol) and potassium carbonate (9.51 g, 68.8 mmol) in acetone was added tert-butyl bromoacetate (6.11 mL, 37.8 mmol). The mixture was stirred at RT for 7 h (0.2 mL extra bromoacetate was added after 4 h). LC-MS showed almost complete conversion to the desired product. The solid was filtered off and the solution was concentrated to give tert-butyl 2-((4-oxo-3,4-dihydroquinazolin-2-yl)thio)acetate (9.16 g, 31.3 mmol, 91% yield) including small amount of impurity as white solid.

STEP 2: To a mixture of tert-butyl 2-((4-oxo-3,4-dihydroquinazolin-2-yl)thio)acetate (9.16 g, 31.3 mmol) in DCM (100 mL) was added trifluoroacetic acid (51.2 mL, 689 mmol). The mixture was stirred at RT overnight. The solution was concentrated and ethyl ether was added. The resulting white precipitate was filtered, washed with MeOH and dried in air to give 2-((4-oxo-3,4-dihydroquinazolin-2-yl)thio)acetic acid (5.11 g, 21.63 mmol, 69.0% yield) as off-white solid. $^1$H NMR (400 MHz, DMSO-d$_6$) δ ppm 8.00-8.09 (m, 1H) 7.72-7.81 (m, 1H) 7.37-7.52 (m, 2H) 4.05 (s, 2H). m/z (ESI) 237.2.

3-((4-oxo-3,4-dihydroquinazolin-2-yl)thio)propanoic acid (n=1)

STEP 1: To a mixture of 2-mercapto-4(3 h)-quinazolinone (2.50 g, 14.03 mmol) and potassium carbonate (3.88 g, 28.1 mmol) in acetone was added tert-butyl 3-bromopropionate (3.52 g, 16.83 mmol). The mixture was stirred at 60° C. for 6 h. The solid was filtered off and the solution was concentrated. The residual material was absorbed onto a plug of silica gel and purified by chromatography through a Redi-Sep pre-packed silica gel column (80 g), eluting with a gradient of 0% to 40% EtOAc in hexane, to provide tert-butyl 3-((4-oxo-3,4-dihydroquinazolin-2-yl)thio)propanoate (1.18 g, 3.85 mmol, 27.5% yield) as a white solid. $^1$H NMR (400 MHz, DMSO-d$_6$) δ ppm 12.53 (br. s., 1H) 8.04 (dd, J=7.92, 1.27 Hz, 1H) 7.77 (ddd, J=8.31, 7.04, 1.66 Hz, 1H) 7.53 (d, J=7.92 Hz, 1H) 7.43 (td, J=7.53, 1.17 Hz, 1H) 3.39 (t, J=6.75 Hz, 2H) 2.73 (t, J=6.75 Hz, 2H) 1.42 (s, 9H). m/z (ESI) 307.2.

STEP 2: To a mixture of tert-butyl 3-((4-oxo-3,4-dihydroquinazolin-2-yl)thio)propanoate (0.49 g, 1.599 mmol) in DCM (8.00 mL) was added trifluoroacetic acid (3.56 mL, 48.0 mmol). The mixture was stirred at RT for 6 h. The solvent and extra TFA was evaporated to give 3-((4-oxo-3,4-dihydroquinazolin-2-yl)thio)propanoic acid (0.39 g, 1.558 mmol, 97% yield) as an off-white solid. $^1$H NMR (400 MHz, DMSO-d$_6$) δ ppm 7.87-8.05 (m, 1H) 7.58-7.76 (m, 1H) 7.38-7.52 (m, 1H) 7.34 (ddd, J=8.00, 7.07, 1.17 Hz, 1H) 3.29 (t, J=6.85 Hz, 2H) 2.66 (t, J=6.85 Hz, 2H). m/z (ESI) 251.2.

4-((4-oxo-3,4-dihydroquinazolin-2-yl)thio)butanoic acid (n=2)

STEP 1: To a mixture of 2-mercapto-4(3H)-quinazolinone (0.706 g, 3.96 mmol) and potassium carbonate (1.094 g, 7.92 mmol) in acetone was added tert-butyl 4-bromobutanoate (1.06 g, 4.75 mmol). The mixture was stirred at 60° C. for 4 h (LC-MS showed complete conversion to the desired product). The solid was filtered off and the solution was concentrated. The residual material was absorbed onto a plug of silica gel and purified by chromatography through a Redi-Sep pre-packed silica gel column (80 g), eluting with a gradient of 0% to 40% EtOAc in hexane, to provide tert-butyl 4-((4-oxo-3,4-dihydroquinazolin-2-yl)thio)butanoate (0.839 g, 2.62 mmol, 66.1% yield) as white solid. $^1$H NMR (400 MHz, DMSO-d$_6$) δ ppm 12.54 (s, 1H) 8.04 (dd, J=7.92, 1.17 Hz, 1H) 7.77 (ddd, J=8.31, 7.04, 1.66 Hz, 1H) 7.52 (d, J=7.82 Hz, 1H) 7.42 (ddd, J=8.00, 7.07, 1.08 Hz, 1H) 3.25 (t, J=7.14 Hz, 2H) 2.37 (t, J=7.29 Hz, 2H) 1.94 (quin, J=7.24 Hz, 2H) 1.41 (s, 9H). m/z (ESI) 321.2.

STEP 2: To a mixture of tert-butyl 4-((4-oxo-3,4-dihydroquinazolin-2-yl)thio)butanoate (0.83 g, 2.59 mmol) in DCM (12.95 mL) was added trifluoroacetic acid (5.77 mL, 78 mmol). The mixture was stirred at RT overnight. The solvent and extra TFA was evaporated to give 4-((4-oxo-3,4-dihydroquinazolin-2-yl)thio)butanoic acid (0.621 g, 2.350 mmol, 91% yield) as a white solid. $^1$H NMR (400 MHz, DMSO-d$_6$) δ ppm 12.53 (br. s., 1H) 12.11 (br. s., 1H) 8.04 (dt, J=7.97, 0.76 Hz, 1H) 7.68-7.85 (m, 1H) 7.54 (d, J=8.22 Hz, 1H) 7.42 (ddd, J=8.00, 7.07, 1.17 Hz, 1H) 3.26 (t, J=7.09 Hz, 2H) 2.39 (t, J=7.29 Hz, 2H) 1.95 (quin, J=7.21 Hz, 2H). m/z (ESI) 265.2.

Intermediate K 3-(4-oxo-3,4-dihydropyrido[2,3-d]pyrimidin-2-yl)propanoic acid

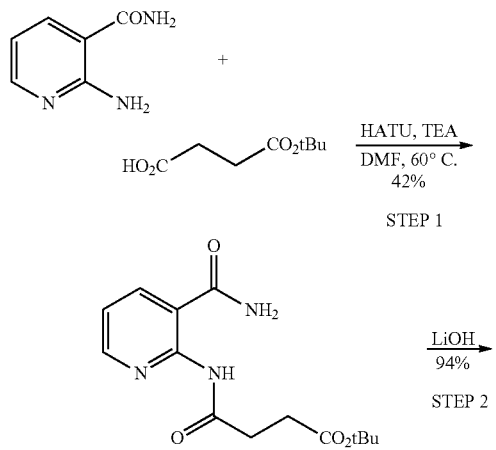

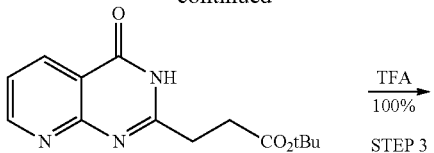

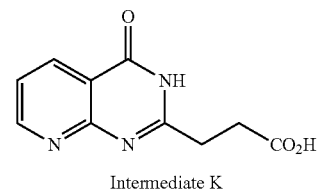

Intermediate K

STEP 1: A mixture of 2-aminonicotinamide (0.85 g, 6.20 mmol), mono-tert-butyl succinate (1.620 g, 9.30 mmol), HATU (3.54 g, 9.30 mmol) and TEA (1.728 mL, 12.40 mmol) in DMF was stirred at 60° C. for 20 h. The mixture was poured into water and extracted with EtOAc. The combined organic layers were washed with brine, dried and concentrated. The residual material was absorbed onto a plug of silica gel and purified by chromatography through a Redi-Sep pre-packed silica gel column (40 g), eluting with a gradient of 0% to 60% 1M NH$_3$.MeOH in DCM, to provide tert-butyl 4-((3-carbamoylpyridin-2-yl)amino)-4-oxobutanoate (0.70 g, 2.386 mmol, 38.5% yield) (including ~30% unidentified compound) as a light-yellow solid.

STEP 2: To a solution of tert-butyl 4-((3-carbamoylpyridin-2-yl)amino)-4-oxobutanoate (0.47 g, 1.602 mmol) in THF (16.02 mL) and water (0.5 mL) at 0° C. was added lithium hydroxide monohydrate (0.336 g, 8.01 mmol). The mixture was stirred at 0° C. to RT for 2 h (LC-MS showed complete conversion). The reaction was quenched by addition of water and extracted with EtOAc. The combined organic layers were washed with brine, dried and concentrated to give tert-butyl 3-(4-oxo-3,4-dihydropyrido[2,3-d]pyrimidin-2-yl)propanoate (0.413 g, 1.500 mmol, 94% yield) as a yellow solid. m/z (ESI) 276.2.

STEP 3: To a mixture of tert-butyl 3-(4-oxo-3,4-dihydropyrido[2,3-d]pyrimidin-2-yl)propanoate (0.413 g, 1.500 mmol) in DCM (15.00 mL) was added trifluoroacetic acid (3.34 mL, 45.0 mmol). The mixture was stirred at RT for 2 h. The solvent and extra TFA was evaporated to give a sticky oil. The oil was treated with MeOH. The resulting yellow precipitate was filtered off and washed with MeOH. The solution was concentrated and the solid was combined. The solid was washed with a small amount of MeOH and dried in air to give 3-(4-oxo-3,4-dihydropyrido[2,3-d]pyrimidin-2-yl)propanoic acid (0.26 g, 1.186 mmol, 79% yield) as a light yellow solid.

$^1$H NMR (400 MHz, DMSO-d$_6$) δ ppm 12.49 (br. s., 1H) 12.21 (br. s., 1H) 8.90 (dd, J=4.60, 2.05 Hz, 1H) 8.47 (dd, J=7.82, 2.05 Hz, 1H) 7.50 (dd, J=7.82, 4.60 Hz, 1H) 2.84-2.99 (m, 2H) 2.68-2.84 (m, 2H). m/z (ESI) 220.2.

Intermediate L

3-(4-oxo-3,4,5,6,7,8-hexahydropyrido[2,3-d]pyrimidin-2-yl) propanoic acid

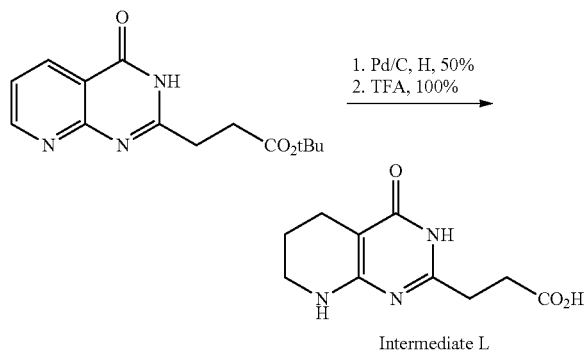

Intermediate L

STEP 1: A mixture of tert-butyl 3-(4-oxo-3,4-dihydropyrido[2,3-d]pyrimidin-2-yl)propanoate (0.296 g, 1.075 mmol) (~45% pure) and palladium 10 wt. % on activated carbon (0.025 mL, 0.237 mmol) in MeOH under hydrogen was stirred at RT overnight. The solid was filtered off and the solution was concentrated. The residual material was absorbed onto a plug of silica gel and purified by chromatography through a Redi-Sep pre-packed silica gel column (12 g), eluting with a gradient of 0% to 50% 1M $NH_3$.MeOH in DCM, to provide tert-butyl 3-(4-oxo-3,4,5,6,7,8-hexahydropyrido[2,3-d]pyrimidin-2-yl)propanoate (0.076 g, 0.272 mmol, 50% yield) as off-white solid. $^1$H NMR (400 MHz, $CDCL_3$-d) δ ppm 4.98 (br. s., 1H) 3.27-3.42 (m, 2H) 2.77-2.85 (m, 2H) 2.65-2.73 (m, 2H) 2.54 (t, J=6.26 Hz, 2H) 1.79-1.94 (m, 2H) 1.41-1.45 (m, 9H). m/z (ESI) 280.2.

STEP 2: To tert-butyl 3-(4-oxo-3,4,5,6,7,8-hexahydropyrido[2,3-d]pyrimidin-2-yl)propanoate (0.075 g, 0.268 mmol) in DCM was added trifluoroacetic acid (0.499 mL, 6.71 mmol). The mixture was stirred at RT for 6 h (LC-MS showed complete conversion). The extra TFA and solvent were evaporated to afford 3-(4-oxo-3,4,5,6,7,8-hexahydropyrido[2,3-d]pyrimidin-2-yl) propanoic acid (0.065 g, 0.291 mmol, 108% yield) as off-white solid. $^1$H NMR (400 MHz, DMSO-$d_6$) δ ppm 3.11-3.20 (m, 2H) 2.58-2.65 (m, 4H) 2.30 (t, J=6.26 Hz, 2H) 1.68 (quin, J=5.89 Hz, 2H). m/z (ESI) 224.2.

Intermediate M

3-(6-fluoro-4-oxo-3,4-dihydroquinazolin-2-yl)propanoic acid

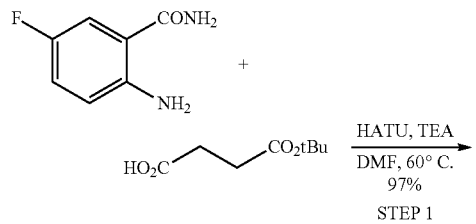

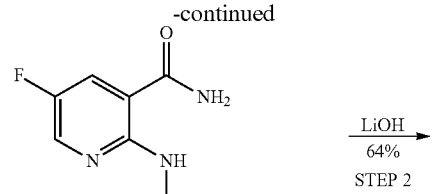

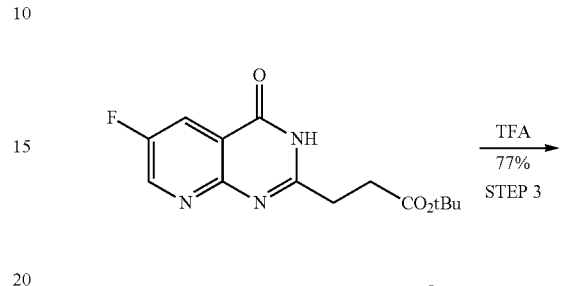

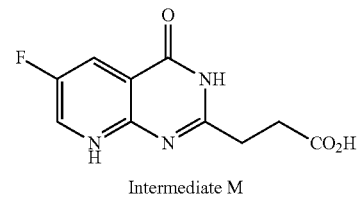

Intermediate M

STEP 1: A mixture of 2-amino-5-fluorobenzamide (0.50 g, 3.24 mmol), mono-tert-butyl succinate (0.678 g, 3.89 mmol), HATU (1.480 g, 3.89 mmol) and TEA (0.904 mL, 6.49 mmol) in DMF was stirred at 60° C. overnight. The mixture was poured into water and then extracted with EtOAc three times. The combined organic layers were washed with brine, dried and concentrated to afford tert-butyl 4-(2-carbamoyl-4-fluorophenyl)amino)-4-oxobutanoate (0.98 g, 3.16 mmol, 97% yield) as an off-white solid, which was used without further purification. m/z (ESI) 255.2.

STEP 2: To a solution of tert-butyl 4-(2-carbamoyl-4-fluorophenyl)amino)-4-oxobutanoate (0.98 g, 3.16 mmol) in THF (15.79 mL) and water (0.5 mL) at 0° C. was added lithium hydroxide monohydrate (0.663 g, 15.79 mmol). The mixture was stirred at 0° C. to RT for 3 h. The reaction was quenched by addition of water and extracted with ethyl acetete three times. The combined organic layers were washed with brine, dried and concentrated to give tert-butyl 3-(6-fluoro-4-oxo-3,4-dihydroquinazolin-2-yl)propanoate (0.59 g, 2.018 mmol, 63.9% yield) as off-white solid, which was used without further purification. m/z (ESI) 293.2.

STEP 3: To a mixture of tert-butyl 3-(6-fluoro-4-oxo-3,4-dihydroquinazolin-2-yl)propanoate (0.59 g, 2.018 mmol) in DCM (10.09 mL) was added trifluoroacetic acid (4.50 mL, 60.6 mmol). The mixture was stirred at RT for 4 h. The solvent and extra TFA were removed providing an oil. Diethyl ether was added to the oil and a solid precipitated. The solid was filtered, washed with ether, and dried in air to give 3-(6-fluoro-4-oxo-3,4-dihydroquinazolin-2-yl)propanoic acid (0.366 g, 1.550 mmol, 77% yield) as an off-white solid. $^1$H NMR (400 MHz, DMSO-$d_6$) δ ppm 12.32 (br. s., 1H) 12.17 (s, 1H) 7.71-7.81 (m, 1H) 7.57-7.71 (m, 2H) 2.80-2.92 (m, 2H) 2.71-2.80 (m, 2H). m/z (ESI) 237.2.

Intermediate N tert-butyl 3-((4-oxo-3,4,5,6,7,8-hexahydroquinazolin-2-yl)thio)propanoate

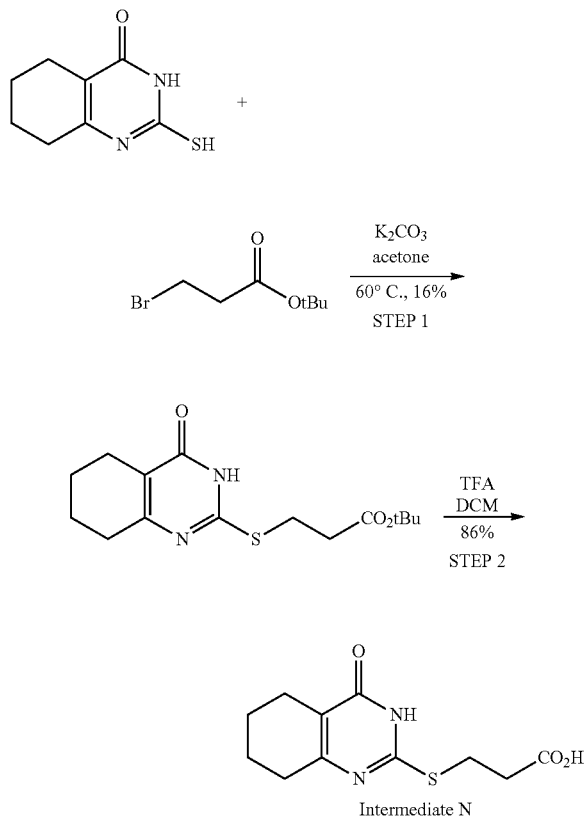

STEP 1: To a mixture of 2-sulfanyl-5,6,7,8-tetrahydro-4-quinazolinol (0.482 g, 2.64 mmol) and potassium carbonate (0.730 g, 5.29 mmol) in acetone was added tert-butyl 3-bromopropionate (0.663 g, 3.17 mmol). The mixture was stirred at 60° C. for 4 h (LC-MS indicated partial conversion to desired product). The solid was filtered off, and the solution was concentrated. The residual material was absorbed onto a plug of silica gel and purified by chromatography through a Redi-Sep pre-packed silica gel column (40 g), eluting with a gradient of 0% to 50% EtOAc in hexane, to provide tert-butyl 3-((4-oxo-3,4,5,6,7,8-hexahydroquinazolin-2-yl)thio)propanoate (0.132 g, 0.425 mmol, 16.09% yield) as white solid. $^1$H NMR (400 MHz, DMSO-$d_6$) δ ppm 12.40 (br. s., 1H) 3.24 (t, J=6.70 Hz, 2H) 2.64 (t, J=6.75 Hz, 2H) 2.42-2.49 (m, 2H) 2.28 (br. s., 2H) 1.60-1.78 (m, 4H) 1.41 (s, 9H). m/z (ESI) 311.2.

STEP 2: To a mixture of tert-butyl 3-((4-oxo-3,4,5,6,7,8-hexahydroquinazolin-2-yl)thio) propanoate (0.13 g, 0.419 mmol) in DCM (2.094 mL) was added trifluoroacetic acid (0.933 mL, 12.56 mmol). The mixture was stirred at RT for 4 h. The solvent and extra TFA was evaporated to give 3-((4-oxo-3,4,5,6,7,8-hexahydroquinazolin-2-yl)thio)propanoic acid (0.092 g, 0.362 mmol, 86% yield) as white solid. $^1$H NMR (400 MHz, DMSO-$d_6$) δ ppm 12.40 (br. s., 1H) 3.25 (t, J=6.80 Hz, 2H) 2.67 (t, J=6.80 Hz, 2H) 2.43-2.50 (m, 2H) 2.29 (t, J=5.77 Hz, 2H) 1.56-1.76 (m, 4H). m/z (ESI) 255.2.

Intermediate O 3-((6-oxo-1,6-dihydropyrimidin-2-yl)thio)propanoic acid

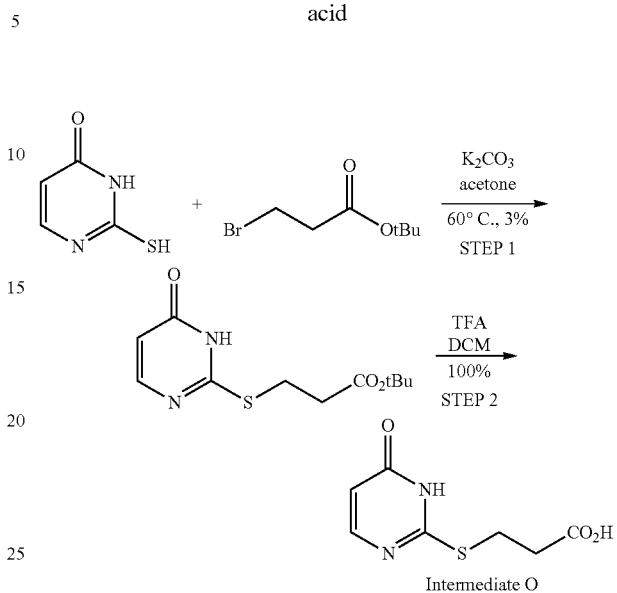

STEP 1: To a mixture of 2-thiouracil (0.93 g, 7.26 mmol) and potassium carbonate (2.006 g, 14.51 mmol) in acetone was added tert-butyl 3-bromopropionate (1.821 g, 8.71 mmol). The mixture was stirred at 60° C. for 6 h. The solid was filtered off and the solution was concentrated. The residual material was absorbed onto a plug of silica gel and purified by chromatography through a Redi-Sep pre-packed silica gel column (40 g), eluting with a gradient of 0% to 50% 1M NH$_3$.MeOH in DCM, to provide tert-butyl 3-((6-oxo-1,6-dihydropyrimidin-2-yl)thio) propanoate (0.062 g, 0.242 mmol, 3.33% yield) as a white solid. $^1$H NMR (400 MHz, DMSO-$d_6$) δ ppm 12.65 (br. s., 1H) 7.87 (br. s., 1H) 6.11 (br. s., 1H) 3.27 (t, J=6.80 Hz, 2H) 2.66 (t, J=6.85 Hz, 2H) 1.42 (s, 10H). m/z (ESI) 257.2.

STEP 2: Trifluoroacetic acid (0.530 mL, 7.14 mmol) was added to tert-butyl 3-((6-oxo-1,6-dihydropyrimidin-2-yl)thio)propanoate (0.061 g, 0.238 mmol) in DCM (2 mL). The mixture was stirred at RT overnight. The excess TFA and solvent were evaporated to give 3-((6-oxo-1,6-dihydropyrimidin-2-yl)thio)propanoic acid (0.048 g, 0.240 mmol, 101% yield) as a white solid, which was used without further purification. m/z (ESI) 201.2.

Intermediate P

N-((1r,4r)-4-(hydrazinecarbonyl)cyclohexyl)-3-(4-oxo-3,4-dihydroquinazolin-2-yl)propanamide

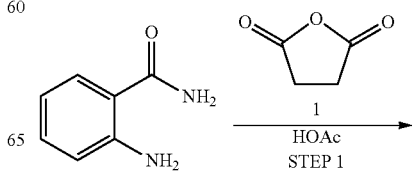

-continued

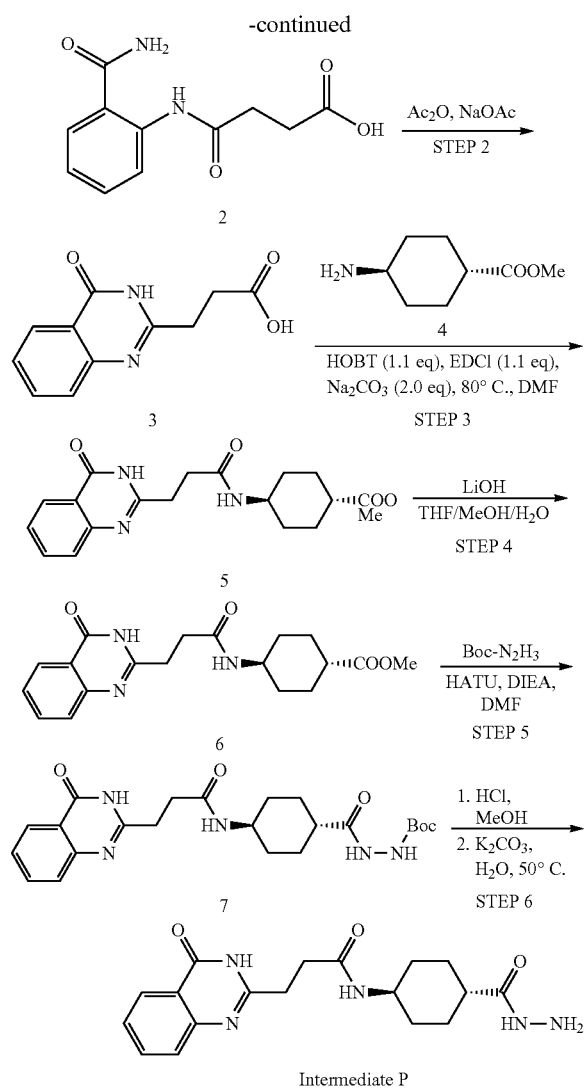

Intermediate P

Step 1: 4-((2-carbamoylphenyl)amino)-4-oxobutanoic acid

Compound 1 (50 g, 367 mmol, 1 eq) was dissolved in 50 mL of glacial AcOH, and a solution of succinic anhydride (36.7 g, 367 mol, 1.0 eq) in 50 mL of AcOH was added. After 30 mins, the mixture was diluted with cold water. The resulting solid was filtered and collected to give the product (120 g, yield 89%). $^1$H NMR (400 MHz, DMSO-$d_6$) δ 12.19 (br s, 1H), 11.74 (s, 1H), 8.45 (d, J=8.4 Hz, 1H), 8.28 (s, 1H), 7.81-7.79 (m, 1H), 7.75 (s, 1H), 7.50-7.46 (m, 1H), 7.13-7.09 (m, 1H), 2.57-2.55 (m, 4H). LC-MS: 237 (M+1).

Step 2: 3-(4-oxo-3,4-dihydroquinazolin-2-yl)propanoic acid

A mixture of Compound 2 (118 g, 0.5 mol), sodium acetate (46 g, 0.5 mol) in 150 mL of acetic anhydride was heated for 30 mins. The mixture was cooled and diluted with cold water. The resulting precipitate was filtered and collected to provide 3-(4-oxo-3,4-dihydroquinazolin-2-yl)propanoic acid (101 g, yield 91%). $^1$H NMR (400 MHz, DMSO-$d_6$) δ 7.90 (br s, 1H), 7.73-7.71 (m, 1H), 7.62-7.58 (m, 1H), 7.54-7.50 (m, 1H), 7.30-7.26 (m, 2H), 2.83-2.65 (m, 4H). LC-MS: 219 (M+1).

Step 3: (1r,4r)-methyl 4-(3-(4-oxo-3,4-dihydroquinazolin-2-yl)propanamido)cyclohexanecarboxylate A solution of 4-amino-cyclohexanecarboxylic acid methyl ester (8 g, 51 mmol), 3-(4-oxo-3,4-dihydro-quinazolin-2-yl)-propionic acid (11.1 g, 51 mmol), HOBT (7.56 g, 56 mmol), EDCI (10.70 g, 56 mmol) and sodium carbonate (11.8 g, 102 mmol) in DMF (100 mL) was stirred at 80° C. overnight. The mixture was poured into water (200 mL) and stirred affording a precipitate. The solid was collected via vacuum filtration and washed with water to provide product (14.0 g, 39 mmol, yield 77%). $^1$H NMR (400 MHz, DMSO-$d_6$) δ 8.06-8.05 (m, 1H), 7.88-7.78 (m, 1H), 7.77-7.70 (m, 1H), 7.58-7.49 (m, 1H), 7.47-7.39 (m, 1H), 3.59 (s, 3H), 3.52-3.46 (m, 1H), 2.85-2.81 (m, 2H), 2.59-2.55 (m, 2H), 2.29-2.21 (m, 1H), 1.91-1.88 (m, 2H), 1.82-1.77 (m, 2H), 1.41-1.31 (m, 2H), 1.23-1.16 (m, 2H). m/z (ESI): 358.

Step 4: (1r,4r)-4-(3-(4-oxo-3,4-dihydroquinazolin-2-yl)propanamido)cyclohexanecarboxylic acid Compound 5 (25 g, 70 mmol) and LiOH (8.8 g, 210 mmol) in THF/MeOH/water (2:2:1) (250 mL) was stirred at 30'C overnight. The reaction mixture was then concentrated under vacuum. The residual product was dissolved in water (100 mL), then adjusted with 1 N HCl to pH=4. The resulting precipitate was collected by filtration and dried to give the product (18 g, 52.5 mmol, yield 75%). $^1$H NMR (400 MHz, DMSO-$d_6$) δ 12.17-12.10 (m, 2H), 8.10-8.07 (m, 1H), 7.84 (d, J=8.0 Hz, 1H), 7.80-7.74 (m, 1H), 7.56 (d, J=8.0 Hz, 1H), 7.48-7.44 (m, 1H), 3.49-3.43 (m, 1H), 2.86-2.82 (m, 2H), 2.60-2.56 (m, 2H), 2.16-2.09 (m, 1H), 1.92-1.87 (m, 2H), 1.81-1.78 (m, 2H), 1.38-1.29 (m, 2H), 1.22-1.12 (m, 2H). m/z (ESI): 346.

Step 5: tert-butyl 2-((1r,4r)-4-(3-(4-oxo-3,4-dihydroquinazolin-2-yl)propanamido)cyclohexanecarbonyl)hydrazinecarboxylate A mixture of hydrazinecarboxylic acid tert-butyl ester (6.16 g, 46.6 mmol), compound 6 (16 g, 46.6 mmol), DIEA (19.9 g, 140 mmol) and HATU (19.5 g, 51.3 mmol) in DMF (200 mL) was stirred at 60'C overnight. The resulting precipitate was collected by filtration and dried to give the product (14.9 g, 32.6 mmol, yield 70%).

$^1$H NMR (400 MHz, DMSO-$d_6$) δ 12.14 (s, 1H), 9.37 (s, 1H); 8.60 (s, 1H), 8.06-8.03 (m, 1H), 7.79-7.72 (m, 2H), 7.52 (d, J=7.6 Hz, 1H), 7.44-7.40 (m, 1H), 3.47-3.40 (m, 1H), 2.82-2.78 (m, 2H), 2.56-2.52 (m, 2H), 2.04-1.98 (m, 1H), 1.79-1.75 (m, 2H), 1.70-1.67 (m, 2H), 1.39-1.35 (m, 11H), 1.16-1.05 (m, 2H). m/z (ESI): 458.

Step 6: N-((1r,4r)-4-(hydrazinecarbonyl)cyclohexyl)-3-(4-oxo-3,4-dihydroquinazolin-2-yl)propanamide Compound 7 (20 g, 43.76 mmol) was dissolved in 4 M HCl/MeOH (150 mL). The solution was stirred at RT overnight. The solvent was removed under reduced pressure to give the product as the HCl salt. To the product thus obtained in water (200 mL), was added $K_2CO_3$ (3eq.). The resulting mixture was heated to 50° C. for 5 hours, and the resulting precipitate was collected by filtration and dried to give the product, Intermediate P (14.8 g, 41.57 mmol, 95%).

$^1$H NMR (400 MHz, DMSO-$d_6$) 11.09 (s, 1H); 8.14-8.07 (m, 2H), 7.95-7.86 (m, 2H), 7.63-7.60 (m, 1H), 3.45-3.40 (m, 1H), 3.05-3.02 (m, 2H), 2.79-2.76 (m, 2H), 2.27-2.21 (m, 1H), 1.79-1.72 (m, 4H), 1.42-1.33 (m, 2H), 1.18-1.09 (m, 2H). m/z (ESI): 358.

Intermediate Q 3-((6-fluoro-4-oxo-3,4-dihydroquinazolin-2-yl)thio) propanoic acid

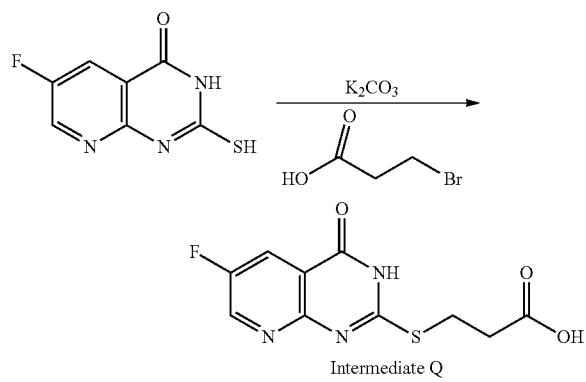

A suspension of 6-fluoro-2-mercaptoquinazolin-4(3H)-one (0.5 g, 2.55 mmol), 3-bromopropanoic acid (0.390 g, 2.55 mmol) (Ukraine organics) and potassium carbonate (1.057 g, 7.65 mmol) in ACN (8.49 ml) and DMF (2 mL) was stirred at ambient temperature for 16 h. The reaction mixture was next acidified with 2 N HCl to pH 2 and extracted with DCM (3×100 mL). The combined organic extracts were passed through a phase separator and concentrated to obtain 3-((6-fluoro-4-oxo-3,4-dihydroquinazolin-2-yl)thio)propanoic acid (99%, initial yield) as white solid. This was used in next step without further purification.

Intermediate R 3-(4-oxo-4H-pyrido[1,2-a]pyrimidin-2-yl)propanoic acid

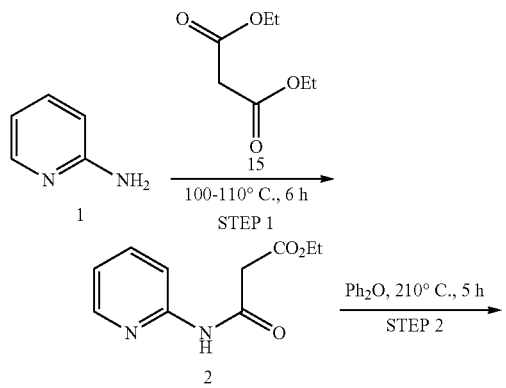

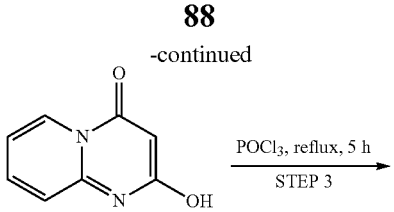

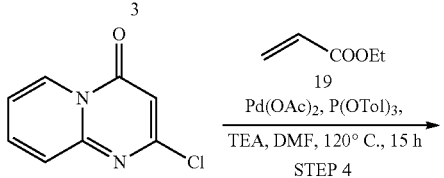

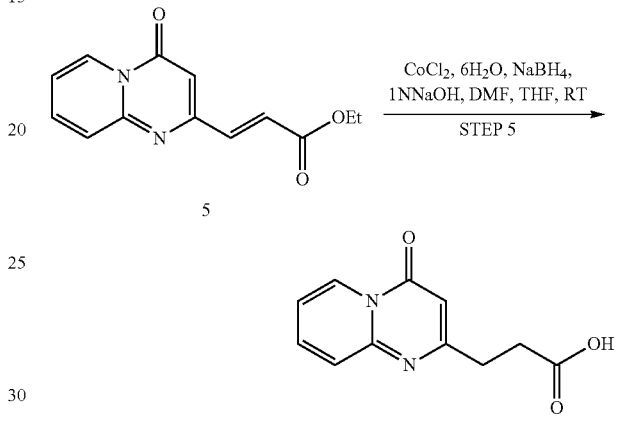

Step 1: Preparation of ethyl 3-oxo-3-(pyridin-2-ylamino) propanoate

A round bottomed flask containing compound 1 (20 g, 0.213 mol) and diethyl malonate (20 mL, 0.212 mol) under argon atmosphere was heated at 120° C. for 24 h and cooled to ambient temperature. The mixture was purified by column chromatography using silica (60-120 mesh) and eluting with hexane and EtOAc (20% to 50%) to afford the ethyl 3-oxo-3-(pyridin-2-ylamino) propanoate (15 g, 0.072 mol, 34% yield) as a colorless oil; $^1$H NMR (300 MHz, CDCl$_3$): δ 9.54 (s, 1H), 8.32 (d, J=3.9 Hz, 1H), 8.19 (d, J=8.1 Hz, 1H), 7.68-7.74 (m, 1H), 7.04-7.08 (m, 1H), 4.27 (q, J=7.2 Hz, 2H), 3.5 (s, 2H), 1.31 (t, J=7.2 Hz 3H).

Step 2: Preparation of 2-hydroxy-4H-pyrido[1,2-a]pyrimidin-4-one

In a round bottom flask, a solution of compound 2 (15 g, 0.072 mol) in diphenyl ether (10 mL) was heated to 210° C. for 5 h. The reaction mixture was then cooled and hexane was added to the reaction mixture. A solid precipitated out. The solid was filtered, washed with hexane and diethyl ether affording a 2-hydroxy-4H-pyrido[1,2-a]pyrimidin-4-one (10 g) as a pale yellow solid The material was taken on to the next step without further purification. $^1$H NMR (300 MHz, DMSO-$d_6$): δ 12.0 (s, 1H), 8.94 (d, J=6.6 Hz, 1H), 8.04-8.12 (t, 1H), 7.33-7.42 (m, 2H).

Step 3: Preparation of 2-chloro-4H-pyrido[1,2-a]pyrimidin-4-one

Compound 3 (300 mg, 1.85 mmol) was suspended in POCl$_3$ (5 mL) and the mixture was heated to 115° C. for 5 h in a round bottom flask. The reaction mixture was concentrated. To this was then added ice water, and the mixture was basified with solid NaHCO₃ providing a yellow precipitate. The precipitate was stirred for 5 min and filtered and was further washed with hexane to afford a 2-chloro-4H-pyrido[1,2-a]pyrimidin-4-one as (70 mg, 0.39 mmol, 21% yield) as pale yellow solid. ¹H NMR (300 MHz, DMSO-d₆): δ 8.97 (d, J=7.2 Hz, 1H), 8.10-8.14 (m, 1H), 7.74 (d, J=9.2 Hz, 1H), 7.50-7.46 (m, 1H), 6.51 (s, 1H). m/z (ESI): 181 (M+1).

Step 4: Preparation of (E)-ethyl 3-(4-oxo-4H-pyrido[1,2-a]pyrimidin-2-yl)acrylate To a sealed tube containing compound 4 (300 mg, 1.67 mmol) and ethyl acrylate (333 mg, 3.33 mmol) in DMF (10 mL), were added TEA (252 mg, 2.499 mg), tritolylphosphine (253 mg, 0.833 mmol), and palladium acetate (187 mg, 0.833 mmol). The tube was purged with argon gas for 5 min, sealed and heated to 120° C. for 15 h. The reaction mixture was cooled to ambient temperature and diluted with water and extracted with EtOAc (20 mL). The organic layer was dried over anhydrous sodium sulfate and concentrated. The residual mixture was then purified using column chromatography (60-120 mesh silica) and using eluent (10-30% EtOAc in hexane) to obtain (E)-ethyl 3-(4-oxo-4H-pyrido[1,2-a]pyrimidin-2-yl) acrylate as an off white solid (40 mg, 0.16 mmol, 10% yield). ¹H NMR (300 MHz, CDCl₃) δ 9.0 (d, J=7.2 Hz, 1H), 7.73-7.75 (m, 1H), 7.64-7.69 (d, J=8.7 Hz, 1H), 7.48-7.54 (m, 1H), 7.01-7.13 (m, 3H), 6.55 (s, 1H), 4.35-4.25 (m, 2H), 1.35 (t, J=6.9 Hz 3H); m/z (ESI): 244.9 (M+1).

Step 5: Preparation of 3-(4-oxo-4H-pyrido[1,2-a]pyrimidin-2-yl) propanoic acid

To a round bottom flask containing a solution of compound 5 (300 mg, 1.23 mmol) in water (0.3 mL) and THF (5 mL), was added 1.0 N sodium hydroxide (0.8 mL). The resulting mixture was then stirred at 25° C. for 10 min and cooled to 10° C. To this was then added the catalyst solution [which was prepared by dissolving dimethyl glyoxime (14 mg, 0.1129 mmol) and cobalt chloride hexahydrate (14 mg, 0.061 mmol) in DMF (0.3 mL)] in one lot. The reaction mixture was stirred for 10 min at ambient temperature and then sodium borohydride (58 mg, 1.54 mmol) was added, and the resulting mixture was stirred at ambient temperature for 2 h. The mixture was then neutralized with AcOH and extracted with 5% MeOH in CHCl₃. The organic layer was washed with water and dried over anhydrous sodium sulfate and concentrated to afford 3-(4-oxo-4H-pyrido[1,2-a]pyrimidin-2-yl) propanoic acid (180 mg) as a solid, which was used without further purification. m/z (ESI): 218.9 (M+1).

Intermediate S (1s,3s)-3-(5-phenyl-1,3,4-oxadiazol-2-yl)cyclobutanamine

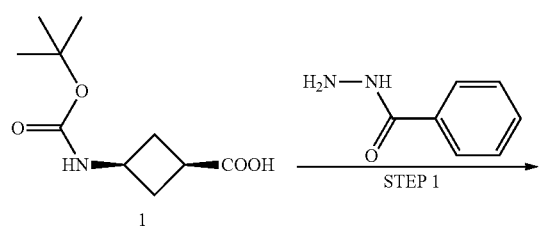

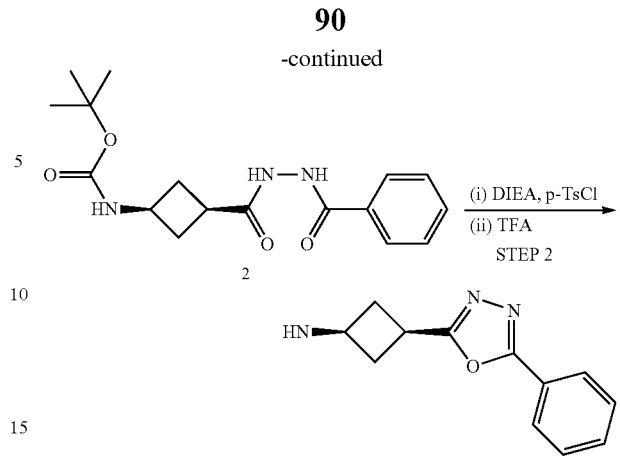

Intermediate S

Step 1: tert-butyl((1s,3s)-3-(2-benzoylhydrazinecarbonyl)cyclobutyl) carbamate

To a solution of DIEA (12.12 mL, 69.7 mmol), (1s,3s)-3-((tert-butoxycarbonyl)amino)cyclobutanecarboxylic acid (3 g, 13.94 mmol) and benzoic hydrazide (2.087 g, 15.33 mmol) in DMF (46.5 ml) was added HATU (5.30 g, 13.94 mmol). The resulting mixture was stirred at ambient temperature for 16 h. The reaction mixture was then diluted with saturated NaHCO₃ (20 mL) and water (50 mL) and extracted with DCM (2×100 mL). The combined organic layers were passed through a phase separator and concentrated. The mixture was purified by nplc by eluting with DCM:MeOH (90:10) up to 70% to obtain tert-butyl((1s,3s)-3-(2-benzoylhydrazinecarbonyl)cyclobutyl)carbamate (4.8 g, 14.40 mmol, 103% yield). m/z (ESI): 278 (M-Boc).

Step 2: (1s,3s)-3-(5-phenyl-1,3,4-oxadiazol-2-yl)cyclobutanamine

To a suspension of compound 2 (4.8 g, 14.40 mmol) and DIEA (12.52 mL, 72.0 mmol) in ACN (313 mL) was added p-toluenesulfonyl chloride (3.68 mL, 28.8 mmol) portion wise over 30 minutes. The resulting mixture was then stirred at ambient temperature for 2 days. The resulting mixture was concentrated and dissolved in DCM (200 mL) and washed with aq NH₄OH (50 mL). The organic layer was passed through a phase separator, concentrated, and the resulting brown oil was purified by nplc eluting with DCM:MeOH (90:10) up to 60% to obtain tert-butyl((1s,3s)-3-(5-phenyl-1,3,4-oxadiazol-2-yl)cyclobutyl)carbamate (2.16 g, 6.85 mmol, 47.6% yield) as yellow brown solid. ¹H NMR (400 MHz, DMSO-d₆) δ ppm 7.96-8.05 (m, 2H) 7.56-7.67 (m, 3H) 7.32 (d, J=8.12 Hz, 1H) 4.00-4.14 (m, 1H) 3.39-3.52 (m, 1H) 2.60-2.71 (m, 2H) 2.26-2.38 (m, 2H) 1.39 (s, 9H); m/z (ESI): 316 (M+1).

The product from the above step was dissolved in DCM (10 mL), TFA (5 mL, 64.9 mmol) was added, and the mixture was stirred at ambient temperature for 16 h. The mixture was then concentrated and loaded on 2, 10 g SCX columns and eluted with MeOH (3 column volumes) and then with ammonical MeOH (3 column volumes). The ammonical washes were collected and concentrated providing a brown oil. The oil was then triturated with MeOH (5 mL) filtered, and washed with EtOAc (2 mL) to obtain (1s,3s)-3-(5-phenyl-1,3,4-oxadiazol-2-yl)cyclobutanamine (1.543 g, 7.17 mmol, 49.8% yield) as a white solid. ¹H NMR (400 MHz, DMSO-d$_6$) δ ppm 7.96-8.05 (m, 2H) 7.55-7.67 (m, 3H) 3.33-3.41 (m, 1H) 3.25-3.30 (m, 1H) 2.59-2.70 (m, 2H) 2.00-2.13 (m, 2H); m/z (ESI): 216 (M+1).

Intermediate T (1r,3r)-3-(5-phenyl-1,3,4-oxadiazol-2-yl)cyclobutan-amine

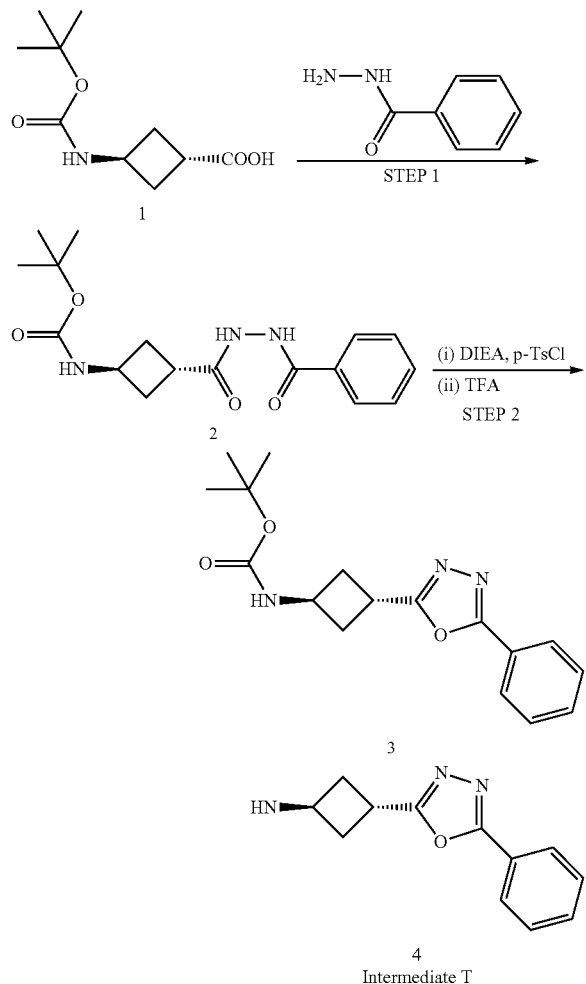

Step 1: tert-butyl((1r,3r)-3-(2-benzoylhydrazinecarbonyl)cyclobutyl)carbamate To a solution of DIEA (8.08 ml, 46.5 mmol), trans-3-(tert-butoxycarbonylamino)cyclobutanecarboxylic acid (2 g, 9.29 mmol) (Pharmasys) and benzoic hydrazide (1.392 g, 10.22 mmol) in DMF (31.0 ml) was added HATU (3.53 g, 9.29 mmol). The resulting mixture was then stirred at ambient temperature for 16 h. The resulting mixture was diluted with water, and a solid precipitated out which was filtered and washed with water (30 mL). The solid was dried under vacuum to obtain tert-butyl((1r,3r)-3-(2-benzoylhydrazinecarbonyl)cyclobutyl)carbamate (3.04 g, 9.12 mmol, 98% yield). The material thus obtained was used in the next step without further purification); m/z (ESI): 356 (M+Na).

Step 2: (1r,3r)-3-(5-phenyl-1,3,4-oxadiazol-2-yl)cyclobutanamine

To a suspension of tert-butyl((1r,3r)-3-(2-benzoylhydrazinecarbonyl)cyclobutyl) carbamate (3.02 g, 9.06 mmol) and DIEA (7.88 mL, 45.3 mmol) in ACN (200 mL) was added p-toluenesulfonyl chloride (2.318 mL, 18.12 mmol) portion wise over 30 min. The resulting mixture was stirred at ambient temperature for 2 days. The resulting mixture was then concentrated and dissolved in DCM (200 mL) and washed with aq NH$_4$OH (50 mL). The organic layer was passed through phase separator and concentrated. The resulting brown oil was purified by nplc eluting with DCM:MeOH (90:10) up to 60% to obtain tert-butyl((1r,3r)-3-(5-phenyl-1,3,4-oxadiazol-2-yl)cyclobutyl)carbamate (3.01 g, 9.54 mmol, 105% yield) as a yellow brown solid. The solid was then dissolved in DCM (10 mL) and TFA (5 mL, 64.9 mmol) was added. The resulting mixture was then stirred at ambient temperature for 16 h. The mixture was concentrated and loaded on 2, 10 g SCX volumes and eluted with MeOH 3 column volumes and then with 3 column ammonical MeOH. The ammonical washes were collected and concentrated and purified by column chromatography to obtain (1r,3r)-3-(5-phenyl-1,3,4-oxadiazol-2-yl)cyclobutanamine (1.965 g, 9.13 mmol, 99% yield) as brown oil. $^1$H NMR (400 MHz, DMSO-d$_6$) δ ppm 7.95-8.05 (m, 2H) 7.55-7.66 (m, 3H) 3.62-3.76 (m, 2H) 2.53-2.64 (m, 2H) 2.19-2.32 (m, 2H); m/z (ESI): 216 (M+1).

General Schemes

General Scheme A:

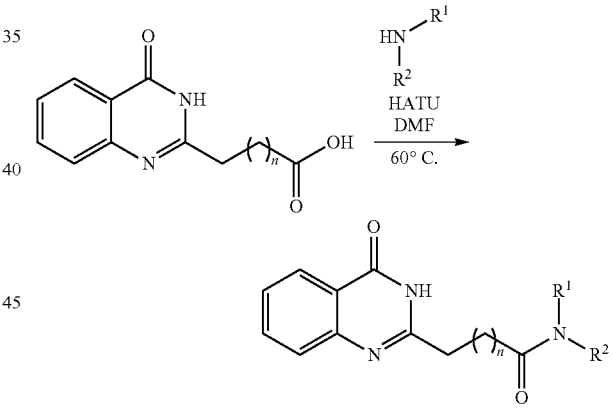

Representative Protocol:

This reaction was typically run in parallel on scales ranging from 0.25 mmol-0.92 mmol, using amines and/or amine salts, with or without added base (DIEA), shaken or stirred, with heating overnight up to several days. Reaction mixtures were purified by MPLC (absorbed onto a plug of silica gel and purified by chromatography through a Redi-Sep pre-packed silica gel column, eluting with a gradient of 0% to 60% 1M NH$_3$.MeOH in CH$_2$Cl$_2$) and/or RP-HPLC and/or ion-exchange chromatography (SCX-2) to obtain product. Alternatively, the reaction was run on larger scale using a round bottom vessel and a heating mantle or oil bath.

3-(4-oxo-3,4-dihydroquinazolin-2-yl)propanoic acid (Enamine) (0.150 g, 0.646 mmol), HATU (Oakwood) (0.246 g, 0.646 mmol) and amine (0.646 mmol) were combined in a 15×75 mm 2 dram screw cap vial and DMF (~3 mL) was added. The tube was sealed, and the mixture was shaken at 60° C. for 20 h in a heating block on a heater/shaker. After cooling to RT, the mixture concentrated and the material thus obtained was purified.

The following examples were all prepared using General Scheme A.

Example 1 trans-N-(2-(4-oxo-3,4-dihydro-2-quinazolinyl)ethyl)-4-(5-phenyl-1,3,4-oxadiazol-2-yl)cyclohexanecarboxamide

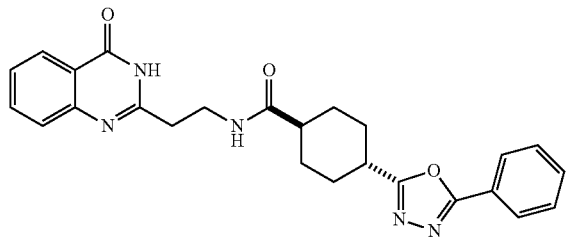

The title compound was prepared using the coupling method described in General Scheme A using 2-(2-aminoethyl)quinazolin-4(3H)-one hydrochloride (Matrix), (trans)-4-(5-phenyl-1,3,4-oxadiazol-2-yl)cyclohexanecarboxylic acid (prepared according to WO 2008/011130) and DIEA. The reaction mixture was concentrated and purified (ISCO: 5 g cartridge, 12 g column, 0 to 100% 90/10 DCM-MeOH in DCM). The solid was triturated with IPA, DCM and MeOH, then concentrated to half volume and filtered. The solid was rinsed with IPA and dried, then repurified (ISCO: 25 g cartridge, 12 g column, 0 to 100% 90/10 DCM-MeOH in DCM. The fractions with product were then slurried in DMSO and then dissolved by addition of DCM and MeOH, loaded on to a 15 mL SCX-2 column, flushed with DCM-MeOH and the product was then eluted with 2.0 M NH$_3$ in MeOH giving trans-N-(2-(4-oxo-3,4-dihydro-2-quinazolinyl)ethyl)-4-(5-phenyl-1,3,4-oxadiazol-2-yl)cyclohexanecarboxamide (49.5 mg, 0.1 mmol, 34%). $^1$H NMR (400 MHz, DMSO-d$_6$) δ ppm 11.92-12.37 (m, 1H), 8.05-8.13 (m, 1H), 7.95-8.03 (m, 2H), 7.87-7.94 (m, 1H), 7.74-7.83 (m, 1H), 7.60 (d, J=0.78 Hz, 4H), 7.42-7.51 (m, 1H), 3.44-3.59 (m, 2H), 2.89-3.05 (m, 1H), 2.68-2.80 (m, 2H), 2.05-2.23 (m, 3H), 1.69-1.91 (m, 2H), 1.38-1.63 (m, 4H); m/z (ESI) 444.2 (M+H)$^+$.

Example 2

3-(4-oxo-3,4-dihydro-2-quinazolinyl)-N-(trans-4-(5-phenyl-1,3,4-oxadiazol-2-yl)cyclohexyl)propanamide

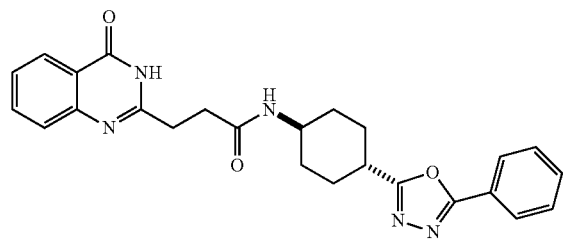

The title compound was prepared as described in General Scheme A using 3-(4-oxo-3,4-dihydroquinazolin-2-yl)propanoic acid (Enamine) and Intermediate C. The reaction was heated at 65° C. for 7 days and 19 h, cooled to RT, and transferred with water into water (~600 mL total). The resulting slurry was stirred at RT for 70 min, filtered, and the solid was rinsed with water, transferred to a round bottom flask with DCM and MeOH, concentrated and purified (ISCO: 25 g cartridge, 120 g column, 0 to 80% 90/10 DCM-MeOH in DCM). The product-containing fractions were combined and concentrated, then taken up in ~7:1 DCM-MeOH and loaded onto a SCX-1 column. The column was flushed with ~2:1 DCM-MeOH, and the product was eluted with ~2:1 DCM-2.0 M NH$_3$ in MeOH and concentrated to afford 3-(4-oxo-3,4-dihydro-2-quinazolinyl)-N-(trans-4-(5-phenyl-1,3,4-oxadiazol-2-yl)cyclohexyl)propanamide (2.78 g, 6.3 mmol, 51%). $^1$H NMR (400 MHz, DMSO-d$_6$) δ ppm 12.18 (s, 1H), 8.08 (dd, J=7.92, 1.08 Hz, 1H), 7.99 (dd, J=7.73, 1.76 Hz, 2H), 7.92 (d, J=7.83 Hz, 1H), 7.73-7.84 (m, 1H), 7.54-7.68 (m, 4H), 7.46 (t, J=7.53 Hz, 1H), 3.50-3.70 (m, 1H), 2.93-3.08 (m, 1H), 2.85 (t, J=7.38 Hz, 2H), 2.60 (t, J=7.29 Hz, 2H), 2.16 (d, J=11.35 Hz, 2H), 1.90 (dd, J=13.20, 2.93 Hz, 2H), 1.54-1.75 (m, 2H), 1.24-1.49 (m, 2H); m/z (ESI) 444.2 (M+H)$^+$.

Example 3

2-(4-(4-(5-(3-chlorophenyl)-1,3,4-oxadiazol-2-yl)-1-piperidinyl)-4-oxobutyl)-4(3H)-quinazolinone

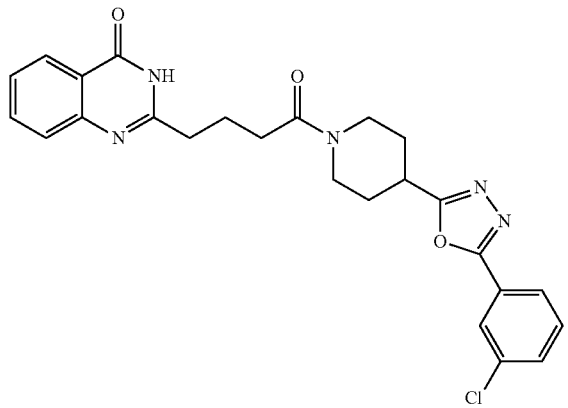 [SMILES: O=C(CCCc1nc2ccccc2c(=O)[nH]1)N1CCC(c2nnc(-c3cccc(Cl)c3)o2)CC1]

The title compound was prepared as described in General Scheme A using 4-(4-oxo-3,4-dihydroquinazolin-2-yl)butanoic acid (Enamine) and 2-(3-chlorophenyl)-5-(piperidin-4-yl)-1,3,4-oxadiazole 2,2,2-trifluoroacetate (HDH Pharma) providing 2-(4-(4-(5-(3-chlorophenyl)-1,3,4-oxadiazol-2-yl)-1-piperidinyl)-4-oxobutyl)-4(3H)-quinazolinone (74.2 mg, 0.15 mmol, 30.4%) after purification using reverse phase mass-directed HPLC. The column used was a Waters Xbridge C18 19×100 mm 10 micron column. The mobile phase was run under gradient conditions using water and ACN with 0.1% NH$_4$OH to provide 2-(4-(4-(5-(3-chlorophenyl)-1,3,4-oxadiazol-2-yl)piperidin-1-yl)-4-oxobutyl)quinazolin-4(3H)-one (74.2 mg, 0.15 mml, 30%). $^1$H NMR (400 MHz, DMSO-d$_6$) δ ppm 8.09 (dd, J=7.96, 1.20 Hz, 1H), 7.99 (d, J=1.83 Hz, 1H), 7.96 (d, J=7.79 Hz, 1H), 7.75-7.81 (m, 1H), 7.67-7.73 (m, 1H), 7.58-7.65 (m, 2H), 7.49 (t, J=7.16 Hz, 1H), 4.27 (d, J=13.29 Hz, 1H), 3.92 (d, J=13.75 Hz, 1H), 3.30-3.42 (m, 1H), 3.25 (t, J=11.40 Hz, 1H), 2.87 (t, J=11.17 Hz, 1H), 2.70 (t, J=7.33 Hz, 2H), 2.42-2.48 (m, 2H), 1.94-2.16 (m, 4H), 1.78 (d, J=10.20 Hz, 1H), 1.62 (d, J=9.85 Hz, 1H); m/z (ESI) 478.2 (M+H)⁺.

Example 4

2-(4-(4-(5-(4-chlorophenyl)-1,3,4-oxadiazol-2-yl)piperidin-1-yl)-4-oxobutyl)quinazolin-4(3H)-one

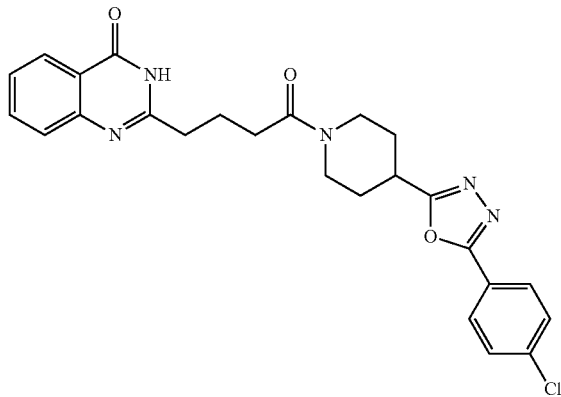 [SMILES: O=C(CCCc1nc2ccccc2c(=O)[nH]1)N1CCC(c2nnc(-c3ccc(Cl)cc3)o2)CC1]

The title compound was prepared as described in General Scheme A using 4-(4-oxo-3,4-dihydroquinazolin-2-yl)butanoic acid (Enamine) and 2-(4-chlorophenyl)-5-(piperidin-4-yl)-1,3,4-oxadiazole 2,2,2-trifluoroacetate (HDH Pharma). The reaction mixture was cooled to RT, poured into 200 mL water and extracted with DCM (500 mL). The organic layer was dried and concentrated. Purification was performed using supercritical fluid chromatography (SFC). The column used was (S,S) Whelk-O 5 micron, 2×25 cm. The mobile phase was run under isocratic conditions ($CO_2$ with 60% MeOH co-solvent containing 0.2% diethylamine modifier). Final purity was improved by recrystallization from hot EtOH to afford 2-(4-(4-(5-(4-chlorophenyl)-1,3,4-oxadiazol-2-yl)piperidin-1-yl)-4-oxobutyl)quinazolin-4(3H)-one (1.09 g, 2.3 mmol, 42%). ¹H NMR (400 MHz, DMSO-d₆) δ ppm 12.15 (br. s., 1H), 8.07 (dd, J=7.97, 1.32 Hz, 1H), 7.98-8.04 (m, 2H), 7.74 (ddd, J=8.31, 7.04, 1.56 Hz, 1H), 7.64-7.70 (m, 2H), 7.58 (d, J=7.73 Hz, 1H), 7.40-7.49 (m, 1H), 4.29 (d, J=13.69 Hz, 1H), 3.93 (d, J=13.60 Hz, 1H), 3.32-3.41 (m, 1H), 3.25 (t, J=11.35 Hz, 1H), 2.81-2.97 (m, 1H), 2.61-2.73 (m, 2H), 2.38-2.47 (m, 2H), 1.92-2.18 (m, 4H), 1.76 (q, J=10.50 Hz, 1H), 1.52-1.69 (m, 1H); m/z (ESI) 478.2 (M+H)⁺.

Example 5

2-(4-(4-(5-(3-fluorophenyl)-1,3,4-oxadiazol-2-yl)-1-piperidinyl)-4-oxobutyl)-4(3H)-quinazolinone

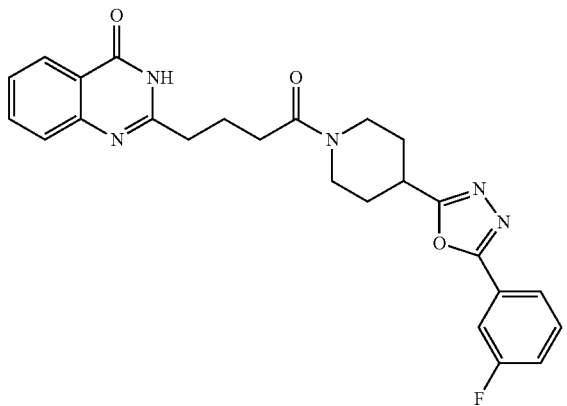 [SMILES: O=C(CCCc1nc2ccccc2c(=O)[nH]1)N1CCC(c2nnc(-c3cccc(F)c3)o2)CC1]

The title compound was prepared as described in General Scheme A using 4-(4-oxo-3,4-dihydroquinazolin-2-yl)butanoic acid (Enamine) and 2-(3-fluorophenyl)-5-(piperidin-4-yl)-1,3,4-oxadiazole 2,2,2-trifluoroacetate (HDH Pharma) providing 2-(4-(4-(5-(3-fluorophenyl)-1,3,4-oxadiazol-2-yl)piperidin-1-yl)-4-oxobutyl)quinazolin-4(3H)-one (125.5 mg, 0.27 mmol, 24.6%) after purification using reverse phase mass-directed HPLC. The column used was a Waters Xbridge C18 19×100 mm 10 micron column. The mobile phase was run under gradient conditions using water and ACN with 0.1% TFA. The free-base was obtained SCX-2 ion exchange column, eluting with 2 M $NH_3$ in MeOH. ¹H NMR (400 MHz, DMSO-d₆) δ ppm 12.14 (br. s., 1H), 8.08 (dd, J=7.92, 1.17 Hz, 1H), 7.86 (dq, J=7.73, 0.82 Hz, 1H), 7.70-7.82 (m, 2H), 7.62-7.70 (m, 1H), 7.56-7.62 (m, 1H), 7.42-7.53 (m, 2H), 4.30 (d, J=12.62 Hz, 1H), 3.93 (d, J=13.60 Hz, 1H), 3.32-3.43 (m, 1H), 3.25 (t, J=11.20 Hz, 1H), 2.88 (t, J=11.00 Hz, 1H), 2.61-2.72 (m, 2H), 2.35-2.48 (m, 2H), 2.09 (t, J=14.28 Hz, 1H), 2.00 (quin, J=7.41 Hz, 2H), 1.71-1.87 (m, 1H), 1.53-1.70 (m, 1H); m/z (ESI) 462.3 (M+H)⁺.

Example 6

2-(4-(4-(5-(4-fluorophenyl)-1,3,4-oxadiazol-2-yl)piperidin-1-yl)-4-oxobutyl)quinazolin-4(3H)-one

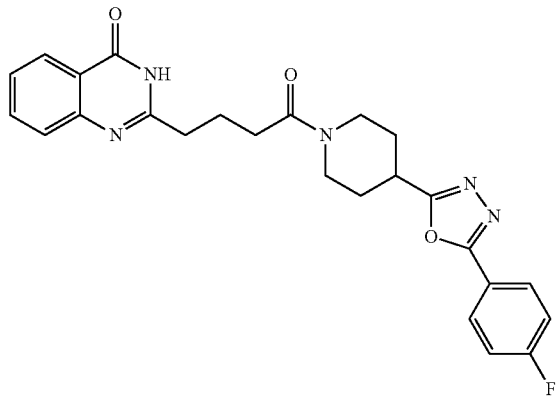 [SMILES: O=C(CCCc1nc2ccccc2c(=O)[nH]1)N1CCC(c2nnc(-c3ccc(F)cc3)o2)CC1]

The title compound was prepared as described in General Scheme A using 4-(4-oxo-3,4-dihydroquinazolin-2-yl)butanoic acid (Enamine) and 2-(4-fluorophenyl)-5-(piperidin-4-yl)-1,3,4-oxadiazole 2,2,2-trifluoroacetate (HDH Pharma). The reaction mixture was stirred at 60° C. for 3 days when 1.5 equivalents of DIEA were added and stirring was continued for an additional 2 h. The reaction mixture was then cooled to RT and poured into 200 mL water. The reaction flask was rinsed with water to bring the total volume to 300 mL resulting in a gum. To this mixture was added DCM to bring the total volume to 500 mL total. The mixture was stirred at RT for 1 h and then transferred to a separatory funnel. The organic layer was dried and concentrated and purified using SFC providing a white solid. The solid was slurried in MTBE on a rotovap (no vacuum) at 45° C. for 3.25 h, and cooled to RT. The solid was filtered, rinsed with MTBE, and dried on a vacuum pump providing 2-(4-(4-(5-(4-fluorophenyl)-1,3,4-oxadiazol-2-yl)piperidin-1-yl)-4-oxobutyl)quinazolin-4(3H)-one (1.37 g, 3.0 mmol, 55%). ¹H NMR (400 MHz, DMSO-d₆) δ ppm 12.14 (br. s., 1H), 8.00-8.12 (m, 3H), 7.74 (td, J=7.65, 1.52 Hz, 1H), 7.58 (d, J=7.83 Hz, 1H), 7.38-7.51 (m, 3H), 4.29 (d, J=13.30 Hz, 1H), 3.93 (d, J=13.69 Hz, 1H), 3.17-3.46 (m, 2H), 2.87 (t, J=11.15 Hz, 1H), 2.66 (t, J=7.34 Hz, 2H), 2.40-2.47 (m, 2H), 1.90-2.18 (m, 4H), 1.70-1.88 (m, 1H), 1.52-1.68 (m, 1H); m/z (ESI) 462.2 (M+H)$^+$.

Example 7

2-(4-(4-(6-methyl-2-oxo-2,3-dihydro-1H-benzimidazol-1-yl)-1-piperidinyl)-4-oxobutyl)-4(3H)-quinazolinone

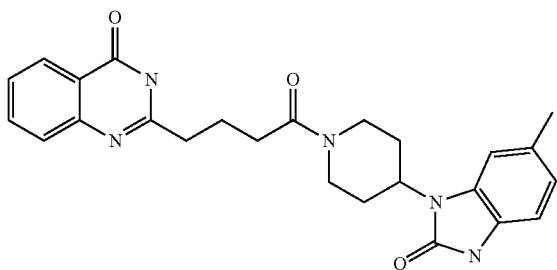 [SMILES: Cc1ccc2[nH]c(=O)n(C3CCN(C(=O)CCCc4nc5ccccc5c(=O)[nH]4)CC3)c2c1]

The title compound was prepared as described in General Scheme A using 4-(4-oxo-3,4-dihydroquinazolin-2-yl)butanoic acid (Enamine) and 6-methyl-1-(piperidin-4-yl)-1H-benzo[d]imidazol-2(3H)-one 2,2,2-trifluoroacetate (HDH Pharma) providing 2-(4-(4-(6-methyl-2-oxo-2,3-dihydro-1H-benzimidazol-1-yl)-1-piperidinyl)-4-oxobutyl)-4(3H)-quinazolinone (65.3 mg, 0.15 mmol, 23%) after purification using reverse phase mass-directed HPLC. The column used was a Waters Xbridge C18 19×100 mm 10 micron column. The mobile phase was run under gradient conditions using water and ACN with 0.1% NH$_4$OH. $^1$H NMR (400 MHz, DMSO-d$_6$) δ ppm 12.14 (br. s., 1H), 10.68 (s, 1H), 8.08 (dd, J=7.90, 1.15 Hz, 1H), 7.69-7.87 (m, 1H), 7.59 (d, J=8.02 Hz, 1H), 7.37-7.51 (m, 1H), 7.04 (s, 1H), 6.81-6.87 (m, 1H), 6.77 (d, J=7.79 Hz, 1H), 4.58 (d, J=12.49 Hz, 1H), 4.31-4.46 (m, 1H), 4.06 (d, J=12.60 Hz, 1H), 3.15 (t, J=12.20 Hz, 1H), 2.57-2.78 (m, 3H), 2.46-2.48 (m, 2H), 2.23-2.34 (m, 4H), 2.07-2.21 (m, 1H), 2.01 (quin, J=7.39 Hz, 2H), 1.60-1.82 (m, 2H); m/z (ESI) 446.1 (M+H)$^+$.

Example 8

2-(4-(4-(5-methoxy-2-oxo-2,3-dihydro-1H-benzimidazol-1-yl)-1-piperidinyl)-4-oxobutyl)-4(3H)-quinazolinone

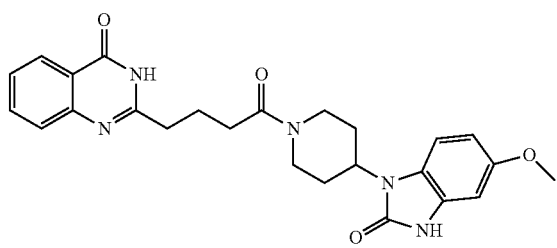 [SMILES: COc1ccc2c(c1)[nH]c(=O)n2C1CCN(C(=O)CCCc2nc3ccccc3c(=O)[nH]2)CC1]

The title compound was prepared as described in General Scheme A using 4-(4-oxo-3,4-dihydroquinazolin-2-yl)butanoic acid (Enamine) and 5-methoxy-1-(piperidin-4-yl)-1H-benzo[d]imidazol-2(3H)-one 2,2,2-trifluoroacetate (HDH Pharma) providing 2-(4-(4-(6-methyl-2-oxo-2,3-dihydro-1H-benzimidazol-1-yl)-1-piperidinyl)-4-oxobutyl)-4(3H)-quinazolinone (34.3 mg, 0.07 mmol, 12%) after purification using reverse phase mass-directed HPLC. The column used was a Waters Xbridge C18 19×100 mm 10 micron column. The mobile phase was run under gradient conditions using water and ACN with 0.1% NH$_4$OH. $^1$H NMR (500 MHz, DMSO-d$_6$) δ ppm 12.15 (br. s., 1H), 10.74 (s, 1H), 8.08 (dd, J=7.90, 1.15 Hz, 1H), 7.70-7.92 (m, 1H), 7.60 (d, J=8.02 Hz, 1H), 7.39-7.50 (m, 1H), 7.09 (d, J=8.48 Hz, 1H), 6.49-6.65 (m, 2H), 4.57 (d, J=12.94 Hz, 1H), 4.25-4.44 (m, 1H), 4.05 (d, J=13.75 Hz, 1H), 3.70 (s, 3H), 3.08-3.20 (m, 1H), 2.57-2.74 (m, 3H), 2.44-2.48 (m, 2H), 2.24 (dd, J=12.26, 3.67 Hz, 1H), 1.95-2.14 (m, 3H), 1.70 (t, J=15.81 Hz, 2H); m/z (ESI) 464.1 (M+H)$^+$.

Example 9

2-(4-oxo-4-(4-(5-phenyl-1,3,4-thiadiazol-2-yl)-1-piperidinyl)butyl)-4(3H)-quinazolinone

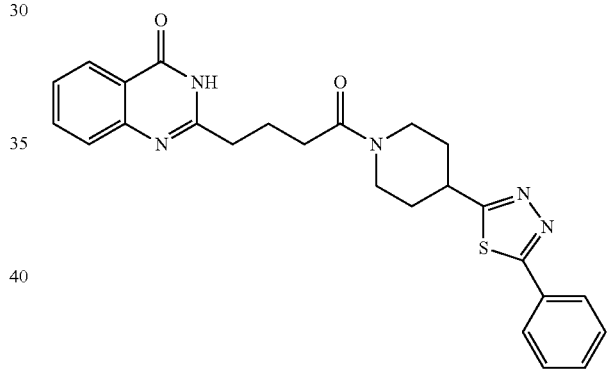

The title compound was prepared as described in General Scheme A using 4-(4-oxo-3,4-dihydroquinazolin-2-yl)butanoic acid (Enamine) and 2-phenyl-5-(piperidin-4-yl)-1,3,4-thiadiazole hydrochloride (Princeton Building Blocks) providing 2-(4-oxo-4-(4-(5-phenyl-1,3,4-thiadiazol-2-yl)-1-piperidinyl)butyl)-4(3H)-quinazolinone (57.8 mg, 0.13 mmol, 19%) after purification using reverse phase mass-directed HPLC. The column used was a Waters Xbridge C18 19×100 mm 10 micron column. The mobile phase was run under gradient conditions using water and ACN with 0.1% NH$_4$OH. $^1$H NMR (500 MHz, DMSO-d$_6$) δ ppm 12.14 (br. s., 1H), 8.08 (dd, J=7.90, 1.26 Hz, 1H), 7.90-8.00 (m, 2H), 7.70-7.85 (m, 1H), 7.52-7.64 (m, 4H), 7.45 (t, J=7.50 Hz, 1H), 4.43 (d, J=12.72 Hz, 1H), 3.99 (d, J=14.55 Hz, 1H), 3.44-3.58 (m, 1H), 3.21 (t, J=12.43 Hz, 1H), 2.73-2.83 (m, 1H), 2.66 (t, J=7.27 Hz, 2H), 2.41-2.48 (m, 2H), 2.07-2.22 (m, 2H), 2.00 (quin, J=7.39 Hz, 2H), 1.74 (d, J=12.14 Hz, 1H), 1.58 (d, J=8.82 Hz, 1H); m/z (ESI) 460.2 (M+H)$^+$.

Example 10

4-(4-oxo-3,4-dihydro-2-quinazolinyl)-N-(trans-4-(5-phenyl-1,3,4-oxadiazol-2-yl)cyclohexyl)butanamide

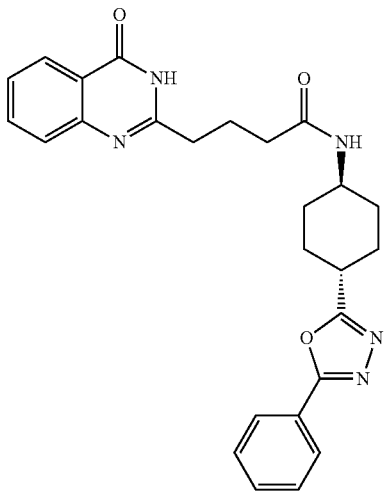 [SMILES: O=C(CCCc1nc2ccccc2c(=O)[nH]1)N[C@H]1CC[C@H](c2nnc(-c3ccccc3)o2)CC1]

The title compound was prepared as described in General Scheme A using 4-(4-oxo-3,4-dihydroquinazolin-2-yl)butanoic acid (Enamine) and Intermediate C providing 4-(4-oxo-3,4-dihydro-2-quinazolinyl)-N-(trans-4-(5-phenyl-1,3,4-oxadiazol-2-yl)cyclohexyl)butanamide (46.5 mg, 0.10 mmol, 16%) after purification using reverse phase mass-directed HPLC. The column used was a Waters Xbridge C18 19×100 mm 10 micron column. The mobile phase was run under gradient conditions using water and ACN with 0.1% $NH_4OH$. $^1H$ NMR (400 MHz, DMSO-$d_6$) δ ppm 12.16 (br. s., 1H), 8.08 (dd, J=7.92, 1.37 Hz, 1H), 7.95-8.03 (m, 2H), 7.78 (td, J=7.65, 1.61 Hz, 2H), 7.54-7.68 (m, 4H), 7.41-7.51 (m, 1H), 3.51-3.66 (m, 1H), 2.90-3.05 (m, 1H), 2.61 (t, J=7.48 Hz, 2H), 2.15 (t, J=7.34 Hz, 4H), 1.85-2.03 (m, 4H), 1.54-1.72 (m, 2H), 1.22-1.41 (m, 2H); m/z (ESI) 458.2 $(M+H)^+$.

Example 11

2-(4-(4-(5-methyl-2-oxo-2,3-dihydro-1H-benzimidazol-1-yl)-1-piperidinyl)-4-oxobutyl)-4(3H)-quinazolinone

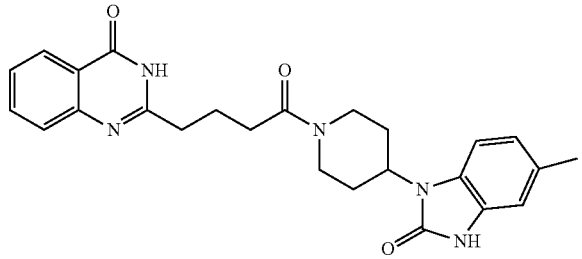 [SMILES: Cc1ccc2c(c1)[nH]c(=O)n2C1CCN(C(=O)CCCc2nc3ccccc3c(=O)[nH]2)CC1]

The title compound was prepared as described in General Scheme A using 4-(4-oxo-3,4-dihydroquinazolin-2-yl)butanoic acid (Enamine) and 5-methyl-1-(piperidin-4-yl)-1H-benzo[d]imidazol-2(3H)-one 2,2,2-trifluoroacetate (HDH Pharma) providing 2-(4-(4-(5-methyl-2-oxo-2,3-dihydro-1H-benzimidazol-1-yl)-1-piperidinyl)-4-oxobutyl)-4(3H)-quinazolinone (61.7 mg, 0.14 mmol, 21%) after purification using reverse phase mass-directed HPLC. The column used was a Waters Xbridge C18 19×100 mm 10 micron column. The mobile phase was run under gradient conditions using water and ACN with 0.1% $NH_4OH$. $^1H$ NMR (500 MHz, DMSO-$d_6$) δ ppm 12.15 (br. s., 1H), 10.72 (s, 1H), 8.08 (dd, J=7.90, 1.15 Hz, 1H), 7.71-7.79 (m, 1H), 7.60 (d, J=8.02 Hz, 1H), 7.45 (t, J=7.50 Hz, 1H), 7.07 (d, J=7.90 Hz, 1H), 6.71-6.84 (m, 2H), 4.57 (d, J=12.37 Hz, 1H), 4.29-4.47 (m, 1H), 3.96-4.18 (m, 2H), 3.18 (s, 2H), 2.58-2.73 (m, 2H), 2.44-2.48 (m, 1H), 2.28 (s, 3H), 2.19-2.26 (m, 1H), 2.09 (dd, J=12.43, 3.95 Hz, 1H), 2.01 (quin, J=7.42 Hz, 2H), 1.63-1.78 (m, 2H); m/z (ESI) 446.1 $(M+H)^+$.

Example 12

2-(4-oxo-4-(4-(5-(2-pyridinyl)-1,3,4-oxadiazol-2-yl)-1-piperidinyl)butyl)-4(3H)-quinazolinone

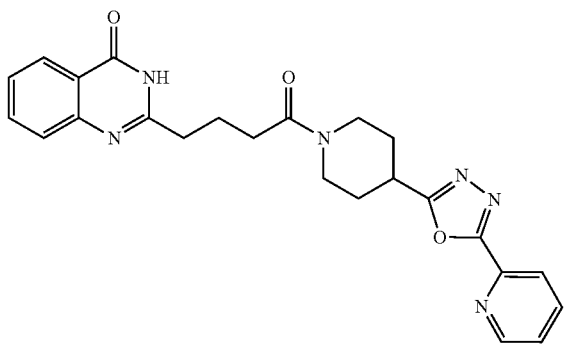 [SMILES: O=C(CCCc1nc2ccccc2c(=O)[nH]1)N1CCC(c2nnc(-c3ccccn3)o2)CC1]

The title compound was prepared as described in General Scheme A using 4-(4-oxo-3,4-dihydroquinazolin-2-yl)butanoic acid (Enamine) and 2-(piperidin-4-yl)-5-(pyridin-2-yl)-1,3,4-oxadiazole 2,2,2-trifluoroacetate (HDH Pharma) providing 2-(4-oxo-4-(4-(5-(2-pyridinyl)-1,3,4-oxadiazol-2-yl)-1-piperidinyl)butyl)-4(3H)-quinazolinone (104.4 mg, 0.24 mmol, 31%) after purification using reverse phase mass-directed HPLC. The column used was a Waters Xbridge C18 19×100 mm 10 micron column. The mobile phase was run under gradient conditions using water and ACN with 0.1% $NH_4OH$. $^1H$ NMR (500 MHz, DMSO-$d_6$) δ ppm 12.13 (br. s., 1H), 8.76 (d, J=4.58 Hz, 1H), 8.16 (d, J=7.79 Hz, 1H), 7.98-8.11 (m, 2H), 7.69-7.82 (m, 1H), 7.60-7.65 (m, 1H), 7.59 (d, J=8.02 Hz, 1H), 7.44 (t, J=7.16 Hz, 1H), 4.29 (d, J=13.06 Hz, 1H), 3.93 (d, J=13.98 Hz, 1H), 3.36-3.45 (m, 1H), 3.25 (t, J=11.57 Hz, 1H), 2.87 (t, J=11.28 Hz, 1H), 2.66 (t, J=7.39 Hz, 2H), 2.39-2.48 (m, 2H), 2.04-2.19 (m, 2H), 1.99 (quin, J=7.36 Hz, 2H), 1.77 (d, J=9.97 Hz, 1H), 1.62 (d, J=9.85 Hz, 1H); m/z (ESI) 445.2 $(M+H)^+$.

Example 13

2-(4-oxo-4-(4-(5-(3-pyridinyl)-1,3,4-oxadiazol-2-yl)-1-piperidinyl)butyl)-4(3H)-quinazolinone

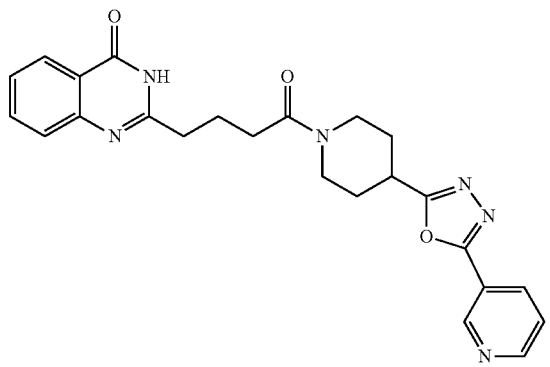 [SMILES: O=C(CCCc1nc2ccccc2c(=O)[nH]1)N1CCC(c2nnc(-c3cccnc3)o2)CC1]

The title compound was prepared as described in General Scheme A using 4-(4-oxo-3,4-dihydroquinazolin-2-yl)butanoic acid (Enamine) and 2-(piperidin-4-yl)-5-(pyridin-3-yl)-1,3,4-oxadiazole 2,2,2-trifluoroacetate (HDH Pharma) providing 2-(4-oxo-4-(4-(5-(3-pyridinyl)-1,3,4-oxadiazol-2-yl)-1-piperidinyl)butyl)-4(3H)-quinazolinone (92.2 mg, 0.21 mmol, 32%) after purification using reverse phase mass-directed HPLC. The column used was a Waters Xbridge C18 19×100 mm 10 micron column. The mobile phase was run under gradient conditions using water and ACN with 0.1% NH$_4$OH. $^1$H NMR (500 MHz, DMSO-d$_6$) δ ppm 12.13 (br. s., 1H), 9.16 (d, J=1.83 Hz, 1H), 8.79 (dd, J=4.81, 1.49 Hz, 1H), 8.36 (dt, J=7.99, 1.85 Hz, 1H), 8.07 (dd, J=7.96, 1.20 Hz, 1H), 7.70-7.81 (m, 1H), 7.63 (dd, J=7.96, 4.87 Hz, 1H), 7.58 (d, J=7.90 Hz, 1H), 7.44 (t, J=7.50 Hz, 1H), 4.29 (d, J=13.17 Hz, 1H), 3.93 (d, J=13.75 Hz, 1H), 3.36-3.44 (m, 1H), 3.26 (t, J=11.51 Hz, 1H), 2.88 (t, J=11.34 Hz, 1H), 2.66 (t, J=7.39 Hz, 2H), 2.45 (td, J=7.39, 1.95 Hz, 2H), 2.04-2.19 (m, 2H), 1.99 (quin, J=7.33 Hz, 2H), 1.72-1.88 (m, 1H), 1.63 (q, J=10.46 Hz, 1H); m/z (ESI) 445.1 (M+H)$^+$.

Example 14

2-(4-oxo-4-(4-(5-(2-pyrazinyl)-1,3,4-oxadiazol-2-yl)-1-piperidinyl)butyl)-4(3H)-quinazolinone

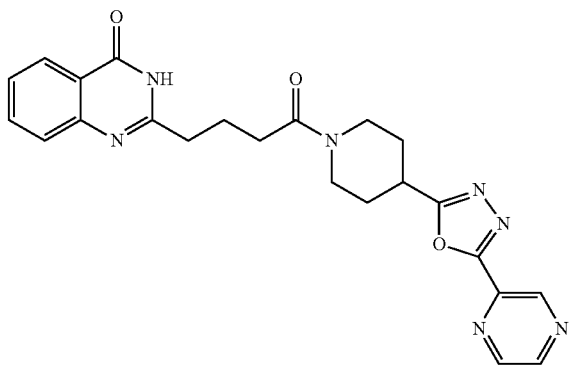 [SMILES: O=C(CCCc1nc2ccccc2c(=O)[nH]1)N1CCC(c2nnc(-c3cnccn3)o2)CC1]

The title compound was prepared as described in General Scheme A using 4-(4-oxo-3,4-dihydroquinazolin-2-yl)butanoic acid (Enamine) and 2-(piperidin-4-yl)-5-(pyrazin-2-yl)-1,3,4-oxadiazole 2,2,2-trifluoroacetate (HDH Pharma) providing 2-(4-oxo-4-(4-(5-(2-pyrazinyl)-1,3,4-oxadiazol-2-yl)-1-piperidinyl)butyl)-4(3H)-quinazolinone (114.5 mg, 0.26 mmol, 40%) after purification using reverse phase mass-directed HPLC. The column used was a Waters Xbridge C18 19×100 mm 10 micron column. The mobile phase was run under gradient conditions using water and ACN with 0.1% NH$_4$OH. $^1$H NMR (500 MHz, DMSO-d$_6$) δ ppm 12.03 (br. s, 1H), 9.35 (d, J=1.03 Hz, 1H), 8.68-9.00 (m, 2H), 8.07 (d, J=6.87 Hz, 1H), 7.70-7.80 (m, 1H), 7.58 (d, J=8.13 Hz, 1H), 7.43 (t, J=7.45 Hz, 1H), 4.29 (d, J=13.29 Hz, 1H), 3.93 (d, J=13.52 Hz, 1H), 3.38-3.49 (m, 1H), 3.20-3.29 (m, 1H), 2.88 (t, J=11.11 Hz, 1H), 2.66 (t, J=7.39 Hz, 2H), 2.38-2.48 (m, 2H), 2.04-2.18 (m, 2H), 1.99 (quin, J=7.33 Hz, 2H), 1.78 (q, J=10.50 Hz, 1H), 1.53-1.70 (m, 1H); m/z (ESI) 446.1 (M+H)$^+$.

Example 15

2-(4-(4-(5-(4-methoxyphenyl)-1,3,4-oxadiazol-2-yl)-1-piperidinyl)-4-oxobutyl)-4(3H)-quinazolinone

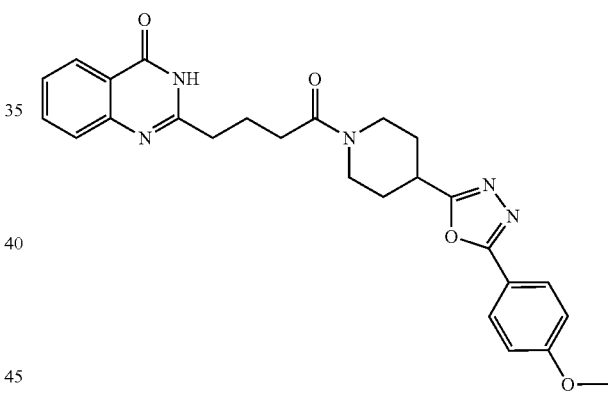

The title compound was prepared as described in General Scheme A using 4-(4-oxo-3,4-dihydroquinazolin-2-yl)butanoic acid (Enamine) and 2-(4-methoxyphenyl)-5-(piperidin-4-yl)-1,3,4-oxadiazole 2,2,2-trifluoroacetate (HDH Pharma) providing 2-(4-(4-(5-(4-methoxyphenyl)-1,3,4-oxadiazol-2-yl)-1-piperidinyl)-4-oxobutyl)-4(3H)-quinazolinone (133.5 mg, 0.28 mmol, 44%) after purification using reverse phase mass-directed HPLC. The column used was a Waters Xbridge C18 19×100 mm 10 micron column. The mobile phase was run under gradient conditions using water and ACN with 0.1% NH$_4$OH. $^1$H NMR (500 MHz, DMSO-d$_6$) δ ppm 12.13 (br. s., 1H), 8.07 (dd, J=7.90, 1.15 Hz, 1H), 7.88-7.99 (m, 2H), 7.70-7.83 (m, 1H), 7.58 (d, J=8.02 Hz, 1H), 7.44 (t, J=7.05 Hz, 1H), 7.13 (d, J=8.94 Hz, 2H), 4.29 (d, J=13.63 Hz, 1H), 3.92 (d, J=13.98 Hz, 1H), 3.85 (s, 3H), 3.34-3.42 (m, 1H), 3.20-3.28 (m, 1H), 2.86 (t, J=11.80 Hz, 1H), 2.66 (t, J=7.45 Hz, 2H), 2.45 (td, J=7.27, 3.32 Hz, 2H), 1.91-2.16 (m, 4H), 1.75 (d, J=10.42 Hz, 1H), 1.60 (d, J=9.51 Hz, 1H); m/z (ESI) 474.2 (M+H)$^+$.

Example 16

2-(4-(4-(5-(2-chlorophenyl)-1,3,4-oxadiazol-2-yl)-1-piperidinyl)-4-oxobutyl)-4(3H)-quinazolinone

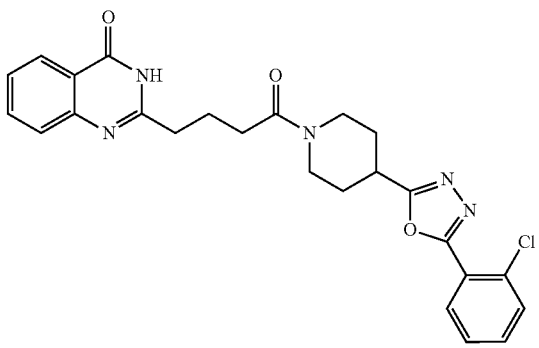 [SMILES: O=C(CCCc1nc2ccccc2c(=O)[nH]1)N1CCC(c2nnc(-c3ccccc3Cl)o2)CC1]

The title compound was prepared as described in General Scheme A using 4-(4-oxo-3,4-dihydroquinazolin-2-yl)butanoic acid (Enamine) and 2-(2-chlorophenyl)-5-(piperidin-4-yl)-1,3,4-oxadiazole 2,2,2-trifluoroacetate (HDH Pharma) providing 2-(4-(4-(5-(2-chlorophenyl)-1,3,4-oxadiazol-2-yl)-1-piperidinyl)-4-oxobutyl)-4(3H)-quinazolinone (129.9 mg, 0.27 mmol, 42%) after purification using reverse phase mass-directed HPLC. The column used was a Waters Xbridge C18 19×100 mm 10 micron column. The mobile phase was run under gradient conditions using water and ACN with 0.1% NH$_4$OH. $^1$H NMR (500 MHz, DMSO-d$_6$) δ ppm 12.12 (br. s., 1H), 8.07 (dd, J=7.85, 1.09 Hz, 1H), 7.97 (dd, J=7.79, 1.60 Hz, 1H), 7.67-7.78 (m, 2H), 7.63 (td, J=7.73, 1.49 Hz, 1H), 7.51-7.60 (m, 2H), 7.44 (t, J=7.45 Hz, 1H), 4.29 (d, J=13.29 Hz, 1H), 3.92 (d, J=13.52 Hz, 1H), 3.36-3.43 (m, 1H), 3.25 (t, J=11.51 Hz, 1H), 2.88 (t, J=11.00 Hz, 1H), 2.65 (t, J=7.33 Hz, 2H), 2.37-2.48 (m, 2H), 2.08 (dd, J=19.70, 14.09 Hz, 2H), 1.99 (quin, J=7.27 Hz, 2H), 1.69-1.85 (m, 1H), 1.53-1.68 (m, 1H); m/z (ESI) 478.1 (M+H)$^+$.

Example 17

2-(4-(4-(5-((4-chlorophenoxy)methyl)-1,3,4-oxadiazol-2-yl)-1-piperidinyl)-4-oxobutyl)-4(3H)-quinazolinone

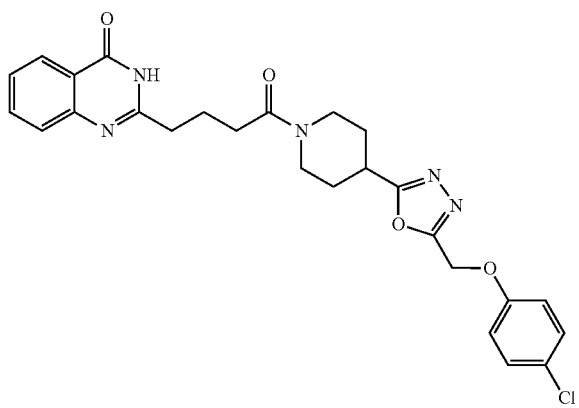 [SMILES: O=C(CCCc1nc2ccccc2c(=O)[nH]1)N1CCC(c2nnc(COc3ccc(Cl)cc3)o2)CC1]

The title compound was prepared as described in General Scheme A using 4-(4-oxo-3,4-dihydroquinazolin-2-yl)butanoic acid (Enamine) and 2-((4-chlorophenoxy)methyl)-5-(piperidin-4-yl)-1,3,4-oxadiazole 2,2,2-trifluoroacetate (HDH Pharma) providing 2-(4-(4-(5-((4-chlorophenoxy)methyl)-1,3,4-oxadiazol-2-yl)-1-piperidinyl)-4-oxobutyl)-4(3H)-quinazolinone (100.6 mg, 0.20 mmol, 31%) after purification using reverse phase mass-directed HPLC. The column used was a Waters Xbridge C18 19×100 mm 10 micron column. The mobile phase was run under gradient conditions using water and ACN with 0.1% NH$_4$OH. $^1$H NMR (500 MHz, DMSO-d$_6$) δ ppm 11.96 (br. s., 1H), 8.07 (dd, J=7.90, 1.15 Hz, 1H), 7.69-7.79 (m, 1H), 7.57 (d, J=8.13 Hz, 1H), 7.40-7.49 (m, 1H), 7.33-7.40 (m, 2H), 7.04-7.15 (m, 2H), 5.38 (s, 2H), 4.25 (d, J=13.40 Hz, 1H), 3.88 (d, J=13.86 Hz, 1H), 3.19-3.29 (m, 2H), 2.82 (t, J=11.05 Hz, 1H), 2.65 (t, J=7.33 Hz, 2H), 2.34-2.47 (m, 2H), 1.89-2.12 (m, 4H), 1.67 (d, J=9.85 Hz, 1H), 1.51 (d, J=9.05 Hz, 1H); m/z (ESI) 508.1 (M+H)$^+$.

Example 18

2-(4-(4-(5-(2-fluorophenyl)-1,3,4-oxadiazol-2-yl)-1-piperidinyl)-4-oxobutyl)-4(3H)-quinazolinone

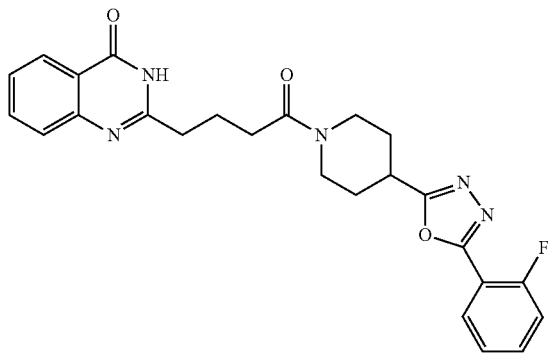 [SMILES: O=C(CCCc1nc2ccccc2c(=O)[nH]1)N1CCC(c2nnc(-c3ccccc3F)o2)CC1]

The title compound was prepared as described in General Scheme A using 4-(4-oxo-3,4-dihydroquinazolin-2-yl)butanoic acid (Enamine) and 2-(2-fluorophenyl)-5-(piperidin-4-yl)-1,3,4-oxadiazole 2,2,2-trifluoroacetate (HDH Pharma) providing 2-(4-(4-(5-(2-fluorophenyl)-1,3,4-oxadiazol-2-yl)-1-piperidinyl)-4-oxobutyl)-4(3H)-quinazolinone (132.5 mg, 0.29 mmol, 45%) after purification using reverse phase mass-directed HPLC. The column used was a Waters Xbridge C18 19×100 mm 10 micron column. The mobile phase was run under gradient conditions using water and ACN with 0.1% NH$_4$OH. $^1$H NMR (500 MHz, DMSO-d$_6$) δ ppm 12.14 (br. s., 1H), 8.07 (dd, J=7.90, 1.26 Hz, 1H), 8.02 (td, J=7.59, 1.66 Hz, 1H), 7.72-7.78 (m, 1H), 7.65-7.72 (m, 1H), 7.58 (d, J=7.90 Hz, 1H), 7.39-7.53 (m, 3H), 4.29 (d, J=13.40 Hz, 1H), 3.93 (d, J=14.89 Hz, 1H), 3.34-3.43 (m, 1H), 3.20-3.28 (m, 1H), 2.88 (t, J=11.00 Hz, 1H), 2.66 (t, J=7.33 Hz, 2H), 2.39-2.48 (m, 2H), 2.03-2.16 (m, 2H), 1.99 (quin, J=7.27 Hz, 2H), 1.76 (d, J=10.31 Hz, 1H), 1.54-1.67 (m, 1H); m/z (ESI) 462.2 (M+H)$^+$.

Example 19

2-(4-oxo-4-(4-(5-(4-pyridinyl)-1,3,4-oxadiazol-2-yl)-1-piperidinyl)butyl)-4(3H)-quinazolinone

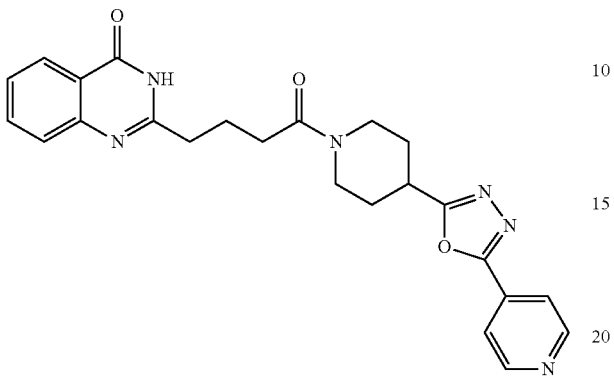

The title compound was prepared as described in General Scheme A using 4-(4-oxo-3,4-dihydroquinazolin-2-yl)butanoic acid (Enamine) and 2-(2-fluorophenyl)-5-(piperidin-4-yl)-1,3,4-oxadiazole 2,2,2-trifluoroacetate (HDH Pharma) providing 2-(4-oxo-4-(4-(5-(4-pyridinyl)-1,3,4-oxadiazol-2-yl)-1-piperidinyl)butyl)-4(3H)-quinazolinone (73.6 mg, 0.17 mmol, 26%) after purification using reverse phase mass-directed HPLC. The column used was a Waters Xbridge C18 19×100 mm 10 micron column. The mobile phase was run under gradient conditions using water and ACN with 0.1% NH$_4$OH. $^1$H NMR (400 MHz, DMSO-d$_6$) δ ppm 11.92 (br. s., 1H), 8.83 (d, J=5.77 Hz, 2H), 8.08 (dd, J=7.92, 1.27 Hz, 1H), 7.88-8.00 (m, 2H), 7.70-7.82 (m, 1H), 7.59 (d, J=8.02 Hz, 1H), 7.40-7.51 (m, 1H), 4.30 (d, J=13.40 Hz, 1H), 3.94 (d, J=13.60 Hz, 1H), 3.36-3.49 (m, 1H), 3.20-3.31 (m, 1H), 2.89 (t, J=11.25 Hz, 1H), 2.66 (t, J=7.34 Hz, 2H), 2.46 (t, J=7.19 Hz, 2H), 1.92-2.22 (m, 4H), 1.72-1.89 (m, 1H), 1.53-1.71 (m, 1H); m/z (ESI) 445.0 (M+H)$^+$.

Example 20

3-(5-(1-(4-(4-oxo-3,4-dihydroquinazolin-2-yl)butanoyl)piperidin-4-yl)-1,3,4-oxadiazol-2-yl)benzonitrile

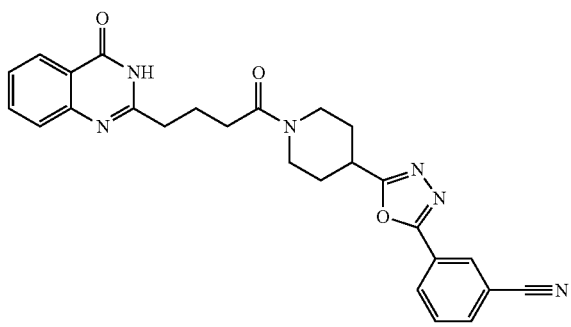 [SMILES: N#Cc1cccc(-c2nnc(C3CCN(C(=O)CCCc4nc5ccccc5c(=O)[nH]4)CC3)o2)c1]

The title compound was prepared as described in General Scheme A using 4-(4-oxo-3,4-dihydroquinazolin-2-yl)butanoic acid (Enamine) and 3-(5-(piperidin-4-yl)-1,3,4-oxadiazol-2-yl)benzonitrile 2,2,2-trifluoroacetate (HDH Pharma) providing 3-(5-(1-(4-(4-oxo-3,4-dihydroquinazolin-2-yl)butanoyl)piperidin-4-yl)-1,3,4-oxadiazol-2-yl)benzonitrile (135.4 mg, 0.29 mmol, 26%), after purification using reverse phase mass-directed HPLC. The column used was a Waters Xbridge C18 19×100 mm 10 micron column. The mobile phase was run under gradient conditions using water and ACN with 0.1% NH$_4$OH. $^1$H NMR (500 MHz, DMSO-d$_6$) δ ppm 12.13 (br. s., 1H), 8.41 (s, 1H), 8.30 (d, J=7.90 Hz, 1H), 8.07 (t, J=7.27 Hz, 2H), 7.80 (t, J=7.90 Hz, 1H), 7.71-7.76 (m, 1H), 7.58 (d, J=8.02 Hz, 1H), 7.44 (t, J=7.45 Hz, 1H), 4.29 (d, J=12.83 Hz, 1H), 3.93 (d, J=13.52 Hz, 1H), 3.34-3.39 (m, 1H), 3.26 (t, J=11.40 Hz, 1H), 2.89 (t, J=11.05 Hz, 1H), 2.66 (t, J=7.33 Hz, 2H), 2.45 (t, J=7.39 Hz, 2H), 2.09 (dd, J=19.24, 14.20 Hz, 2H), 1.99 (quin, J=7.36 Hz, 2H), 1.74-1.83 (m, 1H), 1.60-1.69 (m, 1H); m/z (ESI) 469.2 (M+H)$^+$.

Example 21

4-(5-(1-(4-(4-oxo-3,4-dihydroquinazolin-2-yl)butanoyl)piperidin-4-yl)-1,3,4-oxadiazol-2-yl)benzonitrile

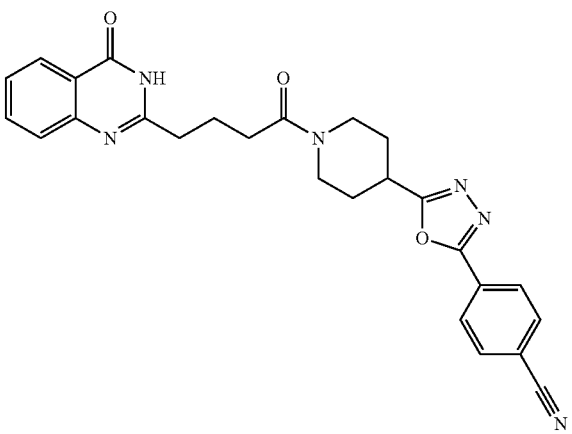 [SMILES: N#Cc1ccc(-c2nnc(C3CCN(C(=O)CCCc4nc5ccccc5c(=O)[nH]4)CC3)o2)cc1]

The title compound was prepared as described in General Scheme A using 4-(4-oxo-3,4-dihydroquinazolin-2-yl)butanoic acid (Enamine) and 4-(5-(piperidin-4-yl)-1,3,4-oxadiazol-2-yl)benzonitrile 2,2,2-trifluoroacetate (HDH Pharma) providing 4-(5-(1-(4-(4-oxo-3,4-dihydroquinazolin-2-yl)butanoyl)piperidin-4-yl)-1,3,4-oxadiazol-2-yl)benzonitrile (118.2 mg, 0.25 mmol, 39%), after purification using reverse phase mass-directed HPLC. The column used was a Waters Xbridge C18 19×100 mm 10 micron column. The mobile phase was run under gradient conditions using water and ACN with 0.1% NH$_4$OH. $^1$H NMR (500 MHz, DMSO-d$_6$) δ ppm 12.12 (br. s., 1H), 8.16 (d, J=8.25 Hz, 2H), 8.03-8.09 (m, 3H), 7.71-7.76 (m, 1H), 7.58 (d, J=8.13 Hz, 1H), 7.43 (t, J=7.56 Hz, 1H), 4.29 (d, J=12.94 Hz, 1H), 3.93 (d, J=13.52 Hz, 1H), 3.35-3.40 (m, 1H), 3.26 (t, J=11.63 Hz, 1H), 2.88 (t, J=11.11 Hz, 1H), 2.66 (t, J=7.39 Hz, 2H), 2.40-2.48 (m, 2H), 2.03-2.15 (m, 2H), 1.99 (quin, J=7.36 Hz, 2H), 1.72-1.83 (m, 1H), 1.57-1.68 (m, 1H); m/z (ESI) 469.2 (M+H)$^+$.

Example 22

2-(4-oxo-4-(4-(5-(m-tolyl)-1,3,4-oxadiazol-2-yl)piperidin-1-yl)butyl)quinazolin-4(3H)-one

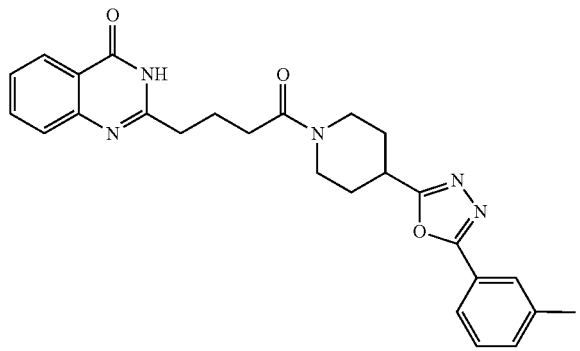 [SMILES: Cc1cccc(-c2nnc(C3CCN(C(=O)CCCc4nc5ccccc5c(=O)[nH]4)CC3)o2)c1]

The title compound was prepared as described in General Scheme A using 4-(4-oxo-3,4-dihydroquinazolin-2-yl)butanoic acid (Enamine) and 2-(piperidin-4-yl)-5-(m-tolyl)-1,3,4-oxadiazole 2,2,2-trifluoroacetate (HDH Pharma) providing 2-(4-oxo-4-(4-(5-(m-tolyl)-1,3,4-oxadiazol-2-yl)piperidin-1-yl)butyl)quinazolin-4(3H)-one (112.5 mg, 0.25 mmol, 38%) after purification using reverse phase mass-directed HPLC. The column used was a Waters Xbridge C18 19×100 mm 10 micron column. The mobile phase was run under gradient conditions using water and ACN with 0.1% NH$_4$OH. $^1$H NMR (500 MHz, DMSO-d$_6$) δ ppm 12.10 (br. s., 1H), 8.07 (dd, J=7.79, 1.03 Hz, 1H), 7.81 (s, 1H), 7.78 (d, J=7.68 Hz, 1H), 7.71-7.76 (m, 1H), 7.58 (d, J=8.13 Hz, 1H), 7.40-7.49 (m, 3H), 4.30 (d, J=12.72 Hz, 1H), 3.93 (d, J=13.75 Hz, 1H), 3.33-3.37 (m, 1H), 3.24 (t, J=11.57 Hz, 1H), 2.87 (t, J=11.11 Hz, 1H), 2.66 (t, J=7.39 Hz, 2H), 2.45 (td, J=7.30, 2.69 Hz, 2H), 2.40 (s, 3H), 2.03-2.14 (m, 2H), 1.99 (quin, J=7.33 Hz, 2H), 1.71-1.81 (m, 1H), 1.57-1.67 (m, 1H); m/z (ESI) 458.1 (M+H)$^+$.

Example 23

2-(4-oxo-4-(4-(5-(p-tolyl)-1,3,4-oxadiazol-2-yl)piperidin-1-yl)butyl)quinazolin-4(3H)-one

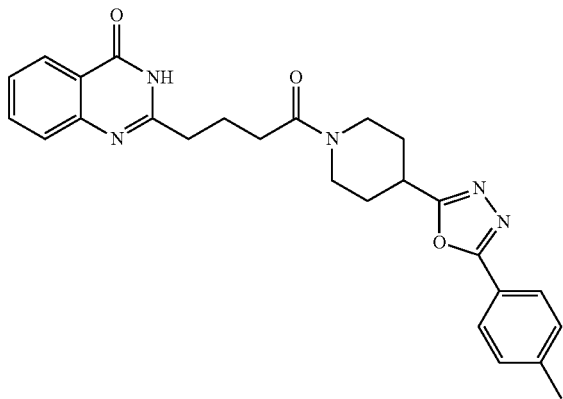 [SMILES: Cc1ccc(-c2nnc(C3CCN(C(=O)CCCc4nc5ccccc5c(=O)[nH]4)CC3)o2)cc1]

The title compound was prepared as described in General Scheme A using 4-(4-oxo-3,4-dihydroquinazolin-2-yl)butanoic acid (Enamine) and 2-(piperidin-4-yl)-5-(p-tolyl)-1,3,4-oxadiazole 2,2,2-trifluoroacetate (HDH Pharma) providing 2-(4-oxo-4-(4-(5-(p-tolyl)-1,3,4-oxadiazol-2-yl)piperidin-1-yl)butyl)quinazolin-4(3H)-one (132.9 mg, 0.29 mmol, 45%) after purification using reverse phase mass-directed HPLC. The column used was a Waters Xbridge C18 19×100 mm 10 micron column. The mobile phase was run under gradient conditions using water and ACN with 0.1% NH$_4$OH. $^1$H NMR (500 MHz, DMSO-d$_6$) δ ppm 12.13 (br. s., 1H), 8.07 (dd, J=7.90, 1.03 Hz, 1H), 7.87 (d, J=8.13 Hz, 2H), 7.70-7.76 (m, 1H), 7.58 (d, J=8.02 Hz, 1H), 7.44 (t, J=7.50 Hz, 1H), 7.39 (d, J=8.13 Hz, 2H), 4.29 (d, J=13.17 Hz, 1H), 3.92 (d, J=13.86 Hz, 1H), 3.34-3.37 (m, 1H), 3.20-3.28 (m, 1H), 2.86 (t, J=11.05 Hz, 1H), 2.66 (t, J=7.33 Hz, 2H), 2.44 (td, J=7.25, 3.26 Hz, 2H), 2.39 (s, 3H), 2.07 (dd, J=19.19, 14.49 Hz, 2H), 1.95-2.03 (m, 2H), 1.70-1.82 (m, 1H), 1.54-1.66 (m, 1H); m/z (ESI) 458.1 (M+H)$^+$.

Example 24

2-(4-(4-(5-(3-methoxyphenyl)-1,3,4-oxadiazol-2-yl)piperidin-1-yl)-4-oxobutyl)quinazolin-4(3H)-one

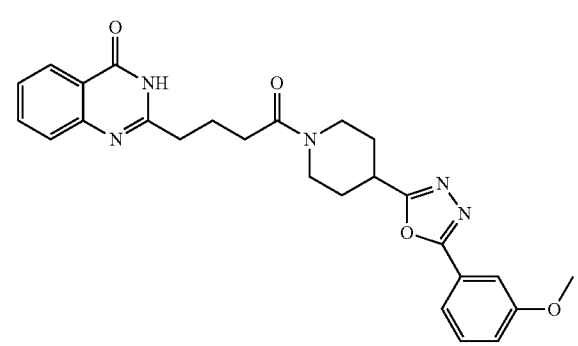 [SMILES: COc1cccc(-c2nnc(C3CCN(C(=O)CCCc4nc5ccccc5c(=O)[nH]4)CC3)o2)c1]

The title compound was prepared as described in General Scheme A using 4-(4-oxo-3,4-dihydroquinazolin-2-yl)butanoic acid (Enamine) and 2-(3-methoxyphenyl)-5-(piperidin-4-yl)-1,3,4-oxadiazole 2,2,2-trifluoroacetate (HDH Pharma) providing 2-(4-(4-(5-(3-methoxyphenyl)-1,3,4-oxadiazol-2-yl)piperidin-1-yl)-4-oxobutyl)quinazolin-4(3H)-one (122.0 mg, 0.26 mmol, 40%) after purification using reverse phase mass-directed HPLC. The column used was a Waters Xbridge C18 19×100 mm 10 micron column. The mobile phase was run under gradient conditions using water and ACN with 0.1% NH$_4$OH. $^1$H NMR (500 MHz, DMSO-d$_6$) δ ppm 12.13 (br. s., 1H), 8.07 (d, J=7.90 Hz, 1H), 7.69-7.76 (m, 1H), 7.54-7.60 (m, 2H), 7.46-7.52 (m, 2H), 7.43 (t, J=7.50 Hz, 1H), 7.18 (dd, J=8.25, 2.52 Hz, 1H), 4.30 (d, J=13.06 Hz, 1H), 3.93 (d, J=13.40 Hz, 1H), 3.84 (s, 3H), 3.29-3.32 (m, 1H), 3.24 (t, J=11.68 Hz, 1H), 2.86 (t, J=11.34 Hz, 1H), 2.66 (t, J=7.39 Hz, 2H), 2.44 (td, J=7.25, 3.04 Hz, 2H), 2.03-2.14 (m, 2H), 1.99 (quin, J=7.33 Hz, 2H), 1.70-1.82 (m, 1H), 1.56-1.67 (m, 1H); m/z (ESI) 474.3 (M+H)$^+$.

Example 25

2-(4-(4-(5-(3-chloro-4-fluorophenyl)-1,3,4-oxadiazol-2-yl)piperidin-1-yl)-4-oxobutyl)quinazolin-4(3H)-one

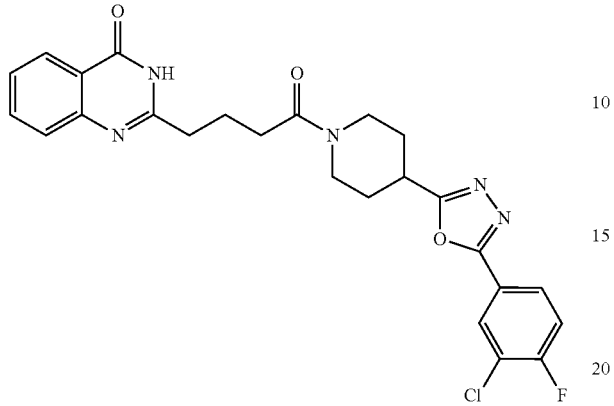

The title compound was prepared as described in General Scheme A using 4-(4-oxo-3,4-dihydroquinazolin-2-yl)butanoic acid (Enamine) and 2-(3-chloro-4-fluorophenyl)-5-(piperidin-4-yl)-1,3,4-oxadiazole 2,2,2-trifluoroacetate (HDH Pharma) providing 2-(4-(4-(5-(3-chloro-4-fluorophenyl)-1,3,4-oxadiazol-2-yl)piperidin-1-yl)-4-oxobutyl)quinazolin-4(3H)-one (141.2 mg, 0.29 mmol, 44%) after purification using reverse phase mass-directed HPLC. The column used was a Waters Xbridge C18 19×100 mm 10 micron column. The mobile phase was run under gradient conditions using water and ACN with 0.1% NH$_4$OH. $^1$H NMR (500 MHz, DMSO-d$_6$) δ ppm 12.13 (br. s., 1H), 8.16 (d, J=6.99 Hz, 1H), 8.07 (d, J=7.90 Hz, 1H), 8.01 (ddd, J=8.53, 4.52, 1.83 Hz, 1H), 7.71-7.76 (m, 1H), 7.64 (t, J=8.94 Hz, 1H), 7.58 (d, J=8.13 Hz, 1H), 7.43 (t, J=7.50 Hz, 1H), 4.29 (d, J=13.06 Hz, 1H), 3.93 (d, J=13.52 Hz, 1H), 3.33-3.39 (m, 1H), 3.25 (t, J=11.51 Hz, 1H), 2.87 (t, J=11.05 Hz, 1H), 2.66 (t, J=7.39 Hz, 2H), 2.40-2.48 (m, 2H), 2.03-2.15 (m, 2H), 1.99 (quin, J=7.39 Hz, 2H), 1.77 (q, J=10.54 Hz, 1H), 1.56-1.68 (m, 1H); m/z (ESI) 496.2 (M+H)$^+$.

Example 26

2-(4-oxo-4-(4-(2-oxo-1,2-dihydro-3H-imidazo[4,5-b]pyridin-3-yl)-1-piperidinyl)butyl)-4(3H)-quinazolinone

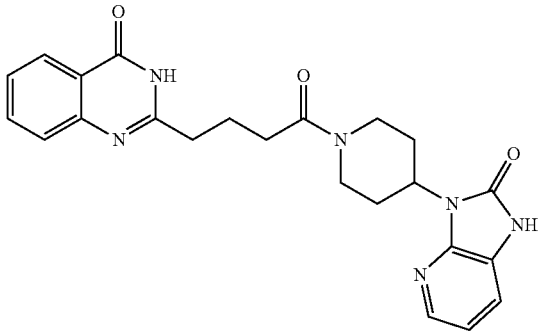 [SMILES: O=C(CCCc1nc2ccccc2c(=O)[nH]1)N1CCC(n2c(=O)[nH]c3cccnc32)CC1]

The title compound was prepared as described in General Scheme A using 4-(4-oxo-3,4-dihydroquinazolin-2-yl)butanoic acid (Enamine) and 3-(piperidin-4-yl)-1H-imidazo[4,5-b]pyridin-2(3H)-one (HDH Pharma) providing 2-(4-oxo-4-(4-(2-oxo-1,2-dihydro-3H-imidazo[4,5-b]pyridin-3-yl)-1-piperidinyl)butyl)-4(3H)-quinazolinone (135.2 mg, 0.31 mmol, 49%) after purification using reverse phase mass-directed HPLC. The column used was a Waters Xbridge C18 19×100 mm 10 micron column. The mobile phase was run under gradient conditions using water and ACN with 0.1% NH$_4$OH. $^1$H NMR (500 MHz, DMSO-d$_6$) δ ppm 12.14 (br. s., 1H), 11.08 (br. s., 1H), 8.08 (dd, J=7.90, 1.15 Hz, 1H), 7.91 (dd, J=5.21, 1.32 Hz, 1H), 7.73-7.79 (m, 1H), 7.61 (d, J=8.02 Hz, 1H), 7.45 (t, J=7.50 Hz, 1H), 7.28 (dd, J=7.68, 1.26 Hz, 1H), 6.98 (dd, J=7.67, 5.27 Hz, 1H), 4.57 (d, J=12.83 Hz, 1H), 4.50 (tt, J=12.04, 4.00 Hz, 1H), 4.05 (d, J=13.06 Hz, 1H), 3.15 (t, J=12.83 Hz, 1H), 2.58-2.71 (m, 3H), 2.42-2.48 (m, 3H), 2.30-2.41 (m, 1H), 2.01 (quin, J=7.45 Hz, 2H), 1.66-1.78 (m, 2H); m/z (ESI) 433.2 (M+H)$^+$.

Example 27

2-(4-(4-(5-chloro-2-oxo-2,3-dihydro-1H-benzimidazol-1-yl)-1-piperidinyl)-4-oxobutyl)-4(3H)-quinazolinone

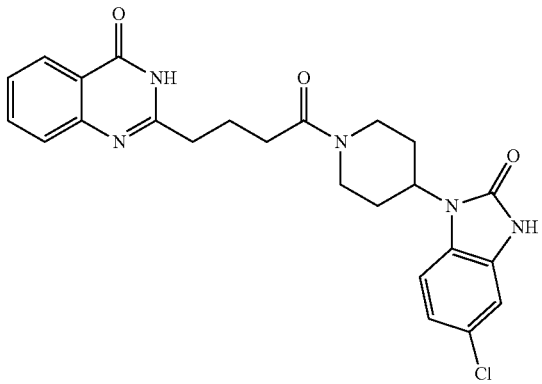 [SMILES: O=C(CCCc1nc2ccccc2c(=O)[nH]1)N1CCC(n2c(=O)[nH]c3cc(Cl)ccc32)CC1]

The title compound was prepared as described in General Scheme A using 4-(4-oxo-3,4-dihydroquinazolin-2-yl)butanoic acid (Enamine) and 5-chloro-1-(piperidin-4-yl)-1H-benzo[d]imidazol-2(3H)-one (Aldrich). The reaction mixture was heated at 65° C. for 43 h, cooled to RT, and poured into 100 mL of water, rinsing the reaction flask bringing the total volume to 200 mL. The mixture was stirred at RT for 1.5 h, then DCM was added and stirring was continued for 15 min. The mixture was then transferred to a separatory funnel. The aqueous layer was extracted with DCM. The combined organic layers were dried and concentrated and purified using supercritical fluid chromatography (SFC). The column used was Chiralpak IC, 2×15 cm. The mobile phase was run under isocratic conditions (CO$_2$ with 60% MeOH co-solvent containing 0.2% diethylamine modifier). The resulting solid was slurried on the rotovap (no vacuum) at 45° C. for 1 h, cooled to RT, filtered, rinsed once with MTBE and dried on a vacuum pump providing 2-(4-(4-(5-chloro-2-oxo-2,3-dihydro-1H-benzimidazol-1-yl)-1-piperidinyl)-4-oxobutyl)-4(3H)-quinazolinone (983 mg, 2.11 mmol, 49%). $^1$H NMR (400 MHz, DMSO-d$_6$) δ ppm 12.11 (br. s, 1H), 11.04 (br. s., 1H), 8.08 (dd, J=7.92, 1.27 Hz, 1H), 7.76 (ddd, J=8.27, 6.99, 1.57 Hz, 1H), 7.60 (d, J=8.02 Hz, 1H), 7.41-7.50 (m, 1H), 7.25 (d, J=8.71 Hz, 1H), 6.95-7.05 (m, 2H), 4.57 (d, J=12.81 Hz, 1H), 4.39 (ddd, J=12.15, 8.19, 4.01 Hz, 1H), 3.98-4.12 (m, 1H), 3.08-3.22 (m, 2H), 2.64-2.72 (m, 2H), 2.57-2.64 (m, 1H), 2.42-2.48 (m, 1H), 2.17-2.31 (m, 1H), 2.05-2.17 (m, 1H), 1.94-2.05 (m, 2H), 1.72 (t, J=13.64 Hz, 2H); m/z (ESI) 466.2 (M+H)$^+$.

Example 28
N-(trans-4-(5-(4-fluorophenyl)-1,3,4-oxadiazol-2-yl)cyclohexyl)-4-(4-oxo-3,4-dihydro-2-quinazolinyl)butanamide

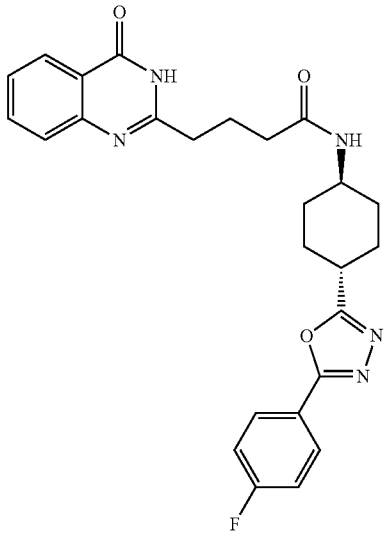 [SMILES: O=C(CCCc1nc2ccccc2c(=O)[nH]1)N[C@H]1CC[C@H](c2nnc(-c3ccc(F)cc3)o2)CC1]

The title compound was prepared as described in General Scheme A using 4-(4-oxo-3,4-dihydroquinazolin-2-yl)butanoic acid (Enamine) and (1r,4r)-4-(5-(4-fluorophenyl)-1,3,4-oxadiazol-2-yl)cyclohexanamine (HDH Pharma) providing N-(trans-4-(5-(4-fluorophenyl)-1,3,4-oxadiazol-2-yl)cyclohexyl)-4-(4-oxo-3,4-dihydro-2-quinazolinyl)butanamide (18.6 mg, 0.04 mmol, 6%) after purification using reverse phase mass-directed HPLC. The column used was a Waters Xbridge C18 19×100 mm 10 micron column. The mobile phase was run under gradient conditions using water and ACN with 0.1% NH$_4$OH. $^1$H NMR (500 MHz, DMSO-d$_6$) δ ppm 12.14 (br. s., 1H), 8.08 (d, J=8.93 Hz, 1H), 8.04 (dd, J=8.88, 5.33 Hz, 2H), 7.73-7.80 (m, 2H), 7.60 (d, J=8.13 Hz, 1H), 7.40-7.49 (m, 3H), 3.52-3.64 (m, 1H), 2.92-3.01 (m, 1H), 2.61 (t, J=7.50 Hz, 2H), 2.10-2.19 (m, 4H), 1.97 (quin, J=7.39 Hz, 2H), 1.90 (d, J=10.31 Hz, 2H), 1.57-1.68 (m, 2H), 1.26-1.36 (m, 2H); m/z (ESI) 476.1 (M+H)$^+$.

Example 29
N-(trans-4-(5-(4-chlorophenyl)-1,3,4-oxadiazol-2-yl)cyclohexyl)-4-(4-oxo-3,4-dihydro-2-quinazolinyl)butanamide

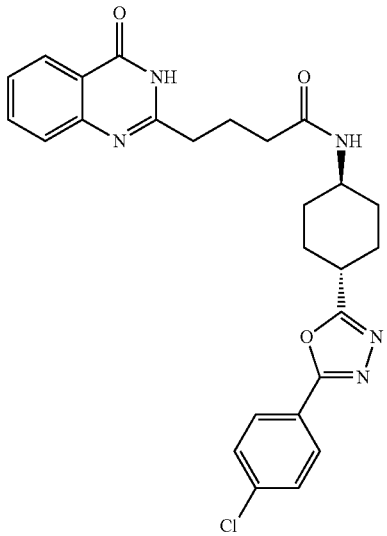 [SMILES: O=C(CCCc1nc2ccccc2c(=O)[nH]1)N[C@H]1CC[C@H](c2nnc(-c3ccc(Cl)cc3)o2)CC1]

The title compound was prepared as described in General Scheme A using 4-(4-oxo-3,4-dihydroquinazolin-2-yl)butanoic acid (Enamine) and (1r,4r)-4-(5-(4-chlorophenyl)-1,3,4-oxadiazol-2-yl)cyclohexanamine (HDH Pharma) providing N-(trans-4-(5-(4-chlorophenyl)-1,3,4-oxadiazol-2-yl)cyclohexyl)-4-(4-oxo-3,4-dihydro-2-quinazolinyl)butanamide (17.3 mg, 0.04 mmol, 5%), after purification using reverse phase mass-directed HPLC. The column used was a Waters Xbridge C18 19×100 mm 10 micron column. The mobile phase was run under gradient conditions using water and ACN with 0.1% NH$_4$OH. $^1$H NMR (500 MHz, DMSO-d$_6$) δ ppm $^1$H NMR (500 MHz, DMSO-d$_6$) δ ppm 12.07 (br. s, 1H), 8.08 (d, J=8.71 Hz, 1H), 8.00 (d, J=8.59 Hz, 2H), 7.74-7.80 (m, 2H), 7.64-7.69 (m, 2H), 7.60 (d, J=7.90 Hz, 1H), 7.46 (t, J=7.50 Hz, 1H), 3.51-3.64 (m, 1H), 2.92-3.02 (m, 1H), 2.61 (t, J=7.39 Hz, 2H), 2.11-2.19 (m, 4H), 1.97 (quin, J=7.50 Hz, 2H), 1.87-1.93 (m, 2H), 1.57-1.69 (m, 2H), 1.25-1.36 (m, 2H); m/z (ESI) 492.0 (M+H)$^+$.

Example 30
N-(trans-4-(5-(4-methoxyphenyl)-1,3,4-oxadiazol-2-yl)cyclohexyl)-4-(4-oxo-3,4-dihydro-2-quinazolinyl)butanamide

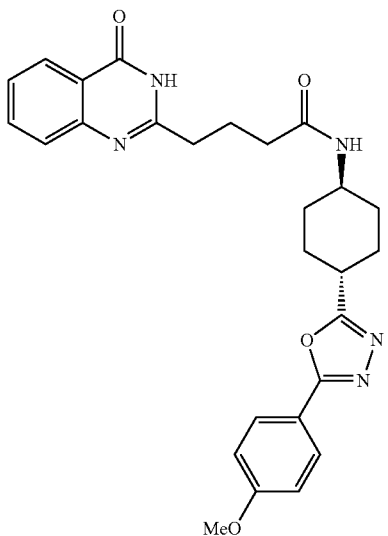 [SMILES: COc1ccc(-c2nnc([C@H]3CC[C@H](NC(=O)CCCc4nc5ccccc5c(=O)[nH]4)CC3)o2)cc1]

The title compound was prepared as described in General Scheme A using 4-(4-oxo-3,4-dihydroquinazolin-2-yl)butanoic acid (Enamine) and (1r,4r)-4-(5-(4-methoxyphenyl)-1,3,4-oxadiazol-2-yl)cyclohexanamine (HDH Pharma) providing N-(trans-4-(5-(4-methoxyphenyl)-1,3,4-oxadiazol-2-yl)cyclohexyl)-4-(4-oxo-3,4-dihydro-2-quinazolinyl)butanamide (102.4 mg, 0.21 mmol, 33%) after purification using reverse phase mass-directed HPLC. The column used was a Waters Xbridge C18 19×100 mm 10 micron column. The mobile phase was run under gradient conditions using water and ACN with 0.1% NH$_4$OH. $^1$H NMR (500 MHz, DMSO-d$_6$) δ ppm 12.13 (br. s., 1H), 8.08 (dd, J=7.90, 1.03 Hz, 1H), 7.87-7.94 (m, 2H), 7.72-7.80 (m, 2H), 7.60 (d, J=8.02 Hz, 1H), 7.42-7.49 (m, 1H), 7.13 (d, J=8.94 Hz, 2H), 3.84 (s, 3H), 3.54-3.63 (m, 1H), 2.88-2.98 (m, 1H), 2.61 (t, J=7.45 Hz, 2H), 2.09-2.19 (m, 4H), 1.97 (quin, J=7.39 Hz, 2H), 1.86-1.93 (m, 2H), 1.55-1.68 (m, 2H), 1.25-1.36 (m, 2H); m/z (ESI) 488.1 (M+H)$^+$.

Example 31

N-(trans-4-(5-(3-fluorophenyl)-1,3,4-oxadiazol-2-yl)cyclohexyl)-4-(4-oxo-3,4-dihydro-2-quinazolinyl)butanamide

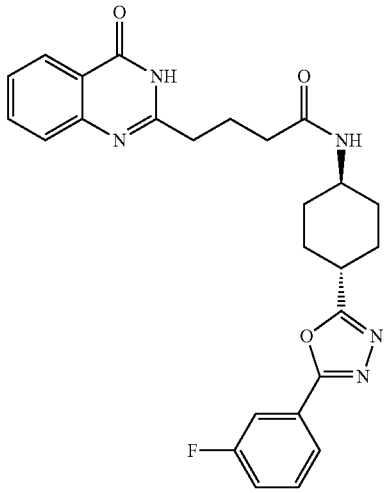 [SMILES: O=C(CCCc1nc2ccccc2c(=O)[nH]1)N[C@H]1CC[C@H](c2nnc(-c3cccc(F)c3)o2)CC1]

The title compound was prepared as described in General Scheme A using 4-(4-oxo-3,4-dihydroquinazolin-2-yl)butanoic acid (Enamine) and (1r,4r)-4-(5-(3-fluorophenyl)-1,3,4-oxadiazol-2-yl)cyclohexanamine (HDH Pharma) providing N-(trans-4-(5-(3-fluorophenyl)-1,3,4-oxadiazol-2-yl)cyclohexyl)-4-(4-oxo-3,4-dihydro-2-quinazolinyl)butanamide (69.8 mg, 0.15 mmol, 23%) after purification using reverse phase mass-directed HPLC. The column used was a Waters Xbridge C18 19×100 mm 10 micron column. The mobile phase was run under gradient conditions using water and ACN with 0.1% NH$_4$OH. $^1$H NMR (500 MHz, DMSO-d$_6$) δ ppm 12.14 (br. s., 1H), 8.08 (dd, J=7.85, 0.97 Hz, 1H), 7.83 (d, J=7.79 Hz, 1H), 7.72-7.80 (m, 3H), 7.65 (td, J=7.99, 6.01 Hz, 1H), 7.60 (d, J=8.13 Hz, 1H), 7.43-7.50 (m, 2H), 3.52-3.64 (m, 1H), 2.93-3.02 (m, 1H), 2.61 (t, J=7.45 Hz, 2H), 2.11-2.19 (m, 4H), 1.97 (quin, J=7.39 Hz, 2H), 1.86-1.93 (m, 2H), 1.57-1.70 (m, 2H), 1.26-1.39 (m, 2H); m/z (ESI) 476.1 (M+H)$^+$.

Example 32

N-(trans-4-(5-(3-methoxyphenyl)-1,3,4-oxadiazol-2-yl)cyclohexyl)-4-(4-oxo-3,4-dihydro-2-quinazolinyl)butanamide

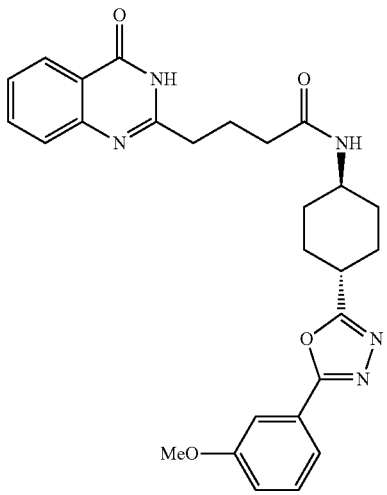 [SMILES: COc1cccc(-c2nnc([C@H]3CC[C@H](NC(=O)CCCc4nc5ccccc5c(=O)[nH]4)CC3)o2)c1]

The title compound was prepared as described in General Scheme A using 4-(4-oxo-3,4-dihydroquinazolin-2-yl)butanoic acid (Enamine) and (1r,4r)-4-(5-(3-methoxyphenyl)-1,3,4-oxadiazol-2-yl)cyclohexanamine (HDH Pharma) providing N-(trans-4-(5-(3-methoxyphenyl)-1,3,4-oxadiazol-2-yl)cyclohexyl)-4-(4-oxo-3,4-dihydro-2-quinazolinyl)butanamide (97.5 mg, 0.20 mmol, 30%) after purification using reverse phase mass-directed HPLC. The column used was a Waters Xbridge C18 19×100 mm 10 micron column. The mobile phase was run under gradient conditions using water and ACN with 0.1% NH$_4$OH. $^1$H NMR (500 MHz, DMSO-d$_6$) δ ppm 12.14 (br. s., 1H), 8.08 (d, J=7.90 Hz, 1H), 7.73-7.81 (m, 2H), 7.60 (d, J=8.02 Hz, 1H), 7.54-7.58 (m, 1H), 7.42-7.53 (m, 3H), 7.19 (dd, J=8.25, 1.72 Hz, 1H), 3.85 (s, 3H), 3.52-3.67 (m, 1H), 2.92-3.03 (m, 1H), 2.61 (t, J=7.45 Hz, 2H), 2.09-2.19 (m, 4H), 1.93-2.02 (m, 2H), 1.86-1.93 (m, 2H), 1.55-1.70 (m, 2H), 1.26-1.37 (m, 2H); m/z (ESI) 488.1 (M+H)$^+$.

Example 33

4-(4-oxo-3,4-dihydro-2-quinazolinyl)-N-(trans-4-(5-(4-pyridinyl)-1,3,4-oxadiazol-2-yl)cyclohexyl)butanamide

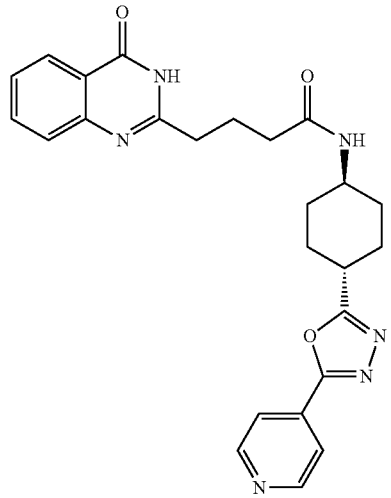 [SMILES: O=C(CCCc1nc2ccccc2c(=O)[nH]1)N[C@H]1CC[C@H](c2nnc(-c3ccncc3)o2)CC1]

The title compound was prepared as described in General Scheme A using 4-(4-oxo-3,4-dihydroquinazolin-2-yl)butanoic acid (Enamine) and (1r,4r)-4-(5-(pyridin-4-yl)-1,3,4-oxadiazol-2-yl)cyclohexanamine (HDH Pharma) providing 4-(4-oxo-3,4-dihydro-2-quinazolinyl)-N-(trans-4-(5-(4-pyridinyl)-1,3,4-oxadiazol-2-yl)cyclohexyl)butanamide (47.3 mg, 0.10 mmol, 16%) after purification using reverse phase mass-directed HPLC. The column used was a Waters Xbridge C18 19×100 mm 10 micron column. The mobile phase was run under gradient conditions using water and ACN with 0.1% NH$_4$OH. $^1$H NMR (500 MHz, DMSO-d$_6$) δ ppm 11.91 (br. s., 1H), 8.78-8.85 (m, 2H), 8.05-8.11 (m, 1H), 7.89-7.95 (m, 2H), 7.73-7.81 (m, 2H), 7.60 (d, J=8.13 Hz, 1H), 7.46 (t, J=7.50 Hz, 1H), 3.50-3.65 (m, 1H), 2.95-3.06 (m, 1H), 2.61 (t, J=7.45 Hz, 2H), 2.11-2.21 (m, 4H), 1.97 (quin, J=7.45 Hz, 2H), 1.87-1.93 (m, 2H), 1.58-1.70 (m, 2H), 1.25-1.36 (m, 2H); m/z (ESI) 459.2 (M+H)$^+$.

Example 34

2-(4-(4-(6-methoxy-2-oxo-2,3-dihydro-1H-benzimidazol-1-yl)-1-piperidinyl)-4-oxobutyl)-4(3H)-quinazolinone

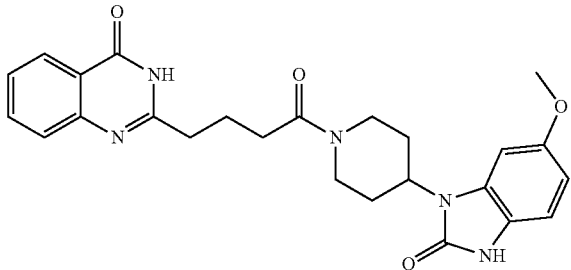 [SMILES: COc1ccc2[nH]c(=O)n(C3CCN(C(=O)CCCc4nc5ccccc5c(=O)[nH]4)CC3)c2c1]

The title compound was prepared as described in General Scheme A using 4-(4-oxo-3,4-dihydroquinazolin-2-yl)butanoic acid (Enamine) and 6-methoxy-1-(piperidin-4-yl)-1H-benzo[d]imidazol-2(3H)-one (Ryan Scientific) providing 2-(4-(4-(6-methoxy-2-oxo-2,3-dihydro-1H-benzimidazol-1-yl)-1-piperidinyl)-4-oxobutyl)-4(3H)-quinazolinone (44.3 mg, 0.10 mmol, 15%) after purification using reverse phase mass-directed HPLC. The column used was a Waters Xbridge C18 19×100 mm 10 micron column. The mobile phase was run under gradient conditions using water and ACN with 0.1% NH$_4$OH. $^1$H NMR (500 MHz, DMSO-d$_6$) δ ppm 12.14 (br. s., 1H), 10.60 (s, 1H), 8.08 (dd, J=7.90, 1.15 Hz, 1H), 7.73-7.79 (m, 1H), 7.60 (d, J=8.02 Hz, 1H), 7.45 (t, J=7.50 Hz, 1H), 6.81-6.89 (m, 2H), 6.56 (dd, J=8.48, 2.29 Hz, 1H), 4.57 (d, J=13.63 Hz, 1H), 4.31-4.41 (m, 1H), 4.05 (d, J=13.40 Hz, 1H), 3.72 (s, 3H), 3.10-3.20 (m, 1H), 2.59-2.71 (m, 3H), 2.44-2.48 (m, 2H), 2.24-2.36 (m, 1H), 2.08-2.19 (m, 1H), 2.01 (quin, J=7.36 Hz, 2H), 1.64-1.78 (m, 2H); m/z (ESI) 462.2 (M+H)$^+$.

Example 35

N-(trans-4-(5-(3-chloro-4-fluorophenyl)-1,3,4-oxadiazol-2-yl)cyclohexyl)-4-(4-oxo-3,4-dihydro-2-quinazolinyl)butanamide 2,2,2-trifluoroacetate

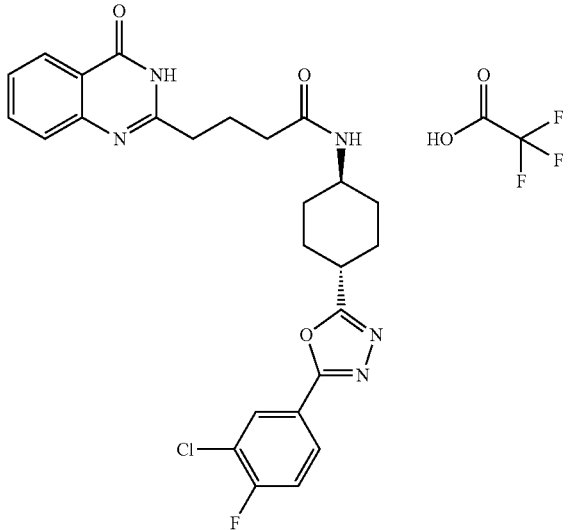 [SMILES: O=C(CCCc1nc2ccccc2c(=O)[nH]1)N[C@H]1CC[C@H](c2nnc(-c3ccc(F)c(Cl)c3)o2)CC1 ; O=C(O)C(F)(F)F]

The title compound was prepared as described in General Scheme A using 4-(4-oxo-3,4-dihydroquinazolin-2-yl)butanoic acid (Enamine) and (1r,4r)-4-(5-(3-chloro-4-fluorophenyl)-1,3,4-oxadiazol-2-yl)cyclohexanamine (HDH Pharma) providing N-(trans-4-(5-(3-chloro-4-fluorophenyl)-1,3,4-oxadiazol-2-yl)cyclohexyl)-4-(4-oxo-3,4-dihydro-2-quinazolinyl)butanamide 2,2,2-trifluoroacetate (8.5 mg, 0.01 mmol, 2%) after purification using reverse phase HPLC. The column used was a Waters Xbridge C18 19×100 mm 10 micron column. The mobile phase was run under gradient conditions using water and ACN with 0.1% TFA. $^1$H NMR (400 MHz, DMSO-d$_6$) δ ppm 12.16 (br. s, 1H), 8.18 (dd, J=6.94, 2.15 Hz, 1H), 8.08 (d, J=7.92 Hz, 1H), 8.02 (ddd, J=8.63, 4.67, 2.25 Hz, 1H), 7.75-7.81 (m, 2H), 7.58-7.70 (m, 2H), 7.46 (t, J=7.04 Hz, 1H), 3.52-3.66 (m, 1H), 2.92-3.03 (m, 1H), 2.58-2.64 (m, 2H), 2.11-2.20 (m, 4H), 1.94-2.01 (m, 2H), 1.86-1.93 (m, 2H), 1.56-1.70 (m, 2H), 1.23-1.37 (m, 2H); m/z (ESI) 510.0 (M+H)$^+$.

Example 36

N-(trans-4-(5-(3-chlorophenyl)-1,3,4-oxadiazol-2-yl)cyclohexyl)-4-(4-oxo-3,4-dihydro-2-quinazolinyl)butanamide 2,2,2-trifluoroacetate

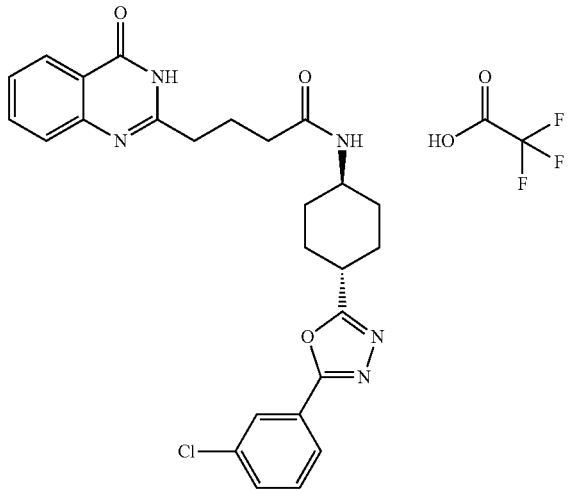 [SMILES: O=C(CCCc1nc2ccccc2c(=O)[nH]1)N[C@H]1CC[C@H](c2nnc(-c3cccc(Cl)c3)o2)CC1 ; O=C(O)C(F)(F)F]

The title compound was prepared as described in General Scheme A using 4-(4-oxo-3,4-dihydroquinazolin-2-yl)butanoic acid (Enamine) and ((1r,4r)-4-(5-(3-chlorophenyl)-1,3,4-oxadiazol-2-yl)cyclohexanamine (HDH Pharma) providing N-(trans-4-(5-(3-chlorophenyl)-1,3,4-oxadiazol-2-yl)cyclohexyl)-4-(4-oxo-3,4-dihydro-2-quinazolinyl)butanamide 2,2,2-trifluoroacetate (12.1 mg, 0.02 mmol, 3%) after purification using reverse phase HPLC. The column used was a Waters Xbridge C18 19×100 mm 10 micron column. The mobile phase was run under gradient conditions using water and ACN with 0.1% TFA. $^1$H NMR (400 MHz, DMSO-d$_6$) δ ppm 12.28 (br. s, 1H), 8.09 (dd, J=7.97, 1.52 Hz, 1H), 8.00 (t, J=1.81 Hz, 1H), 7.96 (dt, J=7.65, 1.16 Hz, 1H), 7.77-7.82 (m, 2H), 7.68-7.73 (m, 1H), 7.59-7.66 (m, 2H), 7.45-7.51 (m, 1H), 3.53-3.62 (m, 1H), 2.93-3.04 (m, 1H), 2.63 (t, J=7.43 Hz, 2H), 2.12-2.20 (m, 4H), 1.94-2.02 (m, 2H), 1.85-1.93 (m, 2H), 1.56-1.70 (m, 2H), 1.25-1.39 (m, 2H); m/z (ESI) 492.2 (M+H)$^+$.

Example 37

3-((4-methyl-6-oxo-1,6-dihydropyrimidin-2-yl)thio)-N-((1r,4r)-4-(5-phenyl-1,3,4-oxadiazol-2-yl)cyclohexyl)propanamide

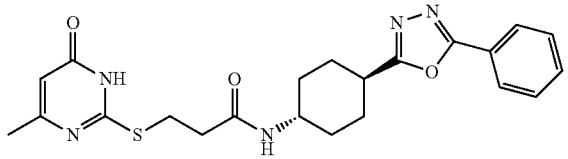 [SMILES: Cc1cc(=O)[nH]c(SCCC(=O)N[C@H]2CC[C@H](c3nnc(-c4ccccc4)o3)CC2)n1]

The title compound was prepared as described in General Scheme A using 3((4-methyl-6-oxo-1,6-dihydropyrimidin-2-yl)thio)propanoic acid (Enamine), and Intermediate C, affording 3-(4-methyl-6-oxo-1,6-dihydropyrimidin-2-yl)thio)-N-((1r,4r)-4-(5-phenyl-1,3,4-oxadiazol-2-yl)cyclohexyl)propanamide (70 mg, 0.16 mmol, 68% yield); m/z (ESI) 440 (M+H)$^+$.

Example 38

3-(4-oxo-4H-pyrido[1,2-a]pyrimidin-2-yl)-N-((1r,4r)-4-(5-phenyl-1,3,4-oxadiazol-2-yl)cyclohexyl)propanamide

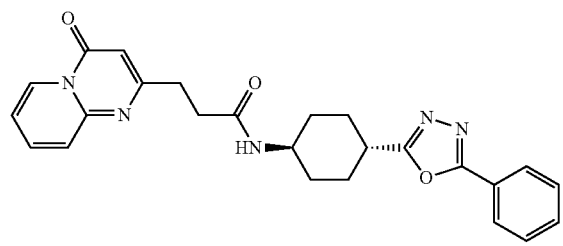 [SMILES: O=C(CCc1cc(=O)n2ccccc2n1)N[C@H]1CC[C@H](c2nnc(-c3ccccc3)o2)CC1]

The title compound was prepared as described in General Scheme A using Intermediate R and Intermediate C, affording 3-(4-oxo-4H-pyrido[1,2-a]pyrimidin-2-yl)-N-((1r,4r)-4-(5-phenyl-1,3,4-oxadiazol-2-yl)cyclohexyl) propanamide (20 mg, 0.045 mmol, 5% yield) as off white solid. $^1$H NMR (400 MHz, DMSO-d$_6$) δ 9.2 (d, J=7.2 Hz, 1H), 8.04-8.02 (m, 2H), 7.70-7.80 (m, 1H), 7.64-7.58 (m, 1H), 7.50-7.52 (m, 3H), 7.10-7.20 (m, 1H), 6.38 (s, 1H), 5.90 (m, 1H), 3.83 (m, 1H), 3.04 (m, 2H), 2.94 (m, 1H), 2.67 (t, J=7.8 Hz, 2H), 2.15-2.26 (m, 4H), 1.75-1.86 (m, 2H), 1.24-1.32 (m, 2H); m/z (ESI) 444.9 (M+H)$^+$.

Example 39

3-((4-oxo-3,4-dihydroquinazolin-2-yl)thio)-N-((1s,3s)-3-(5-phenyl-1,3,4-oxadiazol-2-yl)cyclobutyl)propanamide

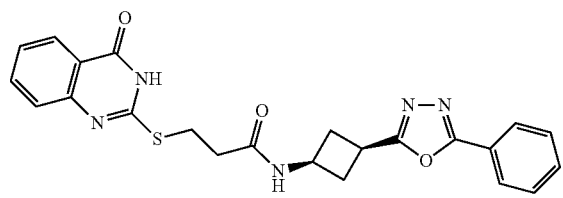 [SMILES: O=C(CCSc1nc2ccccc2c(=O)[nH]1)N[C@H]1C[C@@H](c2nnc(-c3ccccc3)o2)C1]

The title compound was prepared as described in General Scheme A using Intermediate J and Intermediate S, affording 3-((4-oxo-3,4-dihydroquinazolin-2-yl)thio)-N-((1s,3s)-3-(5-phenyl-1,3,4-oxadiazol-2-yl)cyclobutyl)propanamide (89 mg, 199 mmol, 29% yield) as light yellow solid. $^1$H NMR (400 MHz, DMSO-d$_6$) δ ppm 12.52-12.55 (m, 1H), 8.39 (d, J=1.00 Hz, 1H), 8.04 (dd, J=1.30 Hz, 1H), 7.97-8.00 (m, 2H), 7.74-7.80 (m, 1H),7.62 (s, 3H), 7.40-7.45 (m, 1H), 4.32-4.43 (m, 1H), 3.48-3.59 (m, 1H), 3.37-3.43 (m, 2H), 2.66-2.75 (m, 2H), 2.57-2.63 (m, 2H), 2.26-2.38 (m, 2H); LC-MS: 448 (M+1).

Example 40

3-((4-oxo-3,4-dihydroquinazolin-2-yl)thio)-N-((1r,3r)-3-(5-phenyl-1,3,4-oxadiazol-2-yl)cyclobutyl)propanamide

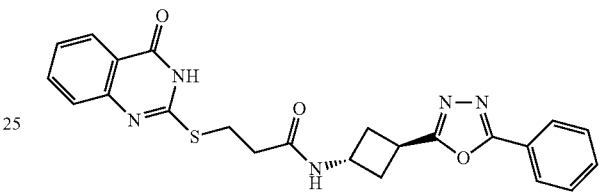

The title compound was prepared as described in General Scheme A using Intermediate J and Intermediate T, affording 3-((4-oxo-3,4-dihydroquinazolin-2-yl)thio)-N-((1r,3r)-3-(5-phenyl-1,3,4-oxadiazol-2-yl)cyclobutyl)propanamide as a light yellow solid (27 mg, 0.061 mmol, 65% yield). $^1$H NMR (400 MHz, DMSO-d$_6$) δ ppm 12.54 (s, 1H), 12.50-12.57 (m, 1H), 8.43 (d, J=1.00 Hz, 1H), 8.43 (d, J=7.73 Hz, 1H), 7.99-8.06 (m, 4H), 7.77 (m, J=1.00, 1.00 Hz, 1H), 7.60-7.65 (m, 3H), 7.55 (d, J=8.31 Hz, 1H), 7.42 (t, J=7.58 Hz, 1H), 4.48-4.57 (m, 1H), 3.70-3.78 (m, 1H), 3.40 (t, J=6.70 Hz, 2H), 2.59-2.70 (m, 4H), 2.42-2.49 (m, 2H); LC-MS: 448 (M+1).

Example 41

2-(4-oxo-4-(4-(2-oxo-2,3-dihydro-1H-benzimidazol-1-yl)-1-piperidinyl)butyl)-4(3H)-quinazolinone trifluoroacetic acid

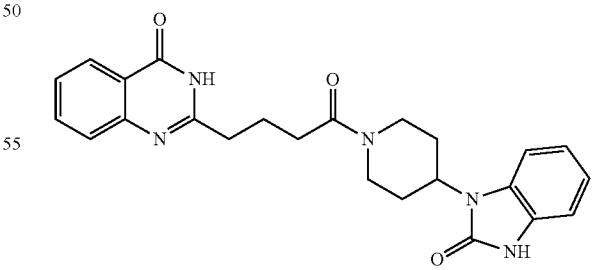

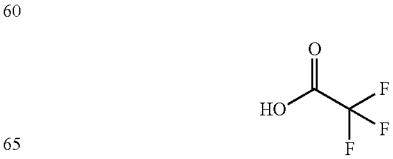

The title compound was prepared as described in General Scheme A using 4-(4-oxo-3,4-dihydroquinazolin-2-yl)butanoic acid (Enamine) and 1-(piperidin-4-yl)-1H-benzo[d]imidazol-2(3H)-one (Aldrich). Purification was accomplished using preparative LC/MS with 0.1% TFA in ACN and water as mobile phase. The pure fractions were dried in vacuo to afford 2-(4-oxo-4-(4-(2-oxo-2,3-dihydro-1H-benzimidazol-1-yl)-1-piperidinyl)butyl)-4(3H)-quinazolinone as the presumed trifluoroacetic acid salt as a solid (194 mg, 0.356 mmol, 44% yield). $^1$H NMR (600 MHz, DMSO-d$_6$) δ=10.82-10.81 (m, 1H), 10.84 (s, 1H), 8.11 (dd, J=1.4, 7.9 Hz, 1H), 7.93-7.78 (m, 1H), 7.64 (d, J=8.1 Hz, 1H), 7.52 (t, J=7.6 Hz, 1H), 7.27-7.12 (m, 1H), 7.03-6.89 (m, 3H), 4.55 (d, J=13.2 Hz, 1H), 4.40 (tt, J=4.1, 12.3 Hz, 1H), 4.04 (d, J=13.7 Hz, 1H), 3.22-3.10 (m, 1H), 2.81-2.70 (m, 2H), 2.69-2.59 (m, 1H), 2.28 (dq, J=4.2, 12.5 Hz, 2H), 2.11 (dd, J=4.4, 12.6 Hz, 1H), 2.03 (quin, J=7.4 Hz, 2H), 1.80-1.65 (m, 2H). m/z (ESI) 432.2 (M+H)$^+$.

Example 42

2-(4-oxo-4-(4-(5-phenyl-1,3,4-oxadiazol-2-yl)-1-piperidinyl)butyl)-4(3H)-quinazolinone

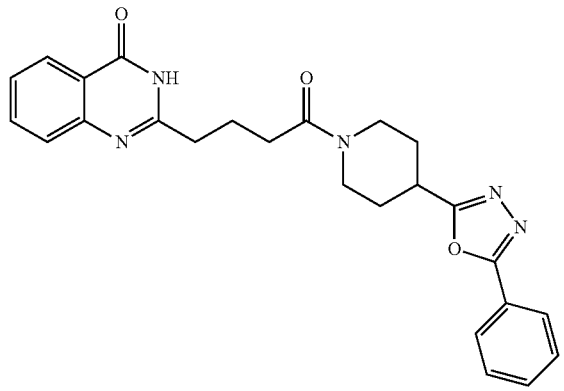 [SMILES: O=C(CCCc1nc2ccccc2c(=O)[nH]1)N1CCC(c2nnc(-c3ccccc3)o2)CC1]

The title compound was prepared as described in General Scheme A using 4-(4-oxo-3,4-dihydroquinazolin-2-yl)butanoic acid (Enamine) and 2-phenyl-5-(piperidin-4-yl)-1,3,4-oxadiazole (ASDI). Purification was accomplished using preparative LC/MS with 0.1% NH$_4$OH in ACN and water as mobile phase. The pure fractions were dried in vacuo to afford 2-(4-oxo-4-(4-(5-phenyl-1,3,4-oxadiazol-2-yl)-1-piperidinyl)butyl)-4(3H)-quinazolinone as a solid (103 mg, 0.232 mmol, 27% yield). $^1$H NMR (500 MHz, DMSO-d$_6$) δ=12.14 (br. s., 1H), 8.07 (d, J=6.9 Hz, 1H), 8.01-7.96 (m, 2H), 7.77-7.71 (m, 1H), 7.63-7.56 (m, 4H), 7.44 (t, J=7.4 Hz, 1H), 4.29 (d, J=13.1 Hz, 1H), 3.93 (d, J=13.5 Hz, 1H), 3.39-3.33 (m, 1H), 3.25 (t, J=12.0 Hz, 1H), 2.95-2.83 (m, 1H), 2.72-2.61 (m, 2H), 2.45 (dt, J=3.0, 7.4 Hz, 2H), 2.17-2.04 (m, 2H), 2.03-1.90 (m, 2H), 1.86-1.71 (m, 1H), 1.68-1.56 (m, 1H). m/z (ESI) 444.2 (M+H)$^+$.

Example 43

2-(4-oxo-4-(4-(2-oxo-2,3-dihydro-1H-indol-1-yl)-1-piperidinyl)butyl)-4(3H)-quinazolinone

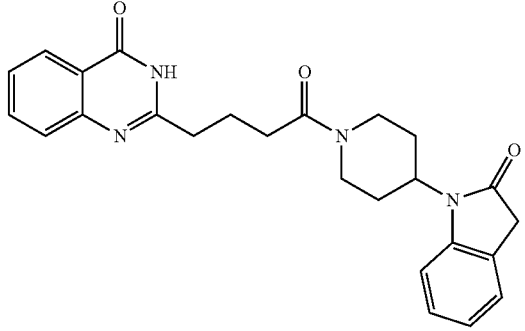

The title compound was prepared as described in General Scheme A using 4-(4-oxo-3,4-dihydroquinazolin-2-yl)butanoic acid (Enamine) and 1-(piperidin-4-yl)indolin-2-one (Aldrich). Purification was accomplished using preparative LC/MS with 0.1% NH$_4$OH in ACN and water as mobile phase. The pure fractions were dried in vacuo to afford 2-(4-oxo-4-(4-(2-oxo-2,3-dihydro-1H-indol-1-yl)-1-piperidinyl)butyl)-4(3H)-quinazolinone as a solid (267 mg, 0.621 mmol, 72% yield). $^1$H NMR (500 MHz, DMSO-d$_6$) δ=12.15 (br. s., 1H), 8.08 (dd, J=1.3, 7.9 Hz, 1H), 7.86-7.71 (m, 1H), 7.60 (d, J=8.0 Hz, 1H), 7.45 (t, J=7.4 Hz, 1H), 7.31-7.18 (m, 3H), 7.13 (d, J=7.9 Hz, 1H), 6.98 (t, J=7.4 Hz, 1H), 4.56 (d, J=12.8 Hz, 1H), 4.33 (ddd, J=4.2, 8.2, 12.1 Hz, 1H), 4.04 (d, J=12.9 Hz, 1H), 3.53 (s, 3H), 3.14 (t, J=12.3 Hz, 1H), 2.76-2.56 (m, 3H), 2.48-2.43 (m, 1H), 2.36-2.22 (m, 1H), 2.20-2.09 (m, 1H), 2.01 (quin, J=7.4 Hz, 2H), 1.76-1.59 (m, 2H). m/z (ESI) 431.2 (M+H)$^+$.

Example 44

2-(4-oxo-4-(4-(2-oxo-1,3-benzoxazol-3(2H)-yl)-1-piperidinyl)butyl)-4(3H)-quinazolinone

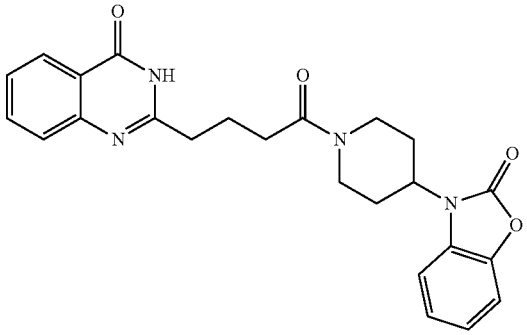 [SMILES: O=C(CCCc1nc2ccccc2c(=O)[nH]1)N1CCC(n2c(=O)oc3ccccc32)CC1]

The title compound was prepared as described in General Scheme A using 4-(4-oxo-3,4-dihydroquinazolin-2-yl)butanoic acid (Enamine) and 3-(piperidin-4-yl)benzo[d]oxazol-2(3H)-one (Oakwood). Purification was accomplished using preparative LC/MS with 0.1% NH$_4$OH in ACN and water as mobile phase. The pure fractions were dried in vacuo to afford 2-(4-oxo-4-(4-(2-oxo-1,3-benzoxazol-3(2H)-yl)-1-piperidinyl)butyl)-4(3H)-quinazolinone as a solid (89 mg, 0.206 mmol, 24% yield). $^1$H NMR (500 MHz, DMSO-d$_6$) δ=12.15 (s, 1H), 8.08 (d, J=6.5 Hz, 1H), 7.82-7.71 (m, 1H), 7.60 (d, J=8.0 Hz, 1H), 7.45 (t, J=7.5 Hz, 1H), 7.40 (s, 1H), 7.34 (d, J=7.6 Hz, 1H), 7.23-7.17 (m, 1H), 7.15-7.10 (m, 1H), 4.58 (d, J=12.6 Hz, 1H), 4.38 (t, J=12.3 Hz, 1H), 4.07 (d, J=13.7 Hz, 1H), 3.18 (t, J=13.6 Hz, 1H), 2.73-2.63 (m, 3H), 2.47 (m, 2H), 2.19 (d, J=12.8 Hz, 1H), 2.06-1.97 (m, 3H), 1.86 (t, J=16.6 Hz, 2H). m/z (ESI) 433.2 (M+H)+.

Example 45

2-(4-(4-(5-chloro-3-methyl-2-oxo-2,3-dihydro-1H-benzimidazol-1-yl)-1-piperidinyl)-4-oxobutyl)-4(3H)-quinazolinone

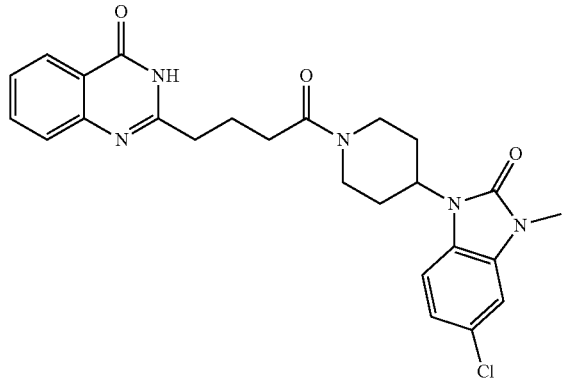 [SMILES: Cn1c(=O)n(C2CCN(C(=O)CCCc3nc4ccccc4c(=O)[nH]3)CC2)c2ccc(Cl)cc21]

The title compound was prepared as described in General Scheme A using 4-(4-oxo-3,4-dihydroquinazolin-2-yl)butanoic acid (Enamine) and 5-chloro-3-methyl-1-(piperidin-4-yl)-1H-benzo[d]imidazol-2(3H)-one (HDH Pharma). Purification was accomplished using preparative LC/MS with 0.1% NH4OH in ACN and water as mobile phase. The pure fractions were dried in vacuo to afford 2-(4-(4-(5-chloro-3-methyl-2-oxo-2,3-dihydro-1H-benzimidazol-1-yl)-1-piperidinyl)-4-oxobutyl)-4(3H)-quinazolinone as a solid (208 mg, 0.433 mmol, 50% yield). 1H NMR (500 MHz, DMSO-d6) δ=12.0 (br. s., 1H), 8.08 (d, J=7.9 Hz, 1H), 7.81-7.73 (m, 1H), 7.60 (d, J=8.1 Hz, 1H), 7.49-7.40 (m, 2H), 7.17-7.12 (m, 1H), 7.11-7.05 (m, 1H), 4.57 (d, J=12.8 Hz, 1H), 4.50-4.40 (m, 1H), 4.05 (d, J=12.1 Hz, 1H), 3.48-3.39 (m, 1H), 3.29 (s, 3H), 3.15 (t, J=12.4 Hz, 1H), 2.75-2.58 (m, 3H), 2.48-2.43 (m, 1H), 2.35-2.22 (m, 1H), 2.20-2.06 (m, 1H), 2.01 (quin, J=7.4 Hz, 2H), 1.80-1.65 (m, 2H). m/z (ESI) 480.2 (M+H)+.

Example 46

2-(4-oxo-4-(4-(2-oxo-2,3-dihydro-1H-benzimidazol-1-yl)-3,6-dihydro-1(2H)-pyridinyl)butyl)-4(3H)-quinazolinone trifluoroacetic acid

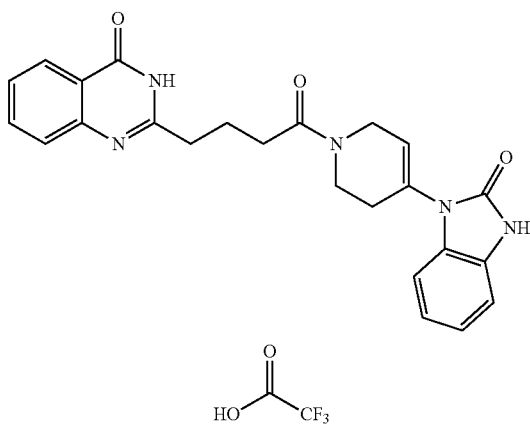 [SMILES: O=C(CCCc1nc2ccccc2c(=O)[nH]1)N1CC=C(n2c(=O)[nH]c3ccccc32)CC1 ; O=C(O)C(F)(F)F]

The title compound was prepared as described in General Scheme A using 4-(4-oxo-3,4-dihydroquinazolin-2-yl)butanoic acid (Enamine) and 1-(1,2,3,6-tetrahydropyridin-4-yl)-1H-benzo[d]imidazol-2(3H)-one (Aldrich). Purification was accomplished using preparative LC/MS with 0.1% TFA in ACN and water as mobile phase. The pure fractions were dried in vacuo to afford 2-(4-oxo-4-(4-(2-oxo-2,3-dihydro-1H-benzimidazol-1-yl)-3,6-dihydro-1(2H)-pyridinyl)butyl)-4(3H)-quinazolinone as the presumed trifluoroacetic acid salt as a solid (4 mg, 0.007 mmol, 1% yield). 1H NMR (500 MHz, DMSO-d6) δ=8.07 (d, J=7.9 Hz, 1H), 7.75 (q, J=6.8 Hz, 1H), 7.66-7.53 (m, 1H), 7.44 (t, J=7.4 Hz, 1H), 7.11-7.04 (m, 1H), 7.03-6.93 (m, 3H), 5.93 (br. s., 1H), 4.27-4.12 (m, 2H), 3.71 (t, J=5.6 Hz, 2H), 2.74-2.61 (m, 2H), 2.56-2.50 (m, 2H), 2.46-2.34 (m, 2H), 2.09-1.93 (m, 2H). m/z (ESI) 430.2 (M+H)+.

Example 47

2-(4-oxo-4-(4-(2-oxo-2,3-dihydro-1H-imidazo[4,5-b]pyridin-1-yl)-1-piperidinyl)butyl)-4(3H)-quinazolinone trifluoroacetic acid

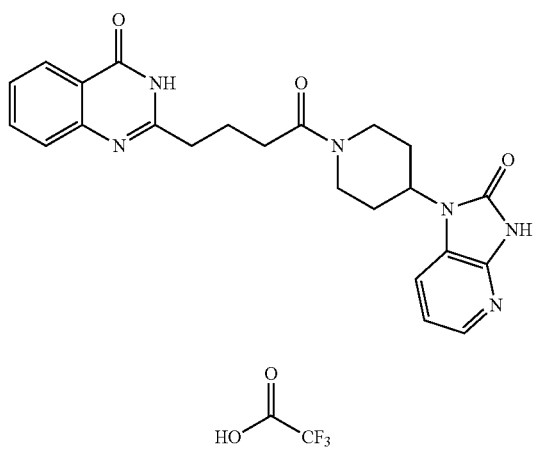 [SMILES: O=C(CCCc1nc2ccccc2c(=O)[nH]1)N1CCC(n2c(=O)[nH]c3ncccc32)CC1 ; O=C(O)C(F)(F)F]

The title compound was prepared as described in General Scheme A using 4-(4-oxo-3,4-dihydroquinazolin-2-yl)butanoic acid (Enamine) and 1-(piperidin-4-yl)-1H-imidazo[4,5-b]pyridin-2(3H)-one (Bionet). Purification was accomplished using preparative LC/MS with 0.1% TFA in ACN and water as mobile phase. The pure fractions were dried in vacuo to afford 2-(4-oxo-4-(4-(2-oxo-2,3-dihydro-1H-imidazo[4,5-b]pyridin-1-yl)-1-piperidinyl)butyl)-4(3H)-quinazolinone as the presumed trifluoroacetic acid salt as a solid (50 mg, 0.092 mmol, 11% yield). 1H NMR (500 MHz, DMSO-d6) (one proton is obscured by solvent peak) δ=12.11 (br. s., 1H), 11.09 (br. s., 1H), 8.20-8.00 (m, 1H), 7.91 (dd, J=1.1, 5.2 Hz, 1H), 7.82-7.70 (m, 1H), 7.61 (d, J=8.1 Hz, 1H), 7.45 (t, J=7.5 Hz, 1H), 7.28 (dd, J=1.1, 7.7 Hz, 1H), 6.98 (dd, J=5.2, 7.6 Hz, 1H), 4.57 (d, J=12.8 Hz, 1H), 4.53-4.44 (m, 1H), 4.05 (d, J=12.8 Hz, 1H), 3.15 (t, J=12.4 Hz, 1H), 2.73-2.58 (m, 3H), 2.48-2.42 (m, 2H), 2.41-2.28 (m, 1H), 2.00 (quin, J=7.4 Hz, 2H), 1.80-1.59 (m, 2H). m/z (ESI) 433.2 (M+H)+.

Example 48

2-(4-(4-(1H-indazol-3-yl)-1-piperidinyl)-4-oxobutyl)-4(3H)-quinazolinone trifluoroacetic acid

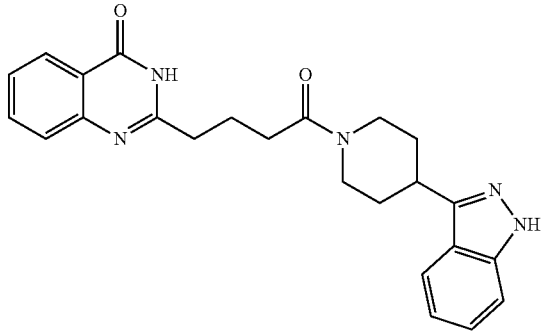

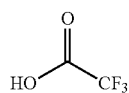

The title compound was prepared as described in General Scheme A using 4-(4-oxo-3,4-dihydroquinazolin-2-yl)butanoic acid (Enamine) and 3-(piperidin-4-yl)-1H-indazole (J&W Pharmlab). Purification was accomplished using preparative LC/MS with 0.1% TFA in ACN and water as mobile phase. The pure fractions were dried in vacuo to afford 2-(4-(4-(1H-indazol-3-yl)-1-piperidinyl)-4-oxobutyl)-4(3H)-quinazolinone as the presumed trifluoroacetic acid salt as a solid (37 mg, 0.070 mmol, 8% yield). $^1$H NMR (500 MHz, DMSO-d$_6$) (one proton is obscured by water peak) δ=12.66 (br. s., 1H), 8.08 (dd, J=1.2, 7.8 Hz, 1H), 7.83-7.70 (m, 2H), 7.59 (d, J=8.0 Hz, 1H), 7.51-7.41 (m, 2H), 7.35-7.26 (m, 1H), 7.06 (t, J=7.4 Hz, 1H), 4.46 (d, J=12.5 Hz, 1H), 4.00 (d, J=13.4 Hz, 1H), 2.85-2.72 (m, 1H), 2.71-2.59 (m, 2H), 2.48-2.36 (m, 2H), 2.25 (t, J=7.3 Hz, 1H), 2.07-1.89 (m, 4H), 1.87-1.74 (m, 1H), 1.72-1.59 (m, 1H). m/z (ESI) 416.2 (M+H)$^+$.

Example 49

2-(4-oxo-4-(4-(2-oxo-4-phenyl-2,3-dihydro-1H-imidazol-1-yl)-1-piperidinyl)butyl)-4(3H)-quinazolinone trifluoroacetic acid

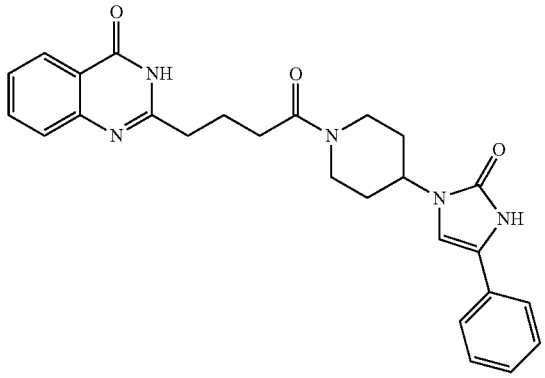

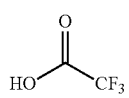

The title compound was prepared as described in General Scheme A using 4-(4-oxo-3,4-dihydroquinazolin-2-yl)butanoic acid (Enamine) and 4-phenyl-1-(4-piperidinyl)-4-imidazolin-2-one (Matrix). Purification was accomplished using preparative LC/MS with 0.1% TFA in ACN and water as mobile phase. The pure fractions were dried in vacuo to afford 4-phenyl-1-(piperidin-4-yl)-1H-imidazol-2(3H)-one as the presumed trifluoroacetic acid salt as a solid (44 mg, 0.086 mmol, 10% yield).

$^1$H NMR (500 MHz, DMSO-d$_6$) δ=12.15 (br. s., 1H), 10.83-10.55 (m, 1H), 8.11-8.05 (m, 1H), 7.80-7.70 (m, 1H), 7.60 (d, J=8.0 Hz, 1H), 7.53-7.48 (m, 2H), 7.45 (t, J=7.4 Hz, 1H), 7.36-7.28 (m, 2H), 7.20-7.11 (m, 2H), 4.53 (d, J=12.7 Hz, 1H), 4.16-3.96 (m, 2H), 3.21-3.08 (m, 1H), 2.74-2.56 (m, 3H), 2.48-2.36 (m, 2H), 2.00 (quin, J=7.4 Hz, 2H), 1.86-1.50 (m, 4H). m/z (ESI) 458.2 (M+H)$^+$.

Example 50

2-(4-oxo-4-(4-(2-oxo-1,3-benzothiazol-3(2H)-yl)-1-piperidinyl)butyl)-4(3H)-quinazolinone trifluoroacetic acid

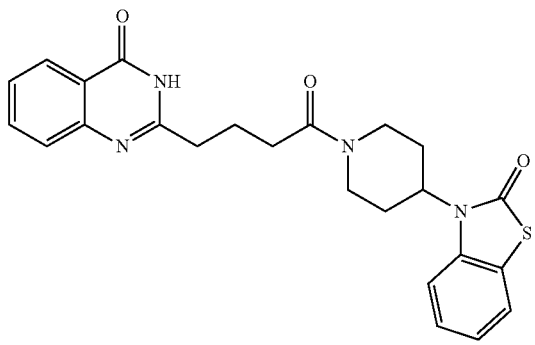

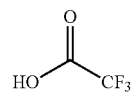

The title compound was prepared as described in General Scheme A using 4-(4-oxo-3,4-dihydroquinazolin-2-yl)butanoic acid (Enamine) and 3-(piperidin-4-yl)benzo[d]thiazol-2(3H)-one (HDH Pharma). Purification was accomplished using preparative LC/MS with 0.1% TFA in ACN and water as mobile phase. The pure fractions were dried in vacuo to afford 2-(4-oxo-4-(4-(2-oxo-1,3-benzothiazol-3(2H)-yl)-1-piperidinyl)butyl)-4(3H)-quinazolinone as the presumed trifluoroacetic acid salt as a solid (91 mg, 0.162 mmol, 19% yield). $^1$H NMR (500 MHz, DMSO-d$_6$) δ=12.14 (br. s., 1H), 8.08 (d, J=7.0 Hz, 1H), 7.82-7.72 (m, 1H), 7.64 (d, J=7.4 Hz, 1H), 7.60 (d, J=8.1 Hz, 1H), 7.54 (d, J=8.2 Hz, 1H), 7.45 (t, J=7.3 Hz, 1H), 7.37 (t, J=7.8 Hz, 1H), 7.19 (t, J=7.6 Hz, 1H), 4.70-4.50 (m, 2H), 4.05 (d, J=13.6 Hz, 1H), 3.19 (t, J=12.8 Hz, 1H), 2.67 (t, J=7.4 Hz, 3H), 2.48-2.44 (m, 2H), 2.44-2.33 (m, 1H), 2.31-2.19 (m, 1H), 2.00 (quin, J=7.4 Hz, 2H), 1.85-1.68 (m, 2H). m/z (ESI) 449.2 (M+H)$^+$.

Example 51

2-(4-(4-(5-fluoro-2-oxo-2,3-dihydro-1H-benzimidazol-1-yl)-1-piperidinyl)-4-oxobutyl)-4(3H)-quinazolinone trifluoroacetic acid

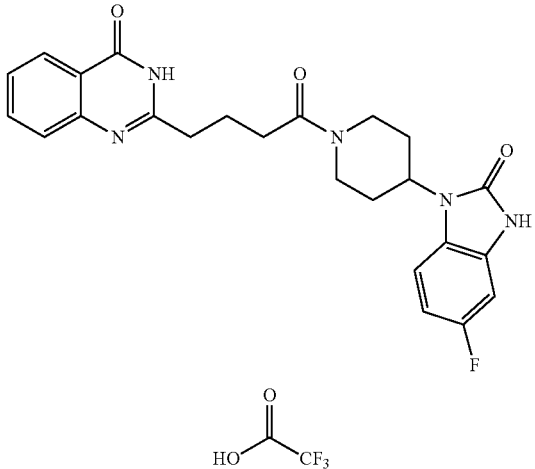 [SMILES: O=C(CCCc1nc2ccccc2c(=O)[nH]1)N1CCC(n2c(=O)[nH]c3cc(F)ccc32)CC1 ; O=C(O)C(F)(F)F]

The title compound was prepared as described in General Scheme A using 4-(4-oxo-3,4-dihydroquinazolin-2-yl)butanoic acid (Enamine) and 5-fluoro-1-(piperidin-4-yl)-1H-benzo[d]imidazol-2(3H)-one (HDH Pharma). Purification was accomplished using preparative LC/MS with 0.1% TFA in ACN and water as mobile phase. The pure fractions were dried in vacuo to afford 2-(4-(4-(5-fluoro-2-oxo-2,3-dihydro-1H-benzimidazol-1-yl)-1-piperidinyl)-4-oxobutyl)-4(3H)-quinazolinone as the presumed trifluoroacetic acid salt as a solid (48 mg, 0.085 mmol, 10% yield). $^1$H NMR (500 MHz, DMSO-$d_6$) δ=12.43-11.90 (m, 1H), 10.99 (br. s., 1H), 8.08 (d, J=7.8 Hz, 1H), 7.81-7.71 (m, 1H), 7.60 (d, J=8.0 Hz, 1H), 7.45 (t, J=7.4 Hz, 1H), 7.21 (dd, J=4.5, 8.7 Hz, 1H), 6.86-6.74 (m, 2H), 4.57 (d, J=12.7 Hz, 1H), 4.39 (tt, J=4.0, 12.1 Hz, 1H), 4.05 (d, J=13.4 Hz, 1H), 3.23-3.05 (m, 1H), 2.73-2.57 (m, 3H), 2.48-2.41 (m, 2H), 2.34-2.18 (m, 1H), 2.16-2.05 (m, 1H), 2.01 (quin, J=7.4 Hz, 2H), 1.72 (t, J=15.7 Hz, 2H). m/z (ESI) 450.2 (M+H)$^+$.

Example 52

2-(4-oxo-4-(4-(2-oxo-5-(trifluoromethyl)-2,3-dihydro-1H-benzimidazol-1-yl)-1-piperidinyl)butyl)-4(3H)-quinazolinone trifluoroacetic acid

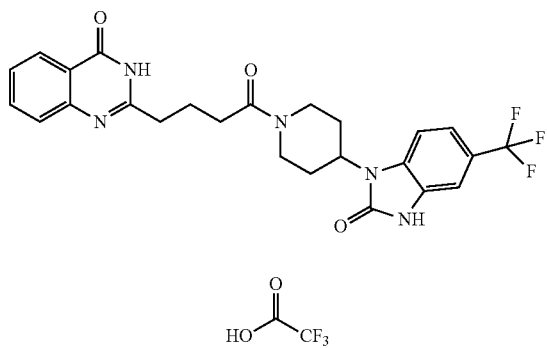 [SMILES: O=C(CCCc1nc2ccccc2c(=O)[nH]1)N1CCC(n2c(=O)[nH]c3cc(C(F)(F)F)ccc32)CC1 ; O=C(O)C(F)(F)F]

The title compound was prepared as described in General Scheme A using 4-(4-oxo-3,4-dihydroquinazolin-2-yl)butanoic acid (Enamine) and 1-(piperidin-4-yl)-5-(trifluoromethyl)-1H-benzo[d]imidazol-2(3H)-one (Chem Pacific). Purification was accomplished using preparative LC/MS with 0.1% TFA in ACN and water as mobile phase. The pure fractions were dried in vacuo to afford 2-(4-oxo-4-(4-(2-oxo-5-(trifluoromethyl)-2,3-dihydro-1H-benzimidazol-1-yl)-1-piperidinyl)butyl)-4(3H)-quinazolinone as the presumed trifluoroacetic acid salt as a solid (52 mg, 0.085 mmol, 10% yield). $^1$H NMR (500 MHz, DMSO-$d_6$) δ=8.08 (dd, J=1.0, 7.9 Hz, 1H), 7.81-7.71 (m, 1H), 7.60 (d, J=8.1 Hz, 1H), 7.50-7.40 (m, 2H), 7.33 (d, J=8.1 Hz, 1H), 7.22 (s, 1H), 4.58 (d, J=12.9 Hz, 1H), 4.46 (ddd, J=4.1, 8.2, 12.2 Hz, 1H), 4.06 (d, J=13.4 Hz, 1H), 3.20-3.11 (m, 2H), 2.73-2.58 (m, 3H), 2.48-2.42 (m, 1H), 2.34-2.20 (m, 1H), 2.20-2.07 (m, 1H), 2.01 (quin, J=7.4 Hz, 2H), 1.75 (t, J=15.2 Hz, 2H). m/z (ESI) 500.2 (M+H)$^+$.

Example 53

2-(4-(4-(6-fluoro-2-oxo-1,3-benzoxazol-3(2H)-yl)-1-piperidinyl)-4-oxobutyl)-4(3H)-quinazolinone trifluoroacetic acid

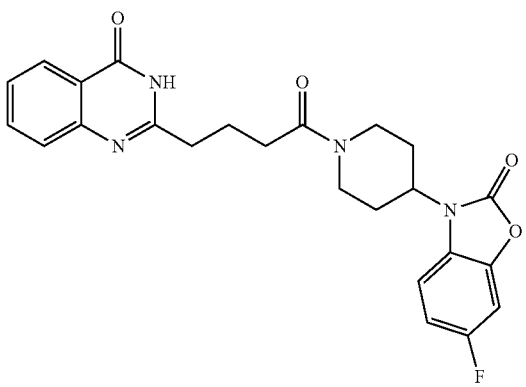

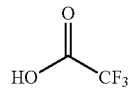

The title compound was prepared as described in General Scheme A using 4-(4-oxo-3,4-dihydroquinazolin-2-yl)butanoic acid (Enamine) and 6-fluoro-3-(piperidin-4-yl)benzo[d]oxazol-2(3H)-one (AB Chem). Purification was accomplished using preparative LC/MS with 0.1% TFA in ACN and water as mobile phase. The pure fractions were dried in vacuo to afford 2-(4-(4-(6-fluoro-2-oxo-1,3-benzoxazol-3(2H)-yl)-1-piperidinyl)-4-oxobutyl)-4(3H)-quinazolinone as the presumed trifluoroacetic acid salt as a solid (180 mg, 0.319 mmol, 37% yield). $^1$H NMR (500 MHz, DMSO-$d_6$) δ=12.15 (br. s., 1H), 8.08 (d, J=7.7 Hz, 1H), 7.81-7.71 (m, 1H), 7.59 (d, J=8.0 Hz, 1H), 7.49-7.34 (m, 3H), 7.10-6.99 (m, 1H), 4.58 (d, J=13.1 Hz, 1H), 4.37 (tt, J=4.0, 12.1 Hz, 1H), 4.06 (d, J=13.4 Hz, 1H), 3.16 (t, J=12.5 Hz, 1H), 2.72-2.59 (m, 3H), 2.48-2.39 (m, 2H), 2.25-2.09 (m, 1H), 2.01 (quin, J=7.4 Hz, 3H), 1.92-1.78 (m, 2H). m/z (ESI) 451.2 (M+H)$^+$.

Example 54

2-(4-(4-(3-methyl-2-oxo-2,3-dihydro-1H-benzimidazol-1-yl)-1-piperidinyl)-4-oxobutyl)-4(3H)-quinazolinone

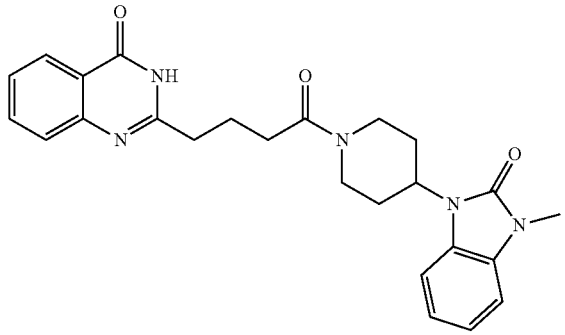 [SMILES: Cn1c(=O)n(C2CCN(C(=O)CCCc3nc4ccccc4c(=O)[nH]3)CC2)c2ccccc21]

The title compound was prepared as described in General Scheme A using 4-(4-oxo-3,4-dihydroquinazolin-2-yl)butanoic acid (Enamine) and 1-methyl-3-(piperidin-4-yl)-1H-benzo[d]imidazol-2(3H)-one (ASDI). Purification was accomplished using preparative LC/MS with 0.1% NH$_4$OH in ACN and water as mobile phase. The pure fractions were dried in vacuo to afford 2-(4-(4-(3-methyl-2-oxo-2,3-dihydro-1H-benzimidazol-1-yl)-1-piperidinyl)-4-oxobutyl)-4(3H)-quinazolinone as a solid (43 mg, 0.097 mmol, 11% yield). $^1$H NMR (500 MHz, DMSO-d$_6$) δ=12.15 (br. s., 1H), 8.08 (d, J=7.8 Hz, 1H), 7.76 (t, J=7.6 Hz, 1H), 7.60 (d, J=8.1 Hz, 1H), 7.45 (t, J=7.4 Hz, 1H), 7.28 (d, J=7.6 Hz, 1H), 7.14 (s, 1H), 7.10-6.96 (m, 2H), 4.58 (d, J=13.2 Hz, 1H), 4.46 (ddd, J=4.0, 8.1, 12.1 Hz, 1H), 4.06 (d, J=12.9 Hz, 1H), 3.3 (s, 3H), 3.24-3.12 (m, 1H), 2.77-2.59 (m, 3H), 2.48-2.46 (m, 2H), 2.36-2.22 (m, 1H), 2.19-2.08 (m, 1H), 2.02 (quin, J=7.4 Hz, 2H), 1.80-1.63 (m, 2H). m/z (ESI) 446.2 (M+H)$^+$.

Example 55

2-(4-(4-(1H-indazol-3-yl)-1-piperazinyl)-4-oxobutyl)-4(3H)-quinazolinone

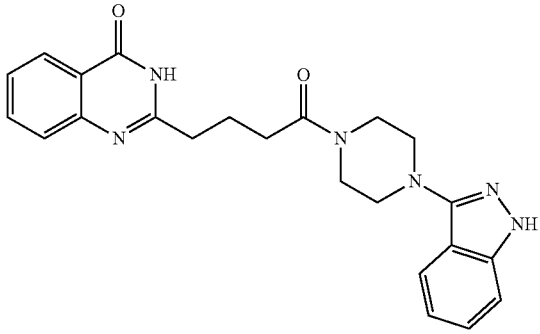 [SMILES: O=C(CCCc1nc2ccccc2c(=O)[nH]1)N1CCN(c2n[nH]c3ccccc23)CC1]

The title compound was prepared as described in General Scheme A using 4-(4-oxo-3,4-dihydroquinazolin-2-yl)butanoic acid (Enamine) and 3-(piperazin-1-yl)-1H-indazole (Anichem). Purification was accomplished using preparative LC/MS with 0.1% NH$_4$OH in ACN and water as mobile phase. The pure fractions were dried in vacuo to afford 2-(4-(4-(3-methyl-2-oxo-2,3-dihydro-1H-benzimidazol-1-yl)-1-piperidinyl)-4-oxobutyl)-4(3H)-quinazolinone as a solid (104 mg, 0.250 mmol, 29% yield). $^1$H NMR (500 MHz, DMSO-d$_6$) δ=12.14 (br. s., 1H), 12.02 (s, 1H), 8.08 (d, J=7.8 Hz, 1H), 7.80-7.70 (m, 2H), 7.60 (d, J=8.1 Hz, 1H), 7.45 (t, J=7.5 Hz, 1H), 7.39-7.33 (m, 1H), 7.32-7.25 (m, 1H), 6.98 (t, J=7.4 Hz, 1H), 3.65 (br. s., 4H), 3.32 (br. s., 4H), 2.67 (t, J=7.4 Hz, 2H), 2.48-2.44 (m, 2H), 2.01 (quin, J=7.4 Hz, 2H). m/z (ESI) 417.2 (M+H)$^+$.

Example 56

4-(4-oxo-3,4-dihydro-2-quinazolinyl)-N-(trans-4-(2-pyridinyloxyl)cyclohexyl)butanamide

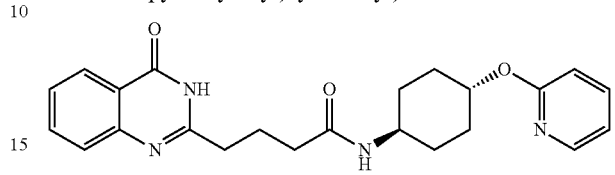

The title compound was prepared as described in General Scheme A using 4-(4-oxo-3,4-dihydroquinazolin-2-yl)butanoic acid (Enamine) and trans-4-(pyridin-2-yloxy)cyclohexanamine (Ryan Scientific). Purification was accomplished using preparative LC/MS with 0.1% NH$_4$OH in ACN and water as mobile phase. The pure fractions were dried in vacuo to afford 4-(4-oxo-3,4-dihydro-2-quinazolinyl)-N-(trans-4-(2-pyridinyloxyl)cyclohexyl)butanamide as a solid (20 mg, 0.049 mmol, 8% yield). $^1$H NMR (500 MHz, DMSO-d$_6$) δ=12.13 (br. s., 1H), 8.13 (dd, J=1.4, 5.0 Hz, 1H), 8.08 (dd, J=1.3, 7.9 Hz, 1H), 7.83-7.74 (m, 1H), 7.71 (d, J=7.8 Hz, 1H), 7.66 (ddd, J=2.0, 6.9, 8.5 Hz, 1H), 7.60 (d, J=8.0 Hz, 1H), 7.46 (t, J=7.5 Hz, 1H), 6.92 (dd, J=5.4, 6.6 Hz, 1H), 6.73 (d, J=8.4 Hz, 1H), 5.01-4.81 (m, 1H), 3.68-3.49 (m, 1H), 2.60 (t, J=7.5 Hz, 2H), 2.18-2.10 (m, 2H), 2.09-2.02 (m, 2H), 1.96 (quin, J=7.4 Hz, 2H), 1.83 (d, J=10.9 Hz, 2H), 1.49-1.38 (m, 2H), 1.36-1.21 (m, 2H). m/z (ESI) 407.2 (M+H)$^+$.

Example 57

N-(trans-4-(2-cyanophenoxy)cyclohexyl)-4-(4-oxo-3,4-dihydro-2-quinazolinyl)butanamide

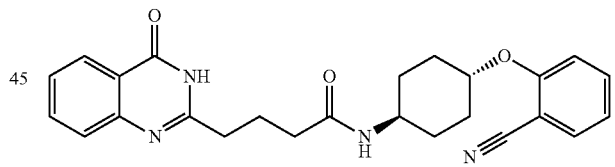

The title compound was prepared as described in General Scheme A using 4-(4-oxo-3,4-dihydroquinazolin-2-yl)butanoic acid (Enamine) and 2-(((trans)-4-aminocyclohexyl)oxy)benzonitrile (HDH Pharma). Purification was accomplished using preparative LC/MS with 0.1% NH$_4$OH in ACN and water as mobile phase. The pure fractions were dried in vacuo to afford N-(trans-4-(2-cyanophenoxy)cyclohexyl)-4-(4-oxo-3,4-dihydro-2-quinazolinyl)butanamide as a solid (97 mg, 0.225 mmol, 35% yield).

$^1$H NMR (500 MHz, DMSO-d$_6$) δ=12.13 (br. s., 1H), 8.08 (dd, J=1.1, 7.9 Hz, 1H), 7.81-7.71 (m, 2H), 7.69 (dd, J=1.6, 7.7 Hz, 1H), 7.65-7.57 (m, 2H), 7.46 (t, J=7.5 Hz, 1H), 7.32 (d, J=8.6 Hz, 1H), 7.06 (t, J=7.6 Hz, 1H), 4.60-4.42 (m, 1H), 3.73-3.51 (m, 1H), 2.61 (t, J=7.4 Hz, 2H), 2.22-2.11 (m, 2H), 2.05 (dd, J=3.0, 12.6 Hz, 2H), 1.96 (quin, J=7.4 Hz, 2H), 1.85 (dd, J=3.4, 13.1 Hz, 2H), 1.60-1.43 (m, 2H), 1.40-1.27 (m, 2H). m/z (ESI) 431.2 (M+H)$^+$.

Example 58

N-(trans-4-(3-cyanophenoxy)cyclohexyl)-4-(4-oxo-3,4-dihydro-2-quinazolinyl)butanamide

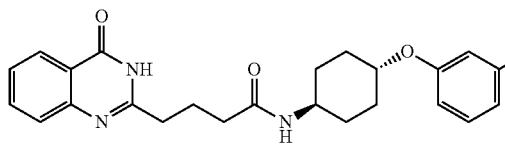

The title compound was prepared as described in General Scheme A using 4-(4-oxo-3,4-dihydroquinazolin-2-yl)butanoic acid (Enamine) and 3-(((trans)-4-aminocyclohexyl)oxy)benzonitrile (HDH Pharma). Purification was accomplished using preparative LC/MS with 0.1% NH$_4$OH in ACN and water as mobile phase. The pure fractions were dried in vacuo to afford N-(trans-4-(3-cyanophenoxy)cyclohexyl)-4-(4-oxo-3,4-dihydro-2-quinazolinyl)butanamide as a solid (30 mg, 0.071 mmol, 11% yield).

$^1$H NMR (500 MHz, DMSO-d$_6$) δ=12.13 (br. s., 1H), 8.08 (dd, J=1.3, 7.9 Hz, 1H), 7.81-7.71 (m, 2H), 7.60 (d, J=8.0 Hz, 1H), 7.49-7.41 (m, 3H), 7.35 (d, J=7.8 Hz, 1H), 7.28 (dd, J=2.2, 8.0 Hz, 1H), 4.50-4.33 (m, 1H), 3.66-3.45 (m, 1H), 2.60 (t, J=7.4 Hz, 2H), 2.23-2.10 (m, 2H), 2.03 (d, J=10.0 Hz, 2H), 1.96 (quin, J=7.4 Hz, 2H), 1.82 (d, J=9.5 Hz, 2H), 1.52-1.23 (m, 4H). m/z (ESI) 431.2 (M+H)$^+$.

Example 59

4-(4-oxo-3,4-dihydro-2-quinazolinyl)-N-(trans-4-(3-pyridinyloxyl)cyclohexyl)butanamide

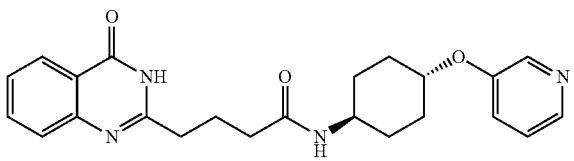 [SMILES: O=C(CCCc1nc2ccccc2c(=O)[nH]1)N[C@H]1CC[C@H](Oc2cccnc2)CC1]

The title compound was prepared as described in General Scheme A using 4-(4-oxo-3,4-dihydroquinazolin-2-yl)butanoic acid (Enamine) and trans-4-(pyridin-3-yloxy)cyclohexanamine (Ryan Scientific). Purification was accomplished using preparative LC/MS with 0.1% NH$_4$OH in ACN and water as mobile phase. The pure fractions were dried in vacuo to afford 4-(4-oxo-3,4-dihydro-2-quinazolinyl)-N-(trans-4-(3-pyridinyloxyl)cyclohexyl)butanamide as a solid (39 mg, 0.096 mmol, 15% yield). $^1$H NMR (500 MHz, DMSO-d$_6$) δ=12.13 (br. s., 1H), 8.26 (d, J=2.9 Hz, 1H), 8.13 (dd, J=1.1, 4.6 Hz, 1H), 8.08 (dd, J=1.3, 7.9 Hz, 1H), 7.82-7.69 (m, 2H), 7.60 (d, J=7.9 Hz, 1H), 7.49-7.43 (m, 1H), 7.41 (ddd, J=1.3, 2.9, 8.4 Hz, 1H), 7.29 (dd, J=4.6, 8.4 Hz, 1H), 4.44-4.30 (m, 1H), 3.64-3.50 (m, 1H), 2.60 (t, J=7.4 Hz, 2H), 2.20-2.09 (m, 2H), 2.04 (d, J=9.9 Hz, 2H), 1.96 (quin, J=7.4 Hz, 2H), 1.82 (d, J=10.2 Hz, 2H), 1.51-1.37 (m, 2H), 1.35-1.23 (m, 2H). m/z (ESI) 407.2 (M+H)$^+$.

Example 60

2-(4-(4-(3,3-difluoro-2-oxo-2,3-dihydro-1H-indol-1-yl)-1-piperidinyl)-4-oxobutyl)-4(3H)-quinazolinone

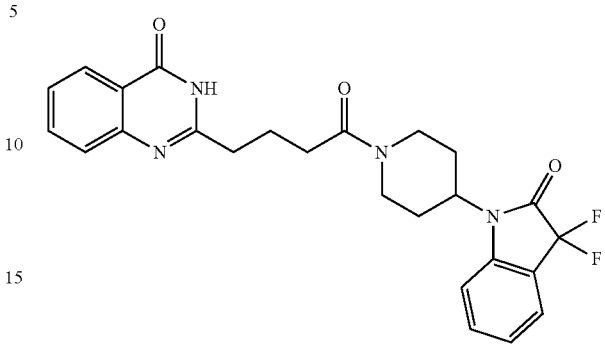

The title compound was prepared as described in General Scheme A using 4-(4-oxo-3,4-dihydroquinazolin-2-yl)butanoic acid (Enamine) and 3,3-difluoro-1-(piperidin-4-yl)indolin-2-one (HDH Pharma). Purification was accomplished using preparative LC/MS with 0.1% NH$_4$OH in ACN and water as mobile phase. The pure fractions were dried in vacuo to afford 2-(4-(4-(3,3-difluoro-2-oxo-2,3-dihydro-1H-indol-1-yl)-1-piperidinyl)-4-oxobutyl)-4(3H)-quinazolinone as a solid (70 mg, 0.150 mmol, 23% yield).
$^1$H NMR (500 MHz, DMSO-d$_6$) δ=12.15 (br. s., 1H), 8.08 (dd, J=1.3, 7.9 Hz, 1H), 7.81-7.74 (m, 1H), 7.70 (d, J=7.1 Hz, 1H), 7.64-7.57 (m, 2H), 7.47-7.40 (m, 2H), 7.23 (t, J=7.5 Hz, 1H), 4.56 (d, J=13.1 Hz, 1H), 4.40-4.24 (m, 1H), 4.13-4.00 (m, 1H), 3.21-3.08 (m, 2H), 2.74-2.58 (m, 3H), 2.48-2.41 (m, 1H), 2.29-2.14 (m, 1H), 2.11-1.94 (m, 3H), 1.80 (t, J=15.3 Hz, 2H). m/z (ESI) 467.2 (M+H)$^+$.

Example 61

2-oxo-1-(1-(4-(4-oxo-3,4-dihydro-2-quinazolinyl)butanoyl)-4-piperidinyl)-2,3-dihydro-1H-benzimidazole-4-carbonitrile

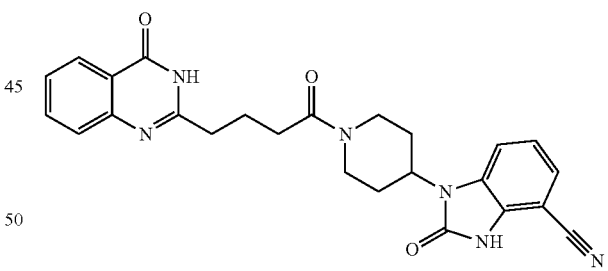

The title compound was prepared as described in General Scheme A using 4-(4-oxo-3,4-dihydroquinazolin-2-yl)butanoic acid (Enamine) and 2-oxo-1-(piperidin-4-yl)-2,3-dihydro-1H-benzo[d]imidazole-4-carbonitrile (HDH Pharma). Purification was accomplished using preparative LC/MS with 0.1% NH$_4$OH in ACN and water as mobile phase. The pure fractions were dried in vacuo to afford 2-oxo-1-(1-(4-(4-oxo-3,4-dihydro-2-quinazolinyl)butanoyl)-4-piperidinyl)-2,3-dihydro-1H-benzimidazole-4-carbonitrile as a solid (61 mg, 0.135 mmol, 21% yield). $^1$H NMR (500 MHz, DMSO-d6) δ ppm 12.17 (br. s., 1H), 11.44 (br. s., 1H), 8.11 (d, J=7.90 Hz, 1H), 7.72-7.85 (m, 1H), 7.63 (d, J=7.96 Hz, 1H), 7.48 (t, J=7.53 Hz, 1H), 7.41 (d, J=7.96 Hz, 1H), 7.30 (d, J=7.79 Hz, 1H), 7.16 (t, J=7.90 Hz, 1H), 4.82 (s, 1H), 4.65 (br. s., 1H), 4.12 (br. s., 1H), 3.10 (br. s., 1H), 2.70 (t, J=7.36 Hz, 2H), 2.57 (br. s., 1H), 2.36 (br. s., 2H), 2.02 (t, J=7.36 Hz, 3H), 1.89 (br. s., 2H). m/z (ESI) 457.2 (M+H)$^+$.

Example 62

N-((1R,3R)-3-(benzyloxy)cyclopentyl)-4-(4-oxo-3,4-dihydroquinazolin-2-yl)butanamide+N-((1S,3S)-3-(benzyloxy)cyclopentyl)-4-(4-oxo-3,4-dihydroquinazolin-2-yl)butanamide

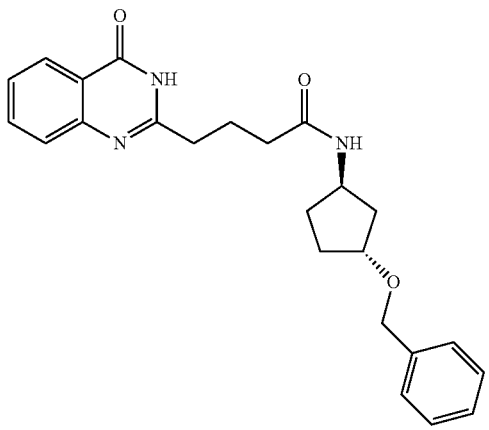

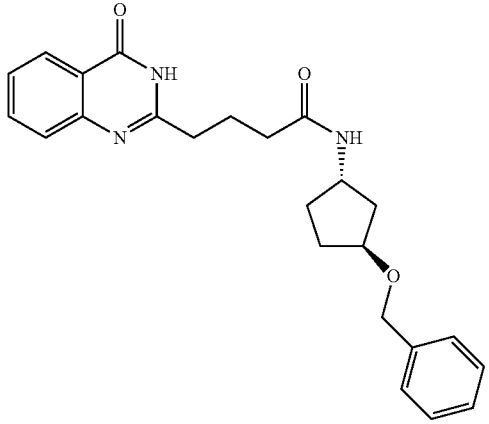

The title compound was prepared as described in General Scheme A using 4-(4-oxo-3,4-dihydroquinazolin-2-yl)butanoic acid (Enamine) and trans-3-(benzyloxy)cyclopentanamine (HDH Pharma). Purification was accomplished using preparative LC/MS with 0.1% NH$_4$OH in ACN and water as mobile phase. The pure fractions were dried in vacuo to afford racemic mixture N-((1R,3R)-3-(benzyloxy)cyclopentyl)-4-(4-oxo-3,4-dihydroquinazolin-2-yl)butanamide+N-((1S,3S)-3-(benzyloxy)cyclopentyl)-4-(4-oxo-3,4-dihydroquinazolin-2-yl)butanamide as a solid (44 mg, 0.108 mmol, 17% yield). $^1$H NMR (500 MHz, DMSO-d6) δ ppm=12.11 (br. s., 1H), 8.08 (d, J=6.70 Hz, 1H), 7.73-7.81 (m, 2H), 7.59 (d, J=8.08 Hz, 1H), 7.45 (t, J=7.50 Hz, 1H), 7.28-7.33 (m, 4H), 7.25 (d, J=6.30 Hz, 1H), 4.40 (s, 2H), 3.89-4.01 (m, 2H), 2.59 (t, J=7.47 Hz, 2H), 2.09-2.22 (m, 3H), 1.94 (t, J=7.36 Hz, 2H), 1.66-1.82 (m, 3H), 1.41-1.59 (m, 2H). m/z (ESI) 406.2 (M+H)$^+$.

Example 63

N-(trans-4-(4-chloro-3-cyanophenoxy)cyclohexyl)-4-(4-oxo-3,4-dihydro-2-quinazolinyl)butanamide

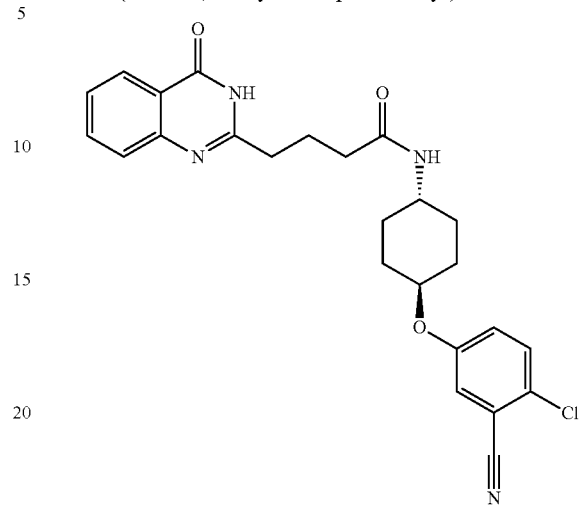

The title compound was prepared as described in General Scheme A using 4-(4-oxo-3,4-dihydroquinazolin-2-yl)butanoic acid (Enamine) and 5-(((trans)-4-aminocyclohexyl)oxy)-2-chlorobenzonitrile (HDH Pharma). Purification was accomplished using preparative LC/MS with 0.1% NH$_4$OH in ACN and water as mobile phase. The pure fractions were dried in vacuo to afford N-(trans-4-(4-chloro-3-cyanophenoxy)cyclohexyl)-4-(4-oxo-3,4-dihydro-2-quinazolinyl)butanamide as a solid (16 mg, 0.035 mmol, 5% yield. $^1$H NMR (500 MHz, DMSO-d6) δ ppm=8.08 (d, J=7.90 Hz, 1H), 7.72-7.79 (m, 2H), 7.55-7.64 (m, 3H), 7.46 (t, J=7.99 Hz, 1H), 7.30 (dd, J=9.02, 3.06 Hz, 1H), 4.39 (br. s., 1H), 2.60 (t, J=7.45 Hz, 2H), 2.07-2.17 (m, 2H), 2.01 (br. s., 2H), 1.96 (t, J=7.36 Hz, 2H), 1.80 (br. s., 2H), 1.41 (d, J=12.89 Hz, 2H), 1.31 (d, J=13.17 Hz, 2H). m/z (ESI) 465.2 (M+H)$^+$.

Example 64

N-(trans-4-(3-chloro-4-cyanophenoxy)cyclohexyl)-4-(4-oxo-3,4-dihydro-2-quinazolinyl)butanamide

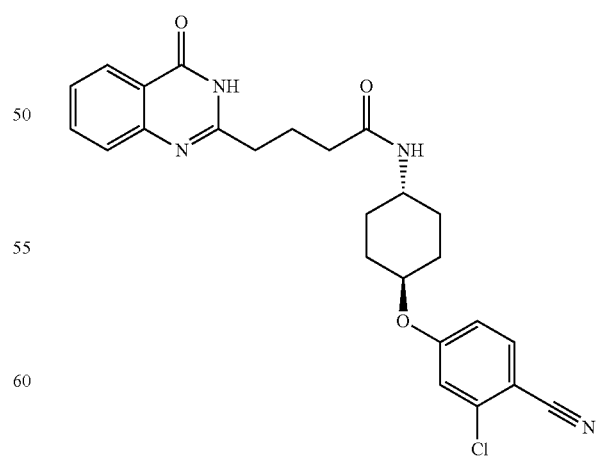

The title compound was prepared as described in General Scheme A using 4-(4-oxo-3,4-dihydroquinazolin-2-yl)butanoic acid (Enamine) and 4-(((trans)-4-aminocyclohexyl)

oxy)-2-chlorobenzonitrile (HDH Pharma). Purification was accomplished using preparative LC/MS with 0.1% NH₄OH in ACN and water as mobile phase. The pure fractions were dried in vacuo to afford N-(trans-4-(3-chloro-4-cyanophenoxy)cyclohexyl)-4-(4-oxo-3,4-dihydro-2-quinazolinyl)butanamide as a solid (17 mg, 0.038 mmol, 6% yield). $^1$H NMR (500 MHz, DMSO-d₆) δ=12.27 (br. s., 1H); 8.09 (dd, J=1.1, 7.9 Hz, 1H), 7.84 (d, J=8.7 Hz, 1H), 7.81-7.71 (m, 2H), 7.61 (d, J=7.9 Hz, 1H), 7.48 (t, J=7.5 Hz, 1H), 7.36 (d, J=2.4 Hz, 1H), 7.11 (dd, J=2.4, 8.8 Hz, 1H), 4.62-4.43 (m, 1H), 3.69-3.56 (m, 1H), 2.63 (t, J=7.4 Hz, 2H), 2.24-2.10 (m, 2H), 2.08-1.90 (m, 4H), 1.81 (d, J=9.7 Hz, 2H), 1.56-1.25 (m, 4H). m/z (ESI) 465.2 (M+H)⁺.

Example 65

4-(4-oxo-3,4-dihydroquinazolin-2-yl)-N-((1S,3S)-3-phenoxycyclopentyl)butanamide+4-(4-oxo-3,4-dihydroquinazolin-2-yl)-N-((1R,3R)-3-phenoxycyclopentyl)butanamide

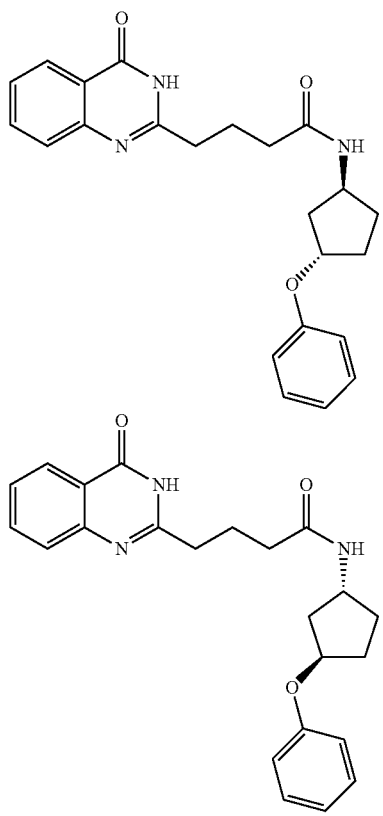

The title compound was prepared as described in General Scheme A using 4-(4-oxo-3,4-dihydroquinazolin-2-yl)butanoic acid (Enamine) and racemic trans-3-phenoxycyclopentanamine (HDH Pharma). Purification was accomplished using preparative LC/MS with 0.1% NH₄OH in ACN and water as mobile phase. The pure fractions were dried in vacuo to afford racemic mixture 4-(4-oxo-3,4-dihydroquinazolin-2-yl)-N-((1S,3S)-3-phenoxycyclopentyl)butanamide+4-(4-oxo-3,4-dihydroquinazolin-2-yl)-N-((1R,3R)-3-phenoxycyclopentyl)butanamide as a solid (37 mg, 0.095 mmol, 16% yield. $^1$H NMR (500 MHz, DMSO-d₆) δ=12.12 (br. s., 1H), 8.08 (d, J=7.96 Hz, 1H), 7.85 (d, J=7.22 Hz, 1H), 7.73-7.79 (m, 1H), 7.59 (d, J=8.08 Hz, 1H), 7.45 (t, J=7.10 Hz, 1H), 7.26 (t, J=7.96 Hz, 2H), 6.83-6.92 (m, 3H), 4.84 (br. s., 1H), 4.15-4.23 (m, 1H), 2.60 (t, J=7.42 Hz, 2H), 2.07-2.17 (m, 3H), 1.87-2.03 (m, 4H), 1.72-1.86 (m, 1H), 1.68 (br. s., 1H), 1.39-1.50 (m, 1H). m/z (ESI) 393.2 (M+H)⁺.

Example 66

N-(trans-4-(3-chlorophenoxy)cyclohexyl)-4-(4-oxo-3,4-dihydro-2-quinazolinyl)butanamide

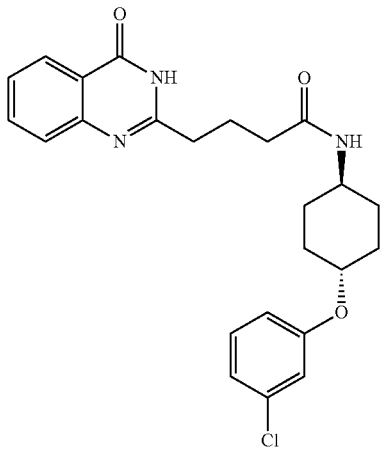 [SMILES: O=C(CCCc1nc2ccccc2c(=O)[nH]1)N[C@H]1CC[C@H](Oc2cccc(Cl)c2)CC1]

The title compound was prepared as described in General Scheme A using 4-(4-oxo-3,4-dihydroquinazolin-2-yl)butanoic acid (Enamine) and trans-4-(3-chlorophenoxy)cyclohexanamine (HDH Pharma). Purification was accomplished using preparative LC/MS with 0.1% NH₄OH in ACN and water as mobile phase. The pure fractions were dried in vacuo to afford N-(trans-4-(3-chlorophenoxy)cyclohexyl)-4-(4-oxo-3,4-dihydro-2-quinazolinyl)butanamide as a solid (12 mg, 0.028 mmol, 4% yield).

$^1$H NMR (500 MHz, DMSO-d₆) One proton is obscured by water peak. δ=8.14-8.06 (m, 1H), 7.85-7.79 (m, 1H), 7.75 (d, J=7.7 Hz, 1H), 7.62 (d, J=8.0 Hz, 1H), 7.51 (t, J=7.3 Hz, 1H), 7.27 (t, J=8.2 Hz, 1H), 7.02 (t, J=2.1 Hz, 1H), 6.93 (ddd, J=1.8, 8.1, 18.1 Hz, 2H), 4.41-4.28 (m, 1H), 2.65 (t, J=7.4 Hz, 2H), 2.23-2.10 (m, 2H), 2.07-1.91 (m, 4H), 1.81 (d, J=10.3 Hz, 2H), 1.48-1.18 (m, 4H). m/z (ESI) 440.2 (M+H)⁺.

Example 67

2-(4-(4-(4-fluoro-2-oxo-2,3-dihydro-1H-benzimidazol-1-yl)-1-piperidinyl)-4-oxobutyl)-4(3H)-quinazolinone

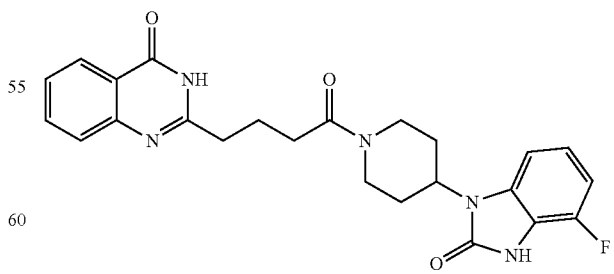

The title compound was prepared as described in General Scheme A using and 4-(4-oxo-3,4-dihydroquinazolin-2-yl) butanoic acid (Enamine) trans-4-(3-chlorophenoxy)cyclohexanamine (HDH Pharma). Purification was accomplished using preparative LC/MS with 0.1% NH$_4$OH in ACN and water as mobile phase. The pure fractions were dried in vacuo to afford 2-(4-(4-(4-fluoro-2-oxo-2,3-dihydro-1H-benzimidazol-1-yl)-1-piperidinyl)-4-oxobutyl)-4(3H)-quinazolinone as a solid (30 mg, 0.067 mmol, 10% yield). $^1$H NMR (500 MHz, DMSO-d$_6$) δ ppm=12.17 (br. s., 1H), 11.42 (s, 1H), 8.10 (d, J=6.76 Hz, 1H), 7.76-7.80 (m, 1H), 7.62 (d, J=7.90 Hz, 1H), 7.47 (t, J=7.05 Hz, 1H), 7.12 (d, J=7.96 Hz, 1H), 6.99 (d, J=5.16 Hz, 1H), 6.86-6.92 (m, 1H), 4.43 (br. s., 1H), 3.18 (br. s., 2H), 2.70 (t, J=7.36 Hz, 4H), 2.48 (br. s., 1H), 2.03 (t, J=7.45 Hz, 4H), 1.75 (br. s., 2H). m/z (ESI) 450.2 (M+H)$^+$.

Example 68

2-oxo-1-(1-(4-(4-oxo-3,4-dihydro-2-quinazolinyl)butanoyl)-4-piperidinyl)-2,3-dihydro-1H-benzimidazole-5-carbonitrile

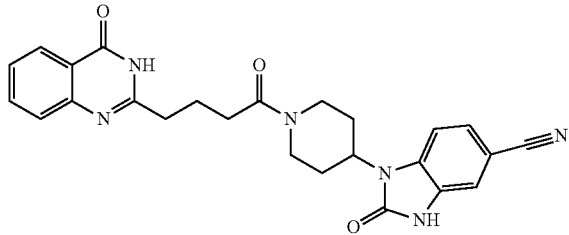 [SMILES: N#Cc1ccc2c(c1)[nH]c(=O)n2C1CCN(C(=O)CCCc2nc3ccccc3c(=O)[nH]2)CC1]

The title compound was prepared as described in General Scheme A using and 4-(4-oxo-3,4-dihydroquinazolin-2-yl)butanoic acid (Enamine) 2-oxo-1-(piperidin-4-yl)-2,3-dihydro-1H-benzo[d]imidazole-5-carbonitrile (HDH Pharma). Purification was accomplished using preparative LC/MS with 0.1% NH$_4$OH in ACN and water as mobile phase. The pure fractions were dried in vacuo to afford 2-oxo-1-(1-(4-(4-oxo-3,4-dihydro-2-quinazolinyl)butanoyl)-4-piperidinyl)-2,3-dihydro-1H-benzimidazole-5-carbonitrile as a solid (65 mg, 0.142 mmol, 22% yield). $^1$H NMR (500 MHz, DMSO-d$_6$) δ ppm=8.08 (d, J=7.90 Hz, 1H), 7.73-7.78 (m, 1H), 7.60 (d, J=7.96 Hz, 1H), 7.41-7.49 (m, 3H), 7.36 (s, 1H), 4.56 (br. s., 1H), 4.46 (br. s., 1H), 4.04 (br. s., 1H), 3.16 (br. s., 1H), 2.52-2.71 (m, 4H), 2.45-2.49 (m, 2H), 2.12 (br. s., 1H), 1.98-2.07 (m, 2H), 1.74 (br. s., 2H), 1.37 (s, 1H). m/z (ESI) 457.2 (M+H)$^+$.

Example 69

2-(4-(4-(1,2-benzisothiazol-3-yl)-1-piperazinyl)-4-oxobutyl)-4(3H)-quinazolinone

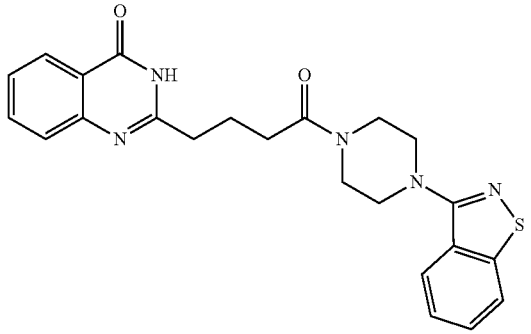 [SMILES: O=C(CCCc1nc2ccccc2c(=O)[nH]1)N1CCN(c2nsc3ccccc23)CC1]

The title compound was prepared as described in General Scheme A using 4-(4-oxo-3,4-dihydroquinazolin-2-yl)butanoic acid (Enamine) and 3-(piperazin-1-yl)benzo[d]isothiazole (Aldrich). Purification was accomplished using preparative LC/MS with 0.1% NH$_4$OH in ACN and water as mobile phase. The pure fractions were dried in vacuo to afford 2-(4-(4-(1,2-benzisothiazol-3-yl)-1-piperazinyl)-4-oxobutyl)-4(3H)-quinazolinone as a solid (130 mg, 0.30 mmol, 36% yield). $^1$H NMR (500 MHz, DMSO-d6) δ ppm=8.05-8.12 (m, 3H), 7.76 (t, J=7.65 Hz, 1H), 7.55-7.62 (m, 2H), 7.45 (t, J=7.53 Hz, 2H), 3.68 (br. s., 4H), 3.46 (br. s., 2H), 3.41 (br. s., 2H), 2.67 (t, J=7.42 Hz, 2H), 2.39-2.49 (m, 2H), 2.02 (t, J=7.33 Hz, 2H). m/z (ESI) 434.2 (M+H)$^+$.

Example 70

4-(4-oxo-3,4-dihydro-2-quinazolinyl)-N-(trans-4-(4-pyridinyloxyl)cyclohexyl)butanamide

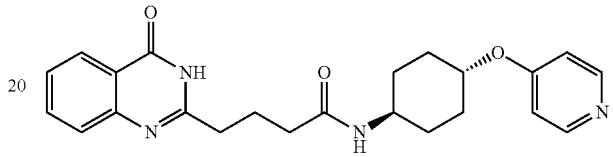

The title compound was prepared as described in General Scheme A using 4-(4-oxo-3,4-dihydroquinazolin-2-yl)butanoic acid (Enamine) and trans-4-(pyridin-4-yloxy)cyclohexanamine (HDH Pharma). Purification was using SFC preparative column chromatography. The pure fractions were dried in vacuo to afford 4-(4-oxo-3,4-dihydro-2-quinazolinyl)-N-(trans-4-(4-pyridinyloxyl)cyclohexyl)butanamide as a solid (46 mg, 0.113 mmol, 18% yield'H NMR (400 MHz, DMSO-d$_6$) δ=12.18 (br. s., 1H), 8.36 (d, J=6.2 Hz, 2H), 8.08 (dd, J=1.3, 7.9 Hz, 1H), 7.86-7.74 (m, 2H), 7.61 (d, J=8.2 Hz, 1H), 7.50-7.42 (m, 1H), 7.06-6.94 (m, 2H), 4.53-4.37 (m, 1H), 3.68-3.48 (m, 1H), 2.61 (t, J=7.4 Hz, 2H), 2.22-2.11 (m, 2H), 2.05 (d, J=11.0 Hz, 2H), 2.01-1.91 (m, 2H), 1.83 (d, J=10.2 Hz, 2H), 1.52-1.26 (m, 4H). m/z (ESI) 407.2 (M+H)$^+$.

Example 71

2-(4-(4-(benzo[d]isoxazol-3-yl)piperazin-1-yl)-4-oxobutyl)quinazolin-4(3H)-one trifluoroacetic acid

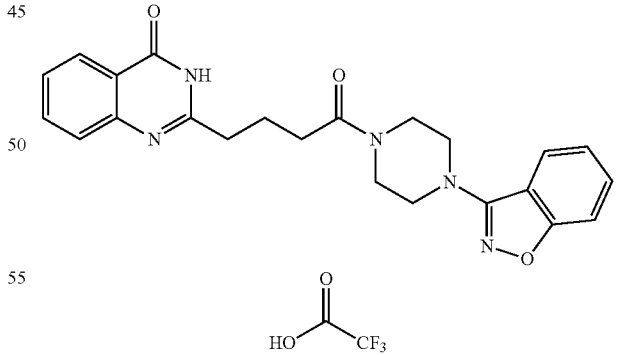

The title compound was prepared as described in General Scheme A using 4-(4-oxo-3,4-dihydroquinazolin-2-yl)butanoic acid (Enamine) and 3-(piperazin-1-yl)benzo[d]isoxazole (Matrix). Purification was accomplished using preparative LC/MS with 0.1% TFA in ACN and water as mobile phase. The pure fractions were dried in vacuo to afford 2-(4-(4-(benzo[d]isoxazol-3-yl)piperazin-1-yl)-4-oxobutyl)quinazolin-4(3H)-one as the presumed trifluoroacetic acid salt as a solid (58 mg, 0.109 mmol, 17% yield). ¹H NMR (500 MHz, DMSO-d$_6$) δ=8.11 (dd, J=1.1, 7.9 Hz, 1H), 7.84-7.77 (m, 1H), 7.63 (d, J=7.9 Hz, 1H), 7.51 (t, J=7.3 Hz, 1H), 7.42 (d, J=7.8 Hz, 1H), 7.31 (d, J=7.3 Hz, 1H), 7.17 (dt, J=1.0, 7.6 Hz, 1H), 7.04 (dt, J=1.1, 7.7 Hz, 1H), 3.72-3.47 (m, 10H), 2.72 (t, J=7.3 Hz, 2H), 2.03 (quin, J=7.3 Hz, 2H). m/z (ESI) 417.2 (M)⁺.

Example 72

2-(4-(4-(5-fluorobenzo[d]isoxazol-3-yl)piperidin-1-yl)-4-oxobutyl)quinazolin-4(3H)-one trifluoroacetic acid

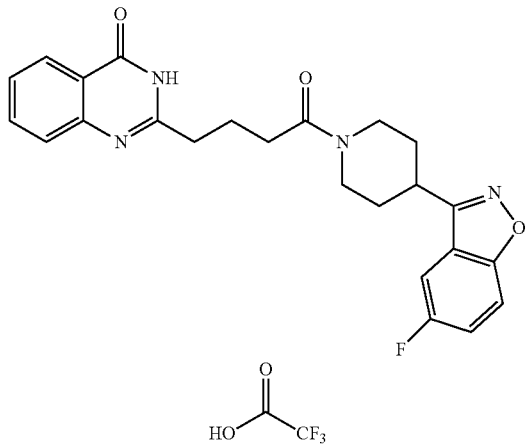

The title compound was prepared as described in General Scheme A using 4-(4-oxo-3,4-dihydroquinazolin-2-yl)butanoic acid (Enamine) and 5-fluoro-3-(piperidin-4-yl)benzo[d]isoxazole (Maybridge). Purification was accomplished using preparative LC/MS with 0.1% TFA in ACN and water as mobile phase. The pure fractions were dried in vacuo to afford 2-(4-(4-(5-fluorobenzo[d]isoxazol-3-yl)piperidin-1-yl)-4-oxobutyl)quinazolin-4(3H)-one as the presumed trifluoroacetic acid salt as a solid (28 mg, 0.051 mmol, 8% yield). ¹H NMR (500 MHz, DMSO-d$_6$) δ=8.15-8.08 (m, 1H), 7.94-7.87 (m, 1H), 7.85-7.74 (m, 2H), 7.63 (d, J=8.0 Hz, 1H), 7.57-7.48 (m, 2H), 4.44 (d, J=13.5 Hz, 1H), 4.00 (d, J=12.8 Hz, 1H), 3.52-3.37 (m, 2H), 3.34-3.16 (m, 2H), 2.83-2.64 (m, 3H), 2.19-1.95 (m, 4H), 1.88-1.70 (m, 1H), 1.62 (dt, J=4.2, 12.3 Hz, 1H). m/z (ESI) 434.2 (M)⁺.

Example 73

N-((1r,4r)-4-(2-oxo-2,3-dihydro-1H-benzo[d]imidazol-1-yl)cyclohexyl)-4-(4-oxo-3,4-dihydroquinazolin-2-yl)butanamide trifluoroacetic acid

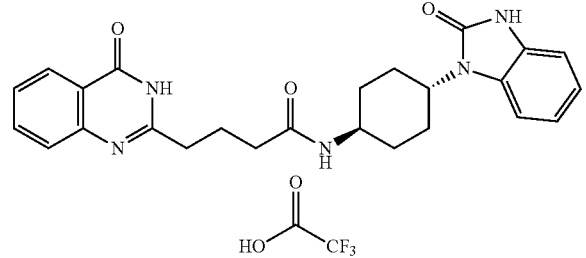

The title compound was prepared as described in General Scheme A using and 4-(4-oxo-3,4-dihydroquinazolin-2-yl) butanoic acid (Enamine) and Intermediate A. Purification was accomplished using preparative LC/MS with 0.1% TFA in ACN and water as mobile phase. The pure fractions were dried in vacuo to afford N-((1r,4r)-4-(2-oxo-2,3-dihydro-1H-benzo[d]imidazol-1-yl)cyclohexyl)-4-(4-oxo-3,4-dihydroquinazolin-2-yl)butanamide as the presumed trifluoroacetic acid salt as a solid (6 mg, 0.011 mmol, 2% yield). ¹H NMR (500 MHz, DMSO-d$_6$) δ=10.78 (s, 1H), 8.10 (d, J=6.8 Hz, 1H), 7.86-7.69 (m, 2H), 7.62 (d, J=7.7 Hz, 1H), 7.49 (t, J=7.4 Hz, 1H), 7.32 (d, J=4.4 Hz, 1H), 7.06-6.85 (m, 3H), 421-4.08 (m, 1H), 3.74-3.64 (m, 1H), 2.64 (t, J=7.4 Hz, 2H), 2.32-2.11 (m, 4H), 1.99 (t, J=7.2 Hz, 2H), 1.91 (d, J=13.4 Hz, 2H), 1.68 (d, J=11.5 Hz, 2H), 1.44-1.26 (m, 2H). m/z (ESI) 445.2 (M)⁺.

Example 74

N-((1r,4r)-4-(5-chloro-2-oxo-2,3-dihydro-1H-benzo[d]imidazol-1-yl)cyclohexyl)-4-(4-oxo-3,4-dihydroquinazolin-2-yl)butanamide trifluoroacetic acid

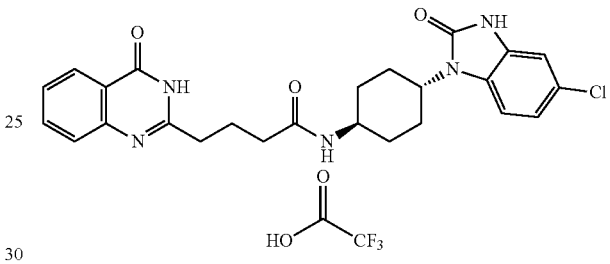

The title compound was prepared as described in General Scheme A using 4-(4-oxo-3,4-dihydroquinazolin-2-yl)butanoic acid (Enamine) and Intermediate E. Purification was accomplished using preparative LC/MS with 0.1% TFA in ACN and water as mobile phase. The pure fractions were dried in vacuo to afford N-((1r,4r)-4-(5-chloro-2-oxo-2,3-dihydro-1H-benzo[d]imidazol-1-yl)cyclohexyl)-4-(4-oxo-3,4-dihydroquinazolin-2-yl)butanamide as the presumed trifluoroacetic acid salt as a solid (5 mg, 0.008 mmol, 1% yield). ¹H NMR (500 MHz, DMSO-d$_6$) δ=12.14 (br. s., 1H), 10.98 (s, 1H), 8.13-8.05 (m, 1H), 7.82-7.69 (m, 2H), 7.60 (d, J=7.9 Hz, 1H), 7.46 (t, J=7.4 Hz, 1H), 7.40-7.33 (m, 1H), 7.02-6.93 (m, 2H), 4.12 (t, J=12.3 Hz, 1H), 3.77-3.61 (m, 1H), 2.61 (t, J=7.4 Hz, 2H), 2.30-2.09 (m, 4H), 2.05-1.84 (m, 4H), 1.67 (d, J=11.8 Hz, 2H), 1.43-1.27 (m, 2H). m/z (ESI) 479.2 (M)⁺.

Example 75

2-(4-(4-(1H-benzo[d][1,2,3]triazol-1-yl)piperidin-1-yl)-4-oxobutyl)quinazolin-4(3H)-one trifluoroacetic acid

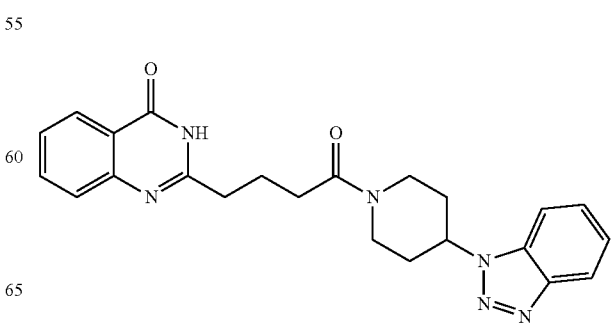

-continued

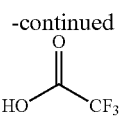

The title compound was prepared as described in General Scheme A using 4-(4-oxo-3,4-dihydroquinazolin-2-yl)butanoic acid (Enamine) and 1-(piperidin-4-yl)-1H-benzo[d][1,2,3]triazole (Butt Park). Purification was accomplished using preparative LC/MS with 0.1% TFA in ACN and water as mobile phase. The pure fractions were dried in vacuo to afford 2-(4-(4-(1H-benzo[d][1,2,3]triazol-1-yl)piperidin-1-yl)-4-oxobutyl)quinazolin-4(3H)-one as the presumed trifluoroacetic acid salt as a solid (34 mg, 0.064 mmol, 10% yield). $^1$H NMR (500 MHz, DMSO-$d_6$) δ=8.15-8.09 (m, 1H), 8.05 (d, J=8.4 Hz, 1H), 7.95 (d, J=8.5 Hz, 1H), 7.82 (t, J=7.6 Hz, 1H), 7.65 (d, J=8.0 Hz, 1H), 7.54 (td, J=7.6, 20.0 Hz, 2H), 7.42 (t, J=7.6 Hz, 1H), 5.29-5.09 (m, 1H), 4.53 (d, J=13.4 Hz, 1H), 4.09 (d, J=13.2 Hz, 1H), 3.41-3.20 (m, 1H), 2.86 (t, J=11.9 Hz, 1H), 2.75 (t, J=7.3 Hz, 2H), 2.61-2.53 (m, 2H), 2.26-2.11 (m, 3H), 2.10-1.89 (m, 3H). m/z (ESI) 416.2 (M)$^+$.

Example 76

2-(4-(4-((3S)-6-chloro-2-oxo-2,3-dihydro-1H-indol-3-yl)-1-piperidinyl)-4-oxobutyl)-4(3H)-quinazolinone trifluoroacetic acid and 2-(4-(4-((3R)-6-chloro-2-oxo-2,3-dihydro-1H-indol-3-yl)-1-piperidinyl)-4-oxobutyl)-4(3H)-quinazolinone trifluoroacetic acid

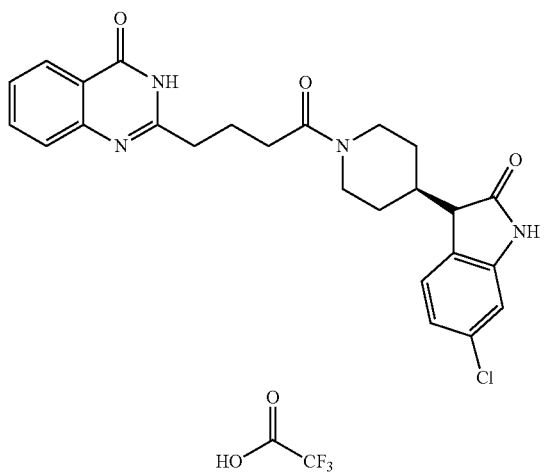

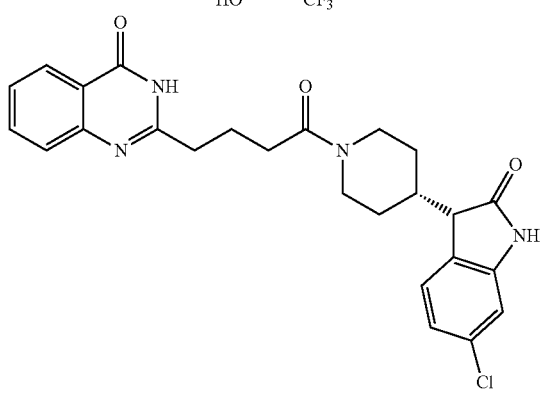

The title compound was prepared as described in General Scheme A using 4-(4-oxo-3,4-dihydroquinazolin-2-yl)butanoic acid (Enamine) and racemic 6-chloro-3-(piperidin-4-yl)indolin-2-one (Enamine). Purification was accomplished using preparative LC/MS with 0.1% TFA in ACN and water as mobile phase. The pure fractions were dried in vacuo to afford racemic mixture 2-(4-(4-((3S)-6-chloro-2-oxo-2,3-dihydro-1H-indol-3-yl)-1-piperidinyl)-4-oxobutyl)-4(3H)-quinazolinone trofluoroacetoc acid+2-(4-(4-((3R)-6-chloro-2-oxo-2,3-dihydro-1H-indol-3-yl)-1-piperidinyl)-4-oxobutyl)-4(3H)-quinazolinone trifluoroacetic acid as a white solid (47 mg, 0.081 mmol, 13% yield). $^1$H NMR (500 MHz, DMSO-$d_6$) δ=10.51 (d, J=5.2 Hz, 1H), 8.10 (d, J=7.9 Hz, 1H), 7.86-7.77 (m, 1H), 7.60 (t, J=9.2 Hz, 1H), 7.51 (t, J=7.3 Hz, 1H), 7.24 (d, J=7.9 Hz, 1H), 6.98 (d, J=7.6 Hz, 1H), 6.82 (d, J=1.7 Hz, 1H), 4.50-4.31 (m, 1H), 3.86 (d, J=12.8 Hz, 2H), 2.92 (t, J=12.8 Hz, 1H), 2.67 (d, J=6.5 Hz, 2H), 2.46-2.30 (m, 3H), 2.22 (m, 1H), 2.05-1.89 (m, 2H), 1.62-1.15 (m, 4H). m/z (ESI) 464.2 (M)$^+$.

Example 77

N-(trans-4-(4-fluorophenoxy)cyclohexyl)-4-(4-oxo-3,4-dihydro-2-quinazolinyl)butanamide

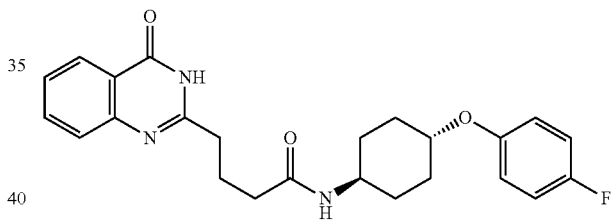

The title compound was prepared as described in General Scheme A using 4-(4-oxo-3,4-dihydroquinazolin-2-yl)butanoic acid (Enamine) and Intermediate B. After 24 h, ~1.2 mL DIPEA was added to the reaction mixture. The mixture was taken up in DCM and washed with water, then concentrated and purified using SFC preparative column chromatography. The pure fractions were dried in vacuo to afford N-(trans-4-(4-fluorophenoxy)cyclohexyl)-4-(4-oxo-3,4-dihydro-2-quinazolinyl)butanamide as a white solid (640 mg, 1.51 mmol, 23% yield). m/z (ESI) 424.2 (M+H)$^+$.

Example 78

N-(trans-4-(4-cyanophenoxy)cyclohexyl)-4-(4-oxo-3,4-dihydro-2-quinazolinyl)butanamide

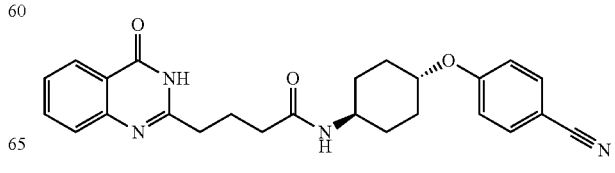

The title compound was prepared as described in General Scheme A using 4-(4-oxo-3,4-dihydroquinazolin-2-yl)butanoic acid (Enamine) and trans-4-(4-fluorophenoxy)cyclohexanamine (HDH Pharma). After 20 h, ~0.5 mL DIPEA was added to the reaction mixture. The mixture was taken up in DCM and washed with water, then concentrated and purified using SFC preparative column chromatography. The pure fractions were dried in vacuo to afford N-(trans-4-(4-cyanophenoxy)cyclohexyl)-4-(4-oxo-3,4-dihydro-2-quinazolinyl)butanamide as a white solid (170 mg, 0.395 mmol, 43% yield). $^1$H NMR (500 MHz, DMSO-$d_6$) δ=12.13 (br. s., 1H), 8.08 (dd, J=1.1, 7.9 Hz, 1H), 7.80-7.68 (m, 3H), 7.59 (d, J=8.1 Hz, 1H), 7.48-7.41 (m, 1H), 7.14-7.07 (m, 2H), 4.53-4.35 (m, 1H), 3.66-3.50 (m, 1H), 2.65-2.57 (m, 2H), 2.54 (d, J=3.7 Hz, 1H), 2.20-2.10 (m, 2H), 2.03 (d, J=10.2 Hz, 2H), 2.00-1.91 (m, 2H), 1.89-1.76 (m, 2H), 1.55-1.25 (m, 4H). m/z (ESI) 431.2 (M+H)$^+$.

Example 79

N-(trans-4-(4-chlorophenoxy)cyclohexyl)-4-(4-oxo-3,4-dihydro-2-quinazolinyl)butanamide

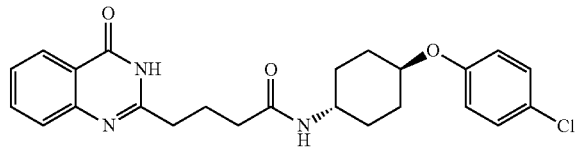 [SMILES: O=C(CCCc1nc2ccccc2c(=O)[nH]1)N[C@H]1CC[C@H](Oc2ccc(Cl)cc2)CC1]

The title compound was prepared as described in General Scheme A using 4-(4-oxo-3,4-dihydroquinazolin-2-yl)butanoic acid (Enamine) and trans-4-(4-chlorophenoxy)cyclohexanamine (HDH Pharma). After 20 h, ~0.5 mL DIPEA was added to the reaction mixture. The mixture was taken up in DCM and washed with water, then concentrated and purified using SFC preparative column chromatography. The pure fractions were dried in vacuo to afford N-(trans-4-(4-chlorophenoxy)cyclohexyl)-4-(4-oxo-3,4-dihydro-2-quinazolinyl)butanamide as a white solid (160 mg, 0.364 mmol, 41% yield). $^1$H NMR (500 MHz, DMSO-$d_6$) δ=12.13 (br. s., 1H), 8.08 (dd, J=1.2, 7.8 Hz, 1H), 7.82-7.75 (m, 1H), 7.72 (d, J=7.6 Hz, 1H), 7.60 (d, J=7.9 Hz, 1H), 7.46 (t, J=7.5 Hz, 1H), 7.33-7.22 (m, 2H), 7.01-6.91 (m, 2H), 4.33-4.19 (m, 1H), 3.64-3.49 (m, 1H), 2.60 (t, J=7.4 Hz, 2H), 2.22-2.09 (m, 2H), 2.07-1.87 (m, 4H), 1.81 (d, J=10.0 Hz, 2H), 1.50-1.12 (m, 4H). m/z (ESI) 440.2 (M+H)$^+$.

Example 80

3-(4-oxo-3,4-dihydroquinazolin-2-yl)-N-yl)-((1r,4r)-4-(2-oxobenzo[d]oxazol-3(2H)-yl)cyclohexyl) propanamide

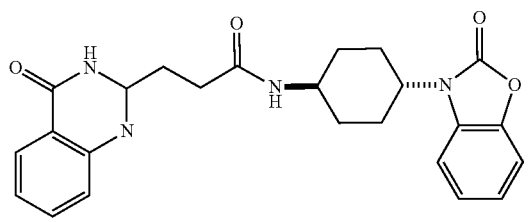

The title compound was prepared as described in General Scheme A using 3-(4-oxo-3,4-dihydroquinazolin-2-yl)propanoic acid (Enamine) and Intermediate D, affording 3-(4-oxo-3,4-dihydroquinazolin-2-yl)-N-((1r,4r)-4-(2-oxobenzo[d]oxazol-3(2H)-yl)cyclohexyl)propanamide (57 mg, 0.132 mmol, 28%) after purification with RP-HPLC.
$^1$H NMR (400 MHz, DMSO-$d_6$) δ ppm 12.01 (br. s., 1H) 7.94 (dd, J=7.97, 1.12 Hz, 1H) 7.75 (d, J=7.63 Hz, 1H) 7.59-7.68 (m, 1H) 7.35-7.46 (m, 2H) 7.25-7.35 (m, 1H) 7.18 (dd, J=7.97, 1.03 Hz, 1H) 6.92-7.09 (m, 2H) 3.93-4.02 (m, 1H) 3.56 (dd, J=8.02, 4.11 Hz, 1H) 3.03 (d, J=5.18 Hz, 2H) 2.72 (t, J=7.43 Hz, 2H) 2.46 (t, J=7.38 Hz, 2H) 1.96-2.12 (m, 2H) 1.78 (d, J=9.78 Hz, 2H) 1.68 (d, J=11.15 Hz, 2H) 1.15-1.33 (m, 2H). m/z (ESI) 433.2 (M+H)$^+$.

Example 81

3-(4-oxo-3,4-dihydropyrido[2,3-d]pyrimidin-2-yl)-N-((1r,4r)-4-(5-phenyl-1,3,4-oxadiazol-2-yl)cyclohexyl) propanamide

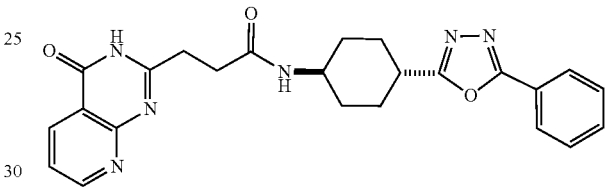

The title compound was prepared as described in General Scheme A using Intermediate K and Intermediate C, affording 3-(4-oxo-3,4-dihydropyrido[2,3-d]pyrimidin-2-yl)-N-((1r,4r)-4-(5-phenyl-1,3,4-oxadiazol-2-yl)cyclohexyl) propanamide (102 mg, 0.229 mmol, 38%) after purification with RP-HPLC. $^1$H NMR (400 MHz, DMSO-$d_6$) δ ppm 12.22 (br. s., 1H) 8.66 (dd, J=4.55, 1.91 Hz, 1H) 8.22 (dd, J=7.87, 2.01 Hz, 1H) 7.72-7.79 (m, 2H) 7.69 (d, J=7.73 Hz, 1H) 7.30-7.43 (m, 3H) 7.24 (dd, J=7.82, 4.60 Hz, 1H) 3.82 (q, J=5.28 Hz, 1H) 3.36 (dtd, J=11.38, 7.54, 7.54, 4.16 Hz, 1H) 2.66 (t, J=7.34 Hz, 2H) 2.41 (t, J=7.38 Hz, 2H) 1.81-2.00 (m, 2H) 1.67 (dd, J=13.40, 3.62 Hz, 2H) 1.29-1.49 (m, 2H) 1.00-1.21 (m, 2H). m/z (ESI) 445.2 (M+H)$^+$.

Example 82

2-((3-(4-(5-chloro-2-oxo-2,3-dihydro-1H-benzo[d]imidazol-1-yl)piperidin-1-yl)-3-oxopropyl)thio)quinazolin-4(3H)-one

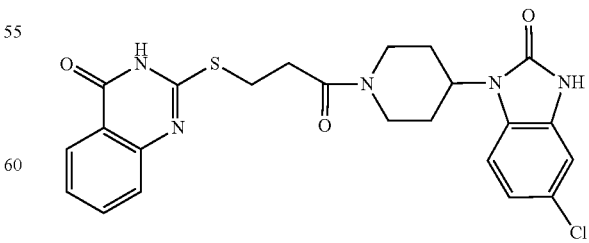

The title compound was prepared as described in General Scheme A using Intermediate I and 5-chloro-1-(piperidin-4-yl)-1H-benzo[d]imidazol-2(3H)-one (Aldrich), affording 2-((3-(4-(5-chloro-2-oxo-2,3-dihydro-1H-benzo[d]imidazol-1-yl)piperidin-1-yl)-3-oxopropyl)thio)quinazolin-4(3H)-one (35 mg, 0.072 mmol, 23%) after purification with RP-HPLC. $^1$H NMR (400 MHz, DMSO-$d_6$) δ ppm 12.53 (br. s., 1H) 11.03 (s, 1H) 8.04 (d, J=6.65 Hz, 1H) 7.66-7.83 (m, 1H) 7.54 (d, J=8.22 Hz, 1H) 7.42 (t, J=7.43 Hz, 1H) 7.25 (d, J=8.22 Hz, 1H) 6.92-7.09 (m, 2H) 4.60 (d, J=13.01 Hz, 1H) 4.42 (t, J=11.88 Hz, 1H) 3.46 (t, J=6.02 Hz, 2H) 3.10-3.24 (m, 1H) 2.82-2.98 (m, 2H) 2.19-2.35 (m, 1H) 2.12 (d, J=8.61 Hz, 1H) 1.74 (d, J=11.64 Hz, 2H). m/z (ESI) 484.2 (M+H)$^+$.

Example 83

2-((3-oxo-3-(4-(5-phenyl-1,3,4-oxadiazol-2-yl)piperidin-1-yl)propyl)thio)quinazolin-4(3H)-one

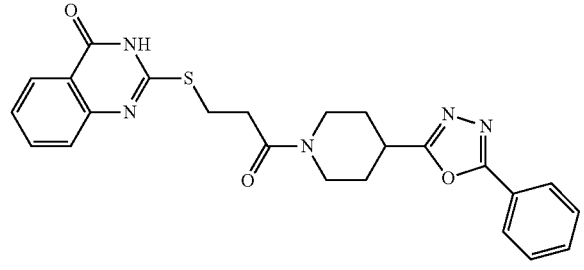 [SMILES: O=C(CCSc1nc2ccccc2c(=O)[nH]1)N1CCC(c2nnc(-c3ccccc3)o2)CC1]

The title compound was prepared as described in General Scheme A using Intermediate I and 2-phenyl-5-(piperidin-4-yl)-1,3,4-oxadiazole (Oakwood), affording 2-((3-oxo-3-(4-(5-phenyl-1,3,4-oxadiazol-2-yl)piperidin-1-yl)propyl)thio)quinazolin-4(3H)-one (12 mg, 0.026 mmol, 6%) after purification with RP-HPLC.

$^1$H NMR (400 MHz, DMSO-$d_6$) δ ppm 12.57 (br. s., 1H) 7.96-8.17 (m, 3H) 7.76-7.87 (m, 1H) 7.62-7.73 (m, 3H) 7.59 (d, J=8.41 Hz, 1H) 7.47 (t, J=7.43 Hz, 1H) 4.39 (d, J=13.30 Hz, 1H) 4.01 (d, J=14.08 Hz, 1H) 3.47-3.56 (m, 2H) 3.40-3.47 (m, 2H) 2.85-3.09 (m, 3H) 2.17 (d, J=12.52 Hz, 2H) 1.85 (d, J=9.88 Hz, 1H) 1.63-1.80 (m, 1H). m/z (ESI) 462.2 (M+H)$^+$.

General Scheme B:

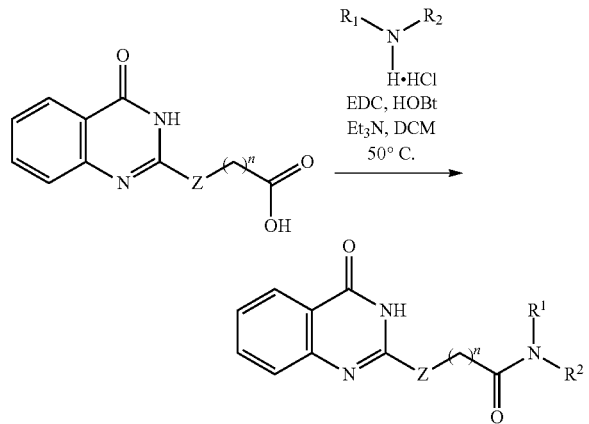

Representative Protocol:
This reaction was typically run in parallel on scales ranging from 0.25 mmol-0.92 mmol, using amines and/or amine salts, with or without added base (TEA), shaken or stirred, with heating overnight up to several days. Reaction mixtures were purified by MPLC (absorbed onto a plug of silica gel and purified by chromatography through a Redi-Sep pre-packed silica gel column, eluting with a gradient of 0% to 60% 1M NH$_3$.MeOH in CH$_2$Cl$_2$) and/or RP-HPLC and/or ion-exchange chromatography (SCX-2) to obtain product. Alternatively, the reaction was run on larger scale using a round bottom vessel and a heating mantle or oil bath.

To a mixture of amine hydrochloride (0.32 mmol) in DCM (2 mL) was added TEA (3.0 equiv.). After being stirred at RT for 5 min, HOBt (1.8 equiv.), EDC (1.8 equiv.), TEA (3.0 equiv.) and 3-(4-oxo-3,4-dihydroquinazolin-2-yl)propanoic acid (1.0 equiv.) were added. The mixture was stirred at 50° C. overnight. The reaction mixture was concentrated and the material thus obtained was purified.

The following examples were all prepared using General Scheme B.

Example 84

N-(trans-4-(2-oxo-2,3-dihydro-1H-benzo[d]imidazol-1-yl)cyclohexyl)-3-(4-oxo-3,4-dihydroquinazolin-2-yl)propanamide

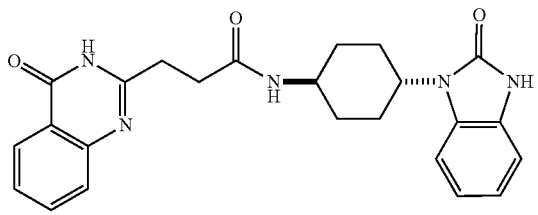

The title compound was prepared as described in General Scheme B using 3-(4-oxo-3,4-dihydroquinazolin-2-yl)propanoic acid (Enamine) and Intermediate A, affording N-(trans-4-(2-oxo-2,3-dihydro-1H-benzo[d]imidazol-1-yl)cyclohexyl)-3-(4-oxo-3,4-dihydroquinazolin-2-yl) propanamide (17 mg, 0.039 mmol, 36%) after purification with HPLC. $^1$H NMR (400 MHz, DMSO-$d_6$) δ ppm 11.95 (br. s., 1H) 10.57 (s, 1H) 7.88 (d, J=7.92 Hz, 1H) 7.68 (d, J=7.43 Hz, 1H) 7.57 (t, J=7.29 Hz, 1H) 7.36 (d, J=8.02 Hz, 1H) 7.25 (t, J=7.34 Hz, 1H) 7.12 (br. s., 1H) 6.74 (br. s., 3H) 3.88-4.08 (m, 1H) 3.51 (br. s., 1H) 2.66 (t, J=7.34 Hz, 2H) 2.40 (t, J=7.34 Hz, 2H) 1.92-2.10 (m, 2H) 1.71 (d, J=10.86 Hz, 2H) 1.48 (d, J=10.95 Hz, 2H) 1.09-1.27 (m, 2H). m/z (ESI) 432.2 (M+H)$^+$.

Example 85

N-((1r,4r)-4-(5-chloro-2-oxo-2,3-dihydro-1H-benzo[d]imidazol-1-yl)cyclohexyl)-3-(4-oxo-3,4-dihydroquinazolin-2-yl)propanamide

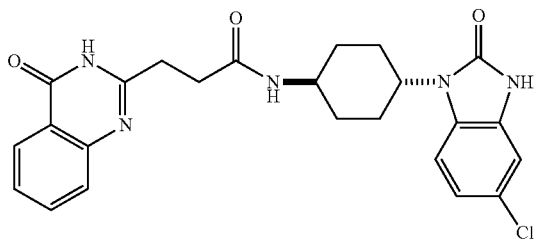

The title compound was prepared as described in General Scheme B using 3-(4-oxo-3,4-dihydroquinazolin-2-yl)propanoic acid (Enamine) and Intermediate E, affording N-((1r,4r)-4-(5-chloro-2-oxo-2,3-dihydro-1H-benzo[d]imidazol-1-yl)cyclohexyl)-3-(4-oxo-3,4-dihydroquinazolin-2-yl)propanamide (146 mg, 0.313 mmol, 53%) after purification with HPLC. $^1$H NMR (400 MHz, DMSO-$d_6$) δ ppm 12.16 (br. s., 1H) 10.98 (br. s., 1H) 8.09 (dd, J=8.02, 1.17 Hz, 1H) 7.88 (d, J=7.82 Hz, 1H) 7.73-7.84 (m, 1H) 7.57 (d, J=8.12 Hz, 1H) 7.41-7.51 (m, 1H) 7.37 (d, J=9.19 Hz, 1H) 6.93-7.05 (m, 2H) 4.15 (t, J=12.52 Hz, 1H) 3.58-3.83 (m, 1H) 2.87 (t, J=7.34 Hz, 2H) 2.61 (t, J=7.34 Hz, 2H) 2.12-2.31 (m, 2H) 1.91 (d, J=11.05 Hz, 2H) 1.69 (d, J=11.54 Hz, 2H) 1.20-1.49 (m, 2H). m/z (ESI) 466.2 (M+H)$^+$.

Example 86

N-((1r,4r)-4-(6-chloro-2-oxo-2,3-dihydro-1H-benzo[d]imidazol-1-yl)cyclohexyl)-3-(4-oxo-3,4-dihydroquinazolin-2-yl)propanamide

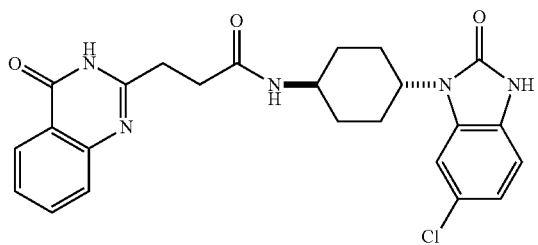

The title compound was prepared as described in General Scheme B using 3-(4-oxo-3,4-dihydroquinazolin-2-yl)propanoic acid (Enamine) and Intermediate F, affording N-((1r,4r)-4-(6-chloro-2-oxo-2,3-dihydro-1H-benzo[d]imidazol-1-yl)cyclohexyl)-3-(4-oxo-3,4-dihydroquinazolin-2-yl)propanamide (45 mg, 0.097 mmol, 38%) after purification with HPLC. $^1$H NMR (400 MHz, DMSO-$d_6$) δ ppm 12.15 (br. s., 1H) 10.96 (br. s., 1H) 8.09 (dd, J=7.87, 1.22 Hz, 1H) 7.83-7.93 (m, 1H) 7.78 (ddd, J=8.29, 7.02, 1.61 Hz, 1H) 7.58 (d, J=8.12 Hz, 1H) 7.42-7.53 (m, 2H) 6.88-7.07 (m, 2H) 3.99-4.26 (m, 1H) 3.75 (td, J=7.95, 4.06 Hz, 1H) 2.87 (t, J=7.34 Hz, 2H) 2.62 (t, J=7.38 Hz, 2H) 2.14-2.32 (m, 2H) 1.91 (d, J=11.44 Hz, 2H) 1.67 (d, J=9.88 Hz, 2H) 1.27-1.48 (m, 2H). m/z (ESI) 466.2 (M+H)$^+$.

Example 87

N-((1r,4r)-4-(5-chloro-2-oxo-2,3-dihydro-1H-benzo[d]imidazol-1-yl)cyclohexyl)-2-((4-oxo-3,4-dihydroquinazolin-2-yl)thio)acetamide

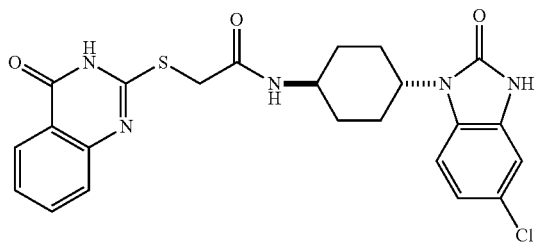

The title compound was prepared as described in General Scheme B using Intermediate H and Intermediate E, affording N-((1r,4r)-4-(6-chloro-2-oxo-2,3-dihydro-1H-benzo[d]imidazol-1-yl)cyclohexyl)-3-(4-oxo-3,4-dihydroquinazolin-2-yl) propanamide (29 mg, 0.060 mmol, 20%) after purification with HPLC. $^1$H NMR (400 MHz, DMSO-$d_6$) δ ppm 10.99 (s, 1H) 8.23 (d, J=7.73 Hz, 1H) 8.05 (dt, J=7.90, 0.79 Hz, 1H) 7.69-7.83 (m, 1H) 7.53 (d, J=8.22 Hz, 1H) 7.32-7.47 (m, 2H) 6.89-7.04 (m, 2H) 4.07-4.26 (m, 1H) 3.95 (s, 2H) 3.62-3.84 (m, 1H) 2.12-2.30 (m, 2H) 1.94 (d, J=10.76 Hz, 2H) 1.70 (d, J=10.47 Hz, 2H) 1.31-1.51 (m, 2H). m/z (ESI) 484.2 (M+H)$^+$.

Example 88

3-(4-oxo-3,4,5,6,7,8-hexahydropyrido[2,3-d]pyrimidin-2-yl)-N-((1r,4r)-4-(5-phenyl-1,3,4-oxadiazol-2-yl)cyclohexyl)propanamide

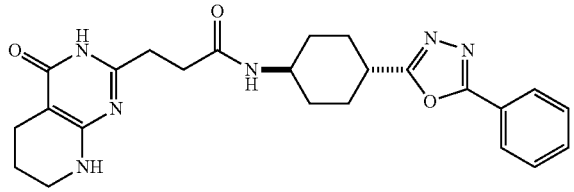

The title compound was prepared as described in General Scheme B using Intermediate L and Intermediate C, affording 3-(4-oxo-3,4,5,6,7,8-hexahydropyrido[2,3-d]pyrimidin-2-yl)-N-((1r,4r)-4-(5-phenyl-1,3,4-oxadiazol-2-yl)cyclohexyl) propanamide (29 mg, 0.060 mmol, 20%) after purification with HPLC. $^1$H NMR (400 MHz, DMSO-$d_6$) δ ppm 11.23 (br. s., 1H) 8.00 (dd, J=7.78, 1.71 Hz, 2H) 7.82 (d, J=7.63 Hz, 1H) 7.56-7.68 (m, 3H) 6.55 (br. s., 1H) 3.52-3.69 (m, 1H) 3.17 (br. s., 2H) 2.93-3.06 (m, 1H) 2.55-2.64 (m, 2H) 2.39-2.49 (m, 2H) 2.29 (t, J=6.11 Hz, 2H) 2.18 (d, J=12.13 Hz, 2H) 1.92 (d, J=10.07 Hz, 2H) 1.56-1.75 (m, 4H) 1.30-1.44 (m, 2H). m/z (ESI) 449.2 (M+H)$^+$.

Example 89

2-((2-oxo-2-(4-(5-phenyl-1,3,4-oxadiazol-2-yl)piperidin-1-yl)ethyl)thio)quinazolin-4(3H)-one

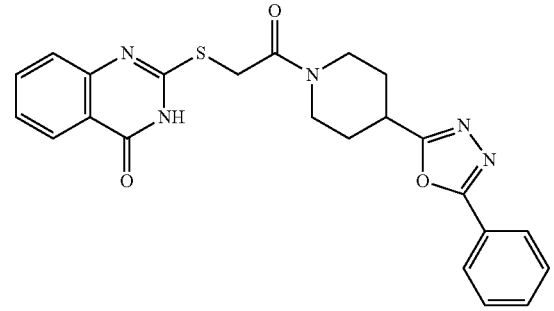 [SMILES: O=C(CSc1nc2ccccc2c(=O)[nH]1)N1CCC(c2nnc(-c3ccccc3)o2)CC1]

The title compound was prepared as described in General Scheme B using Intermediate H and 2-phenyl-5-(piperidin-4-yl)-1,3,4-oxadiazole (Oakwood), affording 2-((2-oxo-2-(4-(5-phenyl-1,3,4-oxadiazol-2-yl)piperidin-1-yl)ethyl)thio)quinazolin-4(3H)-one (28 mg, 0.063 mmol, 9%) after purification with HPLC. $^1$H NMR (400 MHz, DMSO-$d_6$) δ ppm 12.70 (s, 1H) 8.12 (dd, J=7.97, 1.32 Hz, 1H) 8.09-8.11 (m, 1H) 8.07-8.09 (m, 1H) 7.81 (ddd, J=8.34, 7.02, 1.66 Hz, 1H) 7.66-7.74 (m, 3H) 7.61 (d, J=8.22 Hz, 1H) 7.50 (td, J=7.51, 1.12 Hz, 1H) 4.31-4.47 (m, 3H) 4.20 (d, J=13.79 Hz, 1H) 3.46-3.59 (m, 2H) 3.10 (t, J=11.64 Hz, 1H) 2.30 (d, J=10.17 Hz, 1H) 2.20 (d, J=11.15 Hz, 1H) 1.96-2.12 (m, 1H) 1.70-1.87 (m, 1H). m/z (ESI) 448.2 (M+H)$^+$.

Example 90

N-((1r,4r)-4-(5-chloro-2-oxo-2,3-dihydro-1H-benzo[d]imidazol-1-yl)cyclohexyl)-3-((4-oxo-3,4-dihydroquinazolin-2-yl)thio)propanamide

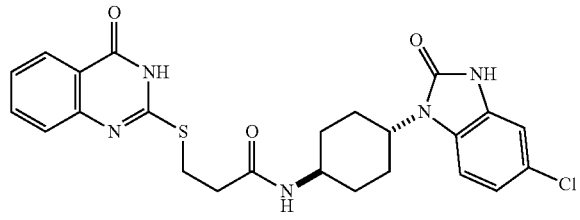

The title compound was prepared as described in General Scheme B using Intermediate I and Intermediate E, affording N-((1r,4r)-4-(5-chloro-2-oxo-2,3-dihydro-1H-benzo[d]imidazol-1-yl)cyclohexyl)-3-((4-oxo-3,4-dihydroquinazolin-2-yl)thio) propanamide (15 mg, 0.030 mmol, 5%) after purification with HPLC. $^1$H NMR (400 MHz, DMSO-d$_6$) δ ppm 12.51 (br. s., 1H) 10.99 (s, 1H) 8.05 (dd, J=7.92, 1.37 Hz, 1H) 7.88 (d, J=7.73 Hz, 1H) 7.71-7.83 (m, 1H) 7.55 (d, J=7.63 Hz, 1H) 7.32-7.48 (m, 2H) 6.89-7.06 (m, 2H) 4.14 (t, J=12.08 Hz, 1H) 3.74 (dd, J=11.49, 3.86 Hz, 1H) 3.42 (t, J=6.85 Hz, 2H) 2.59 (t, J=6.75 Hz, 2H) 2.14-2.31 (m, 2H) 1.93 (d, J=10.56 Hz, 2H) 1.69 (d, J=11.15 Hz, 2H) 1.22-1.46 (m, 2H). m/z (ESI) 498.2 (M+H)$^+$.

General Scheme C:

General Scheme 3:

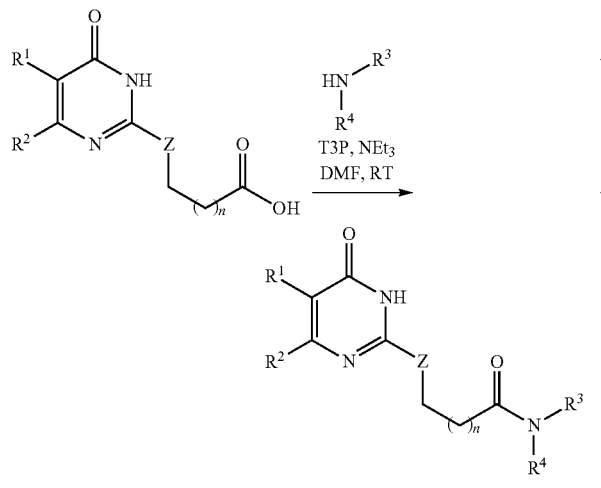

Representative Protocol:

This reaction was typically run in parallel on scales ranging from 0.25 mmol-0.92 mmol, using amines and/or amine salts, with or without added base (TEA), shaken or stirred, with heating overnight up to several days. Reaction mixtures were purified by MPLC (absorbed onto a plug of silica gel and purified by chromatography through a Redi-Sep pre-packed silica gel column, eluting with a gradient of 0% to 60% 1M NH$_3$.MeOH in DCM) and/or RP-HPLC and/or ion-exchange chromatography (SCX-2) to obtain product. Alternatively, the reaction was run on a larger scale using a round bottom vessel and a heating mantle or oil bath.

To a vial charged with amine hydrochloride (1.0 equiv.) in DMF (1.0 mL) was added TEA (0.117 mL, 0.839 mmol), carboxylic acid (64 mg, 0.280 mmol) and 1-propanephosphonic acid cyclic anhydride (50+% soln. in DMF) (0.178 mL, 0.280 mmol). The mixture was stirred overnight at RT. The mixture was then concentrated and the residue was purified.

The following examples were all prepared using General Scheme C.

Example 91

3-((4-amino-6-oxo-1,6-dihydro-2-pyrimidinyl)sulfanyl)-N-(trans-4-(5-phenyl-1,3,4-oxadiazol-2-yl)cyclohexyl)propanamide

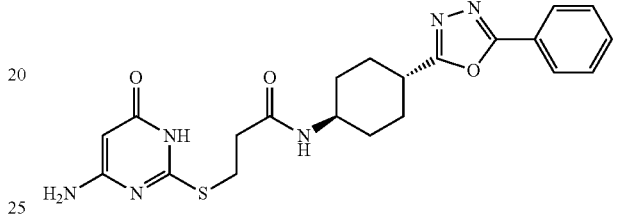

The title compound was prepared as described in General Scheme C using 3-((4-amino-6-oxo-1,6-dihydropyrimidin-2-yl)thio)propanoic acid (Ryan Scientific) and Intermediate C. Purification was accomplished using preparative LC/MS with 0.1% NH$_4$OH in ACN and water as mobile phase. The pure fractions were dried in vacuo to afford 3-((4-amino-6-oxo-1,6-dihydro-2-pyrimidinyl)sulfanyl)-N-(trans-4-(5-phenyl-1,3,4-oxadiazol-2-yl)cyclohexyl)propanamide as a white solid (55 mg, 0.125 mmol, 31% yield). $^1$H NMR (500 MHz, DMSO-d$_6$) δ=7.99 (dd, J=1.5, 7.9 Hz, 2H), 7.87 (d, J=7.6 Hz, 1H), 7.68-7.51 (m, 3H), 6.42 (br. s., 2H), 4.92 (br. s., 1H), 3.69-3.55 (m, 1H), 3.24 (t, J=6.9 Hz, 2H), 3.05-2.93 (m, 1H), 2.50-2.44 (m, 2H), 2.16 (d, J=11.7 Hz, 2H), 1.92 (d, J=9.9 Hz, 2H), 1.74-1.56 (m, 2H), 1.41-1.25 (m, 2H). m/z (ESI) 441.2 (M+H)$^+$.

Example 92

3-(((4-oxo-3,4-dihydro-2-quinazolinyl)methyl)sulfanyl)-N-(trans-4-(5-phenyl-1,3,4-oxadiazol-2-yl)cyclohexyl)propanamide

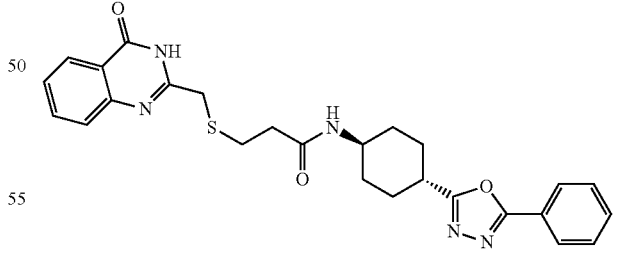

The title compound was prepared as described in General Scheme C using 3-(((4-oxo-3,4-dihydroquinazolin-2-yl)methyl)thio)propanoic acid (Ryan Scientific) and Intermediate C. Purification was accomplished using preparative LC/MS with 0.1% NH$_4$OH in ACN and water as mobile phase. The pure fractions were dried in vacuo to afford 34(4-oxo-3,4-dihydro-2-quinazolinyl)methyl)sulfanyl)-N-(trans-4-(5-phenyl-1,3,4-oxadiazol-2-yl)cyclohexyl)propanamide as a white solid (53 mg, 0.107 mmol, 25% yield).

¹H NMR (500 MHz, DMSO-d₆) δ=12.24 (br. s., 1H), 8.13-8.07 (m, 1H), 7.98 (dd, J=1.5, 7.9 Hz, 2H), 7.86-7.76 (m, 2H), 7.66-7.55 (m, 4H), 7.50 (t, J=7.5 Hz, 1H), 3.67-3.52 (m, 3H), 3.05-2.92 (m, 1H), 2.81 (t, J=7.2 Hz, 2H), 2.39 (t, J=7.3 Hz, 2H), 2.15 (d, J=11.2 Hz, 2H), 1.90 (d, J=10.0 Hz, 2H), 1.77-1.56 (m, 2H), 1.46-1.21 (m, 2H). m/z (ESI) 490.3 (M+H)⁺.

Example 93

2-(((3-(4-(5-(4-fluorophenyl)-1,3,4-oxadiazol-2-yl)-1-piperidinyl)-3-oxopropyl)sulfanyl)methyl)-4(3H)-quinazolinone

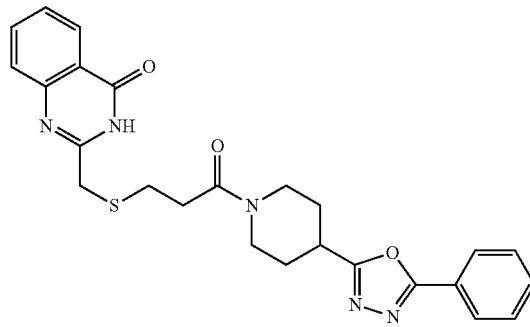

The title compound was prepared as described in General Scheme C using 3-(((4-oxo-3,4-dihydroquinazolin-2-yl)methyl)thio)propanoic acid (Ryan Scientific) and 2-(4-fluorophenyl)-5-(piperidin-4-yl)-1,3,4-oxadiazole (Aldrich). Purification was accomplished using preparative LC/MS with 0.1% NH₄OH in ACN and water as mobile phase. The pure fractions were dried in vacuo to afford 2-(((3-(4-(5-(4-fluorophenyl)-1,3,4-oxadiazol-2-yl)-1-piperidinyl)-3-oxopropyl)sulfanyl)methyl)-4(3H)-quinazolinone as a white solid (58 mg, 0.117 mmol, 28% yield). ¹H NMR (500 MHz, DMSO-d₆) δ=12.25 (br. s., 1H), 8.12-7.99 (m, 3H), 7.80-7.74 (m, 1H), 7.61 (d, J=8.1 Hz, 1H), 7.51-7.38 (m, 3H), 4.36-4.16 (m, 1H), 3.87-3.71 (m, 1H), 3.65 (s, 2H), 3.40-3.32 (m, 1H), 3.19 (t, J=11.3 Hz, 1H), 2.94-2.76 (m, 3H), 2.74-2.61 (m, 2H), 2.03 (t, J=11.2 Hz, 2H), 1.78-1.48 (m, 2H). m/z (ESI) 494.2 (M+H)⁺.

Example 94

2-((3-(4-(1H-indazol-3-yl)-1-piperazinyl)-3-oxopropyl)sulfanyl)-4(3H)-quinazolinone

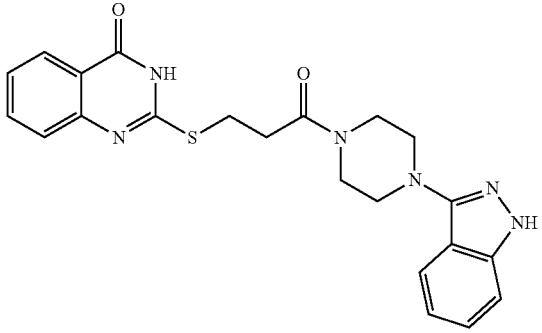

The title compound was prepared as described in General Scheme C using 3-((4-oxo-3,4-dihydroquinazolin-2-yl)thio) propanoic acid (Asinex) and 3-(piperazin-1-yl)-1H-indazole (HDH Pharma). Purification was accomplished using preparative LC/MS with 0.1% NH₄OH in ACN and water as mobile phase. The pure fractions were dried in vacuo to afford 2-((3-(4-(1H-indazol-3-yl)-1-piperazinyl)-3-oxopropyl)sulfanyl)-4(3H)-quinazolinone as a white solid (128 mg, 0.295 mmol, 37% yield). ¹H NMR (400 MHz, DMSO-d₆) δ=12.05 (s, 1H), 8.03 (dd, J=1.5, 7.9 Hz, 1H), 7.82-7.72 (m, 2H), 7.53 (d, J=8.1 Hz, 1H), 7.46-7.35 (m, 2H), 7.33-7.26 (m, 1H), 7.04-6.94 (m, 1H), 3.76-3.64 (m, 4H), 3.45 (t, J=6.7 Hz, 2H), 3.31-3.26 (m, 4H), 2.90 (t, J=6.7 Hz, 2H). m/z (ESI) 435.2 (M+H)⁺.

Example 95

4-(4-oxo-3,4-dihydro-2-quinazolinyl)-N-(trans-4-(5-phenyl-1,3-oxazol-2-yl)cyclohexyl)butanamide

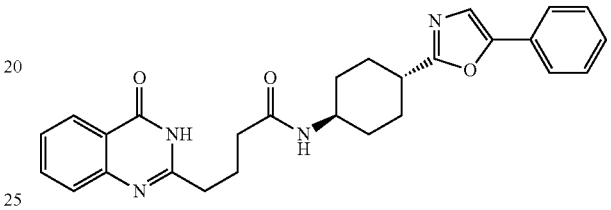

The title compound was prepared as described in General Scheme C using 4-(4-oxo-3,4-dihydroquinazolin-2-yl)butanoic acid (Enamine) and trans-4-(5-phenyloxazol-2-yl)cyclohexanamine (HDH Pharma). Purification was accomplished using preparative LC/MS with 0.1% NH₄OH in ACN and water as mobile phase. The pure fractions were dried in vacuo to afford 4-(4-oxo-3,4-dihydro-2-quinazolinyl)-N-(trans-4-(5-phenyl-1,3-oxazol-2-yl)cyclohexyl)butanamide as a white solid (34 mg, 0.075 mmol, 30% yield). m/z (ESI) 457.2 (M+H)⁺.

Example 96

2-((4-oxo-3,4-dihydroquinazolin-2-yl)thio)-N-((1r,4r)-4-(5-phenyl-1,3,4-oxadiazol-2-yl)cyclohexyl)acetamide

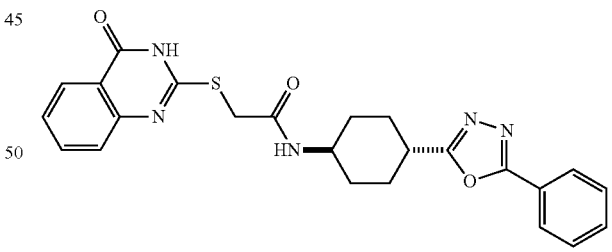

The title compound was prepared as described in General Scheme C using Intermediate H and Intermediate C, affording 2-((4-oxo-3,4-dihydroquinazolin-2-yl)thio)-N-((1r,4r)-4-(5-phenyl-1,3,4-oxadiazol-2-yl)cyclohexyl) acetamide (19 mg, 0.041 mmol, 11%) after purification with RP-HPLC. ¹H NMR (400 MHz, DMSO-d₆) δ ppm 12.53 (br. s., 1H) 8.14 (d, J=7.53 Hz, 1H) 7.80-8.00 (m, 3H) 7.66 (t, J=6.99 Hz, 1H) 7.48 (d, J=6.94 Hz, 4H) 7.40 (d, J=8.12 Hz, 1H) 7.31 (t, J=7.24 Hz, 1H) 3.82 (s, 2H) 3.51 (d, J=6.75 Hz, 1H) 2.80-2.98 (m, 1H) 2.05 (d, J=11.15 Hz, 2H) 1.82 (d, J=10.76 Hz, 2H) 1.41-1.62 (m, 2H) 1.16-1.40 (m, 2H). m/z (ESI) 462.2 (M+H)⁺.

Example 97

3-((4-oxo-3,4-dihydroquinazolin-2-yl)thio)-N-(trans-4-(5-phenyl-1,3,4-oxadiazol-2-yl)cyclohexyl)propanamide

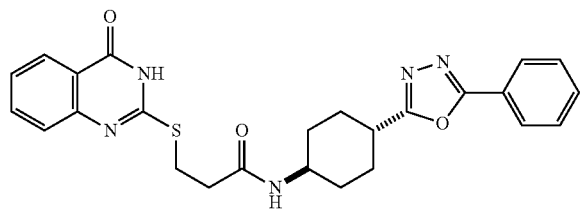

The title compound was prepared as described in General Scheme C using Intermediate I and Intermediate C, affording 3-((4-oxo-3,4-dihydroquinazolin-2-yl)thio)-N-(trans-4-(5-phenyl-1,3,4-oxadiazol-2-yl)cyclohexyl)propanamide (51 mg, 0.107 mmol, 51%) after purification with RP-HPLC. $^1$H NMR (400 MHz, DMSO-$d_6$) δ ppm 12.50 (br. s., 1H) 8.02-8.09 (m, 1H) 7.96-8.02 (m, 2H) 7.90 (d, J=7.63 Hz, 1H) 7.72-7.83 (m, 1H) 7.57-7.66 (m, 3H) 7.50-7.57 (m, 1H) 7.43 (ddd, J=8.00, 7.07, 1.17 Hz, 1H) 3.55-3.71 (m, 1H) 3.41 (t, J=6.75 Hz, 2H) 3.00 (tt, J=11.91, 3.59 Hz, 1H) 2.56-2.63 (m, 2H) 2.12-2.24 (m, 2H) 1.85-2.02 (m, 2H) 1.56-1.75 (m, 2H) 1.22-1.44 (m, 2H). m/z (ESI) 476.2 (M+H)$^+$.

Example 98

2-(3-oxo-3-(4-(5-phenyl-1,3,4-oxadiazol-2-yl)piperidin-1-yl)propyl)quinazolin-4(3H)-one

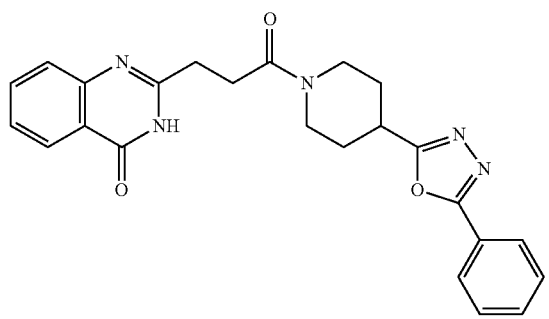 [SMILES: O=C(CCc1nc2ccccc2c(=O)[nH]1)N1CCC(c2nnc(-c3ccccc3)o2)CC1]

The title compound was prepared as described in General Scheme C using 3-(4-oxo-3,4-dihydroquinazolin-2-yl)propanoic acid (Enamine) and 2-phenyl-5-(piperidin-4-yl)-1,3,4-oxadiazole (Oakwood) affording 2-(3-oxo-3-(4-(5-phenyl-1,3,4-oxadiazol-2-yl)piperidin-1-yl)propyl)quinazolin-4(3H)-one (36 mg, 0.084 mmol, 19%) after purification with RP-HPLC. $^1$H NMR (400 MHz, DMSO-$d_6$) δ ppm 12.17 (br. s., 1H) 8.08 (dd, J=7.92, 1.08 Hz, 1H) 7.97-8.05 (m, 2H) 7.73 (ddd, J=8.31, 6.99, 1.61 Hz, 1H) 7.53-7.68 (m, 4H) 7.45 (ddd, J=8.00, 7.07, 1.08 Hz, 1H) 4.30 (d, J=13.11 Hz, 1H) 4.02 (d, J=13.20 Hz, 1H) 3.36-3.45 (m, 3H) 2.78-3.01 (m, 5H) 2.17 (d, J=11.54 Hz, 1H) 2.00-2.12 (m, 1H) 1.79-1.98 (m, 1H) 1.53-1.74 (m, 1H). m/z (ESI) 430.2 (M+H)$^+$.

Example 99

N-((1r,4r)-4-(4-fluorophenoxy)cyclohexyl)-2-((4-oxo-3,4-dihydroquinazolin-2-yl)thio) acetamide

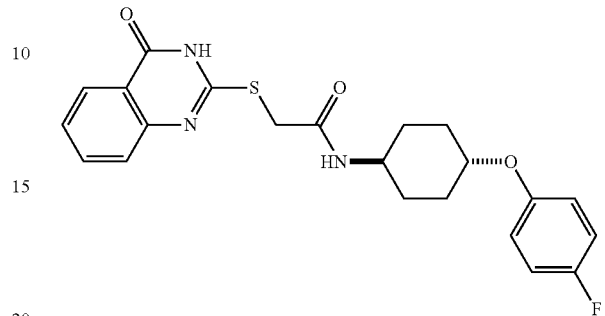

The title compound was prepared as described in General Scheme C using Intermediate H and Intermediate B, affording N-((1r,4r)-4-(4-fluorophenoxy)cyclohexyl)-2-((4-oxo-3,4-dihydroquinazolin-2-yl)thio)acetamide (27 mg, 0.063 mmol, 12%) after purification with RP-HPLC. $^1$H NMR (400 MHz, DMSO-$d_6$) δ ppm 12.65 (br. s., 1H) 8.22 (d, J=7.82 Hz, 1H) 8.04 (d, J=6.85 Hz, 1H) 7.77 (t, J=7.04 Hz, 1H) 7.50 (d, J=7.82 Hz, 1H) 7.43 (t, J=7.48 Hz, 1H) 7.09 (t, J=8.80 Hz, 2H) 6.92-7.01 (m, 2H) 4.24 (br. s., 1H) 3.94 (s, 2H) 3.61 (br. s., 1H) 1.95-2.10 (m, 2H) 1.85 (d, J=9.10 Hz, 2H) 1.30-1.49 (m, 4H). m/z (ESI) 429.2 (M+H)$^+$.

Example 100

N-((1r,4r)-4-(4-fluorophenoxy)cyclohexyl)-3-((4-oxo-3,4-dihydroquinazolin-2-yl)thio) propanamide

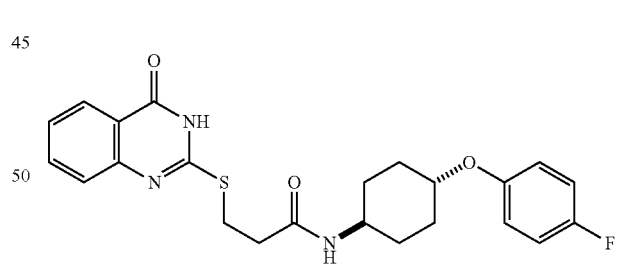

The title compound was prepared as described in General Scheme C using Intermediate I and Intermediate B, affording N-((1r,4r)-4-(4-fluorophenoxy)cyclohexyl)-3-((4-oxo-3,4-dihydroquinazolin-2-yl)thio)propanamide (91 mg, 0.206 mmol, 38%) after purification with RP-HPLC. $^1$H NMR (400 MHz, DMSO-$d_6$) δ ppm 12.50 (br. s., 1H) 8.04 (dd, J=7.97, 1.22 Hz, 1H) 7.85 (d, J=7.63 Hz, 1H) 7.77 (td, J=7.68, 1.56 Hz, 1H) 7.54 (d, J=8.22 Hz, 1H) 7.39-7.46 (m, 1H) 7.05-7.12 (m, 2H) 6.92-6.99 (m, 2H) 4.15-4.30 (m, 1H) 3.54-3.68 (m, 1H) 3.40 (t, J=6.80 Hz, 2H) 2.55-2.62 (m, 2H) 1.99-2.08 (m, 2H) 1.79-1.89 (m, 2H) 1.23-1.48 (m, 4H). m/z (ESI) 442.2 (M+H)$^+$.

Example 101

3-(6-fluoro-4-oxo-3,4-dihydroquinazolin-2-yl)-N-((1r,4r)-4-(5-phenyl-1,3,4-oxadiazol-2-yl)cyclohexyl)propanamide

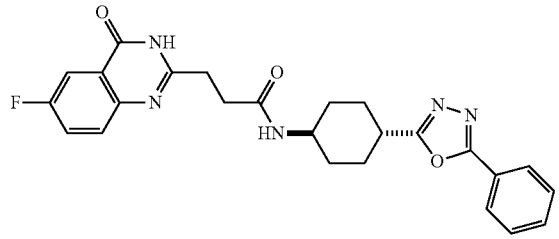

The title compound was prepared as described in General Scheme C using Intermediate M and Intermediate C, affording 3-(6-fluoro-4-oxo-3,4-dihydroquinazolin-2-yl)-N-((1r,4r)-4-(5-phenyl-1,3,4-oxadiazol-2-yl)cyclohexyl)propanamide (55 mg, 0.119 mmol, 33%) after purification with RP-HPLC.

$^1$H NMR (400 MHz, DMSO-$d_6$) δ ppm 12.31 (br. s., 1H) 8.00 (dd, J=7.82, 1.76 Hz, 2H) 7.91 (d, J=7.82 Hz, 1H) 7.76 (dd, J=8.46, 2.49 Hz, 1H) 7.52-7.71 (m, 5H) 3.52-3.69 (m, 1H) 2.93-3.06 (m, 1H) 2.86 (t, J=7.19 Hz, 2H) 2.61 (t, J=7.19 Hz, 2H) 2.17 (d, J=11.64 Hz, 2H) 1.91 (d, J=9.59 Hz, 2H) 1.53-1.75 (m, 2H) 1.24-1.44 (m, 2H). m/z (ESI) 462.2 (M+H)$^+$.

Example 102

N-((1r,4r)-4-(6-chloro-2-oxo-2,3-dihydro-1H-benzo[d]imidazol-1-yl)cyclohexyl)-2-((4-oxo-3,4-dihydroquinazolin-2-yl)thio)acetamide

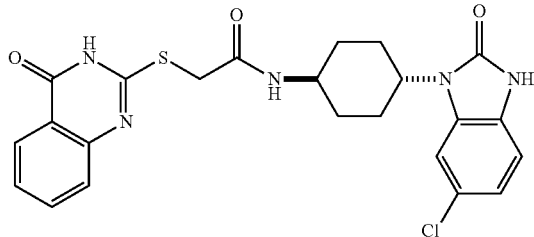

The title compound was prepared as described in General Scheme C using Intermediate H and Intermediate F, affording N-((1r,4r)-4-(6-chloro-2-oxo-2,3-dihydro-1H-benzo[d]imidazol-1-yl)cyclohexyl)-2-((4-oxo-3,4-dihydroquinazolin-2-yl)thio) acetamide (8 mg, 0.017 mmol, 11%) after purification with RP-HPLC. $^1$H NMR (400 MHz, DMSO-$d_6$) δ ppm 12.65 (br. s., 1H) 10.89-11.05 (m, 1H) 8.25 (br. s., 1H) 8.04 (d, J=7.53 Hz, 1H) 7.78 (t, J=7.24 Hz, 1H) 7.47-7.57 (m, 2H) 7.31-7.47 (m, 2H) 6.86-7.06 (m, 2H) 4.17 (br. s., 1H) 3.94 (s, 2H) 3.78 (br. s., 1H) 2.19-2.34 (m, 2H) 1.94 (d, J=10.56 Hz, 2H) 1.68 (d, J=10.66 Hz, 2H) 1.33-1.53 (m, 2H). m/z (ESI) 484.2 (M+H)$^+$.

Example 103

N-((1r,4r)-4-(5-cyano-2-oxo-2,3-dihydro-1H-benzo[d]imidazol-1-yl)cyclohexyl)-2-((4-oxo-3,4-dihydroquinazolin-2-yl)thio)acetamide

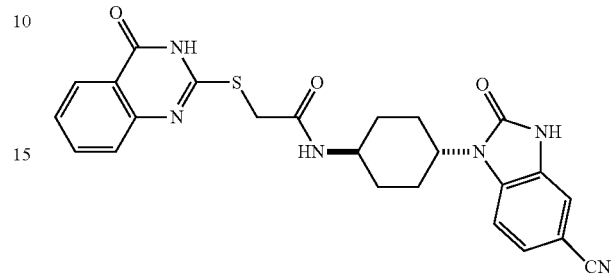

The title compound was prepared as described in General Scheme C using Intermediate H and Intermediate G, affording N-((1r,4r)-4-(5-cyano-2-oxo-2,3-dihydro-1H-benzo[d]imidazol-1-yl)cyclohexyl)-2-((4-oxo-3,4-dihydroquinazolin-2-yl)thio)acetamide (7 mg, 0.015 mmol, 4%) after purification with RP-HPLC. $^1$H NMR (400 MHz, DMSO-$d_6$) δ ppm 12.70 (br. s., 1H) 11.34 (br. s., 1H) 8.31 (d, J=7.82 Hz, 1H) 8.09 (d, J=7.63 Hz, 1H) 7.83 (t, J=7.38 Hz, 1H) 7.52-7.69 (m, 2H) 7.43-7.52 (m, 2H) 7.40 (s, 1H) 4.27 (t, J=11.98 Hz, 1H) 3.99 (s, 2H) 3.82 (br. s., 1H) 2.19-2.38 (m, 2H) 1.99 (d, J=10.76 Hz, 2H) 1.78 (br. s., 2H) 1.38-1.65 (m, 2H). m/z (ESI) 475.2 (M+H)$^+$.

Example 104

N-((1r,4r)-4-(5-cyano-2-oxo-2,3-dihydro-1H-benzo[d]imidazol-1-yl)cyclohexyl)-3-((4-oxo-3,4-dihydroquinazolin-2-yl)thio)propanamide

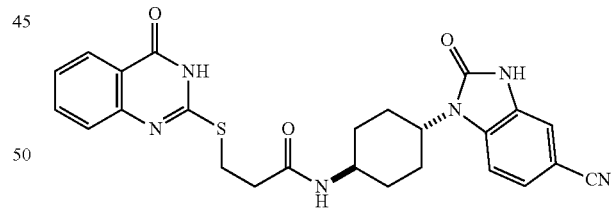

The title compound was prepared as described in General Scheme C using Intermediate I and Intermediate G, affording N-((1r,4r)-4-(5-cyano-2-oxo-2,3-dihydro-1H-benzo[d]imidazol-1-yl)cyclohexyl)-3-((4-oxo-3,4-dihydroquinazolin-2-yl)thio) propanamide (45 mg, 0.092 mmol, 26%) after purification with RP-HPLC. $^1$H NMR (400 MHz, DMSO-$d_6$) δ ppm 12.71 (br. s., 1H) 11.50 (s, 1H) 8.25 (d, J=6.46 Hz, 1H) 8.08 (d, J=7.34 Hz, 1H) 7.91-8.04 (m, 1H) 7.72-7.83 (m, 2H) 7.65 (dd, J=8.31, 1.57 Hz, 2H) 7.56 (d, J=1.57 Hz, 1H) 4.32-4.52 (m, 1H) 3.96 (dd, J=7.58, 4.25 Hz, 1H) 3.62 (t, J=6.60 Hz, 2H) 2.78-2.82 (t, J=6.60 Hz, 2H) 2.34-2.53 (m, 2H) 2.14 (d, J=11.93 Hz, 2H) 1.92 (d, J=11.44 Hz, 2H) 1.48-1.66 (m, 2H). m/z (ESI) 489.2 (M+H)$^+$.

Example 105

N-((1r,4r)-4-(4-chlorophenoxy)cyclohexyl)-3-((4-oxo-3,4-dihydroquinazolin-2-yl)thio) propanamide

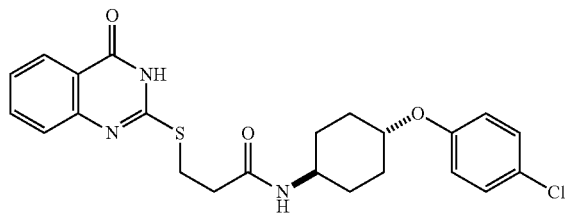

The title compound was prepared as described in General Scheme C using Intermediate I and (1r,4r)-4-(4-chlorophenoxy)cyclohexanamine (HDH Pharma), affording N-((1r,4r)-4-(4-chlorophenoxy)cyclohexyl)-3-((4-oxo-3,4-dihydroquinazolin-2-yl)thio)propanamide (70 mg, 0.153 mmol, 50%) after purification with RP-HPLC. $^1$H NMR (400 MHz, DMSO-$d_6$) δ ppm 12.50 (br. s., 1H) 8.04 (dd, J=7.97, 1.22 Hz, 1H) 7.86 (d, J=7.43 Hz, 1H) 7.73-7.81 (m, 1H) 7.54 (d, J=8.31 Hz, 1H) 7.38-7.46 (m, 1H) 7.25-7.33 (m, 2H) 6.94-7.01 (m, 2H) 4.28 (t, J=4.25 Hz, 1H) 3.53-3.67 (m, 1H) 3.40 (t, J=6.75 Hz, 2H) 2.55-2.62 (m, 2H) 2.03 (d, J=9.78 Hz, 2H) 1.85 (d, J=9.68 Hz, 2H) 1.24-1.52 (m, 4H). m/z (ESI) 458.2 (M+H)$^+$.

Example 106

N-(trans-4-(4-cyanophenoxy)cyclohexyl)-3-((4-oxo-3,4-dihydroquinazolin-2-yl)thio) propanamide

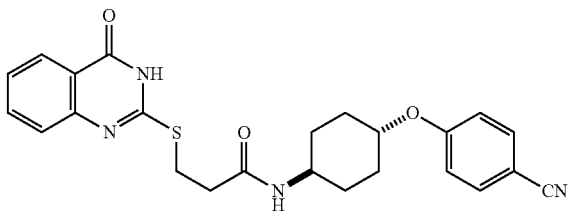

The title compound was prepared as described in General Scheme C using Intermediate I and 4-(((1r,4r)-4-aminocyclohexyl)oxy)benzonitrile (HDH Pharma), affording N-(trans-4-(4-cyanophenoxy)cyclohexyl)-3-((4-oxo-3,4-dihydroquinazolin-2-yl)thio)propanamide (72 mg, 0.161 mmol, 39%) after purification with RP-HPLC. $^1$H NMR (400 MHz, DMSO-$d_6$) δ ppm 12.31 (s, 1H) 7.85 (dd, J=7.92, 1.17 Hz, 1H) 7.69 (d, J=7.53 Hz, 1H) 7.50-7.62 (m, 3H) 7.35 (d, J=8.12 Hz, 1H) 7.20-7.27 (m, 1H) 6.91-6.97 (m, 2H) 4.21-4.34 (m, 1H) 3.37-3.51 (m, 1H) 3.21 (t, J=6.65 Hz, 2H) 2.40 (t, J=6.75 Hz, 2H) 1.87 (d, J=9.68 Hz, 2H) 1.60-1.74 (m, 2H) 1.09-1.35 (m, 4H). m/z (ESI) 449.2 (M+H)$^+$.

Example 107

3-((4-oxo-3,4-dihydroquinazolin-2-yl)thio)-N-((1r,4r)-4-(pyridin-2-yloxy)cyclohexyl) propanamide

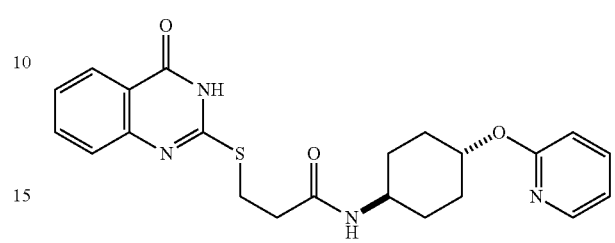

The title compound was prepared as described in General Scheme C using Intermediate I and (1r,4r)-4-(pyridin-2-yloxy)cyclohexanamine (HDH Pharma), affording 3-((4-oxo-3,4-dihydroquinazolin-2-yl)thio)-N-((1r,4r)-4-(pyridin-2-yloxy)cyclohexyl)propanamide (59 mg, 0.139 mmol, 50%) after purification with RP-HPLC.

$^1$H NMR (400 MHz, DMSO-$d_6$) δ ppm 12.50 (br. s., 1H) 8.10-8.18 (m, 1H) 8.04 (dd, J=7.87, 1.22 Hz, 1H) 7.85 (d, J=7.73 Hz, 1H) 7.77 (ddd, J=8.31, 7.04, 1.57 Hz, 1H) 7.63-7.73 (m, 1H) 7.54 (d, J=7.92 Hz, 1H) 7.37-7.50 (m, 1H) 6.93 (ddd, J=7.09, 5.04, 0.88 Hz, 1H) 6.75 (dt, J=8.36, 0.86 Hz, 1H) 4.80-5.02 (m, 1H) 3.53-3.71 (m, 1H) 3.40 (t, J=6.70 Hz, 2H) 2.54-2.63 (m, 2H) 2.01-2.13 (m, 2H) 1.77-1.93 (m, 2H) 1.39-1.56 (m, 2H) 1.23-1.39 (m, 2H). m/z (ESI) 425.2 (M+H)$^+$.

Example 108

3-((4-oxo-3,4-dihydroquinazolin-2-yl)thio)-N-((1r,4r)-4-(pyridin-4-yloxy)cyclohexyl) propanamide

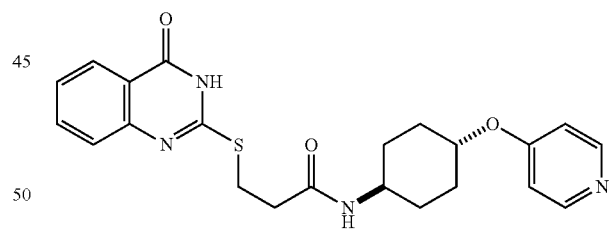

The title compound was prepared as described in General Scheme C using Intermediate I and (1r,4r)-4-(pyridin-4-yloxy)cyclohexanamine (HDH Pharma), affording 3-((4-oxo-3,4-dihydroquinazolin-2-yl)thio)-N-((1r,4r)-4-(pyridin-4-yloxy)cyclohexyl)propanamide (25 mg, 0.059 mmol, 20%) after purification with RP-HPLC.

$^1$H NMR (400 MHz, DMSO-$d_6$) δ ppm 12.50 (br. s., 1H) 8.35 (d, J=6.16 Hz, 2H) 8.04 (d, J=6.94 Hz, 1H) 7.88 (d, J=7.63 Hz, 1H) 7.77 (t, J=6.90 Hz, 1H) 7.53 (d, J=7.92 Hz, 1H) 7.42 (t, J=7.34 Hz, 1H) 6.97 (d, J=5.97 Hz, 2H) 4.34-4.54 (m, 1H) 3.63 (d, J=6.26 Hz, 1H) 3.40 (t, J=6.50 Hz, 2H) 2.59 (t, J=6.75 Hz, 2H) 2.06 (d, J=9.88 Hz, 2H) 1.86 (d, J=9.29 Hz, 2H) 1.29-1.54 (m, 4H). m/z (ESI) 425.2 (M+H)$^+$.

Example 109

(1r,4r)-N-(3-fluorophenyl)-4-(3-(4-oxo-3,4-dihydro-quinazolin-2-yl) propanamido)cyclohexanecarboxamide

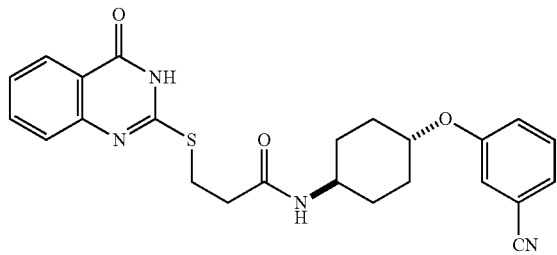

The title compound was prepared as described in General Scheme C using Intermediate I and 3-(((1r,4r)-4-aminocyclohexyl)oxy)benzonitrile (HDH Pharma), affording (1r,4r)-N-(3-fluorophenyl)-4-(3-(4-oxo-3,4-dihydroquinazolin-2-yl)propanamido)cyclohexanecarboxamide (63 mg, 0.140 mmol, 52%) after purification with RP-HPLC. $^1$H NMR (400 MHz, DMSO-$d_6$) δ 12.49 (s, 1H), 8.03 (dd, J=1.27, 7.92 Hz, 1H), 7.86 (d, J=7.34 Hz, 1H), 7.76 (dt, J=1.61, 7.70 Hz, 1H), 7.53 (d, J=7.92 Hz, 1H), 7.38-7.49 (m, 3H), 7.35 (td, J=1.15, 7.68 Hz, 1H), 7.29 (ddd, J=1.03, 2.57, 8.44 Hz, 1H), 4.33-4.49 (m, 1H), 3.55-3.67 (m, 1H), 3.36-3.42 (m, 2H), 2.58 (t, J=6.70 Hz, 2H), 2.00-2.09 (m, 2H), 1.79-1.90 (m, 2H), 1.28-1.50 (m, 4H). m/z (ESI) 449.2 (M+H)$^+$.

Example 110

4-((4-oxo-3,4-dihydroquinazolin-2-yl)thio)-N-((1r,4r)-4-(5-phenyl-1,3,4-oxadiazol-2-yl)cyclohexyl) butanamide

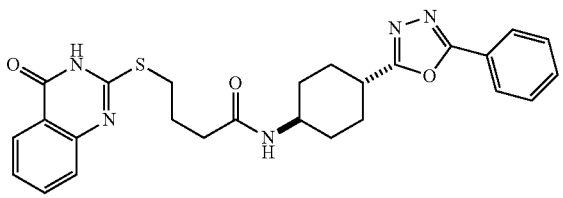

The title compound was prepared as described in General Scheme C using Intermediate J and Intermediate C, affording 4-((4-oxo-3,4-dihydroquinazolin-2-yl)thio)-N-((1r,4r)-4-(5-phenyl-1,3,4-oxadiazol-2-yl)cyclohexyl) butanamide (81 mg, 0.165 mmol, 48%) after purification with RP-HPLC. $^1$H NMR (400 MHz, DMSO-$d_6$) δ ppm 12.52 (br. s., 1H) 7.93-8.08 (m, 3H) 7.82 (d, J=7.63 Hz, 1H) 7.76 (t, J=7.48 Hz, 1H) 7.55-7.66 (m, 3H) 7.52 (d, J=8.02 Hz, 1H) 7.41 (t, J=7.53 Hz, 1H) 3.61 (d, J=7.82 Hz, 1H) 3.19-3.27 (m, 2H) 2.90-3.05 (m, 1H) 2.23 (t, J=7.09 Hz, 2H) 2.16 (d, J=12.52 Hz, 2H) 1.84-2.01 (m, 4H) 1.55-1.73 (m, 2H) 1.26-1.43 (m, 2H). m/z (ESI) 490.2 (M+H)$^+$

Example 111

2-((4-oxo-4-(4-(5-phenyl-1,3,4-oxadiazol-2-yl)piperidin-1-yl)butyl)thio)quinazolin-4(3H)-one

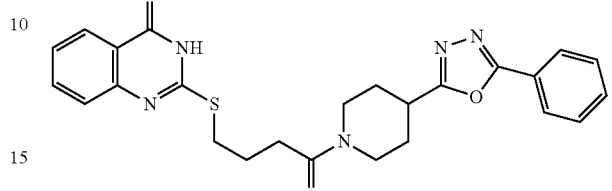

The title compound was prepared as described in General Scheme C using Intermediate J and 2-phenyl-5-(piperidin-4-yl)-1,3,4-oxadiazole (Oakwood), affording 2-((4-oxo-4-(4-(5-phenyl-1,3,4-oxadiazol-2-yl)piperidin-1-yl)butyl)thio)quinazolin-4(3H)-one (271 mg, 0.452 mmol, 78%) after purification with RP-HPLC. $^1$H NMR (400 MHz, DMSO-$d_6$) δ ppm 12.53 (br. s., 1H) 7.93-8.08 (m, 3H) 7.69-7.79 (m, 1H) 7.56-7.67 (m, 3H) 7.51 (d, J=8.12 Hz, 1H) 7.40 (t, J=7.19 Hz, 1H) 4.32 (d, J=13.30 Hz, 1H) 3.91 (d, J=13.40 Hz, 1H) 3.22-3.40 (m, 2H) 3.27 (t, J=7.19 Hz, 2H) 2.91 (t, J=11.44 Hz, 1H) 2.02-2.16 (m, 2H) 1.97 (quin, J=7.12 Hz, 2H) 1.71-1.84 (m, 1H) 1.56-1.71 (m, 1H). m/z (ESI) 476.2 (M+H)$^+$.

Example 112

N-((1r,4r)-4-(3-chlorophenoxy)cyclohexyl)-3-((4-oxo-3,4-dihydroquinazolin-2-yl)thio) propanamide

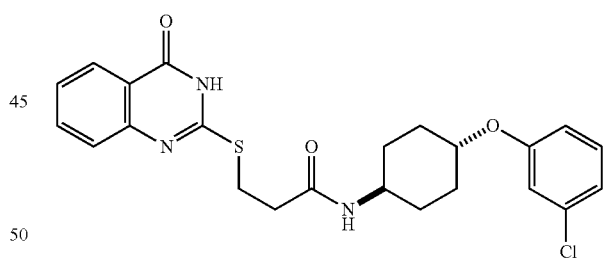

The title compound was prepared as described in General Scheme C using Intermediate I and (1r,4r)-4-(3-chlorophenoxy)cyclohexanamine (HDH Pharma), affording N-((1r,4r)-4-(3-chlorophenoxy)cyclohexyl)-3-((4-oxo-3,4-dihydroquinazolin-2-yl)thio) propanamide (69 mg, 0.151 mmol, 52%) after purification with RP-HPLC. $^1$H NMR (400 MHz, DMSO-$d_6$) δ ppm 12.55 (br. s., 1H) 8.09 (dd, J=7.87, 1.12 Hz, 1H) 7.91 (d, J=7.63 Hz, 1H) 7.82 (ddd, J=8.34, 7.02, 1.56 Hz, 1H) 7.59 (d, J=8.12 Hz, 1H) 7.48 (ddd, J=8.00, 7.12, 1.12 Hz, 1H) 7.34 (t, J=8.17 Hz, 1H) 7.05-7.13 (m, 1H) 7.00 (ddd, J=10.88, 8.19, 0.78 Hz, 1H) 7.00 (ddd, J=15.26, 8.17, 0.83 Hz, 1H) 4.41 (s, 1H) 3.45 (t, J=6.70 Hz, 2H) 2.60-2.68 (m, 2H) 1.99-2.16 (m, 2H) 1.83-1.99 (m, 2H) 1.29-1.57 (m, 4H). m/z (ESI) 458.2 (M+H)$^+$.

Example 113

N-((1r,4r)-4-(4-chloro-3-cyanophenoxy)cyclohexyl)-3-((4-oxo-3,4-dihydroquinazolin-2-yl)thio)propanamide

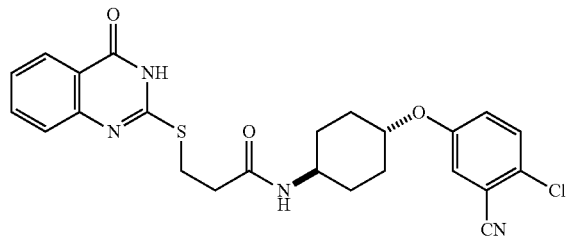

The title compound was prepared as described in General Scheme C using Intermediate I and 5-(((1r,4r)-4-aminocyclohexyl)oxy)-2-chlorobenzonitrile (HDH Pharma), affording N-((1r,4r)-4-(4-chloro-3-cyanophenoxy)cyclohexyl)-3-((4-oxo-3,4-dihydroquinazolin-2-yl)thio)propanamide (73 mg, 0.151 mmol, 57%) after purification with RP-HPLC. $^1$H NMR (400 MHz, DMSO-d$_6$) δ ppm 12.50 (br. s., 1H) 8.04 (dd, J=7.87, 1.12 Hz, 1H) 7.87 (d, J=7.53 Hz, 1H) 7.73-7.81 (m, 1H) 7.64 (d, J=3.03 Hz, 1H) 7.60 (d, J=9.00 Hz, 1H) 7.54 (d, J=8.02 Hz, 1H) 7.38-7.47 (m, 1H) 7.32 (dd, J=9.00, 3.03 Hz, 1H) 4.35-4.50 (m, 1H) 3.55-3.69 (m, 1H) 3.40 (t, J=6.70 Hz, 2H) 2.59 (t, J=6.85 Hz, 2H) 2.04 (d, J=10.27 Hz, 2H) 1.85 (d, J=9.68 Hz, 2H) 1.28-1.50 (m, 4H). m/z (ESI) 483.2 (M+H)$^+$.

Example 114

N-((1r,4r)-4-(3-chloro-4-cyanophenoxy)cyclohexyl)-3-((4-oxo-3,4-dihydroquinazolin-2-yl)thio)propanamide

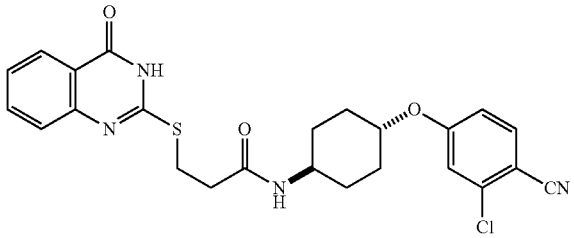

The title compound was prepared as described in General Scheme C using Intermediate I and 4-(((1r,4r)-4-aminocyclohexyl)oxy)-2-chlorobenzonitrile (HDH Pharma), affording N-((1r,4r)-4-(3-chloro-4-cyanophenoxy)cyclohexyl)-3-((4-oxo-3,4-dihydroquinazolin-2-yl)thio)propanamide (80 mg, 0.166 mmol, 59%) after purification with RP-HPLC. $^1$H NMR (400 MHz, DMSO-d$_6$) δ ppm 12.51 (s, 1H) 8.04 (dt, J=7.92, 0.78 Hz, 1H) 7.81-7.92 (m, 2H) 7.77 (ddd, J=8.34, 7.02, 1.57 Hz, 1H) 7.54 (d, J=8.02 Hz, 1H) 7.43 (ddd, J=7.97, 7.09, 1.17 Hz, 1H) 7.37 (d, J=2.45 Hz, 1H) 7.13 (dd, J=8.85, 2.49 Hz, 1H) 4.43-4.65 (m, 1H) 3.52-3.71 (m, 1H) 3.40 (t, J=6.70 Hz, 2H) 2.54-2.63 (m, 2H) 2.05 (d, J=10.17 Hz, 2H) 1.76-1.92 (m, 2H) 1.27-1.56 (m, 4H). m/z (ESI) 483.2 (M+H)$^+$.

Example 115

3-((4-oxo-3,4,5,6,7,8-hexahydroquinazolin-2-yl)thio)-N-(trans-4-(5-phenyl-1,3,4-oxadiazol-2-yl)cyclohexyl)propanamide

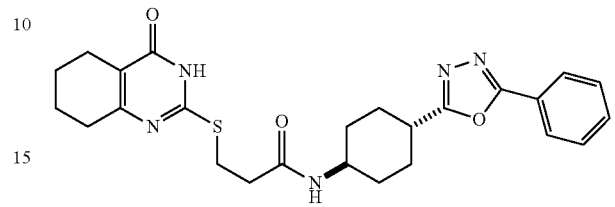

The title compound was prepared as described in General Scheme C using Intermediate N and Intermediate C, affording 3-((4-oxo-3,4,5,6,7,8-hexahydroquinazolin-2-yl)thio)-N-(trans-4-(5-phenyl-1,3,4-oxadiazol-2-yl)cyclohexyl) propanamide (45 mg, 0.094 mmol, 37%) after purification with RP-HPLC. $^1$H NMR (400 MHz, DMSO-d$_6$) δ ppm 12.40 (br. s., 1H) 8.00 (dd, J=7.78, 1.71 Hz, 2H) 7.86 (d, J=7.53 Hz, 1H) 7.52-7.67 (m, 3H) 3.62 (d, J=7.82 Hz, 1H) 3.21-3.29 (m, 2H) 3.00 (t, J=11.79 Hz, 1H) 2.29 (br. s., 2H) 2.18 (d, J=12.62 Hz, 2H) 1.93 (d, J=10.37 Hz, 2H) 1.54-1.77 (m, 6H) 1.24-1.43 (m, 2H). m/z (ESI) 480.2 (M+H)$^+$.

Example 116

N-(trans-4-(4-cyanophenoxy)cyclohexyl)-3-((4-oxo-3,4,5,6,7,8-hexahydroquinazolin-2-yl)thio)propanamide

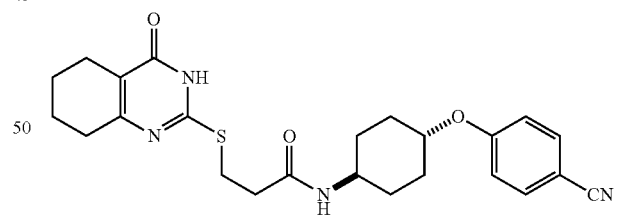

The title compound was prepared as described in General Scheme C using Intermediate N and 4-(((1r,4r)-4-aminocyclohexyl)oxy)benzonitrile (HDH Pharma), affording N-(trans-4-(4-cyanophenoxy)cyclohexyl)-3-((4-oxo-3,4,5,6,7,8-hexahydroquinazolin-2-yl)thio)propanamide (12 mg, 0.027 mmol, 22%) after purification with RP-HPLC. $^1$H NMR (400 MHz, DMSO-d$_6$) δ ppm 12.35 (br. s., 1H) 7.84 (d, J=7.53 Hz, 1H) 7.74 (d, J=8.90 Hz, 2H) 7.13 (d, J=8.90 Hz, 2H) 4.40-4.54 (m, 1H) 3.52-3.70 (m, 1H) 3.26 (t, J=6.75 Hz, 2H) 2.48 (br. s., 4H) 2.28 (br. s., 2H) 2.05 (d, J=10.07 Hz, 2H) 1.84 (d, J=10.17 Hz, 2H) 1.57-1.75 (m, 4H) 1.27-1.53 (m, 4H). m/z (ESI) 453.2 (M+H)$^+$.

Example 117

N-((1r,4r)-4-(5-(4-fluorophenyl)-1,3,4-oxadiazol-2-yl)cyclohexyl)-3-((4-oxo-3,4-dihydroquinazolin-2-yl)thio)propanamide

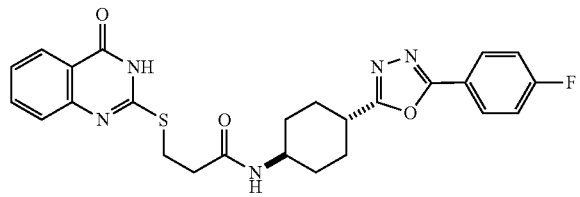

The title compound was prepared as described in General Scheme C using Intermediate I and (1r,4r)-4-(5-(4-fluorophenyl)-1,3,4-oxadiazol-2-yl)cyclohexanamine (HDH Pharma), affording N-((1r,4r)-4-(5-(4-fluorophenyl)-1,3,4-oxadiazol-2-yl)cyclohexyl)-3-((4-oxo-3,4-dihydroquinazolin-2-yl)thio) propanamide (13 mg, 0.026 mmol, 7%) after purification with RP-HPLC. $^1$H NMR (500 MHz, DMSO-d$_6$) δ ppm 12.50 (br. s., 1H) 7.98-8.12 (m, 3H) 7.89 (d, J=7.56 Hz, 1H) 7.77 (t, J=7.68 Hz, 1H) 7.54 (d, J=8.02 Hz, 1H) 7.34-7.50 (m, 3H) 3.62 (dd, J=7.45, 3.55 Hz, 1H) 3.40 (t, J=6.76 Hz, 2H) 2.89-3.06 (m, 1H) 2.58 (t, J=6.64 Hz, 2H) 2.09-2.22 (m, 2H) 1.93 (d, J=13.17 Hz, 2H) 1.65 (q, J=12.83 Hz, 2H) 1.24-1.43 (m, 2H). m/z (ESI) 494.2 (M+H)$^+$.

Example 118

N-((1r,4r)-4-(5-(3-chlorophenyl)-1,3,4-oxadiazol-2-yl)cyclohexyl)-3-((4-oxo-3,4-dihydroquinazolin-2-yl)thio)propanamide

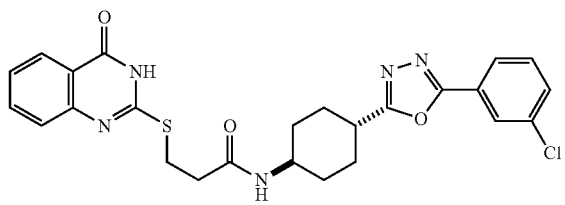

The title compound was prepared as described in General Scheme C using Intermediate I and (1r,4r)-4-(5-(3-chlorophenyl)-1,3,4-oxadiazol-2-yl)cyclohexanamine (HDH Pharma), affording N-((1r,4r)-4-(5-(3-chlorophenyl)-1,3,4-oxadiazol-2-yl)cyclohexyl)-3-((4-oxo-3,4-dihydroquinazolin-2-yl)thio) propanamide (35 mg, 0.069 mmol, 18%) after purification with RP-HPLC. $^1$H NMR (500 MHz, DMSO-d$_6$) δ ppm 12.50 (br. s., 1H) 8.03 (d, J=6.76 Hz, 1H) 7.99 (s, 1H) 7.96 (d, J=7.68 Hz, 1H) 7.89 (d, J=7.68 Hz, 1H) 7.76 (t, J=7.05 Hz, 1H) 7.69 (d, J=8.13 Hz, 1H) 7.63 (t, J=7.90 Hz, 1H) 7.54 (d, J=8.02 Hz, 1H) 7.42 (t, J=7.50 Hz, 1H) 3.57-3.69 (m, 1H) 3.40 (t, J=6.70 Hz, 2H) 2.93-3.06 (m, 1H) 2.58 (t, J=6.70 Hz, 2H) 2.16 (d, J=11.46 Hz, 2H) 1.93 (d, J=12.72 Hz, 2H) 1.66 (q, J=12.91 Hz, 2H) 1.27-1.38 (m, 2H). m/z (ESI) 510.2 (M+H)$^+$.

Example 119

N-((1r,4r)-4-(5-(3-fluorophenyl)-1,3,4-oxadiazol-2-yl)cyclohexyl)-3-((4-oxo-3,4-dihydroquinazolin-2-yl)thio)propanamide

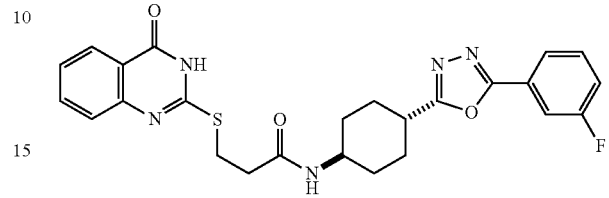

The title compound was prepared as described in General Scheme C using Intermediate I and (1r,4r)-4-(5-(3-fluorophenyl)-1,3,4-oxadiazol-2-yl)cyclohexanamine (HDH Pharma), affording N-((1r,4r)-4-(5-(3-fluorophenyl)-1,3,4-oxadiazol-2-yl)cyclohexyl)-3-((4-oxo-3,4-dihydroquinazolin-2-yl)thio) propanamide (34 mg, 0.069 mmol, 36%) after purification with RP-HPLC. $^1$H NMR (500 MHz, DMSO-d$_6$) δ ppm 12.49 (br. s., 1H) 8.03 (d, J=6.76 Hz, 1H) 7.89 (d, J=7.56 Hz, 1H) 7.84 (d, J=7.79 Hz, 1H) 7.73-7.81 (m, 2H) 7.62-7.70 (m, 1H) 7.54 (d, J=8.13 Hz, 1H) 7.44-7.51 (m, 1H) 7.42 (t, J=7.56 Hz, 1H) 3.60-3.65 (m, 1H) 3.40 (t, J=6.76 Hz, 2H) 2.94-3.03 (m, 1H) 2.58 (t, J=6.76 Hz, 2H) 2.17 (d, J=12.03 Hz, 2H) 1.85-2.00 (m, 2H) 1.59-1.74 (m, 2H) 1.27-1.41 (m, 2H). m/z (ESI) 494.2 (M+H)$^+$.

Example 120

N-((1r,4r)-4-(5-(3-methoxyphenyl)-1,3,4-oxadiazol-2-yl)cyclohexyl)-3-((4-oxo-3,4-dihydroquinazolin-2-yl)thio)propanamide

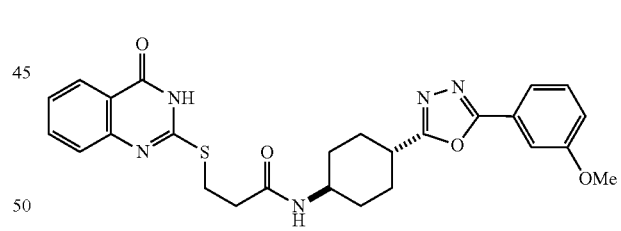

The title compound was prepared as described in General Scheme C using Intermediate I and (1r,4r)-4-(5-(3-methoxyphenyl)-1,3,4-oxadiazol-2-yl)cyclohexanamine (HDH Pharma), affording N-((1r,4r)-4-(5-(3-methoxyphenyl)-1,3,4-oxadiazol-2-yl)cyclohexyl)-3-((4-oxo-3,4-dihydroquinazolin-2-yl)thio) propanamide (30 mg, 0.059 mmol, 15%) after purification with RP-HPLC. $^1$H NMR (500 MHz, DMSO-d$_6$) δ ppm 12.50 (br. s., 1H) 8.03 (d, J=7.33 Hz, 1H) 7.89 (d, J=7.56 Hz, 1H) 7.76 (t, J=7.10 Hz, 1H) 7.45-7.62 (m, 4H) 7.42 (t, J=7.62 Hz, 1H) 7.19 (dd, J=7.85, 2.12 Hz, 1H) 3.85 (s, 3H) 3.57-3.69 (m, 1H) 3.40 (t, J=6.76 Hz, 2H) 2.93-3.05 (m, 1H) 2.58 (t, J=6.76 Hz, 2H) 2.16 (d, J=11.91 Hz, 2H) 1.93 (d, J=9.51 Hz, 2H) 1.57-1.74 (m, 2H) 1.26-1.42 (m, 2H). m/z (ESI) 506.2 (M+H)$^+$.

Example 121

N-((1r,4r)-4-(5-(4-methoxyphenyl)-1,3,4-oxadiazol-2-yl)cyclohexyl)-3-((4-oxo-3,4-dihydroquinazolin-2-yl)thio)propanamide

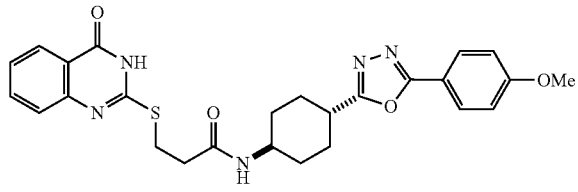

The title compound was prepared as described in General Scheme C using Intermediate I and (1r,4r)-4-(5-(4-methoxyphenyl)-1,3,4-oxadiazol-2-yl)cyclohexanamine (HDH Pharma), affording N-((1r,4r)-4-(5-(4-methoxyphenyl)-1,3,4-oxadiazol-2-yl)cyclohexyl)-3-((4-oxo-3,4-dihydroquinazolin-2-yl)thio) propanamide (10 mg, 0.020 mmol, 10%) after purification with RP-HPLC. $^1$H NMR (500 MHz, DMSO-$d_6$) δ ppm 12.50 (br. s., 1H) 8.03 (d, J=6.87 Hz, 1H) 7.86-7.95 (m, 4H) 7.71-7.81 (m, 1H) 7.54 (d, J=7.90 Hz, 1H) 7.42 (t, J=7.33 Hz, 1H) 7.13 (d, J=8.82 Hz, 3H) 3.80-3.94 (m, 5H) 3.62 (dd, J=11.23, 3.67 Hz, 2H) 3.38-3.41 (m, 5H) 2.96 (t, J=12.03 Hz, 1H) 2.58 (t, J=6.70 Hz, 2H) 2.15 (d, J=11.80 Hz, 3H) 1.93 (d, J=12.37 Hz, 3H) 1.64 (q, J=12.60 Hz, 3H) 1.26-1.40 (m, 3H). m/z (ESI) 506.2 (M+H)$^+$.

Example 122

N-((1r,4r)-4-(5-(3-chloro-4-fluorophenyl)-1,3,4-oxadiazol-2-yl)cyclohexyl)-3-((4-oxo-3,4-dihydroquinazolin-2-yl)thio)propanamide

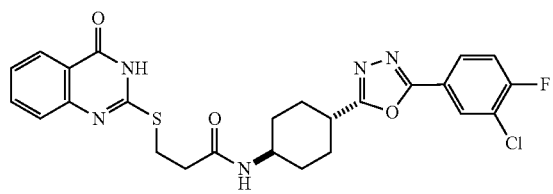

The title compound was prepared as described in General Scheme C using Intermediate I and (1r,4r)-4-(5-(3-chloro-4-fluorophenyl)-1,3,4-oxadiazol-2-yl)cyclohexanamine (HDH Pharma), affording N-((1r,4r)-4-(5-(3-chloro-4-fluorophenyl)-1,3,4-oxadiazol-2-yl)cyclohexyl)-3-((4-oxo-3,4-dihydroquinazolin-2-yl)thio) propanamide (35 mg, 0.066 mmol, 17%) after purification with RP-HPLC. $^1$H NMR (500 MHz, DMSO-$d_6$) δ ppm 12.50 (br. s., 1H) 8.16 (dd, J=6.93, 1.89 Hz, 1H) 7.98-8.05 (m, 2H) 7.89 (d, J=7.68 Hz, 1H) 7.73-7.79 (m, 1H) 7.65 (t, J=8.88 Hz, 1H) 7.53 (d, J=8.02 Hz, 1H) 7.42 (t, J=7.50 Hz, 1H) 3.58-3.68 (m, 1H) 3.35-3.40 (m, 2H) 2.94-3.03 (m, 1H) 2.58 (t, J=6.70 Hz, 2H) 2.16 (d, J=11.80 Hz, 2H) 1.88-1.97 (m, 2H) 1.66 (q, J=12.75 Hz, 2H) 1.27-1.39 (m, 2H). m/z (ESI) 528.2 (M+H)$^+$.

Example 123

3-((6-oxo-1,6-dihydropyrimidin-2-yl)thio)-N-((1r,4r)-4-(5-phenyl-1,3,4-oxadiazol-2-yl)cyclohexyl)propanamide

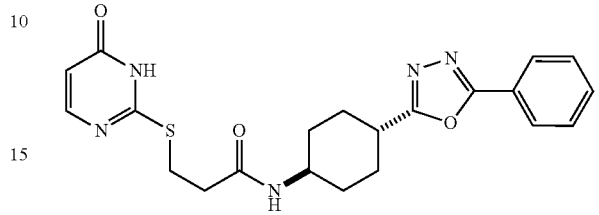

The title compound was prepared as described in General Scheme C using Intermediate O and Intermediate C, affording 3-((6-oxo-1,6-dihydropyrimidin-2-yl)thio)-N-((1r,4r)-4-(5-phenyl-1,3,4-oxadiazol-2-yl)cyclohexyl)propanamide (36 mg, 0.085 mmol, 35% yield) after purification with RP-HPLC. $^1$H NMR (400 MHz, DMSO-$d_6$) δ ppm 12.65 (br. s., 1H) 8.00 (dd, J=7.78, 1.71 Hz, 2H) 7.89 (d, J=7.53 Hz, 2H) 7.53-7.69 (m, 4H) 6.10 (br. s., 1H) 3.62 (dd, J=7.43, 4.21 Hz, 1H) 3.00 (t, J=11.93 Hz, 1H) 2.18 (d, J=12.03 Hz, 2H) 1.84-2.00 (m, 2H) 1.58-1.74 (m, 2H) 1.27-1.45 (m, 2H). m/z (ESI) 426.2 (M+H)$^+$.

Example 124

3-((4-oxo-3,4-dihydroquinazolin-2-yl)thio)-N-(trans-4-(5-(pyridin-4-yl)-1,3,4-oxadiazol-2-yl)cyclohexyl)propanamide

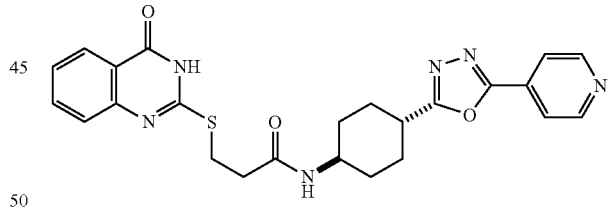

The title compound was prepared as described in General Scheme C using Intermediate I and (1r,4r)-4-(5-(pyridin-4-yl)-1,3,4-oxadiazol-2-yl)cyclohexanamine (HDH Pharma), affording N-((1r,4r)-4-(5-(3-chloro-4-fluorophenyl)-1,3,4-oxadiazol-2-yl)cyclohexyl)-3-((4-oxo-3,4-dihydroquinazolin-2-yl)thio) propanamide (63 mg, 0.132 mmol, 38% yield) after purification with RP-HPLC. $^1$H NMR (400 MHz, DMSO-$d_6$) δ ppm 12.34 (br. s., 1H) 8.59-8.73 (m, 2H) 7.89 (dd, J=7.87, 1.22 Hz, 1H) 7.71-7.80 (m, 3H) 7.61 (td, J=7.65, 1.61 Hz, 1H) 7.39 (d, J=8.12 Hz, 1H) 7.23-7.31 (m, 1H) 3.48 (dtd, J=11.44, 7.53, 7.53, 3.91 Hz, 1H) 3.25 (t, J=6.70 Hz, 2H) 2.88 (ft, J=11.88, 3.47 Hz, 1H) 2.44 (t, J=6.70 Hz, 2H) 2.03 (d, J=11.54 Hz, 2H) 1.71-1.89 (m, 2H) 1.51 (qd, J=12.88, 3.33 Hz, 2H) 1.11-1.31 (m, 2H). m/z (ESI) 478.2 (M+H)$^+$.

Example 125

N-((1r,4r)-4-(5-(4-chlorophenyl)-1,3,4-oxadiazol-2-yl)cyclohexyl)-3-((4-oxo-3,4-dihydroquinazolin-2-yl)thio)propanamide

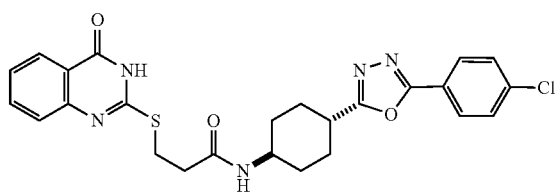

The title compound was prepared as described in General Scheme C using Intermediate I and (1r,4r)-4-(5-(4-chlorophenyl)-1,3,4-oxadiazol-2-yl)cyclohexanamine (HDH Pharma), affording N-((1r,4r)-4-(5-(3-chloro-4-fluorophenyl)-1,3,4-oxadiazol-2-yl)cyclohexyl)-3-((4-oxo-3,4-dihydroquinazolin-2-yl)thio) propanamide (129 mg, 0.253 mmol, 67% yield) after purification with RP-HPLC. $^1$H NMR (400 MHz, DMSO-$d_6$) δ ppm 12.46 (br. s., 1H) 7.90-8.06 (m, 3H) 7.85 (d, J=7.53 Hz, 1H) 7.68-7.77 (m, 1H) 7.63 (d, J=8.51 Hz, 2H) 7.50 (d, J=7.92 Hz, 1H) 7.38 (t, J=7.53 Hz, 1H) 3.51-3.68 (m, 1H) 3.36 (t, J=6.65 Hz, 2H) 2.87-3.01 (m, 1H) 2.55 (t, J=6.70 Hz, 2H) 2.12 (d, J=11.64 Hz, 2H) 1.84-1.97 (m, 2H) 1.51-1.68 (m, 2H) 1.22-1.39 (m, 2H). m/z (ESI) 510.2 (M+H)$^+$.

mixture was irradiated at 150'C in a microwave for 2 h. The mixture was concentrated and purified by preparative HPLC to afford the title compound.

The following examples were all prepared using General Scheme D.

Example 126

N-((1r,4r)-4-(5-(2-fluorophenyl)-1,3,4-oxadiazol-2-yl)cyclohexyl)-3-(4-oxo-3,4-dihydroquinazolin-2-yl)propanamide

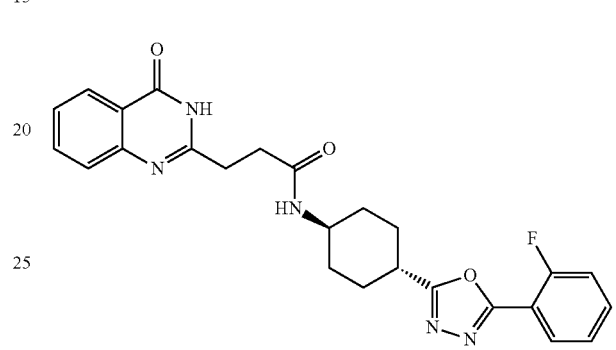

General Scheme D:

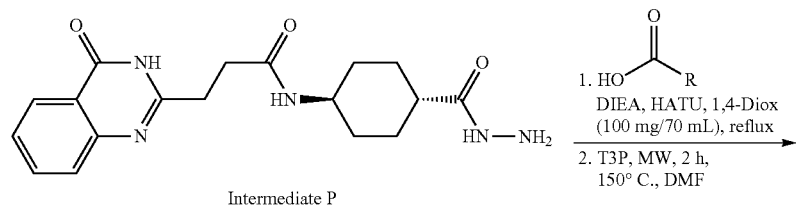

Intermediate P

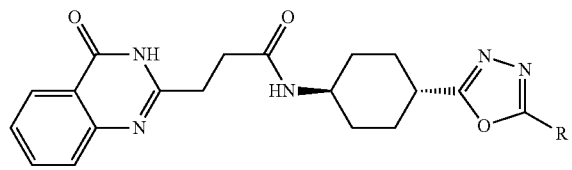

Representative Protocol:

Intermediate P (500 mg, 1.4 mmol), aryl-acetic acid (190 mg, 1.4 mmol) and DIEA (600 mg, 4.2 mmol) were dissolved in 1,4-dioxane (150 mL). HATU (590 mg, 0.85 mmol) was added, and the reaction mixture was stirred at 90'C overnight. The resulting precipitate was collected to give acyl hydrazide (300 mg). To a solution of acyl hydrazide (300 mg) in DMF (10 mL) was added DIEA (162 mg, 1.26 mmol) and T3P (408 mg, 1.26 mmol), and the resulting The title compound was prepared as described in General Scheme D using 2-fluorobenzoic acid, affording N-((1r,4r)-4-(5-(2-fluorophenyl)-1,3,4-oxadiazol-2-yl)cyclohexyl)-3-(4-oxo-3,4-dihydroquinazolin-2-yl)propanamide (32 mg, 0.056 mmol, 28% yield; $^1$H NMR (400 MHz, CD$_3$OD) δ 8.28-8.26 (m, 1H), 8.06-8.02 (m, 1H), 7.96-7.91 (m, 1H), 7.72-7.63 (m, 3H), 7.42-7.35 (m, 2H), 3.76 (s, 1H), 3.14-3.02 (m, 3H), 2.88-2.84 (m, 2H), 2.30-2.26 (m, 2H), 2.10-2.06 (m, 2H), 1.82-1.73 (m, 2H), 1.49-1.41 (m, 2H). LC-MS: 462 (M+1); calcd for $C_{25}H_{24}FN_5O_3$: 461.19.

Example 127

N-((1r,4r)-4-(5-(4-fluorophenyl)-1,3,4-oxadiazol-2-yl)cyclohexyl)-3-(4-oxo-3,4-dihydroquinazolin-2-yl)propanamide

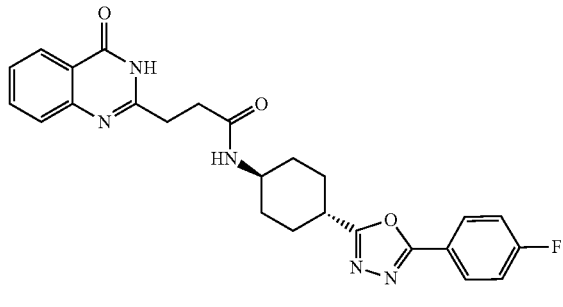

The title compound was prepared as described in General Scheme D using 4-fluorobenzoic acid, affording N-((1r,4r)-4-(5-(4-fluorophenyl)-1,3,4-oxadiazol-2-yl)cyclohexyl)-3-(4-oxo-3,4-dihydroquinazolin-2-yl)propanamide (27 mg, 0.056 mmol, 28% yield; $^1$H NMR (400 MHz, CD$_3$OD) δ 8.30-8.27 (m, 1H), 8.10-8.07 (m, 2H), 7.96-7.93 (m, 1H), 7.73-7.66 (m, 2H), 7.35-7.31 (m, 2H), 3.78-3.72 (m, 1H), 3.17-3.13 (m, 2H), 3.05-2.98 (m, 1H), 2.90-2.86 (m, 2H), 2.29-2.26 (m, 2H), 2.10-2.06 (m, 2H), 1.82-1.70 (m, 2H), 1.50-1.40 (m, 2H). LC-MS: 462 (M+1); calcd for C$_{25}$H$_{24}$FN$_5$O$_3$: 461.2.

Example 128

N-((1r,4r)-4-(5-(2-chlorophenyl)-1,3,4-oxadiazol-2-yl)cyclohexyl)-3-(4-oxo-3,4-dihydroquinazolin-2-yl)propanamide

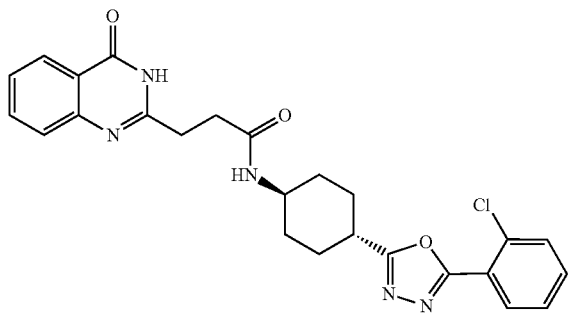 [SMILES: O=C(CCc1nc2ccccc2c(=O)[nH]1)N[C@H]1CC[C@H](c2nnc(-c3ccccc3F)o2)CC1]

The title compound was prepared as described in General Scheme D using 2-chlorobenzoic acid, affording N-((1r,4r)-4-(5-(2-chlorophenyl)-1,3,4-oxadiazol-2-yl)cyclohexyl)-3-(4-oxo-3,4-dihydroquinazolin-2-yl)propanamide (21 mg, 0.044 mmol, 14% yield; $^1$H NMR (400 MHz, CD$_3$OD) δ 8.21-8.19 (m, 1H), 7.97-7.95 (m, 1H), 7.84-7.79 (m, 1H), 7.68-7.60 (m, 3H), 7.58-7.49 (m, 2H), 3.79-3.73 (m, 1H), 3.09-2.97 (m, 3H), 2.78-2.74 (m, 2H), 2.29-2.26 (m, 2H), 2.09-2.05 (m, 2H), 1.83-1.73 (m, 2H), 1.49-1.39 (m, 2H). LC-MS: 478 (M+1); calcd for C$_{25}$H$_{24}$ClN$_5$O$_3$: 477.2.

Example 129

N-((1r,4r)-4-(5-(3-fluorophenyl)-1,3,4-oxadiazol-2-yl)cyclohexyl)-3-(4-oxo-3,4-dihydroquinazolin-2-yl)propanamide

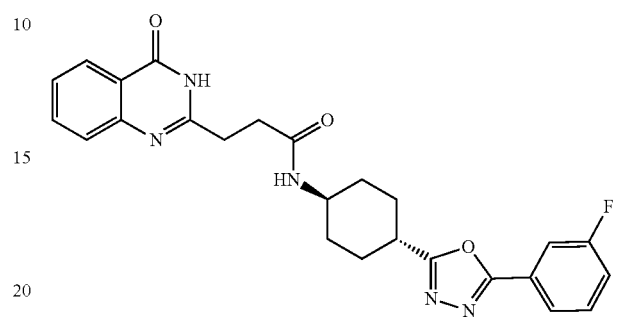

The title compound was prepared as described in General Scheme D using 3-fluorobenzoic acid, affording N-((1r,4r)-4-(5-(3-fluorophenyl)-1,3,4-oxadiazol-2-yl)cyclohexyl)-3-(4-oxo-3,4-dihydroquinazolin-2-yl)propanamide (14 mg, 0.056 mmol, 18% yield; $^1$H NMR (400 MHz, CD$_3$OD) δ 8.19-8.17 (m, 1H), 7.87-7.74 (m, 3H), 7.66-7.47 (m, 3H), 7.38-7.33 (m, 1H), 3.82-3.68 (m, 1H), 3.04-2.97 (m, 3H), 2.76-2.72 (m, 2H), 2.27-2.24 (m, 2H), 2.07-2.03 (m, 2H), 1.80-1.69 (m, 2H), 1.46-1.36 (m, 2H). LC-MS: 462 (M+1); calcd for C$_{25}$H$_{24}$FN$_5$O$_3$: 461.19.

Example 130

N-((1r,4r)-4-(5-(3-chlorophenyl)-1,3,4-oxadiazol-2-yl)cyclohexyl)-3-(4-oxo-3,4-dihydroquinazolin-2-yl)propanamide

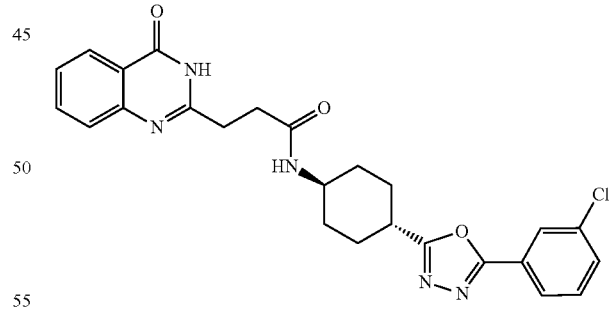

The title compound was prepared as described in General Scheme D using 3-chlorobenzoic acid, affording N-((1r,4r)-4-(5-(3-chlorophenyl)-1,3,4-oxadiazol-2-yl)cyclohexyl)-3-(4-oxo-3,4-dihydroquinazolin-2-yl)propanamide (74 mg, 0.155 mmol, 49% yield; $^1$H NMR (400 MHz, CD$_3$OD) δ 8.04-8.03 (m, 1H), 7.98-7.96 (m, 1H), 7.96-7.92 (m, 2H), 7.73-7.55 (m, 4H), 3.80-3.72 (m, 1H), 3.16-3.13 (m, 2H), 3.12-2.98 (m, 1H), 2.89-2.86 (m, 2H), 2.29-2.27 (m, 2H), 2.10-2.06 (m, 2H), 1.83-1.72 (m, 2H), 1.50-1.40 (m, 2H). LC-MS: 478 (M+1); calcd for C$_{25}$H$_{24}$ClN$_5$O$_3$: 477.2.

Example 131

3-(4-oxo-3,4-dihydroquinazolin-2-yl)-N-((1r,4r)-4-(5-(pyridin-2-yl)-1,3,4-oxadiazol-2-yl)cyclohexyl)propanamide

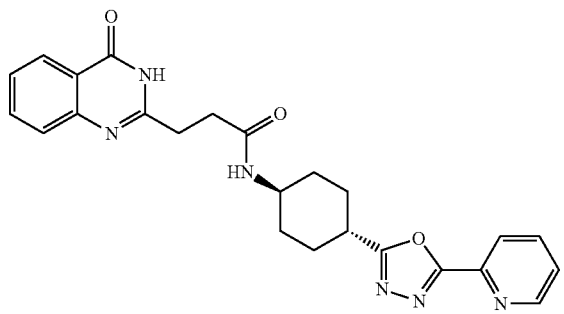 [SMILES: O=C(CCc1nc2ccccc2c(=O)[nH]1)N[C@H]1CC[C@H](c2nnc(-c3ccccn3)o2)CC1]

The title compound was prepared as described in General Scheme D using picolinic acid, affording 3-(4-oxo-3,4-dihydroquinazolin-2-yl)-N-((1r,4r)-4-(5-(pyridin-2-yl)-1,3,4-oxadiazol-2-yl)cyclohexyl)propanamide (90 mg, 0.203 mmol, 64% yield; $^1$H NMR (400 MHz, CD$_3$OD) δ 8.76-8.75 (m, 1H), 8.29-8.27 (m, 1H), 8.23-8.21 (m, 1H), 8.09-8.05 (m, 1H), 7.97-7.93 (m, 1H), 7.73-7.62 (m, 3H), 3.79-3.77 (m, 1H), 3.33-3.03 (m, 3H), 2.89-2.86 (m, 2H), 2.33-2.29 (m, 2H), 2.10-2.06 (m, 2H), 1.85-1.74 (m, 2H), 1.51-1.41 (m, 2H). LC-MS: 445 (M+1); calcd for C$_{24}$H$_{24}$N$_6$O$_3$: 444.

Example 132

3-(4-oxo-3,4-dihydroquinazolin-2-yl)-N-((1r,4r)-4-(5-(pyridin-4-yl)-1,3,4-oxadiazol-2-yl)cyclohexyl)propanamide

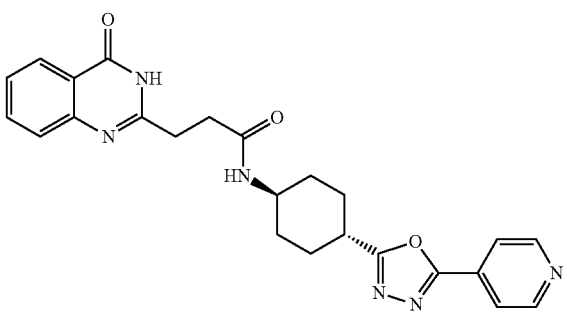 [SMILES: O=C(CCc1nc2ccccc2c(=O)[nH]1)N[C@H]1CC[C@H](c2nnc(-c3ccncc3)o2)CC1]

The title compound was prepared as described in General Scheme D using isonicotinic acid, affording 3-(4-oxo-3,4-dihydroquinazolin-2-yl)-N-((1r,4r)-4-(5-(pyridin-4-yl)-1,3,4-oxadiazol-2-yl)cyclohexyl)propanamide (30 mg, 0.07 mmol, 33% yield; $^1$H NMR (400 MHz, CD$_3$OD) δ 8.81-8.80 (m, 2H), 8.22-8.20 (m, 1H), 8.09-8.07 (m, 2H), 7.88-7.83 (m, 1H), 7.67 (d, J=8.0 Hz, 1H), 7.56 (t, J=7.6 Hz, 1H), 3.78-3.70 (m, 1H), 3.31-3.30 (m, 3H), 3.06-3.03 (m, 2H), 2.28-2.25 (m, 2H), 2.08-2.04 (m, 2H), 1.82-1.71 (m, 2H), 1.48-1.37 (m, 2H). LC-MS: 445 (M+1); calcd for C$_{24}$H$_{24}$N$_6$O$_3$: 444.2.

Example 133

3-(4-oxo-3,4-dihydroquinazolin-2-yl)-N-((1r,4r)-4-(5-(pyrimidin-2-yl)-1,3,4-oxadiazol-2-yl)cyclohexyl)propanamide

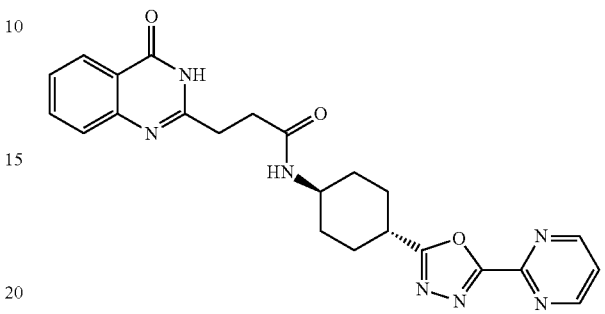

The title compound was prepared as described in General Scheme D using pyrimidine-2-carboxylic acid, affording 3-(4-oxo-3,4-dihydroquinazolin-2-yl)-N-((1r,4r)-4-(5-(pyrimidin-2-yl)-1,3,4-oxadiazol-2-yl)cyclohexyl)propanamide (30 mg, 0.07 mmol, 33% yield; $^1$H NMR (400 MHz, DMSO-d6) δ 9.04 (d, J=4.8 Hz, 2H), 8.10-8.07 (m, 1H), 7.95 (d, J=7.6 Hz, 1H), 7.80-7.72 (m, 2H), 7.57 (d, J=8.0 Hz, 1H), 7.48-7.44 (m, 1H), 3.64-3.57 (m, 1H), 3.10-3.02 (m, 1H), 2.88-2.84 (m, 2H), 2.63-2.59 (m, 2H), 2.18-2.15 (m, 2H), 1.94-1.90 (m, 2H), 1.69-1.59 (m, 2H), 1.41-1.31 (m, 2H). LC-MS: 446 (M+1); calcd for C$_{23}$H$_{23}$N$_7$O$_3$ 445.2.

Example 134

N-((1r,4r)-4-(5-(4-cyanophenyl)-1,3,4-oxadiazol-2-yl)cyclohexyl)-3-(4-oxo-3,4-dihydroquinazolin-2-yl)propanamide

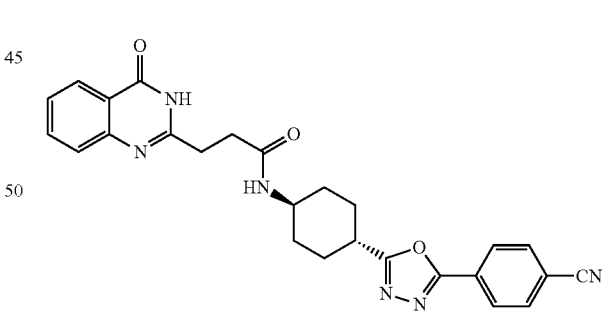

The title compound was prepared as described in General Scheme D using 4-cyanobenzoic acid, affording N-((1r,4r)-4-(5-(4-cyanophenyl)-1,3,4-oxadiazol-2-yl)cyclohexyl)-3-(4-oxo-3,4-dihydroquinazolin-2-yl)propanamide (13 mg, 0.028 mmol, 14% yield; $^1$H NMR (400 MHz, DMSO-d6) δ 12.20 (s, 1H), 818-8.16 (m, 2H), 8.09-8.07 (m, 2H), 7.95 (d, J=7.6 Hz, 1H), 7.80-7.76 (m, 1H), 7.75 (d, J=8.4 Hz, 1H), 7.49-7.45 (m, 1H), 3.61-3.59 (m, 1H), 3.02-2.94 (m, 1H), 2.88-2.84 (m, 2H), 2.9-2.65 (m, 2H), 2.18-2.16 (m, 2H), 1.92-1.89 (m, 2H), 1.69-1.60 (m, 2H), 1.39-1.30 (m, 2H). LC-MS: 469 (M+1); calcd for C$_{26}$H$_{24}$N$_6$O$_3$: 468.19.

Example 135

3-(4-oxo-3,4-dihydroquinazolin-2-yl)-N-((1r,4r)-4-(5-(tetrahydro-2H-pyran-4-yl)-1,3,4-oxadiazol-2-yl)cyclohexyl)propanamide

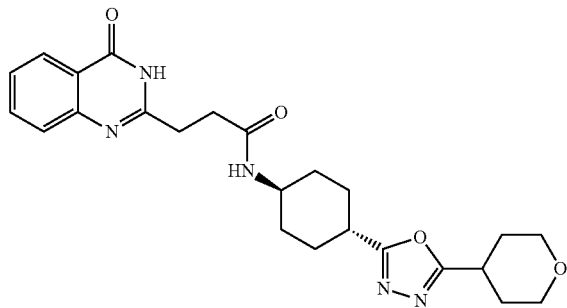 [SMILES: O=C(CCc1nc2ccccc2c(=O)[nH]1)N[C@H]1CC[C@H](c2nnc(C3CCOCC3)o2)CC1]

The title compound was prepared as described in General Scheme D using tetrahydro-2H-pyran-4-carboxylic acid, affording 3-(4-oxo-3,4-dihydroquinazolin-2-yl)-N-((1r,4r)-4-(5-(tetrahydro-2H-pyran-4-yl)-1,3,4-oxadiazol-2-yl)cyclohexyl)propanamide (18 mg, 0.040 mmol, 13% yield; $^1$H NMR (400 MHz, CD$_3$OD) δ 8.20-8.18 (m, 1H), 7.85-7.80 (m, 1H), 7.65 (d, J=8.0 Hz, 1H), 7.55-7.51 (m, 1H), 3.99-3.94 (m, 2H), 3.72-3.66 (m, 1H), 3.58-3.51 (m, 2H), 3.25-3.17 (m, 1H), 3.02-2.99 (m, 2H), 2.89-2.85 (m, 1H), 2.77-2.73 (m, 2H), 2.16-2.13 (m, 2H), 2.01-1.92 (m, 4H), 1.89-1.83 (m, 2H), 1.79-1.64 (m, 2H), 1.47-1.24 (m, 2H). LC-MS: 452 (M+1); calcd for C$_{24}$H$_{29}$N$_5$O$_4$: 451.

Example 136

3-(4-oxo-3,4-dihydroquinazolin-2-yl)-N-((1r,4r)-4-(5-(pyridin-3-yl)-1,3,4-oxadiazol-2-yl)cyclohexyl)propanamide

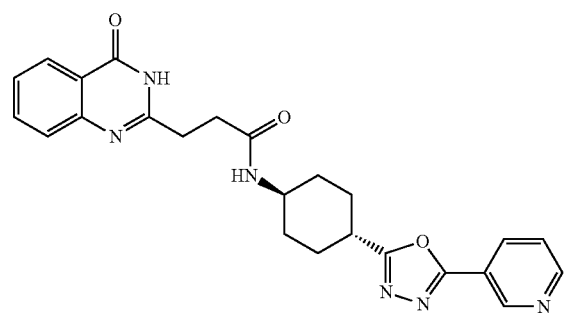 [SMILES: O=C(CCc1nc2ccccc2c(=O)[nH]1)N[C@H]1CC[C@H](c2nnc(-c3cccnc3)o2)CC1]

The title compound was prepared as described in General Scheme D using nictonic acid, affording 3-(4-oxo-3,4-dihydroquinazolin-2-yl)-N-((1r,4r)-4-(5-(pyridin-3-yl)-1,3,4-oxadiazol-2-yl)cyclohexyl)propanamide (58 mg, 0.13 mmol, 59% yield; $^1$H NMR (400 MHz, CD$_3$OD) δ 9.23-9.22 (m, 1H), 8.80-8.78 (m, 1H), 8.57-8.54 (m, 1H), 8.27-8.24 (m, 1H), 7.96-7.94 (m, 1H), 7.93-7.64 (m, 3H), 3.72-3.71 (m, 1H), 3.17-3.14 (m, 2H), 3.03-3.00 (m, 1H), 2.89-2.86 (m, 2H), 2.28-2.23 (m, 2H), 2.07-2.02 (m, 2H), 1.79-1.70 (m, 2H), 1.46-1.40 (m, 2H); m/z (ESI) 445 (M+H)$^+$ calcd for C$_{24}$H$_{24}$N$_6$O$_3$: 444.19.

Example 137

N-((1r,4r)-4-(5-(3-cyanophenyl)-1,3,4-oxadiazol-2-yl)cyclohexyl)-3-(4-oxo-3,4-dihydroquinazolin-2-yl)propanamide

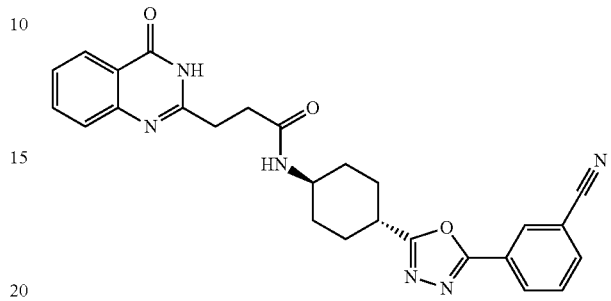

The title compound was prepared as described in General Scheme D using 3-cyano benzoic acid, affording N-((1r,4r)-4-(5-(3-cyanophenyl)-1,3,4-oxadiazol-2-yl)cyclohexyl)-3-(4-oxo-3,4-dihydroquinazolin-2-yl)propanamide (26 mg, 0.056 mmol, 28% yield); $^1$H NMR (400 MHz, CD$_3$OD) δ 8.33-8.31 (m, 3H), 7.97-7.88 (m, 1H), 7.73-7.66 (m, 2H), 7.88-7.83 (m, 2H), 7.03-7.01 (m, 1H), 3.97-3.93 (m, 1H), 3.48-3.46 (m, 2H), 3.02-2.99 (m, 3H), 2.34-2.31 (m, 2H), 2.20-2.17 (m, 2H), 1.89-1.79 (m, 2H), 1.52-1.43 (m, 2H); m/z (ESI) 469 (M+H)$^+$ calcd for C$_{26}$H$_{24}$N$_6$O$_3$: 468.19.

Example 138

N-((1r,4r)-4-(5-cyclohexyl-1,3,4-oxadiazol-2-yl)cyclohexyl)-3-(4-oxo-3,4-dihydroquinazolin-2-yl)propanamide

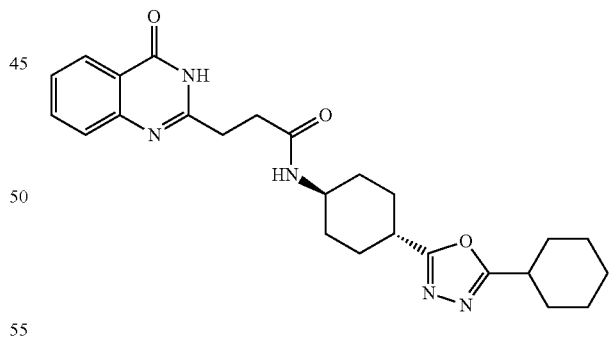

The title compound was prepared as described in General Scheme D using hexanoic acid, affording N-((1r,4r)-4-(5-cyclohexyl-1,3,4-oxadiazol-2-yl)cyclohexyl)-3-(4-oxo-3,4-dihydroquinazolin-2-yl)propanamide (18 mg, 0.040 mmol, 13% yield); $^1$H NMR (400 MHz, CDCl$_3$) δ 8.30-8.28 (m, 1H), 7.78-7.74 (m, 1H), 7.65-7.63 (m, 1H), 7.50-7.46 (m, 1H), 5.90-5.88 (m, 1H); 3.92-3.87 (m, 1H), 3.10-3.07 (m, 2H), 2.92-2.83 (m, 2H), 2.81-2.75 (m, 2H), 2.19-2.14 (m, 3H), 2.09-2.06 (m, 2H), 1.87-1.83 (m, 2H), 1.79-1.56 (m, 5H); 1.46-1.23 (m, 6H); m/z (ESI) 450 (M+H)$^+$; calcd for C$_{25}$H$_{31}$N$_5$O$_3$: 449.

Example 139

N-((1r,4r)-4-(5-benzyl-1,3,4-oxadiazol-2-yl)cyclohexyl)-3-(4-oxo-3,4-dihydroquinazolin-2-yl)propanamide

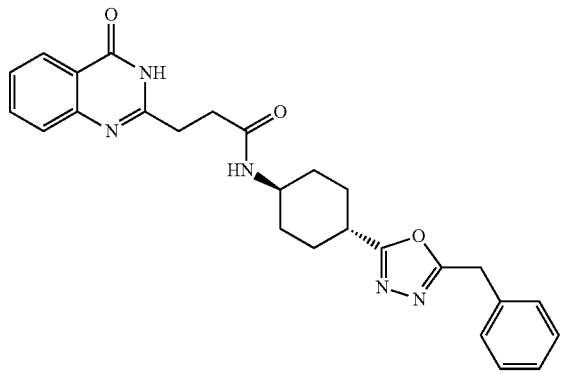 [SMILES: O=C(CCc1nc2ccccc2c(=O)[nH]1)N[C@H]1CC[C@H](c2nnc(Cc3ccccc3)o2)CC1]

The title compound was prepared as described in General Scheme D using 2-phenylacetic acid, affording N-((1r,4r)-4-(5-benzyl-1,3,4-oxadiazol-2-yl)cyclohexyl)-3-(4-oxo-3,4-dihydroquinazolin-2-yl)propanamide (30 mg, 0.066 mmol, 13% yield); $^1$H NMR (400 MHz, CD$_3$OD) δ 8.20-8.18 (m, 1H), 7.83-7.79 (m, 1H), 7.67-7.65 (m, 1H), 7.53-7.48 (m, 1H), 7.38-7.28 (m, 5H), 4.22 (s, 2H), 3.73-3.67 (m, 1H), 3.01-2.97 (m, 2H), 2.92-2.86 (m, 1H), 2.75-2.72 (m, 2H), 2.15-2.12 (m, 2H), 2.03-1.99 (m, 2H), 1.70-1.59 (m, 2H), 1.42-1.31 (m, 2H); m/z (ESI) 458 (M+H)$^+$; calcd for C$_{26}$H$_{27}$N$_5$O$_3$: 457.21.

Example 140

3-(4-oxo-3,4-dihydroquinazolin-2-yl)-N-((1r,4r)-4-(5-(2-phenylpropan-2-yl)-1,3,4-oxadiazol-2-yl)cyclohexyl)propanamide

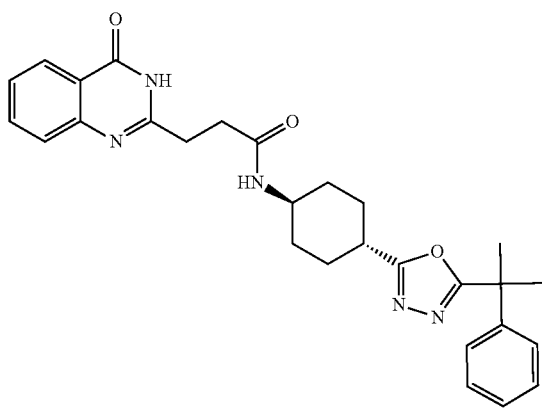 [SMILES: CC(C)(c1ccccc1)c1nnc([C@H]2CC[C@H](NC(=O)CCc3nc4ccccc4c(=O)[nH]3)CC2)o1]

The title compound was prepared as described in General Scheme D using 2-methyl-2-phenylpropanoic acid, affording 3-(4-oxo-3,4-dihydroquinazolin-2-yl)-N-((1r,4r)-4-(5-(2-phenylpropan-2-yl)-1,3,4-oxadiazol-2-yl)cyclohexyl)propanamide (2.7 mg, 0.0056 mmol, 2.8% yield); $^1$H NMR (400 MHz, CD$_3$OD) δ 8.21 (d, J=8.0 Hz, 1H), 7.88-7.84 (m, 1H), 7.66 (d, J=8.0 Hz, 1H), 7.59-7.55 (m, 1H), 7.34-7.30 (m, 2H), 7.26-7.22 (m, 3H), 3.69-3.63 (m, 1H), 3.06-3.02 (m, 2H), 2.89-2.84 (m, 1H), 2.79-2.75 (m, 2H), 2.11-2.08 (m, 2H), 1.99-1.96 (m, 2H), 1.78-1.77 (m, 6H), 1.65-1.58 (m, 2H), 1.39-1.33 (m, 2H); m/z (ESI) 424 (M+H)$^+$; calcd for C$_{28}$H$_{31}$N$_5$O$_3$: 423.

Example 141

N-((1r,4r)-4-(5-(4-chlorophenyl)-1,3,4-oxadiazol-2-yl)cyclohexyl)-3-(4-oxo-3,4-dihydroquinazolin-2-yl)propanamide

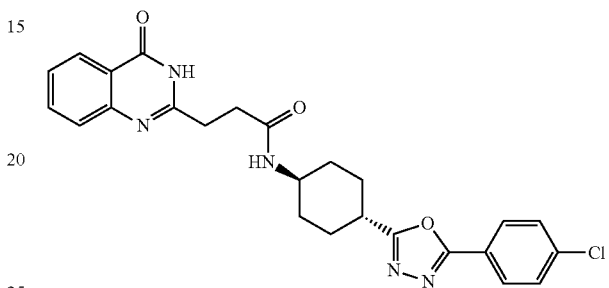

The title compound was prepared according to General Protocol D using 4-chlorobenzoic acid, affording N-((1r,4r)-4-(5-(4-chlorophenyl)-1,3,4-oxadiazol-2-yl)cyclohexyl)-3-(4-oxo-3,4-dihydroquinazolin-2-yl)propanamide 37 mg, 0.078 mmol, 25% yield); $^1$H NMR (400 MHz, CD$_3$OD) δ 8.21-8.19 (m, 1H), 8.04-8.02 (m, 2H), 7.84-7.80 (m, 1H), 7.69-7.67 (m, 1H), 7.62-7.60 (m, 2H), 7.54-7.49 (m, 1H), 3.79-3.72 (m, 1H), 3.06-2.99 (m, 3H), 2.78-2.74 (m, 2H), 2.28-2.25 (m, 2H), 2.09-2.06 (m, 2H), 1.83-1.72 (m, 2H), 1.49-1.39 (m, 2H). m/z (ESI): 478 (M+H)$^+$; calcd for C$_{25}$H$_{24}$ClN$_5$O$_3$: 477.2.

Example 142

3-(4-oxo-3,4-dihydroquinazolin-2-yl)-N-((1r,4r)-4-(5-(pyrazin-2-yl)-1,3,4-oxadiazol-2-yl)cyclohexyl)propanamide

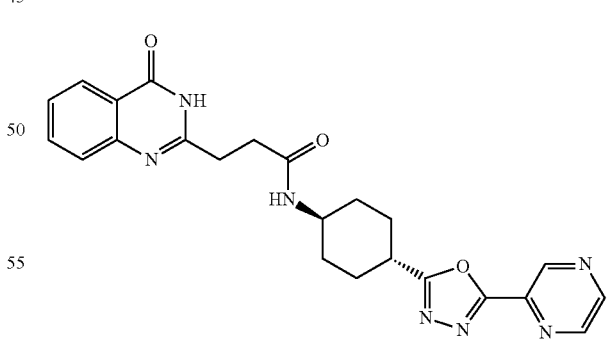

The title compound was prepared according to General Protocol D using pyrazine-2-carboxylic acid, affording 3-(4-oxo-3,4-dihydroquinazolin-2-yl)-N-((1r,4r)-4-(5-(pyrazin-2-yl)-1,3,4-oxadiazol-2-yl)cyclohexyl)propanamide (40 mg, 0.090 mmol, 29% yield); $^1$H NMR (400 MHz, CDCl$_3$) δ 9.47-9.46 (m, 1H), 8.74-8.73 (m, 2H), 8.31-8.29 (m, 1H), 7.88-7.87 (m, 2H), 7.64-7.60 (m, 2H), 6.83-6.81 (m, 1H), 3.98-3.95 (m, 1H), 3.39-3.37 (m, 2H), 2.94-2.93 (m, 3H), 2.34-2.31 (m, 2H), 2.18-2.15 (m, 2H), 1.90-1.82 (m, 2H), 1.45-1.34 (m, 2H). m/z (ESI): (M+H)+; calcd for $C_{23}H_{23}N_7O_3$: 445.

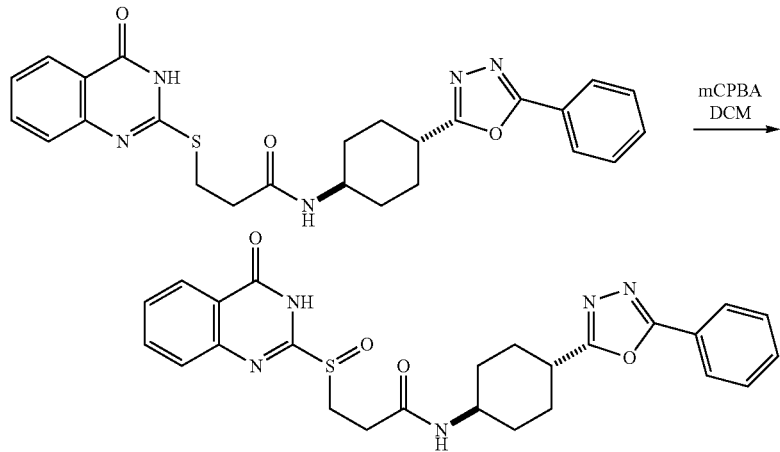

To a mixture of 3-((4-oxo-3,4-dihydroquinazolin-2-yl)thio)-N-((1r,4r)-4-(5-phenyl-1,3,4-oxadiazol-2-yl)cyclohexyl) propanamide (0.083 g, 0.175 mmol) in DCM was added 3-chloroperoxybenzoic acid (0.054 g, 0.314 mmol). The mixture was stirred at RT for 1 h. All starting material was consumed and the desired product was observed on LC-MS with a small amount of overoxidized product. The reaction was quenched with saturated aqueous sodium thiosulfate and extracted with EtOAc. The combined extracts were washed with brine, dried over anhydrous sodium sulfate, and concentrated. The material thus obtained was washed with small amount of MeOH to give 3-((4-oxo-3,4-dihydroquinazolin-2-yl)sulfinyl)-N-((1r,4r)-4-(5-phenyl-1,3,4-oxadiazol-2-yl)cyclohexyl)propanamide (0.020 g, 0.041 mmol, 23.31% yield) as off-white solid. $^1$H NMR (400 MHz, DMSO-$d_6$) δ ppm 12.52 (br. s., 1H) 8.19 (dd, J=7.97, 1.22 Hz, 1H) 8.00-8.09 (m, 3H) 7.83-7.93 (m, 1H) 7.77 (d, J=7.82 Hz, 1H) 7.56-7.70 (m, 4H) 3.47-3.60 (m, 2H) 3.42-3.46 (m, 3H) 2.93-3.10 (m, 1H) 2.10-2.28 (m, 2H) 1.93 (d, J=11.05 Hz, 2H) 1.84 (d, J=10.56 Hz, 2H) 1.53-1.75 (m, 2H) 1.22-1.44 (m, 2H). m/z (ESI) 492.2 (M+H)+.

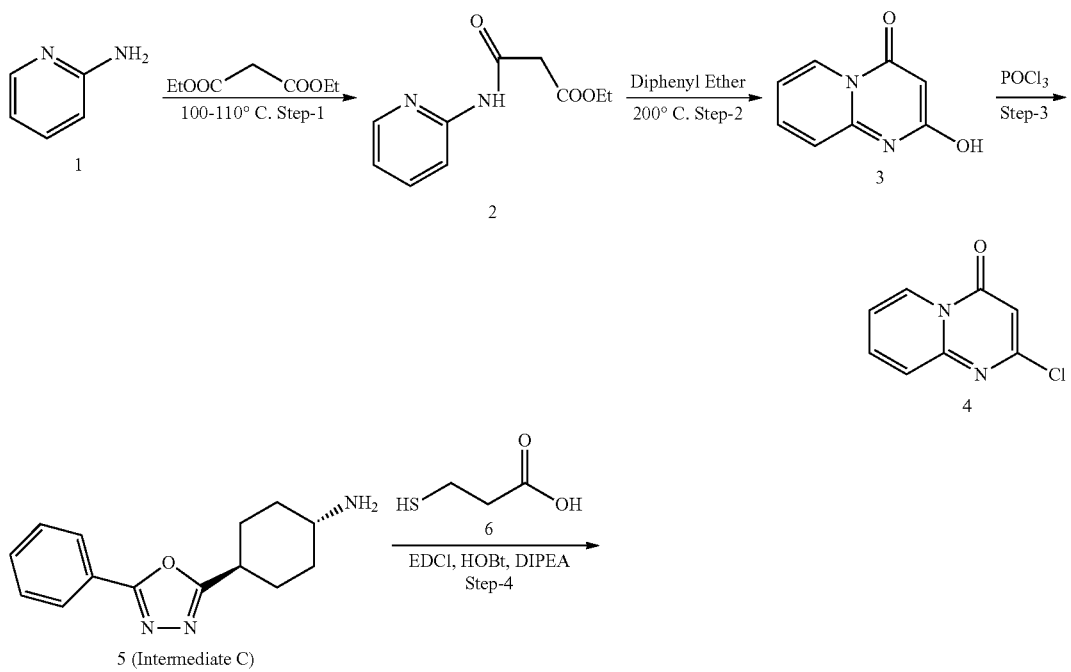

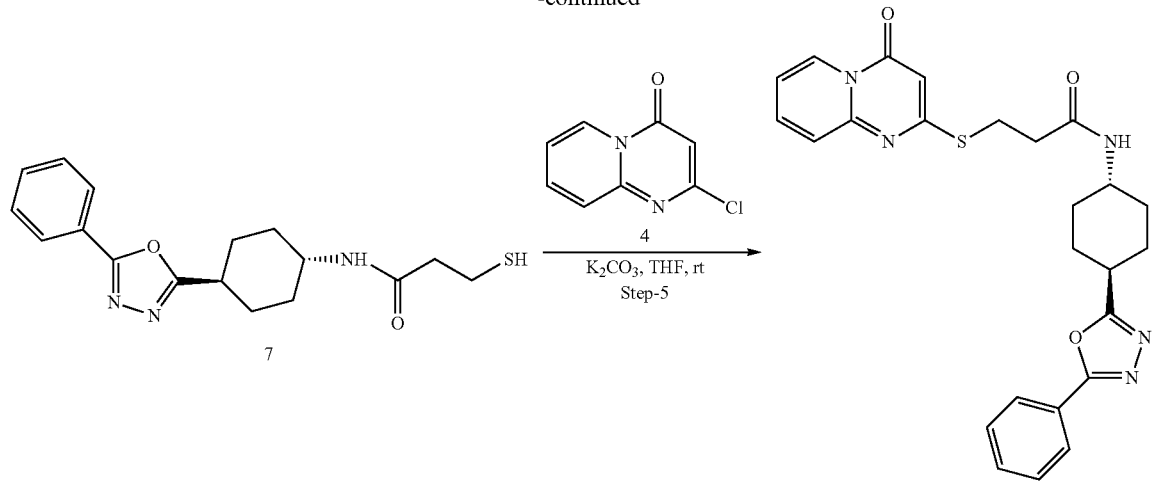

Step-1: Synthesis of Ethyl 3-oxo-3-(pyridin-2-ylamino) propionate

2-Amino pyridine (1) (20.0 g, 212.65 mmol) was dissolved in diethylmalonate (20.0 mL, 212.65 mmol), and the resulting mixture was heated to 110-120° C. for 12 h in a single neck 500 mL round bottom flask. The reaction was monitored by TLC (50% EtOAc in petroleum ether). After reaction completion, the reaction mixture was diluted with DCM (100 mL) and concentrated under reduced pressure to provide a residue. The residue was purified by column chromatography using silica (60-120 mesh) eluting with 50% EtOAc in petroleum ether to obtain ethyl 3-oxo-3-(pyridin-2-ylamino) propanoate (2) as a colorless liquid.

Step-2: Synthesis of 2-hydroxy-4H-pyrido[1,2-a]pyrimidin-4-one

Ethyl 3-oxo-3-(pyridin-2-ylamino)propanoate (2) (20.0 g, 96.11 mmol) was dissolved in diphenyl ether (20 mL) in a single neck 250 mL round bottom flask. The resulting mixture was then heated to 210° C. for 2 h. The progress of the reaction was monitored by TLC (50% EtOAC in hexane). After completion of reaction, the mixture was cooled to 0° C., diluted with hexane (100 mL), and stirred for 1 h affording a precipitate which was collected via vacuum filtration to afford of 2-hydroxy-4H-pyrido[1,2-a]pyrimidin-4-one (3) 5 g (32.25%) as a yellow solid. MS (ESI, pos. ion) m/z: 163.2.

Step-3: Synthesis of 2-chloro-4H-pyrido[1,2-a]pyrimidin-4-one

2-Hydroxy-4H-pyrido[1,2-a]pyrimidin-4-one (5.0 g, 30.864 mmol), was dissolved in phosphorous oxytrichloride (50 mL) in a single neck 100 mL round bottom flask. The resulting reaction mixture was refluxed at 130° C. for 16 h. The reaction progress was monitored by TLC (50% EtOAc in petroleum ether). After completion of the reaction, the volatiles were removed under reduced pressure and the mixture basified with saturated $NaHCO_3$ solution to afford a yellow precipitate. The precipitate was collected by vacuum filtration and triturated with hexane to afford of 2-chloro-4H-pyrido[1,2-a]pyrimidin-4-one (4) 3 g (54.05%) as yellow solid. MS (ESI, pos. ion) m/z: 181.0.

Step-4: Synthesis of 3-mercapto-N-((1r,4r)-4-(5-phenyl-1,3,4-oxadiazol-2-yl)cyclohexyl) propanamide To a solution of (1r, 4r)-4-(5-phenyl-1,3,4-oxadiazol-2-yl)cyclohexanamine (5, intermediate C) (500 mg, 2.05 mmol) and 3-mercaptopropanoic acid (6) (283 mg, 2.67 mmol) in dry THF at 0° C., were added EDC-HCl (591 mg, 3.086 mmol), HOBt (416 mg, 3.086 mmol) and DIPEA (400 mg, 3.086 mmol). The reaction was stirred at ambient temperature for 12 h. The reaction progress was monitored by TLC (10% MeOH in $CHCl_3$). After completion of reaction, the reaction mixture was diluted with and excess of ice water (50 mL) and the product extracted with EtOAc (50 mL). The organic layer was separated and dried using anhydrous sodium sulfate and concentrated under reduced pressure to afford a sticky yellow residual liquid. The material thus obtained was purified using column chromatography silica (60-120 mesh) eluting with 5% MeOH in $CHCl_3$ to afford 3-mercapto-N-((1r,4r)-4-(5-phenyl-1,3,4-oxadiazol-2-yl)cyclohexyl) propanamide (7) 300 mg (44.1%) as yellow solid. $^1$H-NMR (400 MHz, DMSO-$d_6$): δ 8.00-7.98 (m, 2H), 7.95-7.93 (m, 1H), 7.61-7.59 (m, 2H), 3.62-3.51 (m, 1H), 3.05-3.01 (m, 2H), 2.66-2.64 (m, 2H), 2.38-2.37 (m, 2H), 2.25-1.85 (m, 5H), 1.61-1.32 (m, 4H). MS (ESI, pos. ion) m/z: 332.1.

Step-5: Synthesis of 3-((4-oxo-4H-pyrido[1,2-a]pyrimidin-2-yl)thio)-N-((1r,4r)-4-(5-phenyl-1,3,4-oxadiazol-2-yl)cyclohexyl)propanamide To a cooled mixture of 3-mercapto-N-((1r, 4r)-4-(5-phenyl-1,3,4-oxadiazol-2-yl)cyclohexyl) propanamide (200 mg, 0.604 mmol) and $K_2CO_3$ (250 mg, 1.812 mmol) in dry THF (5 mL) in a 100 mL round bottom flask, was added 2-chloro-4H-pyrido[1,2-a]pyrimidin-4-one (129 mg, 0.725 mmol). The resulting mixture was stirred for 12 h at ambient temperature. The progress of the reaction was monitored by TLC (TLC system: 5% MeOH in $CHCl_3$). After completion, the reaction was diluted with ice water (50 mL), and the product was extracted with EtOAc (50 mL). The organic layer was separated and dried over anhydrous sodium sulfate and evaporated under reduced pressure. The product thus obtained was purified by prep HPLC to afford 3-((4-oxo-4H-pyrido[1,2-a]pyrimidin-2-yl)thio)-N-((1r,4r)-4-(5-phenyl-1,3,4-oxadiazol-2-yl)cyclohexyl)propanamide, 75 mg (yield: 24.39%) as yellow solid. $^1$H-NMR (400 MHz, $CDCl_3$): δ 9.03 (d, J=7.2 Hz, 1H), 8.04-8.01 (m, 2H), 7.79-7.49 (m, 1H), 7.56-7.26 (m, 4H), 7.14-7.11 (m, 1H), 6.33 (s, 1H), 5.48-5.46 (d, J=7.6 Hz, 1H), 3.93-3.89 (m, 1H), 3.50-3.47 (m, 2H), 2.96-2.90 (m, 1H), 2.66-2.63 (m, 2H), 2.26-2.17 (m, 4H), 1.86-1.76 (m 2H), 1.33-1.25 (m 2H). MS (ESI, pos. ion) m/z: 476.1.0 (M+1).

Example 145

3-((6-fluoro-4-oxo-3,4-dihydro-2-quinazolinyl)sulfanyl)-N-(trans-4-(5-phenyl-1,3,4-oxadiazol-2-yl)cyclohexyl)propanamide

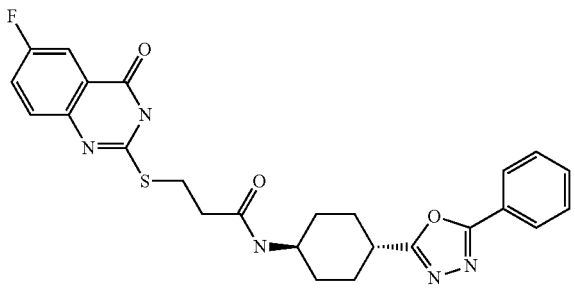 [SMILES: O=C(CCSc1nc2ccc(F)cc2c(=O)[nH]1)N[C@H]1CC[C@H](c2nnc(-c3ccccc3)o2)CC1]

The title compound was prepared as described in General Scheme A using Intermediate Q and Intermediate C. The reaction mixture was diluted with DCM (50 mL) and saturated NaHCO$_3$ (2 mL) and water (20 mL). The organic layer was concentrated and purified by MPLC, eluting with DCM:MeOH (90:10) to obtain 3-((6-fluoro-4-oxo-3,4-dihydroquinazolin-2-yl)thio)-N-((1r,4r)-4-(5-phenyl-1,3,4-oxadiazol-2-yl)cyclohexyl)propanamide as white solid (18 mg, 0.037 mmol, 10%); $^1$H NMR (400 MHz, DMSO-d$_6$) δ ppm 12.66 (s, 1H) 7.99 (dd, J=7.87, 1.81 Hz, 2H) 7.92 (d, J=7.73 Hz, 1H) 7.54-7.75 (m, 6H) 3.62 (dd, J=11.69, 3.77 Hz, 1H) 3.39 (t, J=6.60 Hz, 2H) 2.94-3.04 (m, 1H) 2.58 (t, J=6.85 Hz, 2H) 2.16 (d, J=12.23 Hz, 2H) 1.92 (d, J=10.95 Hz, 2H) 1.57-1.72 (m, 2H) 1.26-1.40 (m, 2H); LC-MS 494.1 (m/z).

The following table provides the name and structure of the Example compounds

TABLE 1

Names and Structures of Example Compounds

| Example | Name | Structure |
|---|---|---|
| 1 | trans-N-(2-(4-oxo-3,4-dihydro-2-quinazolinyl)ethyl)-4-(5-phenyl-1,3,4-oxadiazol-2-yl)cyclohexanecarboxamide | 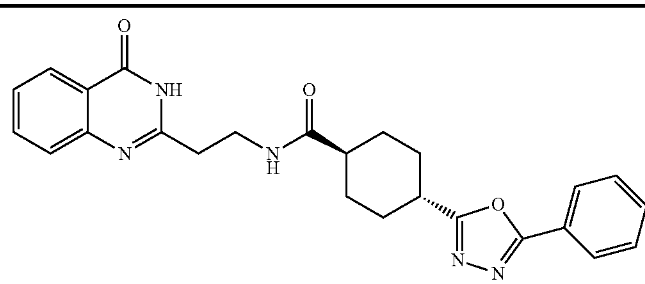 |
| 2 | 3-(4-oxo-3,4-dihydro-2-quinazolinyl)-N-(trans-4-(5-phenyl-1,3,4-oxadiazol-2-yl)cyclohexyl)propanamide | 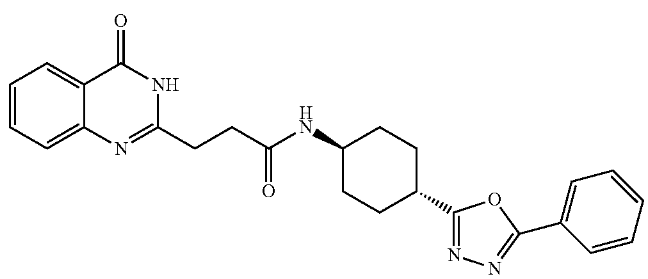 [SMILES: O=C(CCc1nc2ccccc2c(=O)[nH]1)N[C@H]1CC[C@H](c2nnc(-c3ccccc3)o2)CC1] |
| 3 | 2-(4-(4-(5-(3-chlorophenyl)-1,3,4-oxadiazol-2-yl)-1-piperidinyl)-4-oxobutyl)-4(3H)-quinazolinone | 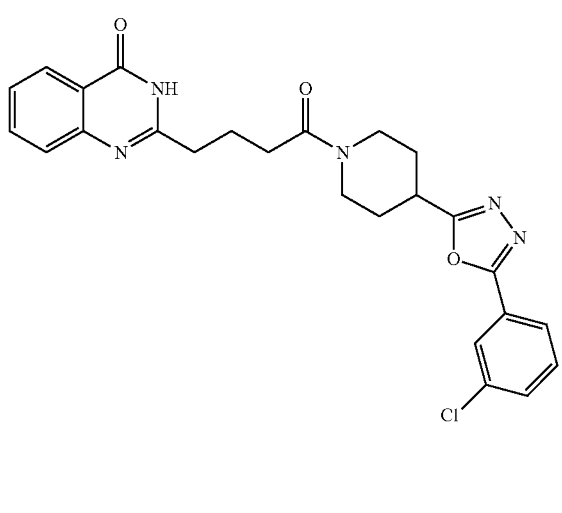 [SMILES: O=C(CCCc1nc2ccccc2c(=O)[nH]1)N1CCC(c2nnc(-c3cccc(Cl)c3)o2)CC1] |

TABLE 1-continued

Names and Structures of Example Compounds

| Example | Name | Structure |
|---|---|---|
| 4 | 2-(4-(4-(5-(4-chlorophenyl)-1,3,4-oxadiazol-2-yl)-1-piperidinyl)-4-oxobutyl)-4(3H)-quinazolinone | 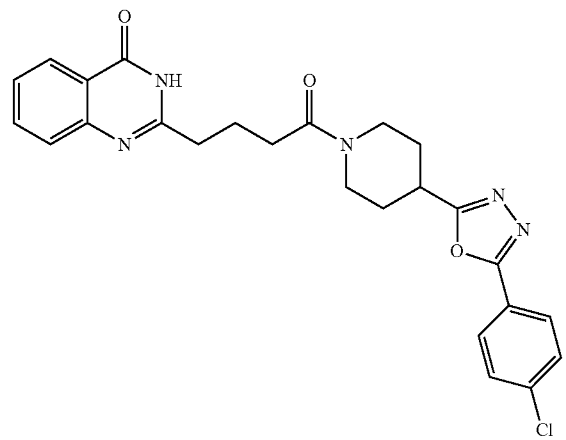 [SMILES: O=C(CCCc1nc2ccccc2c(=O)[nH]1)N1CCC(c2nnc(-c3ccc(Cl)cc3)o2)CC1] |
| 5 | 2-(4-(4-(5-(3-fluorophenyl)-1,3,4-oxadiazol-2-yl)-1-piperidinyl)-4-oxobutyl)-4(3H)-quinazolinone | 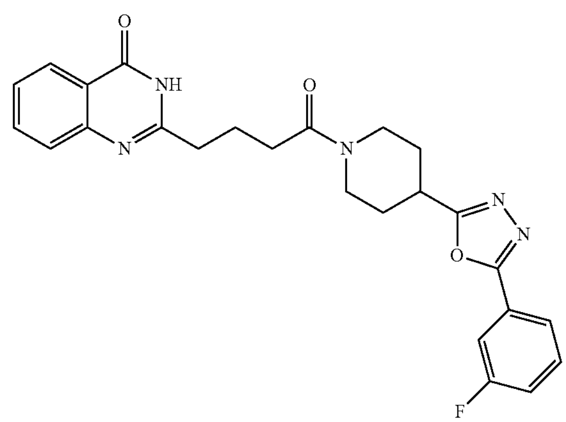 [SMILES: O=C(CCCc1nc2ccccc2c(=O)[nH]1)N1CCC(c2nnc(-c3cccc(F)c3)o2)CC1] |
| 6 | 2-(4-(4-(5-(4-fluorophenyl)-1,3,4-oxadiazol-2-yl)-1-piperidinyl)-4-oxobutyl)-4(3H)-quinazolinone | 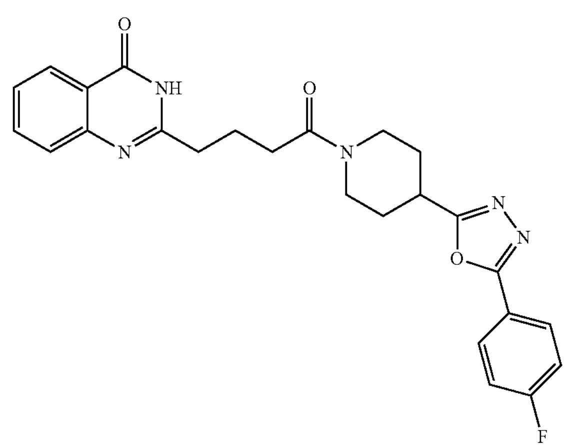 [SMILES: O=C(CCCc1nc2ccccc2c(=O)[nH]1)N1CCC(c2nnc(-c3ccc(F)cc3)o2)CC1] |

TABLE 1-continued

Names and Structures of Example Compounds

| Example | Name | Structure |
|---|---|---|
| 7 | 2-(4-(4-(6-methyl-2-oxo-2,3-dihydro-1H-benzimidazol-1-yl)-1-piperidinyl)-4-oxobutyl)-4(3H)-quinazolinone | 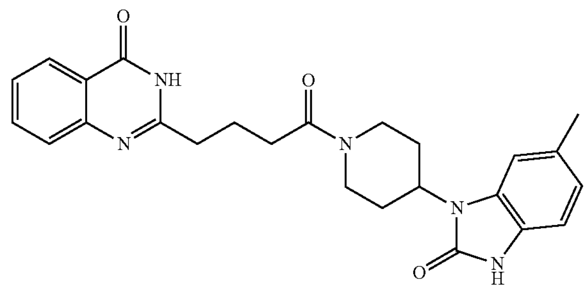 [SMILES: Cc1ccc2[nH]c(=O)n(C3CCN(C(=O)CCCc4nc5ccccc5c(=O)[nH]4)CC3)c2c1] |
| 8 | 2-(4-(4-(5-methoxy-2-oxo-2,3-dihydro-1H-benzimidazol-1-yl)-1-piperidinyl)-4-oxobutyl)-4(3H)-quinazolinone | 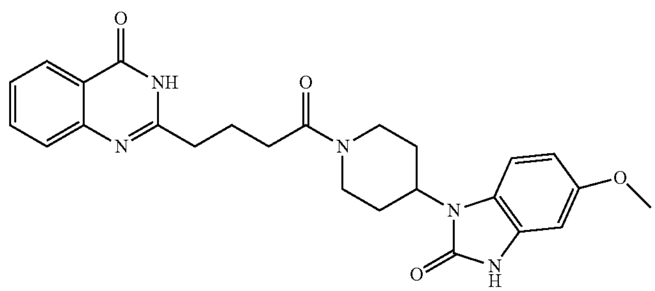 [SMILES: COc1ccc2c(c1)[nH]c(=O)n2C1CCN(C(=O)CCCc2nc3ccccc3c(=O)[nH]2)CC1] |
| 9 | 2-(4-oxo-4-(4-(5-phenyl-1,3,4-thiadiazol-2-yl)-1-piperidinyl)butyl)-4(3H)-quinazolinone | 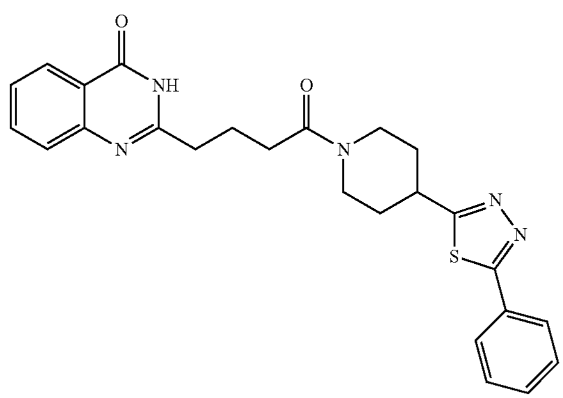 [SMILES: O=C(CCCc1nc2ccccc2c(=O)[nH]1)N1CCC(c2nnc(-c3ccccc3)s2)CC1] |
| 10 | 4-(4-oxo-3,4-dihydro-2-quinazolinyl)-N-(trans-4-(5-phenyl-1,3,4-oxadiazol-2-yl)cyclohexyl)butanamide | 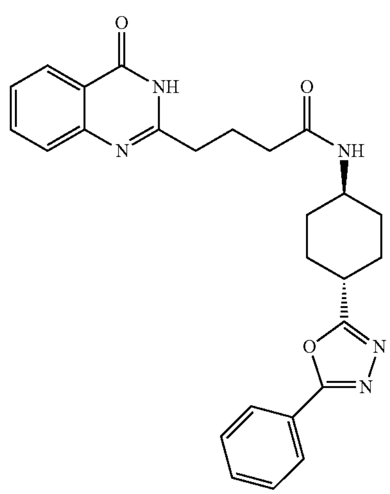 [SMILES: O=C(CCCc1nc2ccccc2c(=O)[nH]1)N[C@H]1CC[C@H](c2nnc(-c3ccccc3)o2)CC1] |

TABLE 1-continued

Names and Structures of Example Compounds

| Example | Name | Structure |
|---|---|---|
| 11 | 2-(4-(4-(5-methyl-2-oxo-2,3-dihydro-1H-benzimidazol-1-yl)-1-piperidinyl)-4-oxobutyl)-4(3H)-quinazolinone | 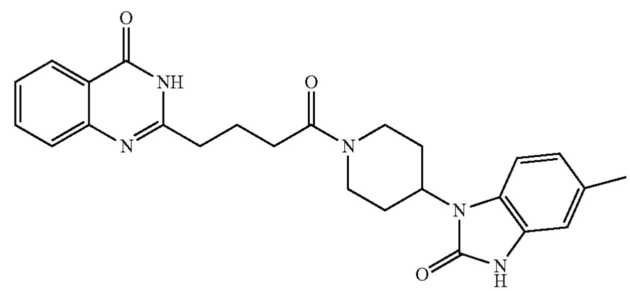 [SMILES: Cc1ccc2c(c1)[nH]c(=O)n2C1CCN(C(=O)CCCc2nc3ccccc3c(=O)[nH]2)CC1] |
| 12 | 2-(4-oxo-4-(4-(5-(2-pyridinyl)-1,3,4-oxadiazol-2-yl)-1-piperidinyl)butyl)-4(3H)-quinazolinone | 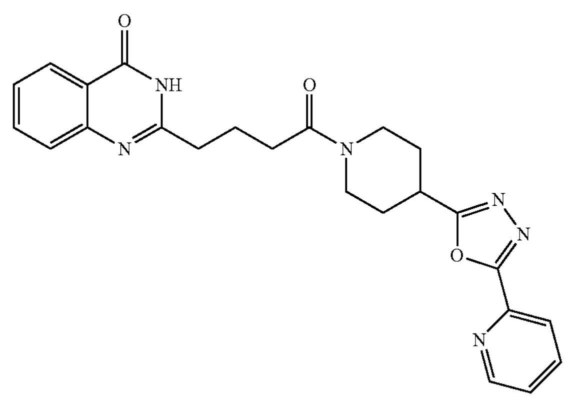 [SMILES: O=C(CCCc1nc2ccccc2c(=O)[nH]1)N1CCC(c2nnc(-c3ccccn3)o2)CC1] |
| 13 | 2-(4-oxo-4-(4-(5-(3-pyridinyl)-1,3,4-oxadiazol-2-yl)-1-piperidinyl)butyl)-4(3H)-quinazolinone | 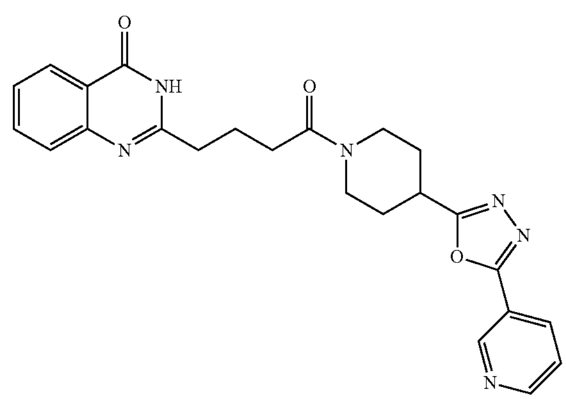 [SMILES: O=C(CCCc1nc2ccccc2c(=O)[nH]1)N1CCC(c2nnc(-c3cccnc3)o2)CC1] |
| 14 | 2-(4-oxo-4-(4-(5-(2-pyrazinyl)-1,3,4-oxadiazol-2-yl)-1-piperidinyl)butyl)-4(3H)-quinazolinone | 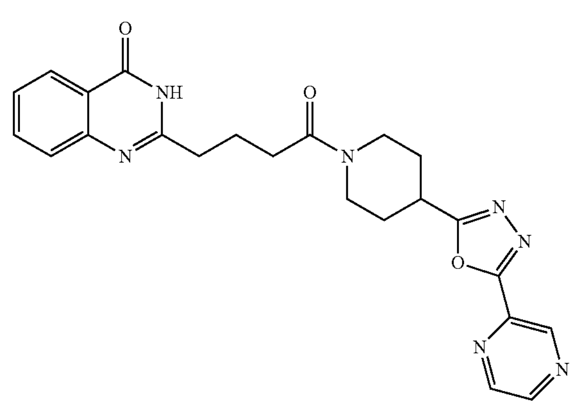 [SMILES: O=C(CCCc1nc2ccccc2c(=O)[nH]1)N1CCC(c2nnc(-c3cnccn3)o2)CC1] |

TABLE 1-continued

Names and Structures of Example Compounds

| Example | Name | Structure |
|---|---|---|
| 15 | 2-(4-(4-(5-(4-methoxyphenyl)-1,3,4-oxadiazol-2-yl)-1-piperidinyl)-4-oxobutyl)-4(3H)-quinazolinone | 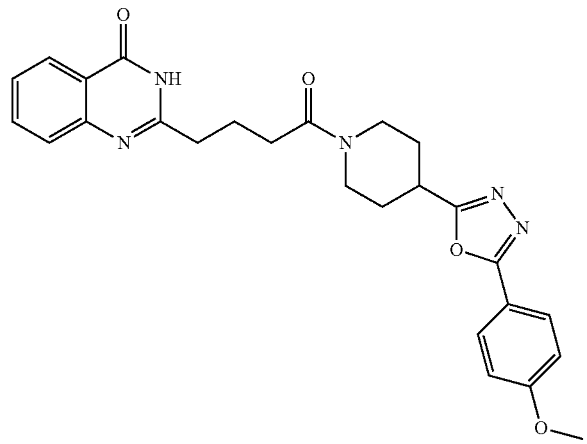 [SMILES: COc1ccc(-c2nnc(C3CCN(C(=O)CCCc4nc5ccccc5c(=O)[nH]4)CC3)o2)cc1] |
| 16 | 2-(4-(4-(5-(2-chlorophenyl)-1,3,4-oxadiazol-2-yl)-1-piperidinyl)-4-oxobutyl)-4(3H)-quinazolinone | 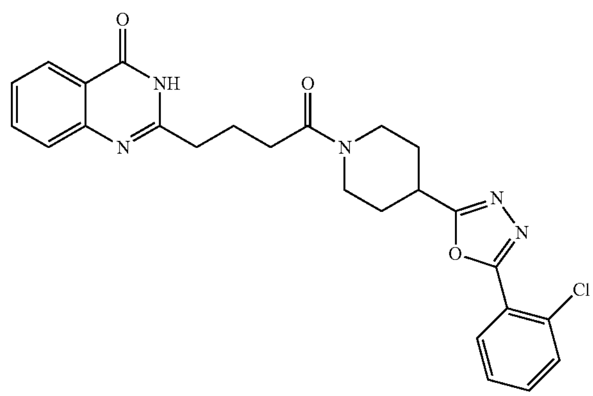 [SMILES: O=C(CCCc1nc2ccccc2c(=O)[nH]1)N1CCC(c2nnc(-c3ccccc3Cl)o2)CC1] |
| 17 | 2-(4-(4-(5-((4-chlorophenoxy)methyl)-1,3,4-oxadiazol-2-yl)-1-piperidinyl)-4-oxobutyl)-4(3H)-quinazolinone | 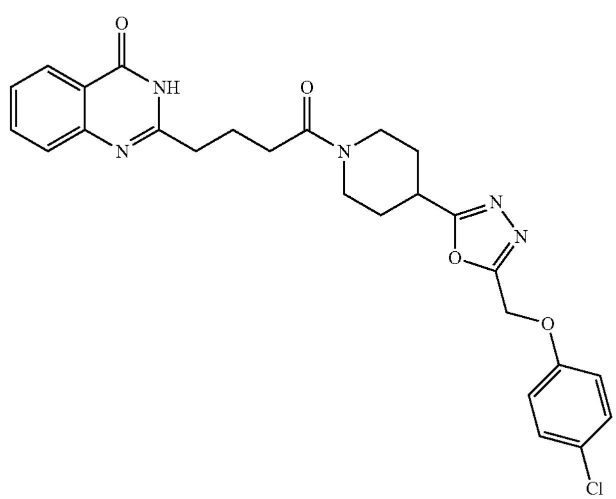 [SMILES: O=C(CCCc1nc2ccccc2c(=O)[nH]1)N1CCC(c2nnc(COc3ccc(Cl)cc3)o2)CC1] |

TABLE 1-continued

Names and Structures of Example Compounds

| Example | Name | Structure |
|---------|------|-----------|
| 18 | 2-(4-(4-(5-(2-fluorophenyl)-1,3,4-oxadiazol-2-yl)-1-piperidinyl)-4-oxobutyl)-4(3H)-quinazolinone | 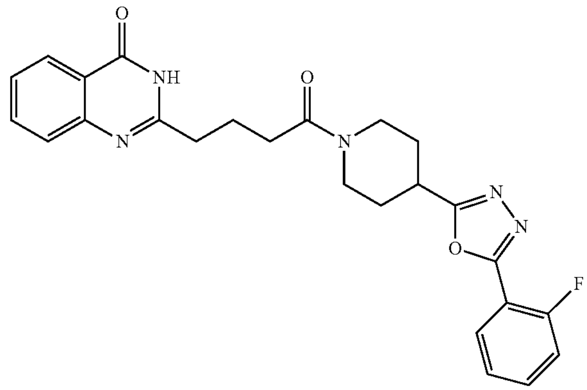 [SMILES: O=C(CCCc1nc2ccccc2c(=O)[nH]1)N1CCC(c2nnc(-c3ccccc3F)o2)CC1] |
| 19 | 2-(4-oxo-4-(4-(5-(4-pyridinyl)-1,3,4-oxadiazol-2-yl)-1-piperidinyl)butyl)-4(3H)-quinazolinone | 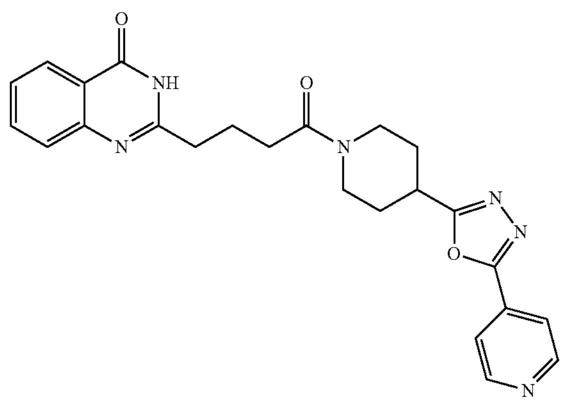 [SMILES: O=C(CCCc1nc2ccccc2c(=O)[nH]1)N1CCC(c2nnc(-c3ccncc3)o2)CC1] |
| 20 | 3-(5-(1-(4-(4-oxo-3,4-dihydro-2-quinazolinyl)butanoyl)-4-piperidinyl)-1,3,4-oxadiazol-2-yl)benzonitrile | 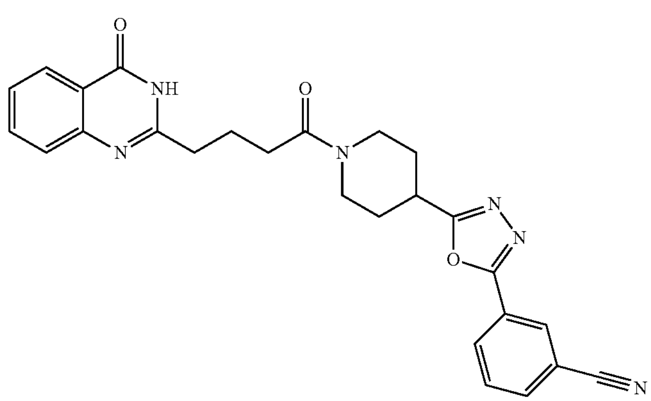 [SMILES: N#Cc1cccc(-c2nnc(C3CCN(C(=O)CCCc4nc5ccccc5c(=O)[nH]4)CC3)o2)c1] |

TABLE 1-continued

Names and Structures of Example Compounds

| Example | Name | Structure |
|---|---|---|
| 21 | 4-(5-(1-(4-(4-oxo-3,4-dihydro-2-quinazolinyl)butanoyl)-4-piperidinyl)-1,3,4-oxadiazol-2-yl)benzonitrile | 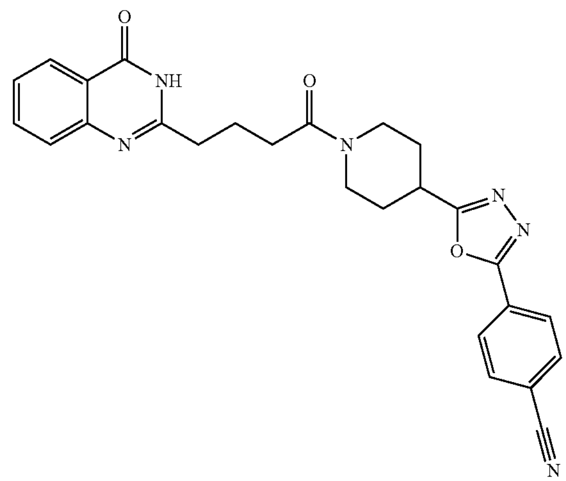 [SMILES: N#Cc1ccc(-c2nnc(C3CCN(C(=O)CCCc4nc5ccccc5c(=O)[nH]4)CC3)o2)cc1] |
| 22 | 2-(4-(4-(5-(3-methylphenyl)-1,3,4-oxadiazol-2-yl)-1-piperidinyl)-4-oxobutyl)-4(3H)-quinazolinone | 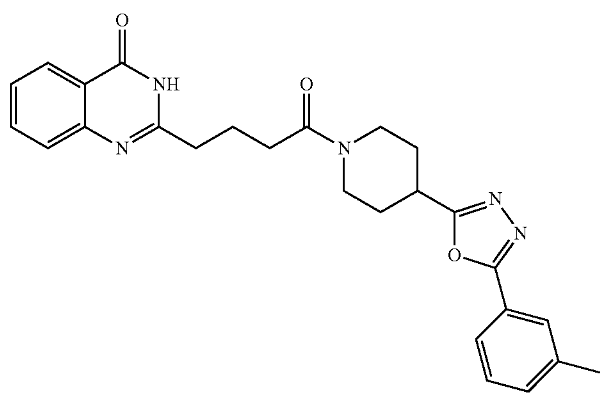 [SMILES: Cc1cccc(-c2nnc(C3CCN(C(=O)CCCc4nc5ccccc5c(=O)[nH]4)CC3)o2)c1] |
| 23 | 2-(4-(4-(5-(4-methylphenyl)-1,3,4-oxadiazol-2-yl)-1-piperidinyl)-4-oxobutyl)-4(3H)-quinazolinone | 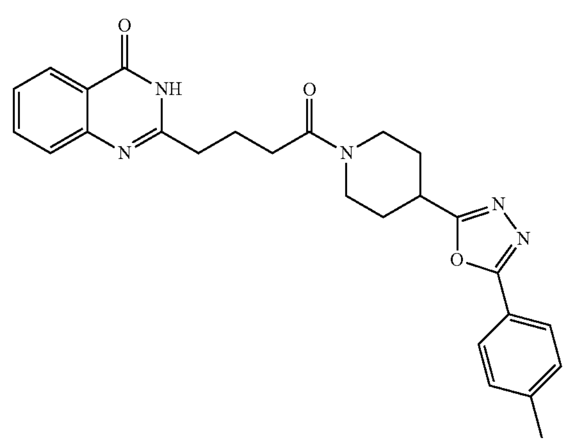 [SMILES: Cc1ccc(-c2nnc(C3CCN(C(=O)CCCc4nc5ccccc5c(=O)[nH]4)CC3)o2)cc1] |

TABLE 1-continued

Names and Structures of Example Compounds

| Example | Name | Structure |
|---|---|---|
| 24 | 2-(4-(4-(5-(3-methoxyphenyl)-1,3,4-oxadiazol-2-yl)-1-piperidinyl)-4-oxobutyl)-4(3H)-quinazolinone | 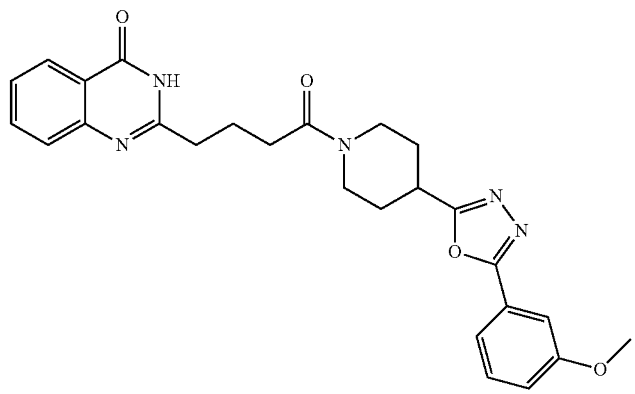 [SMILES: COc1cccc(-c2nnc(C3CCN(C(=O)CCCc4nc5ccccc5c(=O)[nH]4)CC3)o2)c1] |
| 25 | 2-(4-(4-(5-(3-chloro-4-fluorophenyl)-1,3,4-oxadiazol-2-yl)-1-piperidinyl)-4-oxobutyl)-4(3H)-quinazolinone | 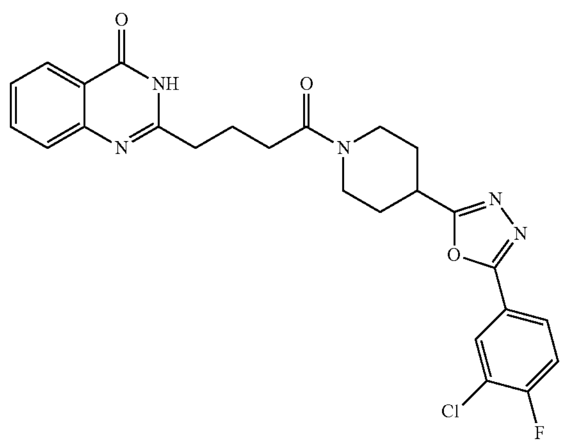 [SMILES: O=C(CCCc1nc2ccccc2c(=O)[nH]1)N1CCC(c2nnc(-c3ccc(F)c(Cl)c3)o2)CC1] |
| 26 | 2-(4-oxo-4-(4-(2-oxo-1,2-dihydro-3H-imidazo[4,5-b]pyridin-3-yl)-1-piperidinyl)butyl)-4(3H)-quinazolinone | 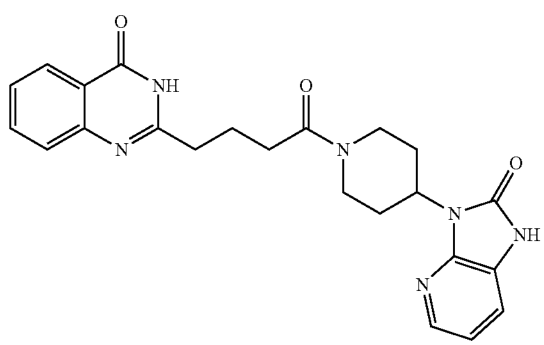 |
| 27 | 2-(4-(4-(5-chloro-2-oxo-2,3-dihydro-1H-benzimidazol-1-yl)-1-piperidinyl)-4-oxobutyl)-4(3H)-quinazolinone | 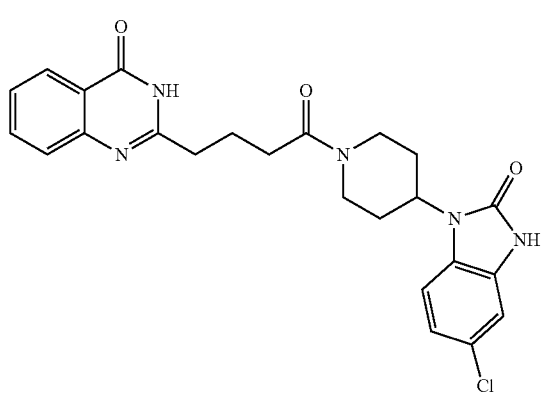 |

TABLE 1-continued

Names and Structures of Example Compounds

| Example | Name | Structure |
|---|---|---|
| 28 | N-(trans-4-(5-(4-fluorophenyl)-1,3,4-oxadiazol-2-yl)cyclohexyl)-4-(4-oxo-3,4-dihydro-2-quinazolinyl)butanamide | 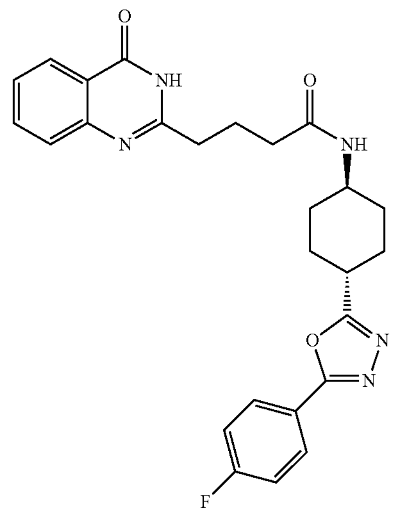 [SMILES: O=C(CCCc1nc2ccccc2c(=O)[nH]1)N[C@H]1CC[C@H](c2nnc(-c3ccc(F)cc3)o2)CC1] |
| 29 | N-(trans-4-(5-(4-chlorophenyl)-1,3,4-oxadiazol-2-yl)cyclohexyl)-4-(4-oxo-3,4-dihydro-2-quinazolinyl)butanamide | 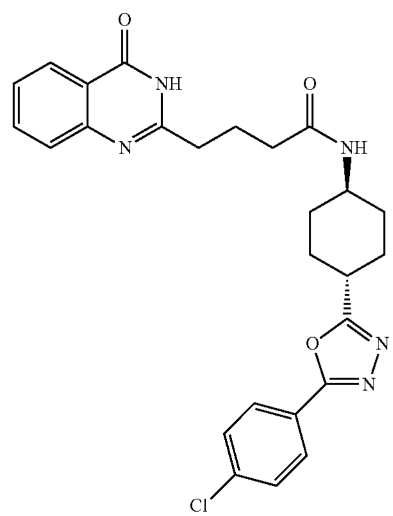 [SMILES: O=C(CCCc1nc2ccccc2c(=O)[nH]1)N[C@H]1CC[C@H](c2nnc(-c3ccc(Cl)cc3)o2)CC1] |
| 30 | N-(trans-4-(5-(4-methoxyphenyl)-1,3,4-oxadiazol-2-yl)cyclohexyl)-4-(4-oxo-3,4-dihydro-2-quinazolinyl)butanamide | 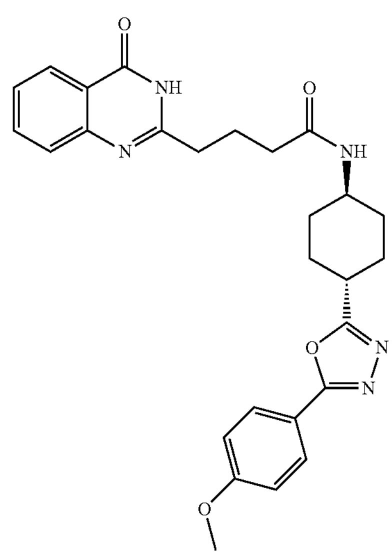 [SMILES: COc1ccc(-c2nnc([C@H]3CC[C@H](NC(=O)CCCc4nc5ccccc5c(=O)[nH]4)CC3)o2)cc1] |

TABLE 1-continued

Names and Structures of Example Compounds

| Example | Name |
|---|---|
| 31 | N-(trans-4-(5-(3-fluorophenyl)-1,3,4-oxadiazol-2-yl)cyclohexyl)-4-(4-oxo-3,4-dihydro-2-quinazolinyl)butanamide |
| 32 | N-(trans-4-(5-(3-methoxyphenyl)-1,3,4-oxadiazol-2-yl)cyclohexyl)-4-(4-oxo-3,4-dihydro-2-quinazolinyl)butanamide |
| 33 | 4-(4-oxo-3,4-dihydro-2-quinazolinyl)-N-(trans-4-(5-(4-pyridinyl)-1,3,4-oxadiazol-2-yl)cyclohexyl)butanamide |

TABLE 1-continued

Names and Structures of Example Compounds

| Example | Name | Structure |
|---|---|---|
| 34 | 2-(4-(4-(6-methoxy-2-oxo-2,3-dihydro-1H-benzimidazol-1-yl)-1-piperidinyl)-4-oxobutyl)-4(3H)-quinazolinone | 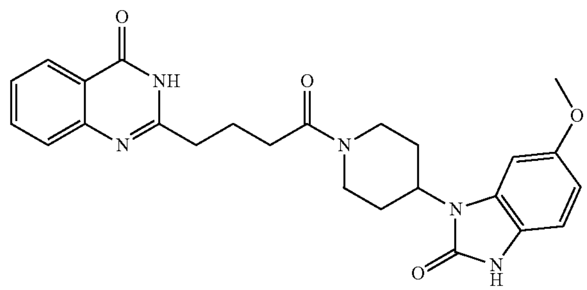 [SMILES: COc1ccc2[nH]c(=O)n(C3CCN(C(=O)CCCc4nc5ccccc5c(=O)[nH]4)CC3)c2c1] |
| 35 | N-(trans-4-(5-(3-chloro-4-fluorophenyl)-1,3,4-oxadiazol-2-yl)cyclohexyl)-4-(4-oxo-3,4-dihydro-2-quinazolinyl)butanamide | 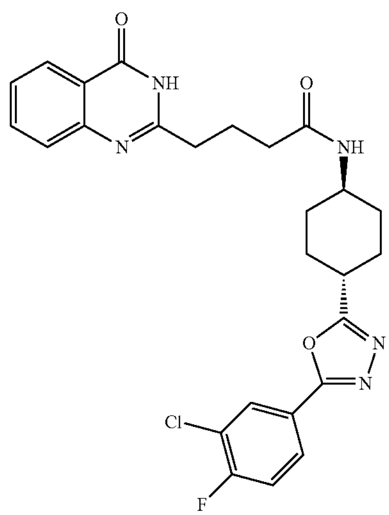 [SMILES: O=C(CCCc1nc2ccccc2c(=O)[nH]1)N[C@H]1CC[C@H](c2nnc(-c3ccc(F)c(Cl)c3)o2)CC1] |
| 36 | N-(trans-4-(5-(3-chlorophenyl)-1,3,4-oxadiazol-2-yl)cyclohexyl)-4-(4-oxo-3,4-dihydro-2-quinazolinyl)butanamide | 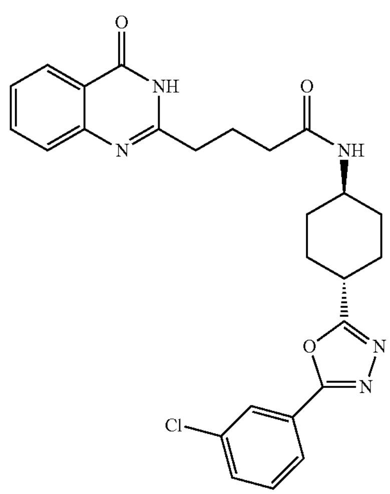 [SMILES: O=C(CCCc1nc2ccccc2c(=O)[nH]1)N[C@H]1CC[C@H](c2nnc(-c3cccc(Cl)c3)o2)CC1] |
| 37 | 3-((4-methyl-6-oxo-1,6-dihydropyrimidin-2-yl)thio)-N-((1r,4r)-4-(5-phenyl-1,3,4-oxadiazol-2-yl)cyclohexyl)propanamide | 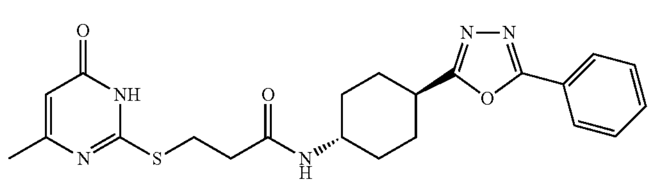 [SMILES: Cc1cc(=O)[nH]c(SCCC(=O)N[C@H]2CC[C@H](c3nnc(-c4ccccc4)o3)CC2)n1] |

TABLE 1-continued

Names and Structures of Example Compounds

| Example | Name | Structure |
|---|---|---|
| 38 | 3-(4-oxo-4H-pyrido[1,2-a]pyrimidin-2-yl)-N-(trans-4-(5-phenyl-1,3,4-oxadiazol-2-yl)cyclohexyl)propanamide | 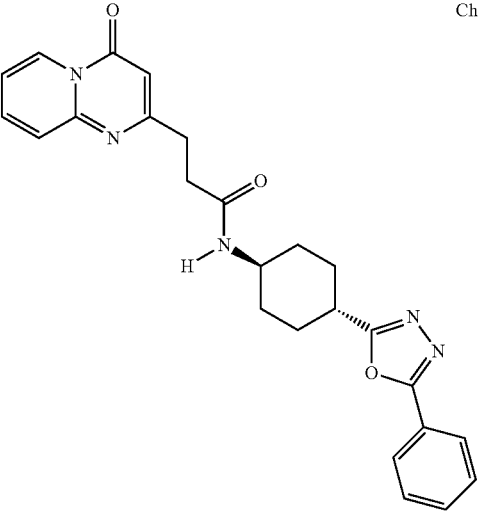 Chiral |
| 39 | 3-((4-oxo-3,4-dihydroquinazolin-2-yl)thio)-N-((1s,3s)-3-(5-phenyl-1,3,4-oxadiazol-2-yl)cyclobutyl)propanamide | 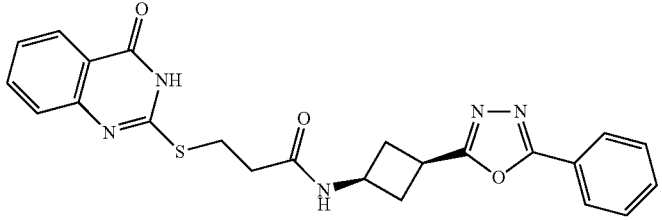 [SMILES: O=C(CCSc1nc2ccccc2c(=O)[nH]1)N[C@H]1C[C@@H](c2nnc(-c3ccccc3)o2)C1] |
| 40 | 3-((4-oxo-3,4-dihydroquinazolin-2-yl)thio)-N-((1r,3r)-3-(5-phenyl-1,3,4-oxadiazol-2-yl)cyclobutyl)propanamide | 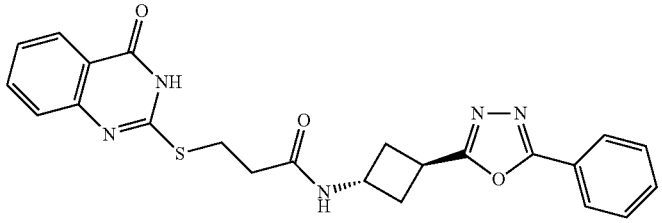 [SMILES: O=C(CCSc1nc2ccccc2c(=O)[nH]1)N[C@H]1C[C@H](c2nnc(-c3ccccc3)o2)C1] |
| 41 | 2-(4-oxo-4-(4-(2-oxo-2,3-dihydro-1H-benzimidazol-1-yl)-1-piperidinyl)butyl)-4(3H)-quinazolinone | 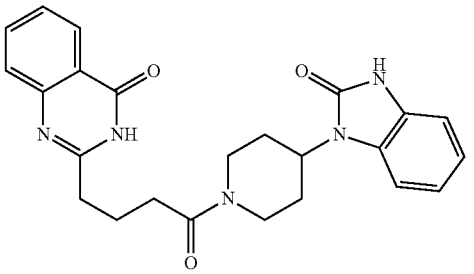 [SMILES: O=C(CCCc1nc2ccccc2c(=O)[nH]1)N1CCC(n2c(=O)[nH]c3ccccc32)CC1] |

TABLE 1-continued
Names and Structures of Example Compounds
| Example | Name | Structure |
|---|---|---|
| 42 | 2-(4-oxo-4-(4-(5-phenyl-1,3,4-oxadiazol-2-yl)-1-piperidinyl)butyl)-4(3H)-quinazolinone | 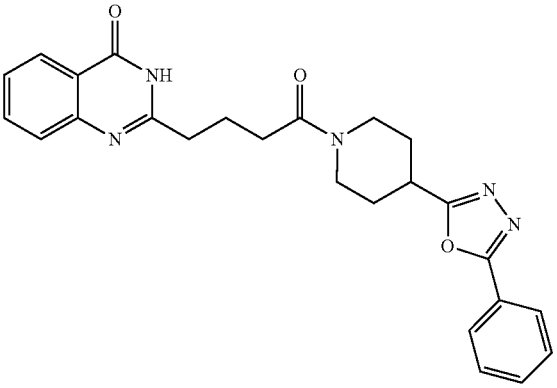 |
| 43 | 2-(4-oxo-4-(4-(2-oxo-2,3-dihydro-1H-indol-1-yl)-1-piperidinyl)butyl)-4(3H)-quinazolinone | 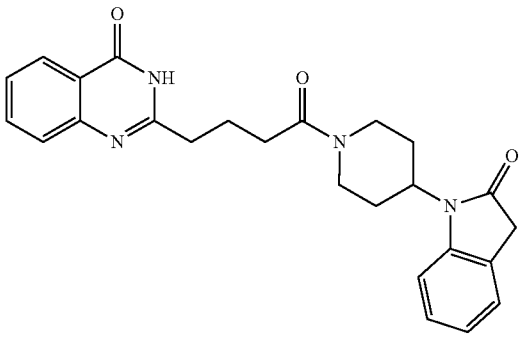 [SMILES: O=C(CCCc1nc2ccccc2c(=O)[nH]1)N1CCC(N2C(=O)Cc3ccccc32)CC1] |
| 44 | 2-(4-oxo-4-(4-(2-oxo-1,3-benzoxazol-3(2H)-yl)-1-piperidinyl)butyl)-4(3H)-quinazolinone | 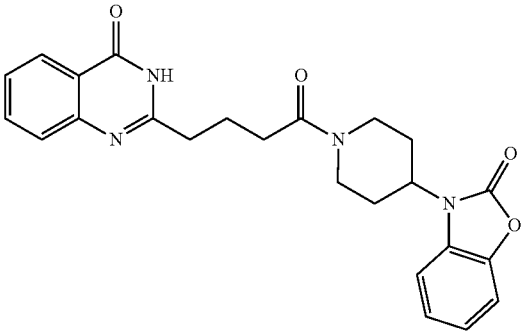 [SMILES: O=C(CCCc1nc2ccccc2c(=O)[nH]1)N1CCC(n2c(=O)oc3ccccc32)CC1] |
| 45 | 2-(4-(4-(5-chloro-3-methyl-2-oxo-2,3-dihydro-1H-benzimidazol-1-yl)-1-piperidinyl)-4-oxobutyl)-4(3H)-quinazolinone | 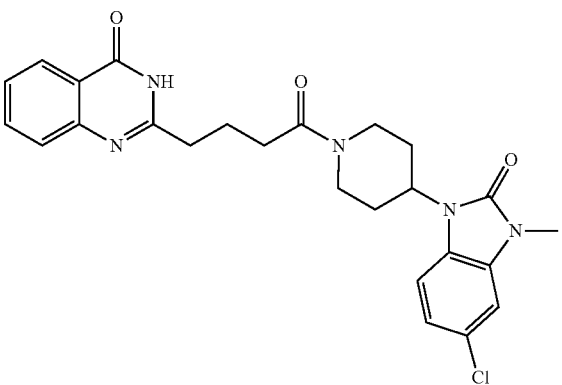 [SMILES: Cn1c(=O)n(C2CCN(C(=O)CCCc3nc4ccccc4c(=O)[nH]3)CC2)c2ccc(Cl)cc21] |

TABLE 1-continued

Names and Structures of Example Compounds

| Example | Name | Structure |
|---|---|---|
| 46 | 2-(4-oxo-4-(4-(2-oxo-2,3-dihydro-1H-benzimidazol-1-yl)-3,6-dihydro-1(2H)-pyridinyl)butyl)-4(3H)-quinazolinone | 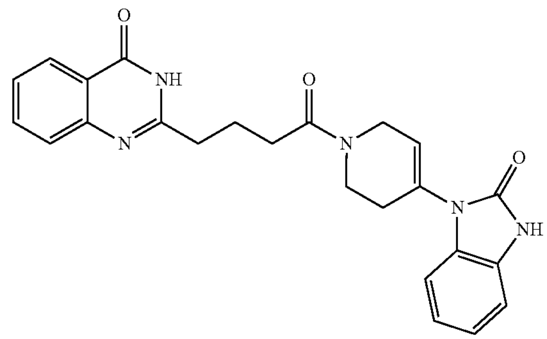 [SMILES: O=C(CCCc1nc2ccccc2c(=O)[nH]1)N1CC=C(n2c(=O)[nH]c3ccccc32)CC1] |
| 47 | 2-(4-oxo-4-(4-(2-oxo-2,3-dihydro-1H-imidazo[4,5-b]pyridin-1-yl)-1-piperidinyl)butyl)-4(3H)-quinazolinone | 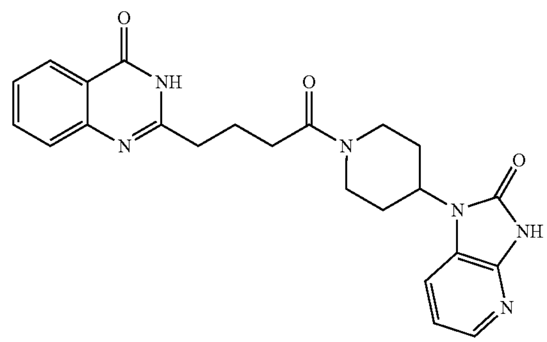 [SMILES: O=C(CCCc1nc2ccccc2c(=O)[nH]1)N1CCC(n2c(=O)[nH]c3ncccc32)CC1] |
| 48 | 2-(4-(4-(1H-indazol-3-yl)-1-piperidinyl)-4-oxobutyl)-4(3H)-quinazolinone | 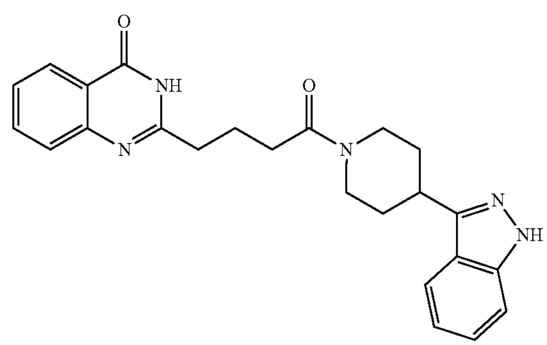 |
| 49 | 2-(4-oxo-4-(4-(2-oxo-4-phenyl-2,3-dihydro-1H-imidazol-1-yl)-1-piperidinyl)butyl)-4(3H)-quinazolinone | 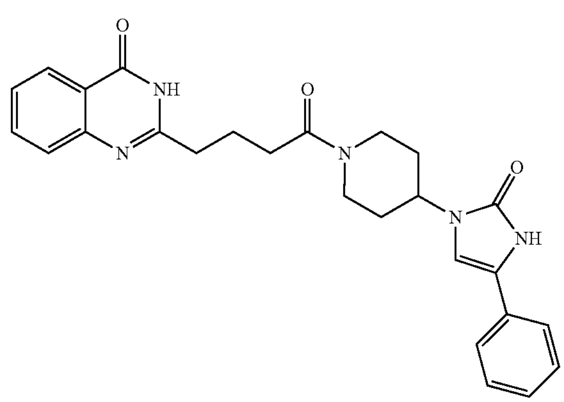 [SMILES: O=C(CCCc1nc2ccccc2c(=O)[nH]1)N1CCC(n2cc(-c3ccccc3)[nH]c2=O)CC1] |

TABLE 1-continued

Names and Structures of Example Compounds

| Example | Name | Structure |
|---|---|---|
| 50 | 2-(4-oxo-4-(4-(2-oxo-1,3-benzothiazol-3(2H)-yl)-1-piperidinyl)butyl)-4(3H)-quinazolinone | 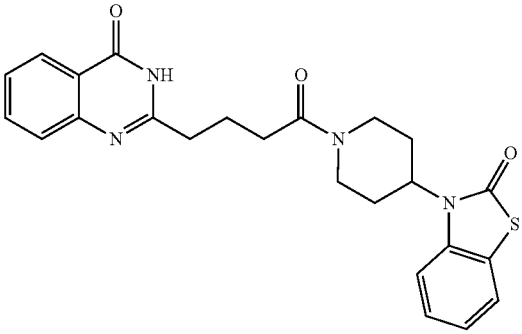 |
| 51 | 2-(4-(4-(5-fluoro-2-oxo-2,3-dihydro-1H-benzimidazol-1-yl)-1-piperidinyl)-4-oxobutyl)-4(3H)-quinazolinone | 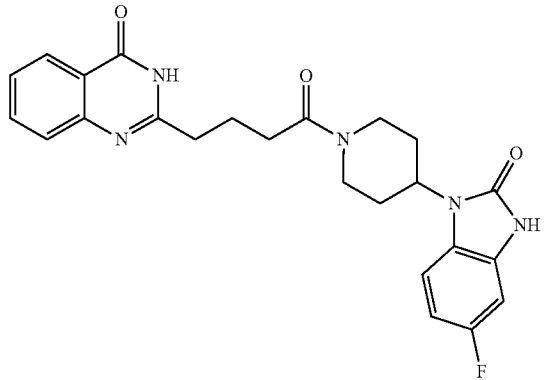 |
| 52 | 2-(4-oxo-4-(4-(2-oxo-5-(trifluoromethyl)-2,3-dihydro-1H-benzimidazol-1-yl)-1-piperidinyl)butyl)-4(3H)-quinazolinone | 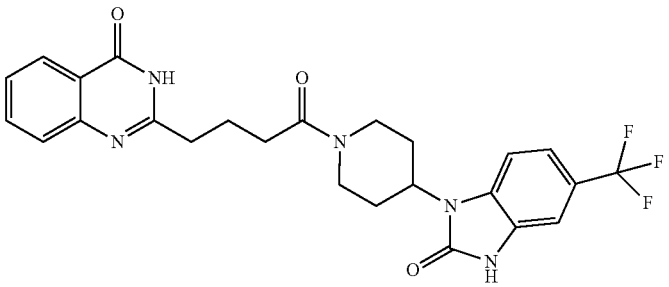 [SMILES: O=C(CCCc1nc2ccccc2c(=O)[nH]1)N1CCC(n2c(=O)[nH]c3cc(C(F)(F)F)ccc32)CC1] |
| 53 | 2-(4-(4-(6-fluoro-2-oxo-1,3-benzoxazol-3(2H)-yl)-1-piperidinyl)-4-oxobutyl)-4(3H)-quinazolinone | 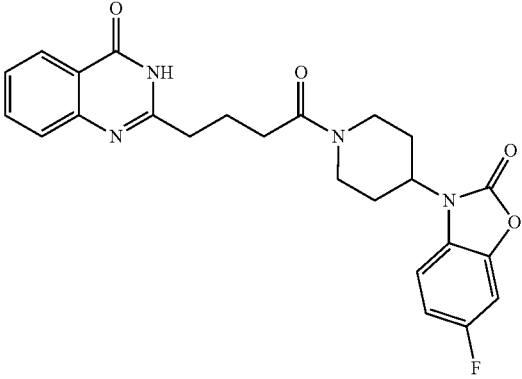 [SMILES: O=C(CCCc1nc2ccccc2c(=O)[nH]1)N1CCC(n2c(=O)oc3cc(F)ccc32)CC1] |

TABLE 1-continued

Names and Structures of Example Compounds

| Example | Name |
|---|---|
| 54 | 2-(4-(4-(3-methyl-2-oxo-2,3-dihydro-1H-benzimidazol-1-yl)-1-piperidinyl)-4-oxobutyl)-4(3H)-quinazolinone |
| 55 | 2-(4-(4-(1H-indazol-3-yl)-1-piperazinyl)-4-oxobutyl)-4(3H)-quinazolinone |
| 56 | 4-(4-oxo-3,4-dihydro-2-quinazolinyl)-N-(trans-4-(2-pyridinyloxy)cyclohexyl)butanamide |
| 57 | N-(trans-4-(2-cyanophenoxy)cyclohexyl)-4-(4-oxo-3,4-dihydro-2-quinazolinyl)butanamide |
| 58 | N-(trans-4-(3-cyanophenoxy)cyclohexyl)-4-(4-oxo-3,4-dihydro-2-quinazolinyl)butanamide |
| 59 | 4-(4-oxo-3,4-dihydro-2-quinazolinyl)-N-(trans-4-(3-pyridinyloxy)cyclohexyl)butanamide |

TABLE 1-continued

Names and Structures of Example Compounds

| Example | Name | Structure |
|---|---|---|
| 60 | 2-(4-(4-(3,3-difluoro-2-oxo-2,3-dihydro-1H-indol-1-yl)-1-piperidinyl)-4-oxobutyl)-4(3H)-quinazolinone | 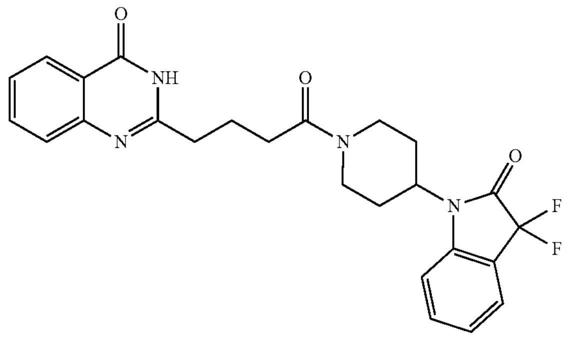 [SMILES: O=C(CCCc1nc2ccccc2c(=O)[nH]1)N1CCC(N2C(=O)C(F)(F)c3ccccc32)CC1] |
| 61 | 2-oxo-1-(1-(4-(4-oxo-3,4-dihydro-2-quinazolinyl)butanoyl)-4-piperidinyl)-2,3-dihydro-1H-benzimidazole-4-carbonitrile | 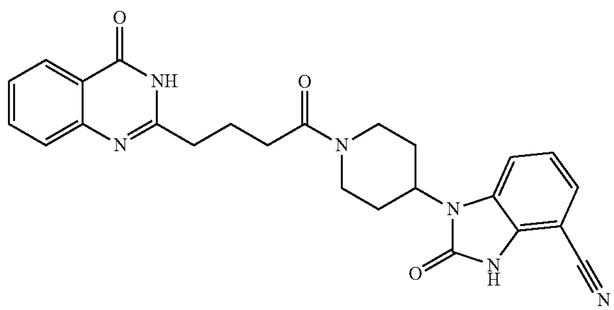 [SMILES: N#Cc1cccc2c1[nH]c(=O)n2C1CCN(C(=O)CCCc2nc3ccccc3c(=O)[nH]2)CC1] |
| 62 | N-((1R,3R)-3-(benzyloxy)cyclopentyl)-4-(4-oxo-3,4-dihydro-2-quinazolinyl)butanamide + N-((1S,3S)-3-(benzyloxy)cyclopentyl)-4-(4-oxo-3,4-dihydro-2-quinazolinyl)butanamide | |

TABLE 1-continued

Names and Structures of Example Compounds

| Example | Name | Structure |
|---|---|---|
| 63 | N-(trans-4-(4-chloro-3-cyanophenoxy)cyclohexyl)-4-(4-oxo-3,4-dihydro-2-quinazolinyl)butanamide | 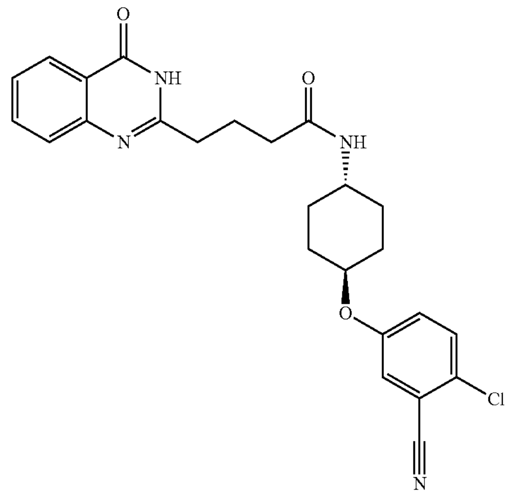 [SMILES: N#Cc1cc(O[C@H]2CC[C@H](NC(=O)CCCc3nc4ccccc4c(=O)[nH]3)CC2)ccc1Cl] |
| 64 | N-(trans-4-(3-chloro-4-cyanophenoxy)cyclohexyl)-4-(4-oxo-3,4-dihydro-2-quinazolinyl)butanamide | 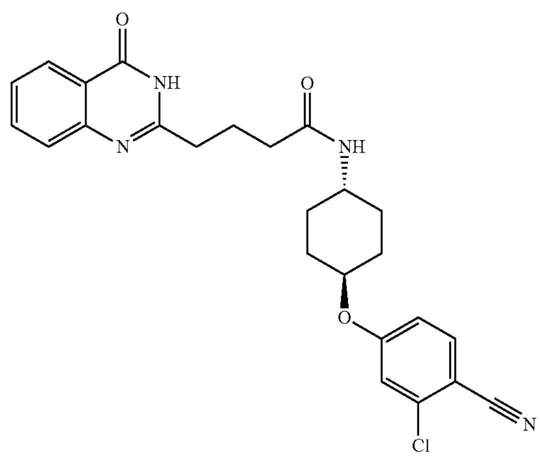 [SMILES: N#Cc1ccc(O[C@H]2CC[C@H](NC(=O)CCCc3nc4ccccc4c(=O)[nH]3)CC2)cc1Cl] |
| 65 | 4-(4-oxo-3,4-dihydro-2-quinazolinyl)-N-((1S,3S)-3-phenoxycyclopentyl)-butanamide + 4-(4-oxo-3,4-dihydro-2-quinazolinyl)-N-((1R,3R)-3-phenoxycyclopentyl)-butanamide | 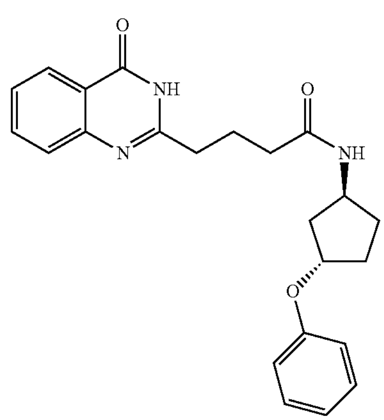 [SMILES: O=C(CCCc1nc2ccccc2c(=O)[nH]1)N[C@H]1CC[C@H](Oc2ccccc2)C1] |

TABLE 1-continued
Names and Structures of Example Compounds
| Example | Name | Structure |
|---|---|---|
| | | 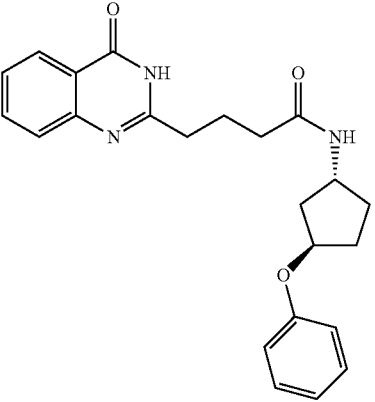 [SMILES: O=C(CCCc1nc2ccccc2c(=O)[nH]1)N[C@@H]1CC[C@@H](Oc2ccccc2)C1] |
| 66 | N-(trans-4-(3-chlorophenoxy)cyclohexyl)-4-(4-oxo-3,4-dihydro-2-quinazolinyl)butanamide | 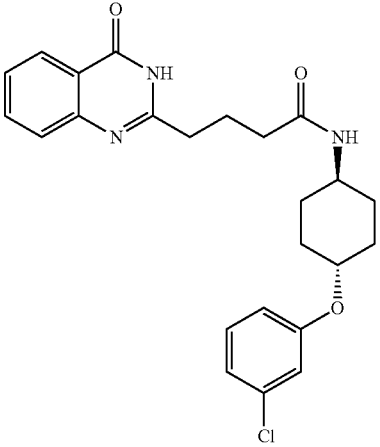 [SMILES: O=C(CCCc1nc2ccccc2c(=O)[nH]1)N[C@H]1CC[C@H](Oc2cccc(Cl)c2)CC1] |
| 67 | 2-(4-(4-(4-fluoro-2-oxo-2,3-dihydro-1H-benzimidazol-1-yl)-1-piperidinyl)-4-oxobutyl)-4(3H)-quinazolinone | 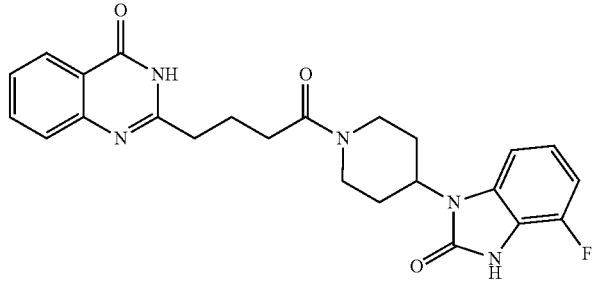 [SMILES: O=C(CCCc1nc2ccccc2c(=O)[nH]1)N1CCC(n2c(=O)[nH]c3c(F)cccc32)CC1] |
| 68 | 2-oxo-1-(1-(4-(4-oxo-3,4-dihydro-2-quinazolinyl)butanoyl)-4-piperidinyl)-2,3-dihydro-1H-benzimidazole-5-carbonitrile | 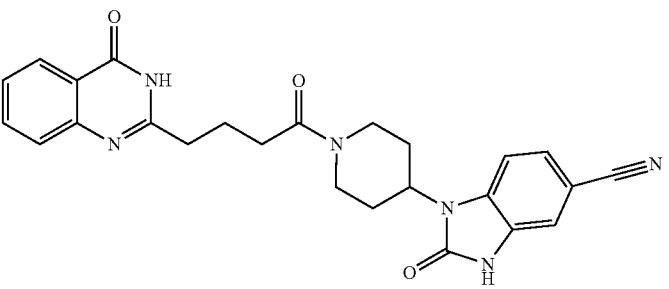 [SMILES: N#Cc1ccc2c(c1)[nH]c(=O)n2C1CCN(C(=O)CCCc2nc3ccccc3c(=O)[nH]2)CC1] |

TABLE 1-continued

Names and Structures of Example Compounds

| Example | Name |
|---|---|
| 69 | 2-(4-(4-(1,2-benzisothiazol-3-yl)-1-piperazinyl)-4-oxobutyl)-4(3H)-quinazolinone |
| 70 | 4-(4-oxo-3,4-dihydro-2-quinazolinyl)-N-(trans-4-(4-pyridinyloxy)cyclohexyl)butanamide |
| 71 | 2-(4-(4-(1,2-benzisoxazol-3-yl)-1-piperazinyl)-4-oxobutyl)-4(3H)-quinazolinone |
| 72 | 2-(4-(4-(5-fluoro-1,2-benzisoxazol-3-yl)-1-piperidinyl)-4-oxobutyl)-4(3H)-quinazolinone |
| 73 | N-(trans-4-(2-oxo-2,3-dihydro-1H-benzimidazol-1-yl)cyclohexyl)-4-(4-oxo-3,4-dihydro-2-quinazolinyl)butanamide |
| 74 | N-(trans-4-(5-chloro-2-oxo-2,3-dihydro-1H-benzimidazol-1-yl)cyclohexyl)-4-(4-oxo-3,4-dihydro-2-quinazolinyl)butanamide |

TABLE 1-continued

Names and Structures of Example Compounds

| Example | Name | Structure |
|---------|------|-----------|
| 75 | 2-(4-(4-(1H-benzotriazol-1-yl)-1-piperidinyl)-4-oxobutyl)-4(3H)-quinazolinone | 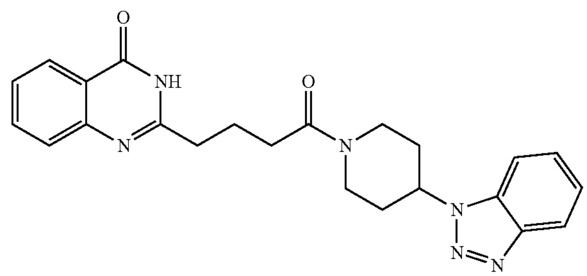 [SMILES: O=C(CCCc1nc2ccccc2c(=O)[nH]1)N1CCC(n2nnc3ccccc32)CC1] |
| 76 | 2-(4-(4-((3S)-6-chloro-2-oxo-2,3-dihydro-1H-indol-3-yl)-1-piperidinyl)-4-oxobutyl)-4(3H)-quinazolinone + 2-(4-(4-((3R)-6-chloro-2-oxo-2,3-dihydro-1H-indol-3-yl)-1-piperidinyl)-4-oxobutyl)-4(3H)-quinazolinone | |
| 77 | N-(trans-4-(4-fluorophenoxy)cyclohexyl)-4-(4-oxo-3,4-dihydro-2-quinazolinyl)butanamide | 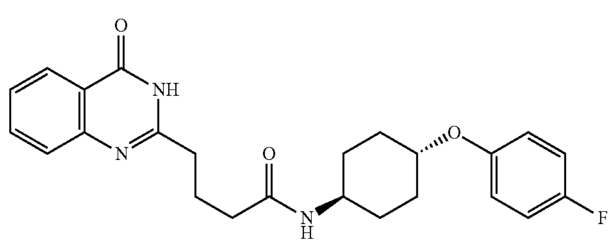 [SMILES: O=C(CCCc1nc2ccccc2c(=O)[nH]1)N[C@H]1CC[C@H](Oc2ccc(F)cc2)CC1] |
| 78 | N-(trans-4-(4-cyanophenoxy)cyclohexyl)-4-(4-oxo-3,4-dihydro-2-quinazolinyl)butanamide | 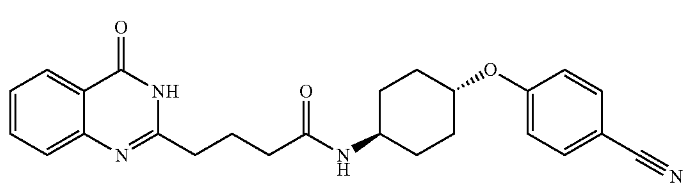 [SMILES: N#Cc1ccc(O[C@H]2CC[C@H](NC(=O)CCCc3nc4ccccc4c(=O)[nH]3)CC2)cc1] |

TABLE 1-continued

Names and Structures of Example Compounds

| Example | Name | Structure |
|---|---|---|
| 79 | N-(trans-4-(4-chlorophenoxy)cyclohexyl)-4-(4-oxo-3,4-dihydro-2-quinazolinyl)butanamide | 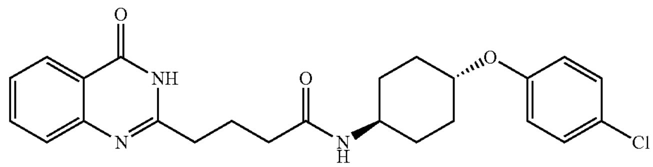 [SMILES: O=C(CCCc1nc2ccccc2c(=O)[nH]1)N[C@H]1CC[C@H](Oc2ccc(Cl)cc2)CC1] |
| 80 | N-(trans-4-(2-oxo-1,3-benzoxazol-3(2H)-yl)cyclohexyl)-3-(4-oxo-3,4-dihydro-2-quinazolinyl)propanamide | 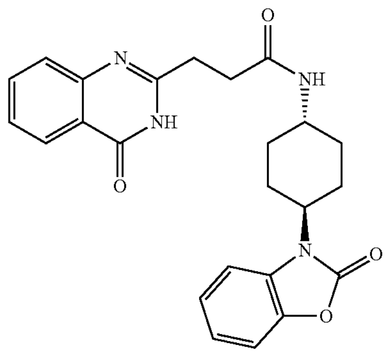 [SMILES: O=C(CCc1nc2ccccc2c(=O)[nH]1)N[C@H]1CC[C@H](n2c(=O)oc3ccccc32)CC1] |
| 81 | 3-(4-oxo-3,4-dihydropyrido[2,3-d]pyrimidin-2-yl)-N-(trans-4-(5-phenyl-1,3,4-oxadiazol-2-yl)cyclohexyl)propanamide | 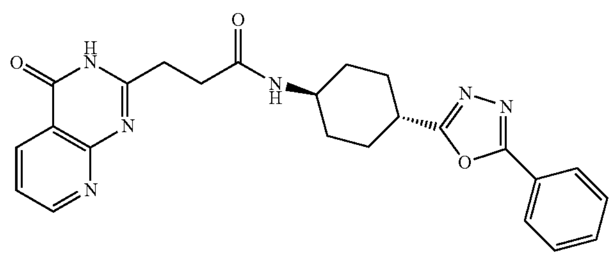 [SMILES: O=C(CCc1nc2ncccc2c(=O)[nH]1)N[C@H]1CC[C@H](c2nnc(-c3ccccc3)o2)CC1] |
| 82 | 2-((3-(4-(5-chloro-2-oxo-2,3-dihydro-1H-benzimidazol-1-yl)-1-piperidinyl)-3-oxopropyl)sulfanyl)-4(3H)-quinazolinone | 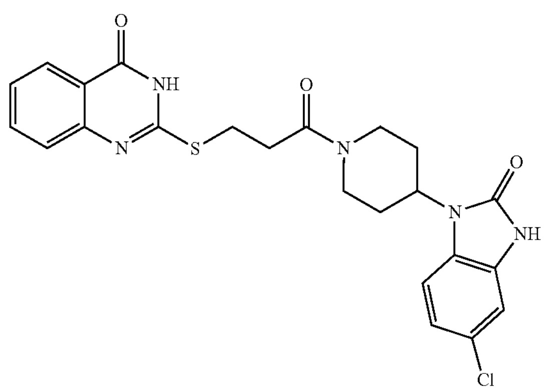 |
| 83 | 2-((3-oxo-3-(4-(5-phenyl-1,3,4-oxadiazol-2-yl)-1-piperidinyl)propyl)sulfanyl)-4(3H)-quinazolinone | 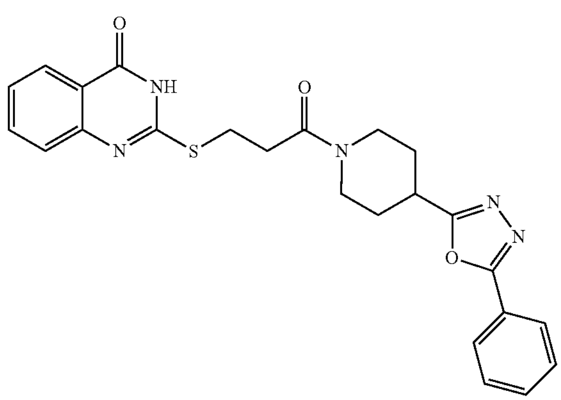 [SMILES: O=C(CCSc1nc2ccccc2c(=O)[nH]1)N1CCC(c2nnc(-c3ccccc3)o2)CC1] |

TABLE 1-continued

Names and Structures of Example Compounds

| Example | Name | Structure |
|---|---|---|
| 84 | N-(trans-4-(2-oxo-2,3-dihydro-1H-benzimidazol-1-yl)cyclohexyl)-3-(4-oxo-3,4-dihydro-2-quinazolinyl)propanamide | 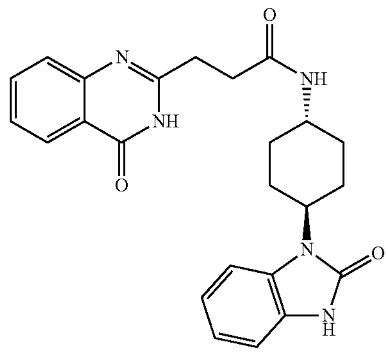 [SMILES: O=C(CCc1nc2ccccc2c(=O)[nH]1)N[C@H]1CC[C@H](n2c(=O)[nH]c3ccccc32)CC1] |
| 85 | N-(trans-4-(5-chloro-2-oxo-2,3-dihydro-1H-benzimidazol-1-yl)cyclohexyl)-3-(4-oxo-3,4-dihydro-2-quinazolinyl)propanamide | 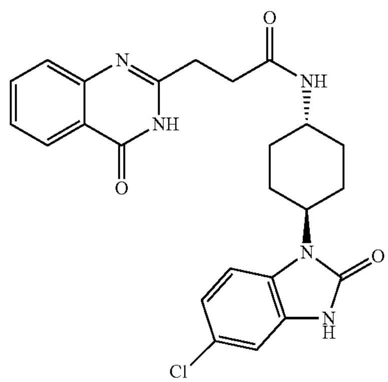 [SMILES: O=C(CCc1nc2ccccc2c(=O)[nH]1)N[C@H]1CC[C@H](n2c(=O)[nH]c3cc(Cl)ccc32)CC1] |
| 86 | N-(trans-4-(6-chloro-2-oxo-2,3-dihydro-1H-benzimidazol-1-yl)cyclohexyl)-3-(4-oxo-3,4-dihydro-2-quinazolinyl)propanamide | 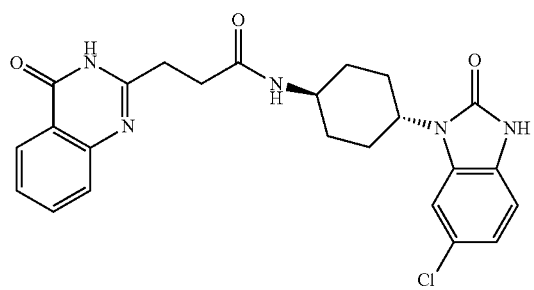 [SMILES: O=C(CCc1nc2ccccc2c(=O)[nH]1)N[C@H]1CC[C@H](n2c(=O)[nH]c3ccc(Cl)cc32)CC1] |
| 87 | N-(trans-4-(5-chloro-2-oxo-2,3-dihydro-1H-benzimidazol-1-yl)cyclohexyl)-2-((4-oxo-3,4-dihydro-2-quinazolinyl)sulfanyl)acetamide | 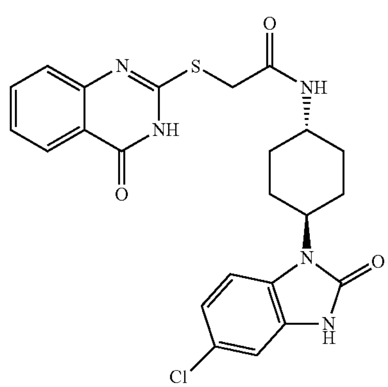 |

TABLE 1-continued

Names and Structures of Example Compounds

| Example | Name | Structure |
|---|---|---|
| 88 | 3-(4-oxo-3,4,5,6,7,8-hexahydropyrido[2,3-d]pyrimidin-2-yl)-N-(trans-4-(5-phenyl-1,3,4-oxadiazol-2-yl)cyclohexyl)propanamide | 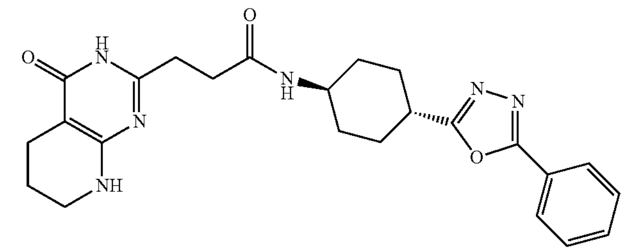 [SMILES: O=C(CCc1nc2c(c(=O)[nH]1)CCCN2)N[C@H]1CC[C@H](c2nnc(-c3ccccc3)o2)CC1] |
| 89 | 2-((2-oxo-2-(4-(5-phenyl-1,3,4-oxadiazol-2-yl)-1-piperidinyl)ethyl)sulfanyl)-4(3H)-quinazolinone | 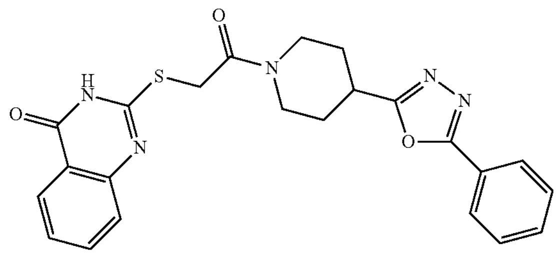 [SMILES: O=C(CSc1nc2ccccc2c(=O)[nH]1)N1CCC(c2nnc(-c3ccccc3)o2)CC1] |
| 90 | N-(trans-4-(5-chloro-2-oxo-2,3-dihydro-1H-benzimidazol-1-yl)cyclohexyl)-3-((4-oxo-3,4-dihydro-2-quinazolinyl)sulfanyl)-propanamide | 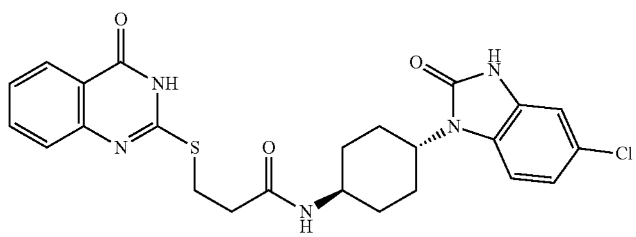 [SMILES: O=C(CCSc1nc2ccccc2c(=O)[nH]1)N[C@H]1CC[C@H](n2c(=O)[nH]c3cc(Cl)ccc32)CC1] |
| 91 | 3-((4-amino-6-oxo-1,6-dihydro-2-pyrimidinyl)sulfanyl)-N-(trans-4-(5-phenyl-1,3,4-oxadiazol-2-yl)cyclohexyl)propanamide | 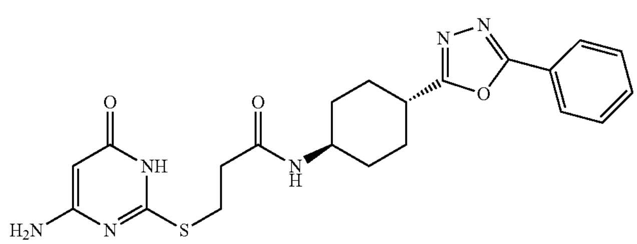 [SMILES: Nc1cc(=O)[nH]c(SCCC(=O)N[C@H]2CC[C@H](c3nnc(-c4ccccc4)o3)CC2)n1] |
| 92 | 3-(((4-oxo-3,4-dihydro-2-quinazolinyl)methyl)sulfanyl)-N-(trans-4-(5-phenyl-1,3,4-oxadiazol-2-yl)cyclohexyl)propanamide | 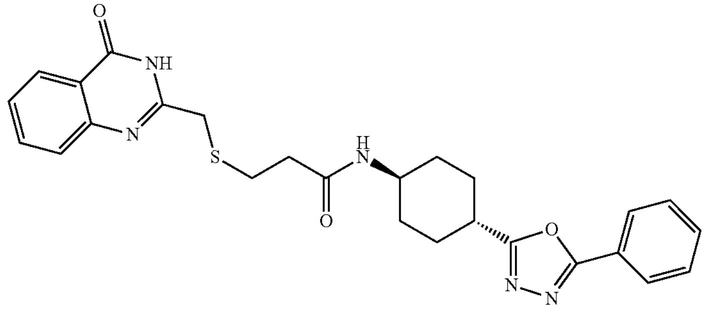 [SMILES: O=C(CCSCc1nc2ccccc2c(=O)[nH]1)N[C@H]1CC[C@H](c2nnc(-c3ccccc3)o2)CC1] |

TABLE 1-continued

Names and Structures of Example Compounds

| Example | Name |
|---|---|
| 93 | 2-(((3-(4-(5-(4-fluorophenyl)-1,3,4-oxadiazol-2-yl)-1-piperidinyl)-3-oxopropyl)sulfanyl)methyl)-4(3H)-quinazolinone |
| 94 | 2-((3-(4-(1H-indazol-3-yl)-1-piperazinyl)-3-oxopropyl)sulfanyl)-4(3H)-quinazolinone |
| 95 | 4-(4-oxo-3,4-dihydro-2-quinazolinyl)-N-(trans-4-(5-phenyl-1,3-oxazol-2-yl)cyclohexyl)butanamide |
| 96 | 2-((4-oxo-3,4-dihydro-2-quinazolinyl)sulfanyl)-N-(trans-4-(5-phenyl-1,3,4-oxadiazol-2-yl)cyclohexyl)acetamide |
| 97 | 3-((4-oxo-3,4-dihydro-2-quinazolinyl)sulfanyl)-N-(trans-4-(5-phenyl-1,3,4-oxadiazol-2-yl)cyclohexyl)propanamide |

TABLE 1-continued

Names and Structures of Example Compounds

| Example | Name | Structure |
|---|---|---|
| 98 | 2-(3-oxo-3-(4-(5-phenyl-1,3,4-oxadiazol-2-yl)-1-piperidinyl)propyl)-4(3H)-quinazolinone | 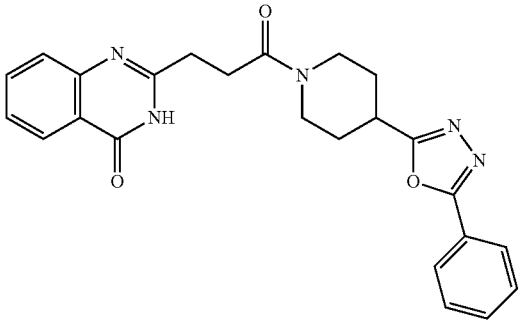 [SMILES: O=C(CCc1nc2ccccc2c(=O)[nH]1)N1CCC(c2nnc(-c3ccccc3)o2)CC1] |
| 99 | N-(trans-4-(4-fluorophenoxy)cyclohexyl)-2-((4-oxo-3,4-dihydro-2-quinazolinyl)sulfanyl)acetamide | 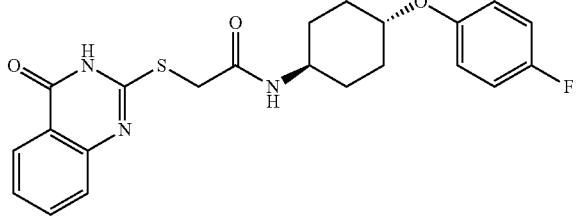 |
| 100 | N-(trans-4-(4-fluorophenoxy)cyclohexyl)-3-((4-oxo-3,4-dihydro-2-quinazolinyl)sulfanyl)propanamide | 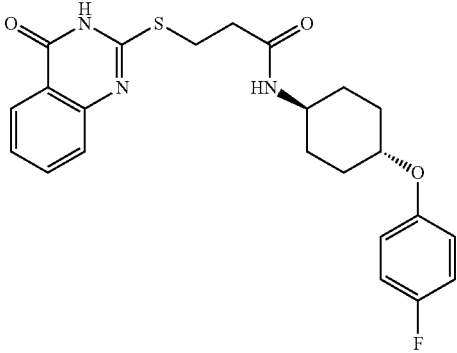 |
| 101 | 3-(6-fluoro-4-oxo-3,4-dihydro-2-quinazolinyl)-N-(trans-4-(5-phenyl-1,3,4-oxadiazol-2-yl)cyclohexyl)propanamide | 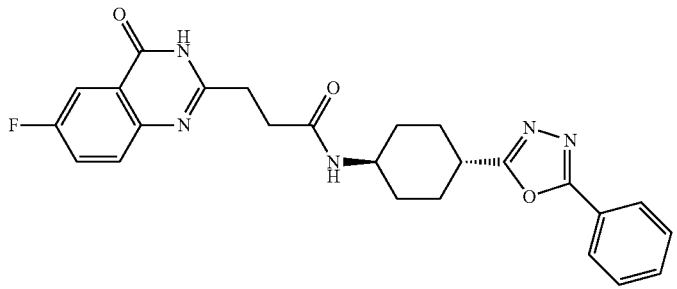 [SMILES: O=C(CCc1nc2ccc(F)cc2c(=O)[nH]1)N[C@H]1CC[C@H](c2nnc(-c3ccccc3)o2)CC1] |
| 102 | N-(trans-4-(6-chloro-2-oxo-2,3-dihydro-1H-benzimidazol-1-yl)cyclohexyl)-2-((4-oxo-3,4-dihydro-2-quinazolinyl)sulfanyl)acetamide | 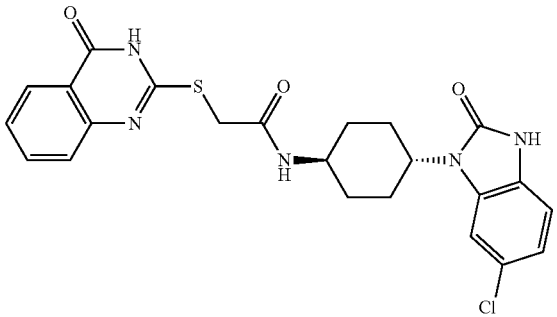 [SMILES: O=C(CSc1nc2ccccc2c(=O)[nH]1)N[C@H]1CC[C@H](n2c(=O)[nH]c3ccc(Cl)cc32)CC1] |

TABLE 1-continued

Names and Structures of Example Compounds

| Example | Name | Structure |
|---|---|---|
| 103 | N-(trans-4-(5-cyano-2-oxo-2,3-dihydro-1H-benzimidazol-1-yl)cyclohexyl)-2-((4-oxo-3,4-dihydro-2-quinazolinyl)sulfanyl)acetamide | 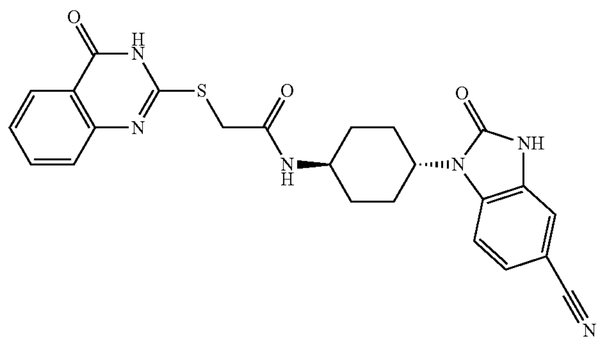 [SMILES: N#Cc1ccc2c(c1)[nH]c(=O)n2[C@H]1CC[C@H](NC(=O)CSc2nc3ccccc3c(=O)[nH]2)CC1] |
| 104 | N-(trans-4-(5-cyano-2-oxo-2,3-dihydro-1H-benzimidazol-1-yl)cyclohexyl)-3-((4-oxo-3,4-dihydro-2-quinazolinyl)sulfanyl)propanamide | 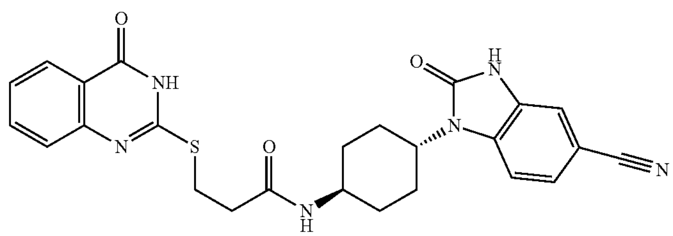 [SMILES: N#Cc1ccc2c(c1)[nH]c(=O)n2[C@H]1CC[C@H](NC(=O)CCSc2nc3ccccc3c(=O)[nH]2)CC1] |
| 105 | N-(trans-4-(4-chlorophenoxy)cyclohexyl)-3-((4-oxo-3,4-dihydro-2-quinazolinyl)sulfanyl)propanamide | 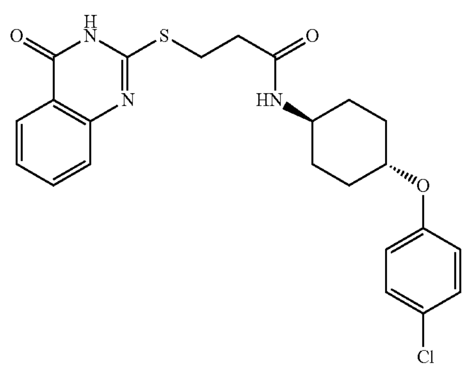 [SMILES: O=C(CCSc1nc2ccccc2c(=O)[nH]1)N[C@H]1CC[C@H](Oc2ccc(Cl)cc2)CC1] |
| 106 | N-(trans-4-(4-cyanophenoxy)cyclohexyl)-3-((4-oxo-3,4-dihydro-2-quinazolinyl)sulfanyl)propanamide | 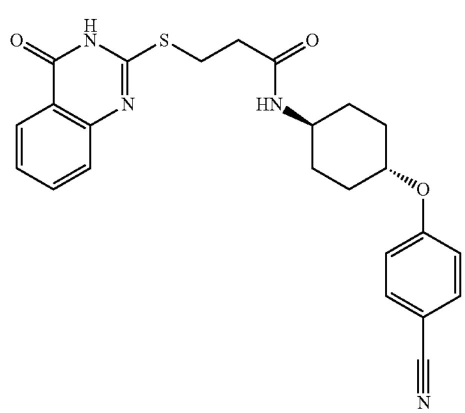 [SMILES: N#Cc1ccc(O[C@H]2CC[C@H](NC(=O)CCSc3nc4ccccc4c(=O)[nH]3)CC2)cc1] |

TABLE 1-continued

Names and Structures of Example Compounds

| Example | Name | Structure |
|---|---|---|
| 107 | 3-((4-oxo-3,4-dihydro-2-quinazolinyl)sulfanyl)-N-(trans-4-(2-pyridinyloxy)cyclohexyl)-propanamide | 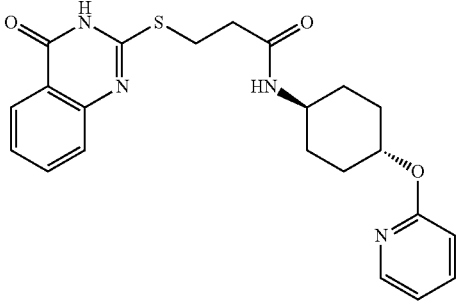 [SMILES: O=C(CCSc1nc2ccccc2c(=O)[nH]1)N[C@H]1CC[C@H](Oc2ccccn2)CC1] |
| 108 | 3-((4-oxo-3,4-dihydro-2-quinazolinyl)sulfanyl)-N-(trans-4-(4-pyridinyloxy)cyclohexyl)-propanamide | 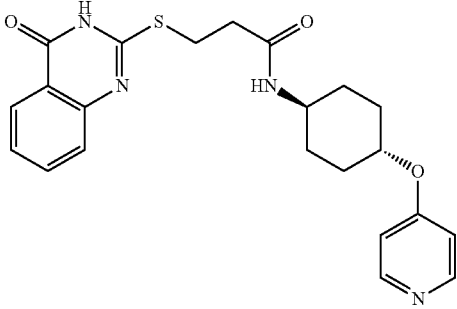 [SMILES: O=C(CCSc1nc2ccccc2c(=O)[nH]1)N[C@H]1CC[C@H](Oc2ccncc2)CC1] |
| 109 | N-(trans-4-(3-cyanophenoxy)cyclohexyl)-3-((4-oxo-3,4-dihydro-2-quinazolinyl)sulfanyl)-propanamide | 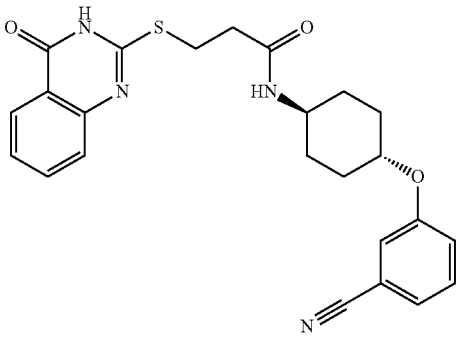 [SMILES: N#Cc1cccc(O[C@H]2CC[C@H](NC(=O)CCSc3nc4ccccc4c(=O)[nH]3)CC2)c1] |
| 110 | 4-((4-oxo-3,4-dihydro-2-quinazolinyl)sulfanyl)-N-(trans-4-(5-phenyl-1,3,4-oxadiazol-2-yl)cyclohexyl)butanamide | 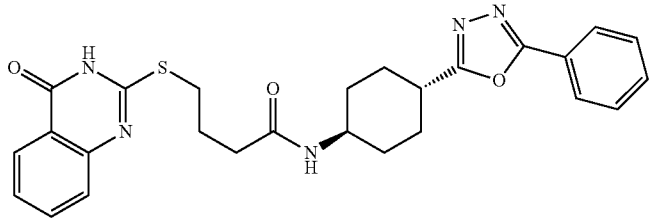 [SMILES: O=C(CCCSc1nc2ccccc2c(=O)[nH]1)N[C@H]1CC[C@H](c2nnc(-c3ccccc3)o2)CC1] |
| 111 | 2-((4-oxo-4-(4-(5-phenyl-1,3,4-oxadiazol-2-yl)-1-piperidinyl)butyl)sulfanyl)-4(3H)-quinazolinone | 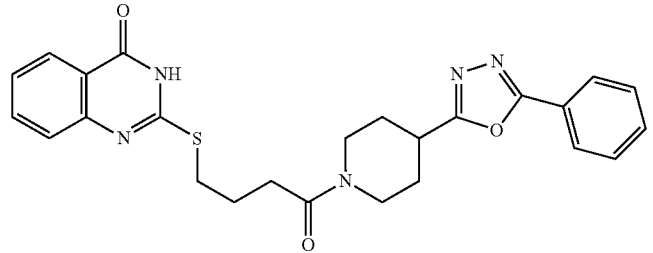 [SMILES: O=C(CCCSc1nc2ccccc2c(=O)[nH]1)N1CCC(c2nnc(-c3ccccc3)o2)CC1] |

TABLE 1-continued

Names and Structures of Example Compounds

| Example | Name | Structure |
|---|---|---|
| 112 | N-(trans-4-(3-chlorophenoxy)cyclohexyl)-3-((4-oxo-3,4-dihydro-2-quinazolinyl)sulfanyl)-propanamide | 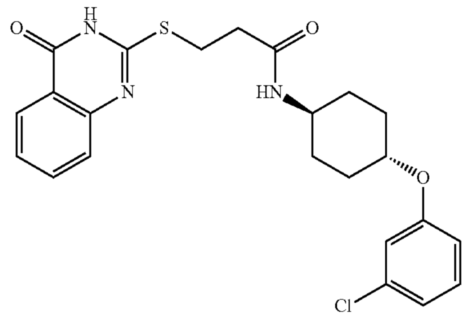 [SMILES: O=C(CCSc1nc2ccccc2c(=O)[nH]1)N[C@H]1CC[C@H](Oc2cccc(Cl)c2)CC1] |
| 113 | N-(trans-4-(4-chloro-3-cyanophenoxy)cyclohexyl)-3-((4-oxo-3,4-dihydro-2-quinazolinyl)sulfanyl)-propanamide | 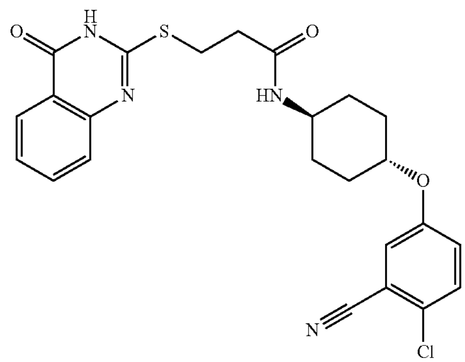 [SMILES: N#Cc1cc(O[C@H]2CC[C@H](NC(=O)CCSc3nc4ccccc4c(=O)[nH]3)CC2)ccc1Cl] |
| 114 | N-(trans-4-(3-chloro-4-cyanophenoxy)cyclohexyl)-3-((4-oxo-3,4-dihydro-2-quinazolinyl)sulfanyl)-propanamide | 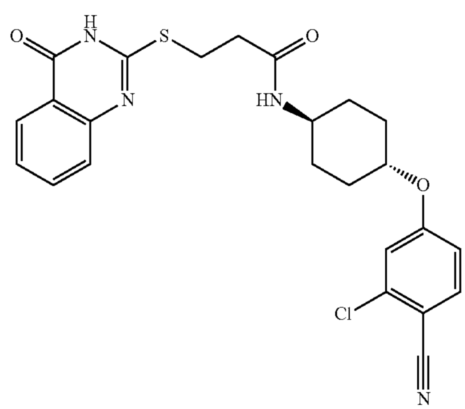 [SMILES: N#Cc1ccc(O[C@H]2CC[C@H](NC(=O)CCSc3nc4ccccc4c(=O)[nH]3)CC2)cc1Cl] |
| 115 | 3-((4-oxo-3,4,5,6,7,8-hexahydro-2-quinazolinyl)sulfanyl)-N-(trans-4-(5-phenyl-1,3,4-oxadiazol-2-yl)cyclohexyl)propanamide | 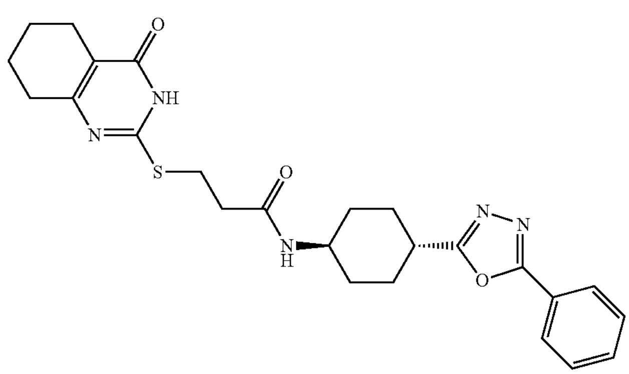 [SMILES: O=C(CCSc1nc2c(c(=O)[nH]1)CCCC2)N[C@H]1CC[C@H](c2nnc(-c3ccccc3)o2)CC1] |

TABLE 1-continued

Names and Structures of Example Compounds

| Example | Name | Structure |
|---|---|---|
| 116 | N-(trans-4-(4-cyanophenoxy)cyclohexyl)-3-((4-oxo-3,4,5,6,7,8-hexahydro-2-quinazolinyl)sulfanyl)-propanamide | 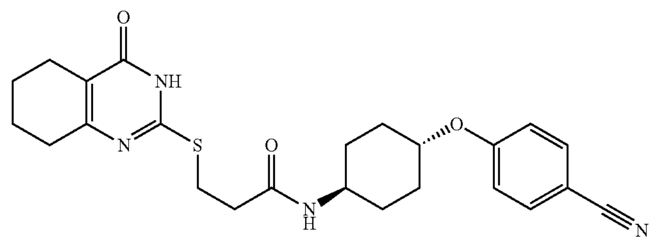 [SMILES: N#Cc1ccc(O[C@H]2CC[C@H](NC(=O)CCSc3nc4c(c(=O)[nH]3)CCCC4)CC2)cc1] |
| 117 | N-(trans-4-(5-(4-fluorophenyl)-1,3,4-oxadiazol-2-yl)cyclohexyl)-3-((4-oxo-3,4-dihydro-2-quinazolinyl)sulfanyl)-propanamide | 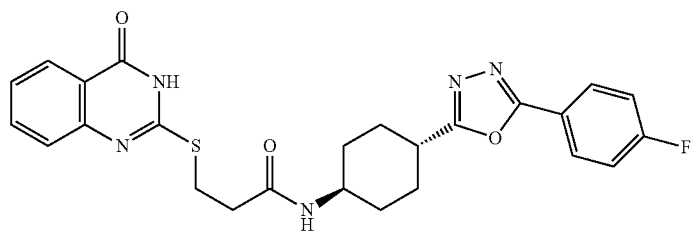 [SMILES: O=C(CCSc1nc2ccccc2c(=O)[nH]1)N[C@H]1CC[C@H](c2nnc(-c3ccc(F)cc3)o2)CC1] |
| 118 | N-(trans-4-(5-(3-chlorophenyl)-1,3,4-oxadiazol-2-yl)cyclohexyl)-3-((4-oxo-3,4-dihydro-2-quinazolinyl)sulfanyl)propanamide | 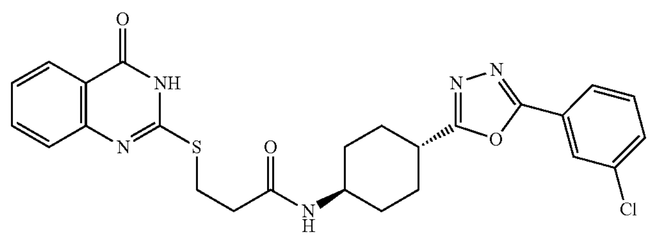 [SMILES: O=C(CCSc1nc2ccccc2c(=O)[nH]1)N[C@H]1CC[C@H](c2nnc(-c3cccc(Cl)c3)o2)CC1] |
| 119 | N-(trans-4-(5-(3-fluorophenyl)-1,3,4-oxadiazol-2-yl)cyclohexyl)-3-((4-oxo-3,4-dihydro-2-quinazolinyl)sulfanyl)-propanamide | 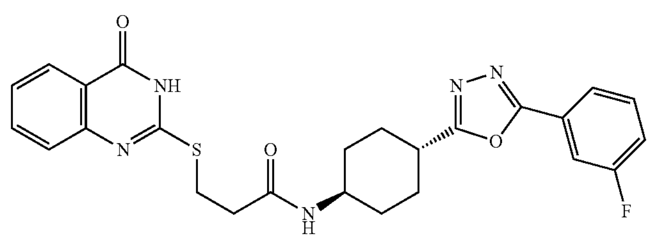 [SMILES: O=C(CCSc1nc2ccccc2c(=O)[nH]1)N[C@H]1CC[C@H](c2nnc(-c3cccc(F)c3)o2)CC1] |
| 120 | N-(trans-4-(5-(3-methoxyphenyl)-1,3,4-oxadiazol-2-yl)cyclohexyl)-3-((4-oxo-3,4-dihydro-2-quinazolinyl)sulfanyl) -propanamide | 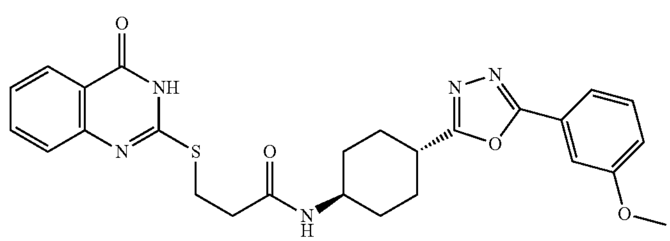 [SMILES: COc1cccc(-c2nnc([C@H]3CC[C@H](NC(=O)CCSc4nc5ccccc5c(=O)[nH]4)CC3)o2)c1] |
| 121 | N-(trans-4-(5-(4-methoxyphenyl)-1,3,4-oxadiazol-2-yl)cyclohexyl)-3-((4-oxo-3,4-dihydro-2-quinazolinyl)sulfanyl)-propanamide | 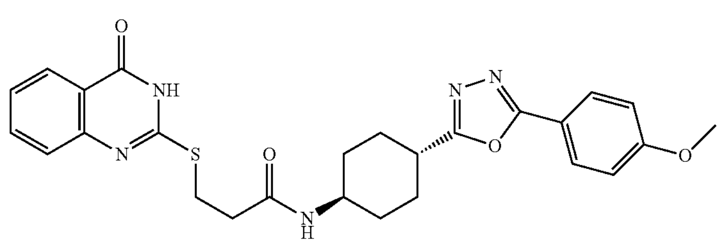 [SMILES: COc1ccc(-c2nnc([C@H]3CC[C@H](NC(=O)CCSc4nc5ccccc5c(=O)[nH]4)CC3)o2)cc1] |

TABLE 1-continued

Names and Structures of Example Compounds

| Example | Name | Structure |
|---|---|---|
| 122 | N-(trans-4-(5-(3-chloro-4-fluorophenyl)-1,3,4-oxadiazol-2-yl)cyclohexyl)-3-((4-oxo-3,4-dihydro-2-quinazolinyl)sulfanyl)-propanamide | 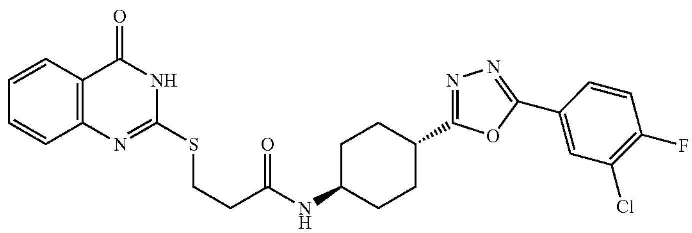 [SMILES: O=C(CCSc1nc2ccccc2c(=O)[nH]1)N[C@H]1CC[C@H](c2nnc(-c3ccc(F)c(Cl)c3)o2)CC1] |
| 123 | 3-((6-oxo-1,6-dihydro-2-pyrimidinyl)sulfanyl)-N-(trans-4-(5-phenyl-1,3,4-oxadiazol-2-yl)cyclohexyl)propanamide | 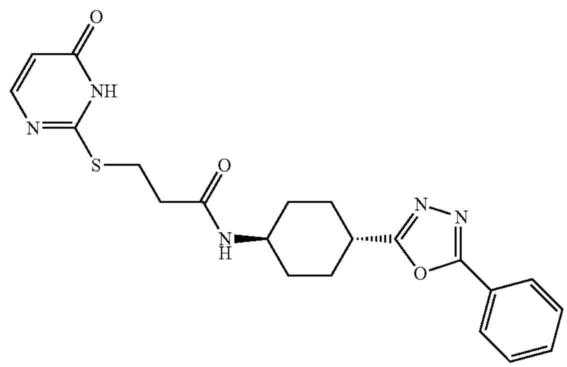 [SMILES: O=C(CCSc1nccc(=O)[nH]1)N[C@H]1CC[C@H](c2nnc(-c3ccccc3)o2)CC1] |
| 124 | 3-((4-oxo-3,4-dihydro-2-quinazolinyl)sulfanyl)-N-(trans-4-(5-(4-pyridinyl)-1,3,4-oxadiazol-2-yl)cyclohexyl)propanamide | 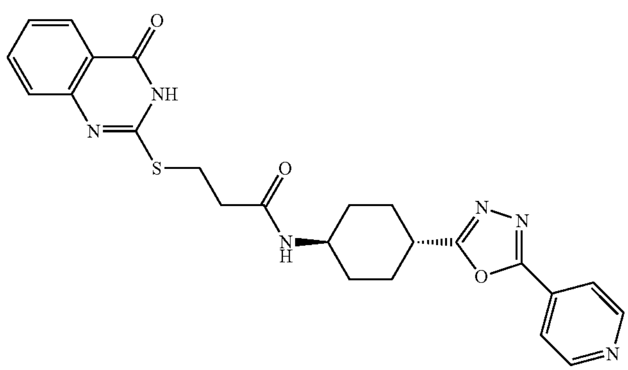 [SMILES: O=C(CCSc1nc2ccccc2c(=O)[nH]1)N[C@H]1CC[C@H](c2nnc(-c3ccncc3)o2)CC1] |
| 125 | N-(trans-4-(5-(4-chlorophenyl)-1,3,4-oxadiazol-2-yl)cyclohexyl)-3-((4-oxo-3,4-dihydro-2-quinazolinyl)sulfanyl)-propanamide | 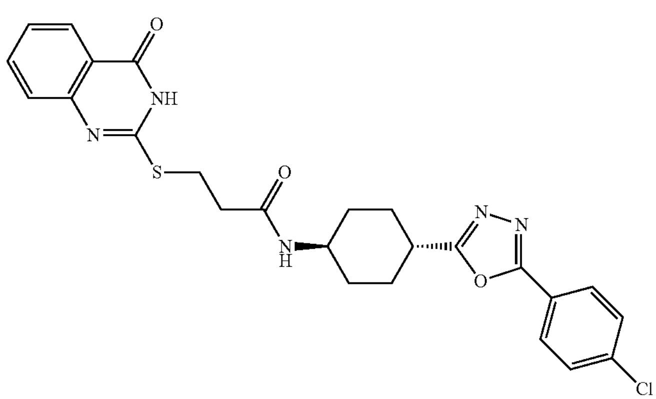 [SMILES: O=C(CCSc1nc2ccccc2c(=O)[nH]1)N[C@H]1CC[C@H](c2nnc(-c3ccc(Cl)cc3)o2)CC1] |

TABLE 1-continued

Names and Structures of Example Compounds

| Example | Name | Structure |
|---|---|---|
| 126 | N-(trans-4-(5-(2-fluorophenyl)-1,3,4-oxadiazol-2-yl)cyclohexyl)-3-(4-oxo-3,4-dihydro-2-quinazolinyl)propanamide | 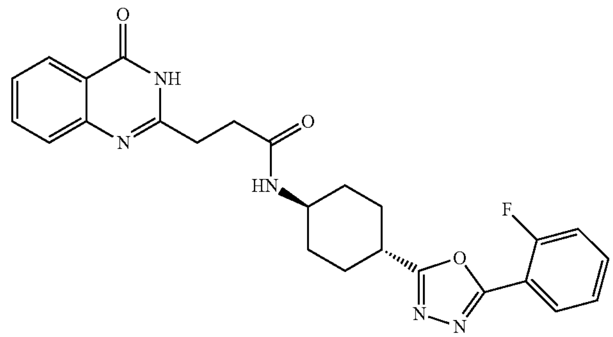 [SMILES: O=C(CCc1nc2ccccc2c(=O)[nH]1)N[C@H]1CC[C@H](c2nnc(-c3ccccc3F)o2)CC1] |
| 127 | N-(trans-4-(5-(4-fluorophenyl)-1,3,4-oxadiazol-2-yl)cyclohexyl)-3-(4-oxo-3,4-dihydro-2-quinazolinyl)propanamide | 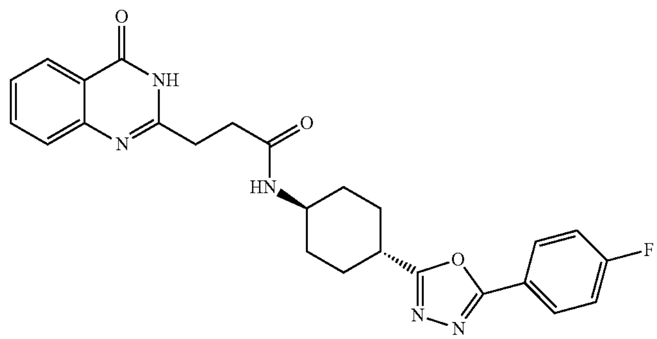 [SMILES: O=C(CCc1nc2ccccc2c(=O)[nH]1)N[C@H]1CC[C@H](c2nnc(-c3ccc(F)cc3)o2)CC1] |
| 128 | N-(trans-4-(5-(2-chlorophenyl)-1,3,4-oxadiazol-2-yl)cyclohexyl)-3-(4-oxo-3,4-dihydro-2-quinazolinyl)propanamide | 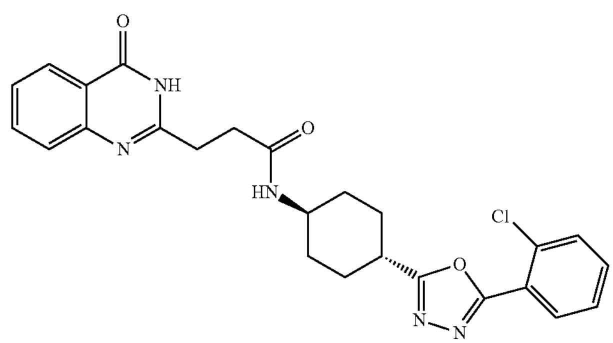 |
| 129 | N-(trans-4-(5-(3-fluorophenyl)-1,3,4-oxadiazol-2-yl)cyclohexyl)-3-(4-oxo-3,4-dihydro-2-quinazolinyl)propanamide | 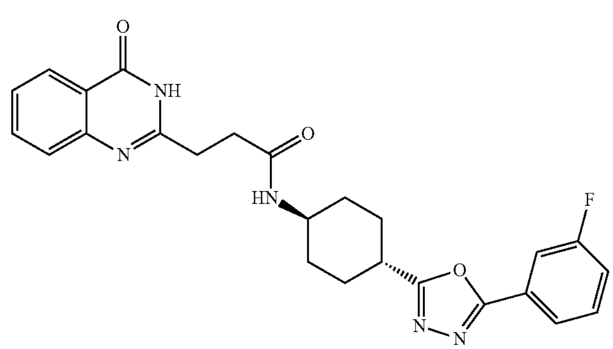 [SMILES: O=C(CCc1nc2ccccc2c(=O)[nH]1)N[C@H]1CC[C@H](c2nnc(-c3cccc(F)c3)o2)CC1] |

TABLE 1-continued

Names and Structures of Example Compounds

| Example | Name | Structure |
|---|---|---|
| 130 | N-(trans-4-(5-(3-chlorophenyl)-1,3,4-oxadiazol-2-yl)cyclohexyl)-3-(4-oxo-3,4-dihydro-2-quinazolinyl)propanamide | 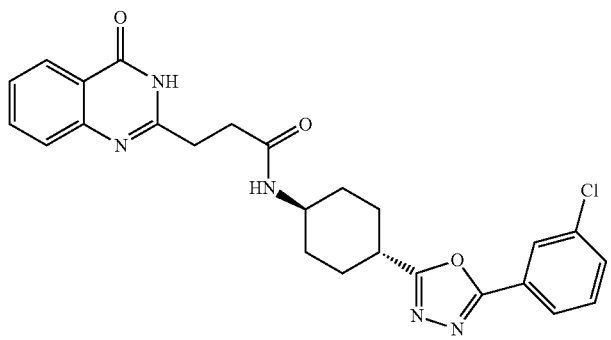 [SMILES: O=C(CCc1nc2ccccc2c(=O)[nH]1)N[C@H]1CC[C@H](c2nnc(-c3cccc(Cl)c3)o2)CC1] |
| 131 | 3-(4-oxo-3,4-dihydro-2-quinazolinyl)-N-(trans-4-(5-(2-pyridinyl)-1,3,4-oxadiazol-2-yl)cyclohexyl)propanamide | 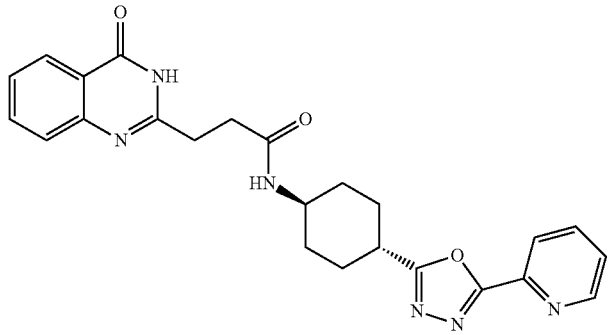 [SMILES: O=C(CCc1nc2ccccc2c(=O)[nH]1)N[C@H]1CC[C@H](c2nnc(-c3ccccn3)o2)CC1] |
| 132 | 3-(4-oxo-3,4-dihydro-2-quinazolinyl)-N-(trans-4-(5-(4-pyridinyl)-1,3,4-oxadiazol-2-yl)cyclohexyl)propanamide | 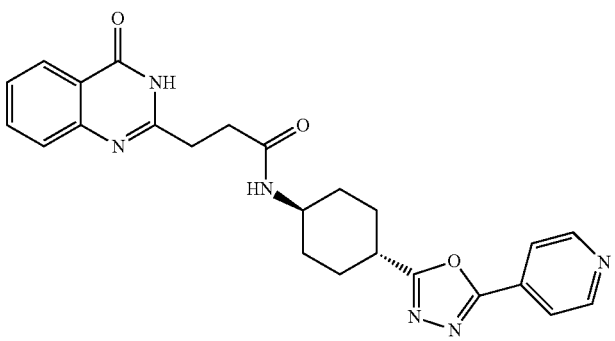 [SMILES: O=C(CCc1nc2ccccc2c(=O)[nH]1)N[C@H]1CC[C@H](c2nnc(-c3ccncc3)o2)CC1] |
| 133 | 3-(4-oxo-3,4-dihydro-2-quinazolinyl)-N-(trans-4-(5-(2-pyrimidinyl)-1,3,4-oxadiazol-2-yl)cyclohexyl)propanamide | 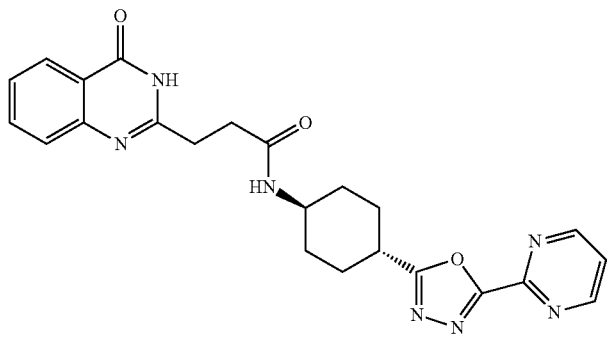 [SMILES: O=C(CCc1nc2ccccc2c(=O)[nH]1)N[C@H]1CC[C@H](c2nnc(-c3ncccn3)o2)CC1] |

TABLE 1-continued

Names and Structures of Example Compounds

| Example | Name |
|---|---|
| 134 | N-((1r,4r)-4-(5-(4-cyanophenyl)-1,3,4-oxadiazol-2-yl)cyclohexyl)-3-(4-oxo-3,4-dihydroquinazolin-2-yl)propanamide |
| 135 | 3-(4-oxo-3,4-dihydroquinazolin-2-yl)-N-((1r,4r)-4-(5-(tetrahydro-2H-pyran-4-yl)-1,3,4-oxadiazol-2-yl)cyclohexyl)propanamide |
| 136 | 3-(4-oxo-3,4-dihydro-2-quinazolinyl)-N-(trans-4-(5-(3-pyridinyl)-1,3,4-oxadiazol-2-yl)cyclohexyl)propanamide |
| 137 | N-(trans-4-(5-(3-cyanophenyl)-1,3,4-oxadiazol-2-yl)cyclohexyl)-3-(4-oxo-3,4-dihydro-2-quinazolinyl)propanamide |

TABLE 1-continued

Names and Structures of Example Compounds

| Example | Name | Structure |
|---|---|---|
| 138 | N-(trans-4-(5-cyclohexyl-1,3,4-oxadiazol-2-yl)cyclohexyl)-3-(4-oxo-3,4-dihydro-2-quinazolinyl)propanamide | 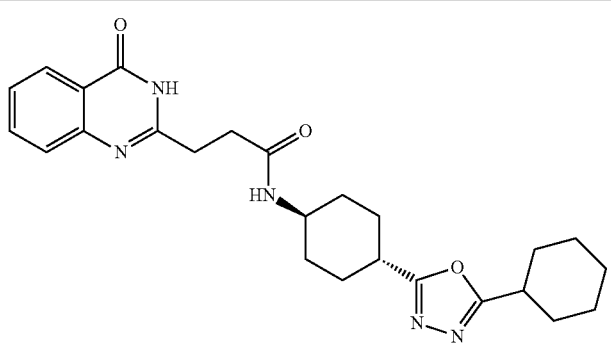 [SMILES: O=C(CCc1nc2ccccc2c(=O)[nH]1)N[C@H]1CC[C@H](c2nnc(C3CCCCC3)o2)CC1] |
| 139 | N-(trans-4-(5-benzyl-1,3,4-oxadiazol-2-yl)cyclohexyl)-3-(4-oxo-3,4-dihydro-2-quinazolinyl)propanamide | 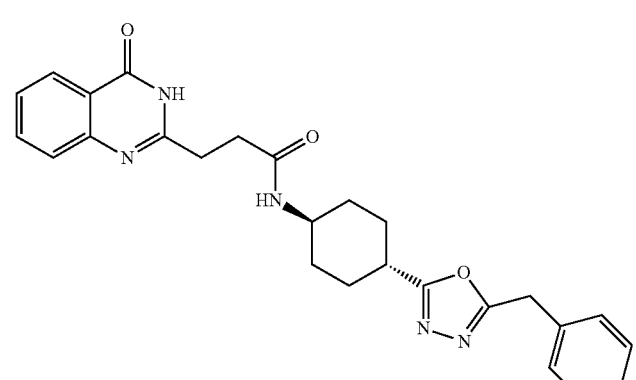 |
| 140 | 3-(4-oxo-3,4-dihydroquinazolin-2-yl)-N-((1r,4r)-4-(5-(2-phenylpropan-2-yl)-1,3,4-oxadiazol-2-yl)cyclohexyl)propanamide | 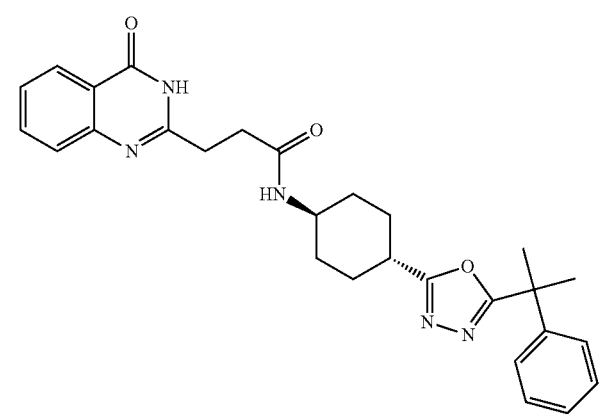 [SMILES: CC(C)(c1ccccc1)c1nnc([C@H]2CC[C@H](NC(=O)CCc3nc4ccccc4c(=O)[nH]3)CC2)o1] |
| 141 | N-(trans-4-(5-(4-chlorophenyl)-1,3,4-oxadiazol-2-yl)cyclohexyl)-3-(4-oxo-3,4-dihydro-2-quinazolinyl)propanamide | 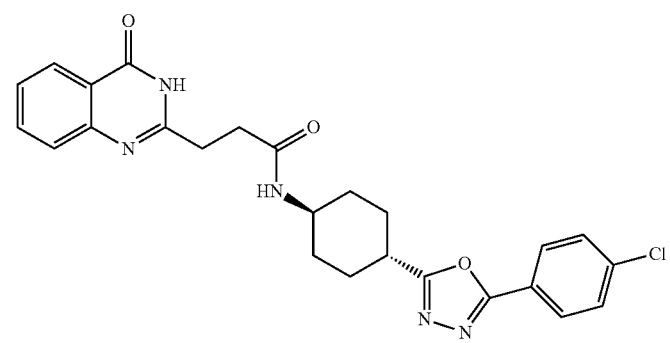 [SMILES: O=C(CCc1nc2ccccc2c(=O)[nH]1)N[C@H]1CC[C@H](c2nnc(-c3ccc(Cl)cc3)o2)CC1] |

TABLE 1-continued

Names and Structures of Example Compounds

| Example | Name | Structure |
|---|---|---|
| 142 | 3-(4-oxo-3,4-dihydro-2-quinazolinyl)-N-(trans-4-(5-(2-pyrazinyl)-1,3,4-oxadiazol-2-yl)cyclohexyl)propanamide | 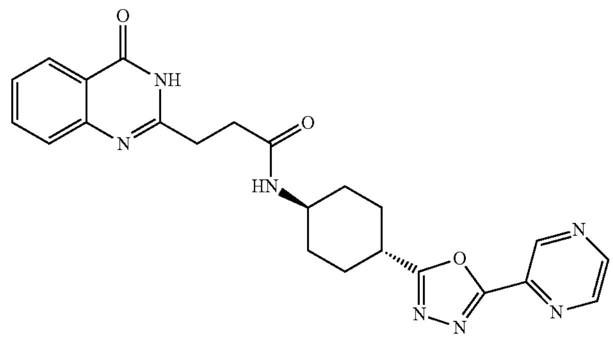 [SMILES: O=C(CCc1nc2ccccc2c(=O)[nH]1)N[C@H]1CC[C@H](c2nnc(-c3cnccn3)o2)CC1] |
| 143 | 3-((4-oxo-3,4-dihydro-2-quinazolinyl)sulfinyl)-N-(trans-4-(5-phenyl-1,3,4-oxadiazol-2-yl)cyclohexyl)propanamide | 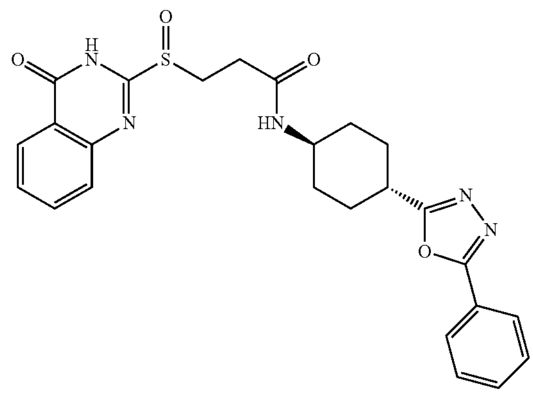 [SMILES: O=C(CCS(=O)c1nc2ccccc2c(=O)[nH]1)N[C@H]1CC[C@H](c2nnc(-c3ccccc3)o2)CC1] |
| 144 | 3-((4-oxo-4H-pyrido[1,2-a]pyrimidin-2-yl)sulfanyl)-N-(trans-4-(5-phenyl-1,3,4-oxadiazol-2-yl)cyclohexyl)propanamide | 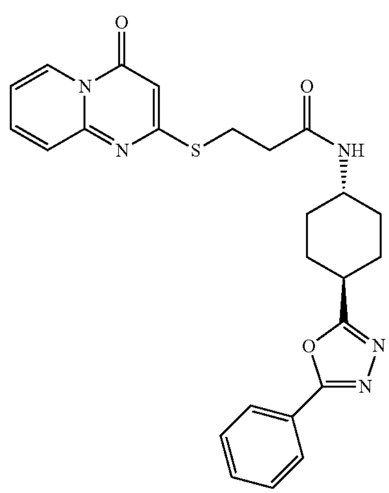 [SMILES: O=C(CCSc1cc(=O)n2ccccc2n1)N[C@H]1CC[C@H](c2nnc(-c3ccccc3)o2)CC1] |
| 145 | 3-((6-fluoro-4-oxo-3,4-dihydro-2-quinazolinyl)sulfanyl)-N-(trans-4-(5-phenyl-1,3,4-oxadiazol-2-yl)cyclohexyl)propanamide | 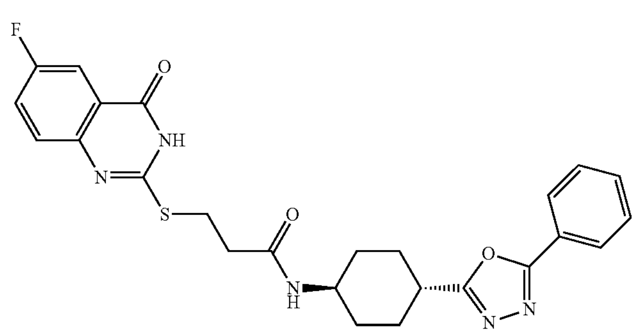 [SMILES: O=C(CCSc1nc2ccc(F)cc2c(=O)[nH]1)N[C@H]1CC[C@H](c2nnc(-c3ccccc3)o2)CC1] |

Biological Activity

Axin2 384 Immunofluorescence Protocol

SW480 cells were grown in RPMI 1640 (Invitrogen, 72400-047), 10% HI FBS (Invitrogen, 16140-071), 1× sodium pyruvate (Invitrogen, 11360-070), 750 ug/mL Geneticin® antibiotic (Invitrogen, 10131-027) and 10 mg/mL Blasticidin S antibiotic (Invitrogen, R210-01). On the day of the assay, cells were trypsinized (Invitrogen, 25200-056) to remove cells from flask and media was added. The cells were then centrifuged at 300 RCF for 5 minutes, and the media was removed and replaced with assay media (RPMI 1640 (Invitrogen, 72400-047), 10% HI FBS (Invitrogen, 16140-071), and 1× sodium pyruvate (Invitrogen, 11360-070)). The cells were then counted using a ViCell and plated at 2,500 cells per well in 60 μL of assay media in Perkin Elmer Black 384 ViewPlates (Fisher, 509052489). Compounds (0.5 μL in 100% DMSO) were diluted using a FlexDrop by adding 13.8 μL of assay media to columns 1-22 (resulting in 3.5% DMSO). Control compound was added to column 23 at a concentration of 14 μM, and 3.5% DMSO (HI). DMSO in assay media (3.5%) was added to column 24 (LO). Using a VPrep, 10 μL of compound/controls was transferred from the compound plate to 60 μL in the cell plate (final 0.5% DMSO, 70 μL). The mixture was incubated for 24 hours at 37° C. at 5% $CO_2$.

The assay media was aspirated off the cells using a BioTek plate washer, and the cells were then washed with 50 μL of PBS (Invitrogen, 14040-117). The extra media was tapped out. 50 μL of 4% paraformaldehyde (Fisher, AA433689M), 0.1% Triton (Sigma, X100-100 ML) in PBS were added, and the mixture was incubated for 15 minutes at RT. The cells were then washed with PBS, 0.1% Tween-20 (BioRad, 1610781), and 1% Normal Goat Serum (Fisher, NC9270494). The extra media was tapped out and to this was added 50 μL of buffer containing Axin2 Antibody (Sigma, SAB1100677-200 UL) at 1:10000 in PBS, 0.1% Tween-20, 1% Normal Goat Serum. The mixture was incubated for 2 hours at RT or overnight at 4° C. The cells were then washed twice with PBS, 0.1% Tween-20, and 1% Normal Goat Serum. To the cells was added 50 μL Secondary Alexa 488 Antibody (Invitrogen, A11008) at 0.5 μg/mL and Hoechst (Invitrogen, H3570) at 1 μg/mL in PBS, 0.1% Tween-20, and 1% Normal Goat Serum. The mixture was then incubated for 30 minutes at RT. The cells were then washed twice with PBS, 0.1% Tween-20, and 1% Normal Goat Serum. 50-100 μL PBS was added, and the mixture was covered with a plate seal (Fisher, NC9425162). An ArrayScan (a variation of the compartmental analysis protocol was optimized) was used to scan the plates, and data was analyzed using MEAN_RingSpotAvgIntenCh2). The Axin2 accumulation POC was calculated, and the EC50 was determined using Genedata Screener software to report Axin2 activity.

Total β-Catenin MSD 96-Well Plate Assay for SW480 Cells

SW480 colorectal cells were seeded at a density of 10,000/well in CellBIND 96-well plates (Corning catalog no. 3300) in 60 μL of normal growth medium (MEM alpha supplemented with 10% heat inactivated FBS, GlutaMAX, pyruvate, and 10 mM HEPES).

A 10-point, 3-fold dilution series for each TNKS inhibitor was constructed in a 96-well "stock" plate. Twenty microliters of each diluted compound was transferred from the "stock" plate into the plate containing the SW-480 cells resulting in a 1:4 dilution of the compounds and resulted in final vehicle (DMSO) concentration of 0.1%. The top concentration of TNKS inhibitors tested was 10 μM. DMSO alone (0.1%) served as the "HI" control and a potent tankyrase inhibitor at a final concentration of 20 μM served as the "LO" control for $IC_{50}$ calculations. The plates were incubated at 37° C. for 40 to 48 hours. The media was removed from the CellBIND plate via plate inversion and gentle shaking and the inverted plate was touched to a paper towel and immediately placed on ice. Cell lysis was achieved with 75 μL/well MSD lysis buffer containing following protease and phosphatase inhibitors (Protease inhibitor tablet, Roche catalog no. 11836153001; PhosSTOP phosphatase inhibitor tablet, Roche cat. No. 04906845001; 10 mM NaF) as well as 1 mM EDTA and 1 mM EGTA. Plates containing cell lysates were sealed and shaken for one hour at 4° C. and then quickly frozen in a −80° C. for approximately 15 to 30 minutes followed by gradually thawing at 4° C. Finally, lysate containing plates were centrifuged @ 1000×g (2073 rpm) for 10 minutes at 4° C.

A goat anti-rabbit MSD plate (catalog no. L41RA-1) was coated with 25 μL of 5 μg/mL of Cell Signaling anti-total β-catenin polyclonal (catalog no. 9562, lyophilized, carrier-free special order) which had been reconstituted with TBS. The sealed MSD plate was incubated overnight in a cold room with gentle shaking. The MSD plate was then blocked with 150 μL of Blocker "A" per well and incubated overnight at 4° C. with vigorous shaking. The blocked MSD plate was washed 4 times with 150 μL/well TBS-T wash buffer (150 mM NaCl, 50 mM Tris, pH 7.5, 0.02% Tween-20). Cell lysates (75 μL) were transferred to prepared MSD plates and incubated at 4° C. ON with gentle shaking. The next day MSD plates were washed 4 times with TBS-T wash buffer and 25 μL/well of detection antibody at a concentration of 1 μg/mL BD Biosciences anti-total β-catenin mAb (catalog no. 610153) conjugated to SULFO-TAG in MSD Antibody Diluent (catalog no. R50AA-2) was added. The detection antibody was incubated for 1 hour at RT with vigorous shaking after which plates were washed 3 times with 150 μL/well TBS-T wash buffer. Plates were processed for analysis by the addition of 150 μL/well MSD Read 4× Buffer T with surfactant (catalog no. R92TC-2; diluted 1:3 in deionized water) and were read on the SECTOR Imager 6000.

Tankyrase 1 and 2 Assays

The tankyrase 1 biochemical activity of the compounds was assayed in the following assay buffer (50 mM MOPS pH7.5, 100 mM NaCl, 2.5 mM $MgCl_2$, 0.01% Tween-20, 0.05% BSA, and 1 mM DTT) as follows: 0.25 nM of 6×HIS-tankyrase1 (1091-1325) was incubated in the presence of compound (DMSO 1.85% final) in a Perkin Elmer 384 well Proxiplate Plus™ (cat.no. 6008289) with 400 nM of NAD for 60 minutes at RT. The assay was then stopped with the above assay buffer containing a 0.6 μM inhibitor and the following detection components: 0.05 μg/mL monoclonal anti-PAR antibody (Trevigen cat.no. 4335-MC-01K-AC) prebound for 60 minutes with 0.63 μg/mL protein G AlphaLisa® acceptor bead (Perkin Elmer cat.no. AL102M) and 5 μg/mL AlphaLisa® nickel chelate donor bead (Perkin Elmer cat.no. AS 101M). The assay was incubated for 16 hours at RT in the dark and read on a Perkin Elmer Envision® multi label reader using the default program set with laser excitation at 680 nM and emission at 615 nM.

The tankyrase 2 biochemical assay was performed using the procedure set forth above with respect to tankyrase 1 except that 4 nM 6×HIS-tankyrase 2 (946-1162) and 250 nM NAD were used.

PARP 1 and 2 Assays

PARP1 biochemical assay was purchased as a kit from Trevigen (cat.#4676-096-K) and used per manufacturers recommendations.

PARP2 biochemical assay was purchased as a kit from BPS (cat.#80552) and used per manufacturers recommendations.

DLD-1-STF Assay. Constitutively Activated Wnt Pathway Assay in Mutant APC Cancer Cell Context DLD-1 colorectal cells engineered with an 8×TCF promoter-driven Firefly (FF) luciferase gene (Wnt reporter) along with an EF1a promoter-driven Renilla (RN) luciferase gene (control reporter) were used to measure the potency of tankyrase compounds in the context of the constitutively activated Wnt pathway due to mutated APC in colorectal cancer cells. The engineered DLD-1 cells were plated (45 µL) at a density of 10,000 cells/well in black, clear-bottom, 96-well View plates (PerkinElmer) in normal growth medium (RPMI with 10% FBS with no antibiotics). Tankyrase inhibitors (5 µL) were transferred to cells from a three-fold serially diluted compound plate. A 10-point dilution series was tested starting at a concentration (10 µM final concentration in assay). Column 6 contained only DMSO and served as the "HI" control. A potent Tankyrase inhibitor was used at a final concentration of 10 uM in column 12 which served as the "LO" control. The plates were incubated at 37° C. for 40 to 48 hours. The Dual-Glo Reagents (Promega) were added as directed by manufacturer to assay the FF and RN luciferase activity. Luciferase activity was measures using the EnVision multilabel plate reader (PerkinElmer).

The following tables includes biological activity data obtained using the procedures and assays set forth above for the Example compounds described herein.

TABLE 2

Biological Activity Information for Example Compounds in TNKS1, TNKS 2, SW480-TBC, Axin2 384 IF, DLD1-STF FF/RL, PARP1 and PARP2 Assays.

| Example | TNKS1 IC50 (µM) | TNKS2 IC50 (µM) | SW480-Total beta-catenin (TBC) IC50 IP (µM) | Axin2 384 IF EC50 (µM) | DLD1-STF-FF/RL*100 IC50 (µM) | PARP1- IC50 (µM) | PARP2 IC50 (µM) |
|---|---|---|---|---|---|---|---|
| 1 | 0.0666 | 0.0225 | 0.142 | 1.39 | ***** | Undefined | 3.22 |
| 2 | 0.0581 | 0.014 | 0.0797 | 0.642 | ***** | 2.7 | 0.982 |
| 3 | 0.011 | 0.00254 | 0.0417 | 0.26 | ***** | 3.05 | 0.414 |
| 4 | 0.011 | 0.00206 | 0.0364 | 0.21 | ***** | 2.41 | 0.961 |
| 5 | 0.0318 | 0.00484 | 0.0922 | 0.771 | ***** | 3.76 | 2.35 |
| 6 | 0.0188 | 0.00259 | 0.0639 | 0.247 | ***** | 5.41 | 0.783 |
| 7 | 0.00694 | 0.00338 | 0.626 | 0.651 | ***** | 1.93 | 0.192 |
| 8 | 0.00231 | 0.000475 | 0.0454 | 0.0818 | ***** | 1.78 | 0.16 |
| 9 | 0.168 | 0.0185 | 0.0566 | 1.23 | ***** | 2.86 | 0.471 |
| 10 | 0.00152 | 0.000461 | 0.0167 | 0.0739 | ***** | Undefined | 0.461 |
| 11 | 0.00276 | 0.0016 | 0.157 | 0.247 | ***** | 0.867 | 0.103 |
| 12 | 0.0897 | 0.0159 | 1.84 | 1.22 | ***** | 6.29 | 1.92 |
| 13 | 0.0428 | 0.00654 | 0.358 | 0.461 | ***** | 7.09 | 1.24 |
| 14 | 0.0797 | 0.0155 | 0.837 | 1.25 | ***** | 8.54 | 2.18 |
| 15 | 0.015 | 0.00335 | 0.0869 | 0.126 | ***** | 3.17 | 1.2 |
| 16 | 0.107 | 0.0179 | 1.19 | 1.9 | ***** | 5.07 | 0.56 |
| 17 | 0.646 | 0.152 | 2.19 | 6.39 | ***** | 3.79 | 0.916 |
| 18 | 0.0544 | 0.0209 | 0.76 | 0.732 | ***** | 4.47 | 1.12 |
| 19 | 0.015 | 0.00486 | 0.248 | 0.291 | ***** | 4.92 | 1.12 |
| 20 | 0.0113 | 0.00319 | 0.151 | 0.166 | ***** | 2.85 | 0.37 |
| 21 | 0.0171 | 0.00489 | 0.154 | 0.242 | ***** | 2.03 | 1.45 |
| 22 | 0.0194 | 0.00413 | 0.217 | 0.333 | ***** | 3.13 | 1.59 |
| 23 | 0.656 | 0.00631 | 0.152 | 0.601 | ***** | 3.3 | 0.455 |
| 24 | 0.0188 | 0.00495 | 0.226 | 0.257 | ***** | 1.69 | 1.11 |
| 25 | 0.00961 | 0.00391 | 0.224 | 0.24 | ***** | 2.3 | 1.36 |
| 26 | 0.00507 | 0.00151 | 0.361 | 1.41 | ***** | 4.93 | 0.397 |
| 27 | 0.00134 | 0.000478 | 0.0637 | 0.114 | ***** | 0.887 | 0.0997 |
| 28 | 0.000531 | 0.000303 | 0.0159 | 0.0185 | ***** | Undefined | 1.76 |
| 29 | 0.000549 | 0.00043 | 0.0149 | 0.0302 | ***** | 1.67 | 0.889 |
| 30 | 0.000567 | 0.000191 | 0.0106 | 0.0139 | ***** | 1.06 | 1.27 |
| 31 | 0.000469 | 0.000237 | 0.0248 | 0.0309 | ***** | 1.05 | 1.15 |
| 32 | 0.000495 | 0.000301 | 0.0157 | 0.0325 | ***** | 0.801 | 0.828 |
| 33 | 0.000453 | 0.000341 | 0.0348 | 0.0257 | ***** | 2.84 | 1.14 |
| 34 | 0.00197 | 0.000981 | 0.101 | 0.0969 | ***** | 0.629 | 0.431 |
| 35 | 0.000277 | 0.000196 | 0.0197 | 0.0108 | ***** | Undefined | 0.923 |
| 36 | 0.000367 | 0.00027 | 0.0299 | 0.022 | ***** | 1.14 | 0.701 |
| 37 | 0.0037 | 0.00348 | 0.738 | ***** | ***** | >85.0 | >170.0 |
| 38 | 0.901 | 0.489 | 1.43 | 8.19 | ***** | >85.0 | Undefined |
| 39 | 0.000405 | 0.000389 | ***** | ***** | ***** | Undefined | 1.9 |
| 40 | 0.0000891 | ***** | ***** | ***** | ***** | Undefined | 3.97 |
| 41 | 0.00805 | 0.00491 | 1.71 | 3.38 | ***** | 1.49 | 0.5 |
| 42 | 0.0282 | 0.00826 | 0.132 | 0.843 | ***** | 7.47 | 0.825 |
| 43 | 0.0335 | 0.0166 | 1.91 | 3.88 | ***** | 6.42 | 1.06 |
| 44 | 0.00897 | 0.00353 | 0.681 | 2.93 | ***** | 7.61 | 0.363 |
| 45 | 0.0737 | 0.0525 | 2.34 | 4.63 | ***** | Undefined | 1.02 |
| 46 | 0.0177 | 0.00401 | 1.36 | 4.78 | ***** | 2.05 | |
| 47 | 0.00397 | 0.00118 | 0.233 | 1.27 | ***** | 2.44 | 1.59 |
| 48 | 0.00515 | 0.000596 | 0.111 | 0.417 | ***** | 1.98 | 1.35 |
| 49 | 0.118 | ***** | 0.53 | 5.33 | ***** | ***** | ***** |

TABLE 2-continued

Biological Activity Information for Example Compounds in TNKS1, TNKS 2, SW480-TBC, Axin2 384 IF, DLD1-STF FF/RL, PARP1 and PARP2 Assays.

| Example | TNKS1 IC50 (µM) | TNKS2 IC50 (µM) | SW480-Total beta-catenin (TBC) IC50 IP (µM) | Axin2 384 IF EC50 (µM) | DLD1-STF-FF/RL*100 IC50 (µM) | PARP1-IC50 (µM) | PARP2 IC50 (µM) |
|---|---|---|---|---|---|---|---|
| 50 | 0.00649 | 0.00181 | 0.256 | 1.55 | ***** | 10.7 | 0.748 |
| 51 | 0.00409 | 0.000517 | 0.348 | 0.661 | ***** | 0.894 | 0.553 |
| 52 | 0.0013 | 0.000193 | 0.0252 | 0.0947 | ***** | 3.83 | 1.02 |
| 53 | 0.00317 | 0.000593 | 0.0503 | 0.359 | ***** | 2.57 | 0.998 |
| 54 | 0.0391 | 0.017 | 1.12 | 3.63 | ***** | 3.2 | 0.673 |
| 55 | 0.00176 | 0.000401 | 0.0465 | 0.193 | ***** | 1.8 | 0.284 |
| 56 | 0.00251 | 0.000719 | 0.0736 | 0.266 | ***** | 5.82 | 1.1 |
| 57 | 0.0312 | 0.0125 | 0.51 | 1.71 | ***** | 5.96 | 0.905 |
| 58 | 0.00326 | 0.00125 | 0.0989 | 0.354 | ***** | 1.58 | 0.983 |
| 59 | 0.0118 | 0.00239 | 0.208 | 0.951 | ***** | 1.9 | 0.371 |
| 60 | 0.046 | 0.0289 | Undefined [2] | 2.41 | ***** | 4.53 | |
| 61 | 0.000873 | 0.000206 | 0.302 | 0.217 | ***** | 0.464 | 0.349 |
| 62 | 0.587 | 0.138 | >10.0 | Undefined | ***** | 7.68 | 2.84 |
| 63 | 0.00233 | 0.000653 | 0.211 | 0.27 | ***** | 0.586 | 0.802 |
| 64 | 0.00105 | 0.00052 | 0.0266 | 0.0609 | 0.00126 | 0.257 | 0.288 |
| 65 | 1.6 | 0.318 | >10.0 | Undefined | ***** | 1.29 | 0.893 |
| 66 | 0.00311 | 0.00102 | 0.614 | 0.628 | ***** | 1.39 | 0.998 |
| 67 | 0.00393 | 0.00168 | 0.98 | 0.552 | ***** | 1.28 | 0.681 |
| 68 | 0.000783 | 0.000292 | 0.161 | 0.239 | ***** | 0.636 | 0.227 |
| 69 | 0.407 | 0.451 | 2.56 | 0.686 | ***** | 1.76 | 0.317 |
| 70 | 0.0051 | 0.000826 | 0.252 | 0.191 | ***** | 0.723 | 1.81 |
| 71 | 0.0726 | 0.06 | 3.44 | 4.17 | ***** | 0.992 | 0.333 |
| 72 | 0.00672 | 0.00424 | 1.13 | 0.63 | ***** | 5.57 | 1.44 |
| 73 | 0.000186 | ***** | 0.021 | 0.0296 | ***** | ***** | ***** |
| 74 | 0.000161 | ***** | 0.00662 | 0.00534 | 0.00159 | ***** | ***** |
| 75 | 0.00475 | 0.00275 | 0.623 | 0.383 | ***** | 2.26 | 1.37 |
| 76 | 0.0658 | 4.98 | 3.02 | 2.95 | ***** | 7.35 | 0.251 |
| 77 | 0.00437 | 0.000601 | 0.119 | 0.601 | ***** | 1.71 | 1.82 |
| 78 | 0.00223 | 0.000434 | 0.00714 | 0.0492 | ***** | 0.558 | 0.246 |
| 79 | 0.00285 | 0.000614 | 0.0423 | 0.192 | ***** | 2.55 | 0.292 |
| 80 | 0.00315 | 0.000626 | 0.0423 | 0.225 | ***** | 2.26 | 3.08 |
| 81 | 0.798 | 0.099 | 1.95 | 8.75 | ***** | Undefined | 8.45 |
| 82 | 0.128 | 0.0737 | 3.31 | Undefined [2] | ***** | 1.47 | 0.0994 |
| 83 | 0.0314 | 0.0125 | 0.726 | 2.68 | ***** | 1.51 | 0.345 |
| 84 | 0.00144 | 0.000671 | 0.433 | 1.78 | ***** | Undefined [2] | 1.03 |
| 85 | 0.000524 | 0.000227 | 0.0141 | 0.0597 | ***** | >85.0 | 0.47 |
| 86 | 0.00101 | 0.000347 | 0.0326 | 0.207 | ***** | Undefined | 0.279 |
| 87 | 0.0000597 | 0.00252 | 0.00727 | 0.0258 | ***** | >85.0 | Undefined |
| 88 | 0.0371 | 0.0141 | 1.02 | Undefined [2] | ***** | 3.5 | 0.53 |
| 89 | 0.0166 | 0.00633 | 1.71 | 2.33 | ***** | 1.39 | 0.35 |
| 90 | 0.000127 | 0.000796 | 0.00784 | 0.00342 | ***** | Undefined | 0.72 |
| 91 | 0.00397 | 0.00878 | 1.68 | 1.02 | ***** | >85.0 | >170.0 |
| 92 | 0.0158 | 0.00444 | 0.145 | 0.287 | ***** | 2.27 | 2.42 |
| 93 | 0.0952 | 0.0851 | 1.2 | 1.23 | ***** | 8.29 | >170.0 |
| 94 | 0.0121 | 0.0063 | 2.22 | Undefined | ***** | 1.23 | 0.0895 |
| 95 | 0.0000979 | 0.00016 | 0.00483 | ***** | ***** | 1.93 | 1.07 |
| 96 | 0.0159 | 0.00359 | 0.0912 | 0.536 | ***** | 28.8 | 1.57 |
| 97 | 0.000109 | 0.0041 | 0.00369 | 0.00388 | 0.000608 | Undefined | 2.45 |
| 98 | 0.161 | 0.199 | 2.73 | 3.99 | ***** | 3.46 | 0.806 |
| 99 | 0.00687 | 0.00238 | 2.42 | 2.16 | ***** | Undefined | Undefined |
| 100 | 0.000237 | 0.000362 | 0.0167 | 0.0227 | ***** | Undefined | 4.95 |
| 101 | 0.0499 | 0.0152 | 0.252 | 0.783 | ***** | 0.936 | 0.421 |
| 102 | 0.000118 | 0.000458 | 0.0554 | 0.0381 | ***** | >85.0 | 1.65 |
| 103 | 0.000129 | 0.00992 | 0.138 | 0.198 | ***** | Undefined | 2.28 |
| 104 | 0.000045 | 0.00131 | 0.00842 | 0.00945 | ***** | 1.35 | 1.18 |
| 105 | 0.000145 | 0.0000982 | 0.02 | 0.0359 | ***** | >85.0 | Undefined |
| 106 | 0.0000973 | 0.00757 | 0.0019 | 0.00401 | 0.000275 | Undefined | 1.76 |
| 107 | 0.000176 | 0.0000882 | 0.0154 | 0.0166 | 0.00133 | >85.0 | 3.35 |
| 108 | 0.000153 | 0.00624 | 0.0069 | 0.00679 | 0.000682 | 2.76 | 3.22 |
| 109 | 0.000206 | 0.000302 | 0.0478 | 0.0509 | Undefined | >85.0 | >170.0 |
| 110 | 0.00105 | 0.000533 | 0.104 | 0.132 | 0.00178 | 0.376 | 1.44 |
| 111 | 0.0884 | 0.0295 | >10.0 [2] | 2.95 | ***** | 7.63 | 4.67 |
| 112 | 0.000224 | 0.000264 | 0.12 | 0.105 | >0.05 | >85.0 | Undefined |
| 113 | 0.000323 | 0.000294 | 0.0242 | 0.056 | >0.05 | >85.0 | Undefined |
| 114 | 0.000176 | 0.000431 | 0.00808 | 0.00842 | 0.00108 | >85.0 | Undefined |
| 115 | 0.000187 | 0.00251 | 0.011 | 0.0144 | 0.0013 | 3.86 | 1.12 |
| 116 | 0.000167 | 0.00313 | 0.00379 | 0.0107 | ***** | 2.5 | 0.319 |

TABLE 2-continued

Biological Activity Information for Example Compounds in TNKS1, TNKS 2, SW480-TBC, Axin2 384 IF, DLD1-STF FF/RL, PARP1 and PARP2 Assays.

| Example | TNKS1 IC50 (µM) | TNKS2 IC50 (µM) | SW480- Total beta- catenin (TBC) IC50 IP (µM) | Axin2 384 IF EC50 (µM) | DLD1- STF-FF/ RL*100 IC50 (µM) | PARP1- IC50 (µM) | PARP2 IC50 (µM) |
|---|---|---|---|---|---|---|---|
| 117 | 0.000269 | 0.00398 | 0.00123 | 0.00278 | ***** | ***** | ***** |
| 118 | 0.000107 | 0.00498 | 0.0012 | 0.00334 | ***** | Undefined | 3.28 |
| 119 | 0.000194 | 0.00334 | 0.003 | 0.00572 | ***** | ***** | ***** |
| 120 | 0.0000647 | 0.00535 | 0.00203 | 0.00233 | ***** | Undefined | 3.73 |
| 121 | 0.0000724 | 0.0181 | 0.0011 | 0.00198 | ***** | 4.43 | 6.78 |
| 122 | 0.000153 | 0.00138 | 0.00304 | 0.00447 | ***** | >9.440001 | 7.69 |
| 123 | 0.0312 | 0.0347 | 2.13 | 3.33 | ***** | >85.0 | >170.0 |
| 124 | 0.000287 | 0.00311 | 0.00192 | 0.000666 | ***** | 10.2 | 3.02 |
| 125 | 0.00152 | 0.000179 | 0.00193 | 0.00168 | ***** | Undefined | Undefined |
| 126 | 0.201 | 0.137 | 1.02 | 2.72 | ***** | 5.1 | 1.07 |
| 127 | 0.0262 | 0.0127 | 0.157 | 0.307 | ***** | 1.97 | 2.31 |
| 128 | 0.168 | 0.0813 | 0.592 | 1.75 | ***** | 3.89 | 0.276 |
| 129 | 0.0386 | 0.0128 | 0.124 | 0.435 | ***** | 1.09 | 1.96 |
| 130 | 0.0173 | 0.00792 | 0.11 | 0.24 | ***** | 0.998 | 0.944 |
| 131 | 0.46 | 0.187 | 1.77 | 12.1 | ***** | 5.65 | 0.537 |
| 132 | 0.016 | 0.017 | 0.488 | ***** | ***** | 2.45 | 2.64 |
| 133 | 0.178 | Undefined | >10.0 | ***** | ***** | 4.62 | 1.87 |
| 134 | 0.021 | 0.0142 | 0.253 | ***** | ***** | Undefined | 2.11 |
| 135 | 1.33 | Undefined | >10.0 | ***** | ***** | Undefined | Undefined |
| 136 | 0.098 | 0.0327 | 0.96 | 1.19 | ***** | 10.8 | 1.06 |
| 137 | 0.217 | 0.0998 | 0.741 | 1.82 | ***** | Undefined | 4.68 |
| 138 | 1.9 | 0.282 | Undefined | >25.0 | ***** | 5.45 | 2.61 |
| 139 | 1.59 | 0.624 | Undefined [2] | >25.0 | ***** | 8.22 | 1.13 |
| 140 | 1.21 | ***** | ***** | ***** | ***** | 7.45 | 1.29 |
| 141 | 0.00713 | 0.00592 | 0.118 | 0.228 | ***** | Undefined | 0.677 |
| 142 | 0.258 | 0.203 | Undefined | 6.49 | ***** | 5.47 | 1.7 |
| 143 | 0.0179 | 0.0523 | 0.929 | 0.97 | ***** | Undefined [2] | Undefined |
| 144 | 0.00478 | 0.00546 | 0.349 | ***** | ***** | >85.0 | >170.0 |
| 145 | 0.000148 | 0.00502 | 0.00766 | ***** | ***** | 3.54 | 1.12 |

All publications and patent applications cited in this specification are hereby incorporated by reference herein in their entireties and for all purposes as if each individual publication or patent application were specifically and individually indicated as being incorporated by reference and as if each reference was fully set forth in its entirety. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. A compound of Formula I:

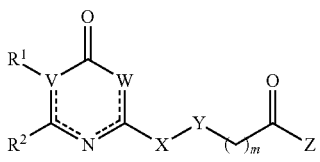

I or a pharmaceutically acceptable salt thereof, a tautomer thereof, a pharmaceutically acceptable salt of the tautomer, a stereoisomer of any of the foregoing, or a mixture thereof, wherein:

$R^1$ is selected from —H, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —($C_1$-$C_6$ alkyl)-S—($C_1$-$C_6$ alkyl), —($C_1$-$C_6$ alkyl)-NH—($C_1$-$C_6$ alkyl), or ($C_1$-$C_6$ alkyl)-$NH_2$, or $R^1$ may additionally be selected from —O—($C_1$-$C_6$ alkyl), —NH—($C_1$-$C_6$ alkyl), or —N($C_1$-$C_6$ alkyl)$_2$;

$R^2$ is selected from —H, —$NH_2$, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —($C_1$-$C_6$ alkyl)-S—($C_1$-$C_6$ alkyl), —($C_1$-$C_6$ alkyl)-NH—($C_1$-$C_6$ alkyl), or —($C_1$-$C_6$ alkyl)-$NH_2$;

or $R^1$ and $R^2$, together with the atoms to which they are attached, join to form a 6 membered ring comprising 0, 1, or 2 heteroatoms selected from N, O, or S; wherein the 6-membered ring is optionally substituted with one or two substituents selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), or —$NH_2$;

V is C;

W is CH or NH;

X is $CH_2$, S, or $SO_2$;

Y is $CH_2$ or S;

one or two of X and Y are $CH_2$;

m is 0, 1, or 2;

Z is a group of formula II or formula III

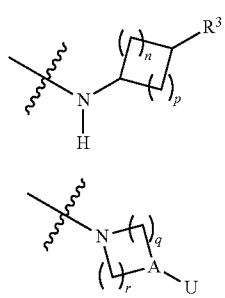

wherein

R³ is selected from —O—R⁴ᵃ, —O—CH₂—R⁴ᵃ or —R⁴ᵃ;

R⁴ᵃ is selected from a $C_6$-$C_{10}$ aryl group, a heteroaryl group with 5 to 10 ring members containing 1, 2, or 3 heteroatoms independently selected from N, O, or S, or a heterocyclyl group with 5 to 10 ring members containing 1, 2, 3, or 4 heteroatoms independently selected from N, O, or S, or a —CH₂-phenyl group, wherein the $C_6$-$C_{10}$ aryl group, the heteroaryl group, or the heterocyclyl group are unsubstituted or are substituted with 1, 2, or 3 substituents independently selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —R⁴ᵇ, —OCH₂—R⁴ᵇ, —CH₂O—R⁴ᵇ, or —($C_1$-$C_4$ alkylene)-R⁴ᵇ, and the heterocyclyl group may be further substituted with 1 oxo substituent;

R⁴ᵇ is selected from $C_6$-$C_{10}$ aryl group, a $C_3$-$C_8$ cycloalkyl group, a heteroaryl group with 5 to 10 ring members containing 1, 2, or 3 heteroatoms independently selected from N, O, or S, or a heterocyclyl group with 5 to 10 ring members containing 1, 2, 3, or 4 heteroatoms independently selected from N, O, or S, wherein the $C_6$-$C_{10}$ aryl group, the $C_3$-$C_8$ cycloalkyl group, the heteroaryl group, and the heterocyclyl group are unsubstituted or are substituted with 1, 2, or 3 substituents independently selected from —F, —Cl, —Br, —I, —CN, —$C_1$-$C_6$ alkyl, —$C_1$-$C_6$ haloalkyl, —$C_1$-$C_6$ perhaloalkyl, —OH, or —O—($C_1$-$C_6$ alkyl, and the heterocyclyl group or cycloalkyl group may be further substituted with 1 oxo substituent n is 0, 1, 2, or 3;

p is 1, 2, or 3;

q is 1 or 2;

r is 1, 2, or 3;

A is CH or N;

wherein when Z is a group of formula III, R¹ and R², together with the atoms to which they are attached, join to form a 6-membered ring;

wherein the ring that includes the A variable in the group of formula III may include 0 or 1 double bond and A is C if the bond between an adjacent ring member and A is a double bond;

U is a heterocyclic or heteroaromatic group selected from

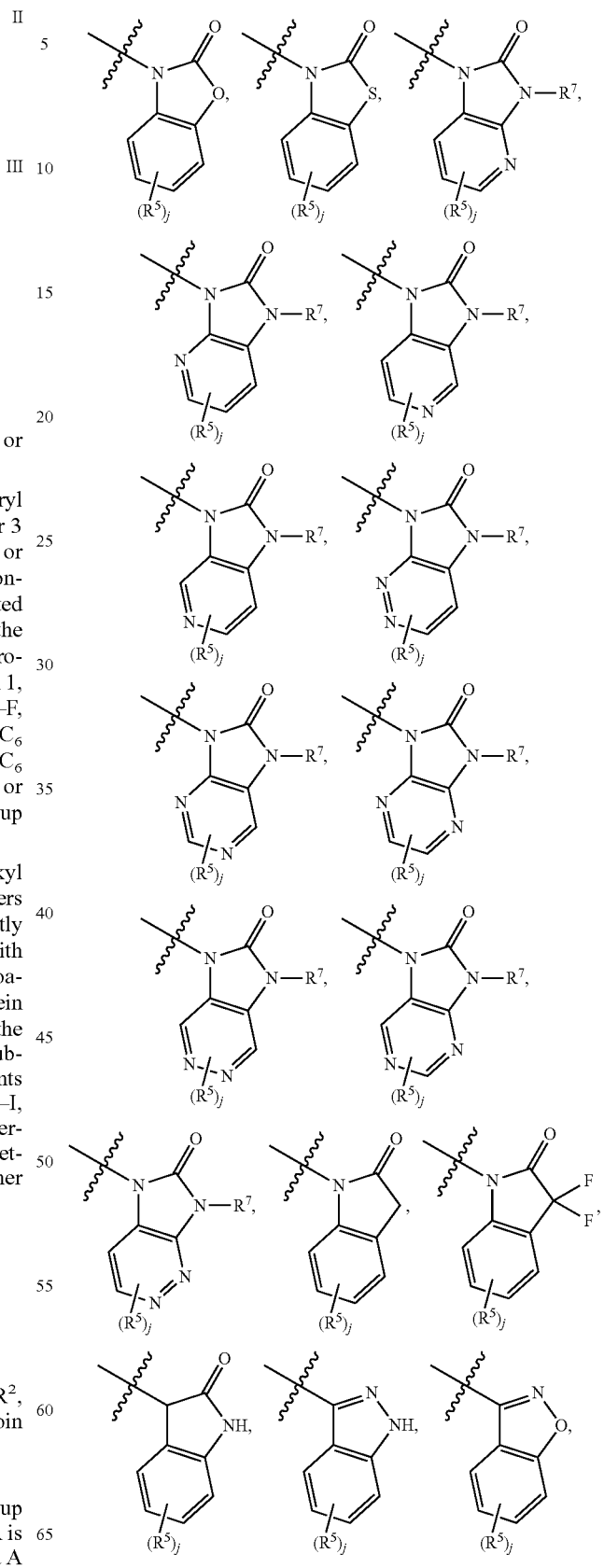

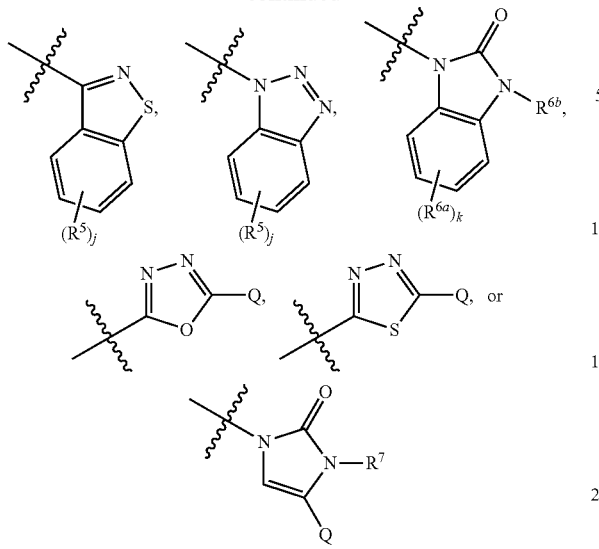

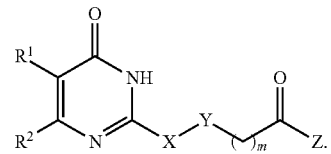

IA $R^5$ and $R^{6a}$ are independently in each instance selected from —F, —Cl, —Br, —I, —CN, —$C_1$-$C_6$ alkyl, —$C_1$-$C_6$ haloalkyl, —$C_1$-$C_6$ perhaloalkyl, —OH, or —O—($C_1$-$C_6$ alkyl);

$R^{6b}$ and $R^7$ are selected from —H and —$C_1$-$C_6$ alkyl;

j is 0, 1, or 2;

k is 0, 1, or 2 and is 1 or 2 if X and Y are both carbon and m is 0; and

Q is selected from Q' or —$CH_2$O-Q'; and

Q' is selected from $C_6$-$C_{10}$ aryl group or a heteroaryl group with 5 to 10 ring members containing 1, 2, or 3 heteroatoms independently selected from N, O, or S, wherein the $C_6$-$C_{10}$ aryl group and the heteroaryl group are unsubstituted or are substituted with 1, 2, or 3 substituents independently selected from —F, —Cl, —Br, —I, —CN, —$C_1$-$C_6$ alkyl, —$C_1$-$C_6$ haloalkyl, —$C_1$-$C_6$ perhaloalkyl, —OH, or —O—($C_1$-$C_6$ alkyl);

wherein the symbol ∼∼∼, when drawn across a bond, indicates the point of attachment to the rest of the molecule.

2. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^1$ is selected from —H, —$C_1$-$C_6$ alkyl, —$C_1$-$C_6$ haloalkyl, —$C_1$-$C_6$ perhaloalkyl, —($C_1$-$C_6$ alkyl)-O-($C_1$-$C_6$ alkyl), —($C_1$-$C_6$ alkyl)-S—($C_1$-$C_6$ alkyl), —($C_1$-$C_6$ alkyl)-NH—($C_1$-$C_6$ alkyl), or —($C_1$-$C_6$ alkyl)-$NH_2$, or $R^1$ may additionally be selected from —O—($C_1$-$C_6$ alkyl), —NH—($C_1$-$C_6$ alkyl), or —N($C_1$-$C_6$ alkyl)$_2$; and $R^2$ is selected from —H, —$CH_3$, or —$NH_2$.

3. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^1$ is —H.

4. The compound of claim 1 or the pharmaceutically acceptable salt thereof, the tautomer thereof, the pharmaceutically acceptable salt of the tautomer, the stereoisomer of any of the foregoing, or the mixture thereof, wherein the compound of formula I, has the formula IA 5. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^1$ and $R^2$, together with the atoms to which they are attached, join to form a 6 membered ring comprising 0 or 1 heteroatoms selected from N, O, or S; wherein the 6-membered ring is optionally substituted with one or two substituents selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), or —$NH_2$.

6. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^1$ and $R^2$, together with the atoms to which they are attached, join to form a 6 membered ring comprising 0 heteroatoms, wherein the 6-membered ring is optionally substituted with one or two substituents selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), or —$NH_2$.

7. The compound of claim 1 or the pharmaceutically acceptable salt thereof, the tautomer thereof, the pharmaceutically acceptable salt of the tautomer, the stereoisomer of any of the foregoing, or the mixture thereof, wherein the compound of formula I, has the formula IB

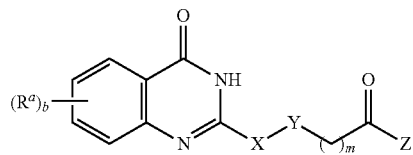

IB wherein b is 0, 1, or 2; and $R^a$ is independently selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), or —$NH_2$.

8. The compound of claim 1 or the pharmaceutically acceptable salt thereof, the tautomer thereof, the pharmaceutically acceptable salt of the tautomer, the stereoisomer of any of the foregoing, or the mixture thereof, wherein the compound of formula I, has the formula IC

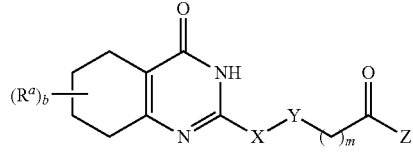

IC wherein b is 0, 1, or 2; and
R$^a$ is independently selected from —F, —Cl, —Br, —I, —CN, —C$_1$-C$_6$ alkyl, —C$_1$-C$_6$ haloalkyl, —C$_1$-C$_6$ perhaloalkyl, —OH, —O—(C$_1$-C$_6$ alkyl), or —NH$_2$.

9. The compound of claim 7 or the pharmaceutically acceptable salt thereof, the tautomer thereof, the pharmaceutically acceptable salt of the tautomer, the stereoisomer of any of the foregoing, or the mixture thereof, wherein b is 0, or b is 1 and R$^a$ is —F.

10. The compound of claim 1 or the pharmaceutically acceptable salt thereof, the tautomer thereof, the pharmaceutically acceptable salt of the tautomer, the stereoisomer of any of the foregoing, or the mixture thereof, wherein W is NH.

11. The compound of claim 1 or the pharmaceutically acceptable salt thereof, the tautomer thereof, the pharmaceutically acceptable salt of the tautomer, the stereoisomer of any of the foregoing, or the mixture thereof, wherein X is S and Y is CH$_2$.

12. The compound of claim 1 or the pharmaceutically acceptable salt thereof, the tautomer thereof, the pharmaceutically acceptable salt of the tautomer, the stereoisomer of any of the foregoing, or the mixture thereof, wherein Y is S and X is CH$_2$.

13. The compound of claim 1 or the pharmaceutically acceptable salt thereof, the tautomer thereof, the pharmaceutically acceptable salt of the tautomer, the stereoisomer of any of the foregoing, or the mixture thereof, wherein X is CH$_2$ and Y is CH$_2$.

14. The compound of claim 1 or the pharmaceutically acceptable salt thereof, the tautomer thereof, the pharmaceutically acceptable salt of the tautomer, the stereoisomer of any of the foregoing, or the mixture thereof, wherein X is SO$_2$ and Y is CH$_2$.

15. The compound of claim 1 or the pharmaceutically acceptable salt thereof, the tautomer thereof, the pharmaceutically acceptable salt of the tautomer, the stereoisomer of any of the foregoing, or the mixture thereof, wherein m is 0.

16. The compound of claim 1 or the pharmaceutically acceptable salt thereof, the tautomer thereof, the pharmaceutically acceptable salt of the tautomer, the stereoisomer of any of the foregoing, or the mixture thereof, wherein m is 1.

17. The compound of claim 1 or the pharmaceutically acceptable salt thereof, the tautomer thereof, the pharmaceutically acceptable salt of the tautomer, the stereoisomer of any of the foregoing, or the mixture thereof, wherein m is 2.

18. The compound of claim 1 or the pharmaceutically acceptable salt thereof, the tautomer thereof, the pharmaceutically acceptable salt of the tautomer, the stereoisomer of any of the foregoing, or the mixture thereof, wherein Z is a group of formula II.

19. The compound of claim 18 or the pharmaceutically acceptable salt thereof, the tautomer thereof, the pharmaceutically acceptable salt of the tautomer, the stereoisomer of any of the foregoing, or the mixture thereof, wherein Z is

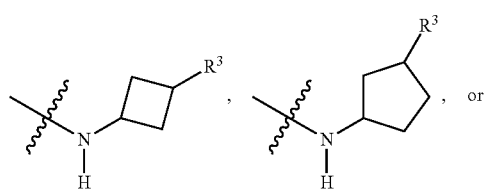, or

-continued

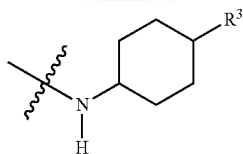

and the symbol ∿, when drawn across a bond, indicates the point of attachment to the rest of the molecule.

20. The compound of claim 1 or the pharmaceutically acceptable salt thereof, the tautomer thereof, the pharmaceutically acceptable salt of the tautomer, the stereoisomer of any of the foregoing, or the mixture thereof, wherein Z is

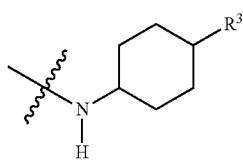

and the symbol ∿, when drawn across a bond, indicates the point of attachment to the rest of the molecule.

21. The compound of claim 20 or the pharmaceutically acceptable salt thereof, the tautomer thereof, the pharmaceutically acceptable salt of the tautomer or the mixture thereof, wherein Z is

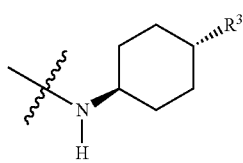

and the symbol ∿, when drawn across a bond, indicates the point of attachment to the rest of the molecule.

22. The compound of claim 20 or the pharmaceutically acceptable salt thereof, the tautomer thereof, the pharmaceutically acceptable salt of the tautomer, or the mixture thereof, wherein Z is

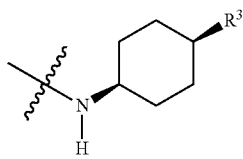

and the symbol ∿, when drawn across a bond, indicates the point of attachment to the rest of the molecule.

23. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^3$ is
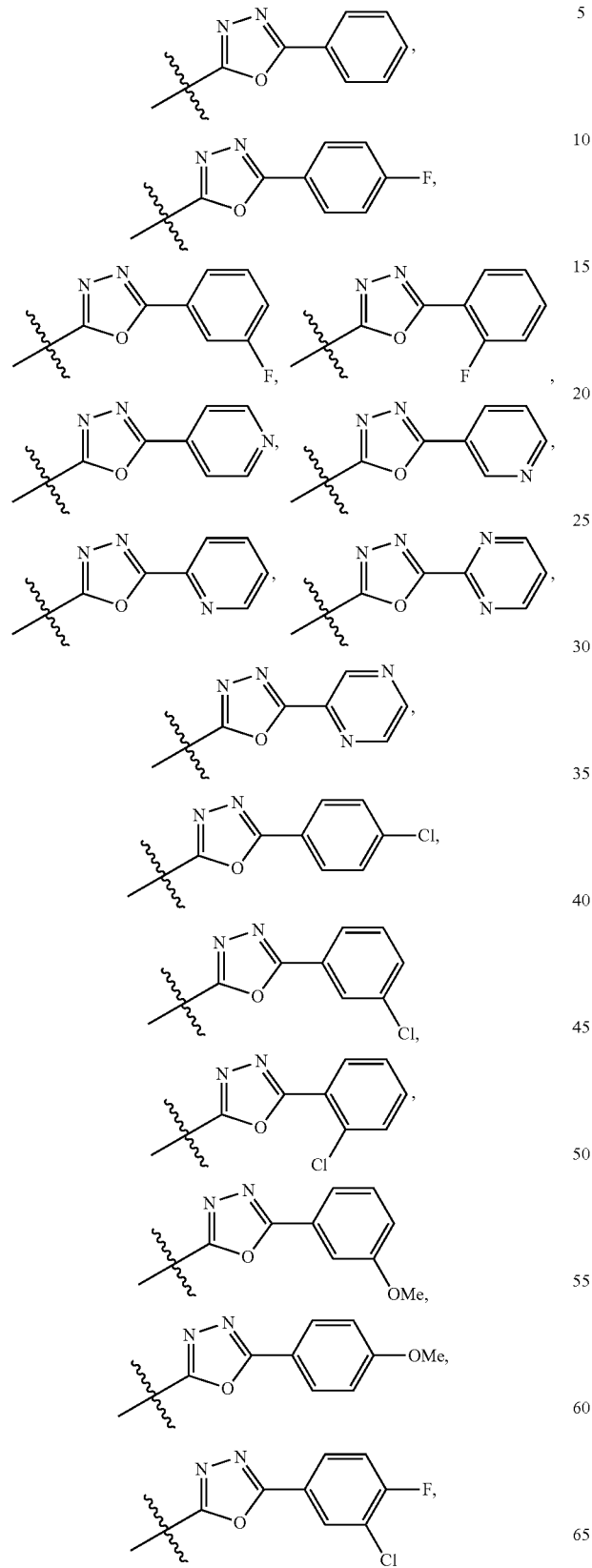
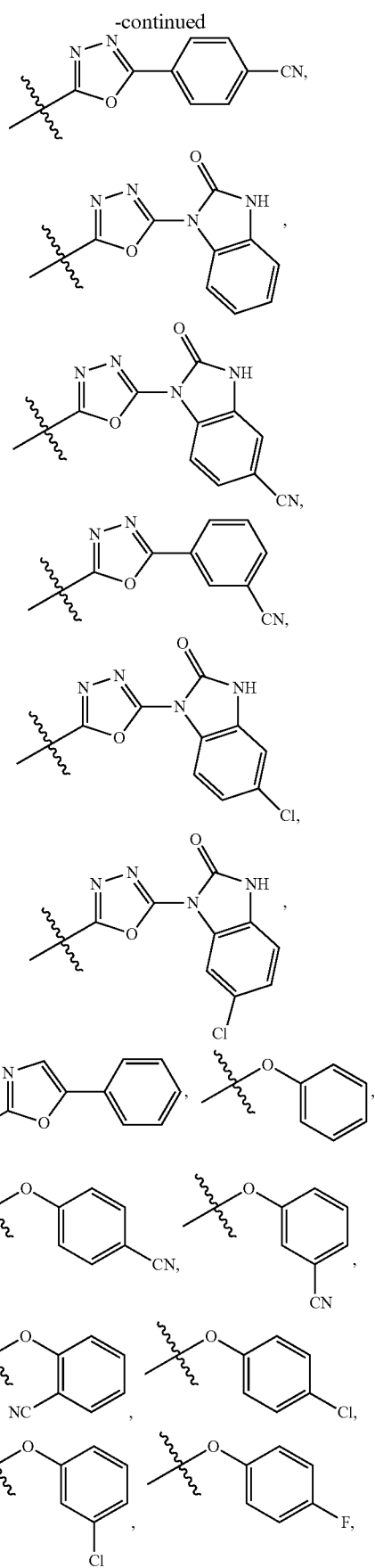

-continued

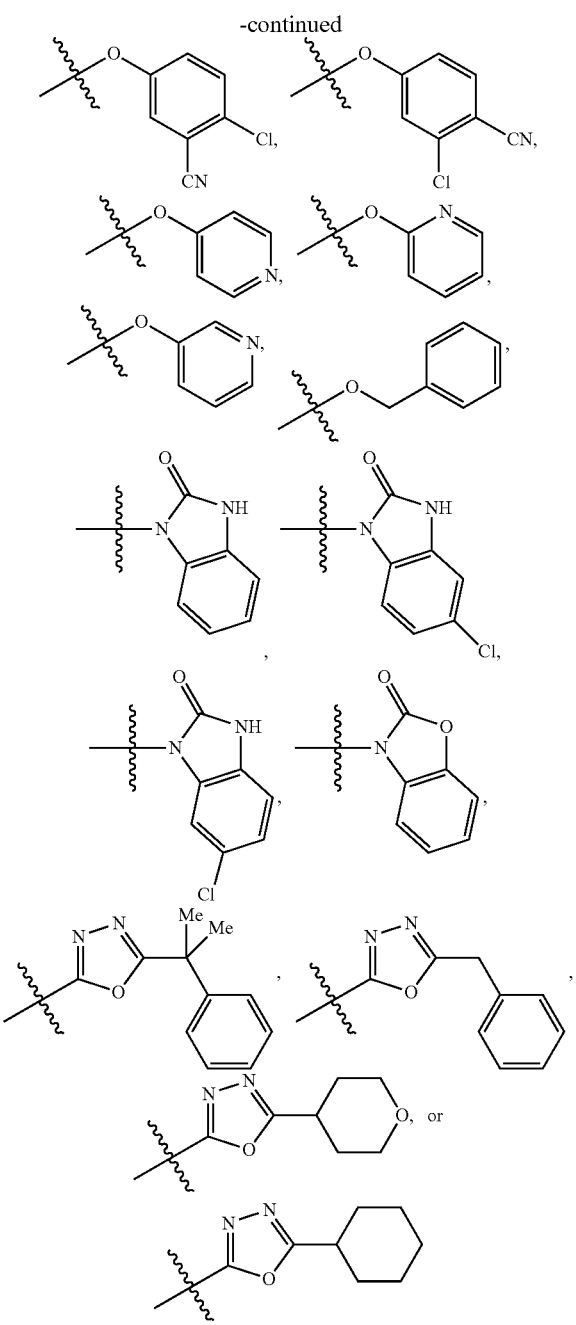

and the symbol ∽, when drawn across a bond, indicates the point of attachment to the rest of the molecule.

24. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^3$ is —O—$R^{4a}$ or —$R^{4a}$.

25. The compound of claim 24 or the pharmaceutically acceptable salt thereof, the tautomer thereof, the pharmaceutically acceptable salt of the tautomer, the stereoisomer of any of the foregoing, or the mixture thereof, wherein $R^3$ is —O—$R^{4a}$.

26. The compound of claim 24 or the pharmaceutically acceptable salt thereof, the tautomer thereof, the pharma-ceutically acceptable salt of the tautomer, the stereoisomer of any of the foregoing, or the mixture thereof, wherein $R^3$ is —$R^{4a}$.

27. The compound of claim 26 or the pharmaceutically acceptable salt thereof, the tautomer thereof, the pharmaceutically acceptable salt of the tautomer, the stereoisomer of any of the foregoing, or the mixture thereof, wherein —$R^{4a}$ is

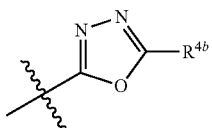

and the symbol ∽, when drawn across a bond, indicates the point of attachment to the rest of the molecule.

28. The compound of claim 27 or the pharmaceutically acceptable salt thereof, the tautomer thereof, the pharmaceutically acceptable salt of the tautomer, the stereoisomer of any of the foregoing, or the mixture thereof, wherein $R^{4b}$ is a $C_6$-$C_{10}$ aryl group or a heteroaryl group with 5 to 10 ring members containing 1, 2, or 3 heteroatoms independently selected from N, O, or S, and the $C_6$-$C_{10}$ aryl group and the heteroaryl group are unsubstituted or are substituted with 1, 2, or 3 substituents independently selected from —F, —Cl, —CN, —$C_1$-$C_6$ alkyl, —$C_1$-$C_6$ haloalkyl, —$C_1$-$C_6$ perhaloalkyl, or —O—($C_1$-$C_6$ alkyl).

29. The compound of claim 26 or the pharmaceutically acceptable salt thereof, the tautomer thereof, the pharmaceutically acceptable salt of the tautomer, the stereoisomer of any of the foregoing, or the mixture thereof, wherein —$R^{4a}$ is

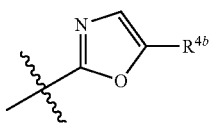

and the symbol ∽, when drawn across a bond, indicates the point of attachment to the rest of the molecule.

30. The compound of claim 26 or the pharmaceutically acceptable salt thereof, the tautomer thereof, the pharmaceutically acceptable salt of the tautomer, the stereoisomer of any of the foregoing, or the mixture thereof, wherein —$R^{4a}$ is

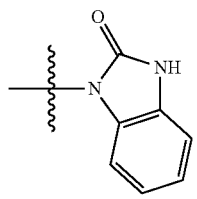 [SMILES: *n1c(=O)[nH]c2ccccc21]

and $R^{4a}$ is unsubstituted or is substituted with 1, 2, or 3 substituents independently selected from —F, —Cl, —CN, —$C_1$-$C_6$ alkyl, —$C_1$-$C_6$ haloalkyl, —$C_1$-$C_6$ perhaloalkyl, or —O—($C_1$-$C_6$ alkyl), and the symbol ∽, when drawn across a bond, indicates the point of attachment to the rest of the molecule.

31. The compound of claim 26 or the pharmaceutically acceptable salt thereof, the tautomer thereof, the pharmaceutically acceptable salt of the tautomer, the stereoisomer of any of the foregoing, or the mixture thereof, wherein —$R^{4a}$ is selected from a heteroaryl group with 5 to 10 ring members containing 1, 2, or 3 heteroatoms independently selected from N, O, or S, or a heterocyclyl group with 5 to 10 ring members containing 1, 2, 3, or 4 heteroatoms independently selected from N, O, or S, wherein the heteroaryl group or the heterocyclyl group are unsubstituted or are substituted with 1, 2, or 3 substituents independently selected from —F, —Cl, —Br, —I, —CN, —$C_1$-$C_6$ alkyl, —$C_1$-$C_6$ haloalkyl, —$C_1$-$C_6$ perhaloalkyl, —OH, —O—($C_1$-$C_6$ alkyl), or —$R^{4b}$, and the heterocyclyl group may additionally be substituted with 1 oxo substituent.

32. The compound of claim 31 or the pharmaceutically acceptable salt thereof, the tautomer thereof, the pharmaceutically acceptable salt of the tautomer, the stereoisomer of any of the foregoing, or the mixture thereof, wherein —$R^{4a}$ is a heteroaryl group with 5 ring members comprising 2 or 3 heteroatoms independently selected from N, O, or S, or —$R^{4a}$ is a heterocyclyl group with 9 ring members comprising 1, 2, or 3 heteroatoms independently selected from N, O, or S, wherein the heteroaryl group or the heterocyclyl group are unsubstituted or are substituted with 1, 2, or 3 substituents independently selected from —F, —Cl, —Br, —I, —CN, —$CH_3$, —$CF_3$, —OH, —O—$CH_3$, or —$R^{4b}$ and the heterocyclyl group may additionally be substituted with 1 oxo substituent.

33. The compound of claim 31 or the pharmaceutically acceptable salt thereof, the tautomer thereof, the pharmaceutically acceptable salt of the tautomer, the stereoisomer of any of the foregoing, or the mixture thereof, wherein —$R^{4a}$ is substituted with an $R^{4b}$ substituent and —$R^{4b}$ is selected from a phenyl, pyridyl, pyrazinyl, pyrimidinyl, or benzoimidazolonyl group, wherein the phenyl, pyridyl, pyrazinyl, pyrimidinyl, or benzoimidazolonyl group are unsubstituted or are substituted with 1, 2, or 3 substituents independently selected from —F, —Cl, —CN, —$CH_3$, —$CF_3$, or —O—$CH_3$.

34. The compound of claim 18 or the pharmaceutically acceptable salt thereof, the tautomer thereof, the pharmaceutically acceptable salt of the tautomer, the stereoisomer of any of the foregoing, or the mixture thereof, wherein n is 1 or 2.

35. The compound of claim 18, or the pharmaceutically acceptable salt thereof, the tautomer thereof, the pharmaceutically acceptable salt of the tautomer, the stereoisomer of any of the foregoing, or the mixture thereof, wherein p is 1 or 2.

36. The compound of claim 1 or the pharmaceutically acceptable salt thereof, the tautomer thereof, the pharmaceutically acceptable salt of the tautomer, the stereoisomer of any of the foregoing, or the mixture thereof, wherein Z is a group of formula III.

37. The compound of claim 36 or the pharmaceutically acceptable salt thereof, the tautomer thereof, the pharmaceutically acceptable salt of the tautomer, the stereoisomer of any of the foregoing, or the mixture thereof, wherein q is 1 or 2.

38. The compound of claim 36 or the pharmaceutically acceptable salt thereof, the tautomer thereof, the pharmaceutically acceptable salt of the tautomer, the stereoisomer of any of the foregoing, or the mixture thereof, wherein r is 1 or 2.

39. The compound of claim 36 or the pharmaceutically acceptable salt thereof, the tautomer thereof, the pharmaceutically acceptable salt of the tautomer, the stereoisomer of any of the foregoing, or the mixture thereof, wherein Z is

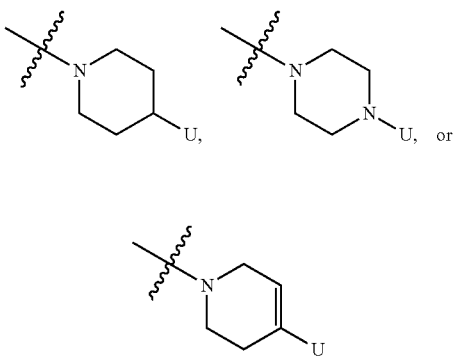

and the symbol ⌇, when drawn across a bond, indicates the point of attachment to the rest of the molecule.

40. The compound of claim 1 or the pharmaceutically acceptable salt thereof, the tautomer thereof, the pharmaceutically acceptable salt of the tautomer, the stereoisomer of any of the foregoing, or the mixture thereof, wherein U is selected from

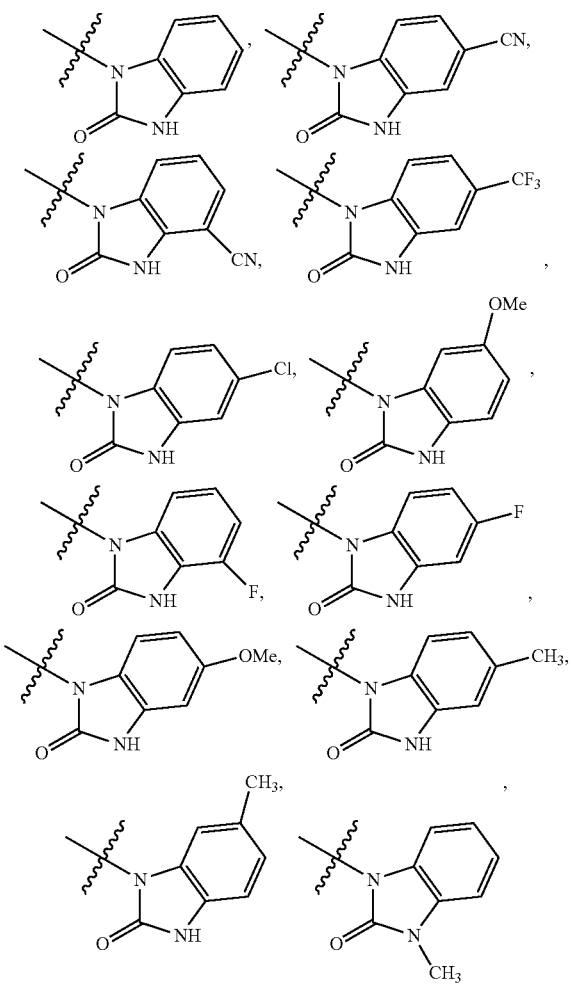

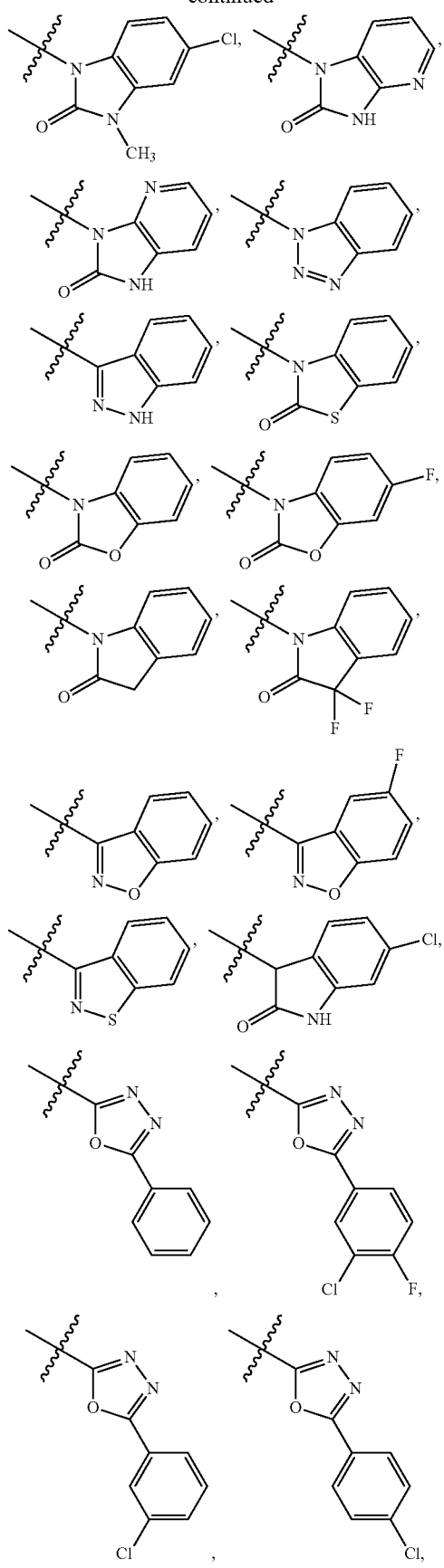
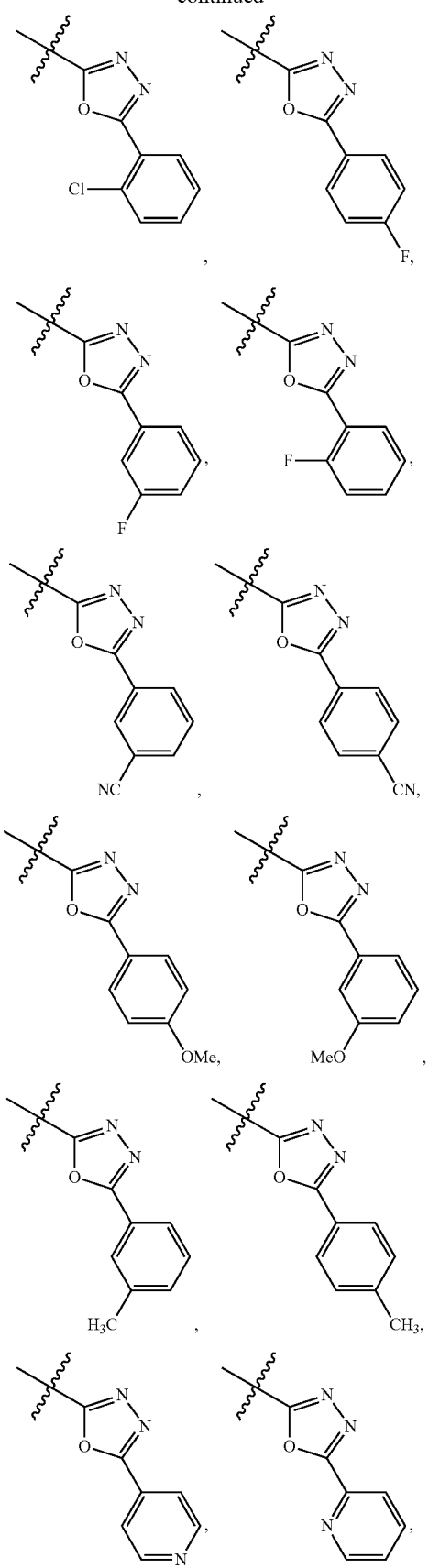

-continued

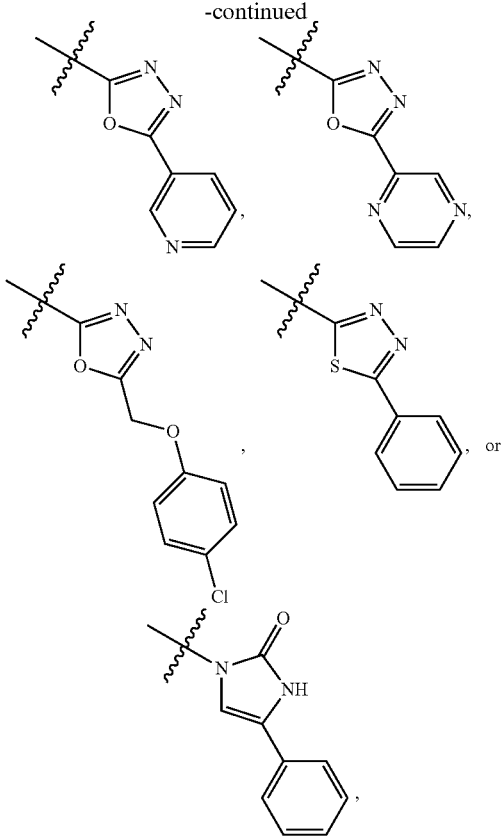

and the symbol ∿, when drawn across a bond, indicates the point of attachment to the rest of the molecule.

41. The compound of claim 1 or the pharmaceutically acceptable salt thereof, the tautomer thereof, the pharmaceutically acceptable salt of the tautomer, the stereoisomer of any of the foregoing, or the mixture thereof, wherein U is

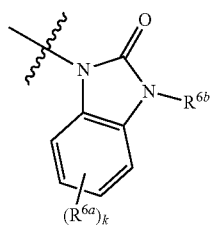

wherein
$R^{ha}$ is independently selected from —F, —Cl, —CN, —$C_1$-$C_6$ alkyl, —$C_1$-$C_6$ perhaloalkyl, or —O—($C_1$-$C_6$ alkyl);
k is 1 or 2;
$R^{6b}$ is —H; and
the symbol ∿, when drawn across a bond, indicates the point of attachment to the rest of the molecule.

42. The compound of claim 41 or the pharmaceutically acceptable salt thereof, the tautomer thereof, the pharmaceutically acceptable salt of the tautomer, the stereoisomer of any of the foregoing, or the mixture thereof, wherein $R^{6a}$ is —F, —Cl, —CN, —$CF_3$, —$CH_3$, or —O—$CH_3$.

43. The compound of claim 42 or the pharmaceutically acceptable salt thereof, the tautomer thereof, the pharmaceutically acceptable salt of the tautomer, the stereoisomer of any of the foregoing, or the mixture thereof, wherein $R^{6a}$ is —F, —Cl, —CN, —$CF_3$, or —O—$CH_3$.

44. The compound of claim 1 or the pharmaceutically acceptable salt thereof, the tautomer thereof, the pharmaceutically acceptable salt of the tautomer, the stereoisomer of any of the foregoing, or the mixture thereof wherein U is

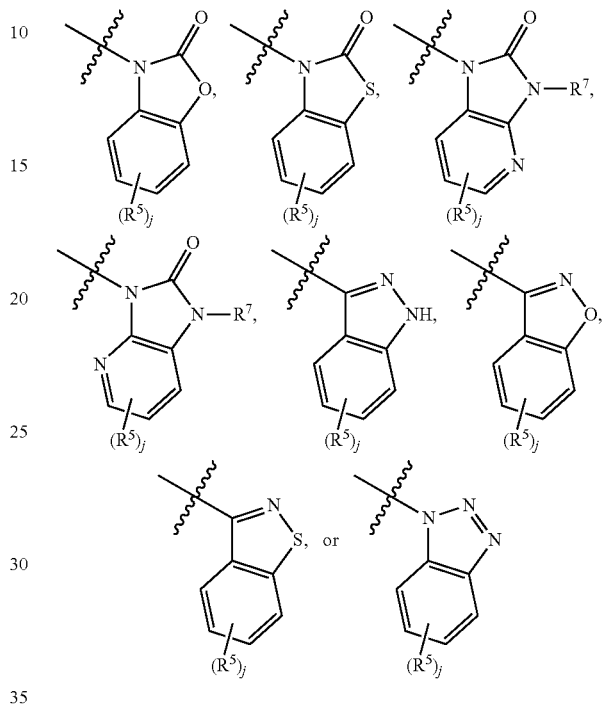

and the symbol ∿, when drawn across a bond, indicates the point of attachment to the rest of the molecule.

45. The compound of claim 1 or the pharmaceutically acceptable salt thereof, the tautomer thereof, the pharmaceutically acceptable salt of the tautomer, the stereoisomer of any of the foregoing, or the mixture thereof, wherein U is

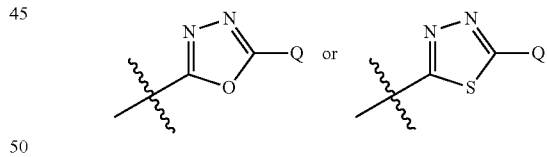

and the symbol ∿, when drawn across a bond, indicates the point of attachment to the rest of the molecule.

46. The compound of claim 45 or the pharmaceutically acceptable salt thereof, the tautomer thereof, the pharmaceutically acceptable salt of the tautomer, the stereoisomer of any of the foregoing, or the mixture thereof, wherein Q is Q' and Q' is a phenyl or a heteroaryl group with 6 ring members containing 1 or 2 N heteroatoms, wherein the phenyl group and the heteroaryl group are unsubstituted or are substituted with 1 or 2 substituents independently selected from —F, —Cl, —CN, —$CH_3$, —$CF_3$, or —$OCH_3$.

47. The compound of claim 1 or the pharmaceutically acceptable salt thereof, the tautomer thereof, the pharmaceutically acceptable salt of the tautomer, the stereoisomer of any of the foregoing, or the mixture thereof, wherein U is and the symbol ⌇, when drawn across a bond, indicates the point of attachment to the rest of the molecule.

48. The compound of claim 1 or the pharmaceutically acceptable salt thereof, the tautomer thereof, the pharmaceutically acceptable salt of the tautomer, the stereoisomer of any of the foregoing, or the mixture thereof, wherein the compound is trans-N-(2-(4-oxo-3,4-dihydro-2-quinazolinypethyl)-4-(5-phenyl-1,3,4-oxadiazol-2-yl)cyclohexanecarboxamide;
3-(4-oxo-3,4-dihydro-2-quinazolinyl)-N-(trans-4-(5-phenyl-1,3,4-oxadiazol-2-yl)cyclohexyl)propanamide;
2-(4-(4-(5-(3-chlorophenyl)-1,3,4-oxadiazol-2-yl)-1-piperidinyl)-4-oxobutyl)-4(3H)-quinazolinone;
2-(4-(4-(5-(4-chlorophenyl)-1,3,4-oxadiazol-2-yl)-1-piperidinyl)-4-oxobutyl)-4(3H)-quinazolinone;
2-(4-(4-(5-(3-fluorophenyl)-1,3,4-oxadiazol-2-yl)-1-piperidinyl)-4-oxobutyl)-4(3H)-quinazolinone;
2-(4-(4-(5-(4-fluorophenyl)-1,3,4-oxadiazol-2-yl)-1-piperidinyl)-4-oxobutyl)-4(3H)-quinazolinone;
2-(4-(4-(6-methyl-2-oxo-2,3-dihydro-1H-benzimidazol-1-yl)-1-piperidinyl)-4-oxobutyl)-4(3H)-quinazolinone;
2-(4-(4-(5-methoxy-2-oxo-2,3-dihydro-1H-benzimidazol-1-yl)-1-piperidinyl)-4-oxobutyl)-4(3H)-quinazolinone;
2-(4-oxo-4-(4-(5-phenyl-1,3,4-thiadiazol-2-yl)-1-piperidinyl)butyl)-4(3H)-quinazolinone;
4-(4-oxo-3,4-dihydro-2-quinazolinyl)-N-(trans-4-(5-phenyl-1,3,4-oxadiazol-2-yl)cyclohexyl)butanamide;
2-(4-(4-(5-methyl-2-oxo-2,3-dihydro-1H-benzimidazol-1-yl)-1-piperidinyl)-4-oxobutyl)-4(3H)-quinazolinone;
2-(4-oxo-4-(4-(5-(2-pyridinyl)-1,3,4-oxadiazol-2-yl)-1-piperidinyl)butyl)-4(3H)-quinazolinone;
2-(4-oxo-4-(4-(5-(3-pyridinyl)-1,3,4-oxadiazol-2-yl)-1-piperidinyl)butyl)-4(3H)-quinazolinone;
2-(4-oxo-4-(4-(5-(2-pyrazinyl)-1,3,4-oxadiazol-2-yl)-1-piperidinyl)butyl)-4(3H)-quinazolinone;
2-(4-(4-(5-(4-methoxyphenyl)-1,3,4-oxadiazol-2-yl)-1-piperidinyl)-4-oxobutyl)-4(3H)-quinazolinone;
2-(4-(4-(5-(2-chlorophenyl)-1,3,4-oxadiazol-2-yl)-1-piperidinyl)-4-oxobutyl)-4(3H)-quinazolinone;
2-(4-(4-(5-((4-chlorophenoxy)methyl)-1,3,4-oxadiazol-2-yl)-1-piperidinyl)-4-oxobutyl)-4(3H)-quinazolinone;
2-(4-(4-(5-(2-fluorophenyl)-1,3,4-oxadiazol-2-yl)-1-piperidinyl)-4-oxobutyl)-4(3H)-quinazolinone;
2-(4-oxo-4-(4-(5-(4-pyridinyl)-1,3,4-oxadiazol-2-yl)-1-piperidinyl)butyl)-4(3H)-quinazolinone;
3-(5-(1-(4-(4-oxo-3,4-dihydro-2-quinazolinyl)butanoyl)-4-piperidinyl)-1,3,4-oxadiazol-2-yl)benzonitrile;
4-(5-(1-(4-(4-oxo-3,4-dihydro-2-quinazolinyl)butanoyl)-4-piperidinyl)-1,3,4-oxadiazol-2-yl)benzonitrile;
2-(4-(4-(5-(3-methylphenyl)-1,3,4-oxadiazol-2-yl)-1-piperidinyl)-4-oxobutyl)-4(3H)-quinazolinone;
2-(4-(4-(5-(4-methylphenyl)-1,3,4-oxadiazol-2-yl)-1-piperidinyl)-4-oxobutyl)-4(3H)-quinazolinone;
2-(4-(4-(5-(3-methoxyphenyl)-1,3,4-oxadiazol-2-yl)-1-piperidinyl)-4-oxobutyl)-4(3H)-quinazolinone;
2-(4-(4-(5-(3-chloro-4-fluorophenyl)-1,3,4-oxadiazol-2-yl)-1-piperidinyl)-4-oxobutyl)-4(3H)-quinazolinone;
2-(4-oxo-4-(4-(2-oxo-1,2-dihydro-3H-imidazo[4,5-b]pyridin-3-yl)-1-piperidinyl)butyl)-4(3H)-quinazolinone;
2-(4-(4-(5-chloro-2-oxo-2,3-dihydro-1H-benzimidazol-1-yl)-1-piperidinyl)-4-oxobutyl)-4(3H)-quinazolinone;
N-(trans-4-(5-(4-fluorophenyl)-1,3,4-oxadiazol-2-yl)cyclohexyl)-4-(4-oxo-3,4-dihydro-2-quinazolinyl)butanamide;
N-(trans-4-(5-(4-chlorophenyl)-1,3,4-oxadiazol-2-yl)cyclohexyl)-4-(4-oxo-3,4-dihydro-2-quinazolinyl)butanamide;
N-(trans-4-(5-(4-methoxyphenyl)-1,3,4-oxadiazol-2-yl)cyclohexyl)-4-(4-oxo-3,4-dihydro-2-quinazolinyl)butanamide;
N-(trans-4-(5-(3-fluorophenyl)-1,3,4-oxadiazol-2-yl)cyclohexyl)-4-(4-oxo-3,4-dihydro-2-quinazolinyl)butanamide;
N-(trans-4-(5-(3-methoxyphenyl)-1,3,4-oxadiazol-2-yl)cyclohexyl)-4-(4-oxo-3,4-dihydro-2-quinazolinyl)butanamide;
4-(4-oxo-3,4-dihydro-2-quinazolinyl)-N-(trans-4-(5-(4-pyridinyl)-1,3,4-oxadiazol-2-yl)cyclohexyl)butanamide;
2-(4-(4-(6-methoxy-2-oxo-2,3-dihydro-1H-benzimidazol-1-yl)-1-piperidinyl)-4-oxobutyl)-4(3H)-quinazolinone;
N-(trans-4-(5-(3-chloro-4-fluorophenyl)-1,3,4-oxadiazol-2-yl)cyclohexyl)-4-(4-oxo-3,4-dihydro-2-quinazolinyl)butanamide;

N-(trans-4-(5-(3-chlorophenyl)-1,3,4-oxadiazol-2-yl)cyclohexyl)-4-(4-oxo-3,4-dihydro-2-quinazolinyl)butanamide;
3-((4-methyl-6-oxo-1,6-dihydropyrimidin-2-yl)thio)-N-((1 r,4r)-4-(5-phenyl-1,3,4-oxadiazol-2-yl)cyclohexyl) propanamide;
3-((4-oxo-3,4-dihydroquinazolin-2-yl)thio)-N-((1 s,3s)-3-(5-phenyl-1,3,4-oxadiazol-2-yl)cyclobutyl)propanamide;
3-((4-oxo-3,4-dihydroquinazolin-2-yl)thio)-N-((1 r,3r)-3-(5-phenyl-1,3,4-oxadiazol-2-yl)cyclobutyl)propanamide;
2-(4-oxo-4-(4-(2-oxo-2,3-dihydro-1H-benzimidazol-1-yl)-1-piperidinyl)butyl)-4(3H)-quinazolinone;
2-(4-oxo-4-(4-(5-phenyl-1,3,4-oxadiazol-2-yl)-1-piperidinyl)butyl)-4(3H)-quinazolinone;
2-(4-oxo-4-(4-(2-oxo-2,3-dihydro-1H-indol-1-yl)-1-piperidinyl)butyl)-4(3H)-quinazolinone;
2-(4-oxo-4-(4-(2-oxo-1,3-benzoxazol-3(2H)-yl)-1-piperidinyl)butyl)-4(3H)-quinazolinone;
2-(4-(4-(5-chloro-3-methyl-2-oxo-2,3-dihydro-1H-benzimidazol-1-yl)-1-piperidinyl)-4-oxobutyl)-4(3H)-quinazolinone;
2-(4-oxo-4-(4-(2-oxo-2,3-dihydro-1H-benzimidazol-1-yl)-3,6-dihydro-1 (2H)-pyridinyl)butyl)-4(3H)-quinazolinone;
2-(4-oxo-4-(4-(2-oxo-2,3-dihydro-1H-imidazo[4,5-b]pyridin-1-yl)-1-piperidinyl)butyl)-4(3H)-quinazolinone;
2-(4-(4-(1H-indazol-3-yl)-1-piperidinyl)-4-oxobutyl)-4(3H)-quinazolinone;
2-(4-oxo-4-(4-(2-oxo-4-phenyl-2,3-dihydro-1H-imidazol-1-yl)-1-piperidinyl)butyl)-4(3H)-quinazolinone;
2-(4-oxo-4-(4-(2-oxo-1,3-benzothiazol-3(2H)-yl)-1-piperidinyl)butyl)-4(3H)-quinazolinone;
2-(4-(4-(5-fluoro-2-oxo-2,3-dihydro-1H-benzimidazol-1-yl)-1-piperidinyl)-4-oxobutyl)-4(3H)-quinazolinone;
2-(4-oxo-4-(4-(2-oxo-5-(trifluoromethyl)-2,3-dihydro-1H-benzimidazol-1-yl)-1-piperidinyl)butyl)-4(3H)-quinazolinone;
2-(4-(4-(6-fluoro-2-oxo-1,3-benzoxazol-3(2H)-yl)-1-piperidinyl)-4-oxobutyl)-4(3H)-quinazolinone;
2-(4-(4-(3-methyl-2-oxo-2,3-dihydro-1H-benzimidazol-1-yl)-1-piperidinyl)-4-oxobutyl)-4(3H)-quinazolinone;
2-(4-(4-(1H-indazol-3-yl)-1-piperazinyl)-4-oxobutyl)-4 (3H)-quinazolinone;
4-(4-oxo-3,4-dihydro-2-quinazolinyl)-N-(trans-4-(2-pyridinyloxy)cyclohexyl)butanamide;
N-(trans-4-(2-cyanophenoxy)cyclohexyl)-4-(4-oxo-3,4-dihydro-2-quinazolinyl)butanamide;
N-(trans-4-(3-cyanophenoxy)cyclohexyl)-4-(4-oxo-3,4-dihydro-2-quinazolinyl)butanamide;
4-(4-oxo-3,4-dihydro-2-quinazolinyl)-N-(trans-4-(3-pyridinyloxy)cyclohexyl)butanamide;
2-(4-(4-(3,3-difluoro-2-oxo-2,3-dihydro-1H-indol-1-yl)-1-piperidinyl)-4-oxobutyl)-4(3H)-quinazolinone;
2-oxo-1-(1-(4-(4-oxo-3,4-dihydro-2-quinazolinyl)butanoyl)-4-piperidinyl)-2,3-dihydro-1H-benzimidazole-4-carbonitrile;
N-((1R,3R)-3-(benzyloxy)cyclopentyl)-4-(4-oxo-3,4-dihydro-2-quinazolinyl)butanamide;
N-((1 S,3S)-3-(benzyloxy)cyclopentyl)-4-(4-oxo-3,4-dihydro-2-quinazolinyl)butanamide;
N-(trans-4-(4-chloro-3-cyanophenoxy)cyclohexyl)-4-(4-oxo-3,4-dihydro-2-quinazolinyl)butanamide;
N-(trans-4-(3-chloro-4-cyanophenoxy)cyclohexyl)-4-(4-oxo-3,4-dihydro-2-quinazolinyl)butanamide;
4-(4-oxo-3,4-dihydro-2-quinazolinyl)-N-((1 S,3S)-3-phenoxycyclopentyl)butanamide;
4-(4-oxo-3,4-dihydro-2-quinazolinyl)-N-((1R,3R)-3-phenoxycyclopentyl)butanamide;
N-(trans-4-(3-chlorophenoxy)cyclohexyl)-4-(4-oxo-3,4-dihydro-2-quinazolinyl)butanamide;
2-(4-(4-(4-fluoro-2-oxo-2,3-dihydro-1H-benzimidazol-1-yl)-1-piperidinyl)-4-oxobutyl)-4(3H)-quinazolinone;
2-oxo-1-(1-(4-(4-oxo-3,4-dihydro-2-quinazolinyl)butanoyl)-4-piperidinyl)-2,3-dihydro-1H-benzimidazole-5-carbonitrile;
2-(4-(4-(1,2-benzisothiazol-3-yl)-1-piperazinyl)-4-oxobutyl)-4(3H)-quinazolinone;
4-(4-oxo-3,4-dihydro-2-quinazolinyl)-N-(trans-4-(4-pyridinyloxy)cyclohexyl)butanamide;
2-(4-(4-(1,2-benzisoxazol-3-yl)-1-piperazinyl)-4-oxobutyl)-4(3H)-quinazolinone;
2-(4-(4-(5-fluoro-1,2-benzisoxazol-3-yl)-1-piperidinyl)-4-oxobutyl)-4(3H)-quinazolinone;
N-(trans-4-(2-oxo-2,3-dihydro-1H-benzimidazol-1-yl)cyclohexyl)-4-(4-oxo-3,4-dihydro-2-quinazolinyl)butanamide;
N-(trans-4-(5-chloro-2-oxo-2,3-dihydro-1H-benzimidazol-1-yl)cyclohexyl)-4-(4-oxo-3,4-dihydro-2-quinazolinyl)butanamide;
2-(4-(4-(1H-benzotriazol-1-yl)-1-piperidinyl)-4-oxobutyl)-4(3H)-quinazolinone;
2-(4-(4-((3S)-6-chloro-2-oxo-2,3-dihydro-1H-indol-3-yl)-1-piperidinyl)-4-oxobutyl)-4(3H)-quinazolinone;
2-(4-(4-((3R)-6-chloro-2-oxo-2,3-dihydro-1H-indol-3-yl)-1-piperidinyl)-4-oxobutyl)-4(3H)-quinazolinone;
N-(trans-4-(4-fluorophenoxy)cyclohexyl)-4-(4-oxo-3,4-dihydro-2-quinazolinyl)butanamide;
N-(trans-4-(4-cyanophenoxy)cyclohexyl)-4-(4-oxo-3,4-dihydro-2-quinazolinyl)butanamide;
N-(trans-4-(4-chlorophenoxy)cyclohexyl)-4-(4-oxo-3,4-dihydro-2-quinazolinyl)butanamide;
N-(trans-4-(2-oxo-1,3-benzoxazol-3(2H)-yl)cyclohexyl)-3-(4-oxo-3,4-dihydro-2-quinazolinyl)propanamide;
3-(4-oxo-3,4-dihydropyrido[2,3-d]pyrimidin-2-yl)-N-(trans-4-(5-phenyl-1,3,4-oxadiazol-2-yl)cyclohexyl) propanamide;
2-((3-(4-(5-chloro-2-oxo-2,3-dihydro-1H-benzimidazol-1-yl)-1-piperidinyl)-3-oxopropyl)sulfanyl)-4(3H)-quinazolinone;
2-((3-oxo-3-(4-(5-phenyl-1,3,4-oxadiazol-2-yl)-1-piperidinyl)propyl)sulfanyl)-4(3H)-quinazolinone;
N-(trans-4-(2-oxo-2,3-dihydro-1H-benzimidazol-1-yl) cyclohexyl)-3-(4-oxo-3,4-dihydro-2-quinazolinyl)propanamide;
N-(trans-4-(5-chloro-2-oxo-2,3-dihydro-1H-benzimidazol-1-yl)cyclohexyl)-3-(4-oxo-3,4-dihydro-2-quinazolinyl)propanamide;
N-(trans-4-(6-chloro-2-oxo-2,3-dihydro-1H-benzimidazol-1-yl)cyclohexyl)-3-(4-oxo-3,4-dihydro-2-quinazolinyl)propanamide;
N-(trans-4-(5-chloro-2-oxo-2,3-dihydro-1H-benzimidazol-1-yl)cyclohexyl)-2-((4-oxo-3,4-dihydro-2-quinazolinyl)sulfanyl)acetamide;
3-(4-oxo-3,4,5,6,7,8-hexahydropyrido[2,3-d]pyrimidin-2-yl)-N-(trans-4-(5-phenyl-1,3,4-oxadiazol-2-yl)cyclohexyl)propanamide;
2-((2-oxo-2-(4-(5-phenyl-1,3,4-oxadiazol-2-yl)-1-piperidinypethyl)sulfanyl)-4(3H)-quinazolinone;
N-(trans-4-(5-chloro-2-oxo-2,3-dihydro-1H-benzimidazol-1-yl)cyclohexyl)-3-((4-oxo-3,4-dihydro-2-quinazolinyl)sulfanyl)propanamide;

3-((4-amino-6-oxo-1,6-dihydro-2-pyrimidinyl)sulfanyl)-N-(trans-4-(5-phenyl-1,3,4-oxadiazol-2-yl)cyclohexyl)propanamide;

3-(((4-oxo-3,4-dihydro-2-quinazolinyl)methyl)sulfanyl)-N-(trans-4-(5-phenyl-1,3,4-oxadiazol-2-yl)cyclohexyl)propanamide;

2-(((3-(4-(5-(4-fluorophenyl)-1,3,4-oxadiazol-2-yl)-1-piperidinyl)-3-oxopropyl)sulfanyl)methyl)-4(3H)-quinazolinone;

2-((3-(4-(1H-indazol-3-yl)-1-piperazinyl)-3-oxopropyl)sulfanyl)-4(3H)-quinazolinone;

4-(4-oxo-3,4-dihydro-2-quinazolinyl)-N-(trans-4-(5-phenyl-1,3-oxazol-2-yl)cyclohexyl)butanamide;

2-((4-oxo-3,4-dihydro-2-quinazolinyl)sulfanyl)-N-(trans-4-(5-phenyl-1,3,4-oxadiazol-2-yl)cyclohexyl)acetamide;

3-((4-oxo-3,4-dihydro-2-quinazolinyl)sulfanyl)-N-(trans-4-(5-phenyl-1,3,4-oxadiazol-2-yl)cyclohexyl)propanamide;

2-(3-oxo-3-(4-(5-phenyl-1,3,4-oxadiazol-2-yl)-1-piperidinyl)propyl)-4(3H)-quinazolinone;

N-(trans-4-(4-fluorophenoxy)cyclohexyl)-2-((4-oxo-3,4-dihydro-2-quinazolinyl)sulfanyl)acetamide;

N-(trans-4-(4-fluorophenoxy)cyclohexyl)-3-((4-oxo-3,4-dihydro-2-quinazolinyl)sulfanyl)propanamide;

3-(6-fluoro-4-oxo-3,4-dihydro-2-quinazolinyl)-N-(trans-4-(5-phenyl-1,3,4-oxadiazol-2-yl)cyclohexyl)propanamide;

N-(trans-4-(6-chloro-2-oxo-2,3-dihydro-1H-benzimidazol-1-yl)cyclohexyl)-2-((4-oxo-3,4-dihydro-2-quinazolinyl)sulfanyl)acetamide;

N-(trans-4-(5-cyano-2-oxo-2,3-dihydro-1H-benzimidazol-1-yl)cyclohexyl)-2-((4-oxo-3,4-dihydro-2-quinazolinyl)sulfanyl)acetamide;

N-(trans-4-(5-cyano-2-oxo-2,3-dihydro-1H-benzimidazol-1-yl)cyclohexyl)-3-((4-oxo-3,4-dihydro-2-quinazolinyl)sulfanyl)propanamide;

N-(trans-4-(4-chlorophenoxy)cyclohexyl)-3-((4-oxo-3,4-dihydro-2-quinazolinyl)sulfanyl)propanamide;

N-(trans-4-(4-cyanophenoxy)cyclohexyl)-3-((4-oxo-3,4-dihydro-2-quinazolinyl)sulfanyl)propanamide;

3-((4-oxo-3,4-dihydro-2-quinazolinyl)sulfanyl)-N-(trans-4-(2-pyridinyloxy)cyclohexyl)propanamide;

3-((4-oxo-3,4-dihydro-2-quinazolinyl)sulfanyl)-N-(trans-4-(4-pyridinyloxy)cyclohexyl)propanamide;

N-(trans-4-(3-cyanophenoxy)cyclohexyl)-3-((4-oxo-3,4-dihydro-2-quinazolinyl)sulfanyl)propanamide;

4-((4-oxo-3,4-dihydro-2-quinazolinyl)sulfanyl)-N-(trans-4-(5-phenyl-1,3,4-oxadiazol-2-yl)cyclohexyl)butanamide;

2-((4-oxo-4-(4-(5-phenyl-1,3,4-oxadiazol-2-yl)-1-piperidinyl)butyl)sulfanyl)-4(3H)-quinazolinone;

N-(trans-4-(3-chlorophenoxy)cyclohexyl)-3-((4-oxo-3,4-dihydro-2-quinazolinyl)sulfanyl)propanamide;

N-(trans-4-(4-chloro-3-cyanophenoxy)cyclohexyl)-3-((4-oxo-3,4-dihydro-2-quinazolinyl)sulfanyl)propanamide;

N-(trans-4-(3-chloro-4-cyanophenoxy)cyclohexyl)-3-((4-oxo-3,4-dihydro-2-quinazolinyl)sulfanyl)propanamide;

3-((4-oxo-3,4,5,6,7,8-hexahydro-2-quinazolinyl)sulfanyl)-N-(trans-4-(5-phenyl-1,3,4-oxadiazol-2-yl)cyclohexyl)propanamide;

N-(trans-4-(4-cyanophenoxy)cyclohexyl)-34(4-oxo-3,4,5,6,7,8-hexahydro-2-quinazolinyl)sulfanyl)propanamide;

N-(trans-4-(5-(4-fluorophenyl)-1,3,4-oxadiazol-2-yl)cyclohexyl)-3-((4-oxo-3,4-dihydro-2-quinazolinyl)sulfanyl)propanamide;

N-(trans-4-(5-(3-chlorophenyl)-1,3,4-oxadiazol-2-yl)cyclohexyl)-3-((4-oxo-3,4-dihydro-2-quinazolinyl)sulfanyl)propanamide;

N-(trans-4-(5-(3-fluorophenyl)-1,3,4-oxadiazol-2-yl)cyclohexyl)-3-((4-oxo-3,4-dihydro-2-quinazolinyl)sulfanyl)propanamide;

N-(trans-4-(5-(3-methoxyphenyl)-1,3,4-oxadiazol-2-yl)cyclohexyl)-3-((4-oxo-3,4-dihydro-2-quinazolinyl)sulfanyl)propanamide;

N-(trans-4-(5-(4-methoxyphenyl)-1,3,4-oxadiazol-2-yl)cyclohexyl)-3-((4-oxo-3,4-dihydro-2-quinazolinyl)sulfanyl)propanamide;

N-(trans-4-(5-(3-chloro-4-fluorophenyl)-1,3,4-oxadiazol-2-yl)cyclohexyl)-3-((4-oxo-3,4-dihydro-2-quinazolinyl)sulfanyl)propanamide;

3-((6-oxo-1,6-dihydro-2-pyrimidinyl)sulfanyl)-N-(trans-4-(5-phenyl-1,3,4-oxadiazol-2-yl)cyclohexyl)propanamide;

3-((4-oxo-3,4-dihydro-2-quinazolinyl)sulfanyl)-N-(trans-4-(5-(4-pyridinyl)-1,3,4-oxadiazol-2-yl)cyclohexyl)propanamide;

N-(trans-4-(5-(4-chlorophenyl)-1,3,4-oxadiazol-2-yl)cyclohexyl)-3-((4-oxo-3,4-dihydro-2-quinazolinyl)sulfanyl)propanamide;

N-(trans-4-(5-(2-fluorophenyl)-1,3,4-oxadiazol-2-yl)cyclohexyl)-3-(4-oxo-3,4-dihydro-2-quinazolinyl)propanamide;

N-(trans-4-(5-(4-fluorophenyl)-1,3,4-oxadiazol-2-yl)cyclohexyl)-3-(4-oxo-3,4-dihydro-2-quinazolinyl)propanamide;

N-(trans-4-(5-(2-chlorophenyl)-1,3,4-oxadiazol-2-yl)cyclohexyl)-3-(4-oxo-3,4-dihydro-2-quinazolinyl)propanamide;

N-(trans-4-(5-(3-fluorophenyl)-1,3,4-oxadiazol-2-yl)cyclohexyl)-3-(4-oxo-3,4-dihydro-2-quinazolinyl)propanamide;

N-(trans-4-(5-(3-chlorophenyl)-1,3,4-oxadiazol-2-yl)cyclohexyl)-3-(4-oxo-3,4-dihydro-2-quinazolinyl)propanamide;

3-(4-oxo-3,4-dihydro-2-quinazolinyl)-N-(trans-4-(5-(2-pyridinyl)-1,3,4-oxadiazol-2-yl)cyclohexyl)propanamide;

3-(4-oxo-3,4-dihydro-2-quinazolinyl)-N-(trans-4-(5-(4-pyridinyl)-1,3,4-oxadiazol-2-yl)cyclohexyl)propanamide;

3-(4-oxo-3,4-dihydro-2-quinazolinyl)-N-(trans-4-(5-(2-pyrimidinyl)-1,3,4-oxadiazol-2-yl)cyclohexyl)propanamide;

N-((1 r,4r)-4-(5-(4-cyanophenyl)-1,3,4-oxadiazol-2-yl)cyclohexyl)-3-(4-oxo-3,4-dihydroquinazolin-2-yl)propanamide;

3-(4-oxo-3,4-dihydroquinazolin-2-yl)-N-((1 r,4r)-4-(5-(tetrahydro-2H-pyran-4-yl)-1,3,4-oxadiazol-2-yl)cyclohexyl)propanamide;

3-(4-oxo-3,4-dihydro-2-quinazolinyl)-N-(trans-4-(5-(3-pyridinyl)-1,3,4-oxadiazol-2-yl)cyclohexyl)propanamide;

N-(trans-4-(5-(3-cyanophenyl)-1,3,4-oxadiazol-2-yl)cyclohexyl)-3-(4-oxo-3,4-dihydro-2-quinazolinyl)propanamide;

N-(trans-4-(5-cyclohexyl-1,3,4-oxadiazol-2-yl)cyclohexyl)-3-(4-oxo-3,4-dihydro-2-quinazolinyl)propanamide;

N-(trans-4-(5-benzyl-1,3,4-oxadiazol-2-yl)cyclohexyl)-3-(4-oxo-3,4-dihydro-2-quinazolinyl)propanamide;

3-(4-oxo-3,4-dihydroquinazolin-2-yl)-N-((1 r,4r)-4-(5-(2-phenylpropan-2-yl)-1,3,4-oxadiazol-2-yl)cyclohexyl)propanamide;

N-(trans-4-(5-(4-chlorophenyl)-1,3,4-oxadiazol-2-yl)cyclohexyl)-3-(4-oxo-3,4-dihydro-2-quinazolinyl)propanamide;

3-(4-oxo-3,4-dihydro-2-quinazolinyl)-N-(trans-4-(5-(2-pyrazinyl)-1,3,4-oxadiazol-2-yl)cyclohexyl)propanamide;

3-((4-oxo-3,4-dihydro-2-quinazolinyl)sulfinyl)-N-(trans-4-(5-phenyl-1,3,4-oxadiazol-2-yl)cyclohexyl)propanamide; or 3-((6-fluoro-4-oxo-3,4-dihydro-2-quinazolinyl)sulfanyl)-N-(trans-4-(5-phenyl-1,3,4-oxadiazol-2-yl)cyclohexyl)propanamide.

49. A pharmaceutical composition, comprising the compound of claim 1 or the pharmaceutically acceptable salt thereof, the tautomer thereof, the pharmaceutically acceptable salt of the tautomer, the stereoisomer of any of the foregoing, or the mixture thereof, and at least one pharmaceutically acceptable excipient, carrier, or diluent.

* * * * *